US010106543B2

(12) United States Patent
Kanyo et al.

(10) Patent No.: US 10,106,543 B2
(45) Date of Patent: Oct. 23, 2018

(54) ANTIMICROBIAL COMPOUNDS AND METHODS OF MAKING AND USING THE SAME

(71) Applicant: Melinta Therapeutics, Inc., New Haven, CT (US)

(72) Inventors: Zoltan F. Kanyo, New Haven, CT (US); Ashoke Bhattacharjee, New Haven, CT (US); Erin M. Duffy, New Haven, CT (US); Andrea Marra, New Haven, CT (US)

(73) Assignee: Melinta Therapeutics, Inc., New Haven, CT (US)

( * ) Notice: Subject to any disclaimer, the term of this patent is extended or adjusted under 35 U.S.C. 154(b) by 0 days.

(21) Appl. No.: 14/917,921

(22) PCT Filed: Sep. 9, 2014

(86) PCT No.: PCT/US2014/054869
§ 371 (c)(1),
(2) Date: Mar. 9, 2016

(87) PCT Pub. No.: WO2015/035426
PCT Pub. Date: Mar. 12, 2015

(65) Prior Publication Data
US 2016/0214988 A1    Jul. 28, 2016

Related U.S. Application Data

(60) Provisional application No. 61/875,643, filed on Sep. 9, 2013.

(51) Int. Cl.
*C07D 487/04* (2006.01)
*A61K 31/519* (2006.01)
*C07D 239/47* (2006.01)
*C07D 519/00* (2006.01)

(52) U.S. Cl.
CPC ......... *C07D 487/04* (2013.01); *C07D 239/47* (2013.01); *C07D 519/00* (2013.01)

(58) Field of Classification Search
None
See application file for complete search history.

(56) References Cited

U.S. PATENT DOCUMENTS

| 2,624,731 | A | 1/1953 | Hitchings et al. |
| 3,673,184 | A | 6/1972 | Minami |
| 3,980,781 | A | 9/1976 | Snell et al. |
| 4,361,557 | A | 11/1982 | Nagabhushan |
| 4,522,811 | A | 6/1985 | Eppstein et al. |
| 4,971,965 | A | 11/1990 | Ono et al. |
| 5,208,141 | A | 5/1993 | Ikesu et al. |
| 5,434,257 | A | 7/1995 | Matteucci et al. |
| 5,567,844 | A | 10/1996 | Jommi et al. |
| 5,567,884 | A | 10/1996 | Jommi et al. |
| 5,763,263 | A | 6/1998 | Dehlinger |
| 5,763,588 | A | 6/1998 | Matteucci et al. |
| 5,766,855 | A | 6/1998 | Buchardt et al. |
| 5,958,930 | A | 9/1999 | Gangjee |
| 6,028,183 | A | 2/2000 | Lin et al. |
| 6,110,925 | A | 8/2000 | Williams et al. |
| 6,162,925 | A | 12/2000 | Williams et al. |
| 6,617,332 | B1 | 9/2003 | Brands et al. |
| 6,875,764 | B1 | 4/2005 | Muzi et al. |
| 7,282,327 | B2 | 10/2007 | McGall et al. |
| 9,023,843 | B2 | 5/2015 | Duffy et al. |
| 9,193,731 | B2 | 11/2015 | Duffy et al. |
| 9,216,979 | B2 | 12/2015 | Duffy et al. |
| 9,221,827 | B2 | 12/2015 | Duffy et al. |
| 9,573,962 | B2 | 2/2017 | Duffy et al. |
| 2002/0016297 | A1 | 2/2002 | Linde, II et al. |
| 2002/0193385 | A1 | 12/2002 | Chambers et al. |
| 2003/0158403 | A1 | 8/2003 | Manoharan et al. |
| 2005/0153992 | A1 | 7/2005 | Tsutsumi et al. |
| 2006/0014743 | A1 | 1/2006 | Boojamra et al. |
| 2006/0100224 | A1 | 5/2006 | Svenstrup et al. |
| 2007/0206054 | A1 | 9/2007 | Watanbe |
| 2008/0221095 | A1 | 9/2008 | Gege et al. |
| 2008/0255164 | A1 | 10/2008 | Albert et al. |
| 2010/0190747 | A1 | 7/2010 | Suzuki et al. |
| 2010/0249126 | A1 | 9/2010 | Burger et al. |
| 2016/0214988 | A1 | 7/2016 | Kanyo et al. |
| 2016/0220568 | A1 | 8/2016 | Kanyo et al. |
| 2018/0065966 | A1 | 3/2018 | Bhattacharjee et al. |

FOREIGN PATENT DOCUMENTS

| CN | 1871240 | 11/2006 |
| CN | 101535311 | 9/2009 |
| CN | 102712647 | 10/2012 |
| DE | 10061537 | 6/2002 |
| DE | 10061538 | 6/2002 |

(Continued)

OTHER PUBLICATIONS

Aguilar et al., "Toward a library synthesis of the natural dipeptide antibiotic TAN 1057 A, B," Molecules. Jun. 30, 2002; 7(6):469-474.
Angelino et al., "On the oxidation of N-methyl and N-benzylpyrimidin-2-and-4-ones by rabbit liver aldehyde oxidase," Journal of heterocyclic chemistry. 1984; 21:749-752.
Ausín et al., "Synthesis of amino-and guanidino-G-clamp PNA monomers," Organic letters. Nov. 14, 2002; 4(23):4073-4075.
Babic et al., "What's new in antibiotic resistance? Focus on beta-lactamases/'" Drug resistance updates. Jun. 30, 2006; 9(3):142-156.
Bandow et al., "Proteomic approach to understanding antibiotic action," Antimicrobial agents and chemotherapy. Mar. 1, 2003; 47(3):948-955.

(Continued)

*Primary Examiner* — Nyeemah A Grazier
(74) *Attorney, Agent, or Firm* — Fish & Richardson P.C.

(57) ABSTRACT

The present invention relates generally to the field of antimicrobial compounds and to methods of making and using them. These compounds are useful for treating, preventing, reducing the risk of, and delaying the onset of microbial infections in humans and animals.

17 Claims, No Drawings

(56) References Cited

FOREIGN PATENT DOCUMENTS

| | | |
|---|---|---|
| DE | 10061541 | 6/2002 |
| DE | 10061542 | 6/2002 |
| DE | 10133277 | 1/2003 |
| DE | 10141271 | 3/2003 |
| EP | 0339596 | 11/1989 |
| EP | 1113008 | 7/2001 |
| JP | S42025913 | 9/1965 |
| JP | 61091184 | 5/1986 |
| JP | 04077488 | 3/1992 |
| JP | H09506859 | 7/1997 |
| JP | H10503759 | 4/1998 |
| JP | 2001522369 | 11/2001 |
| JP | 2001522860 | 11/2001 |
| JP | 2004533406 | 11/2004 |
| JP | 2004537503 | 12/2004 |
| JP | 2005504020 | 2/2005 |
| JP | 2007270087 | 10/2007 |
| JP | 2008222557 | 9/2008 |
| JP | S5821681 | 10/2015 |
| KR | 20060118416 | 11/2006 |
| TW | 424090 | 3/2001 |
| TW | 99135283 | 10/2010 |
| TW | 201124417 | 7/2011 |
| WO | WO1994026722 | 11/1994 |
| WO | WO1995029894 | 11/1995 |
| WO | WO1997001562 | 1/1997 |
| WO | WO1998049177 | 11/1998 |
| WO | WO1999007685 | 2/1999 |
| WO | WO1999024452 | 5/1999 |
| WO | WO2000012484 | 3/2000 |
| WO | WO2001030749 | 5/2001 |
| WO | WO2001060825 | 8/2001 |
| WO | WO2002032920 | 4/2002 |
| WO | WO2002048138 | 6/2002 |
| WO | WO2002061110 | 8/2002 |
| WO | WO2002074773 | 9/2002 |
| WO | WO2002097134 | 12/2002 |
| WO | WO2003004602 | 1/2003 |
| WO | WO2003072574 | 9/2003 |
| WO | WO2004080466 | 9/2004 |
| WO | WO2005019228 | 3/2005 |
| WO | WO2005037801 | 4/2005 |
| WO | WO2006/002627 | 1/2006 |
| WO | WO2007014308 | 2/2007 |
| WO | WO2007069923 | 6/2007 |
| WO | WO2007084786 | 7/2007 |
| WO | WO2008004796 | 1/2008 |
| WO | WO2008030119 | 3/2008 |
| WO | WO2008082440 | 7/2008 |
| WO | WO2008104279 | 9/2008 |
| WO | WO2008143729 | 11/2008 |
| WO | WO2008/156610 | 12/2008 |
| WO | WO2008150406 | 12/2008 |
| WO | WO2008154642 | 12/2008 |
| WO | WO2009074812 | 6/2009 |
| WO | WO2009113828 | 9/2009 |
| WO | WO2011/017319 | 2/2011 |
| WO | WO2011045415 | 4/2011 |
| WO | WO2011047319 | 4/2011 |
| WO | WO2012125832 | 9/2012 |
| WO | WO2012173689 | 12/2012 |
| WO | WO2015035421 | 3/2015 |
| WO | WO2015035426 | 3/2015 |

OTHER PUBLICATIONS

Banker et al, "Modern Pharmaceutics, 3ed.," Marcel Dekker, New York. 1996, pp. 451 and 596.
Bassetti et al., "New antibiotics for bad bugs: where are we," Ann Clin Microbiol Antimicrob. Aug. 28, 2013; 12(1):22.
Becker, "Antimicrobial drugs," Anesth Prog. 2013 Fall;60(3):111-122; quiz 123.
Belov et al., "First enantioselective synthesis of the novel antiinfective TAN-1057A via its aminomethyl-substituted dihydropyrimidinone heterocycle," Tetrahedron. Aug. 23, 2004; 60(35):7579-7589.
Berlinck, "Natural guanidine derivatives," Natural Product Reports. 1999; 16(3):339-365.
Böddeker et al., "Characterization of a novel antibacterial agent that inhibits bacterial translation," RNA. Sep. 1, 2002; 8(09):1120-1128.
Bondock et al., "Synthesis and antimicrobial activity of some new heterocycles incorporating antipyrine moiety," European journal of medicinal chemistry. Oct. 31, 2008; 43(10):2122-2129.
Brackmann et al., "Titanium-mediated cyclopropanation of N, N-dibenzylcarboxamides towards functionally substituted 2-(1'-aminocyclopropyl) acetic acids1," Synthesis. 2005(12):2008-2014.
Brands et al., "Dihydropyrimidinones-a new class of anti-Staphylococcal antibiotics," Bioorganic & medicinal chemistry letters. Jan. 20, 2003; 13(2):241-245.
Brands et al., "Novel antibiotics for the treatment of gram-positive bacterial infections," Journal of medicinal chemistry. Sep. 12, 2002; 45(19):4246-4253.
Brands et al., "Pyrimidinone antibiotics—heterocyclic analogues with improved antibacterial spectrum," Bioorganic & medicinal chemistry letters. Aug. 18, 2003; 13(16):2641-2645.
Budesinsky et al., Cesko-Slovenska Farmacie (1966), 15(8), 432-7; CA 67:90756, 1967. CAPLUS Abstract provided, 3 pages.
Buděsínský et al., "[5-Aryl-pyrimidines. 3. 5-Aryl-isocytosines and 5-aryl-4-thio-isocytosines]," Cesk Farm., 15(8):432-437, Oct. 1966.
Cahn and Ingold, "131. Specification of configuration about quadricovalent asymmetric atoms," Journal of the Chemical Society (Resumed). 1951:612-622.
Cahn et al., "Specification of Molecular Chirality" Angew. Chem. Int. Ed. Engl., 5(4):385-415, Apr. 1966.
Cahn et al., "The specification of asymmetric configuration in organic chemistry," Experientia. Mar. 1, 1956; 12(3):81-94.
Cahn. "An Introduction to the Sequence Rule: A System for the Specification of Absolute Configuration," J. Chem. Educ. 1964; 41(3):116-125.
CAS Registry No. 1056628-47-7, 1 page, Oct. 3, 2008.
CAS Registry No. 1056628-57-9, 2 pages, 2008.
CAS Registry No. 1056628-60-4, 2 pages, 2008.
CAS Registry No. 646521-61-1, 2 pages, 2003.
CAS Registry No. 646521-62-2, "(2R,4S,5R)-2-[2-(N-benzoylamino)-4-oxo-3,4-dihydropyrimidin-5-yl]-4-hydroxy-5-hydroxymethyl pyrrolidine," 3 pages, 2005.
CAS Registry No. 646521-63-3, "(2R,4S,5R)-N-[(9-fluorenylmethoxy)carbonyl]-2-[2-(N-benzoylamino)-4-oxo-3,4-dihydropyrimidin-5-yl]-4-hydroxy-5-hydroxymethyl pyrrolidine," 2 pages, 2005.
CAS Registry No. 646521-64-4, "(2R,4S,5R)-N-[(9-fluorenylmethoxy)carbonyl]-2-[2-(N-benzoylamino)-4-oxo-3,4-dihydropyrimidin-5-yl]-5-[(4,4'-dimethoxy)triphenylmethyl]-oxymethyl-4-hydroxy pyrrolidine," 2 pages, 2005.
CAS Registry No. 646521-65-5, 2 pages, Feb. 5, 2004.
CAS Registry No. 667411-76-9, "2-benzoylamino-5-[2'-deoxy-3',5'-bis-O-(tert-butyldimethylsilyl)-β-D-erythro-pent-2-enofuranosyl]-3Hpyrimidin-4-one," 3 pages, 2003.
CAS Registry No. 667411-77-0, "N4-benzoyl-2'-deoxypseudoisocytidine," 3 pages, 2003.
CAS Registry No. 667411-78-1, 3 pages, 2003.
CAS Registry No. 667411-79-2, 1 page, Mar. 25, 2004.
CAS Registry No. 751437-20-4, 1 page, Sep. 24, 2004.
CAS Registry No. 646521-58-6, "(2R,5R)-N-(benzyloxy)carbonyl-2-[2-(N-benzoylamino)-4-oxo-3,4-dihydropyrimidin-5-yl]-4-[(tertbutyl)dimethylsilyl]oxy-5-[(tert-butyl)dimethylsilyl]oxymethyl-aza-cyclopent-3-ene," 3 pages, 2003.
Champney et al., "TAN-1057A: A translational inhibitor with a specific inhibitory effect on 50S ribosomal subunit formation," Current microbiology. Nov. 1, 2001; 43(5):340-345.
Chemical Abstracts Accession No. 1967:490756, 3 pages, 1966.
Chemical Abstracts Accession No. 2004:353887, 1 page, 2004.
Chou et al., "Quantitative analysis of dose-effect relationships: the combined effects of multiple drugs or enzyme inhibitors," Advances in enzyme regulation. Dec. 31, 1984; 22:27-55.
Chu et al., "Nucleosides XCII. A facile synthesis of 5-(β-d-ribofuranosyl)- isocytosine (ψ-isocytidine)," J Heterocycl Chem., Jan. 1, 1975;12(4):817-818.

(56) References Cited

OTHER PUBLICATIONS

Chu et al., Journal of Heterocyclic Chemistry (1975), 12(4), 817-18; CA 83:179473, 1975. CAPLUS Abstract provided, 3 pages.
Chu, "Acyclopyrimidine C-nucleosides. Synthesis of acyclopseudoisocytidine and its derivatives," J. Heterocyclic Chem., 21: 9-11, 1984.
Debaene et al., "Expanding the scope of PNA-encoded libraries: divergent synthesis of libraries targeting cysteine, serine and metalloproteases as well as tyrosine phosphatases," Tetrahedron. Jul. 9, 2007; 63(28):6577-6586.
Dermer, "Another anniversary for the war on cancer," Nature Biotechnology. Mar. 1, 1994; 12(3):320.
Dyer et al., "Carbamates and Ureas Derived from Amino- and Oxopyrimidines," Journal of Organic Chemistry 27:982-985 (1962).
Fattori et al., "Drug-eluting stents in vascular intervention," The Lancet. Jan. 18, 2003; 361(9353):247-249.
Franceschi et al., "Structure-based drug design meets the ribosome," Biochemical pharmacology. Mar. 30, 2006; 71(7):1016-1025.
Freshney et al.,Culture of Animal Cells, A Manual of Basic Technique, Alan R. Liss, Inc., 1983, New York, p. 4.
Funabashi et al., "A new anti-MRSA dipeptide, TAN-1057 A," Tetrahedron. Jan. 1, 1993; 49(1):13-28.
Gangjee et al., "Synthesis of classical, three-carbon-bridged 5-substituted furo[2,3-d]pyrimidine and 6-substituted pyrrolo[2,3-d]pyrimidine analogues as antifolates," J Med Chem., 47(27):6893-6901, Dec. 30, 2004.
Gnad et al., "Synthesis and applications of β-aminocarboxylic acids containing a cyclopropane ring," Chemical reviews. Apr. 9, 2003; 103(4):1603-1624.
Gold et al., "Antimicrobial-drug resistance," New England Journal of Medicine. Nov. 7, 1996; 335(19):1445-1453.
Häberli et al., "Pyrrolidino-DNA," Nucleosides Nucleotides Nucleic Acids. May-Aug. 2003; 22(5-8):1187-1189.
Hershfield et al., "Antibacterial Activity of Novel RX-04 Compounds Against Biodefense Pathogens," Poster F-1522, 52nd ICAAC, 2012.
Housman et al., "In Vitro Evaluation of Rib-X Novel Compounds Against Selected Resistant Pseudomonas aeruginosa Isolates," Antimicrob. Agents Chemother., 05944, Dec. 27, 2011, 17 pages.
Hudson et al., "Fluorescent 7-deazapurine derivatives from 5-iodocytosine via a tandem cross-coupling-annulation reaction with terminal alkynes," Synlett. 2004(13):2400-2402.
Hudson et al., "Nucleobase modified peptide nucleic acid," Nucleosides, Nucleotides and Nucleic Acids. Oct. 1, 2003; 22(5-8):1029-1033.
Janeba et al., "Synthesis and Biological Evaluation of Acyclic 3-[(2-Hydroxyethoxy) methyl] Analogues of Antiviral Furo-and Pyrrolo [2, 3-d] pyrimidine Nucleosides 1," Journal of medicinal chemistry. Jul. 14, 2005; 48(14):4690-4696.
Katayama et al., "TAN-1057 AD, new antibiotics with potent antibacterial activity against methicillin-resistant Staphylococcus aureus. Taxonomy, fermentation and biological activity," The Journal of antibiotics. 1993; 46(4):606-613.
Kawahara et al., "Computer-Aided Molecular Design of Hydrogen Bond Equivalents of Nucleobases: Theoretical Study of Substituent Effects on the Hydrogen Bond Energies of Nucleobase Pairs," European Journal of Organic Chemistry. Jul. 1, 2003; 2003(14):2577-2584.
Kint et al., "New-found fundamentals of bacterial persistence," Trends in microbiology. Dec. 31, 2012;20(12):577-585.
Kordes et al., "Preparation of Cyclopropane Analogues of the Natural AntibioticTAN 1057 A/B," European journal of organic chemistry. Jul. 1, 2005; 2005(14):3008-3016.
Kosegi et al., JP 61091184; CA: 105:208920, 1986. CAPLUS Abstract provided.
Laufersweiler et al., "Synthesis and evaluation of tricyclic pyrrolopyrimidinones as dipeptide mimetics: Inhibition of interleukin-1β-converting enzyme," Bioorganic & medicinal chemistry letters. Oct. 1, 2005; 15(19):4322-4326.

Limburg et al., "Ribosomal alterations contribute to bacterial resistance against the dipeptide antibiotic TAN 1057," Antimicrobial agents and chemotherapy. Feb. 1, 2004; 48(2):619-622.
Lin et al., "Assembly of the TAN-1057 A/B heterocycle from a dehydroalanine precursor," Synthesis, 2000(14):2127-2130, 2000.
Lin et al., "Tricyclic 2'-deoxycytidine analogs: syntheses and incorporation into oligodeoxynucleotides which have enhanced binding to complementary RNA," Journal of the American Chemical Society. Apr. 1995; 117(13):3873-3874.
Liu et al., "Recent advances in the stereoselective synthesis of β-amino acids," Tetrahedron. Sep. 30, 2002; 58(40):7991-8035.
Lowy, "Antimicrobial resistance: the example of Staphylococcus aureus," Journal of Clinical Investigation. May 1, 2003;111(9):1265.
Lukin et al, "Rationalizing the strength of hydrogen-bonded complexes. Ab initio HF and DFT studies," The Journal of Physical Chemistry A. Jul. 25, 2002;106(29):6775-6782.
Magiorakos et al., "Multidrug-resistant, extensively drug-resistant and pandrug-resistant bacteria: an international expert proposal for interim standard definitions for acquired resistance," Clinical Microbiology and Infection. Mar. 1, 2012; 18(3):268-281.
Maguire, "Inhibition of bacterial ribosome assembly: a suitable drug target?" Microbiology and Molecular Biology Reviews. Mar. 1, 2009;73(1):22-35.
Matsuda et al., "Nucleosides. 120. Syntheses of 2'-deoxy-. psi.-isocytidine and 2'-deoxy-1-methyl-. psi.-uridine from. psi.-uridine," The Journal of Organic Chemistry. Aug. 1981;46(18):3603-3609.
Matsuda et al., Journal of Organic Chemistry (1981), 46(18), 3603-9; CA: 95:98205, 1981. CAPLUS Abstract provided.
Mayer et al., "Synthesis and triplex forming properties of pyrrolidino pseudoisocytidine containing oligodeoxynucleotides," Organic & biomolecular chemistry. 2005;3(9):1653-1658.
Mishra et al., "Dry Media Synthesis of Novel Pyrrolo-pyrimidines," Journal of Nepal Chemical Society. 2010; 25:83-88.
Miyaura et al., "A new stereospecific cross-coupling by the palladium-catalyzed reaction of 1-alkenylboranes with 1-alkenyl or 1-alkynyl halides," Tetrahedron Letters. Dec. 31, 1979; 20(36):3437-3440.
Moellering, "Linezolid: the first oxazolidinone antimicrobial," Annals of internal medicine. Jan. 21, 2003; 138(2):135-142.
Morice, "A new era in the treatment of coronary disease?" European heart journal. Feb. 1, 2003;24(3):209-211.
National Center for Biotechnology Information. PubChem Compound Database; CID=1112068, create date Jul. 10, 2005, 10 pages.
National Center for Biotechnology Information. PubChem Compound Database; CID=23522053, create date Dec. 6, 2007, 11 pages.
Nett, "The chemistry of gliding bacteria," Natural product reports. 2007; 24(6):1245-1261.
Orner et al., "The guanidinium group in molecular recognition: design and synthetic approaches," Journal of inclusion phenomena and macrocyclic chemistry. Dec. 1, 2001; 41(1-4):141-147.
Ortega et al., "Binding affinities of oligonucleotides and PNAs containing phenoxazine and G-clamp cytosine analogues are unusually sequence-dependent," Organic letters. Oct. 25, 2007; 9(22):4503-4506.
Paterson et al., "Extended-spectrum β-lactamases: a clinical update," Clinical microbiology reviews. Oct. 1, 2005;18(4):657-686.
Phillips, "Reactivity of 5-Bromoisocytosine with Some Amines," Journal of the American Chemical Society. Aug. 1953;75(16):4092.
Phillips, A. P., Journal of the American Chemical Society (1953), 75, 4092; CA 49:42634, 1955. CAPLUS Abstract provided, 1 page.
Pohl, "Zur Kenntnis des Dicyandiamids," [Investigations from the Organic Chemistry Laboratory of the Technical University of Dresden], Journal für Praktische Chemie., 77(1):533-548, May 14, 1908 [English machine translation], 30 pages.
Rajeev et al., "High-affinity peptide nucleic acid oligomers containing tricyclic cytosine analogues," Organic letters. Dec. 12, 2002; 4(25):4395-4398.
Ravin et al., "Preformulation," Remington's Pharm. Sci., Chapter 75, 1435-1450 (1990).
Rehm et al., "Staphylococcus aureus: methicillin-susceptible S. aureus to methicillin-resistant S. aureus and vancomycin-resistant S. aureus," Clinical Infectious Diseases. Sep. 15, 2010;51(Supplement 2):S176-S182.

(56) References Cited

OTHER PUBLICATIONS

Reigan et al., "Synthesis and enzymatic evaluation of xanthine oxidase-activated prodrugs based on inhibitors of thymidine phosphorylase," Bioorganic & medicinal chemistry letters. Nov. 1, 2004; 14(21):5247-5250.
Remington's Pharmaceutical Sciences, 18th ed. (Mack Publishing Company, 1990) Table of Contents p. xv, and chapter 75 pp. 1435-1450.
Rival et al., "Synthesis and antibacterial activity of some imidazo[1,2-a]pyrimidine derivatives," *Chem Pharm Bull (Tokyo).*, 40(5):1170-1176, May 1992.
Šála et al., "Synthesis of racemic 2-hydroxy-4-and 2-hydroxy-5-(hydroxymethyl) cyclohexane pyrimidine C-nucleoside analogues," Collection of Czechoslovak chemical communications, 69(4): 918-932, 2004.
Sala et al., Collection of Czechoslovak Chemical Communications (2004), 69(4), Abstract provided. 918-932; CA: 141:314551, 2004. CAPLUS Abstract provided, 3 pages.
Samir Bondock et al., "Synthesis and antimicrobial activity of some new heterocycles incorporating antipyrine moiety", European Journal of Medicinal Chemistry, 43:10, Oct. 1, 2008, pp. 2022-21229, XP055132947.
Sanders et al., "Disease-related misassembly of membrane proteins," Annu. Rev. Biophys. Biomol. Struct. Jun. 9, 2004; 33:25-51.
Sato et al., "A stereocontrolled synthesis of C-4' alkylated pyrimidine C-nucleosides," Tetrahedron Letters. Dec. 31, 1979;20(31):2897-2900.
Sato et al., "A Convenient Route to 5'-Modified Pseudoisocytidines and 2-Thiopseudouridines," Chemistry Letters. 1978; 7(11):1297-1300.
Sato et al., Chemistry Letters (1978), (11), 1297-300; CA 90:87793, 1979. CAPLUS Abstract provided, 4 pages.
Sato et al., Tetrahedron Letters (1979), (31), 2897-900; CA 92:164211, 1980. CAPLUS Abstract provided, 2 pages.
Shaffer, "The challenge of antibiotic-resistant *Staphylococcus*: lessons from hospital nurseries in the mid-20th century," The Yale journal of biology and medicine. Jun. 2013; 86(2):261.
Singh, "Confronting the challenges of discovery of novel antibacterial agents," Bioorganic & medicinal chemistry letters. Aug. 15, 2014; 24(16):3683-3689.
Sniady et al., "Zinc-catalyzed cycloisomerizations. Synthesis of substituted furans and furopyrimidine nucleosides," The Journal of organic chemistry. Jul. 3, 2008; 73(15):5881-5889.
Sokolov et al., "Total Synthesis of TAN-1057 A/B, a New Dipeptide Antibiotic from *Flexibacter* sp. PK-74," European journal of organic chemistry. May 1, 1998; 1998(5):777-783.
Stoss et al., "Novel pyrimidine and pyrimido[1, 2-a]pyrimidine derivatives. By-products of a guanidine based thymine synthesis," Journal of Heterocyclic Chemistry, 28(2):231-236, Feb./Mar. 1991.
Theuretzbacher et al., "Update on antibacterial and antifungal drugs—can we master the resistance crisis?" Current opinion in pharmacology. Oct. 31, 2011; 11(5):429-432.
Toutouzas et al., "Sirolimus-eluting stents: a review of experimental and clinical findings," Zeitschrift für Kardiologie. Jul. 1, 2002; 91(3):49-57.
Tsiodras et al., "Linezolid resistance in a clinical isolate of *Staphylococcus aureus*," The Lancet. Jul. 21, 2001;358(9277):207-8.
Wang et al., "A highly enantioselective hetero-Diels-Alder reaction of aldehydes with Danishefsky's diene catalyzed by chiral titanium (IV) 5, 5', 6, 6', 7, 7', 8, 8'-octahydro-1, 1'-bi-2-naphthol complexes," The Journal of organic chemistry. Apr. 5, 2002;67(7):2175-2182.
Wang, TW 424090; CA: 138:205080, 2003. CAPLUS Abstract provided, 1 page.
Williams et al., "Synthesis and antimicrobial evaluation of TAN-1057A/B analogs," The Journal of antibiotics. 1998; 51(2):189-201.
Wilson, "The A-Z of bacterial translation inhibitors. Critical Reviews in Biochemistry and Molecular Biology," Dec. 1, 2009; 44(6):393-433.
Wojciechowski et al., "Exceptional Fluorescence and Hybridization Properties of a Phenylpyrrolocytosine in Peptide Nucleic Acid," InNucleic Acids Symposium Series Sep. 1, 2008 (vol. 52, No. 1, pp. 401-402). Oxford University Press.
Wojciechowski et al., "Peptide nucleic acid containing a meta-substituted phenylpyrrolocytosine exhibits a fluorescence response and increased binding affinity toward RNA," Organic letters. Sep. 29, 2009; 11(21):4878-4881.
Wojciechowski, "Fluorescence and hybridization properties of peptide nucleic acid containing a substituted phenylpyrrolocytosine designed to engage guanine with an additional H-bond," Journal of the American Chemical Society. Aug. 30, 2008; 130(38):12574-12575.
Wolff Manfred E. "Burger's Medicinal Chemistry, 5ed, Part 1", John Wiley & Sons, 1995, pp. 975-977.
Xu et al., "A new and convergent synthesis for 2, 5-diamino-tetrahydropyrimidones," Tetrahedron letters. Mar. 17, 2003; 44(12):2601-2604.
Xu et al., "SAR studies on dihydropyrimidinone antibiotics," Bioorganic & medicinal chemistry letters. Mar. 15, 2011; 21(6):1670-1674.
Yuan et al., "Total synthesis of the anti methicillin-resistant *Staphylococcus aureus* peptide antibiotics TAN-1057A-D," Journal of the American Chemical Society. Dec. 10, 1997; 119(49):11777-11784.
Zhang et al., "A facile construction of the 3, 6-diamino-1, 2, 3, 4-tetrahydropyridine-4-one scaffold: synthesis of N-3 to carbon replacement analog of TAN-1057A/B," Tetrahedron letters. Apr. 30, 2007; 48(18):3273-3275.
Zhang et al., "A new approach to the 2, 5-diamino-5, 6-dihydro-1H-pyrimidine-4-one derivatives: synthesis of TAN-1057A/B and analogs," Tetrahedron letters. Jul. 28, 2003; 44(31):5871-5873.
Zhou et al., "Design at the atomic level: design of biaryloxazolidinones as potent orally active antibiotics," Bioorg Med Chem Lett., 18(23):6175-6178, Epub Oct. 7, 2008.
Zhou et al., "Design at the atomic level: generation of novel hybrid biaryloxazolidinones as promising new antibiotics," Bioorg Med Chem Lett., 18(23):6179-6183, Epub Oct. 7, 2008.
Zlatko Janeba., "Synthesis and Biological Evaluation of Acyclic 3-[(2-Hydroxyethoxy) methyl] Analogues of Antiviral Furo- and Pyrrolo [2,3-d] pyrimidine Nucleosides". J Med Chem, Jul. 14, 2005; 14:48(14): 4690-6.
Anonymous: "U.S. Government Lists of 1-12 Bioterrorism Agents and Diseases", Biosecurity and Biodefense Resource, Jan. 1, 2007 (Jan. 1, 2007), XP055352854, Retrieved from the Internet:URL:https://fas.org/biosecurity/resource/lists.htm [retrieved on Mar. 8, 2017].
Biochemistry, 2009, 48, pp. 7547-7555.
Biopolymers and Cell, 2009, 25(6), pp. 491-499.
Corriere, M.D., et al, MRSA: An Evolving Pathogen: Disease-A-Month, vol. 54 pp. 751-755. Published 2008.
Extended European Search Report for Application No. 14841546.6, dated Apr. 28, 2017, 10 pages.
Hudson et al., Canadian Journal of Chemistry, 86(11): 1026-1029, 2008.
JACS, 2009, 131(12), pp. 4288-4293.
Japanese Office Action in Japanese Application No. 2016-37911, dated Feb. 7, 2017, 17 pages.
Taiwan Office Action in Japanese Application No. 104131806, dated Jul. 4, 2017, 56 pages.
Merriam-Webster Definition of Prophylaxis.
PNAS, 2006, 103(17), pp. 6665-6669.
Supplementary European Search Report in European Application No. EP14841940, dated Mar. 8, 2017, 5 pages.
Chu, Chung K. et al., Journal of Heterocyclic Chemistry, 1986, 23(6), 1621-4.
Indian Journal of Chemistry, Section B: Organic Chemistry Including Medicinal Chemistry, 1992, 31B(2), pp. 105-108.
International Search Report and Written Opinion in PCT/US2014/054869, dated Oct. 29, 2014, 13 pages.
Golovan et al., Mikrobiologichnii Zhurnal, 2010, 72(2), pp. 36-42.
Perin et al., Bulletin de la Societe Chimique de France 1964, vol. 8, p. 1877-1880 (English translation).
European Search Report issued in European Patent Application No. 10824207.4-1452 dated Jul. 24, 2017.
Zeitschrift fuer Analytische Chemie 1976, vol. 281 p. 302.

(56) References Cited

OTHER PUBLICATIONS

Australian Office Action in Australian Application No. 2016266048, dated Jun. 26, 2017.
Zanatta, N. et al, Synthesis, 2006, 14, 2305-2312.
Anwar, H.F. et al, Journal of Chemical Research, 2005, 29-31.
Matteucci, M.D. et al, Tetrahedron Letters, 1996, 37(29), 5057-5060.
LaMattina, J.L. et al, Tetrahedron, 1988, 44(11), 3073-3078.
Sato, Y. et al, Yakugaku Zasshi, 1970, 90(5), 618-28".
Chinese Examination Report in Chinese Application No. CPCH1660525P, dated Nov. 1, 2017, 10 pages.
Mexican Office Action in Mexican Application No. MX/a/2013/012015, dated Apr. 11, 2012, 3 pages.
Morimoto et al., "Successful management of severe L-asparaginase-associated pancreatits by continuous regional arterial infusion of protease inhibitor and antibiotiv", Cancer, 113(6), pp. 1362-1369, 2008.
Sandrini et al., "Deoxyribonucleoside kinases activate nucleoside antibiotics in severely pathogenic bacteria", Antimicrobial Agents and Chemotherapy, 51(8), pp. 2726-2732, 2007.
CAS RN: 359851-13-1, STN Entry Date Oct. 3, 2001.
CAS RN: 221555-28-8, STN Entry Date Apr. 22, 1999.
Hanessian et al., "On the binding site of quinolone antibacterials. An attempt to probe the Shen model", Bioorganic & Medicinal Chemistry Letters, 6(19), pp. 2333-2338, 1996.
Abdel- Megid, Mohamed, Nitrogen bridgehead compounds, facile synthesis of bioactive cyanopyrimido [1,2-a]pyrimidinones, Pharmazie, 2000, vol. 55, No. 4, pp. 263-268.
Angier, Robert et al., "Alkylation of 2-amino-4-hydroxypyrimidines with acrylonitrile and with dimethyl sulfate: Two pyrimido [1,2-a] pryimidinediones", Journal of Organic Chemistry, 1961, vol. 26, pp. 1891-1895.
Abdel-Fattah, A. M. et al., "New synthesis of imidazo [1,2-a]- and pyrimido [1,2-a] pyrimidines", Phosphorus, Sulfur and Silicon and the Related Elements, 1992, vol. 70, No. 1, pp. 67-73.
Minami, Shinsaku et al., "Pyrido [2,3-d] pyrimidine antibacterial agents. I. 8-alkyl-5,8-dihydro-5-oxopyrido[2,3-d]-pryimidine-6-carboxylic acids and related compounds", Chemical & Pharmaceutical Bulletin, 1971, vol. 19, No. 7, pp. 1482-1486.

ANTIMICROBIAL COMPOUNDS AND METHODS OF MAKING AND USING THE SAME

RELATED APPLICATIONS

This application is a U.S. national stage under 35 U.S.C. § 371 of International Application No. PCT/US2014/054869, filed on Sep. 9, 2014, which claims priority to, and the benefit of, U.S. Provisional Application No. 61/875,643, filed Sep. 9, 2013, the entire contents of which are incorporated herein by reference in their entireties.

BACKGROUND

Since the discovery of penicillin in the 1920s and streptomycin in the 1940s, many new compounds have been discovered or specifically designed for use as antibiotic agents. It was once thought that infectious diseases could be completely controlled or eradicated with the use of such therapeutic agents. However, such views have been challenged because strains of cells or microorganisms resistant to currently effective therapeutic agents continue to evolve. Almost every antibiotic agent developed for clinical use has ultimately encountered problems with the emergence of resistant bacteria. For example, resistant strains of Gram-positive bacteria such as methicillin-resistant staphylococci, penicillin-resistant streptococci, and vancomycin-resistant *enterococci* have developed. Resistant bacteria can cause serious and even fatal results for infected patients. See, e.g., Lowry, F. D. "Antimicrobial Resistance: The Example of *Staphylococcus aureus*," *J. Clin. Invest.*, vol. 111, no. 9, pp. 1265-1273 (2003); and Gold, H. S. and Moellering, R. C., Jr., "Antimicrobial-Drug Resistance," *N. Engl. J. Med.*, vol. 335, pp. 1445-53 (1996).

The discovery and development of new antibacterial agents have been for decades a major focus of many pharmaceutical companies. Nonetheless, in more recent years there has been an exodus from this area of research and drug development resulting in very few new antibiotics entering the market. This lack of new antibiotics is particularly disturbing, especially at a time when bacterial resistance to current therapies is increasing both in the hospital and community settings.

One approach to developing new antimicrobial compounds is to design modulators, for example, inhibitors, of bacterial ribosome function. By modulating or inhibiting bacterial ribosome function, antimicrobial compounds could interfere with essential processes such as RNA translation and protein synthesis, thereby providing an antimicrobial effect. In fact, some antibiotic compounds such as erythromycin, clindamycin, and linezolid are known to bind to the ribosome.

SUMMARY OF THE INVENTION

The present invention relates generally to the field of antimicrobial compounds and to methods of making and using them. These compounds and tautomers thereof are useful for treating, preventing, reducing the risk of, or delaying the onset of microbial infections in humans and animals. The present invention also provides pharmaceutically acceptable salts, esters, and prodrugs of these compounds and tautomers.

In one aspect, the present invention relates to a compound having any one of the formulae (I)-(V) below:

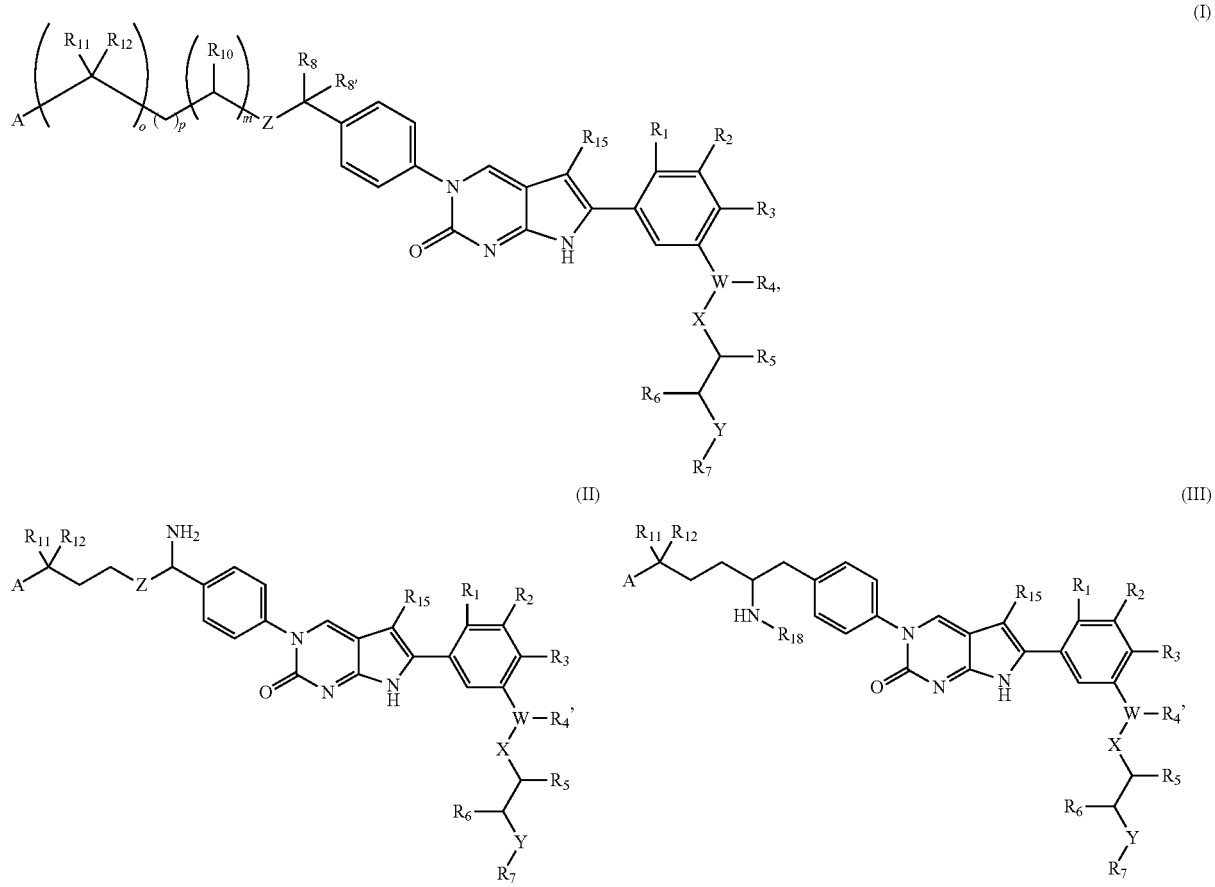

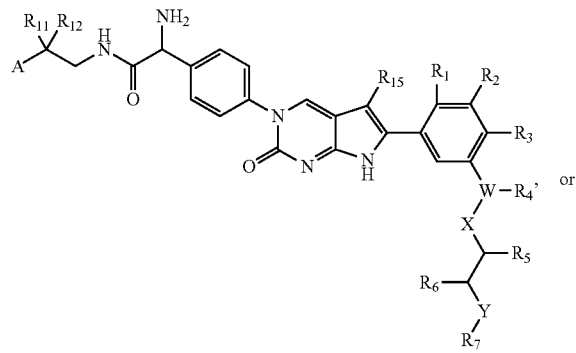
(IV)

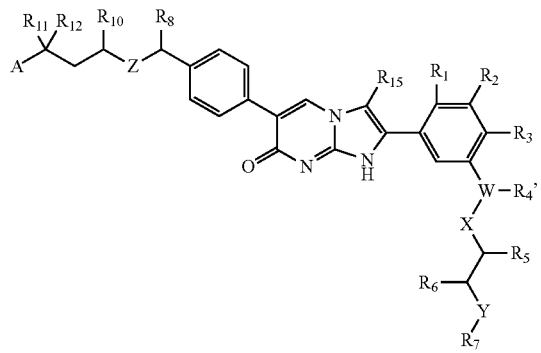
(V)

or a tautomer thereof, or a pharmaceutically acceptable salt, or ester of said compound or tautomer wherein:

$R_1$ is H or F, wherein when $R_1$ is H, then $R_2$ is $CF_3$, $OCF_3$, $SCF_3$, $SOCF_3$ or halo and $R_3$ is H; and when $R_1$ is F, then (i) $R_2$ is Cl or $OCF_3$ and $R_3$ is H; or (ii) $R_2$ is H and $R_3$ is $C_1$-$C_6$ alkyl; or (iii) $R_2$ is $C_1$-$C_6$ alkyl optionally substituted with one or more halo and $R_3$ is halo;

$R_4$ is H, OH, $NH_2$, or $C_1$-$C_6$ alkoxyl, or when X is O or $CHR_{17}$, $R_4$ and $R_5$ together with the two atoms to which they are attached and the atom connecting said two atoms form a 5- to 8-membered heterocycloalkyl ring having 1 to 2 heteroatoms; or when X is a bond, $R_4$ and $R_6$ together with the two carbon atoms to which they are attached and the carbon atoms connecting said two carbon atoms, form a 5- to 12-membered saturated heterocycloalkyl ring having 1 to 2 heteroatoms;

$R_5$ is H, $CH_2OH$ or $CH_2OC_1$-$C_6$ alkyl, or when X is O or $CHR_{17}$, $R_4$ and $R_5$ together with the two atoms to which they are attached and the atom connecting said two atoms form a 5- to 8-membered heterocycloalkyl ring having 1 to 2 heteroatoms;

$R_6$ is $C_1$-$C_3$ alkyl optionally substituted with one or more substituents independently selected from the group consisting of halo, OH, azido, amino, $C_1$-$C_6$ alkoxyl, $C_1$-$C_6$ alkylthio, $C_2$-$C_3$ alkenyl, $OCOR_a$, $CH_2OCOR_a$, and $-OP(O)(OR_a)_2$, in which $R_a$ is $C_1$-$C_6$ alkyl, amino, or phenyl, and $R_a$ is optionally substituted with COOH, $COOC_1$-$C_6$ alkyl, $OCOC_1$-$C_6$ alkyl, phenyl, or $C_7$-$C_{12}$ arylalkyl; or $R_6$ and $R_7$ together with the two atoms to which they are attached, form a 5- to 12-membered heterocycloalkyl ring having 0 to 1 additional heteroatom optionally substituted with an oxo group; or $R_6$ and $R_{17}$ together with the two carbon atoms to which they are attached and the carbon atom connecting said two carbon atoms, form a 5- to 12-membered saturated heterocycloalkyl ring having 1 to 2 heteroatoms; or when X is a bond, $R_4$ and $R_6$ together with the two carbon atoms to which they are attached and the carbon atom connecting said two carbon atoms, form a 5- to 12-membered saturated heterocycloalkyl ring having 1 to 2 heteroatoms;

$R_7$ is H, $C(=NH)NH_2$, or $COR_b$ in which $R_b$ is $C_1$-$C_6$ alkyl optionally substituted with $C_1$-$C_6$ alkoxyl or amino; or $R_6$ and $R_7$ together with the two atoms to which they are attached, form a 5- to 12-membered heterocycloalkyl ring having 0 to 1 additional heteroatom optionally substituted with an oxo group;

each of $R_8$, $R_{10}$, and $R_{11}$, independently is $-Q_1$-$T_1$, in which $Q_1$ is a bond or $C_1$-$C_3$ alkyl linker optionally substituted with one or more halo or hydroxyl, and $T_1$ is H, halo, OH, COOH, cyano, azido, $C_1$-$C_3$ alkyl, $C_2$-$C_6$ alkenyl, $C_2$-$C_6$ alkynyl, $C_1$-$C_6$ alkoxyl, $C_2$-$C_6$ haloalkenyl, $C_1$-$C_6$ alkylthio, $COOC_1$-$C_6$ alkyl, $-NHC(O)CH_2NH_2$, $NHS(O)C_1$-$C_3$ alkyl, $SO_2C_1$-$C_6$ alkyl, or $R_c$, in which $R_c$ is amino, $C_3$-$C_8$ cycloalkyl, $C_6$-$C_{10}$ aryl, 4 to 12-membered heterocycloalkyl, 5- or 6-membered heteroaryl, $-$O-heteroaryl, $-$NH-heteroaryl, $-$S-heteroaryl, or $C(O)NR_dR_e$, each of $R_d$ and $R_e$ independently being H or $C_1$-$C_6$ alkyl, or $R_d$ and $R_e$ together with the nitrogen atom to which they are attached forming a 5- to 12-membered heterocycloalkyl ring having 0 to 2 additional heteroatoms; and $R_c$ is optionally substituted with $-Q_2$-$T_2$, in which $Q_2$ is a bond or $C_1$-$C_3$ alkyl and $T_2$ is H, halo, $C_1$-$C_3$ alkyl, amino, 5- or 6-membered heteroaryl or $C_6$-$C_{10}$ aryl wherein the aryl and heteroaryl are optionally substituted with $C_1$-$C_6$ alkoxyl or $C_1$-$C_4$ aminoalkyl; or $R_8$ and $R_{10}$, together with the two carbon atoms to which they are attached and the Z atom connecting said two carbon atoms, form a 5- to 12-membered heterocycloalkyl ring having 0 to 2 additional heteroatoms optionally substituted with one more substituents independently selected from $C_1$-$C_6$ alkyl or $-C(=N)NH_2$;

$R_8$ is H; or $R_{8'}$ and $R_8$ together with the carbon to which they are attached form a $C_3$-$C_8$ heterocycloalkyl having 1 to 2 heteroatoms optionally substituted with $C_1$-$C_3$ alkyl or $C(=NH)NH_2$; or $R_8$ and $R_{8'}$ together form $=O$ or $=NH$;

$R_{12}$ is H or $C_1$-$C_6$ alkyl, or $R_{12}$ and $R_{11}$ together with the carbon atom to which they are attached form a 4- to 12-membered saturated heterocycloalkyl ring having 1 to 2 heteroatoms optionally substituted with $C(=NH)NH_2$; or $R_{12}$ and $R_{10}$ together with the two carbon atoms to which they are attached and the atom(s), if present, connecting the two carbon atoms form a $C_3$-$C_8$ cycloalkyl ring;

each of $R_9$ and $R_{13}$ independently is H, $C_1$-$C_3$ alkyl, $C_2$-$C_4$ alkenyl or $-C(O)H$, or $R_9$ and $R_{13}$, when Z is $NR_9$, together with the two nitrogen atoms to which they are attached and the carbon atoms connecting said two nitrogen atoms, form a 7- to 12-membered saturated heterocycloalkyl ring having 0 to 1 additional heteroatom, or $R_9$ and $R_8$, when Z is $NR_9$, together with the two atoms to which they are attached form a 5- to 12-membered heterocycloalkyl ring having 0 to 1 additional heteroatom optionally substituted with an oxo group; or $R_9$ and A, when Z is $NR_9$ and A is $NR_{14}$, together with the two atoms to which they are attached and the atoms connecting said two atoms form a 5- to 8-membered heterocycloalkyl ring having 2 to 3 heteroatoms optionally substituted with an oxo or an imino group;

$R_{11}$ and $R_{13}$, when A is $NR_{13}NR_{14}$, together with the atoms to which they are attached form a 5- to 8-membered heterocycloalkyl ring having 0 to 2 additional heteroatoms optionally substituted with oxo;

$R_{14}$ is H, $C(O)C_1$-$C_3$ alkyl, $C(O)NH_2$, $C(CH=NO_2)NHCH_3$, $C(=NH)H$, $C(=NH)C_1$-$C_3$ alkyl, 5- or 6-membered heteroaryl having 1 to 3 heteroatoms, 5 or 6-membered heterocycloalkyl having 1 to 3 heteroatoms, $C_1$-$C_6$ alkyl optionally substituted with one or more substituents independently selected from 5- or 6-membered heteroaryl having 1 to 3 heteroatoms, $C_3$-$C_8$ cycloalkyl, and 5 or 6-membered heterocycloalkyl having 1 to 3 heteroatoms, or $C(=NR_{16})NH_2$, in which $R_{16}$ is H, $C_1$-$C_3$ alkyl, $C_2$-$C_4$ alkenyl, $C_3$-$C_8$ cycloalkyl, or 4- to 12-membered saturated heterocycloalkyl ring having 1 to 2 heteroatoms, or $R_{16}$ and $R_{11}$ together with the two atoms to which they are attached and the atoms connecting said two carbon atoms, form a 5- to 12-membered heterocycloalkyl ring having 0 to 1 additional heteroatom;

$R_{14}$ and $R_{13}$ together with the nitrogen atom to which they are attached form a 5- or 6-membered heteroaryl having 1 to 3 additional heteroatoms optionally substituted with oxo; or $R_{14}$ and $R_{13}$ together with the nitrogen atom to which they are attached form a 5- or 6-membered heterocycloalkyl having 1 to 3 additional heteroatoms optionally substituted with oxo;

$R_{15}$ is H or halo;

A is $C(O)NH_2$, $NR_{13}R_{14}$, $NR_{14}C(O)NHC_1$-$C_3$ alkyl, $C(O)OH$, OH, CN, $C_3$-$C_8$ cycloalkyl, —$OP(O)(OR_b)_2$, in which $R_b$ is $C_1$-$C_6$ alkyl, amino, or phenyl, 5 or 6-membered heterocycloalkyl having 1 to 3 heteroatoms optionally substituted with oxo, or 5- or 6-membered heteroaryl having 1 to 4 heteroatoms optionally substituted with $C_1$-$C_4$ alkyl, $C_1$-$C_4$ alkylenyl-aryl, $NO_2$, or amino, wherein the alkyl, alkylenyl, and aryl are optionally substituted with one or more substituents independently selected from $C_1$-$C_3$ alkyl, $C_2$-$C_4$ alkenyl, $C_1$-$C_3$ alkoxy, or halo; or $R_9$ and A, when Z is $NR_9$ and A is $NR_{14}$, together with the two carbon atoms to which they are attached and the atoms connecting said carbon atoms form a 5- to 8-membered heterocycloalkyl ring having 2 to 3 heteroatoms optionally substituted with an oxo or an imino group;

W is CH or C; or W and Y, when W is C, together with the atoms to which they are attached, form a 5- to 12-membered heterocycloalkyl ring having 0 to 1 additional heteroatom;

X is a bond, O, or $CHR_{17}$, in which $R_{17}$ is H, or $R_{17}$ and $R_6$ together with the two carbon atoms to which they are attached and the carbon atom connecting said two carbon atoms, form a 5- to 12-membered saturated heterocycloalkyl ring having 1 to 2 heteroatoms; or when X is a bond, $R_4$ and $R_6$ together with the two carbon atoms to which they are attached and the carbon atom connecting said two carbon atoms, form a 5- to 12-membered saturated heterocycloalkyl ring having 1 to 2 heteroatoms;

Y is NH; or Y and W together with the atoms to which they are attached, form a 5- to 12-membered heterocycloalkyl ring having 0 to 1 additional heteroatom;

Z is a bond, O, $NR_9$, NH, CH, or $CH_2$; or $R_{11}$ and Z, when Z is NH or CH, together with the atoms to which they are attached and the atoms connecting said two atoms form a 5- to 8-membered heterocycloalkyl ring having 0 to 2 additional heteroatoms;

each m and o is independently 0 or 1;

p is 0, 1, or 2; and $R_{18}$ is H or $C(=NH)NH_2$;

provided that for a compound of Formula (I)

(a) when $R_{14}$ is $C(=NR_{16})NH_2$, X is $CH_2$, $R_6$ is methyl and $R_8$ is H, $C_1$-$C_3$ alkyl, $C_2$-$C_3$ alkenyl, cyclopropyl, $CH_2CH_2OH$, COOH, $COOCH_3$, $CH_2COOH$, $CH_2COOCH_3$, or 4-methoxyphenyl, then at least one of $R_4$, $R_5$, $R_7$, $R_{10}$, $R_{11}$, $R_{12}$, or $R_{15}$ is not H;

(b) when $R_{14}$ is $C(=NR_{16})NH_2$, X is $CH_2$, $R_6$ is $CH_2OH$ and $R_8$ is H, methyl or ethyl, then at least one of $R_4$, $R_5$, $R_7$, $R_{10}$, $R_{11}$, $R_{12}$, or $R_{15}$ is not H;

(c) when $R_{14}$ is $C(=NR_{16})NH_2$, X is $CH_2$, and $R_6$ is $CH_2OCH_3$, then at least one of $R_4$, $R_5$, $R_7$, $R_8$, $R_{10}$, $R_{11}$, $R_{12}$, or $R_{15}$ is not H;

(d) when $R_{14}$ is $C(=NR_{16})NH_2$, X is a bond, $R_6$ is methyl, and $R_8$ is H or methyl then at least one of $R_4$, $R_5$, $R_7$, $R_8$, $R_{10}$, $R_{11}$, $R_{12}$, or $R_{15}$ is not H;

(e) when $R_{14}$ is $C(=NR_{16})NH_2$, X is O, $R_5$ is H or methyl, $R_6$ is methyl, and $R_8$ is H or methyl then at least one of $R_4$, $R_7$, $R_8$, $R_{10}$, $R_{11}$, $R_{12}$, or $R_{15}$ is not H;

(f) when $R_{14}$ is $C(=NR_{16})NH_2$, X is $CH_2$, $R_6$ is methyl, $R_8$ is H or methyl, and $R_7$ is $C(=NH)NH_2$, then at least one of $R_4$, $R_5$, $R_8$, $R_{10}$, $R_{11}$, $R_{12}$, or $R_{15}$ is not H; or (g) when $R_{14}$ is $C(=O)CH_3$, X is $CH_2$, $R_6$ is methyl, and $R_8$ is H, then at least one of $R_4$, $R_5$, $R_7$, $R_8$, $R_{10}$, $R_{11}$, $R_{12}$, or $R_{15}$ is not H.

In another aspect, the invention features a compound of Formula (VIII) or (IX):

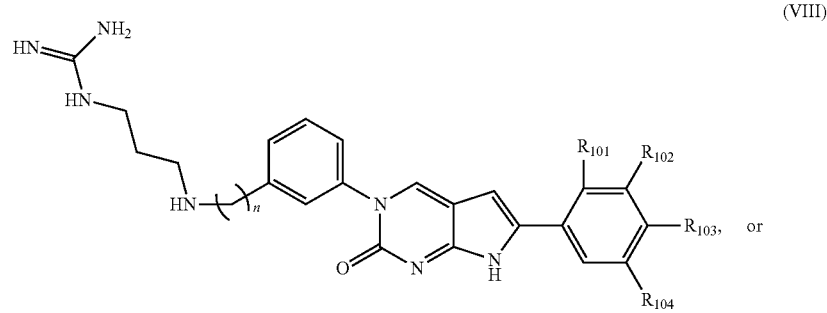

(VIII)

or

(IX)

or a tautomer thereof, or a pharmaceutically acceptable salt, or ester of said compound or tautomer, wherein:

m is 0 or 1;
n is 1 or 2;

$R_{101}$ is H or F, wherein when $R_{101}$ is H, then (i) $R_{102}$ is $CF_3$, $OCF_3$, $SCF_3$, or $SOCF_3$, $R_{103}$ is H, and $R_{104}$ is $(CH_2)_3CH(CH_3)NH_2$; or (ii) each of $R_{102}$ and $R_{104}$ is H, and $R_{103}$ is $CH(R_p)NHR_q$, in which is $R_p$ is $C_1$-$C_6$ alkyl optionally substituted with one or more halo and $R_q$ is 4- to 12-membered saturated heterocycloalkyl ring having 1 to 2 heteroatoms optionally substituted with $C(=NH)NH_2$; and when $R_{101}$ is F, then $R_{102}$ is Cl or $OCF_3$, $R_{103}$ is H, and $R_{104}$ is $(CH_2)_3CH(CH_3)NH_2$;

$R_{105}$ is $CH(R_p)NHR_q$, $CH=CHR_q$, $CH=NO(CH_2)_2NHC(=NH)NH_2$, or $CONHCH_2R_s$ in which $R_s$ is 5- or 6-membered heteroaryl optionally substituted with 5- to 12-membered saturated heterocycloalkyl ring having 1 to 2 heteroatoms, and each of $R_{106}$ and $R_{107}$ is H or $C_1$-$C_6$ alkyl, or $R_{106}$ and $R_{107}$ together with the two nitrogen atoms to which they are attached and the carbon atom connecting said two nitrogen atoms, form a 6- to 12-membered saturated heterocycloalkyl ring having 0 to 1 additional heteroatom.

In yet another aspect, the invention also provides a compound of Formula (X):

or a tautomer thereof, or a pharmaceutically acceptable salt, or ester of said compound or tautomer, wherein:

$R_{201}$ is H or F, wherein when $R_{201}$ is H, then $R_{202}$ is $CF_3$, $OCF_3$, $SCF_3$, $SOCF_3$ or halo, and $R_{203}$ is H; and when $R_{201}$ is F, then (i) $R_{202}$ is Cl or $OCF_3$, and $R_3$ is H; or (ii) $R_{202}$ is H and $R_{203}$ is $C_1$-$C_6$ alkyl; or (iii) $R_{202}$ is $C_1$-$C_6$ alkyl optionally substituted with one or more halo, and $R_{203}$ is halo;

$R_{206}$ is $C_1$-$C_3$ alkyl optionally substituted with one or more substituents independently selected from the group consisting of halo, OH, amino, $C_1$-$C_6$ alkoxyl and $C_1$-$C_6$ alkylthio, $C_2$-$C_3$ alkenyl, or $CH_2OCOR_{aa}$, in which $R_{aa}$ is $C_1$-$C_6$ alkyl, amino, or phenyl, and $R_{aa}$ is optionally substituted with COOH, $COOC_1$-$C_6$ alkyl, $OCOC_1$-$C_6$ alkyl, or $C_7$-$C_{12}$ arylalkyl;

$R_{207}$ is H, $C(=NH)NH_2$, or $COR_b$, in which $R_b$ is $C_1$-$C_6$ alkyl optionally substituted with amino, $C_1$-$C_6$ alkoxyl, or amino; or $R_{206}$ and $R_{207}$ together with the two atoms to which they are attached, form a 5- to 12-membered heterocycloalkyl ring having 0 to 1 additional heteroatom optionally substituted with an oxo group;

$R_{208}$ is H, $C_1$-$C_6$ alkyl or $C_2$-$C_6$ alkenyl; and
$R_{214}$ is H or $C(=NH)NH_2$.

Further, the invention relates to a compound of Formula (XIa), (XIb), (XIc), or (XId):

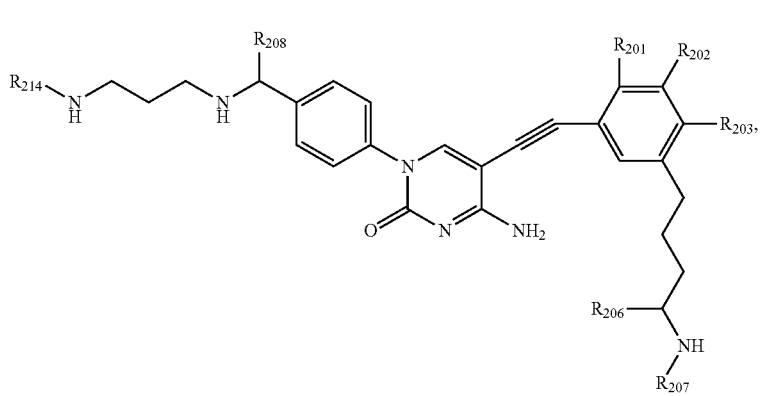

(X)

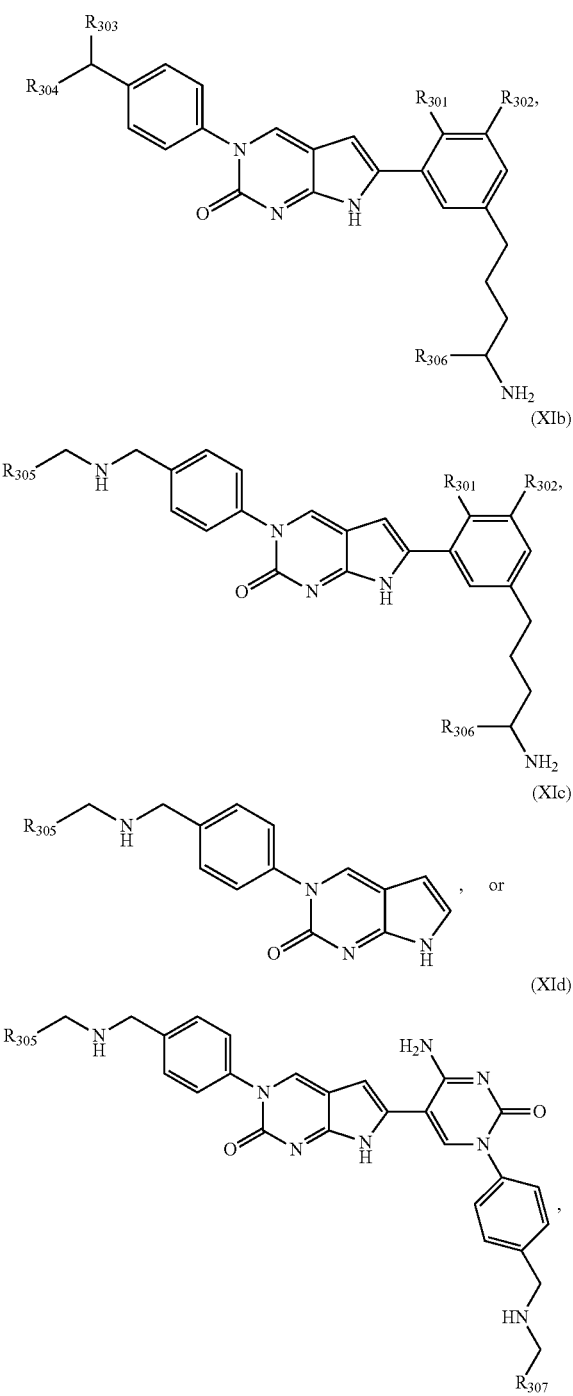

or a tautomer thereof, or a pharmaceutically acceptable salt, or ester of said compound or tautomer, wherein:

$R_{301}$ is H or F, wherein when $R_{301}$ is H, then $R_{302}$ is $CF_3$, $OCF_3$, $SCF_3$, or $SOCF_3$; and when $R_{301}$ is F, then $R_{302}$ is Cl or $OCF_3$;

each of $R_{303}$ and $R_{304}$ independently is phenyl or 5- or 6-membered heteroaryl, each of which is optionally substituted with one or more substituents independently selected from halo, OH, amino, $C_1$-$C_6$ alkoxyl and $C_1$-$C_6$ alkylthio; or one of $R_{303}$ and $R_{304}$ is amino and the other is $CH_2CH_2NR_fR_g$ in which $R_f$ is H, $C_1$-$C_6$ alkyl, $COC_1$-$C_6$ alkyl or $COC_6$-$C_{10}$ aryl and $R_g$ is 5- or 6-membered heteroaryl;

each of $R_{305}$ and $R_{307}$ independently is cyano, COOH, $COC_1$-$C_6$ alkoxyl, $C(=NH)C_1$-$C_6$ alkoxyl, $C(=NH)NH_2$, amino, $CH_2COOH$, $CH_2COC_1$-$C_6$ alkoxyl, $CH_2NH_2$, $CH_2NHC_1$-$C_6$ alkyl, or 5- or 6-membered heteroaryl optionally substituted with one or more substituents independently selected from halo, OH, amino, $C_1$-$C_6$ alkoxyl, $C_1$-$C_6$ alkylthio, and $C_7$-$C_{12}$ arylalkyl that is optionally further substituted with one or more substituents independently selected from halo, OH, amino, $C_1$-$C_6$ alkoxyl, and $C_1$-$C_6$ alkylthio; and $R_{306}$ is $C_1$-$C_3$ alkyl optionally substituted with one or more substituents independently selected from the group consisting of halo, OH, amino, $C_1$-$C_6$ alkoxyl and $C_1$-$C_6$ alkylthio, $C_2$-$C_3$ alkenyl, or $CH_2OCOR_{aaa}$, in which $R_{aaa}$ is $C_1$-$C_6$ alkyl, amino, or phenyl, and $R_{aaa}$ is optionally substituted with COOH, $COOC_1$-$C_6$ alkyl, $OCOC_1$-$C_6$ alkyl, or $C_7$-$C_{12}$ arylalkyl.

In another aspect, the present invention relates to a pharmaceutical composition comprising a pharmaceutically acceptable carrier and a compound of the present invention or a tautomer thereof, or a pharmaceutically acceptable salt, or ester of said compound or tautomer.

In another aspect, the present invention relates to a method of treating a microbial infection comprising administering to a subject in need thereof an effective amount of a compound of the present invention, or a tautomer thereof, or a pharmaceutically acceptable salt, or ester of said compound or tautomer.

In another aspect, the present invention relates to a method of preventing a microbial infection comprising administering to a subject in need thereof an effective amount of a compound of the present invention, or a tautomer thereof, or a pharmaceutically acceptable salt, or ester of said compound or tautomer.

In yet another aspect, the present invention relates to a method of reducing the risk of a microbial infection comprising administering to a subject in need thereof an effective amount of a compound of the present invention, or a tautomer thereof, or a pharmaceutically acceptable salt, or ester of said compound or tautomer.

In another aspect, the present invention relates to a method of delaying the onset of a microbial infection comprising administering to a subject in need thereof an effective amount of a compound of the present invention, or a tautomer thereof, or a pharmaceutically acceptable salt, or ester of said compound or tautomer.

In yet another aspect, the present invention relates to a compound for use in the manufacture of a medicament for treating a microbial infection in a subject, wherein the compound is selected from a compound of the present invention, or a tautomer thereof, or a pharmaceutically acceptable salt, or ester of said compound or tautomer.

In another aspect, the present invention relates to a compound for use in the manufacture of a medicament for preventing a microbial infection in a subject, wherein the compound is selected from a compound of the present invention, or a tautomer thereof, or a pharmaceutically acceptable salt, or ester of said compound or tautomer.

In yet another aspect, the present invention relates to a compound for use in the manufacture of a medicament for reducing the risk of a microbial infection in a subject, wherein the compound is selected from a compound of the present invention, or a tautomer thereof, or a pharmaceutically acceptable salt, or ester of said compound or tautomer.

In another aspect, the present invention relates to a compound for use in the manufacture of a medicament for delaying the onset of a microbial infection in a subject, wherein the compound is selected from a compound of the present invention, or a tautomer thereof, or a pharmaceutically acceptable salt, or ester of said compound or tautomer.

In yet another aspect, the present invention relates to a compound for use in a method for treating, preventing, reducing the risk of, and/or delaying the onset of a microbial infection in a subject, wherein the compound is selected from a compound of the present invention, or a tautomer thereof, or a pharmaceutically acceptable salt, or ester of said compound or tautomer.

In addition, the invention provides methods of synthesizing the foregoing compounds and tautomers thereof, and pharmaceutically acceptable salts, esters and prodrugs of said compounds and tautomers. Following synthesis, an effective amount of one or more of the compounds or tautomers thereof, or pharmaceutically acceptable salts, esters or prodrugs of said compounds or tautomers can be formulated with a pharmaceutically acceptable carrier for administration to a human or animal for use as antimicrobial agents, particularly as antibacterial agents. In certain embodiments, the compounds of the present invention are useful for treating, preventing, reducing the risk of, or delaying the onset of microbial infections or for the manufacture of a medicament for treating, preventing, reducing the risk of, or delaying the onset of microbial infections.

Accordingly, the compounds or tautomers thereof, or pharmaceutically acceptable salts, esters, or prodrugs of said compounds or tautomers or their formulations can be administered, for example, via oral, parenteral, intravenous, otic, ophthalmic, nasal, or topical routes, to provide an effective amount of the compound or tautomer thereof, or pharmaceutically acceptable salt, ester or prodrug of said compound or tautomer to the human or animal.

The foregoing and other aspects and embodiments of the invention can be more fully understood by reference to the following detailed description and claims.

DETAILED DESCRIPTION OF THE INVENTION

The present invention utilizes a structure based drug design approach for discovering and developing new antimicrobial agents. This approach starts with a high resolution X-ray crystal of a ribosome to design new classes of antimicrobial compounds having specific chemical structures, ribosome binding characteristics, and antimicrobial activity. This structure based drug discovery approach is described in the following publication: Franceschi, F. and Duffy, E. M., "Structure-based drug design meets the ribosome", *Biochemical Pharmacology*, vol. 71, pp. 1016-1025 (2006).

Based on this structure based drug design approach, the present invention describes new chemical classes of antimicrobial compounds useful for treating bacterial infections in humans and animals. Without being limited by theories, these compounds are believed to inhibit bacterial ribosome function by binding to the ribosome. By taking advantage of these ribosome binding sites, the antimicrobial compounds of the present invention can provide better activity, especially against resistant strains of bacteria, than currently available antibiotic compounds.

The present invention therefore fills an important ongoing need for new antimicrobial agents, particularly for antimicrobial agents, having activity against resistant pathogenic bacterial organisms.

The present invention provides a family of compounds or tautomers thereof, that can be used as antimicrobial agents, more particularly as antibacterial agents.

The present invention also includes pharmaceutically acceptable salts, esters, and prodrugs of said compounds and tautomers.

The compounds or tautomers thereof, or pharmaceutically acceptable salts, esters, or prodrugs of said compounds or tautomers described herein can have asymmetric centers. Compounds or tautomers thereof, or pharmaceutically acceptable salts, esters, or prodrugs of said compounds or tautomers of the present invention containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds or tautomers thereof, or pharmaceutically acceptable salts, esters, or prodrugs of said compounds or tautomers described herein, and all such stable isomers are contemplated in the present invention. Cis and trans geometric isomers of the compounds or tautomers thereof, or pharmaceutically acceptable salts, esters, or prodrugs of said compounds or tautomers of the present invention are described and can be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds or tautomers thereof, or pharmaceutically acceptable salts, esters, or prodrugs of said compounds or tautomers of the present invention and intermediates made herein are considered to be part of the present invention. All tautomers of shown or described compounds are also considered to be part of the present invention. Furthermore, the invention also includes metabolites of the compounds described herein.

The invention also comprehends isotopically-labeled compounds or tautomers thereof, or pharmaceutically acceptable salts, esters, or prodrugs of said compounds or tautomers, which are identical to those recited in formulae of the invention, but for the replacement of one or more atoms by an atom having an atomic mass or mass number different from the atomic mass or mass number most commonly found in nature. Examples of isotopes that can be incorporated into compounds or tautomers thereof, or pharmaceutically acceptable salts, esters, or prodrugs of said compounds or tautomers of the invention include isotopes of hydrogen, carbon, nitrogen, fluorine, such as $^3$H, $^{11}$C, $^{14}$C and $^{18}$F.

The compounds of the present invention or tautomers thereof, or pharmaceutically acceptable salts, esters, or prodrugs of said compounds or tautomers that contain the aforementioned isotopes and/or isotopes of other atoms are within the scope of the present invention. Isotopically-labeled compounds or tautomers thereof, or pharmaceutically acceptable salts, esters, or prodrugs of said compounds or tautomers of the present invention, for example, those into which radioactive isotopes such as $^3$H and $^{14}$C are incorporated, are useful in drug and/or substrate tissue distribution assays. Tritium, i.e., $^3$H, and carbon-14, i.e., $^{14}$C, isotopes are are particularly preferred due to their ease of preparation and detectability. $^{11}$C and $^{18}$F isotopes are particularly useful in PET (positron emission tomography). PET is useful in brain imaging. Further, substitution with heavier isotopes such as deuterium, i.e., $^2$H, can afford certain therapeutic advantages resulting from greater metabolic stability, i.e., increased in vivo half-life or reduced dosage requirements and, hence, may be preferred in some circumstances. Isotopically labeled compounds or tautomers thereof, or pharmaceutically acceptable salts, esters, or prodrugs of said compounds or tautomers having a formula of the invention can generally be prepared as described in the procedures, Schemes and/or in the Examples disclosed herein, by substituting a non-isotopically labeled reagent with a readily available isotopically labeled reagent. In one embodiment, the compounds or tautomers thereof, or pharmaceutically acceptable salts, esters, or prodrugs of said compounds or tautomers of the invention are not isotopically labeled.

When any variable (e.g., R) occurs more than one time in any constituent or formulae of the invention, its definition at each occurrence is independent of its definition at every other occurrence. Thus, for example, if a group is shown to be substituted with one or more R moieties, then R at each occurrence is selected independently from the definition of R. Also, combinations of substituents and/or variables are permissible, but only if such combinations result in stable compounds within a designated atom's normal valence.

A chemical structure showing a dotted line representation for a chemical bond indicates that the bond is optionally present. For example, a dotted line drawn next to a solid single bond indicates that the bond can be either a single bond or a double bond.

When a bond to a substituent is shown to cross a bond connecting two atoms in a ring, then such substituent can be bonded to any atom on the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

In cases wherein compounds of the present invention, or tautomers thereof, or pharmaceutically acceptable salts, esters, or prodrugs of said compounds or tautomers thereof, contain nitrogen atoms, these, where appropriate, can be converted to N-oxides by treatment with an oxidizing agent (e.g., meta-chloroperoxybenzoic acid (mCPBA) and/or hydrogen peroxides). Thus, shown and claimed nitrogen atoms are considered to cover both the shown nitrogen and its N-oxide (N→O) derivative, as appropriate. In some embodiments, the present invention relates to N-oxides of the compounds or tautomers thereof, or pharmaceutically acceptable salts, esters, or prodrugs of said compounds or tautomers disclosed herein.

One approach to developing improved anti-proliferative and anti-infective agents is to provide modulators (for example, inhibitors) of ribosome function.

Ribosomes are ribonucleoproteins, which are present in both prokaryotes and eukaryotes. Ribosomes are the cellular organelles responsible for protein synthesis. During gene expression, ribosomes translate the genetic information encoded in a messenger RNA into protein (Garrett et al. (2000) "*The Ribosome: Structure, Function, Antibiotics and Cellular Interactions,*" American Society for Microbiology, Washington, D.C.).

Ribosomes comprise two nonequivalent ribonucleoprotein subunits. The larger subunit (also known as the "large ribosomal subunit") is about twice the size of the smaller subunit (also known as the "small ribosomal subunit"). The small ribosomal subunit binds messenger RNA (mRNA) and mediates the interactions between mRNA and transfer RNA (tRNA) anticodons on which the fidelity of translation depends. The large ribosomal subunit catalyzes peptide bond formation, i.e., the peptidyl-transferase reaction of protein synthesis, and includes, at least, three different tRNA binding sites known as the aminoacyl, peptidyl, and exit sites. The aminoacyl site or A-site accommodates the incoming aminoacyl-tRNA that is to contribute its amino acid to the growing peptide chain. Also, the A space of the A-site is important. The peptidyl site or P-site accommodates the peptidyl-tRNA complex, i.e., the tRNA with its amino acid that is part of the growing peptide chain. The exit or E-site accommodates the deacylated tRNA after it has donated its amino acid to the growing polypeptide chain.

1. DEFINITIONS

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. A compound with one chiral center has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, J., *Chem. Educ.* 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however, as a result of recent advances in chromatography techniques, it has been possible to separate mixtures of two atropic isomers in select cases.

Some compounds of the present invention can exist in a tautomeric form which is also intended to be encompassed within the scope of the present invention. "Tautomers" refers to compounds whose structures differ markedly in the arrangement of atoms, but which exist in easy and rapid equilibrium. It is to be understood that compounds of present invention may be depicted as different tautomers. It should also be understood that when compounds have tautomeric forms, all tautomeric forms are intended to be within the scope of the invention, and the naming of the compounds does not exclude any tautomeric form.

The compounds, pharmaceutically acceptable salts, esters and prodrugs of the present invention can exist in one or more tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the compounds of the invention.

A tautomer is one of two or more structural isomers that exist in equilibrium and are readily converted from one isomeric form to another. This reaction results in the formal migration of a hydrogen atom accompanied by a shift of adjacent conjugated double bonds. In solutions where tautomerization is possible, a chemical equilibrium of the tautomers can be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism, a simultaneous shift of electrons and a hydrogen atom occurs. Ring-chain tautomerism, exhibited by glucose and other sugars, arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

Common tautomeric pairs include: ketone-enol, amide-nitrile, lactam-lactim, amide-imidic acid tautomerism in heterocyclic rings (e.g., in the nucleobases guanine, thymine, and cytosine), amine-enamine and enamine-enamine. Examples below are included for illustrative purposes, and the present invention is not limited to the examples:

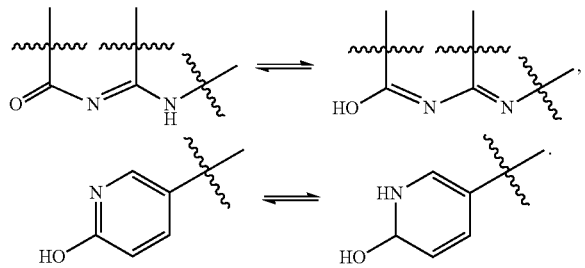

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate over another crystal form. Crystal polymorphs of the compounds can be prepared by crystallization under different conditions.

The term "substituted," as used herein, means that any one or more hydrogens on the designated atom, usually a carbon, oxygen, or nitrogen atom, is replaced with a selection from the indicated group, provided that the designated atom's normal valency is not exceeded, and that the substitution results in a stable compound. When a substituent is keto or oxo (i.e., =O), then 2 hydrogens on the atom are replaced. Ring double bonds, as used herein, are double bonds that are formed between two adjacent ring atoms (e.g., C=C, C=N, N=N, etc.).

As used herein, "alkyl" is intended to include both branched and straight-chain saturated aliphatic hydrocarbon groups having the specified number of carbon atoms. For example $C_{1-4}$ is intended to include $C_1$, $C_2$, $C_3$, and $C_4$ $C_{1-6}$ alkyl is intended to include $C_1$, $C_2$, $C_3$, $C_4$, $C_5$, and $C_6$ alkyl groups and $C_{1-8}$ is intended to include $C_1$, $C_2$, $C_3$, $C_4$, $C_5$, $C_6$, $C_7$, and $C_8$. Some examples of alkyl include, but are not limited to, methyl, ethyl, n-propyl, i-propyl, n-butyl, s-butyl, t-butyl, n-pentyl, s-pentyl, n-hexyl, n-heptyl, and n-octyl.

As used herein, "alkenyl" is intended to include hydrocarbon chains of either straight or branched configuration and one or more unsaturated carbon-carbon bonds that can occur in any stable point along the chain, such as ethenyl and propenyl. For example $C_{2-6}$ alkenyl is intended to include $C_2$, $C_3$, $C_4$, $C_5$, and $C_6$ alkenyl groups and $C_{2-8}$ alkenyl is intended to include $C_2$, $C_3$, $C_4$, $C_5$, $C_6$, $C_7$, and $C_8$.

As used herein, "alkynyl" is intended to include hydrocarbon chains of either straight or branched configuration and one or more triple carbon-carbon bonds that can occur in any stable point along the chain, such as ethynyl and propynyl. For example, $C_{2-6}$ alkynyl is intended to include $C_2$, $C_3$, $C_4$, $C_5$, and $C_6$ alkynyl groups and $C_{2-8}$ alkynyl is intended to include $C_2$, $C_3$, $C_4$, $C_5$, $C_6$, $C_7$, and $C_8$.

Furthermore, "alkyl", "alkenyl", and "alkynyl" are intended to include moieties which are diradicals, i.e., having two points of attachment. A nonlimiting example of such an alkyl moiety that is a diradical is —CH$_2$CH$_2$—, i.e., a $C_2$ alkyl group that is covalently bonded via each terminal carbon atom to the remainder of the molecule. The alkyl diradicals are also known as "alkylenyl" radicals. The alkenyl diradicals are also known as "alkenylenyl" radicals. The alkynyl diradicals are also known as "alkynylenyl" radicals.

As used herein, "cycloalkyl" is intended to include saturated ring groups, such as cyclopropyl, cyclobutyl, or cyclopentyl. $C_{3-8}$ cycloalkyl is intended to include $C_3$, $C_4$, $C_5$, $C_6$, $C_7$, and $C_8$ cycloalkyl groups. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "amine" or "amino" refers to unsubstituted —$NH_2$ unless otherwise specified.

As used herein, "halo" or "halogen" refers to fluoro, chloro, bromo, and iodo substituents.

As used herein, "haloalkyl" is intended to include both branched and straight-chain saturated aliphatic hydrocarbon groups having the specified number of carbon atoms, substituted with one or more halogen (for example —$C_vF_wH_{2v-w+1}$ wherein v=1 to 3 and w=1 to (2v+1)). Examples of haloalkyl include, but are not limited to, trifluoromethyl, trichloromethyl, pentafluoroethyl, and pentachloroethyl.

As used herein, "haloalkenyl" is intended to include both branched and straight-chain unsaturated hydrocarbon groups having the specified number of carbon atoms, substituted with one or more halogen. Examples of haloalkyl include, but are not limited to, —CH=CHF, —CH=CHCl, —CH=$CF_2$, —CH=$CCl_2$, $CH_2$CH=CHF, $CH_2$CH=CHCl, $CH_2$CH=$CF_2$, and $CH_2$CH=$CCl_2$.

As used herein, "alkoxyl" refers to an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. $C_{1-8}$ alkoxy, is intended to include $C_1$, $C_2$, $C_3$, $C_4$, $C_5$, $C_6$, $C_7$, and $C_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "alkylthio" refers to an alkyl group as defined above with the indicated number of carbon atoms attached through a sulfur bridge. $C_{1-6}$ alkylthio, is intended to include $C_1$, $C_2$, $C_3$, $C_4$, $C_5$, and $C_6$ alkylthio groups. $C_{1-8}$ alkylthio, is intended to include $C_1$, $C_2$, $C_3$, $C_4$, $C_5$, $C_6$, $C_7$, and $C_8$ alkylthio groups.

As used herein, "carbocycle" or "carbocyclic ring" is intended to mean, unless otherwise specified, any stable 3, 4, 5, 6, 7, 8, 9, 10, 11, or 12-membered monocyclic, bicyclic or tricyclic ring, any of which can be saturated, unsaturated (including partially and fully unsaturated), or aromatic and said ring consists of carbon atoms in its core ring structure. Examples of such carbocycles or carbocyclic rings include, but are not limited to, cyclopropyl, cyclobutyl, cyclobutenyl, cyclopentyl, cyclopentenyl, cyclohexyl, cyclohexenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring can also be present on the bridge. Fused (e.g., naphthyl and tetrahydronaphthyl) and spiro rings are also included.

As used herein, the term "heterocycle" or "heterocyclic" ring means, unless otherwise stated, a stable 3, 4, 5, 6, 7, 8, 9, 10, 11, or 12-membered monocyclic, bicyclic or tricyclic ring which is saturated, unsaturated (including partially and fully unsaturated), or aromatic, and said ring consists of carbon atoms and one or more heteroatoms in its core ring structure, e.g., 1 or 1-2 or 1-3 or 1-4 or 1-5 or 1-6 heteroatoms, independently selected from nitrogen, oxygen, and sulfur, and including any bicyclic or tricyclic group in which any of the above-defined heterocyclic rings is fused or attached to a second ring (e.g., a benzene ring). The nitrogen and sulfur heteroatoms can optionally be oxidized (i.e., N→O and $S(O)_p$, wherein p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom can be substituted or unsubstituted (i.e., N or NR wherein R is H or another substituent, as defined). The heterocycle or heterocyclic ring can be attached to its pendant group at any heteroatom or carbon atom that results in a stable structure. The heterocycle or heterocyclic rings described herein can be substituted on carbon or on a nitrogen atom if the resulting compound is stable. A nitrogen in the heterocycle or heterocyclic ring can optionally be quaternized. Bridged rings are also included in the definition of heterocycle or heterocyclic ring. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. When a ring is bridged, the substituents recited for the ring can also be present on the bridge. Spiro and fused rings are also included.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

As used herein, the term "aromatic heterocycle", "aromatic heterocylic" or "heteroaryl" ring is intended to mean a stable 5, 6, 7, 8, 9, 10, 11, or 12-membered monocyclic or bicyclic aromatic ring which consists of carbon atoms and one or more heteroatoms, e.g., 1 or 1-2 or 1-3 or 1-4 or 1-5 or 1-6 heteroatoms, independently selected from nitrogen, oxygen, and sulfur. In the case of bicyclic aromatic heterocyclic or heterocycle or heteroaryl rings, only one of the two rings needs to be aromatic (e.g., 2,3-dihydroindole), though both can be (e.g., quinoline). The second ring can also be fused or bridged as defined above for heterocycles. The nitrogen atom can be substituted or unsubstituted (i.e., N or NR wherein R is H or another substituent, as defined). The nitrogen and sulfur heteroatoms can optionally be oxidized (i.e., N→O and S(O)$_p$, wherein p=1 or 2). In certain compounds, the total number of S and O atoms in the aromatic heterocycle is not more than 1.

Examples of aromatic heterocycles, aromatic heterocyclics or heteroaryls include, but are not limited to, acridinyl, azabicyclooctanonyl, azepanyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, benzodioxoly, benzooxadiazoly, carbazolyl, 4aH-carbazolyl, carbolinyl, chromanyl, chromenyl, cinnolinyl, cycloheptyl, decahydroquinolinyl, dihydrobenzodioxinyl, 2H,6H-1,5,2-dithiazinyl, dihydrofuro[2,3-b]tetrahydrofuran, furanyl, furazanyl, imidazolidinyl, imidazolidinylimine, imidazolinyl, imidazolyl, imidazolonyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, methylbenztriazolyl, methylfuranyl, methylimidazolyl, methylthiazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolidinonyl, oxazolyl, oxindolyl, phenanthridinyl, phenanthrolinyl, phenazinyl, phenothiazinyl, phenoxathinyl, phenoxazinyl, phthalazinyl, piperazinyl, piperazinonyl, piperidinyl, piperidenyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridinonyl, pyridyl, pyrimidinyl, pyrroldionyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, thiomorpholinyldioxidyl, triazinyl, triazolopyrimidinyl, 1,2,3-triazolyl, 1,2,4-triazolyl, 1,2,5-triazolyl, 1,3,4-triazolyl, and xanthenyl.

As used herein, the phrase "pharmaceutically acceptable" refers to those compounds or tautomers thereof, or salts, esters, or prodrugs thereof, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds or tautomers thereof, wherein the parent compound or a tautomer thereof, is modified by making of the acid or base salts thereof of the parent compound or a tautomer thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound, or a tautomer thereof, formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic.

The pharmaceutically acceptable salts of the present invention can be synthesized from the parent compound or a tautomer thereof, that contains a basic or acidic moiety by conventional chemical methods. Generally, such pharmaceutically acceptable salts can be prepared by reacting the free acid or base forms of these compounds or tautomers thereof with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., USA, p. 1445 (1990).

Since prodrugs are known to enhance numerous desirable qualities of pharmaceuticals (e.g., solubility, bioavailability, manufacturing, etc.), the compounds or tautomers thereof of the present invention can be delivered in prodrug form. Thus, the present invention is intended to cover prodrugs of the presently claimed compounds or tautomers thereof, methods of delivering the same, and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound or a tautomer thereof in such a way that the modified functional groups are cleaved, either in routine manipulation or in vivo, to the release, form, or produce the parent compound or a tautomer thereof. Prodrugs include compounds or tautomers thereof of the present invention wherein a hydroxy, amino, or sulfhydryl group is bonded to any group to produce a prodrug of the compound or tautomer thereof that when administered to a mammalian subject is cleaved to form a free hydroxyl, free amino, or free sulfhydryl group, respectively. Examples of prodrugs include, but are not limited to, acetate, formate, and benzoate derivatives of alcohol and amine functional groups in the compounds of the present invention.

As used herein, "stable compound" and "stable structure" are meant to indicate a compound that is sufficiently robust to survive isolation to a useful degree of purity from a reaction mixture, and formulation into an efficacious therapeutic agent.

As used herein, the term "patient", as used herein, means the human or animal (in the case of an animal, more typically a mammal) subject that would be subjected to a surgical or invasive medical procedure. Such patient or subject could be considered to be in need of the methods of treating, reducing the risk of or preventing the infection due to a surgical procedure or an invasive medical procedure. Such patient or subject can also be considered to be in need of peri-operative prophylaxis.

As used herein, the term "treating" means to provide a therapeutic intervention to cure or ameliorate an infection.

As used herein, the term "preventing", as used herein, means, to completely or almost completely stop an infection from occurring, for example when the patient or subject is predisposed to an infection or at risk of contracting an infection. Preventing can also include inhibiting, i.e., arresting the development, of an infection.

As used herein, the term "reducing the risk of", as used herein, means to lower the likelihood or probability of an infection occurring, for example when the patient or subject is predisposed to an infection or at risk of contracting an infection.

As used herein, "unsaturated" refers to compounds having at least one degree of unsaturation (e.g., at least one multiple bond) and includes partially and fully unsaturated compounds.

As used herein, the term "effective amount" refers to an amount of a compound or a tautomer thereof, or a pharmaceutically acceptable salt, ester, or prodrug of said compound or tautomer (including combinations of compounds and/or tautomers thereof, and/or pharmaceutically acceptable salts, esters, or prodrugs of said compound or tautomer) of the present invention that is effective when administered alone or in combination as an antimicrobial agent. For example, an effective amount refers to an amount of the compound or tautomer thereof, or a pharmaceutically acceptable salt, ester, or prodrug said compound or tautomer that is present in a composition, a formulation or on a medical device given to a recipient patient or subject sufficient to elicit biological activity, for example, anti-infective activity, such as e.g., anti-microbial activity, anti-bacterial activity, anti-fungal activity, anti-viral activity, or anti-parasitic activity.

The term "prophylactically effective amount" means an amount of a compound or a tautomer of said compound or tautomer, or a pharmaceutically acceptable salt, ester, or prodrug of said compound or tautomer (including combinations of compounds and/or tautomers thereof, and/or pharmaceutically acceptable salts, esters, or prodrugs thereof), of the present invention that is effective prophylactically when administered alone or in combination as an antimicrobial agent. For example, a prophylactically effective amount refers to an amount of the compound or tautomer thereof, or a pharmaceutically acceptable salt, ester, or prodrug of said compound or tautomer that is present in a composition, a formulation, or on a medical device given to a recipient patient or subject sufficient to prevent or reduce the risk of an infection due to a surgical procedure or an invasive medical procedure.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control. As used herein, "mammal" refers to human and non-human patients.

As used herein, the term "therapeutically effective amount" refers to an amount of a compound or a tautomer thereof or a pharmaceutically acceptable salt, ester, or prodrug of said compound or tautomer, (also including combinations of compounds and/or tautomers thereof, and/or pharmaceutically acceptable salts, esters, or prodrugs or said compounds or tautomers), of the present invention that is effective when administered alone or in combination as an antimicrobial agent. For example, a therapeutically effective amount refers to an amount of the compound or tautomer thereof, or a pharmaceutically acceptable salt, ester, or prodrug of said compound or tautomer that is present in a composition, a formulation, or on a medical device given to a recipient patient or subject in an amount sufficient to elicit biological activity, for example, anti-microbial activity, anti-fungal activity, anti-viral activity, anti-parasitic activity, anti-diarrheal activity, and/or anti-proliferative activity. In one aspect, the combination of compounds and/or tautomers thereof, and/or pharmaceutically acceptable salts, esters, or prodrugs or said compounds or tautomers is a synergistic combination. Synergy, as described, for example, by Chou and Talalay, *Adv. Enzyme Regul.* vol. 22, pp. 27-55 (1984), occurs when the effect of the compounds or tautomers thereof or pharmaceutically acceptable salts, esters, or prodrugs of said compounds or tautomers when administered in combination is greater than the additive effect of the compounds or tautomers thereof, or pharmaceutically acceptable salts, esters, or prodrugs of said compounds or tautomers when administered alone as a single agent. In general, a synergistic effect is most clearly demonstrated at sub-optimal concentrations of the compounds or tautomers thereof, or pharmaceutically acceptable salts, esters, or prodrugs of said compounds or tautomers. Synergy can be in terms of lower cytotoxicity, increased anti-proliferative and/or anti-infective effect, or some other beneficial effect of the combination compared with the individual components.

As used herein, the term ESBL is extended spectrum beta-lactamase. The term KPC is *Klebsiella pneumonia* carbapenemase.

As used herein, the term acute bacterial skin and skin structure infection (ABSSSI) encompasses complicated skin and skin structure infections (cSSSI) and complication skin and soft tissue infections (cSSTI), which have been used interchangeably. The terms uncomplicated skin and skin structure infections (uCSSSI) and uncomplicated skin and soft tissue infections (uCSSTI) have been used interchangeably.

As used herein, the term "spp." is the abbreviation for species.

As used herein, the term "formulae of the invention" includes one or more of the formulae: I, Ia, Ib, Ic, Id, Ie, If, Ig, Ih, Ii, Ij, Ik, Il, Im, In, Io, Ip, Iq, Ir, Is, It, Iu, Iv, Iw, Ix, Iy, Iz, IA, IB, IC, ID, IE, IF, IG, IH, IJ, IK, IM, IN, IL, II, IIA, IIa, III, IIIA, IIIa, IV, IVA, IVa, V, VA, Va, VIII, IX, X, XIa, XIb, XIc, and XId.

As used herein, the term "compound of the invention" includes one or more compounds of the formulae of the invention or a compound explicitly disclosed herein.

All percentages and ratios used herein, unless otherwise indicated, are by weight.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions can be conducted simultaneously.

2. COMPOUNDS OF THE INVENTION

In some embodiments, the present invention relates to a compound having any one of the formulae (IA)-(VA) below:

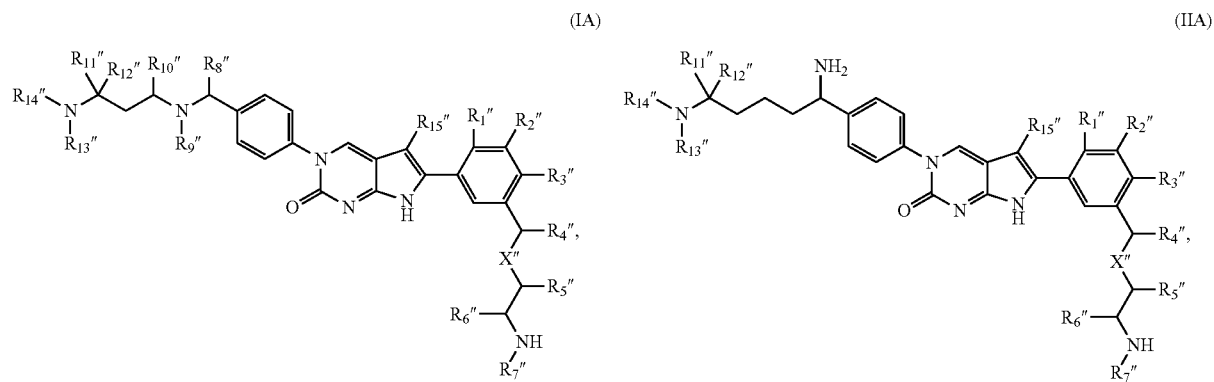
(IA)
(IIA)
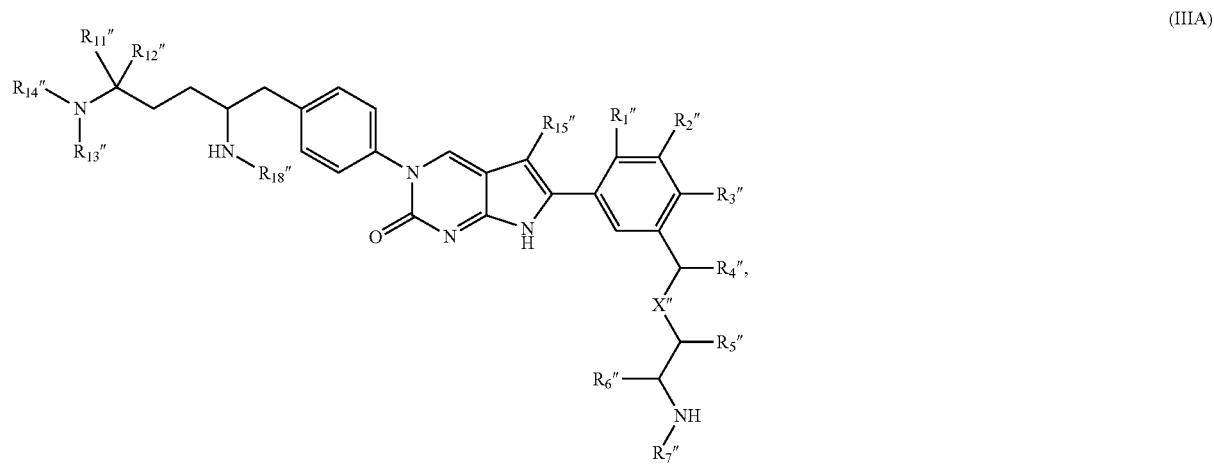
(IIIA)
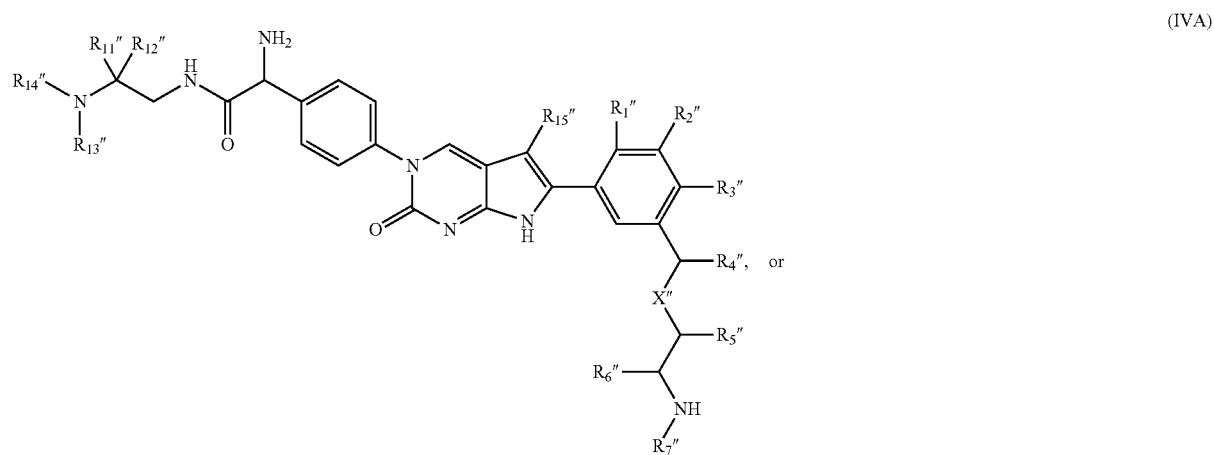
(IVA)

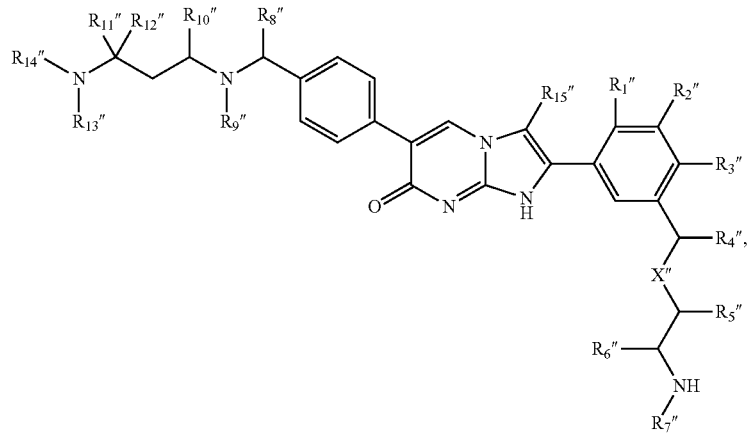

(VA)

or a tautomer thereof, or a pharmaceutically acceptable salt, or ester of said compound or tautomer wherein:

$R_{1''}$ is H or F, wherein when $R_{1''}$ is H, then $R_{2''}$ is $CF_3$, $OCF_3$, $SCF_3$, $SOCF_3$ or halo and $R_{3''}$ is H; and when $R_{1''}$ is F, then (i) $R_{2''}$ is Cl or $OCF_3$ and $R_{3''}$ is H; or (ii) $R_{2''}$ is H and $R_{3''}$ is $C_1$-$C_6$ alkyl; or (iii) $R_{2''}$ is $C_1$-$C_6$ alkyl optionally substituted with one or more halo and $R_{3''}$ is halo;

$R_{4''}$ is H, OH, or $C_1$-$C_6$ alkoxyl;

$R_{5''}$ is H, $CH_2OH$ or $CH_2OC_1$-$C_6$ alkyl;

$R_{6''}$ is $C_1$-$C_3$ alkyl optionally substituted with one or more substituents selected from the group consisting of halo, OH, amino, $C_1$-$C_6$ alkoxyl and $C_1$-$C_6$ alkylthio, $C_2$-$C_3$ alkenyl, or $CH_2OCOR_{a''}$, in which $R_{a''}$ is $C_1$-$C_6$ alkyl, amino, or phenyl, and $R_{a''}$ is optionally substituted with COOH, $COOC_1$-$C_6$ alkyl, $OCOC_1$-$C_6$ alkyl, or $C_7$-$C_{12}$ arylalkyl;

$R_{7''}$ is H, C(=NH)$NH_2$, or $COR_{b''}$ in which $R_{b''}$ is $C_1$-$C_6$ alkyl optionally substituted with $C_1$-$C_6$ alkoxyl or amino; or $R_{6''}$ and $R_{7''}$ together with the two atoms to which they are attached, form a 5- to 12-membered heterocycloalkyl ring having 0 to 1 additional heteroatom optionally substituted with an oxo group;

each of $R_{8'''}$, $R_{10'''}$, and $R_{11'''}$, independently is -$Q_{1''}$-$T_{1'''}$, in which $Q_{1''}$ is a bond or $C_1$-$C_3$ alkyl linker optionally substituted with one or more halo or hydroxyl, and $T_{1'''}$ is H, halo, OH, COOH, cyano, azido, $C_1$-$C_3$ alkyl, $C_2$-$C_6$ alkenyl, $C_2$-$C_6$ alkynyl, $C_1$-$C_6$ alkoxyl, $C_1$-$C_6$ alkylthio, $COOC_1$-$C_6$ alkyl, $SO_2C_1$-$C_6$ alkyl, or $R_{c''}$, in which $R_{c''}$ is amino, $C_3$-$C_8$ cycloalkyl, $C_6$-$C_{10}$ aryl, 4 to 12-membered heterocycloalkyl, 5- or 6-membered heteroaryl, or C(O)$NR_{d''}R_{e''}$, each of $R_{d''}$ and $R_{e''}$ independently being H or $C_1$-$C_6$ alkyl, or $R_{d''}$ and $R_{e''}$ together with the nitrogen atom to which they are attached forming a 5- to 12-membered heterocycloalkyl ring having 0 to 2 additional heteroatoms; and $R_{c''}$ is optionally substituted with -$Q_{2''}$-$T_{2''}$, in which $Q_{2''}$ is a bond or $C_1$-$C_3$ alkyl and $T_{2''}$ is H, halo, amino, 5- or 6-membered heteroaryl or $C_6$-$C_{10}$ aryl optionally substituted with $C_1$-$C_6$ alkoxyl; or $R_{8''}$ and $R_{10''}$, together with the two carbon atoms to which they are attached and the nitrogen atom connecting said two carbon atoms, form a 5- to 12-membered heterocycloalkyl ring having 0 to 1 additional heteroatom;

$R_{12''}$ is H or $C_1$-$C_6$ alkyl, or $R_{12''}$ and $R_{11''}$ together with the carbon atom to which they are attached form a 4- to 12-membered saturated heterocycloalkyl ring having 1 to 2 heteroatoms optionally substituted with C(=NH)$NH_2$;

each of $R_{9''}$ and $R_{13''}$, independently is, H, $C_1$-$C_3$ alkyl, or $C_2$-$C_4$ alkenyl, or $R_{9''}$ and $R_{13''}$ together with the two nitrogen atoms to which they are attached and the carbon atom connecting said two nitrogen atoms, form a 7- to 12-membered saturated heterocycloalkyl ring having 0 to 1 additional heteroatom, or $R_{9''}$ and $R_{8''}$ together with the two atoms to which they are attached form a 5- to 12-membered heterocycloalkyl ring having 0 to 1 additional heteroatom optionally substituted with an oxo group;

$R_{14''}$ is H or C(=$NR_{16''}$)$NH_2$, in which $R_{16''}$ is H, $C_1$-$C_3$ alkyl, $C_2$-$C_4$ alkenyl, $C_3$-$C_8$ cycloalkyl, or 4- to 12-membered saturated heterocycloalkyl ring having 1 to 2 heteroatoms, or $R_{16''}$ and $R_{11''}$ together with the two atoms to which they are attached and the atoms connecting said two carbon atoms, form a 5- to 12-membered heterocycloalkyl ring having ring having 0 to 1 additional heteroatom;

$R_{15''}$ is H or halo;

X" is a bond, O, or $CHR_{17''}$, in which $R_{17''}$ is H or $R_{17''}$ and $R_{6''}$ together with the two carbon atoms to which they are attached and the carbon atom connecting said two carbon atoms, form a 5- to 12-membered saturated heterocycloalkyl ring having 1 to 2 heteroatoms, and when X" is a bond, $R_{4''}$ and $R_{6''}$ together with the two carbon atoms to which they are attached and the carbon atom connecting said two carbon atoms, form a 5- to 12-membered saturated heterocycloalkyl ring having 1 to 2 heteroatoms; and $R_{18''}$ is H or C(=NH)$NH_2$;

provided that for a compound of Formula (I)

(a) when $R_{14''}$ is C(=$NR_{16''}$)$NH_2$, X" is $CH_2$, $R_{6''}$ is methyl and $R_{8''}$ is H, $C_1$-$C_3$ alkyl, $C_2$-$C_3$ alkenyl, cyclopropyl, $CH_2CH_2OH$, COOH, $COOCH_3$, $CH_2COOH$, $CH_2COOCH_3$, or 4-methoxyphenyl, then at least one of $R_{4''}$, $R_{5''}$, $R_{7''}$, $R_{10''}$, $R_{11''}$, $R_{12''}$, or $R_{15''}$ is not H;

(b) when $R_{14''}$ is C(=$NR_{16''}$)$NH_2$, X" is $CH_2$, $R_{6''}$ is $CH_2OH$ and $R_{8''}$ is H, methyl or ethyl, then at least one of $R_{4''}$, $R_{5''}$, $R_{7''}$, $R_{10''}$, $R_{11''}$, $R_{12''}$, or $R_{15''}$ is not H; or (c) when $R_{14''}$ is C(=$NR_{16''}$)$NH_2$, X" is $CH_2$, $R_{6''}$ is $CH_2OCH_3$, then at least one of $R_{4''}$, $R_{5''}$, $R_{7''}$, $R_{8''}$, $R_{10''}$, $R_{11''}$, $R_{12''}$, or $R_{15''}$ is not H.

In some embodiments, the present invention relates to a compound having the formula: (Ia):

(Ia)

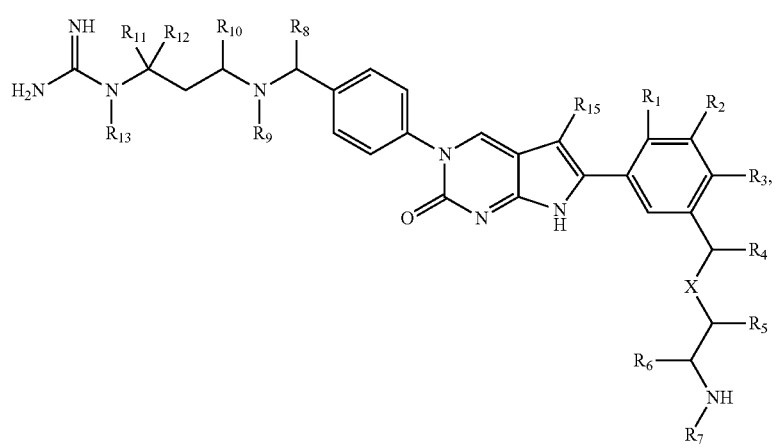

or a tautomer thereof, or a pharmaceutically acceptable salt, ester, or prodrug of said compound or tautomer, wherein $R_1$ is H or F, wherein when $R_1$ is H, then $R_2$ is $CF_3$, $OCF_3$, $SCF_3$, $SOCF_3$ or halo and $R_3$ is H; and when $R_1$ is F, then (i) $R_2$ is Cl or $OCF_3$ and $R_3$ is H; or (ii) $R_2$ is H and $R_3$ is $C_1$-$C_6$ allyl; or (iii) $R_2$ is $C_1$-$C_6$ alkyl optionally substituted with one or more halo and $R_3$ is halo;

$R_4$ is H, OH, $NH_2$, or $C_1$-$C_6$ alkoxyl, or when X is O or $CHR_{17}$, $R_4$ and $R_5$ together with the two atoms to which they are attached and the atom connecting said two atoms form a 5- to 8-membered heterocycloalkyl ring having 1 to 2 heteroatoms; or when X is a bond, $R_4$ and $R_6$ together with the two carbon atoms to which they are attached and the carbon atom connecting said two carbon atoms, form a 5- to 12-membered saturated heterocycloalkyl ring having 1 to 2 heteroatoms;

$R_5$ is H, $CH_2OH$ or $CH_2OC_1$-$C_6$ allyl, or when X is O or $CHR_{17}$, $R_4$ and $R_5$ together with the two atoms to which they are attached and the atom connecting said two atoms form a 5- to 8-membered heterocycloalkyl ring having 1 to 2 heteroatoms;

$R_6$ is $C_1$-$C_3$ allyl optionally substituted with one or more substituents independently selected from the group consisting of halo, OH, azido, amino, $C_1$-$C_6$ alkoxyl, $C_1$-$C_6$ allylthio, $C_2$-$C_3$ alkenyl, $OCOR_a$ $CH_2OCOR_a$, and —OP(O)$(OR_a)_2$, in which $R_a$ is $C_1$-$C_6$ allyl, amino, or phenyl, and $R_a$ is optionally substituted with COOH, $COOC_1$-$C_6$ allyl, $OCOC_1$-$C_6$ allyl, phenyl, or $C_7$-$C_{12}$ arylalkyl; or $R_6$ and $R_7$ together with the two atoms to which they are attached, form a 5- to 12-membered heterocycloalkyl ring having 0 to 1 additional heteroatom optionally substituted with an oxo group; or $R_6$ and $R_{17}$ together with the two carbon atoms to which they are attached and the carbon atom connecting said two carbon atoms, form a 5- to 12-membered saturated heterocycloalkyl ring having 1 to 2 heteroatoms; or when X is a bond, $R_4$ and $R_6$ together with the two carbon atoms to which they are attached and the carbon atom connecting said two carbon atoms, form a 5- to 12-membered saturated heterocycloalkyl ring having 1 to 2 heteroatoms;

$R_7$ is H, C(=NH)$NH_2$, or $COR_b$ in which $R_b$ is $C_1$-$C_6$ alkyl optionally substituted with $C_1$-$C_6$ alkoxyl or amino; or $R_6$ and $R_7$ together with the two atoms to which they are attached, form a 5- to 12-membered heterocycloalkyl ring having 0 to 1 additional heteroatom optionally substituted with an oxo group;

each of $R_8$, $R_{10}$, and $R_{11}$, independently is -$Q_1$-$T_1$, in which $Q_1$ is a bond or $C_1$-$C_3$ alkyl linker optionally substituted with one or more halo or hydroxyl, and $T_1$ is H, halo, OH, COOH, cyano, azido, $C_1$-$C_3$ alkyl, $C_2$-$C_6$ alkenyl, $C_2$-$C_6$ alkynyl, $C_1$-$C_6$ alkoxyl, $C_2$-$C_6$ haloalkenyl, $C_1$-$C_6$ alkylthio, $COOC_1$-$C_6$ alkyl, —NHC(O)$CH_2NH_2$, NHS(O) $C_1$-$C_3$ alkyl, $SO_2C_1$-$C_6$ alkyl, or $R_c$, in which $R_c$ is amino, $C_3$-$C_8$ cycloalkyl, $C_6$-$C_{10}$ aryl, 4 to 12-membered heterocycloalkyl, 5- or 6-membered heteroaryl, —O-heteroaryl, —NH-heteroaryl, —S-heteroaryl, or C(O)$NR_dR_e$, each of $R_d$ and $R_e$ independently being H or $C_1$-$C_6$ alkyl, or $R_d$ and $R_e$ together with the nitrogen atom to which they are attached forming a 5- to 12-membered heterocycloalkyl ring having 0 to 2 additional heteroatoms; and $R_c$ is optionally substituted with -$Q_2$-$T_2$, in which $Q_2$ is a bond or $C_1$-$C_3$ alkyl and $T_2$ is H, halo, $C_1$-$C_3$ alkyl, amino, 5- or 6-membered heteroaryl or $C_6$-$C_{10}$ aryl wherein the aryl and heteroaryl are optionally substituted with $C_1$-$C_6$ alkoxyl or $C_1$-$C_4$ aminoalkyl; or $R_8$ and $R_{10}$, together with the two carbon atoms to which they are attached and the Z atom connecting said two carbon atoms, form a 5- to 12-membered heterocycloalkyl ring having 0 to 2 additional heteroatoms optionally substituted with one more substituents independently selected from $C_1$-$C_6$ alkyl or —C(=N)$NH_2$;

$R_{12}$ is H or $C_1$-$C_6$ alkyl, or $R_{12}$ and $R_{11}$ together with the carbon atom to which they are attached form a 4- to 12-membered saturated heterocycloalkyl ring having 1 to 2 heteroatoms optionally substituted with C(=NH)$NH_2$; or $R_{12}$ and $R_{10}$ together with the two carbon atoms to which they are attached and the atoms, if present, connecting said two carbon atoms form a $C_3$-$C_8$ cycloalkyl ring;

each of $R_9$ and $R_{13}$ independently is H, $C_1$-$C_3$ alkyl, $C_2$-$C_4$ alkenyl or —C(O)H, or $R_9$ and $R_{13}$ together with the two nitrogen atoms to which they are attached and the carbon atoms connecting said two nitrogen atoms, form a 7- to 12-membered saturated heterocycloalkyl ring having 0 to 1 additional heteroatom, or $R_9$ and $R_8$ together with the two atoms to which they are attached form a 5- to 12-membered heterocycloalkyl ring having 0 to 1 additional heteroatom optionally substituted with an oxo group;

$R_{11}$ and $R_{13}$ together with the atoms to which they are attached form a 5- to 8-membered heterocycloalkyl ring having 0 to 2 additional heteroatoms optionally substituted with oxo;

$R_{15}$ is H or halo;

X is a bond, O, or $CHR_{17}$, in which $R_{17}$ is H, or $R_{17}$ and $R_6$ together with the two carbon atoms to which they are attached and the carbon atom connecting said two carbon atoms, form a 5- to 12-membered saturated heterocycloalkyl ring having 1 to 2 heteroatoms; or when X is a bond, $R_4$ and $R_6$ together with the two carbon atoms to which they are attached and the carbon atom connecting said two carbon atoms, form a 5- to 12-membered saturated heterocycloalkyl ring having 1 to 2 heteroatoms; and provided that for a compound of Formula (I)

(a) X is $CH_2$, $R_6$ is methyl and $R_8$ is H, $C_1$-$C_3$ alkyl, $C_2$-$C_3$ alkenyl, cyclopropyl, $CH_2CH_2OH$, COOH, $COOCH_3$, $CH_2COOH$, $CH_2COOCH_3$, or 4-methoxyphenyl, then at least one of $R_4$, $R_5$, $R_7$, $R_{10}$, $R_{11}$, $R_{12}$, or $R_{15}$ is not H;

(b) when X is $CH_2$, $R_6$ is $CH_2OH$ and $R_8$ is H, methyl or ethyl, then at least one of $R_4$, $R_5$, $R_7$, $R_{10}$, $R_{11}$, $R_{12}$, or $R_{15}$ is not H;

(c) when X is $CH_2$ and $R_6$ is $CH_2OCH_3$, then at least one of $R_4$, $R_5$, $R_7$, $R_8$, $R_{10}$, $R_{11}$, $R_{12}$, or $R_{15}$ is not H;

(d) when X is a bond, $R_6$ is methyl, and $R_8$ is H or methyl then at least one of $R_4$, $R_5$, $R_7$, $R_8$, $R_{10}$, $R_{11}$, $R_{12}$, or $R_{15}$ is not H;

(e) when X is O, $R_5$ is H or methyl, $R_6$ is methyl, and $R_8$ is H or methyl then at least one of $R_4$, $R_7$, $R_8$, $R_{10}$, $R_{11}$, $R_{12}$, or $R_{15}$ is not H;

(f) when X is $CH_2$, $R_6$ is methyl, $R_8$ is H or methyl, and $R_7$ is C(=NH)$NH_2$, then at least one of $R_4$, $R_5$, $R_8$, $R_{10}$, $R_{11}$, $R_{12}$, or $R_{15}$ is not H; or (g) when X is $CH_2$, $R_6$ is methyl, and $R_8$ is H, then at least one of $R_4$, $R_5$, $R_7$, $R_8$, $R_{10}$, $R_{11}$, $R_{12}$, or $R_{15}$ is not H.

In some embodiments, the present invention relates to a compound of Formula (Ib):

carbon atom connecting said two carbon atoms, form a 5- to 12-membered saturated heterocycloalkyl ring having 1 to 2 heteroatoms;

$R_5$ is H, $CH_2OH$ or $CH_2OC_1$-$C_6$ alkyl, or when X is O or $CHR_{17}$, $R_4$ and $R_5$ together with the two atoms to which they are attached and the atom connecting said two atoms form a 5- to 8-membered heterocycloalkyl ring having 1 to 2 heteroatoms;

$R_6$ is $C_1$-$C_3$ alkyl optionally substituted with one or more substituents independently selected from the group consisting of halo, OH, azido, amino, $C_1$-$C_6$ alkoxyl, $C_1$-$C_6$ alkylthio, $C_2$-$C_3$ alkenyl, $OCOR_a$, $CH_2OCOR_a$, and —OP(O)$(OR_a)_2$, in which $R_a$ is $C_1$-$C_6$ alkyl, amino, or phenyl, and $R_a$ is optionally substituted with COOH, $COOC_1$-$C_6$ alkyl, $OCOC_1$-$C_6$ alkyl, phenyl, or $C_7$-$C_{12}$ arylalkyl; or $R_6$ and $R_7$ together with the two atoms to which they are attached, form a 5- to 12-membered heterocycloalkyl ring having 0 to 1 additional heteroatom optionally substituted with an oxo group; or $R_6$ and $R_{17}$ together with the two carbon atoms to which they are attached and the carbon atom connecting said two carbon atoms, form a 5- to 12-membered saturated heterocycloalkyl ring having 1 to 2 heteroatoms; or when X is a bond, $R_4$ and $R_6$ together with the two carbon atoms to which they are attached and the carbon atom connecting said two carbon atoms, form a 5- to 12-membered saturated heterocycloalkyl ring having 1 to 2 heteroatoms;

$R_7$ is H, C(=NH)$NH_2$, or $COR_b$ in which $R_b$ is $C_1$-$C_6$ alkyl optionally substituted with $C_1$-$C_6$ alkoxyl or amino; or $R_6$ and $R_7$ together with the two atoms to which they are attached, form a 5- to 12-membered heterocycloalkyl ring having 0 to 1 additional heteroatom optionally substituted with an oxo group;

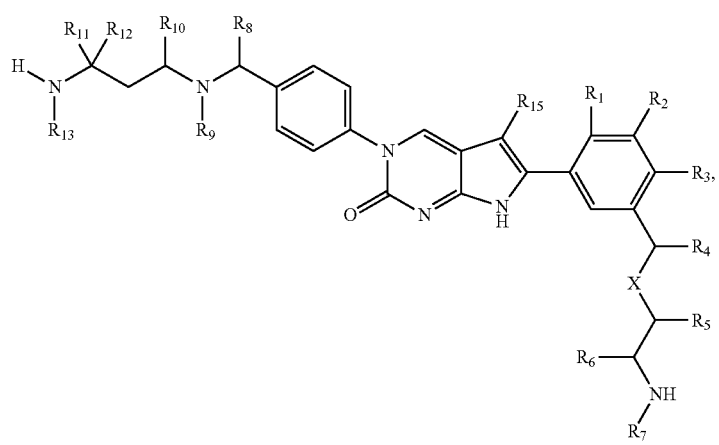

(Ib)

or a tautomer thereof, or a pharmaceutically acceptable salt, ester, or prodrug of said compound or tautomer, wherein $R_1$ is H or F, wherein when $R_1$ is H, then $R_2$ is $CF_3$, $OCF_3$, $SCF_3$, $SOCF_3$ or halo and $R_3$ is H; and when $R_1$ is F, then (i) $R_2$ is Cl or $OCF_3$ and $R_3$ is H; or (ii) $R_2$ is H and $R_3$ is $C_1$-$C_6$ alkyl; or (iii) $R_2$ is $C_1$-$C_6$ alkyl optionally substituted with one or more halo and $R_3$ is halo;

$R_4$ is H, OH, $NH_2$, or $C_1$-$C_6$ alkoxyl, or when X is O or $CHR_{17}$, $R_4$ and $R_5$ together with the two atoms to which they are attached and the atom connecting said two atoms form a 5- to 8-membered heterocycloalkyl ring having 1 to 2 heteroatoms; or when X is a bond, $R_4$ and $R_6$ together with the two carbon atoms to which they are attached and the each of $R_8$, $R_{10}$, and $R_{11}$, independently is $-Q_1$-$T_1$, in which $Q_1$ is a bond or $C_1$-$C_3$ alkyl linker optionally substituted with one or more halo or hydroxyl, and $T_1$ is H, halo, OH, COOH, cyano, azido, $C_1$-$C_3$ alkyl, $C_2$-$C_6$ alkenyl, $C_2$-$C_6$ alkynyl, $C_1$-$C_6$ alkoxyl, $C_2$-$C_6$ haloalkenyl, $C_1$-$C_6$ alkylthio, $COOC_1$-$C_6$ alkyl, —NHC(O)$CH_2NH_2$, NHS(O) $C_1$-$C_3$ alkyl, $SO_2C_1$-$C_6$ alkyl, or $R_c$, in which $R_c$ is amino, $C_3$-$C_8$ cycloalkyl, $C_6$-$C_{10}$ aryl, 4 to 12-membered heterocycloalkyl, 5- or 6-membered heteroaryl, —O-heteroaryl, —NH-heteroaryl, —S-heteroaryl, or C(O)$NR_dR_e$, each of $R_d$ and $R_e$ independently being H or $C_1$-$C_6$ alkyl, or $R_d$ and $R_e$ together with the nitrogen atom to which they are attached forming a 5- to 12-membered heterocycloalkyl ring having 0 to 2 additional heteroatoms; and $R_c$ is optionally substituted with -Q$_2$-T$_2$, in which Q$_2$ is a bond or C$_1$-C$_3$ alkyl and T$_2$ is H, halo, C$_1$-C$_3$ alkyl, amino, 5- or 6-membered heteroaryl or C$_6$-C$_{10}$ aryl wherein the aryl and heteroaryl are optionally substituted with C$_1$-C$_6$ alkoxyl or C$_1$-C$_4$ aminoalkyl; or R$_8$ and R$_{10}$, together with the two carbon atoms to which they are attached and the Z atom connecting said two carbon atoms, form a 5- to 12-membered heterocycloalkyl ring having 0 to 2 additional heteroatoms optionally substituted with one more substituents independently selected from C$_1$-C$_6$ alkyl or —C(=N)NH$_2$;

R$_{12}$ is H or C$_1$-C$_6$ alkyl, or R$_{12}$ and R$_{11}$ together with the carbon atom to which they are attached form a 4- to 12-membered saturated heterocycloalkyl ring having 1 to 2 heteroatoms optionally substituted with C(=NH)NH$_2$; or R$_{12}$ and R$_{10}$ together with the two carbon atoms to which they are attached and the atoms, if present, connecting said two carbon atoms form a C$_3$-C$_8$ cycloalkyl ring;

each of R$_9$ and R$_{13}$ independently is H, C$_1$-C$_3$ alkyl, C$_2$-C$_4$ alkenyl or —C(O)H, or R$_9$ and R$_{13}$ together with the two nitrogen atoms to which they are attached and the carbon atoms connecting said two nitrogen atoms, form a 7- to 12-membered saturated heterocycloalkyl ring having 0 to 1 additional heteroatom, or R$_9$ and R$_8$ together with the two atoms to which they are attached form a 5- to 12-membered heterocycloalkyl ring having 0 to 1 additional heteroatom optionally substituted with an oxo group;

R$_{11}$ and R$_{13}$ together with the atoms to which they are attached form a 5- to 8-membered heterocycloalkyl ring having 0 to 2 additional heteroatoms optionally substituted with oxo;

R$_{15}$ is H or halo;

X is a bond, O, or CHR$_{17}$, in which R$_{17}$ is H, or R$_{17}$ and R$_6$ together with the two carbon atoms to which they are attached and the carbon atom connecting said two carbon atoms, form a 5- to 12-membered saturated heterocycloalkyl ring having 1 to 2 heteroatoms; or when X is a bond, R$_4$ and R$_6$ together with the two carbon atoms to which they are attached and the carbon atom connecting said two carbon atoms, form a 5- to 12-membered saturated heterocycloalkyl ring having 1 to 2 heteroatoms;

In some embodiments, the present invention relates to a compound having any of Formulae (Ic)-(If):

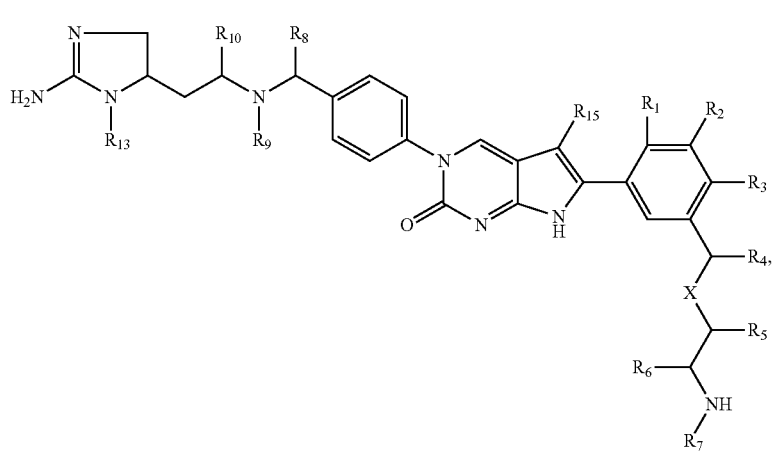

(Ic)

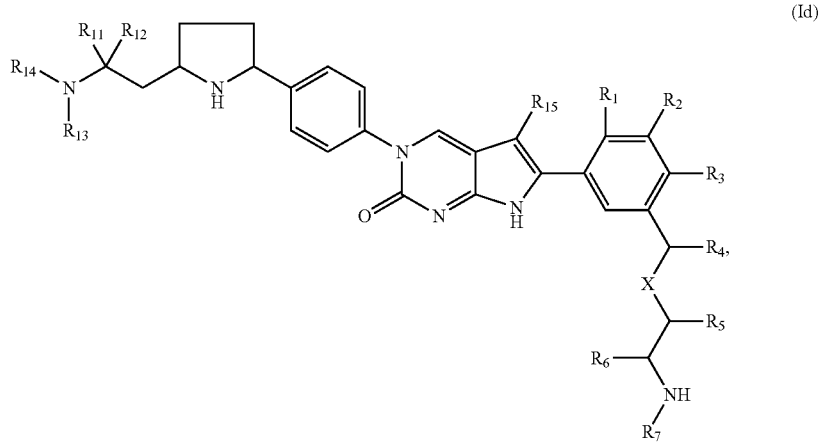

(Id)

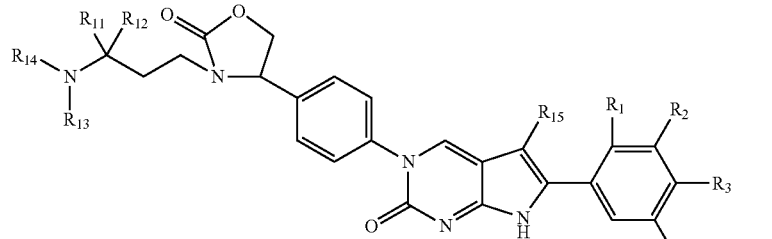

(Ie)

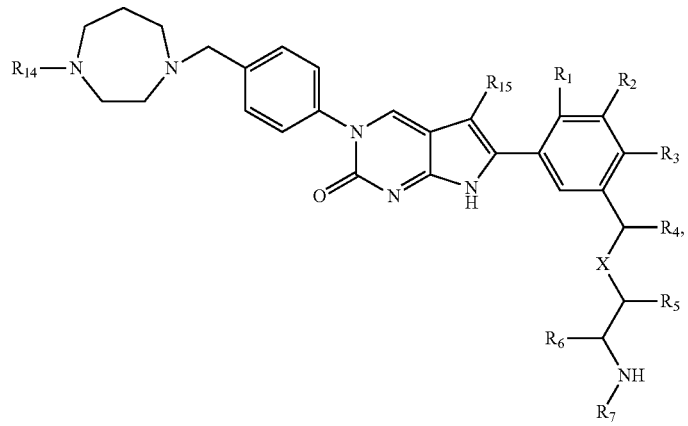

(If)

or a tautomer thereof, or a pharmaceutically acceptable salt, ester, or prodrug of said compound or tautomer, wherein X and $R_1$ through $R_{15}$ are as defined herein for Formula (I).

In some embodiments, the present invention relates to a compound having Formula (Ig):

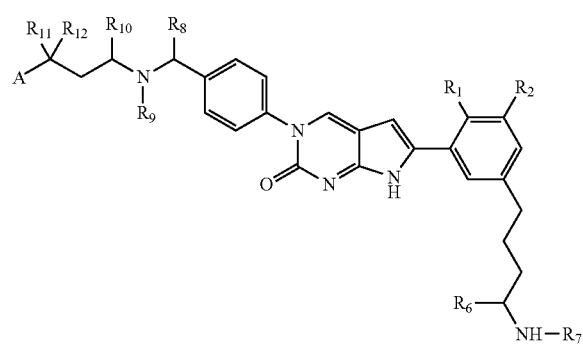

(Ig)

or a tautomer thereof, or a pharmaceutically acceptable salt, ester, or prodrug of said compound or tautomer,
wherein:
$R_1$ is F;
$R_2$ is Cl or $OCF_3$;

$R_6$ is $C_1$-$C_3$ alkyl, optionally substituted with one or more substituents independently selected from the group consisting of halo, OH, azido, amino, $C_1$-$C_6$ alkoxyl, $C_1$-$C_6$ alkylthio, $C_2$-$C_3$ alkenyl, $OCOR_a$, $CH_2OCOR_a$, and $-OP(O)(OR_a)_2$, in which $R_a$ is $C_1$-$C_6$ alkyl, amino, or phenyl, and $R_a$ is optionally substituted with COOH, $COOC_1$-$C_6$ alkyl, $OCOC_1$-$C_6$ alkyl, or $C_7$-$C_{12}$ arylalkyl; or $R_6$ and $R_7$ together with the two atoms to which they are attached, form a 5- to 12-membered heterocycloalkyl ring having 0 to 1 additional heteroatom optionally substituted with an oxo group;

$R_7$ is H, C(=NH)$NH_2$, or $COR_b$ in which $R_b$ is $C_1$-$C_6$ alkyl optionally substituted with $C_1$-$C_6$ alkoxyl or amino; or $R_6$ and $R_7$ together with the two atoms to which they are attached, form a 5- to 12-membered heterocycloalkyl ring having 0 to 1 additional heteroatom optionally substituted with an oxo group;

$R_8$ is -$Q_1$-$T_1$, in which $Q_1$ is a bond or $C_1$-$C_3$ alkyl linker optionally substituted with one or more halo or hydroxyl, and $T_1$ is H, halo, OH, COOH, cyano, azido, $C_1$-$C_3$ alkyl, $C_2$-$C_6$ alkenyl, $C_2$-$C_6$ alkynyl, $C_1$-$C_6$ alkoxyl, $C_2$-$C_6$ haloalkenyl, $C_1$-$C_6$ alkylthio, $COOC_1$-$C_6$ alkyl, —NHC(O)$CH_2NH_2$, NHS(O)$C_1$-$C_3$ alkyl, $SO_2C_1$-$C_6$ alkyl, or $R_c$, in which $R_c$ is amino, $C_3$-$C_8$ cycloalkyl, $C_6$-$C_{10}$ aryl, 4 to 12-membered heterocycloalkyl, 5- or 6-membered heteroaryl, —O-heteroaryl, —NH-heteroaryl, —S— heteroaryl, or C(O)$NR_dR_e$, each of $R_d$ and $R_e$ independently being H or $C_1$-$C_6$ alkyl, or $R_d$ and $R_e$ together with the nitrogen atom to which they are attached forming a 5- to 12-membered heterocycloalkyl ring having 0 to 2 additional heteroatoms; and $R_c$ is optionally substituted with -$Q_2$-$T_2$, in which $Q_2$ is a bond or $C_1$-$C_3$ alkyl and $T_2$ is H, halo, $C_1$-$C_3$ alkyl, amino, 5- or 6-membered heteroaryl or $C_6$-$C_{10}$ aryl wherein the aryl and heteroaryl are optionally substituted with $C_1$-$C_6$ alkoxyl or $C_1$-$C_4$ aminoalkyl;

$R_9$ is H, $C_1$-$C_3$ alkyl, $C_2$-$C_4$ alkenyl or —C(O)H;

$R_{10}$ is $C_1$-$C_6$ alkyl, $C_2$-$C_6$ alkenyl, $C_2$-$C_6$ alkynyl —C(=O)OH, —C(=O)O$C_1$-$C_3$ alkyl, -or C(=O)NH$_2$, wherein the alkyl and alkenyl are optionally substituted with one or more substituents independently selected from $C_1$-$C_3$ alkoxy, OH, amino, —NHS(O)$_2$$C_1$-$C_6$ alkyl, —NH-heteroaryl, —O— heteroaryl, and 5 to 6-membered heteroaryl, wherein the heteroaryl is optionally substituted with one or more substituents independently selected from $C_1$-$C_3$ alkyl, amino, and CH$_2$NH$_2$, $R_{11}$ is H, $C_1$-$C_3$ alkyl or $C_2$-$C_3$ alkenyl wherein the alkyl and alkenyl are optionally substituted with one or more substituents independently selected from $C_1$-$C_3$ alkoxy, OH, amino, CN, halo, —C(=O)NH$_2$, —NHC(=O)CH$_2$NH$_2$, 4- to 7-membered heterocycloalkyl, 5 to 6-membered heteroaryl, and S-heteroaryl, wherein the heteroaryl is optionally substituted with one or more substituents independently selected from $C_1$-$C_3$ alkyl, amino, and —CH$_2$NH$_2$;

$R_{12}$ is H or $C_1$-$C_6$ alkyl;

$R_{13}$ independently is H, $C_1$-$C_3$ alkyl, $C_2$-$C_4$ alkenyl or —C(O)H; or $R_{13}$ and $R_{14}$ together with the nitrogen atom to which they are attached form a 5- or 6-membered heteroaryl having 1 to 3 additional heteroatoms optionally substituted with oxo or nitro; $R_{13}$ and $R_{14}$ together with the nitrogen atom to which they are attached form a 5- or 6-membered heterocycloalkyl having 1 to 3 additional heteroatoms optionally substituted with oxo;

$R_{14}$ is H, C(O)$C_1$-$C_3$ alkyl, C(O)NH$_2$, C(CH=NO$_2$)NHCH$_3$, C(=NH)H, C(=NH)$C_1$-$C_3$ alkyl, 5- or 6-membered heteroaryl having 1 to 3 heteroatoms, 5 or 6-membered heterocycloalkyl having 1 to 3 heteroatoms, $C_1$-$C_6$ alkyl optionally substituted with one or more substituents independently selected from 5- or 6-membered heteroaryl having 1 to 3 heteroatoms, $C_3$-$C_8$ cycloalkyl, and 5 or 6-membered heterocycloalkyl having 1 to 3 heteroatoms, or C(=NR$_{16}$)NH$_2$, in which R$_{16}$ is H, $C_1$-$C_3$ alkyl, $C_2$-$C_4$ alkenyl, $C_3$-$C_8$ cycloalkyl, or 4- to 12-membered saturated heterocycloalkyl ring having 1 to 2 heteroatoms; or $R_{14}$ and $R_{13}$ together with the nitrogen atom to which they are attached form a 5- or 6-membered heteroaryl having 1 to 3 additional heteroatoms optionally substituted with oxo; or $R_{14}$ and $R_{13}$ together with the nitrogen atom to which they are attached form a 5- or 6-membered heterocycloalkyl having 1 to 3 additional heteroatoms optionally substituted with oxo;

A is C(O)NH$_2$, NR$_{13}$R$_{14}$, C(O)NH$C_1$-$C_3$ alkyl, C(O)OH, OH, CN, $C_3$-$C_8$ cycloalkyl, —OP(O)(OR$_b$)$_2$, in which R$_b$ is $C_1$-$C_6$ alkyl, amino, or phenyl, 5 or 6-membered heterocycloalkyl having 1 to 3 heteroatoms optionally substituted with oxo, or 5- or 6-membered heteroaryl having 1 to 4 heteroatoms optionally substituted with $C_1$-$C_4$ alkyl, $C_1$-$C_4$ alkyl, $C_1$-$C_4$ alkylenyl-aryl, NO$_2$, or amino, wherein the alkyl, alkylenyl, and aryl are optionally substituted with one or more substituents independently selected from $C_1$-$C_3$ alkyl, $C_2$-$C_4$ alkenyl, $C_1$-$C_3$ alkoxy, or halo;

In some embodiments, the present invention relates to a compound having any of Formulae (Ih)-(Ii) and (Ik)-(Iw):

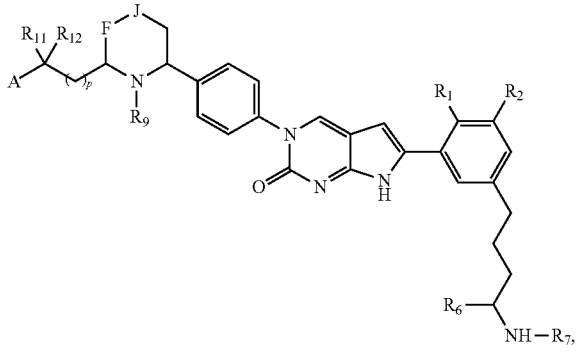

(Ih)

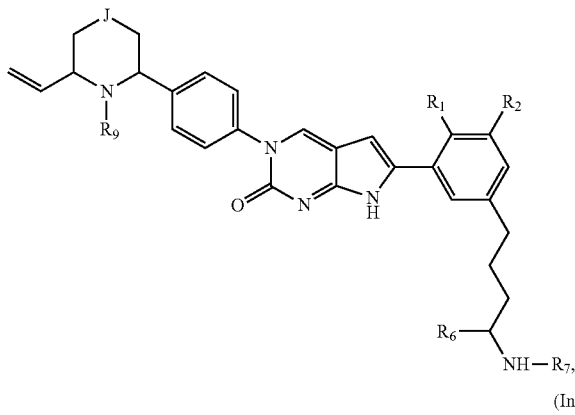

(Ii)

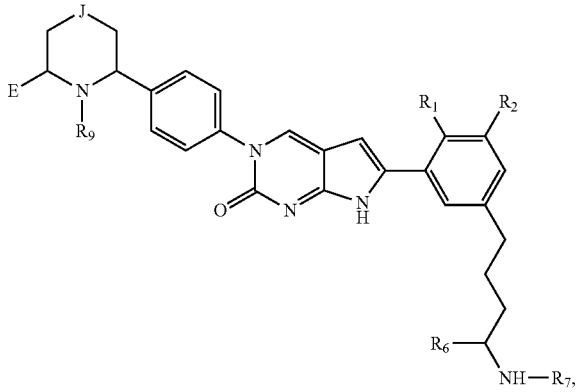

(In)

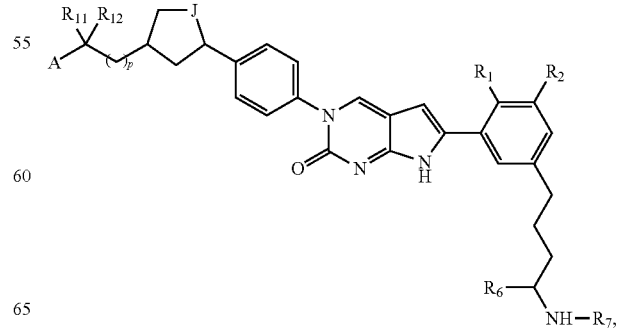

(Ik)

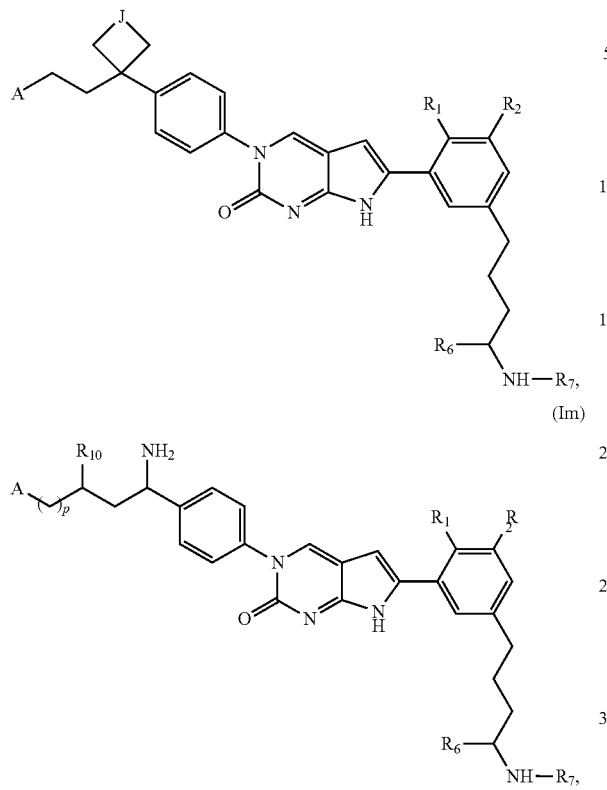
(Il)
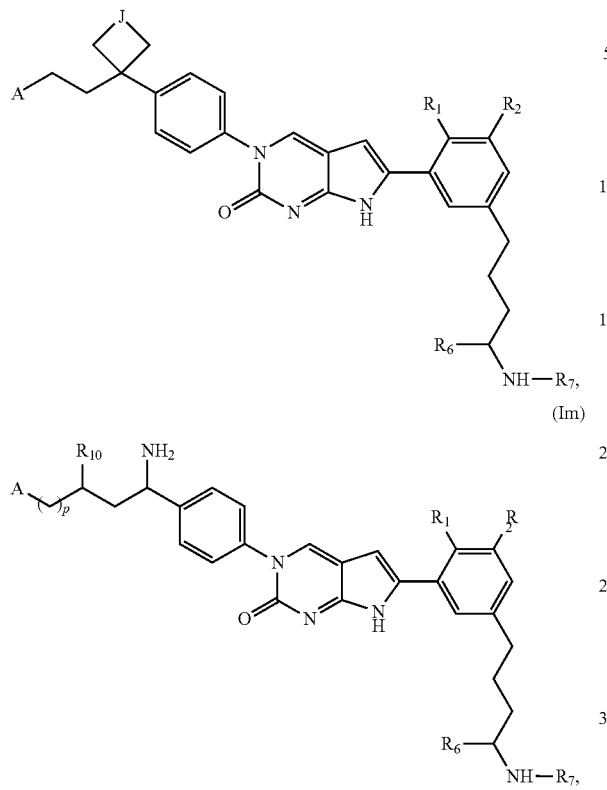
(Im)
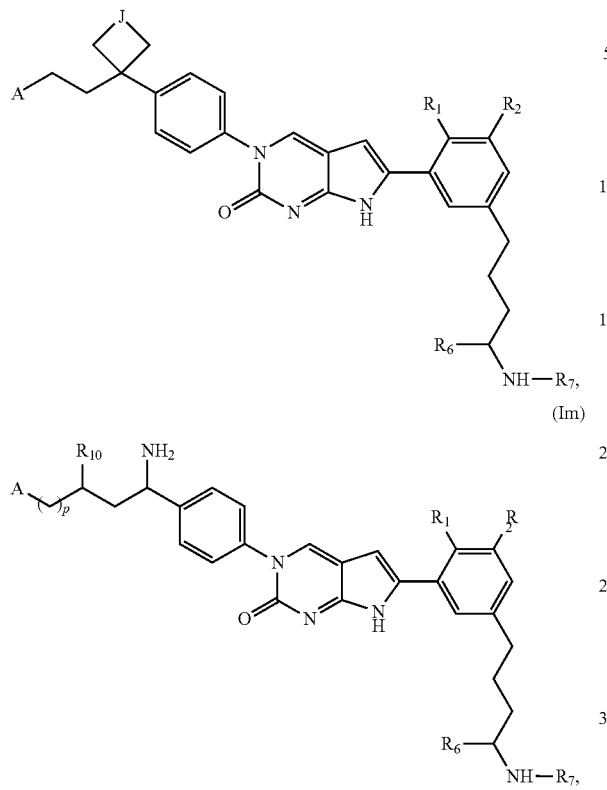
(In)
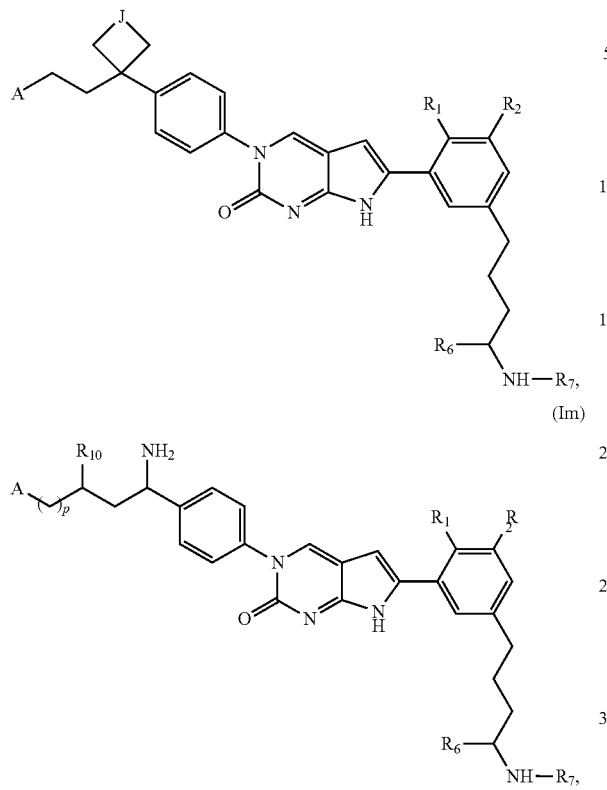
(Io)
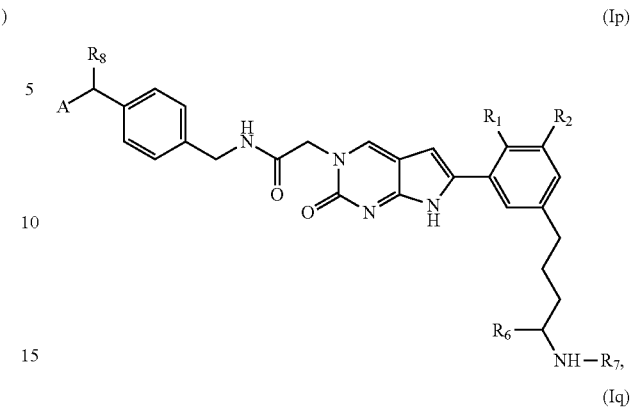
(Ip)
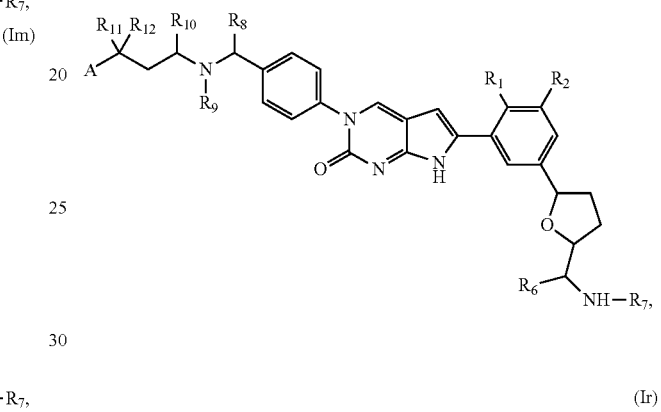
(Iq)
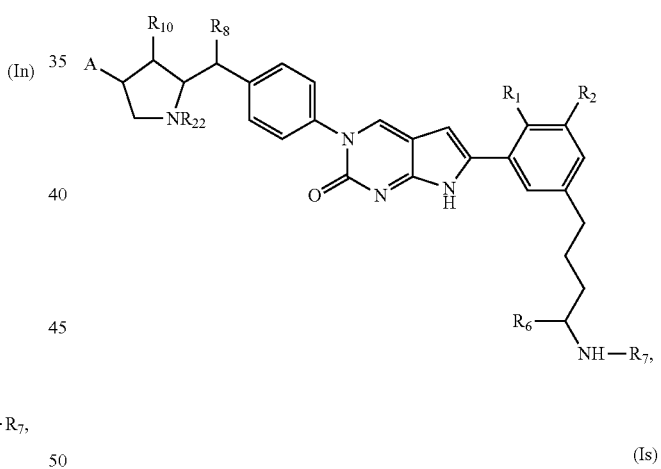
(Ir)
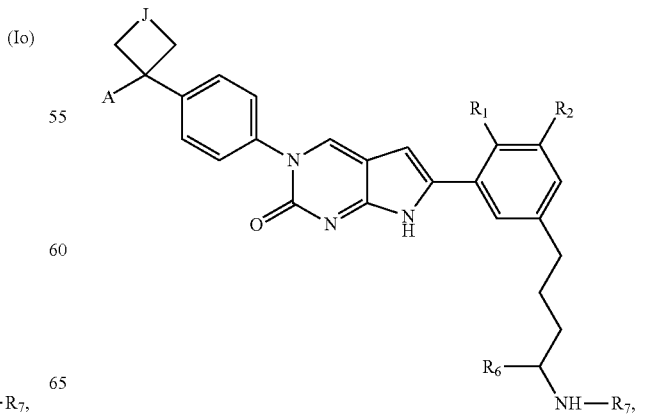
(Is)

-continued

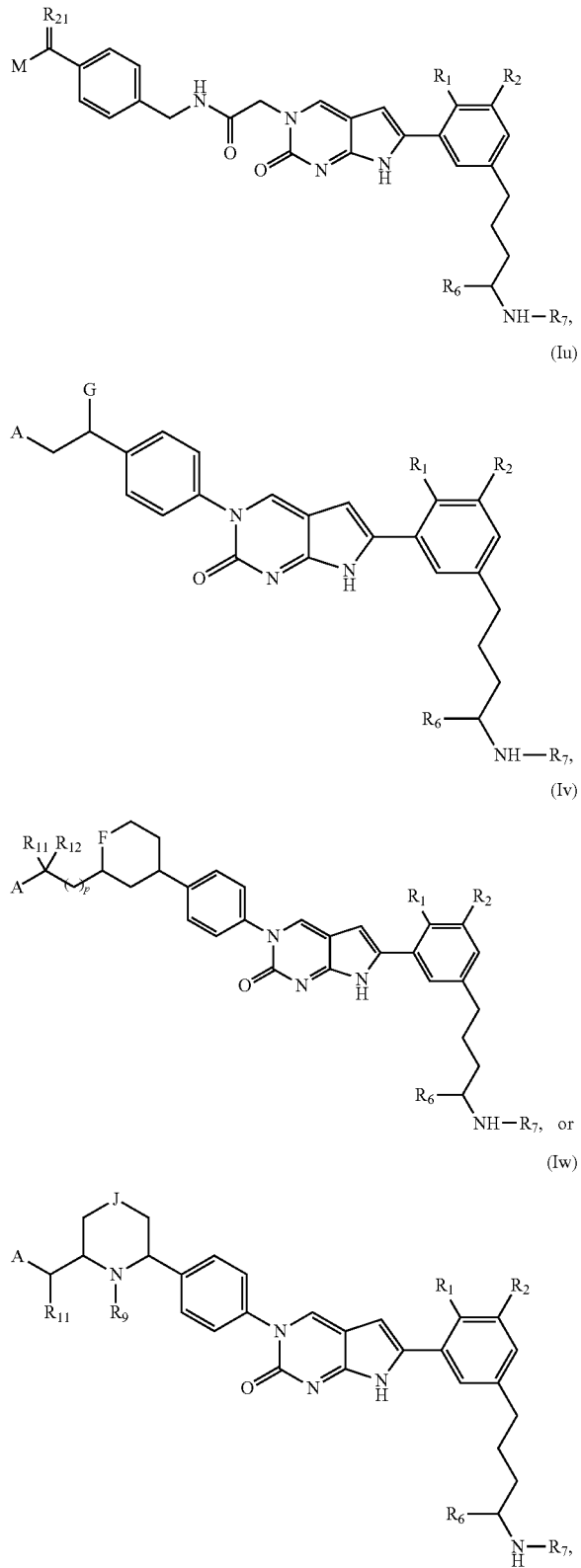

or a tautomer thereof, or a pharmaceutically acceptable salt, ester, or prodrug of said compound or tautomer, wherein:
J is $NR_{20}$, O or $CH_2$;
F is O or $CH_2$;
$R_1$ is H or F;
$R_2$ is $CF_3$, Cl or $OCF_3$;
$R_6$ is $C_1$-$C_3$ alkyl, optionally substituted with one or more substituents independently selected from the group consisting of halo, OH, azido, amino, $C_1$-$C_6$ alkoxyl, $C_1$-$C_6$ alkylthio, $C_2$-$C_3$ alkenyl, $OCOR_a$, $CH_2OCOR_a$, and —OP(O)($OR_a$)$_2$, in which $R_a$ is $C_1$-$C_6$ alkyl, amino, or phenyl, and $R_a$ is optionally substituted with COOH, $COOC_1$-$C_6$ alkyl, $OCOC_1$-$C_6$ alkyl, or $C_7$-$C_{12}$ arylalkyl; or $R_6$ and $R_7$ together with the two atoms to which they are attached, form a 5- to 12-membered heterocycloalkyl ring having 0 to 1 additional heteroatom optionally substituted with an oxo group;
$R_7$ is H, C(=NH)$NH_2$, or $COR_b$ in which $R_b$ is $C_1$-$C_6$ alkyl optionally substituted with amino, $C_1$-$C_6$ alkoxyl, or amino; or $R_6$ and $R_7$ together with the two atoms to which they are attached, form a 5- to 12-membered heterocycloalkyl ring having 0 to 1 additional heteroatom optionally substituted with an oxo group;
$R_8$ is -$Q_1$-$T_1$, in which $Q_1$ is a bond or $C_1$-$C_3$ alkyl linker optionally substituted with one or more halo or hydroxyl, and $T_1$ is H, halo, OH, COOH, cyano, azido, $C_1$-$C_3$ alkyl, $C_2$-$C_6$ alkenyl, $C_2$-$C_6$ alkynyl, $C_1$-$C_6$ alkoxyl, $C_2$-$C_6$ haloalkenyl, $C_1$-$C_6$ alkylthio, $COOC_1$-$C_6$ alkyl, —NHC(O)$CH_2NH_2$, NHS(O)$C_1$-$C_3$ alkyl, $SO_2C_1$-$C_6$ alkyl, or $R_c$, in which $R_c$ is amino, $C_3$-$C_8$ cycloalkyl, $C_6$-$C_{10}$ aryl, 4 to 12-membered heterocycloalkyl, 5- or 6-membered heteroaryl, —O-heteroaryl, —NH-heteroaryl, —S— heteroaryl, or C(O)$NR_dR_e$, each of $R_d$ and $R_e$ independently being H or $C_1$-$C_6$ alkyl, or $R_d$ and $R_e$ together with the nitrogen atom to which they are attached forming a 5- to 12-membered heterocycloalkyl ring having 0 to 2 additional heteroatoms; and $R_c$ is optionally substituted with -$Q_2$-$T_2$, in which $Q_2$ is a bond or $C_1$-$C_3$ alkyl and $T_2$ is H, halo, $C_1$-$C_3$ alkyl, amino, 5- or 6-membered heteroaryl or $C_6$-$C_{10}$ aryl wherein the aryl and heteroaryl are optionally substituted with $C_1$-$C_6$ alkoxyl or $C_1$-$C_4$ aminoalkyl;
$R_9$ is H, $C_1$-$C_3$ alkyl, $C_2$-$C_4$ alkenyl or —C(O)H; or $R_9$ and A form a 5- to 6-membered heterocycloalkyl ring with 0 to 1 additional heteroatom optionally substituted with one or more $C_1$-$C_3$ alkyl;
$R_{10}$ is -$Q_1$-$T_1$, in which $Q_1$ is a bond or $C_1$-$C_3$ alkyl linker optionally substituted with one or more halo or hydroxyl, and $T_1$ is H, halo, OH, COOH, cyano, azido, $C_1$-$C_3$ alkyl, $C_2$-$C_6$ alkenyl, $C_2$-$C_6$ alkynyl, $C_1$-$C_6$ alkoxyl, $C_2$-$C_6$ haloalkenyl, $C_1$-$C_6$ alkylthio, $COOC_1$-$C_6$ alkyl, —NHC(O)$CH_2NH_2$, NHS(O)$C_1$-$C_3$ alkyl, $SO_2C_1$-$C_6$ alkyl, or $R_c$, in which $R_c$ is amino, $C_3$-$C_8$ cycloalkyl, $C_6$-$C_{10}$ aryl, 4 to 12-membered heterocycloalkyl, 5- or 6-membered heteroaryl, —O-heteroaryl, —NH-heteroaryl, —S— heteroaryl, or C(O)$NR_dR_e$, each of $R_d$ and $R_e$ independently being H or $C_1$-$C_6$ alkyl, or $R_d$ and $R_e$ together with the nitrogen atom to which they are attached forming a 5- to 12-membered heterocycloalkyl ring having 0 to 2 additional heteroatoms; and $R_c$ is optionally substituted with -$Q_2$-$T_2$, in which $Q_2$ is a bond or $C_1$-$C_3$ alkyl and $T_2$ is H, halo, $C_1$-$C_3$ alkyl, amino, 5- or 6-membered heteroaryl or $C_6$-$C_{10}$ aryl wherein the aryl and heteroaryl are optionally substituted with $C_1$-$C_6$ alkoxyl or $C_1$-$C_4$ aminoalkyl;
$R_{11}$ is H, $C_1$-$C_3$ alkyl or $C_2$-$C_3$ alkenyl, wherein the alkyl and alkenyl are optionally substituted with one or more substituents independently selected from $C_1$-$C_3$ alkoxy, OH, amino, CN, halo, —C(=O)NH$_2$, —NHC(=O)CH$_2$NH$_2$, 4- to 7-membered heterocycloalkyl, 5 to 6-membered heteroaryl, and S-heteroaryl, wherein the heteroaryl is optionally substituted with one or more substituents independently selected from C$_1$-C$_3$ alkyl, amino, and —CH$_2$NH$_2$;

R$_{12}$ is H or C$_1$-C$_6$ alkyl;

R$_{13}$ independently is H, C$_1$-C$_3$ alkyl, C$_2$-C$_4$ alkenyl or —C(O)H; or R$_{13}$ and R$_{14}$ together with the nitrogen atom to which they are attached form a 5- or 6-membered heteroaryl having 1 to 3 additional heteroatoms optionally substituted with oxo; or R$_{14}$ and R$_{13}$ together with the nitrogen atom to which they are attached form a 5- or 6-membered heterocycloalkyl having 1 to 3 additional heteroatoms optionally substituted with oxo;

R$_{14}$ is H, C(O)C$_1$-C$_3$ alkyl, C(O)NH$_2$, C(CH=NO$_2$)NHCH$_3$, C(=NH)H, C(=NH)C$_1$-C$_3$ alkyl, 5- or 6-membered heteroaryl having 1 to 3 heteroatoms, 5 or 6-membered heterocycloalkyl having 1 to 3 heteroatoms, C$_1$-C$_6$ alkyl optionally substituted with one or more substituents independently selected from 5- or 6-membered heteroaryl having 1 to 3 heteroatoms, C$_3$-C$_8$ cycloalkyl, and 5 or 6-membered heterocycloalkyl having 1 to 3 heteroatoms, or C(=NR$_{16}$)NH$_2$, in which R$_{16}$ is H, C$_1$-C$_3$ alkyl, C$_2$-C$_4$ alkenyl, C$_3$-C$_8$ cycloalkyl, or 4- to 12-membered saturated heterocycloalkyl ring having 1 to 2 heteroatoms; or R$_{14}$ and R$_{13}$ together with the nitrogen atom to which they are attached form a 5- or 6-membered heteroaryl having 1 to 3 additional heteroatoms optionally substituted with oxo; or R$_{14}$ and R$_{13}$ together with the nitrogen atom to which they are attached form a 5- or 6-membered heterocycloalkyl having 1 to 3 additional heteroatoms optionally substituted with oxo;

R$_{20}$ is H, C$_1$-C$_6$ alkyl, —C(=O) C$_1$-C$_4$ alkyl, or —C(=O)NH C$_1$-C$_4$ alkyl;

R$_{21}$ is NH or O;

R$_{22}$ is H or C$_1$-C$_6$ alkyl;

p is 0 or 1;

A is C(O)NH$_2$, NR$_{13}$R$_{14}$, C(O)NHC$_1$-C$_3$ alkyl, C(O)OH, OH, CN, C$_3$-C$_8$ cycloalkyl, —OP(O)(OR$_b$)$_2$, in which R$_b$ is C$_1$-C$_6$ alkyl, amino, or phenyl, 5 or 6-membered heterocycloalkyl having 1 to 3 heteroatoms optionally substituted with oxo, or 5- or 6-membered heteroaryl having 1 to 4 heteroatoms optionally substituted with C$_1$-C$_4$ alkyl, C$_1$-C$_4$ alkylenyl-aryl, NO$_2$, or amino, is selected from C$_1$-C$_3$ alkyl, C$_2$-C$_4$ alkenyl, C$_1$-C$_3$ alkoxy, or halo; or A is N, when R$_9$ and A form a 5- to 6-membered heterocycloalkyl ring with 0 to 1 additional heteroatom optionally substituted with one or more C$_1$-C$_3$ alkyl;

E is CH$_2$OH or 5- or 6-membered heteroaryl having 1 to 4 heteroatoms optionally substituted with C$_1$-C$_3$ alkyl, C$_1$-C$_4$ alkylenyl-aryl or amino, wherein the alkyl, alkylenyl, and aryl are optionally substituted with one or more substituents independently selected from C$_1$-C$_3$ alkyl, C$_2$-C$_4$ alkenyl, C$_1$-C$_3$ alkoxy, or halo;

M is —NH—C$_0$-C$_3$ alkylenyl-heteroaryl, NH$_2$, or —NH—C$_3$-C$_8$ cycloalkyl; and G is CH$_2$OH, OH or NH$_2$.

In some embodiments, the present invention relates to a compound having any of Formulae (Ix)-(Iz) and (IB)-(ID):

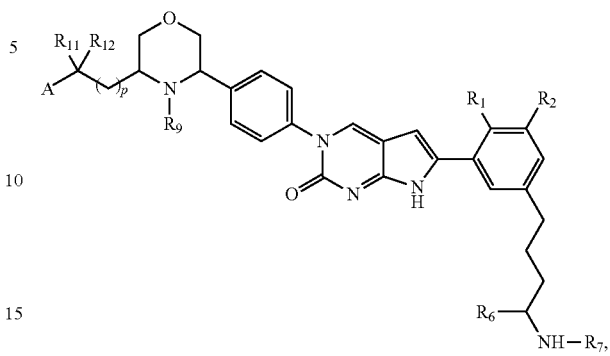

(Ix)

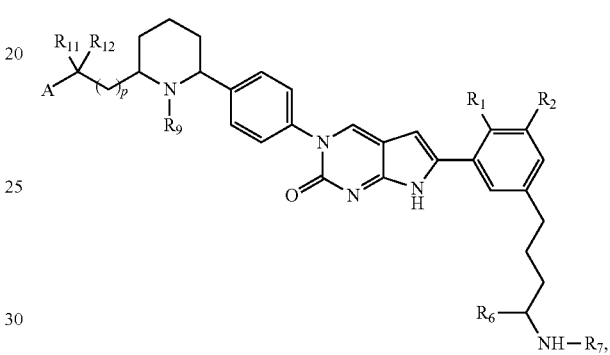

(Iy)

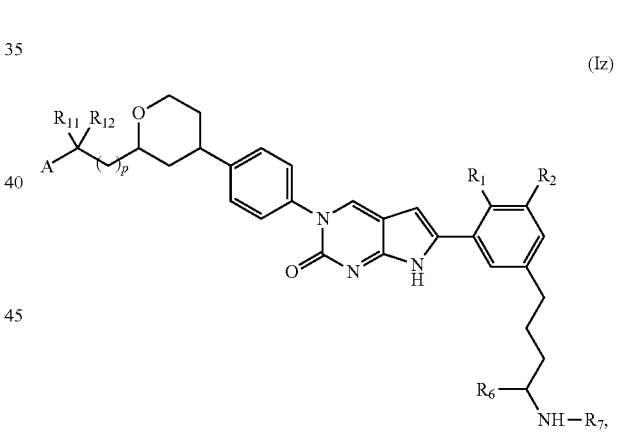

(Iz)

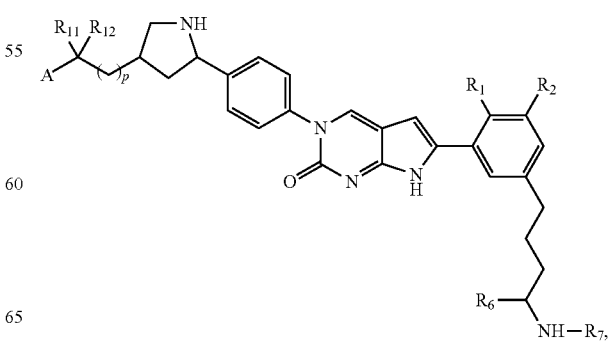

(IB)

-continued (IC)

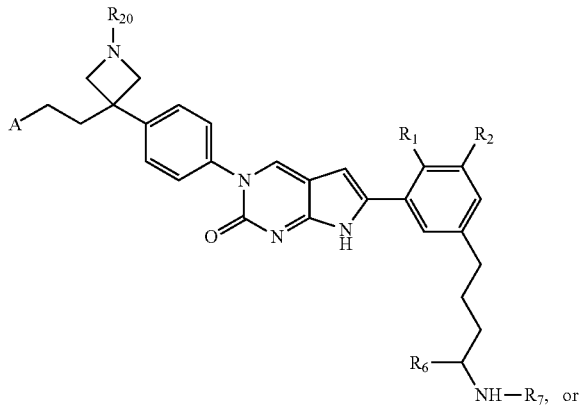

(ID)

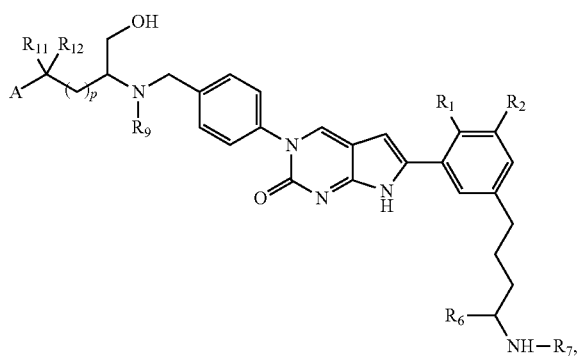

or a tautomer thereof, or a pharmaceutically acceptable salt, ester, or prodrug of said compound or tautomer, wherein $R_1$, $R_2$, $R_6$, $R_7$, $R_9$, $R_{11}$, $R_{12}$, p, and A are as defined herein for Formula (I) and $R_{20}$ is as defined for Formulae (Ih)-(Ii) and (Ik)-(Iw).

In some embodiments, the present invention relates to a compound having Formula (IE) or (IF):

(IE)

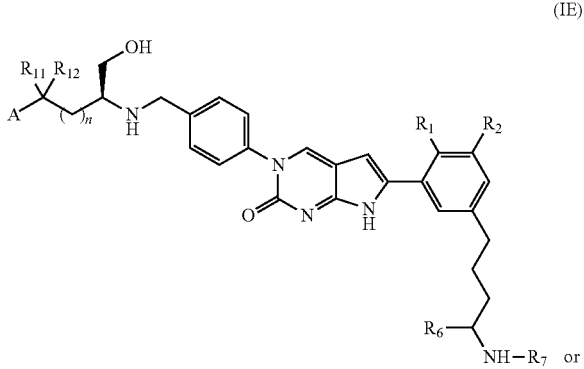

-continued (IF)

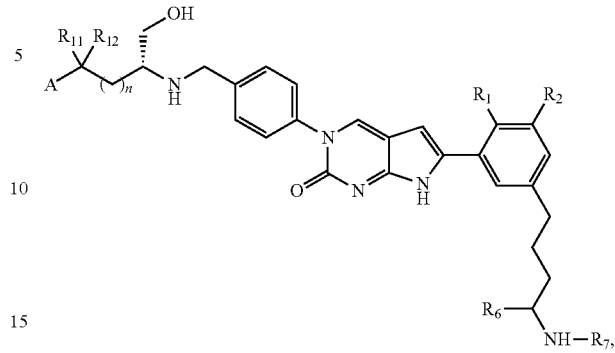

or a tautomer thereof, or a pharmaceutically acceptable salt, ester, or prodrug of said compound or tautomer, wherein $R_1$, $R_2$, $R_6$, $R_7$, $R_{11}$, $R_{12}$, and A are as defined herein for Formula (I).

In some embodiments, the present invention relates to a compound having the Formula (IG) or (IH):

(IG)

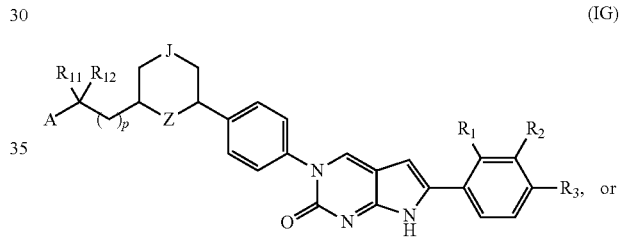

(IH)

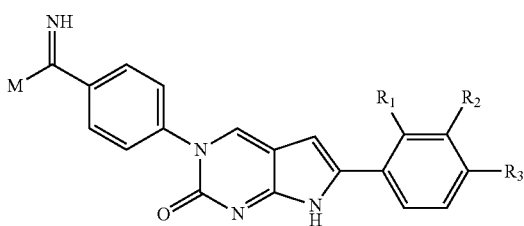

or a tautomer thereof, or a pharmaceutically acceptable salt, ester, or prodrug of said compound or tautomer, wherein:

$R_3$ is H or $S(O)_2$N-heterocycloalkyl optionally substituted with $C_1$-$C_6$ alkyl, C(O)OH, or C(O)O$C_1$-$C_3$alkyl, and $R_1$, $R_2$, $R_{11}$, $R_{12}$, p, Z, and A are as defined in Formula (I) and M and J are as defined herein above for Formulae (Ih)-(Ii) and (Ik)-(Iw).

In some embodiments, the present invention relates to a compound having the Formula (IJ) or (IK):

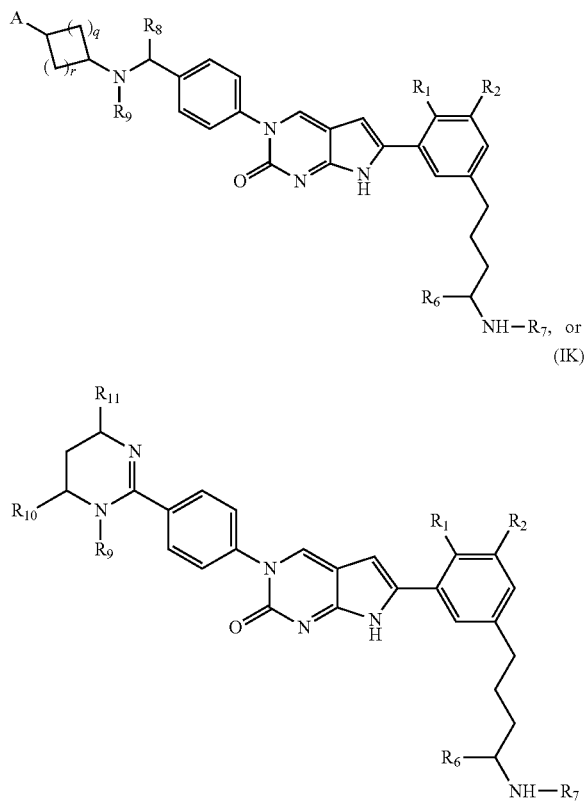

or a tautomer thereof, or a pharmaceutically acceptable salt, ester, or prodrug of said compound or tautomer, wherein:

each of $R_8$, $R_{10}$, and $R_{11}$, independently is $-Q_1-T_1$, in which $Q_1$ is a bond or $C_1-C_3$ alkyl linker optionally substituted with one or more halo or hydroxyl, and $T_1$ is H, halo, OH, COOH, cyano, azido, $C_1-C_3$ alkyl, $C_2-C_6$ alkenyl, $C_2-C_6$ alkynyl, $C_1-C_6$ alkoxyl, $C_2-C_6$ haloalkenyl, $C_1-C_6$ alkylthio, $COOC_1-C_6$ alkyl, $-NHC(O)CH_2NH_2$, $NHS(O) C_1-C_3$ alkyl, $SO_2C_1-C_6$ alkyl, or $R_c$, in which $R_c$ is amino, $C_3-C_8$ cycloalkyl, $C_6-C_{10}$ aryl, 4 to 12-membered heterocycloalkyl, 5- or 6-membered heteroaryl, —O-heteroaryl, —NH-heteroaryl, —S-heteroaryl, or $C(O)NR_dR_e$, each of $R_d$ and $R_e$ independently being H or $C_1-C_6$ alkyl, or $R_d$ and $R_e$ together with the nitrogen atom to which they are attached forming a 5- to 12-membered heterocycloalkyl ring having 0 to 2 additional heteroatoms; and $R_c$ is optionally substituted with $-Q_2-T_2$, in which $Q_2$ is a bond or $C_1-C_3$ alkyl and $T_2$ is H, halo, $C_1-C_3$ alkyl, amino, 5- or 6-membered heteroaryl or $C_6-C_{10}$ aryl wherein the aryl and heteroaryl are optionally substituted with $C_1-C_6$ alkoxyl or $C_1-C_4$ aminoalkyl;

$R_9$ is H, $C_1-C_3$ alkyl, $C_2-C_4$ alkenyl or —C(O)H;

each q and r is independently 1 or 2; and $R_1$, $R_2$, $R_6$, $R_7$, and A are as defined herein for Formula (I).

In some embodiments, the present invention relates to a compound having the Formula (IL) or (IM):

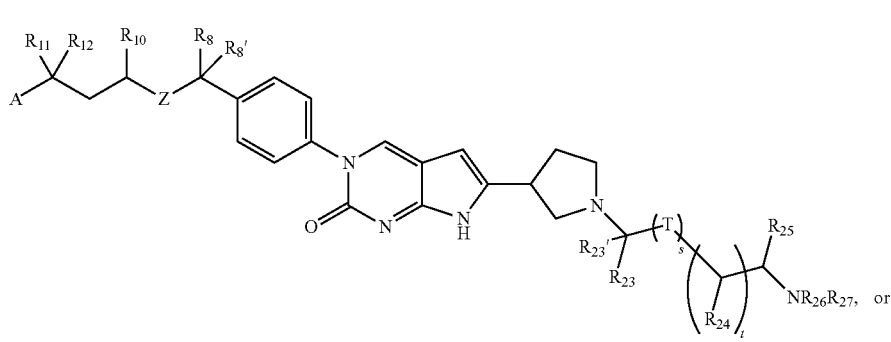

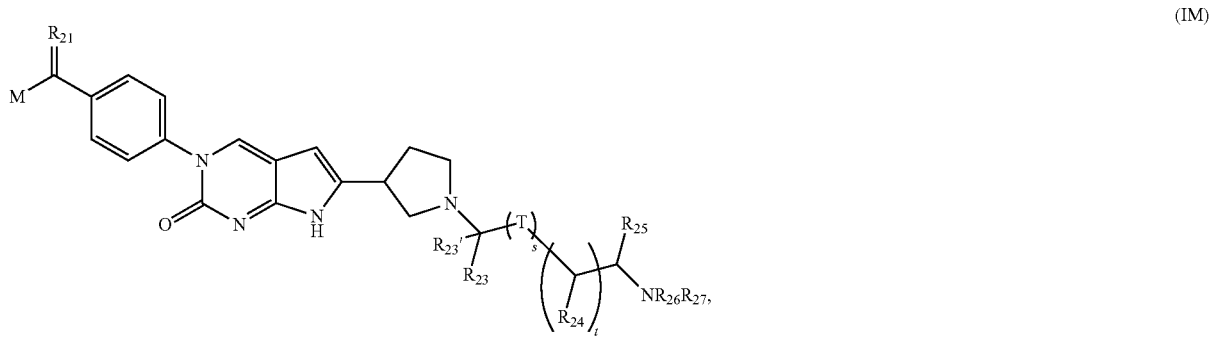

or a tautomer thereof, or a pharmaceutically acceptable salt, ester, or prodrug of said compound or tautomer, wherein:

each $R_{23}$ and $R_{23'}$ is independently H, $C_1$-$C_3$ alkyl, or $C_2$-$C_4$ alkenyl; or $R_{23}$ and $R_{23'}$ together form an oxo or imino;

each $R_{24}$ is independently H, $C_1$-$C_3$ alkyl, or $C_2$-$C_4$ alkenyl;

$R_{25}$ is H, $C_1$-$C_3$ alkyl, or $C_2$-$C_4$ alkenyl;

each $R_{27}$ and $R_{28}$ is independently H, $C_1$-$C_3$ alkyl, or $C(=NH)NH_2$;

T is $CH_2$ or O;

s is 0, 1, or 2;

t is 1 or 2; and $R_8$, $R_{8'}$, $R_{10}$, $R_{11}$, $R_{12}$, A, and Z are as defined herein for Formula (I) and $R_{21}$ and M are as defined herein above for Formulae (Ih)-(Ii) and (Ik)-(Iw).

In some embodiments, the present invention relates to a compound having the Formula (IN):

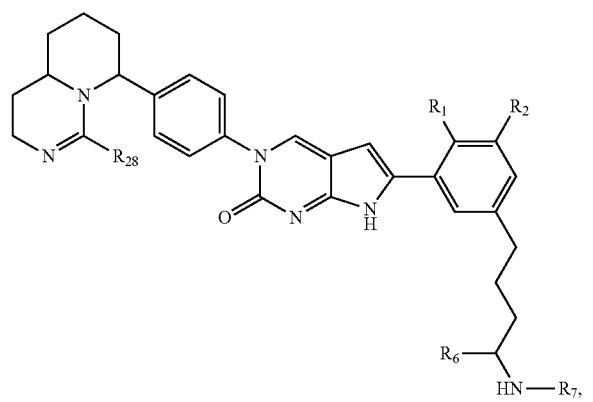

(IN)

or a tautomer thereof, or a pharmaceutically acceptable salt, ester, or prodrug of said compound or tautomer, wherein:

$R_{28}$ is H, $C_1$-$C_3$ alkyl optionally substituted with one or more halo or hydroxyl, $C_2$-$C_6$ alkenyl, $C_2$-$C_6$ alkynyl, or $C_1$-$C_6$ alkoxyl; and $R_1$, $R_2$, $R_6$, and $R_7$ are as defined for Formula (I).

In some embodiments, the present invention relates to a compound having Formula (IIa):

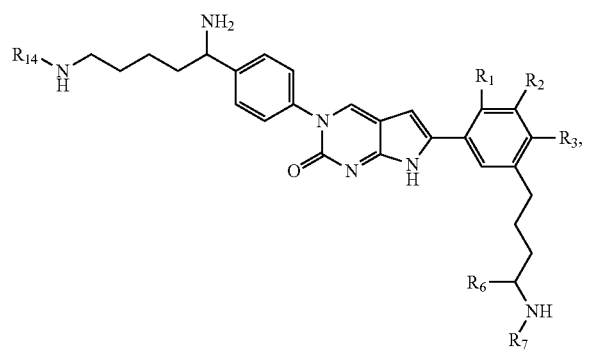

(IIa)

or a tautomer thereof, or a pharmaceutically acceptable salt, ester, or prodrug of said compound or tautomer, wherein $R_1$, $R_2$, $R_3$, $R_6$, $R_7$, and $R_{14}$ are as defined for Formula (I) herein.

In some embodiments, the present invention relates to a compound having Formula (IIIa):

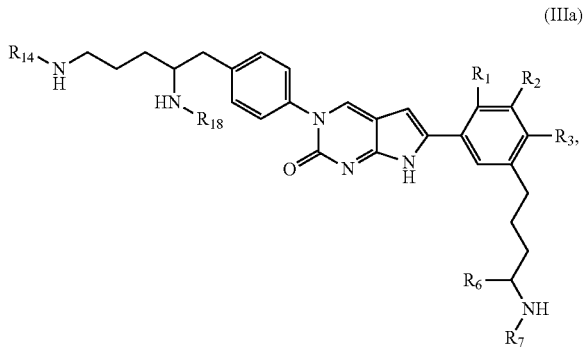

(IIIa)

or a tautomer thereof, or a pharmaceutically acceptable salt, ester, or prodrug of said compound or tautomer, wherein $R_1$, $R_2$, $R_3$, $R_6$, $R_7$, $R_{14}$, and $R_{18}$ are as defined herein for Formula (I).

In some embodiments, the present invention relates to a compound having Formula (IVa):

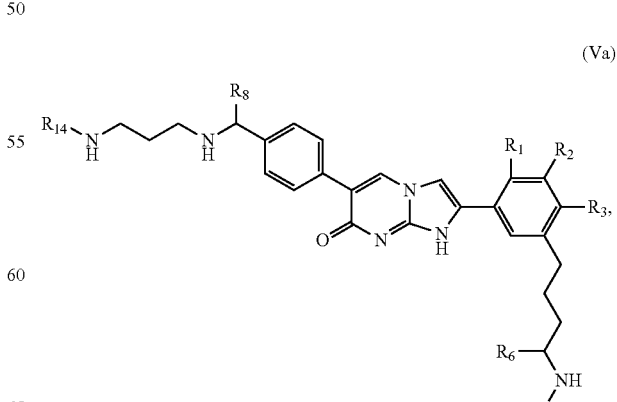

(IVa)

or a tautomer thereof, or a pharmaceutically acceptable salt, ester, or prodrug of said compound or tautomer, wherein $R_1$, $R_2$, $R_3$, $R_6$, $R_7$, and $R_{14}$ are as defined herein for Formula (I).

In some embodiments, the present invention relates to a compound having Formula (Va):

(Va)

or a tautomer thereof, or a pharmaceutically acceptable salt, ester, or prodrug of said compound or tautomer, wherein $R_1$, $R_2$, $R_3$, $R_6$, $R_7$, and $R_{14}$ are as defined herein for Formula (I).

The compounds of any of Formulae I, Ia, Ib, Ic, Id, Ie, If, Ih, Ig, Ii, Ij, Ik, Il, Im, In, Io, Ip, Iq, Ir, Is, It, Iu, Iv, Iw, Ix, Iy, Iz, IA, IB, IC, ID, IE, IF, IG, IH, IJ, IK, IM, IL, IN, II, IIA, IIa, III, IIIA, IIIa, IV, IVA, IVa, V, VA, and Va or tautomers thereof, or pharmaceutically acceptable salts, esters, or prodrugs of said compounds or tautomers, can include one or more of the following features, when applicable.

For example, $R_1$ and $R_3$ is H and $R_2$ is $CF_3$, $OCF_3$, $SCF_3$, $SOCF_3$ or Cl.

For example, each of $R_1$ and $R_3$ is H and $R_2$ is $CF_3$, $OCF_3$, $SCF_3$, $SOCF_3$ or Cl.

For example, $R_1$ is F, $R_3$ is H and $R_2$ is $OCF_3$ or Cl.

For example, each of $R_1$ and $R_3$ is F, and $R_2$ is $CF_3$ or ethyl.

For example, $R_1$ is F, $R_2$ is H, and $R_3$ is methyl.

For example, $R_4$ is H or amino.

For example, $R_5$ is H.

For example, $R_4$ and $R_5$ together with the carbon atoms to which they are attached form a 5-membered heterocycloalkyl ring.

For example, X is $CH_2$ or O.

For example, $R_6$ is methyl, ethyl, ethenyl, $CH_2OH$, $CH_2CH_2OH$, $CH_2F$, $CH_2OCH_3$, $CH_2SCH_3$, $CH(OH)CH_2OH$, $CH_2NH_2$, $CH_2N_3$, $CH_2OCOCH_3$, $CH_2OCOC_6H_5$, $CH_2OCONHCH_2C_6H_5$, $CH_2OCOCH_2CH_2COOH$, $CH_2OCOC_6H_4OCOCH_3$, $CH_2OCOCH_2C_6H_4$, $CH_2OP(O)(OH)_2$, or $CH_2OP(O)(OPh)_2$.

For example, $R_6$ is ethenyl, $CH_2CH_2OH$, $CH_2F$, $CH_2SCH_3$, $CH(OH)CH_2OH$, $CH_2NH_2$, $CH_2OCOCH_3$, $CH_2OCOC_6H_5$, $CH_2OCONHCH_2C_6H_5$, $CH_2OCOCH_2CH_2COOH$, $CH_2OCOC_6H_4OCOCH_3$, $CH_2OCOCH_2C_6H_4$, $CH_2OP(O)(OH)_2$, or $CH_2OP(O)(OPh)_2$.

For example, $R_7$ is H, $C(=NH)NH_2$, $COOCH_2CH_3$, $COCH_2NH_2$, or $COCH_3$.

For example, $R_6$ and $R_7$ together with the atoms to which they are attached, form

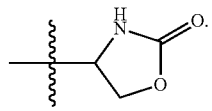

For example, X is a bond, and $R_4$ and $R_6$ together with the two carbon atoms to which they are attached and the carbon atom connecting said two carbon atoms, form

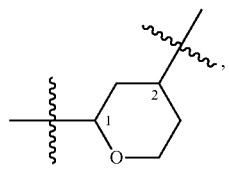 [SMILES: *C1CCOC(*)C1]

with carbon 1 connected to phenyl and carbon 2 connected to $NHR_7$, as in e.g., Compound 35 or 36 in Table 1.

For example, each of $R_4$ and $R_5$ is H, X is $CHR_{17}$, in which $R_{17}$ and $R_6$ together with the two carbon atoms to which they are attached and the carbon atom connecting said two carbon atoms, form

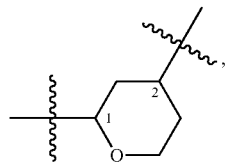 [SMILES: *C1CCOC(*)C1]

with carbon 1 connected to phenyl and carbon 2 connected to $NHR_7$, as in e.g., Compound 37 or 38 in Table 1.

For example, X is O.

For example, $R_5$ is H and $R_6$ is methyl, ethyl, ethenyl, $CH_2OH$, $CH_2CH_2OH$, $CH_2F$, $CH_2OCH_3$, $CH_2SCH_3$, $CH(OH)CH_2OH$, $CH_2NH_2$, $CH_2OCOCH_3$, $CH_2OCOC_6H_5$, $CH_2OCONHCH_2C_6H_5$, $CH_2OCOCH_2CH_2COOH$, or $CH_2OCOC_6H_4OCOCH_3$.

For example, $R_6$ is H and $R_5$ is $CH_2OH$.

For example, one of $R_4$, $R_5$ and $R_{17}$ is not H and the others are H.

For example, each of $R_4$, $R_5$ and $R_{17}$ is H.

For example, two of $R_8$, $R_{10}$, $R_{11}$, and $R_{12}$ are not H and the others are H.

For example, one of $R_8$, $R_{10}$, $R_{11}$, and $R_{12}$ are not H and the others are H.

For example, each of $R_8$, $R_{10}$, $R_{11}$, and $R_{12}$ is H.

For example, when A is $-NH_2$, $-C(O)NH_2$, $-NHC(=NH)H$, $-NHC(=N)CH_3$, $-NHC(O)NHCH_3$, $-NHC(=O)H$, $-NHC(=O)NH_2$, $-NHC(CH=NO_2)NHCH_3$, $-C(=O)NHCH_3$, $-NHC(=O)NHCH_3$, $C(O)OH$, OH, CN, cyclopropyl, cyclobutyl, or cyclopentyl, $R_8$ is H, methyl, ethyl, propyl, isopropyl, ethylenyl, propylenyl cyclopropyl, $CH_2CO_2CH_3$, $CH_2CO_2H$, $CO_2H$, $CO_2CH_3$, $CH_2CH_2OH$, or $4-CH_3C_6H_5$.

For example, when A is $-NHC(=NH)NH_2$, $R_8$ is not H, methyl, ethyl, propyl, isopropyl, ethylenyl, propylenyl cyclopropyl, $CH_2CO_2CH_3$, $CH_2CO_2H$, $CO_2H$, $CO_2CH_3$, $CH_2CH_2OH$, or $4-CH_3C_6H_5$.

For example, when A is $-NHC(=NH)NH_2$, $R_8$ is not $CF_3$, $CHF_2$, $CH_2F$, or F.

For example, when A is $-NHC(=NH)NH_2$, $R_8$ and $R_{8'}$ together is not oxo.

For example, when A is $-NHC(=NH)NH_2$, $R_{10}$ is not H, methyl, $CHF_2$, F, or $CF_3$.

For example, when A is $-NHC(=NH)NH_2$, $R_{11}$ is not H, methyl, $CH_2F$, or $CF_3$.

For example, when A is $-NHC(=NH)NH_2$, $R_{19}$ is not O.

For example, $R_{10}$ is H, methyl, $CH_2OH$, or $CH_2CH_2OH$.

For example, one of $R_8$ and $R_{11}$ is H or $CH_3$ and the other is $-Q_1-T_1$.

For example, A $-NHC(=NH)NH_2$ or $NH_2$.

For example, A is 5 or 6-membered heterocycloalkyl having 1 to 3 heteroatoms optionally substituted with oxo, or 5- or 6-membered heteroaryl having 1 to 4 heteroatoms optionally substituted with $C_1$-$C_4$ alkyl, $C_1$-$C_4$ alkylenyl-aryl, or amino, wherein the alkyl, alkylenyl, and aryl are optionally substituted with one or more substituents independently selected from $C_1$-$C_3$ alkyl, $C_2$-$C_4$ alkenyl, $C_1$-$C_3$ alkoxy, or halo.

For example, $R_8$ and $R_{8'}$ together together with the carbon atom to which they are attached form

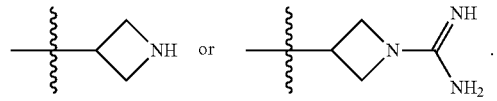

For example, each of $R_{11}$ and $R_{12}$ is H or $CH_3$, or $R_{11}$ and $R_{12}$ together with the carbon atom to which they are attached form

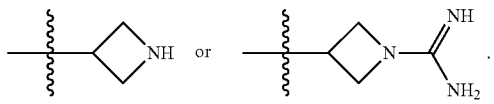

For example, $R_{15}$ is H.

For example, $R_{15}$ is Cl or Br.

For example, when X is O, $R_4$ and $R_5$ together with the two carbon atoms to which they are attached and the X atom connecting said two carbon atoms, form

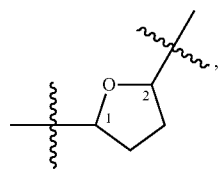 [SMILES: *C1CCC(*)O1]

with carbon 1 connected to phenyl and carbon 2 connected to —$CH(R_6)YR_7$.

For example, in Formula (Ip) $R_8$ is H.

For example, in Formula (Ip) $R_8$ is H and A is —NHC(=NH)$NH_2$.

For example, in Formula (Ip) $R_1$ is H and $R_2$ is $CF_3$.

For example, in Formula (It) M is $NH_2$, —NH-cyclopropyl, —NH-cyclobutyl or —NH— cyclopentyl.

For example, in Formula (It) M is —NH—$CH_2$-heteroaryl —NH—$CH_2CH_2$-heteroaryl, or —NH—$CH_2CH_2CH_2$-heteroaryl.

In some embodiments, the present invention relates to a compound having Formula (VIII) or (IX):

m is 0 or 1;

n is 1 or 2;

$R_{101}$ is H or F, wherein when $R_{101}$ is H, then (i) $R_{102}$ is $CF_3$, $OCF_3$, $SCF_3$, or $SOCF_3$, $R_{103}$ is H, and $R_{104}$ is $(CH_2)_3CH(CH_3)NH_2$; or (ii) each of $R_{102}$ and $R_{104}$ is H, and $R_{103}$ is $CH(R_p)NHR_q$, in which is $R_p$ is $C_1$-$C_6$ alkyl optionally substituted with one or more halo and $R_q$ is 4- to 12-membered saturated heterocycloalkyl ring having 1 to 2 heteroatoms optionally substituted with C(=NH)$NH_2$; and when $R_{101}$ is F, then $R_{102}$ is Cl or $OCF_3$, $R_{103}$ is H, and $R_{104}$ is $(CH_2)_3CH(CH_3)NH_2$;

$R_{105}$ is $CH(R_p)NHR_q$, CH=$CHR_q$, CH=NO$(CH_2)_2$NHC(=NH)$NH_2$, or CONH$CH_2R_s$ in which $R_s$ is 5- or 6-membered heteroaryl optionally substituted with 5- to 12-membered saturated heterocycloalkyl ring having 1 to 2 heteroatoms, and each of $R_{106}$ and $R_{107}$ is H or $C_1$-$C_6$ alkyl, or $R_{106}$ and $R_{107}$ together with the two nitrogen atoms to which they are attached and the carbon atom connecting said two nitrogen atoms, form a 6- to 12-membered saturated heterocycloalkyl ring having 0 to 1 additional heteroatom.

The compound of Formula (VIII) or (IX) above or tautomers thereof, or pharmaceutically acceptable salts, esters, or prodrugs of said compounds or tautomers, can include one or more of the following features when applicable.

For example, $R_q$ is

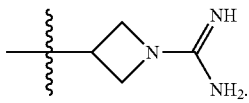

For example, $R_p$ is $CF_3$.

For example, m is 1 and each of $R_{106}$ and $R_{107}$ is H.

For example, m is 0 and $R_{106}$ and $R_{107}$ together with the two nitrogen atoms to which they are attached and the carbon atom connecting said two nitrogen atoms, form a 6-membered saturated heterocycloalkyl ring having 0 additional heteroatom.

(VIII)

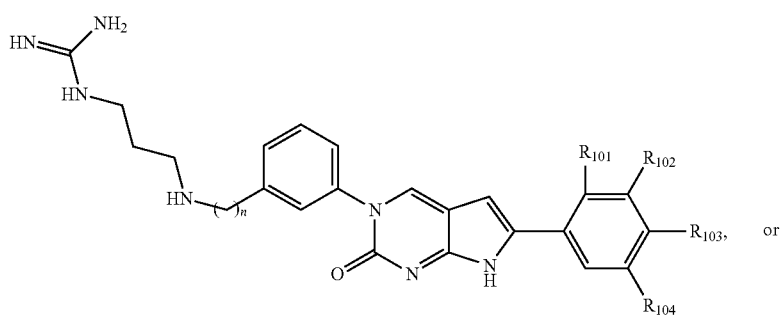

or (IX)

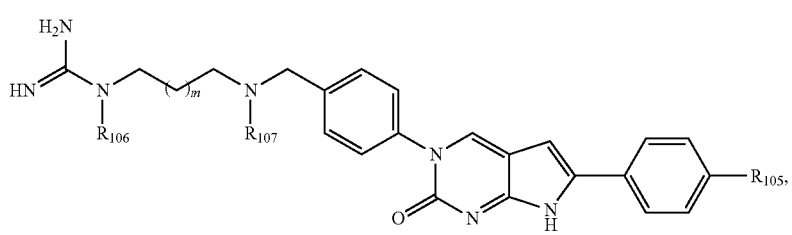

or a tautomer thereof, or a pharmaceutically acceptable salt, or ester of said compound or tautomer, wherein:

In some embodiments, the present invention relates to a compound having Formula (X):

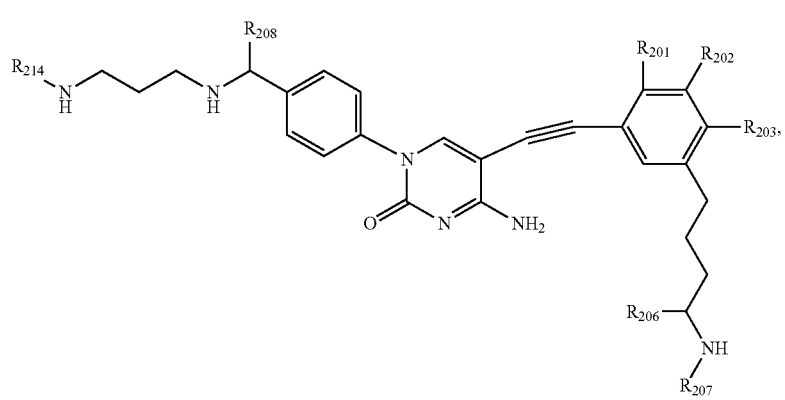

(X)

or a tautomer thereof, or a pharmaceutically acceptable salt, or ester of said compound or tautomer, wherein:

$R_{201}$ is H or F, wherein when $R_{201}$ is H, then $R_{202}$ is $CF_3$, $OCF_3$, $SCF_3$, $SOCF_3$ or halo, and $R_{203}$ is H; and when $R_{201}$ is F, then (i) $R_{202}$ is Cl or $OCF_3$, and $R_3$ is H; or (ii) $R_{202}$ is H and $R_{203}$ is $C_1$-$C_6$ alkyl; or (iii) $R_{202}$ is $C_1$-$C_6$ alkyl optionally substituted with one or more halo, and $R_{203}$ is halo;

$R_{206}$ is $C_1$-$C_3$ alkyl optionally substituted with one or more substituents independently selected from the group consisting of halo, OH, amino, $C_1$-$C_6$ alkoxyl and $C_1$-$C_6$ alkylthio, $C_2$-$C_3$ alkenyl, or $CH_2OCOR_{aa}$, in which $R_{aa}$ is $C_1$-$C_6$ alkyl, amino, or phenyl, and $R_{aa}$ is optionally substituted with COOH, $COOC_1$-$C_6$ alkyl, $OCOC_1$-$C_6$ alkyl, or $C_7$-$C_{12}$ arylalkyl;

$R_{207}$ is H, C(=NH)NH$_2$, or COR$_b$ in which R$_b$ is $C_1$-$C_6$ alkyl optionally substituted with amino, $C_1$-$C_6$ alkoxyl, or amino; or $R_{206}$ and $R_{207}$ together with the two atoms to which they are attached, form a 5- to 12-membered heterocycloalkyl ring having 0 to 1 additional heteroatom optionally substituted with an oxo group;

$R_{208}$ is H, $C_1$-$C_6$ alkyl or $C_2$-$C_6$ alkenyl; and $R_{214}$ is H or C(=NH)NH$_2$.

The compounds of Formula (X) above or tautomers thereof, or pharmaceutically acceptable salts, esters, or prodrugs of said compounds or tautomers, can include one or more of the following features when applicable.

For example, $R_{201}$ and $R_{203}$ is H and $R_{202}$ is $CF_3$, $OCF_3$, $SCF_3$, $SOCF_3$ or Cl.

For example, each of $R_{201}$ and $R_{203}$ is H and $R_{202}$ is $CF_3$, $OCF_3$, $SCF_3$, $SOCF_3$ or Cl.

For example, $R_{201}$ is F, $R_{203}$ is H and $R_{202}$ is $OCF_3$ or Cl.

For example, each of $R_{201}$ and $R_{203}$ is F, and $R_{202}$ is $CF_3$ or ethyl.

For example, $R_{201}$ is F, $R_{202}$ is H, and $R_{203}$ is methyl.

For example, $R_{208}$ is methyl.

For example, $R_{214}$ is C(=NH)NH$_2$.

For example, $R_{206}$ is methyl, ethyl, ethenyl, $CH_2OH$, $CH_2CH_2OH$, $CH_2F$, $CH_2OCH_3$, $CH_2SCH_3$, CH(OH)$CH_2OH$, $CH_2NH_2$, $CH_2OCOCH_3$, $CH_2OCOC_6H_5$, $CH_2OCONHCH_2C_6H_5$, $CH_2OCOCH_2CH_2COOH$, or $CH_2OCOC_6H_4OCOCH_3$.

For example, $R_{206}$ is ethenyl, $CH_2CH_2OH$, $CH_2F$, $CH_2SCH_3$, CH(OH)$CH_2OH$, $CH_2NH_2$, $CH_2OCOCH_3$, $CH_2OCOC_6H_5$, $CH_2OCONHCH_2C_6H_5$, $CH_2OCOCH_2CH_2COOH$, or $CH_2OCOC_6H_4OCOCH_3$.

For example, $R_{207}$ is H, C(=NH)NH$_2$, $COOCH_2CH_3$, $COCH_2NH_2$, or $COCH_3$.

For example, $R_{207}$ and $R_{206}$ together with the atoms to which they are attached, form

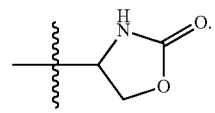 [SMILES: *C1COC(=O)N1]

In some embodiments, the present invention relates to a compound having compound of Formula (XIa), (XIb), (XIc), or (XId):

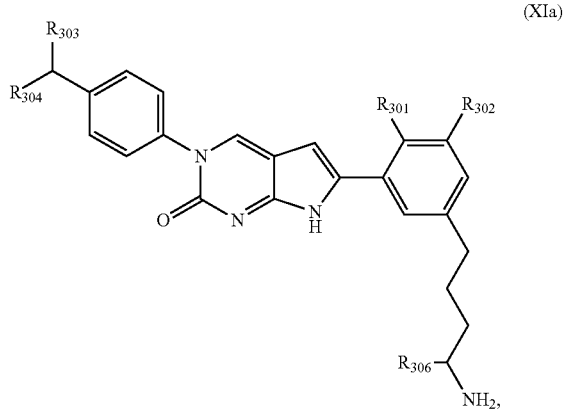

(XIa)

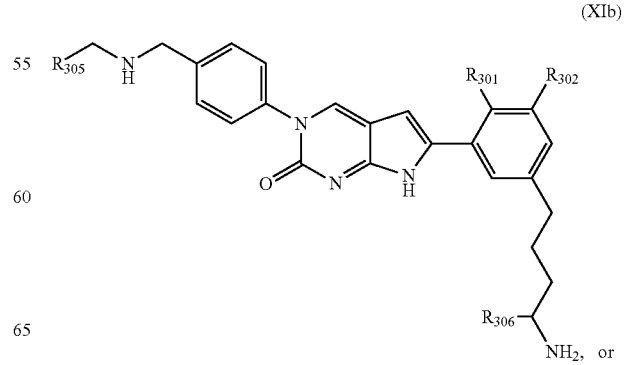

(XIb)

-continued

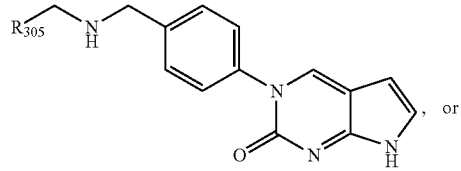

(XIc)

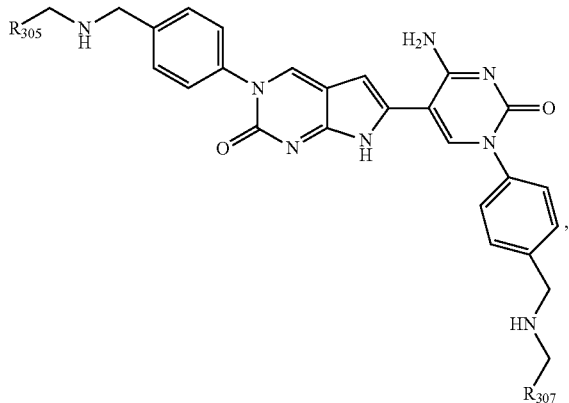

(XId)

or a tautomer thereof, or a pharmaceutically acceptable salt, or ester of said compound or tautomer, wherein:

$R_{301}$ is H or F, wherein when $R_{301}$ is H, then $R_{302}$ is $CF_3$, $OCF_3$, $SCF_3$, or $SOCF_3$; and when $R_{301}$ is F, then $R_{302}$ is Cl or $OCF_3$;

each of $R_{303}$ and $R_{304}$ independently is phenyl or 5- or 6-membered heteroaryl, each of which is optionally substituted with one or more substituents independently selected from halo, OH, amino, $C_1$-$C_6$ alkoxyl and $C_1$-$C_6$ alkylthio; or one of $R_{303}$ and $R_{304}$ is amino and the other is $CH_2CH_2NR_fR_g$ in which $R_f$ is H, $C_1$-$C_6$ alkyl, $COC_1$-$C_6$ alkyl or $COC_6$-$C_{10}$ aryl and $R_g$ is 5- or 6-membered heteroaryl;

each of $R_{305}$ and $R_{307}$ independently is cyano, COOH, $COC_1$-$C_6$ alkoxyl, C(=NH)$C_1$-$C_6$ alkoxyl, C(=NH)NH$_2$, amino, $CH_2COOH$, $CH_2COC_1$-$C_6$ alkoxyl, $CH_2NH_2$, $CH_2NHC_1$-$C_6$ alkyl, or 5- or 6-membered heteroaryl optionally substituted with one or more substituents independently selected from halo, OH, amino, $C_1$-$C_6$ alkoxyl, $C_1$-$C_6$ alkylthio, and $C_7$-$C_{12}$ arylalkyl that is optionally further substituted with one or more substituents independently selected from halo, OH, amino, $C_1$-$C_6$ alkoxyl, and $C_1$-$C_6$ alkylthio; and $R_{306}$ is $C_1$-$C_3$ alkyl optionally substituted with one or more substituents independently selected from the group consisting of halo, OH, amino, $C_1$-$C_6$ alkoxyl and $C_1$-$C_6$ alkylthio, $C_2$-$C_3$ alkenyl, or $CH_2OCOR_{aa}$, in which $R_{aa}$ is $C_1$-$C_6$ alkyl, amino, or phenyl, and $R_{aaa}$ is optionally substituted with COOH, $COOC_1$-$C_6$ alkyl, $OCOC_1$-$C_6$ alkyl, or $C_7$-$C_{12}$ arylalkyl.

The compounds of Formula (XIa), (XIb), (XIc), or (XId) above or tautomers thereof, or pharmaceutically acceptable salts, esters, or prodrugs of said compounds or tautomers, can include one or more of the following features when applicable.

For example, $R_{301}$ is H and $R_{302}$ is $SCF_3$.
For example, $R_{301}$ is F and $R_{302}$ is Cl.
For example, $R_{303}$ is phenyl substituted with $SCH_3$ or $OCH_3$.

For example, $R_{304}$ is phenyl substituted with $SCH_3$ or $OCH_3$.

For example, $R_{303}$ is amino and $R_{304}$ is $CH_2CH_2NH(2$-thiazole).

For example, $R_{303}$ is amino and $R_{304}$ is $CH_2CH_2N$ ($COC_6H_5$)(2-thiazole).

For example, $R_{305}$ is 5- or 6-membered heteroaryl (e.g., pyridyl, tetrazolyl, or thiazolyl) optionally substituted with one $C_7$-$C_{12}$ arylalkyl (e.g., benzyl) that is optionally further substituted with one OH or $C_1$-$C_6$ alkoxyl (e.g., methoxyl).

For example, $R_{306}$ is methyl, ethyl, ethenyl, $CH_2OH$, $CH_2CH_2OH$, $CH_2F$, $CH_2OCH_3$, $CH_2SCH_3$, CH(OH)$CH_2OH$, $CH_2NH_2$, $CH_2OCOCH_3$, $CH_2OCOC_6H_5$, $CH_2OCONHCH_2C_6H_5$, $CH_2OCOCH_2CH_2COOH$, or $CH_2OCOC_6H_4OCOCH_3$.

For example, $R_{307}$ is $CH_2NHC_1$-$C_6$ alkyl, e.g., $CH_2NHCH_3$.

In some embodiments, the present invention relates to a compound or a tautomer thereof, or a pharmaceutically acceptable salt, ester, or prodrug of said compound or tautomer, according to any one the compounds in Table 1.

In some embodiments, the present invention relates to a compound or a tautomer thereof, or a pharmaceutically acceptable salt, ester, or prodrug of said compound or tautomer that binds the ribosome. In some embodiments, the ribosome is a bacterial ribosome.

In some embodiments, the present invention relates to a pharmaceutical composition comprising a compound of the invention, or a tautomer thereof, or a pharmaceutically acceptable salt, ester, or prodrug of said compound or tautomer, and a pharmaceutically acceptable carrier. In some embodiments, the present invention relates to a compound or a tautomer thereof, or a pharmaceutically acceptable salt, ester, or prodrug of said compound or tautomer of the invention and a means for delivery.

In some embodiments, the present invention relates to a method of treating, preventing, reducing the risk of or delaying the onset of a disease state in a human or animal comprising administering to the human or animal in need thereof an effective amount of a compound of the invention, or a tautomer thereof, or a pharmaceutically acceptable salt, ester, or prodrug of said compound or tautomer.

In some embodiments, the present invention relates to a method of treating, preventing, reducing the risk of, or delaying the onset of a microbial infection in a human or animal comprising administering to the human or animal an effective amount of a compound of the invention, or a tautomer thereof, or a pharmaceutically acceptable salt, ester, or prodrug of said compound or tautomer.

In some embodiments, the present invention relates to use of a compound of the invention, or a tautomer thereof, or a pharmaceutically acceptable salt, ester, or prodrug of said compound or tautomer, in the manufacture of a medicament for treating, preventing, reducing the risk of, or delaying the onset of, a microbial infection in a human or animal.

In some embodiments, the present invention relates to a compound of the invention, or a tautomer thereof, or a pharmaceutically acceptable salt, ester, or prodrug of said compound or tautomer, for use in treating, preventing, reducing the risk of, or delaying the onset of a microbial infection in a human or animal.

In some embodiments, the present invention relates to a method of treating, preventing, reducing the risk of, or delaying the onset of a microbial infection in a human or animal comprising administering to the human or animal an effective amount of a compound or a tautomer thereof, or a pharmaceutically acceptable salt, ester, or prodrug of said compound or tautomer, wherein said microbial infection is caused by one or more of the following microorganisms: *Acinetobacter* spp. (*Acinetobacter baumanni*), *Bacteroides distasonis*, *Bacteroides fragilis*, *Bacteroides ovatus*, *Bacteroides thetaiotaomicron*, *Bacteroides uniformis*, *Bacteroides vulgatus*, *Citrobacter freundii*, *Citrobacter koser*, *Clostridium clostridioforme*, *Clostridium perfringens*, *Enterobacter aerogenes*, *Enterobacter cloacae*, *Enterococcus faecalis*, *Enterococcus* spp. (vancomycin susceptible and resistant isolates), *Escherichia coli* (including ESBL and KPC producing isolates), *Eubacterium lentum*, *Fusobacterium* spp., *Haemophilus influenzae* (including beta-lactamase positive isolates), *Haemophilus parainfluenzae*, *Klebsiella pneumoniae* (including ESBL and KPC producing isolates), *Klebsiella oxytoca* (including ESBL and KPC producing isolates), *Legionella pneumophilia Moraxella catarrhalis*, *Morganella morganii*, *Mycoplasma* spp., *Peptostreptococcus* spp., *Porphyromonas asaccharolytica*, *Prevotella bivia*, *Proteus mirabilis*, *Proteus vulgaris*, *Providencia rettgeri*, *Providencia stuartii*, *Pseudomonas aeruginosa*, *Serratia marcescens*, *Streptococcus anginosus*, *Staphylococcus aureus* (methicillin susceptible and resistant isolates), *Staphylococcus epidermidis* (methicillin susceptible and resistant isolates), *Stenotrophomonas maltophilia*, *Streptococcus agalactiae*, *Streptococcus constellatus*, *Streptococcus pneumoniae* (penicillin susceptible and resistant isolates), *Streptococcus pyogenes*, or *Streptococcus pyogenes*.

In some embodiments, the present invention relates to a method of treating, preventing, reducing the risk of, or delaying the onset of a microbial infection in a human or animal comprising administering to the human or animal an effective amount of a compound or a tautomer thereof, or a pharmaceutically acceptable salt, ester, or prodrug of said compound or tautomer, wherein said infection is caused by or involves one or more microorganisms selected from: *Acinetobacter* spp. (*Acinetobacter baumanni*), *Bacteroides distasonis*, *Bacteroides fragilis*, *Bacteroides ovatus*, *Bacteroides thetaiotaomicron*, *Bacteroides uniformis*, *Bacteroides vulgatus*, *Citrobacter freundii*, *Citrobacter koser*, *Clostridium clostridioforme*, *Clostridium perfringens*, *Enterobacter aerogenes*, *Enterobacter cloacae*, *Enterococcus faecalis*, *Enterococcus* spp., *Escherichia coli*, *Eubacterium lentum*, *Fusobacterium* spp., *Haemophilus influenzae*, *Haemophilus parainfluenzae*, *Klebsiella pneumoniae*, *Klebsiella oxytoca*, *Legionella pneumophilia*, *Moraxella catarrhalis*, *Morganella morganii*, *Mycoplasma* spp., *Peptostreptococcus* spp., *Porphyromonas asaccharolytica*, *Prevotella bivia*, *Proteus mirabilis*, *Proteus vulgaris*, *Providencia rettgeri*, *Providencia stuartii*, *Pseudomonas aeruginosa*, *Serratia marcescens*, *Streptococcus anginosus*, *Staphylococcus aureus*, *Staphylococcus epidermidis*, *Stenotrophomonas maltophilia*, *Streptococcus agalactiae*, *Streptococcus constellatus*, *Streptococcus pneumoniae*, *Streptococcus pyogenes*, and *Streptococcus pyogenes*.

In some embodiments, the present invention relates to a method wherein said infection is caused by or involves one or more of aerobic and facultative gram-positive microorganism selected from: *Staphylococcus aureus*, *Streptococcus pneumoniae*, *Enterococcus* spp., *Streptococcus agalactiae*, *Streptococcus pyogenes*, and *Staphylococcus epidermidis*.

In some embodiments, the present invention relates to a method wherein said infection is caused by or involves one or more of aerobic and facultative gram-negative microorganism selected from: *Escherichia coli*, *Haemophilus influenzae*, *Klebsiella pneumoniae*, *Citrobacter freundii*, *Enterobacter aerogenes*, *Enterobacter cloacae*, *Morganella morganii*, *Serratia marcescens*, *Pseudomonas aeruginosa*, *Acinetobacter baumanni*, *Moraxella catarrhalis*, *Proteus mirabilis*, *Citrobacter koseri*, *Haemophilus parainfluenzae*, *Klebsiella oxytoca*, *Proteus vulgaris*, *Providencia rettgeri*, and *Providencia stuartii*.

In some embodiments, the present invention relates to a method wherein, said infection is caused by or involves one or more of anaerobic microorganism: *Bacteroides fragilis*, *Bacteroides distasonis*, *Bacteroides ovatus*, *Bacteroides thetaiotaomicron*, *Bacteroides uniformis*, *Clostridium clostridioforme*, *Eubacterium lentum*, *Peptostreptococcus* spp., *Porphyromonas asaccharolytica*, *Prevotella bivia*, *Bacteroides vulgatus*, *Clostridium perfringens*, and *Fusobacterium* spp.

In some embodiments, the present invention relates to a method, wherein the microorganism *Enterococcus* spp. is selected from vancomycin susceptible isolate and vancomycin resistant isolate.

In some embodiments, the present invention relates to a method wherein, the microorganism *Escherichia coli* is selected from extended spectrum beta-lactamase (ESBL) producing isolate and *Klebsiella pneumoniae* carbapenemase (KPC) producing isolate.

In some embodiments, the present invention relates to a method wherein, the microorganism *Haemophilus influenzae* is a beta-lactamase positive isolate.

In some embodiments, the present invention relates to a method wherein, the microorganism *Klebsiella pneumoniae* is selected from extended spectrum beta-lactamase (ESBL) producing isolate and *Klebsiella pneumoniae* carbapenemase (KPC) producing isolate.

In some embodiments, the present invention relates to a method wherein, the microorganism *Klebsiella oxytoca* selected from extended spectrum beta-lactamase (ESBL) producing isolate and *Klebsiella pneumoniae* carbapenemase (KPC) producing isolate.

In some embodiments, the present invention relates to a method wherein, the microorganism *Staphylococcus aureus* is selected from methicillin susceptible isolate and methicillin resistant isolate.

In some embodiments, the present invention relates to a method wherein, the microorganism *Staphylococcus epidermidis* is selected from methicillin susceptible isolate and methicillin resistant isolate.

In some embodiments, the present invention relates to a method wherein, the microorganism *Streptococcus pneumoniae* is selected from penicillin susceptible isolate and penicillin resistant isolate.

In some embodiments, the present invention relates to a method of treating, preventing, reducing the risk of, or delaying the onset of a microbial infection in a human or animal comprising administering to the human or animal an effective amount of a compound of the invention, or a tautomer thereof, or a pharmaceutically acceptable salt, ester, or prodrug of said compound or tautomer, or use of a compound of the invention, or a tautomer thereof, or a pharmaceutically acceptable salt, ester, or prodrug of said compound or tautomer, in the manufacture of a medicament for treating, preventing, reducing the risk of, or delaying the onset of a microbial infection in a human or animal, wherein the microbial infection is selected from the group consisting of: a skin infection, a Gram positive infection, a Gram negative infection, nosocomial pneumonia, community acquired pneumonia, post-viral pneumonia, hospital acquired pneumonia/ventilator associated pneumonia, a respiratory tract infection such as chronic respiratory tract infection (CRTI), acute pelvic infection, a complicated skin and skin structure infection, a skin and soft tissue infection (SSTI) including uncomplicated skin and soft tissue infections (uSSTI)s and complicated skin and soft tissue infections, an abdominal infection, a complicated intra-abdominal infection, a urinary tract infection, bacteremia, septicemia, endocarditis, an atrioventricular shunt infection, a vascular access infection, meningitis, surgical prophylaxis, a peritoneal infection, a bone infection, a joint infection, a methicillin-resistant *Staphylococcus aureus* infection, a vancomycin-resistant *Enterococci* infection, a linezolid-resistant organism infection, and tuberculosis.

The compounds of the present invention can be used, for example for the treatment of patients with moderate to severe infections, which may be caused by susceptible isolates of the indicated microorganisms.

In some embodiments, the present invention relates to a method of treating, preventing, reducing the risk of, or delaying the onset of a complicated intra-abdominal infection in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing, reducing the risk of, or delaying the onset of a complicated intra-abdominal infection in a human or animal.

In some embodiments, the complicated intra-abdominal infection is selected from polymicrobial infections such as abscess due to *Escherichia coli, Clostridium clostridioforme, Eubacterium lentum, Peptostreptococcus* spp., *Bacteroides fragilis, Bacteroides distasonis, Bacteroides ovatus, Bacteroides thetaiotaomicron, Bacteroides uniformis, Streptococcus anginosus, Streptococcus constellatus, Enterococcus faecalis, Proteus mirabilis*, or *Clostridium perfringens*.

In some embodiments, the present invention relates to a method of treating, preventing, reducing the risk of, or delaying the onset of a complicated skin and skin structure infection (cSSSI, also known as acute bacterial skin and skin structure infections or ABSSSI) in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing, reducing the risk of, or delaying the onset of a complicated skin and skin structure infection.

In some embodiments, the complicated skin and skin structure infection is selected from diabetic foot infections without osteomyelitis due to *Staphylococcus aureus* (methicillin susceptible and resistant isolates), *Streptococcus agalactiae, Streptococcus pyogenes, Escherichia coli, Klebsiella pneumoniae, Proteus mirabilis, Bacteroides fragilis, Peptostreptococcus* species, *Porphyromonas asaccharolytica*, or *Prevotella bivia*.

In some embodiments, the present invention relates to a method of treating, preventing, reducing the risk of, or delaying the onset of a community acquired pneumonia (CAP) in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing, reducing the risk of, or delaying the onset of community acquired pneumonia.

In some embodiment, the community acquired pneumonia is due to *Streptococcus pneumoniae* (penicillin susceptible and resistant isolates) including cases with concurrent bacteremia, *Haemophilus influenzae* (including beta-lactamase positive isolates), *Moraxella catarrhalis*, or atypical bacteria like *Mycoplasma* spp.

In some embodiments, the present invention relates to a method of treating, preventing, reducing the risk of, or delaying the onset of a complicated urinary tract infection (cUTI) in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing, reducing the risk of, or delaying the onset of a complicated urinary tract infection.

In some embodiment, the complicated urinary tract infection is selected from pyelonephritis due to *Escherichia coli*, concurrent bacteremia, or *Klebsiella pneumoniae*.

In some embodiments, the present invention relates to a method of treating, preventing, reducing the risk of, or delaying the onset of an acute pelvic infection in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing, reducing the risk of, or delaying the onset of an cute pelvic infection.

In some embodiments, the acute pelvic infection is selected from postpartum endomyometritis, septic abortion and post-surgical gynecologic infections and the infection is due to a microorganism selected from *Streptococcus agalactiae, Escherichia coli, Bacteroides fragilis, Porphyromonas asaccharolytica, Peptostreptococcus* spp., and *Prevotella bivia*.

In some embodiments, the present invention relates to a method of treating, preventing, reducing the risk of, or delaying the onset of a hospital acquired pneumonia (HAP)/ventilator associated pneumonia (VAP) in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing, reducing the risk of, or delaying the onset of hospital acquired pneumonia/ventilator associated pneumonia.

In some embodiments, the hospital acquired pneumonia/ventilator associated pneumonia is due to a microorganism selected from *Streptococcus pneumoniae* (penicillin susceptible and resistant isolates), *Staphylococcus aureus* (methicillin susceptible and resistant isolates), *Klebsiella pneumoniae, Pseudomonas aeruginosa, Acinetobacter* spp.,

*Stenotrophomonas maltophilia, Haemophilus influenzae* (including beta-lactamase positive isolates), and *Legionella pneumophilia*.

The compounds or tautomers or pharmaceutically acceptable salts, esters or prodrugs of said compounds or tautomers of the present invention may also be useful for the prevention, prophylaxis, or reduction of surgical site infections. In some embodiments, the compounds or tautomers or pharmaceutically acceptable salts, esters or prodrugs of said compounds or tautomers of the present invention are useful following elective colorectal surgery.

Appropriate specimens for bacteriological examination should be obtained in order to isolate and identify the causative organisms and to determine their susceptibility to the compounds of the present invention. Therapy with the compounds or tautomers or pharmaceutically acceptable salts, esters or prodrugs of said compounds or tautomers of the present invention may be initiated empirically before results of these tests are known; once results become available, antimicrobial therapy should be adjusted accordingly.

To reduce the development of drug-resistant bacteria and maintain the effectiveness of the compounds or tautomers or pharmaceutically acceptable salts, esters or prodrugs of said compounds or tautomers of the present invention and other antibacterial drugs, the compounds or tautomers or pharmaceutically acceptable salts, esters or prodrugs of said compounds or tautomers should be used only to treat or prevent infections that are proven or strongly suspected to be caused by susceptible bacteria. When culture and susceptibility information are available, they should be considered in selecting or modifying antibacterial therapy. In the absence of such data, local epidemiology and susceptibility patterns may contribute to the empiric selection of therapy.

In some embodiments, the present invention relates to a method of treating, preventing, reducing the risk of, or delaying the onset of a microbial infection due to an aerobic or facultative gram-positive microorganism in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing, reducing the risk of, or delaying the onset of a microbial infection due to an aerobic or facultative gram-positive microorganism.

In some embodiments, the aerobic or facultative gram-positive microorganism is selected from: *Staphylococcus aureus* (methicillin susceptible and resistant isolates), *Streptococcus pneumoniae* (penicillin susceptible and resistant isolates), *Enterococcus* spp. (vancomycin susceptible and resistant isolates), *Streptococcus agalactiae, Streptococcus pyogenes*, and *Staphylococcus epidermidis* (methicillin susceptible and resistant isolates).

In some embodiments, the present invention relates to a method of treating, preventing, reducing the risk of, or delaying the onset of a microbial infection due to an aerobic and facultative gram-negative microorganism in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing, reducing the risk of, or delaying the onset of a microbial infection due to an aerobic or facultative gram-positive microorganism.

In some embodiments, the aerobic and facultative gram-negative microorganism is selected from: *Escherichia coli* [including extended spectrum beta-lactamase (ESBL) and *Klebsiella pneumonia* (KPC) producing isolates), *Haemophilus influenzae* (including Beta-lactamase positive isolates), *Klebsiella pneumoniae* (including ESBL and KPC producing isolates), *Citrobacter freundii, Enterobacter aerogenes, Enterobacter cloacae, Morganella morganii, Serratia marcescens, Pseudomonas aeruginosa, Acinetobacter baumanni, Moraxella catarrhalis, Proteus mirabilis, Citrobacter koseri, Haemophilus parainfluenzae, Klebsiella oxytoca* (including ESBL and KPC producing isolates), *Proteus vulgaris, Providencia rettgeri*, and *Providencia stuartii*.

In some embodiments, the present invention relates to a method of treating, preventing, reducing the risk of, or delaying the onset of a microbial infection due to an anaerobic microorganism in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing, reducing the risk of, or delaying the onset of a microbial infection due to an anaerobic microorganism.

In some embodiments, the anaerobic microorganism is selected from: *Bacteroides fragilis, Bacteroides distasonis, Bacteroides ovatus, Bacteroides thetaiotaomicron, Bacteroides uniformis, Clostridium clostridioforme, Eubacterium lentum, Peptostreptococcus* species, *Porphyromonas asaccharolytica, Prevotella bivia, Bacteroides vulgates, Clostridium perfringens*, and *Fusobacterium* spp.

In some embodiments, the present invention relates to a method of treating or reducing the risk of a microbial infection in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing, reducing the risk of, or delaying the onset of of a microbial infection.

In some embodiments, the microorganism is *Legionella pneumophilia*.

In some embodiments, the microorganism *Enterococcus* spp. is selected from vancomycin susceptible isolate and vancomycin resistant isolate. In some embodiments, the microorganism *Escherichia coli* is selected from extended spectrum beta-lactamase (ESBL) producing isolate and *Klebsiella pneumoniae* carbapenemase (KPC) producing isolate. In some embodiments, the microorganism *Haemophilus influenzae* is a beta-lactamase positive isolate. In some embodiments, the microorganism *Klebsiella pneumoniae* is selected from extended spectrum beta-lactamase (ESBL) producing isolate and *Klebsiella pneumoniae* carbapenemase (KPC) producing isolate. In some embodiments, the microorganism *Klebsiella oxytoca* selected from extended spectrum beta-lactamase (ESBL) producing isolate and *Klebsiella pneumoniae* carbapenemase (KPC) producing isolate. In some embodiments, the microorganism *Staphylococcus aureus* is selected from methicillin susceptible isolate and methicillin resistant isolate. In some embodiments, the microorganism *Staphylococcus epidermidis* is selected from methicillin susceptible isolate and methicillin resistant isolate. In some embodiments, the microorganism *Streptococcus pneumoniae* is selected from penicillin susceptible isolate and penicillin resistant isolate.

In some embodiments, the present invention relates to a method, use, or compound of the invention, wherein the amount of compound or a tautomer thereof, or a pharmaceutically acceptable salt, ester, or prodrug of said compound or tautomer comprises from 0.1 mg to 1500 mg.

In some embodiments, the present invention relates to a method, use, or compound of the invention wherein the amount of compound or a tautomer thereof, or a pharmaceutically acceptable salt, ester, or prodrug of said compound or tautomer comprises about 25 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg, or about 325, or about 350 mg, or about 375 mg, or about 400 mg, or about 425 mg, or about 450 mg, or about 475 mg, or about 500 mg, or about 525 mg, or about 550 mg, or about 575 mg, or about 600 mg, or about 625 mg, or about 650 mg, or about 675 mg, or about 700 mg, or about 725 mg, or about 750 mg, or about 775 mg, or about 800 mg, or about 825 mg, or about 850 mg, or about 875 mg, or about 900 mg, or about 925 mg, or about 950 mg, or about 975 mg, or about 1000 mg, or about 1025 mg, or about 1050, mg, or about 1075 mg, or about 1100 mg, or about 1125 mg, or about 1150 mg, or about 1175 mg, or about 1200 mg, or about 1225 mg, or about 1250 mg, or about 1275 mg, or about 1300 mg, or about 1325 mg, or about 1350 mg, or about 1375 mg, or about 1400 mg, or about 1425 mg, or about 1450 mg, or about 1475 mg, or about 1500 mg.

In some embodiments, the present invention relates to a method, use, or compound of the invention wherein the compound, or a tautomer thereof, or a pharmaceutically acceptable salt, ester, or prodrug of said compound or tautomer, is administered otically, ophthalmically, nasally, orally, parenterally, topically, or intravenously.

In some embodiments, the present invention relates to a method of synthesizing a compound of the invention, or a tautomer thereof, or a pharmaceutically acceptable salt, ester, or prodrug of said compound or tautomer.

In some embodiments, the present invention relates to a medical device containing a compound of the invention or a tautomer thereof, or a pharmaceutically acceptable salt, ester, or prodrug of said compound or tautomer. In some embodiments, the device is a stent.

3. SYNTHESIS OF THE COMPOUNDS OF THE INVENTION

The compounds of the present invention can be synthesized by using art recognized techniques, such as those described in US 2012-0220566 or WO 2012/173689, the contents of each of which are incorporated herein by reference in their entirety. The compounds thus obtained can be further purified, for example, by flash column chromatography, high performance liquid chromatography, crystallization, or any known purification method.

In one embodiment, the compounds of the present invention can be synthesized according to the synthetic Schemes 1-10 below:

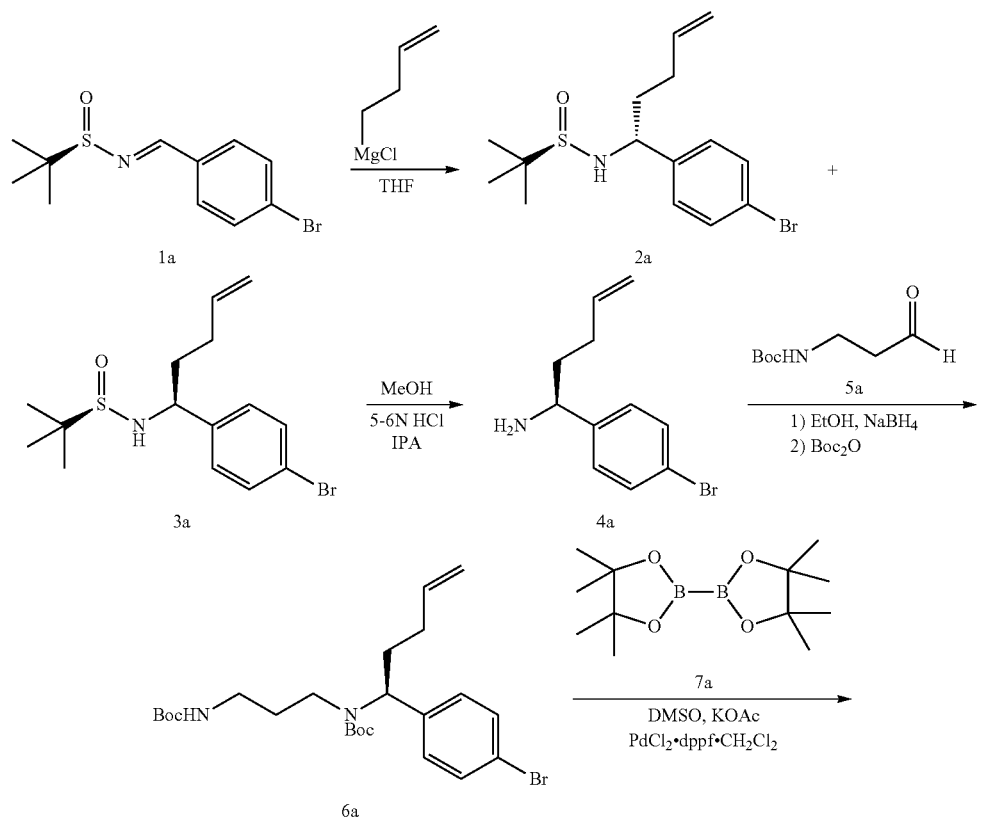

-continued
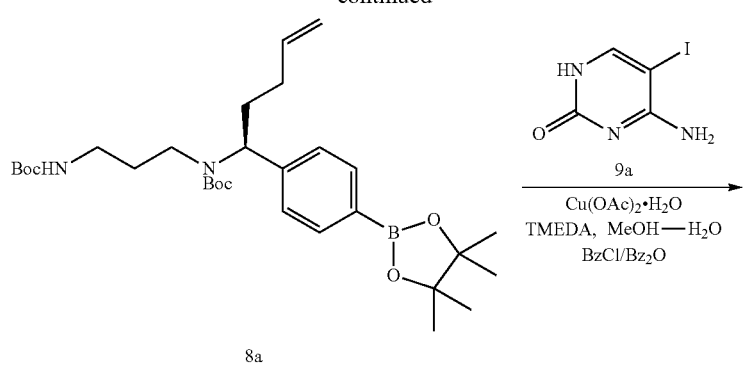
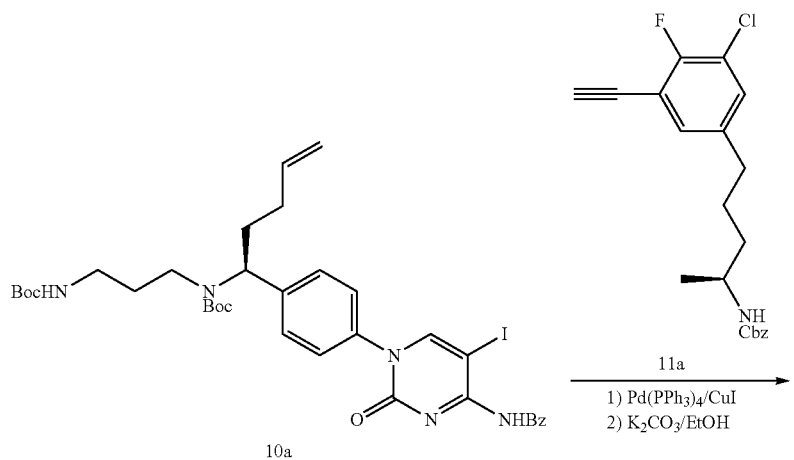
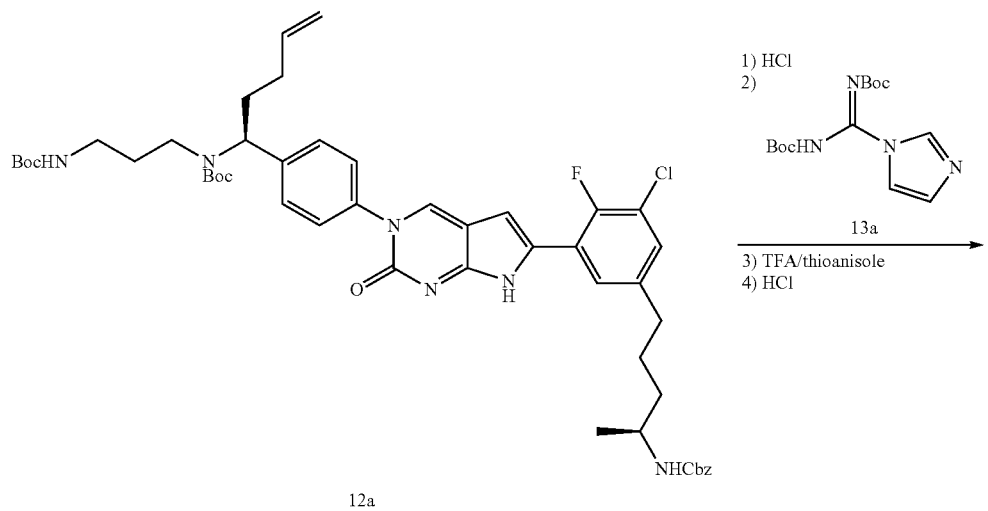

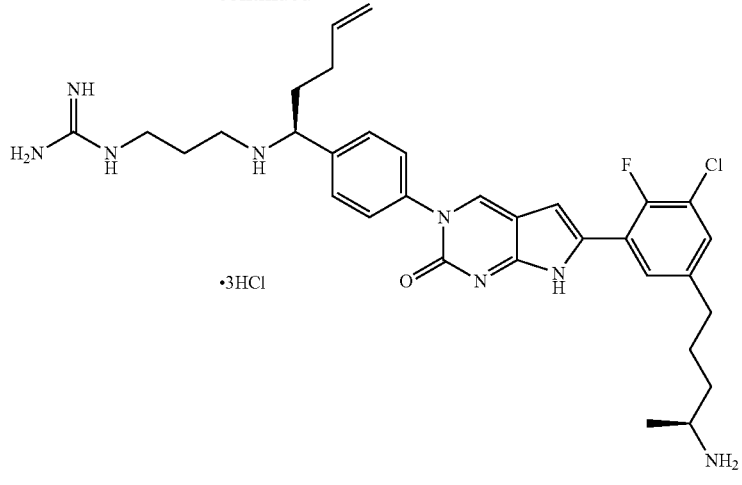

Compound 81

Pyridine para-toluenesulfonate and magnesium sulfate are added to a solution of (R)-(+)-2-methyl-2-propanesulfinamide and 4-bromobenzaldehyde in, e.g., dichloromethane. The resulting mixture is stirred overnight at, e.g., ambient temperature. The mixture is then be filtered, concentrated and purified by, e.g., flash chromatography over silica gel (5% ethyl acetate in dichloromethane) to yield compound 1a. A solution of compound 1a in tetrahydrofuran (THF) is then treated with 3-butenyl magnesium bromide at, e.g., −75° C. The resulting mixture is then slowly warmed up to, e.g., ambient temperature and, e.g., stirred overnight. The reaction is then quenched with saturated ammonium chloride solution and extracted with an organic solvent, e.g., ethyl acetate. The combined organic layers are then dried (with, e.g., anhydrous sodium sulfate), concentrated, and purified to afford 2a and 3a. Compound 3a in methanol is then treated with an acid, e.g., 5-6 N HCl in e.g., isopropanol (IPA) and/or methanol (MeOH) to afford amine 4a as a hydrochloride salt. Compound 4a is then further converted to Compound 81 (ESI, m/z 607.1 [M+H]$^+$) as shown Scheme 1 above using a method similar to that described in WO 2012/173689.

Scheme 2

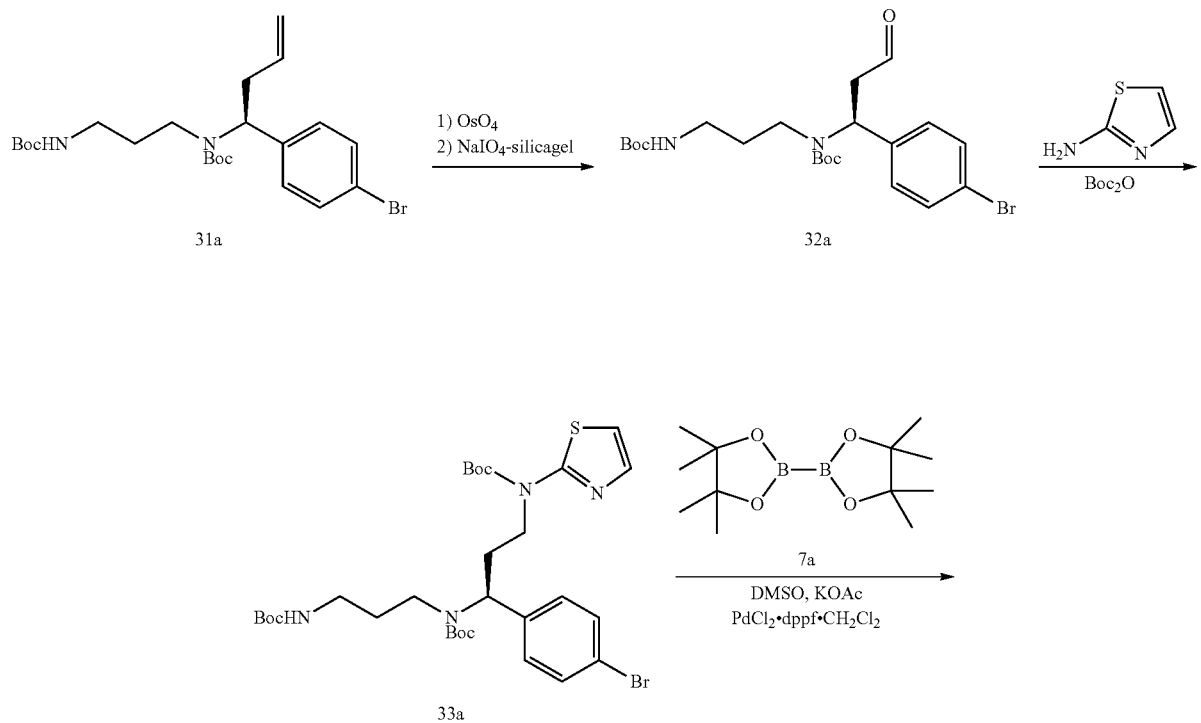

-continued
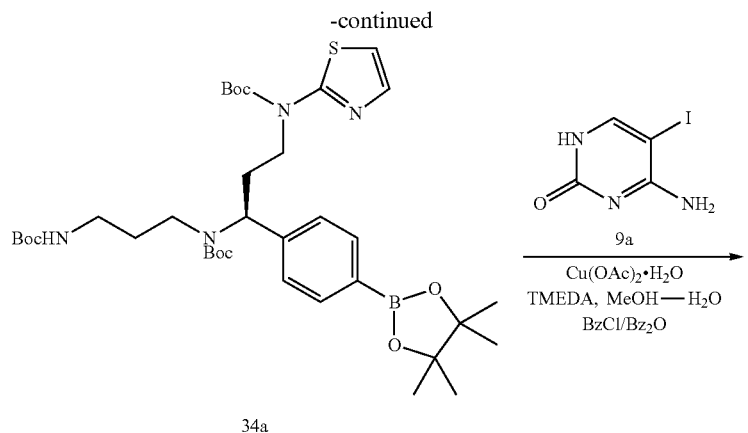
34a
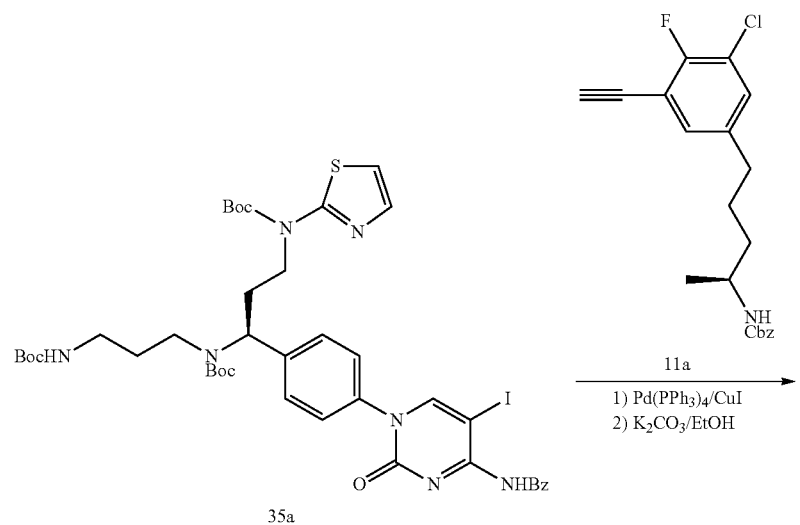
35a
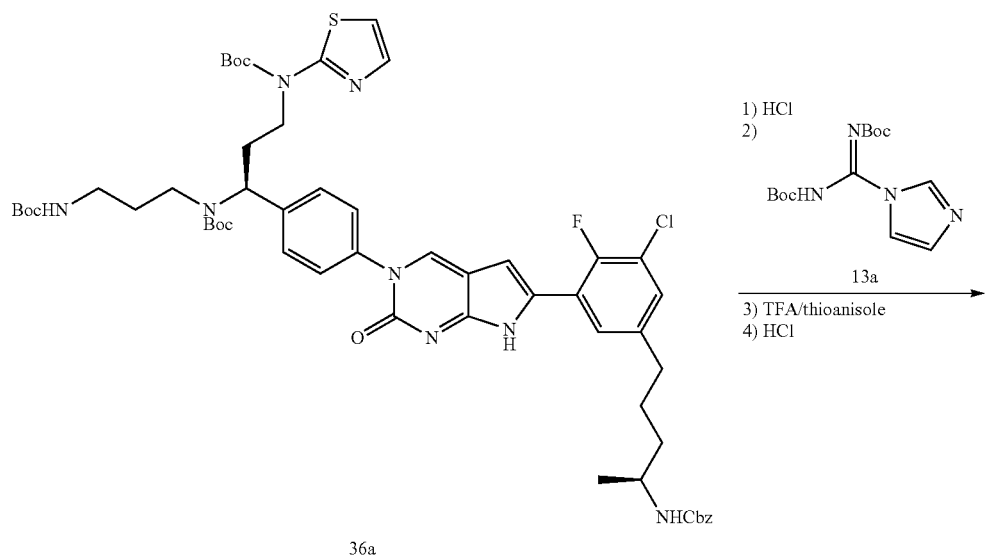
36a

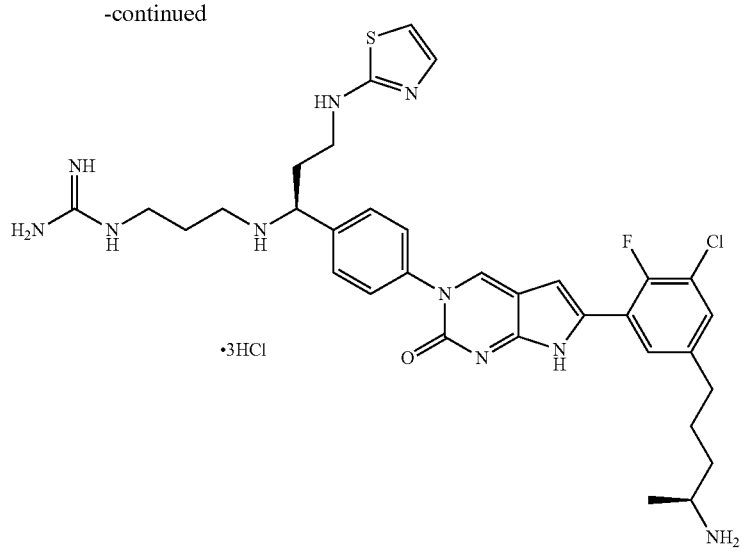

Compound 85

Compound 31a is synthesized using a method similar to that used to synthesize compound 6a in Scheme 1. Compound 31a is then converted to aldehyde 32a by oxidation, e.g., with osmium tetroxide and sodium periodate-silica gel ($OsO_4/SiO_2$). Reductive amination of aldehyde 32a with 2-amino thiazole followed by protection affords 33a. Intermediate 33a is then converted to Compound 85 (ESI, m/z 340.1 $[M+H]^{+2}$) using a method similar to that described in WO 2012/173689.

Scheme 3

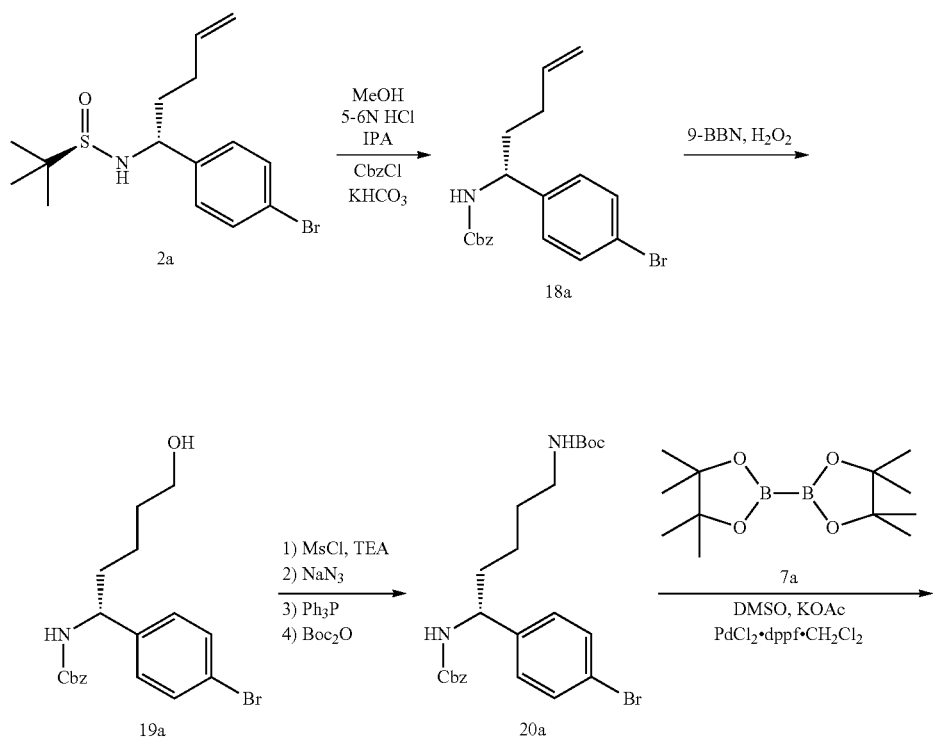

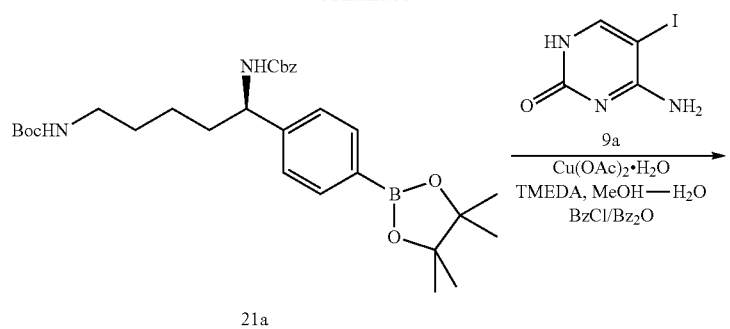
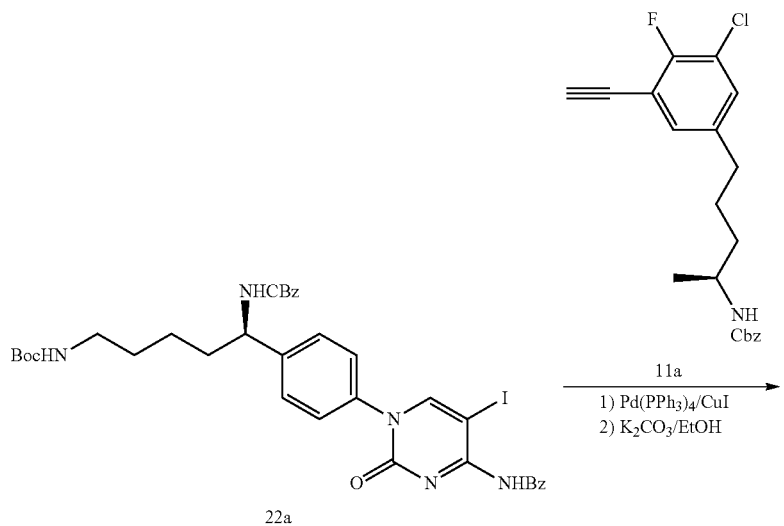
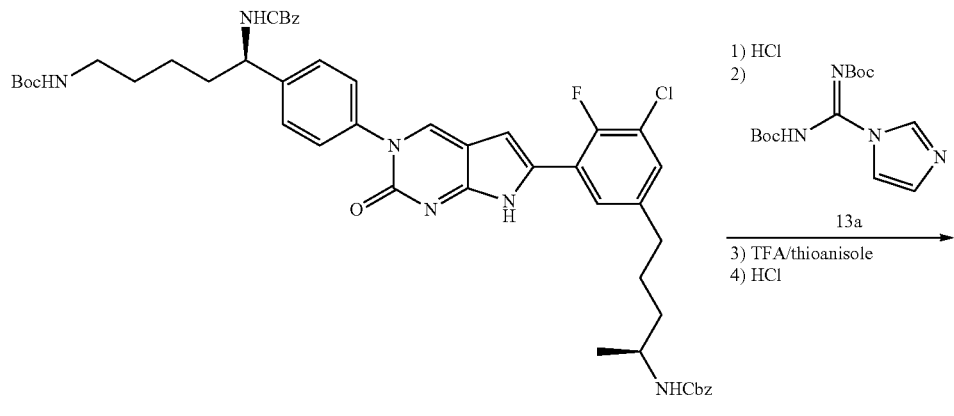

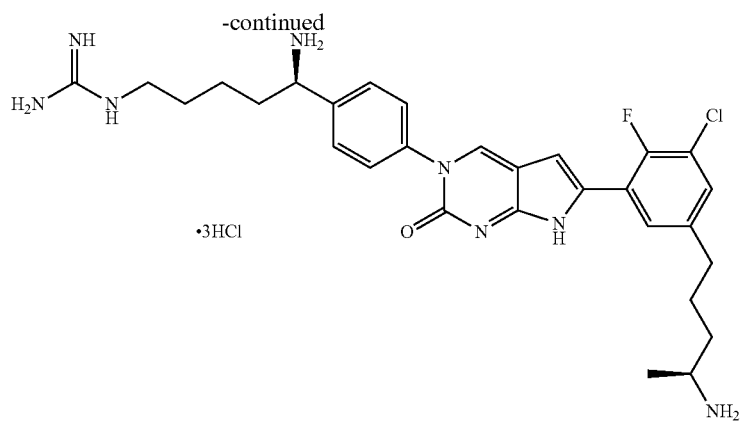

Compound 92

As shown in Scheme 3 above, compound 2a is treated with HCl in isopropanol, to afford the corresponding amine which is isolated as protected amine 18a. 9-BBN is then added to a solution of 18a in THF and the resulting mixture is stirred overnight at ambient temperature. The solution is then quenched with hydrogen peroxide ($H_2O_2$) and worked up to afford 19a. The alcohol 19a can then be converted to 20a using the standard synthetic protocol shown in Scheme 3. Compound 20a is then converted to Compound 92 (ESI, m/z 567.1 [M+H]$^+$) using a method similar to that described in WO 2012/173689.

Scheme 4

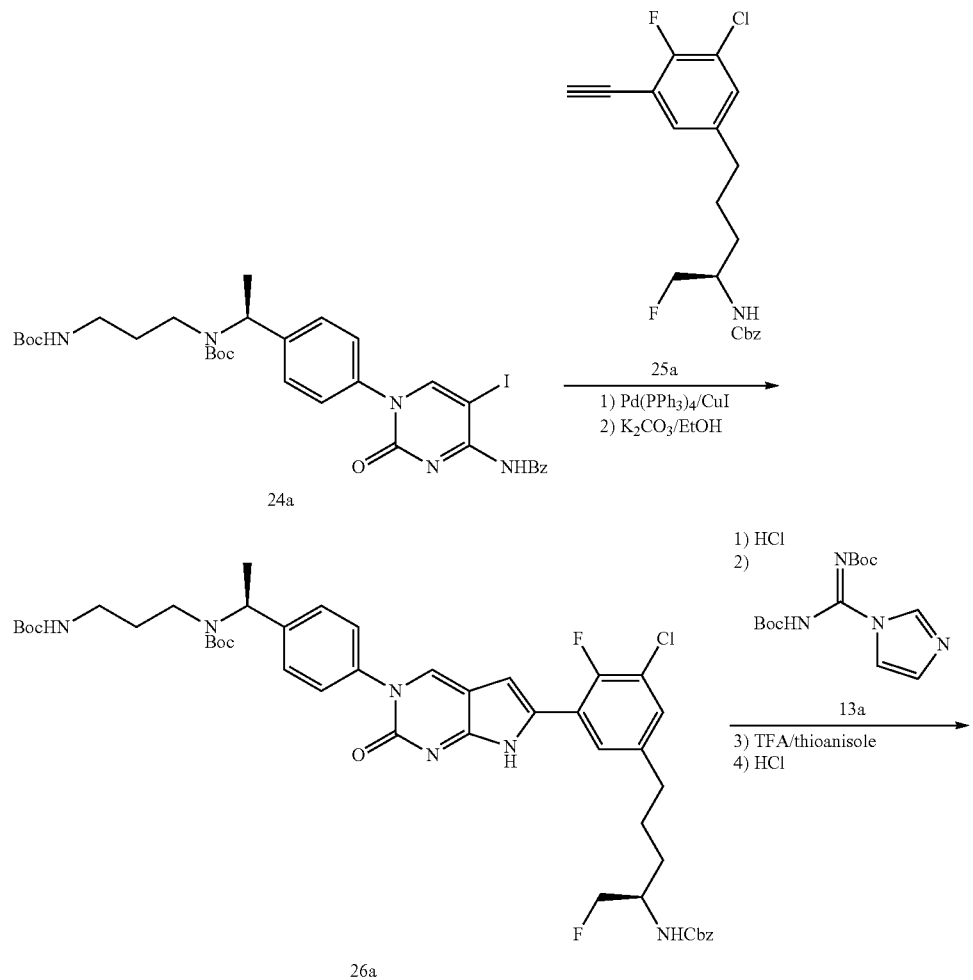

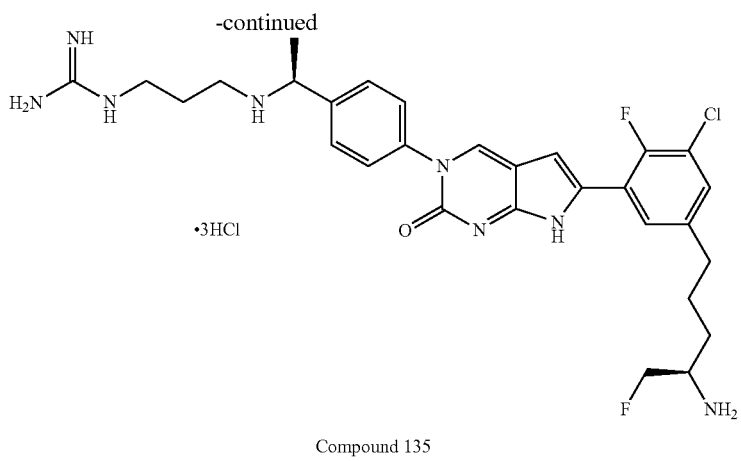

Compound 135

As shown in Scheme 4, intermediate 24a (synthesis of which is described in WO 2012/173689) is converted to Compound 135 (ESI, m/z 585.1 [M+H]$^+$) using a method similar to that described in WO 2012/173689. The alkyne derivative 25a can be made using the procedure shown in Scheme 5 below.

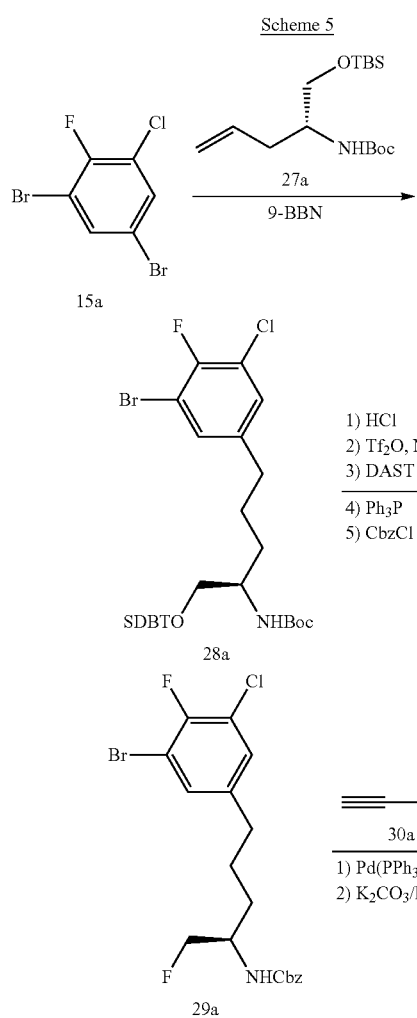

9-BBN is added to a solution of 27a in, e.g., toluene and THF and the resulting mixture is stirred, e.g., overnight at ambient temperature. The mixture is then concentrated, 15a in, e.g., toluene and 1N NaOH is then added followed by Pd(PPh$_3$)$_4$, and the resulting mixture is heated to, e.g., 60° C. for 24 hours. After standard work up and purification procedures, 28a is obtained. This intermediate is then treated with, e.g., 6N HCl to form the corresponding amino alcohol which is then treated with trifluoromethyl sulfonic anhydride and sodium azide to afford the corresponding azide. The azide is then treated with diethylaminosulfur trifluoride (DAST) followed by triphenyl phosphine and benzyl chloroformate (CbzCl) to afford 29a. The polyhalogenated derivative 29a is coupled with 30a as shown above to afford 25a.

Scheme 6
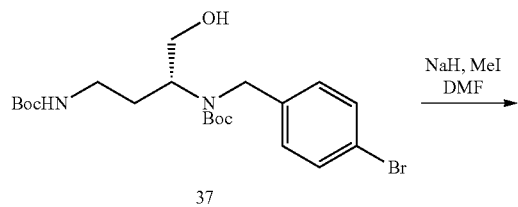
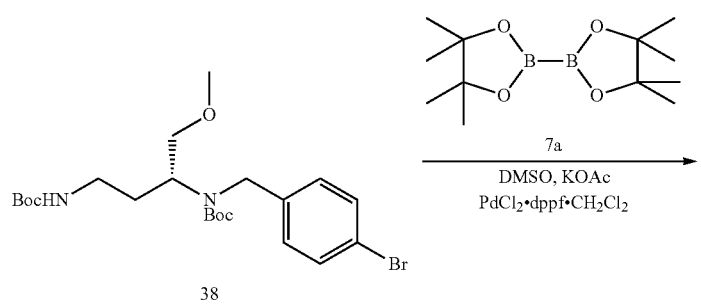
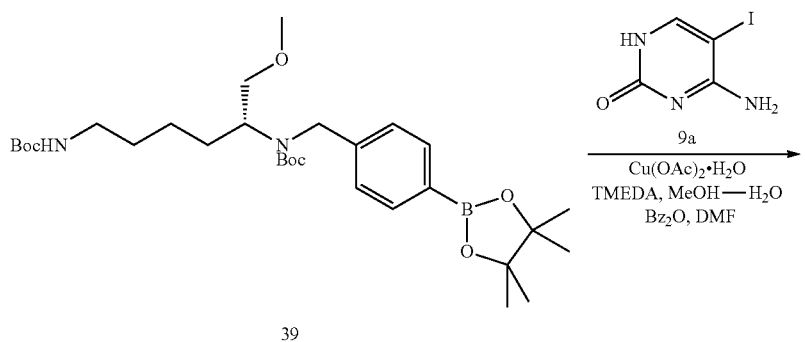
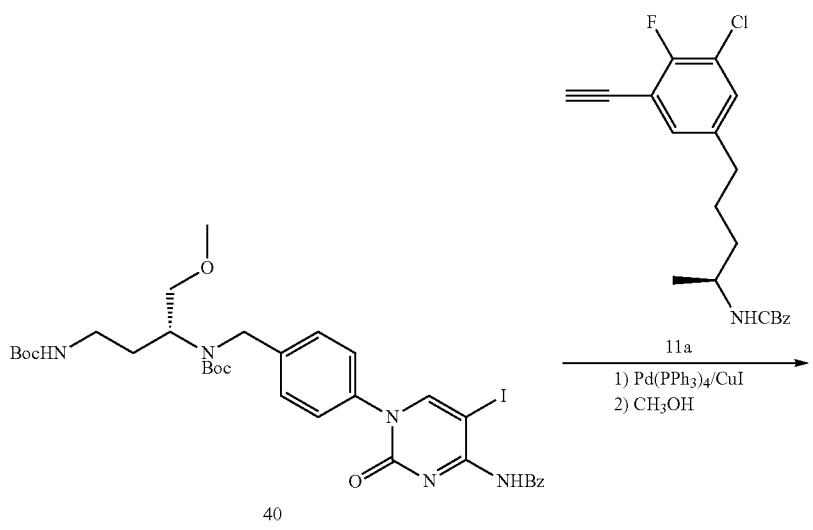

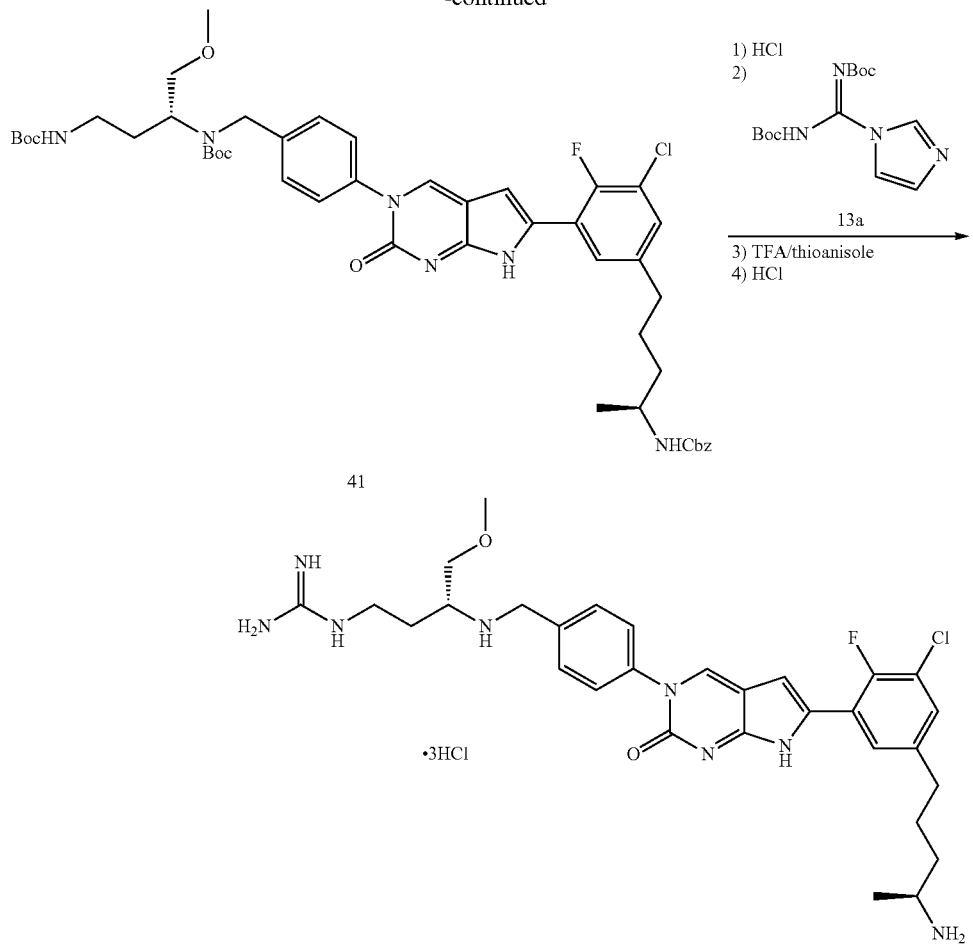

Compound 340

To a stirred solution of 37 in a solvent, e.g., DMF is added CH₃I at 0° C. followed by NaH. The resulting mixture is then warmed up to room temperature after which the reaction is slowly quenched with cold water and brine. The solution is extracted with EtOAc and the combined organic layers are washed with brine, dried, concentrated, and purified by, e.g., flash chromatography over silica gel to yield 38. A mixture of 38, bis(pinacolato)diborane 9a, Pd(dppf)Cl₂.CH₂Cl₂, and potassium acetate (KOAc) in, e.g., DMF is degassed and then heated to, e.g., 85° C. under an atmosphere of argon overnight. The mixture is then diluted with EtOAc, washed with water, dried over, e.g., MgSO₄, filtered, and concentrated. The crude product is purified by, e.g., flash chromatography over silica gel to afford 39. Cu(OAc)₂ is added to a mixture of 39, 4-amino-5-iodo-1H-pyrimidin-2-one 9a, in solvent, e.g., MeOH and H₂O, followed by N,N,N'N'-tetramethyl-ethane-1,2-diamine. The mixture is then stirred at room temperature under air for, e.g., 48 hours before concentrated to a volume of ca. 130 mL. The residue is partitioned between EtOAc and 20% NH₄OH in saturated NH₄Cl solution. The organic layer is separated and the aqueous layer is extracted with EtOAc. The combined organics are then washed with brine, dried and concentrated. This material is dissolved in, e.g., EtOAc, treated with benzoic anhydride, Et₃N and stirred for, e.g., 24 hours. The reaction mixture is then partitioned between EtOAc and saturated Na₂CO₃ solution. The organic layer is separated, dried, concentrated, and purified by, e.g., flash chromatography over silica gel to afford 40. Compound 40 and compound 11a are dissolved in, e.g., anhydrous DMF and the resulting solution is then purged with argon. CuI, Pd(PPh₃)₄, and Et₃N are then added and the resulting mixture is stirred at, e.g., 80-85° C. overnight. The mixture is then cooled to room temperature, CH₃OH and Et₃N are added, and the resulting mixture is stirred at, e.g., 80° C. for 6 hours. After cooling to ambient temperature, the mixture is partitioned between EtOAc and 20% NH₄OH in saturated NH₄Cl solution. The organic layer is separated, dried, concentrated, and purified by, e.g., preparative Thin Layer Chromatography to yield 41.

Intermediate 41 is dissolved in, e.g., CH₃OH and HCl and heated to, e.g., 40° C. for 5 hours. The reaction mixture is then concentrated to dryness, re-dissolved in CH₃OH and Hunig's base is added followed by 13a. The resulting mixture is stirred for, e.g., 24 hours at room temperature. The mixture is then partitioned between EtOAc and brine and the organic layer is separated, washed with water, dried, concentrated, and purified by, e.g., flash chromatography over silica gel. This material thus obtained is treated with thioanisole and TFA and heated to, e.g., 50° C. until the starting material disappears. The reaction mixture is then concentrated and purified by, e.g., a Shimadzu 10A-VP HPLC instrument using a Varian L4002 column (50 mm I.D.×300 mm) packed with 8 micron irregular C-18 coated silica. The pure fractions (by LCMS and/or HPLC assay) are collected and concentrated in vacuo. The residue is then treated with HCl/H$_2$O and concentrated almost to dryness. The latter step is repeated and the residue is dissolved in H$_2$O. MeCN is then added, and the mixture is lyophilized overnight affording desired compound 340 as the hydrochloride salt (3 HCl). (ESI, m/z 597.8 [M+H]$^+$).

Compounds 349 and 352 were made as illustrated in Scheme 7 below.

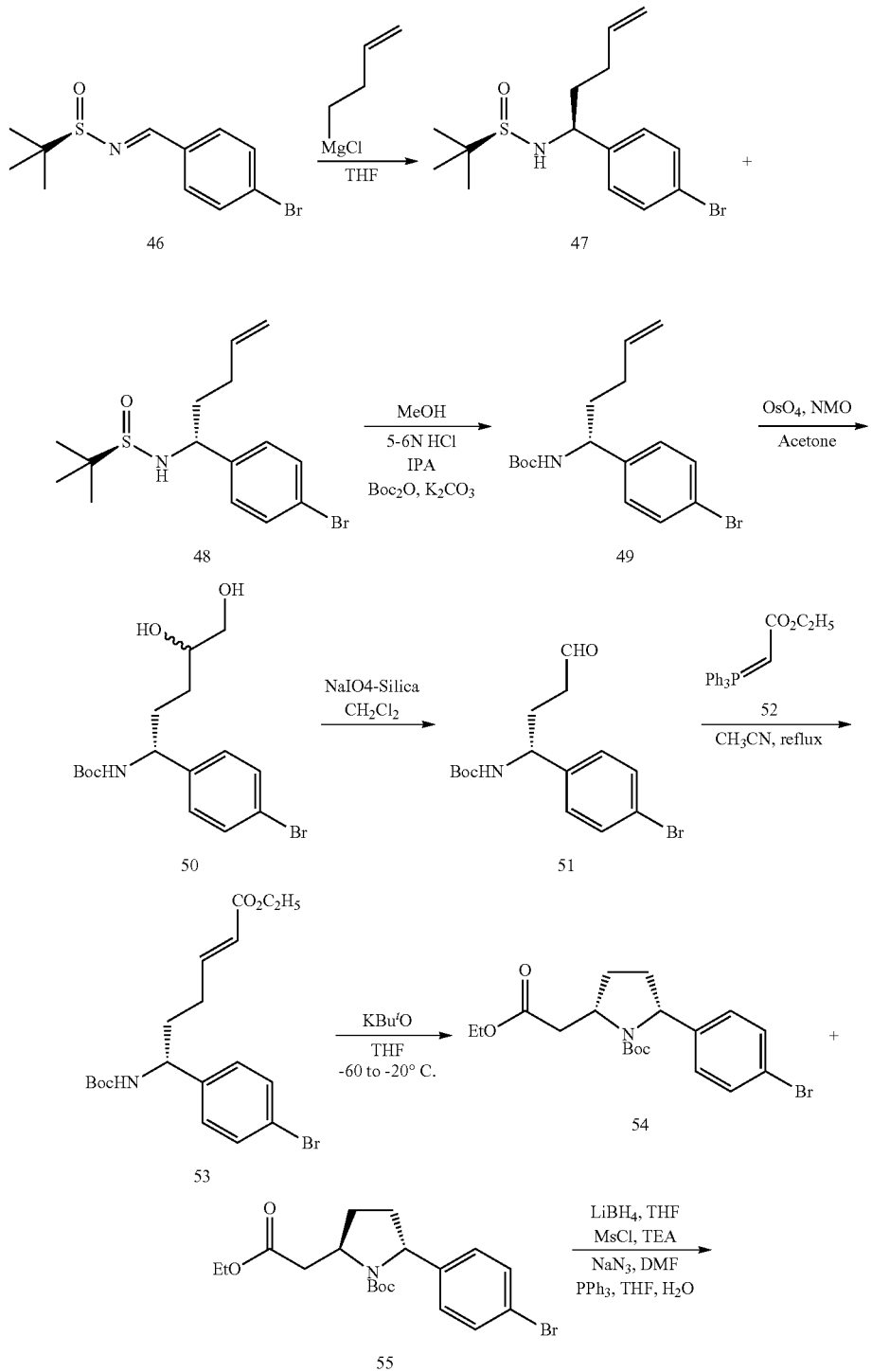

-continued
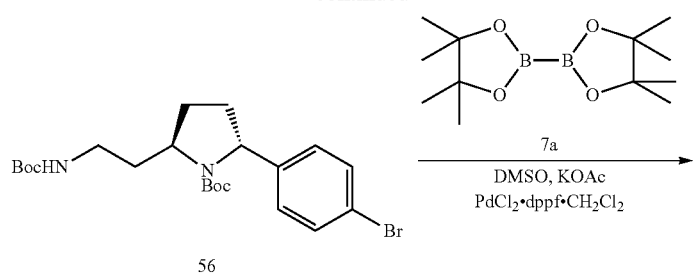
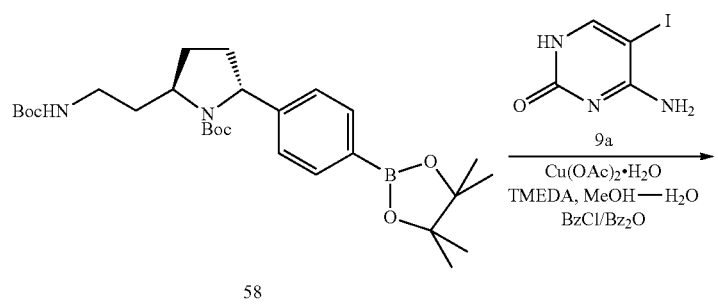
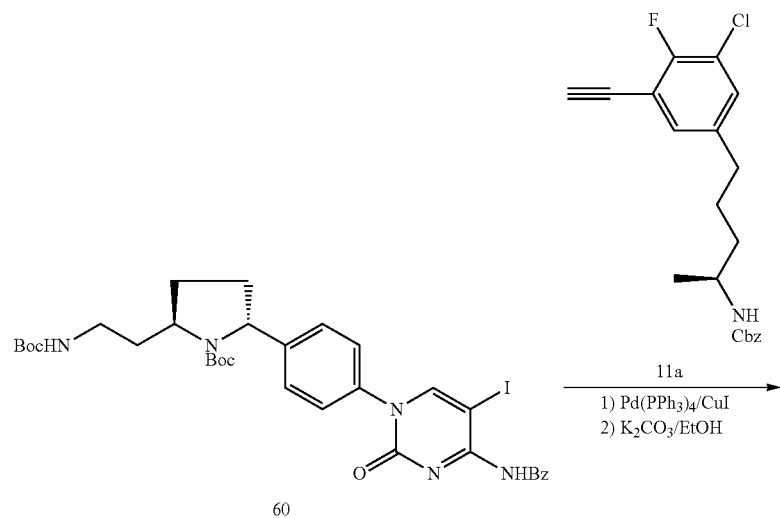
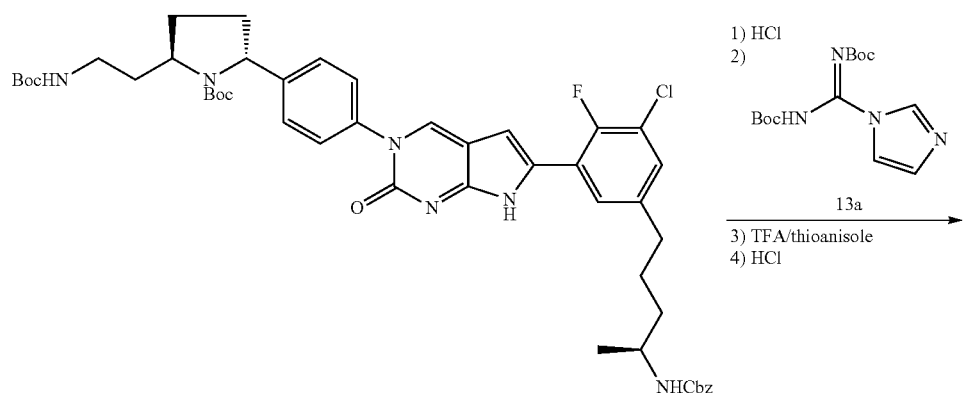

-continued

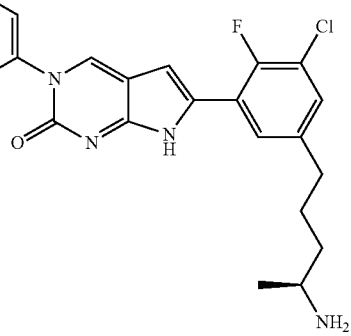

Compound 349

To a solution of (R)-(+)-2-Methyl-2-propanesulfinamide and 4-bromobenzaldehyde in, e.g., dichloromethane is added pyridine para-toluenesulfonate and magnesium sulfate and the resulting mixture is stirred overnight at, e.g., ambient temperature. The mixture is then filtered, concentrated, and purified by, e.g., flash chromatography over silica gel to afford compound 46. A solution of compound 46 in tetrahydrofuran is then treated with 3-butenyl magnesium bromide at, e.g., −75° C. The resulting mixture is slowly warmed up to ambient temperature and stirred overnight. The reaction is then quenched with saturated ammonium chloride solution, extracted with ethyl acetate and the combined organic layers are dried (with, e.g., anhydrous sodium sulfate), concentrated, and purified by, e.g., flash chromatography over silica gel to yield 47 and 48.

Compound 48 in methanol is treated with 5-6 N HCl in isopropanol to afford the intermediate amine which is then treated with a saturated solution of $K_2CO_3$ and with di-tert-butyl dicarbonate ($(Boc)_2O$) and stirred for, e.g., 72 hours. The resulting solution is then concentrated and extracted with EtOAc. The combined organic layers are washed with brine, dried, concentrated, and purified by, e.g., flash chromatography over silica gel to yield 49.

To a mixture of 49 and N-methyl morpholine oxide (NMO) is added acetone followed by osmium tetroxide ($OsO_4$) and the resulting mixture is stirred overnight at ambient temperature. The reaction mixture is then quenched with saturated of sodium thiosulphate solution, extracted with ethyl acetate, washed with brine, dried, concentrated, and purified by, e.g., flash chromatography over silica gel to afford 50 quantitatively. A mixture of 50 and sodium periodate-silica gel ($NaIO_4$—$SiO_2$) in $CH_2Cl_2$ is stirred for, e.g., 5 hours, filtered, and, concentrated to afford 51. A mixture of 51 and Wittig salt 52 is placed in a sealed tube with $CH_3CN$ and heated to reflux for, e.g., 72 hours. The solution is then concentrated, extracted with EtOAc, washed with brine, dried, and purified by, e.g., flash chromatography over silica gel to afford 53.

To a solution of 53 in, e.g., THF cooled in an acetone-dry ice bath −60° C. is added potassium tert-butoxide ($KO^tBu$) in one portion and the resulting mixture is stirred at, e.g., −60° C. The acetone-dry ice bath temperature is allowed to warm to, e.g., ~−20° C. and it is maintained at ~−20° C. by addition of dry ice as required. After 2 hours of stirring at that temperature, the reaction is quenched by the addition of water and the resulting solution is allowed to warm to room temperature. The reaction mixture is then diluted with, e.g., ether, the layers are separated, and the aqueous layer is extracted with ethyl acetate. The combined organic layers are then dried over, e.g., anhydrous $Na_2SO_4$, filtered, and concentrated afford a pale yellow crude viscous liquid which is purified using, e.g., Combiflash chromatography to afford 54 and 55.

To a solution of 55 in THF cooled in ice bath is added $LiBH_4$ in one portion and the resulting solution is allowed to warm to room temperature and stir under an atmosphere of argon. If the reaction is not complete by LC/MS (liquid chromatography/mass spectroscopy), additional $LiBH_4$ can be added to push the reaction to completion. Upon reaction completion, the reaction is cooled in ice bath and slowly quenched by the slow addition of ice and HCl solution (*caution: add HCl very slowly as there is exothermic reaction with vigorous effervescences). The reaction mixture is then extracted with EtOAc and the combined organic layers are dried over anhydrous $Na_2SO_4$, filtered and concentrated to afford a pale yellow viscous liquid (the alcohol) which can be used in next step without any further purification.

The primary alcohol is dissolved in, e.g., $CH_2Cl_2$ and $Et_3N$ is added. The mixture is cooled in ice bath (e.g., 0° C.) and MsCl is added. The resulting solution is allowed to warm to room temperature and stirred for, e.g., 24 hours under argon (additional equivalents of MsCl and $Et_3N$ are added if necessary to push the reaction to completion; reaction monitored by LC/MS and TLC). The reaction is then quenched with cold water, the layers are separated and the aqueous layer is extracted with $CH_2Cl_2$. The combined organic layers are then dried over anhydrous, e.g., $Na_2SO_4$ and concentrated on to afford the mesylate which can be used for next step without any further purification.

A solution of the mesylate obtained in the prior step and $NaN_3$ in DMF is heated to, e.g., 70-75° C. in an oil bath under an atmosphere of argon. Once LC/MS shows complete conversion of starting material, the reaction mixture is cooled to room temperature, diluted with water, and extracted with EtOAc. The combined organic layers are then dried (e.g., $Na_2SO_4$) and concentrated to afford a viscous liquid (the azide) which can be used in next step without any further purification.

To solution of the crude azide in THF and water at room temperature is added triphenylphosphine and the resulting mixture is heated to, e.g., 60-65° C. in an oil bath for, e.g., 16 hours (monitored by LC/MS for conversion of starting material). Once reaction is complete, the heating is stopped and the reaction mixture is cooled to room temperature. Saturated NaHCO₃ solution and EtN$^i$Pr₂ is added followed by di-tert-butyl dicarbonate ((Boc)₂O) and the resulting mixture is heated to, e.g., 45-50° C. in oil bath for, e.g., 46 hours. The reaction mixture is then cooled to room temperature, diluted with water and EtOAc, and the layers are separated. The aqueous layer is extracted with EtOAc and the combined organic layers are dried (e.g., Na₂SO₄) and concentrated to afford a viscous liquid which is purified using, e.g., Combiflash chromatography to afford 56.

To a solution of 56 in DMSO under an atmosphere of argon is added bispinacalatodiborane 7a and potassium acetate (KOAc) followed by PdCl₂(dppf).CH₂Cl₂. The resulting mixture is heated with stirring under an atmosphere of argon to, e.g., 80-85° C. for, e.g., 20 hours. Once LC/MS shows reaction completion, the reaction mixture is cooled to room temperature, diluted with water and 60-70% EtOAc in heptane. The layers are then separated and the aqueous layer is extracted with 60% EtOAc in heptane. The combined organic layers are dried (e.g., Na₂SO₄) and concentrated to provide a dark brown viscous liquid which is purified using, e.g., Combiflash chromatography to afford 58.

To a solution of 58 in, e.g., MeOH:H₂O is added iodocytosine, 9a, followed by Cu(OAc)₂, H₂O and TMEDA. The resulting solution is stirred at room temperature and air is bubbled very slowly through reaction mixture. After stirring for, e.g., 19 hours at room temperature, the reaction mixture is concentrated to remove any MeOH and diluted with water. The CH₂Cl₂, layers are separated and the aqueous later is extracted two more times with CH₂Cl₂. The combined organic layers are then dried (e.g., anhydrous Na₂SO₄) and concentrated to afford the coupled product which can be used in next step without further purification.

To a solution in EtOAc is added Bz₂O and the resulting solution is heated in an oil bath to, e.g., 70-75° C. under argon atmosphere for, e.g., 3 hours. Once LC/MS shows reaction completion, the reaction mixture is cooled to room temperature and diluted with saturated NaHCO₃ solution. The layers are separated and the aqueous layer is extracted with EtOAc. The combined organics are then dried (e.g., Na₂SO₄) and concentrated to provide a viscous liquid which is purified using, e.g., Combiflash chromatography to afford 60.

To a degassed solution of 60 in DMF under an atmosphere of argon is added alkyne 11a and EtN$^i$Pr₂ followed by Pd(PPh₃)₄ and CuI. The resulting solution is flushed with argon and heated to, e.g., 70-75° C. with stirring under an atmosphere of argon for, e.g., 16 hours. Once LC/MS shows complete conversion of 60, the reaction mixture is cooled to room temperature and MeOH is added. The resulting solution is then heated under argon to, e.g., 75-80° C. for, e.g., 9 hours (and checked by LC/MS for complete conversion of intermediate). The reaction mixture is cooled to room temperature, concentrated to remove MeOH, and diluted with water. The EtOAc layer is separated and the organic layer is extracted once with EtOAc. The combined organic layers are washed with NH₄OH, water and brine, dried (e.g., Na₂SO₄), and concentrated to provide a dark brown viscous liquid which is purified by using, e.g., prep TLC to afford protected intermediate 62.

To a solution of 62 in CH₂Cl₂ is added an acid, e.g., 4N solution of HCl in dioxane and the resulting solution is stirred at room temperature for, e.g., 2 hours. Once LC/MS shows complete conversion of starting material, the reaction mixture is concentrated and dried under vacuum to provide the deprotected amine intermediate as a foam which can be used in next step without any further purification.

To a solution of the deprotected amine intermediate in MeOH at room temperature is added EtN$^i$Pr₂ and bis-boc-guanylpyrazole 13a and the resulting reaction mixture is stirred at room temperature. Once LC/MS shows reaction completion, the reaction mixture is concentrated to afford a viscous liquid which can be used in next step without any further purification.

To a solution of the above compound in trifluoroacetic acid is added thioanisole and the resulting mixture is stirred with heating to, e.g., 45° C. in an oil bath for, e.g., 3 hours. Once LC/MS shows reaction completion, the reaction mixture is cooled to room temperature, concentrated, and purified using, e.g., Varian prep HPLC. HPLC fractions are collected and concentrated and the obtained TFA salt is converted to the HCl salt by treatment with, e.g., 6 N HCl (2×). The resulting solid is then lyophilized to afford 349.

Scheme 8

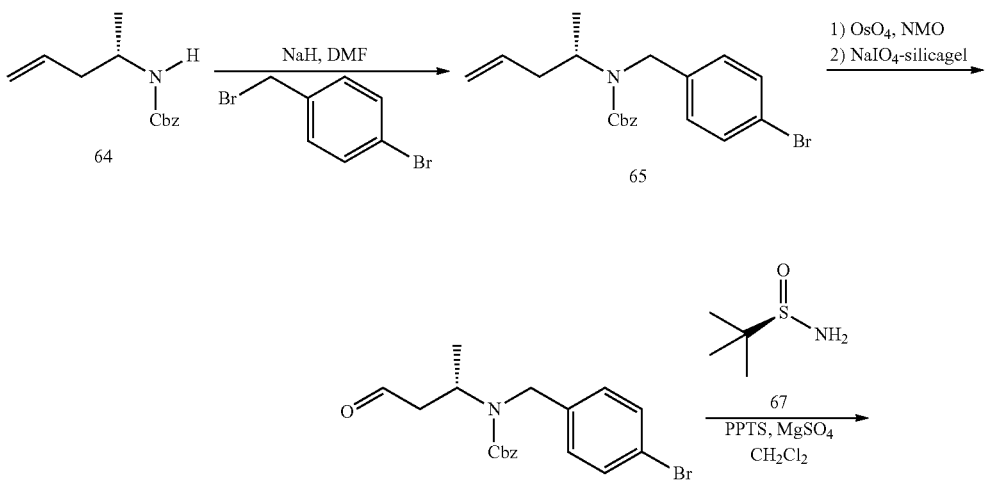

-continued
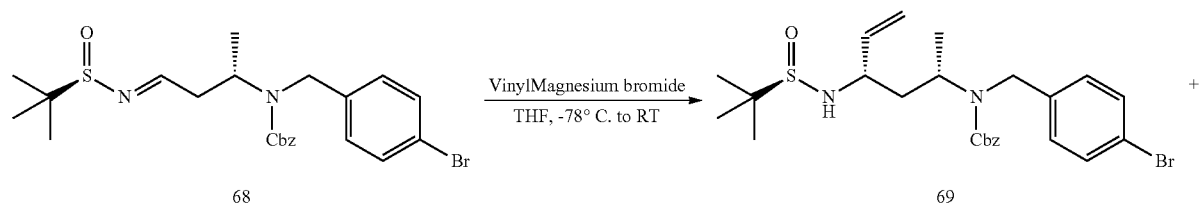
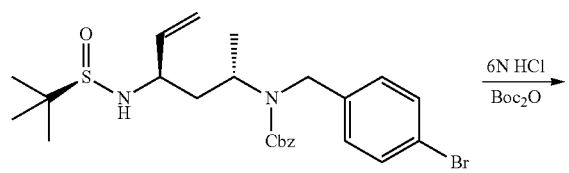
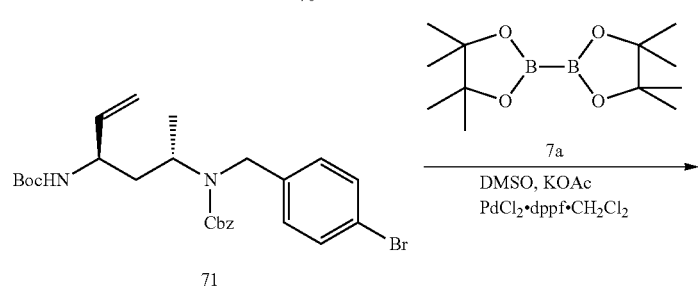
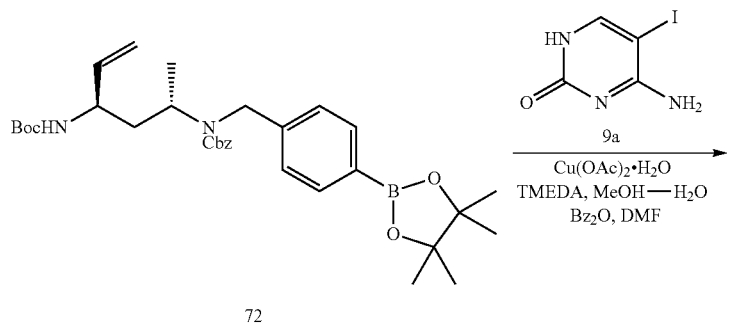
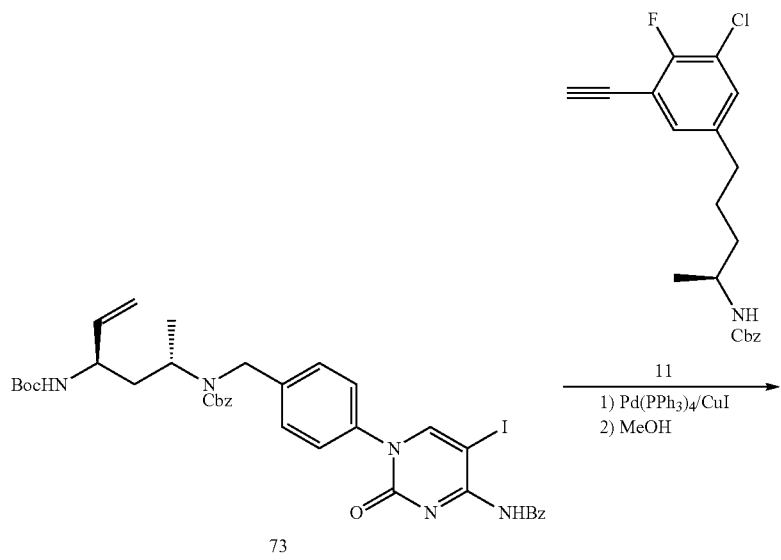

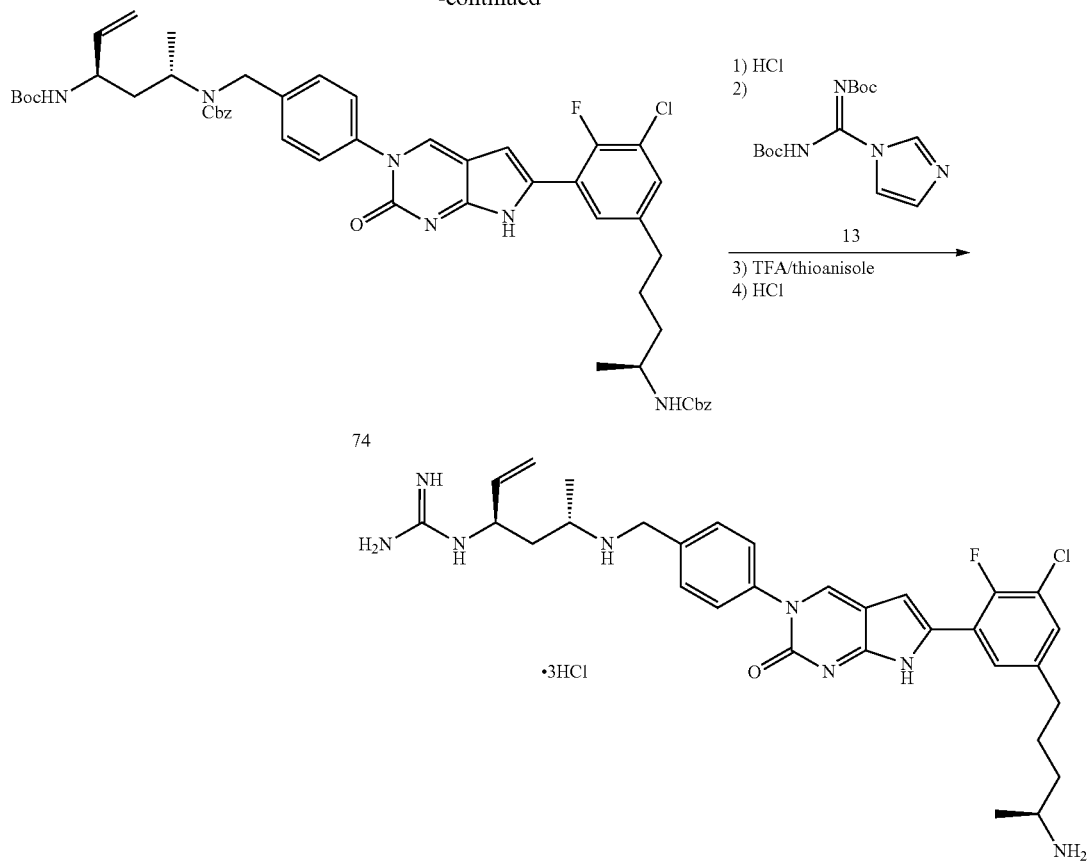

Compound 336

To a solution of (1-methyl-but-3-enyl)-carbamic acid benzyl ester 64 in DMF is added NaH at, e.g., 0° C. and the resulting mixture is stirred for, e.g., 30 minutes. The solution is then slowly warmed up to ambient temperature after which 4-bromo benzyl bromide is added and the mixture is stirred overnight under an inert atmosphere. The mixture is then partitioned between EtOAc and brine and the organic layer is separated. The aqueous layer is extracted with EtOAc and the combined organic layers are dried with anhydrous Na$_2$SO$_4$, concentrated under reduced pressure and purified by, e.g., flash chromatography over silica gel to yield (4-bromo-benzyl)-(1-methyl-but-3-enyl)-carbamic acid benzyl ester 65. A solution of 65 in acetone is then treated with OsO$_4$ followed by N-methyl morpholine N-oxide and stirred at ambient temperature overnight. The reaction is quenched with saturated Na$_2$S$_2$O$_3$ solution in water and extracted with EtOAc. The combined organic layers are washed with water, dried with, e.g., anhydrous Na$_2$SO$_4$, evaporated to dryness and purified by, e.g., flash chromatography over silica gel. This material is then dissolved in CH$_2$Cl$_2$ and treated with NaIO$_4$-silica gel reagent. Once starting material is consumed (e.g., 2 hours), the resulting solution is filtered and concentrated to provide a 66, (4-bromo-benzyl)-(1-methyl-3-oxo-propyl)-carbamic acid benzyl ester, which can be used in the next step without further purification.

A mixture of 66, (R)-(+)-2-methyl-2-propanesulfinamide, pyridine para-toluene sulfonate, and MgSO$_4$ is stirred vigorously in CH$_2$Cl$_2$ at ambient temperature overnight. The reaction mixture is then partitioned between CH$_2$Cl$_2$ and water and the organic layer is separated. The aqueous layer is then extracted with CH$_2$Cl$_2$ and the combined organic layers are washed with brine, dried with, e.g., anhydrous Na$_2$SO$_4$, and evaporated to afford 68, (4-bromobenzyl)-[1-methyl-3-(2-methyl-propane-2-sulfinylimino)-propyl]-carbamic acid benzyl ester.

Vinyl magnesium bromide is added drop wise to solution of 68 in, e.g., THF at, e.g., −78° C. and stirred at that temperature until starting material disappears. The solution is then warmed up to 0° C. and quenched with NH$_4$Cl solution. The resulting mixture is extracted with EtOAc, dried with, e.g., anhydrous Na$_2$SO$_4$, concentrated under reduced pressure, and purified by, e.g., flash chromatography over silica gel to afford 69, (4-bromobenzyl)-[1-methyl-3-(2-methyl-propane-2-sulfinylimino)-pent-4-enyl]-carbamic acid benzyl ester and isomeric 70. The isomer 70 is dissolved in CH$_3$OH and stirred with 5-6 N HCl (in, e.g., 2-propanol) at ambient temperature (for, e.g., 4 hours). The solution is then concentrated and re-dissolved in THF and water. To this solution is added K$_2$CO$_3$ and di-tert-butyl dicarbonate ((Boc)$_2$O) and the resulting mixture is stirred at ambient temperature overnight. The reaction mixture is then concentrated and partitioned between EtOAc and water. The organic layer is separated, washed with brine, dried and concentrated to afford 71. A mixture of 71, bis(pinacolato) diborane 7a, Pd(dppf)Cl$_2$.CH$_2$Cl$_2$, potassium acetate (KOAc) in DMSO is degassed and heated to, e.g., 85° C. under an atmosphere of argon overnight. The mixture is diluted with EtOAc, washed with water, dried over, e.g., MgSO₄, filtered and concentrated. The crude product is then purified by, e.g., flash chromatography over silica gel to afford 72.

Cu(OAc)₂ is added to a mixture of 72, 4-amino-5-iodo-1H-pyrimidin-2-one 9a, CH₃OH and H₂O followed by N,N,N',N'-tetramethyl-ethane-1,2-diamine and the resulting mixture is stirred at room temperature under air for, e.g., 48 hours before it is concentrated to a volume of ca. 130 mL. The residue is then partitioned between EtOAc and 20% NH₄OH in saturated NH₄Cl solution, the organic layer is separated, and aqueous layer is extracted with EtOAc. All of the organic layers are combined and washed with brine, dried, and concentrated. This material is then dissolved in DMF and treated with benzoic anhydride and stirred for, e.g., 72 hours at room temperature. The reaction mixture is then partitioned between EtOAc and saturated Na₂CO₃ solution. The organic layer is separated, dried, concentrated and purified by flash chromatography over silica gel to afford 73. Compound 73 and compound 11a are dissolved in anhydrous DMF. The solution is purged with argon, and then CuI, Pd(PPh₃)₄, and Et₃N are added and the resulting mixture is stirred at, e.g., 80-85° C. overnight. The solution is then cooled to room temperature, CH₃OH is added and the mixture is stirred again at, e.g., 85° C. for 3 hours. After cooling to ambient temperature, the mixture is partitioned between EtOAc and 20% NH₄OH in saturated NH₄Cl solution. The organic layer is separated, dried, concentrated and purified by, e.g., flash chromatography over silica gel to yield 74.

74 is dissolved in ethanol and 6N HCl and heated to, e.g., 65° C. for, e.g., 1 hour. The reaction mixture is then concentrated to dryness, re-dissolved in CH₃OH and Hunig's base after which 13a is added and the resulting mixture is stirred for, e.g., 96 hours at room temperature. The solution is then partitioned between EtOAc and brine. The organic layer is separated, washed with water, dried, concentrated, and purified by, e.g., flash chromatography over silica gel. This material thus obtained is treated with thioanisole and TFA and heated to 50° C. until the starting material disappears. The reaction mixture is then concentrated and purified. The pure fractions are collected and concentrated in vacuo and the resulting residue is treated with 1.0 N HCl/H₂O and concentrated almost to dryness. The latter step is repeated. The residue is then dissolved in H₂O, CH₃CN is added, and the resulting mixture is lyophilized overnight affording desired compound 336×3 HCl salt.

Compounds 353 and 357 were made as shown in Schemes 9 and 10 below.

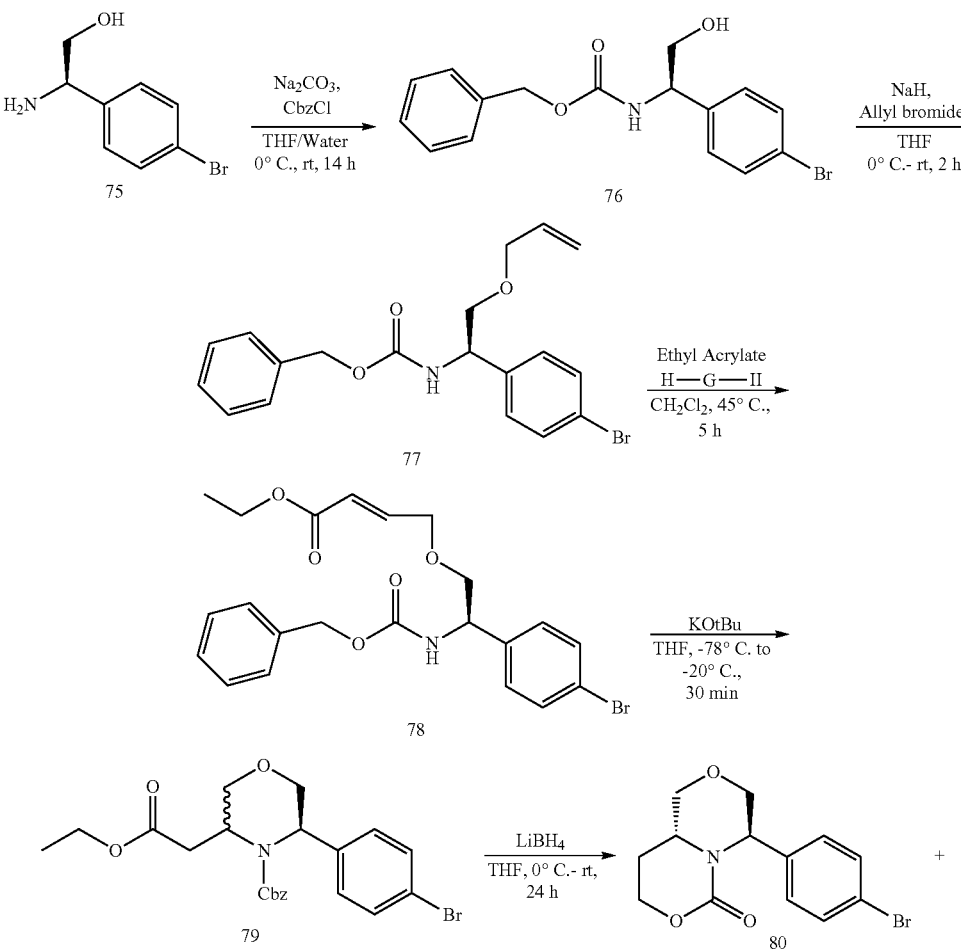

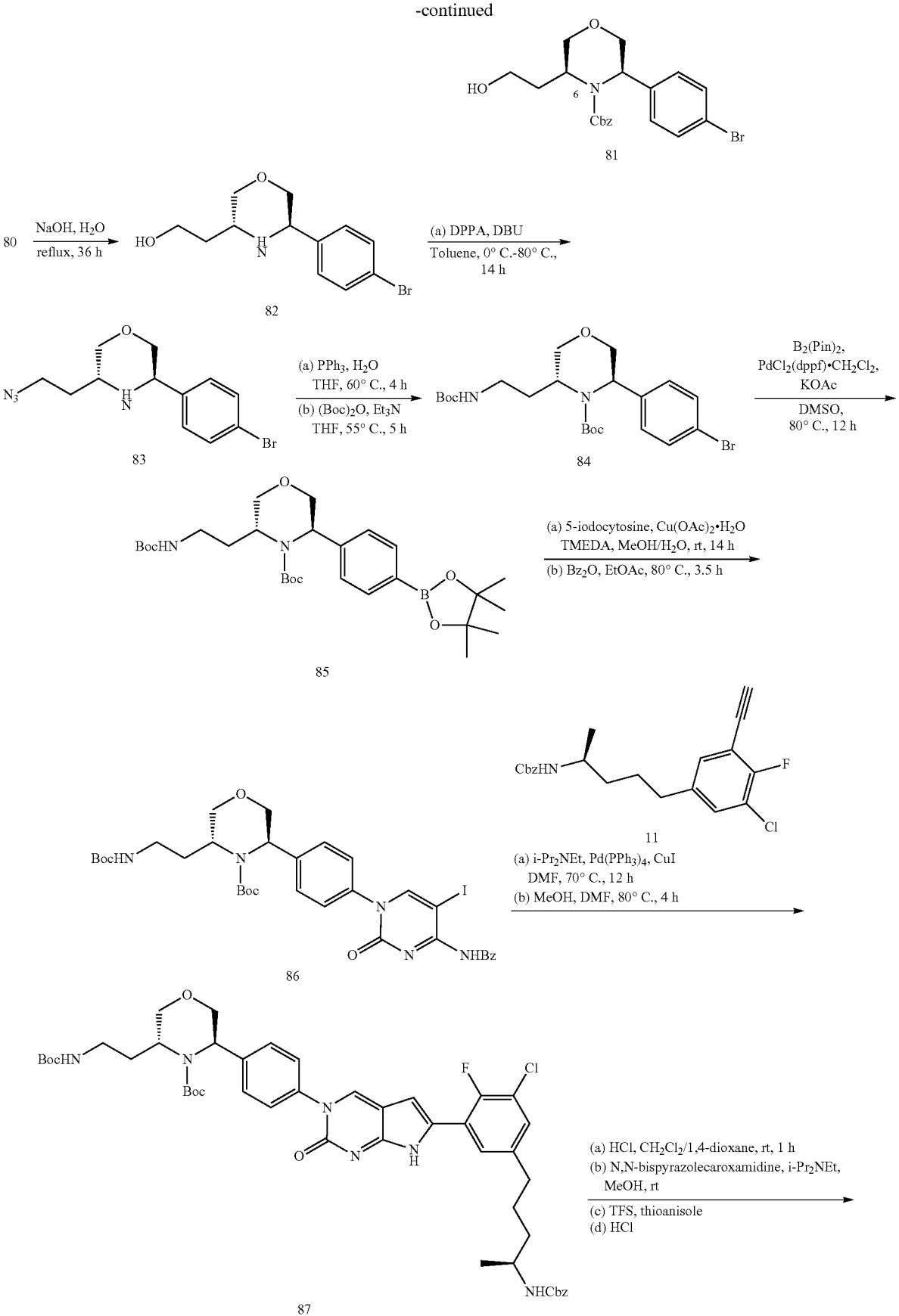

-continued

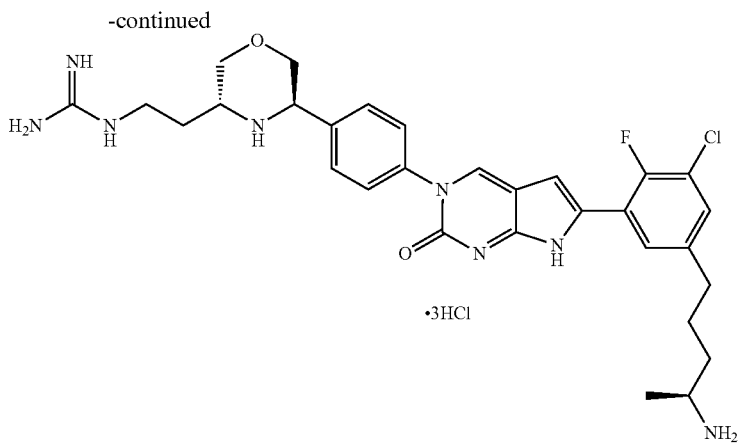

Compound 353

To the solution of 2-Amino-2-(4-bromo-phenyl)-ethanol in, e.g., THF is added a saturated sodium bicarbonate solution followed by benzyl chloroformate (CbzCl). The reaction mixture is stirred at room temperature for, e.g., 14 hours. Ethyl acetate is then added and the organic layer is separated, washed with brine, dried over MgSO$_4$ and concentrated to afford 76.

To a stirring solution of [1-(4-Bromo-phenyl)-2-hydroxyethyl]-carbamic acid benzyl ester (76) in, e.g., anhydrous DMF at, e.g., 0° C. under an atmosphere of argon is added allyl bromide and the resulting mixture is stirred for, e.g., 15 min. Sodium tert-butoxide (NaO$^t$Bu) is then added in 5 portions over a, e.g., 2 min interval. The mixture is then stirred for, e.g., 2 hours at 0° C. Ice is then added to the reaction mixture. The cooling bath is removed and the mixture is extracted with ethyl acetate. The combined organic layers are then washed with brine, dried over, e.g., Na$_2$SO$_4$, concentrated, and purified by, e.g., flash column chromatography. Fractions are collected, combined and concentrated to obtain 77.

To stirred solution of 4-[2-Benzyloxycarbonylamino-2-(4-bromo-phenyl)-ethoxy]-but-2-enoic acid ethyl ester (77) in, e.g., anhydrous dichloromethane under an atmosphere of argon is added ethyl acrylate and the resulting mixture is stirred for, e.g., 15 minutes. Hoveyda-Grubbs-II catalyst (H-G-II) is then added and the mixture is stirred at, e.g., 45° C. for 3 hours. An additional amount of Hoveyda-Grubbs-II catalyst is then added and the reaction is stirred for, e.g., 2 hours at 45° C. Once, e.g., LCMS shows complete consumption of starting material 77 and formation of 78, the mixture is cooled down, the solvent is evaporated and the product is purified by, e.g., flash chromatography. The fractions are combined and concentrated to obtain 78.

To a solution of 4-[2-Benzyloxycarbonylamino-2-(4-bromo-phenyl)-ethoxy]-but-2-enoic acid ethyl ester (78) in anhydrous THF at, e.g., −78° C. under an atmosphere of argon is added potassium tert-butoxide (KO$^t$Bu) and the resulting mixture is stirred for 30 min. The cooling bath is then removed and the reaction mixture is allowed to warm up to, e.g., −20° C. (over, e.g., 30 min). Once, e.g., LCMS shows complete consumption of 78 and formation of the product 79, ice is added followed by water. The aqueous phase is extracted with ethyl acetate and the combined organic phases are washed with brine, dried over sodium sulfate, concentrated, and purified by, e.g., flash chromatography to afford 79.

To the solution of 3-(4-Bromo-phenyl)-5-ethoxycarbonyl-methyl-morpholine-4-carboxylic acid (79) in anhydrous THF is added LiBH$_4$ at, e.g., 0° C. under an atmosphere of argon and the resulting mixture is stirred at, e.g., 0° C. for, e.g., 2 hours. The cooling bath is removed and the reaction mixture is then stirred overnight (e.g., ~14 hours). Once, e.g., LCMS shows complete disappearance of the ester, the mixture is cooled to 0° C. and 20 ml of water is slowly added. After, e.g., 30 min, the cooling bath is removed and reaction is stirred for, e.g., another 4 hours. Water is added and the product is extracted with ethyl acetate. The combined organic phases are then washed with water and brine, dried over, e.g., sodium sulfate, concentrated, and purified by, e.g., flash chromatography to obtain 81 and 80.

To the solution of 4-(4-Bromo-phenyl)-hexahydro-[1,4]oxazino[4,3-c][1,3]oxazin-6-one (80) in, e.g., methanol is added sodium hydroxide in water and the resulting mixture is heated to, e.g., reflux for, e.g., 36 hours. Once, e.g., LCMS shows complete hydrolysis of the carbamate 80, the mixture is concentrated and water is added. The aqueous phase is extracted with, e.g., dichloromethane and the combined organic phases are washed with brine, dried over, e.g., sodium sulfate, and concentrated to afford 82.

To a stirred solution of 2-[5-(4-Bromo-phenyl)-morpholin-3-yl]-ethanol (82) in, e.g., anhydrous toluene at, e.g., 0° C. is added diphenylphosphoryl azide (DPPA) followed by 1,8-diazabicyclo[5.4.0]undec-7-ene (DBU) and the resulting mixture is stirred for, e.g., 10 min under an atmosphere of argon. The cooling bath is removed and after 10 min the mixture is placed in an 80° C. oil bath and stirred under argon for, e.g., 14 hours. Once, e.g., LCMS shows complete conversion of the alcohol to the azide, ethyl acetate and water are added. The organic phase is separated and the aqueous phase is extracted with additional ethyl acetate. The combined organic phases are washed with saturated sodium bicarbonate, water and brine, dried over, e.g., sodium sulfate, concentrated, and purified by, e.g., flash chromatography to obtain 83.

To the solution of 3-(2-Azido-ethyl)-5-(4-bromo-phenyl)-morpholine (83) in THF and water is added triphenylphosphine and the resulting mixture is stirred at, e.g., 60° C. for, e.g., 4 hours. Once, e.g., LCMS shows complete reduction of the azide to the amine, the solvent is evaporated and the residue is dried under high vacuum for, e.g., 3 hours. The crude product is then dissolved in, e.g., anhydrous THF, Et$_3$N is added and the resulting mixture is cooled to, e.g., 0°

C. To this cold solution, di-tert-butyl dicarbonate ((Boc)₂O) is added and the reaction mixture is stirred for, e.g., 10 min. The cooling bath is removed and the solution is stirred at, e.g., 55° C. under an atmosphere of argon for, e.g., 5 hours. Once, e.g., LCMS shows complete protection of both amines, the reaction mixture is cooled and ethyl acetate and water are added. The organic layer is separated and the aqueous layer is extracted with ethyl acetate. The combined organic layers are washed with water and brine, dried over, e.g., sodium sulfate, concentrated, and purified by, e.g., flash chromatography to obtain 84.

To a solution of 3-(4-Bromo-phenyl)-5-(2-tert-butoxycarbonylamino-ethyl)-morpholine-4-carboxylic acid tert-butyl ester (84) in, e.g., DMSO is added B₂(Pin)₂ (7a), potassium acetate (KOAc), and PdCl₂(dppf).CH₂Cl₂ and the resulting mixture is degassed using high vacuum, purged with argon twice and stirred at, e.g., 80° C. under an atmosphere argon for, e.g., 12 hours. Once, e.g., LCMS shows complete consumption of 84, the solution is cooled down, water is added, and the aqueous phase is extracted with EtOAc. The combined organic phases are then washed with water, ammonium hydroxide, water, and brine, dried over, e.g., sodium sulfate, concentrated, and purified by, e.g., flash chromatography to obtain pure 85.

To a solution of 3-(2-tert-Butoxycarbonylamino-ethyl)-5-[4-(4,4,5,5-tetramethyl-[1,3,2]dioxaborolan-2-yl)-phenyl]-morpholine-4-carboxylic acid tert-butyl ester (85) in methanol is added water, 5-iodocytosine, and Cu(OAc)₂.H₂O followed by TMEDA and the mixture is then stirred in open air for, e.g., 14 hours. Once, e.g., LCMS shows complete consumption of 85, the mixture is concentrated, water is added, and the aqueous phase is extracted with ethyl acetate. The combined organic phases are then washed with ammonium hydroxide, water and brine, dried over, e.g., sodium sulfate and concentrated to obtain the crude product. This crude product is dissolved in ethyl acetate, benzoic anhydride is added, and the mixture is stirred at, e.g., 80° C. for, e.g., 3 hours and 30 min. Once, e.g., LCMS shows complete benzoylation of the intermediate amine, the reaction mixture is cooled down to room temperature, washed with saturated sodium bicarbonate, water, and brine, dried over, e.g., sodium sulfate, concentrated, and purified by, e.g., flash chromatography to obtain 86.

A solution of 3-[4-(4-Benzoylamino-5-iodo-2-oxo-2H-pyrimidin-1-yl)-phenyl]-5-(2-tert-butoxycarbonylamino-ethyl)-morpholine-4-carboxylic acid tert-butyl ester (86) and alkyne 11a in anhydrous, e.g., DMF is degassed under high vacuum and purged with argon. To this solution is added DIPEA followed by Pd(PPh₃)₄ and CuI. The mixture is then stirred at, e.g., 70° C. for, e.g., 12 hours. Once, e.g., LCMS shows complete consumption of 86, the reaction mixture is cooled to room temperature, methanol is added, and the mixture is stirred at, e.g., 80° C. for, e.g., 4 hours. Once, e.g., LCMS shows complete consumption of the Sonogashira coupled intermediate and formation of debenzoylated cyclized product 87, the mixture is cooled down to room temperature and concentrated. Water is then added and the aqueous phase is extracted with ethyl acetate. The combined organic phases are washed with water, ammonium hydroxide, water, and brine, dried over sodium sulfate, concentrated, and purified by, e.g., flash chromatography to afford 87.

To a stirred solution of 3-(4-{6-[5-(4-Benzyloxycarbonylamino-pentyl)-3-chloro-2-fluoro-phenyl]-2-oxo-2,7-dihydro-pyrrolo[2,3-d]pyrimidin-3-yl}-phenyl)-5-(2-tert-butoxycarbonylamino-ethyl)-morpholine-4-carboxylic acid tert-butyl ester (87) in dichloromethane is added a 4 N solution of HCl in 1,4-dioxane and the resulting mixture is stirred for, e.g., 50 min. Once, e.g., LCMS shows complete deprotection of the tert-butyl carbonyl (Boc) groups, the mixture is concentrated to dryness and the resulting residue is dissolved in anhydrous methanol. To this solution is added N,N'-di-Boc-1H-pyrazole-1-carboxamidine and i-Pr₂NEt and the resulting mixture is stirred at room temperature for, e.g., 14 hours. Once, e.g., LCMS shows complete consumption of the intermediate amine, the mixture is concentrated and the resulting residue is dissolved in trifluoroacetic acid.

Thioanisole is then added to the solution and the resulting mixture is stirred at room temperature for, e.g., 24 hours. Once, e.g., LCMS shows complete deprotection of the Cbz and Boc groups, the mixture is concentrated and the product is purified by, e.g., HPLC chromatography. Product fractions are collected and concentrated to dryness, suspended in ethanol and concentrated to dryness. The TFA salt of the product is then converted to the HCl salt by treating the TFA product with HCl and the reaction mixture is then concentrated and lyophilized to afford compound 353.

Scheme 10

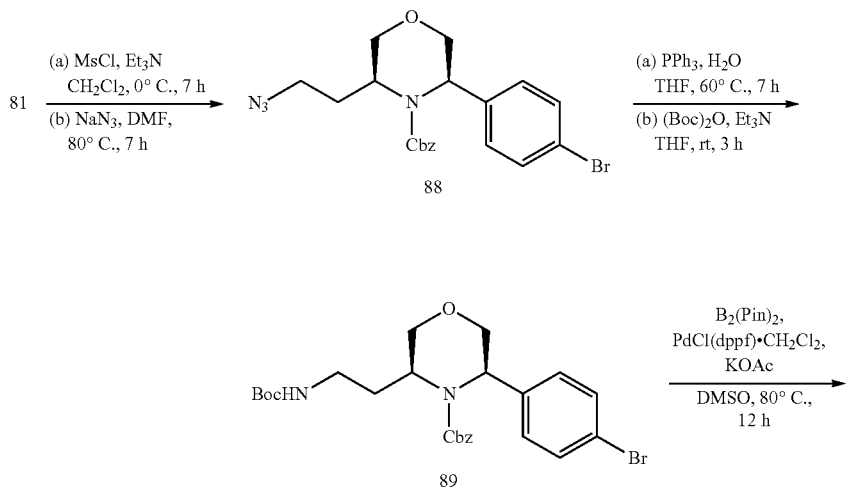

-continued

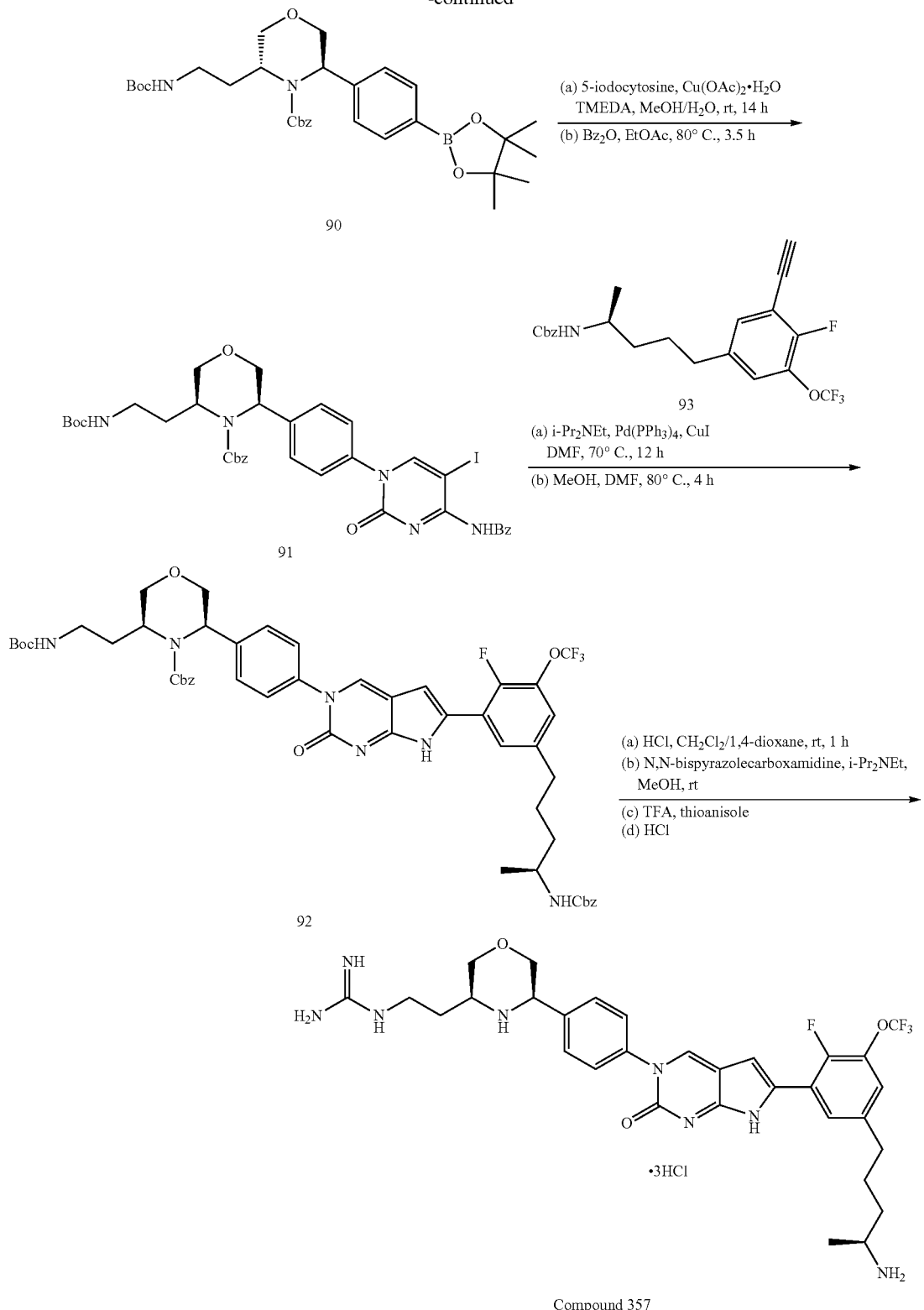

Compound 357

A solution of 3-(4-Bromo-phenyl)-5-(2-hydroxy-ethyl)-morpholine-4-carboxylic acid benzyl ester (81) in, e.g., anhydrous dichloromethane is cooled to, e.g., 0° C. under an atmosphere of argon and Et₃N is added followed by methanesulfonyl chloride (MsCl). The resulting mixture is then stirred in an ice bath for, e.g., 7 hours. Upon complete consumption of 81, the mixture is concentrated. The residue is then dissolved in of ethyl acetate, washed with water and brine, dried over, e.g., sodium sulfate, and concentrated to obtain crude mesylated product. The crude mesylated product is then dissolved in anhydrous DMF, sodium azide is then added and the resulting mixture is stirred at, e.g., 80° C. under an atmosphere of argon for, e.g., 7 hours. Once, e.g., LCMS indicates complete consumption of the mesylate, the mixture is cooled to room temperature. Water is then added and the aqueous phase is extracted with ethyl acetate. The combined organic phases are then washed with water and brine, dried over, e.g., sodium sulfate, concentrated, and purified by, e.g., flash chromatography to afford 88.

To a stirred solution of 3-(2-azido-ethyl)-5-(4-bromo-phenyl)-morpholine-4-carboxylic acid benzyl ester (88) in THF (9 ml) is added PPh$_3$ and water and the resulting mixture is heated to, e.g., 55° C. for, e.g., 4 hours. Once, e.g., LCMS shows complete consumption of the azide 88, the solvent is evaporated and the resulting crude product is dried under high vacuum. The crude product is then dissolved in, e.g., anhydrous THF, Et$_3$N (0.79 g, 7.9 mmol) is added, and the mixture is cooled to, e.g., 0° C. To this cold mixture is added di-tert-butyl dicarbonate ((Boc)$_2$O) and the resulting mixture is stirred for, e.g., 10 min. The cooling bath is removed and the mixture is stirred for, e.g., 3 hours. Once, e.g., LCMS shows complete consumption of amine, water is added and the product is extracted with ethyl acetate. The combined organic phases are then washed with water and brine, dried over, e.g., sodium sulfate, and concentrated. The product is then purified by, e.g., flash chromatography to obtain 89 a.

To a solution of 3-(4-Bromo-phenyl)-5-(2-tert-butoxycarbonylamino-ethyl)-morpholine-4-carboxylic acid tert-butyl ester (89), e.g., in DMSO is added B$_2$(Pin)$_2$ (11a), potassium acetate (KOAc) and PdCl$_2$(dppf).CH$_2$Cl$_2$ and the resulting mixture is degassed using high vacuum, purged with argon, and stirred at, e.g., 80° C. under an atmosphere of argon for, e.g., 12 hours. Once, e.g., LCMS shows the complete consumption of 89, the reaction solution is cooled down, water is added, and the aqueous phase is extracted with EtOAc. The combined organic phases are washed with water, ammonium hydroxide, water and brine, dried over, e.g., sodium sulfate, concentrated and purified by, e.g., flash chromatography to obtain 90.

To a solution of 3-(2-tert-Butoxycarbonylamino-ethyl)-5-[4-(4,4,5,5-tetramethyl-[1,3,2]dioxaborolan-2-yl)-phenyl]-morpholine-4-carboxylic acid tert-butyl ester (90) in methanol is added water, 5-iodocytosine, and Cu(OAc)$_2$.H$_2$O followed by TMEDA and the mixture is then stirred in open air for, e.g., 14 hours. Once, e.g., LCMS shows complete consumption of 90, the mixture is concentrated, water is added, and the aqueous phase is extracted with ethyl acetate. The combined organic phases are then washed with ammonium hydroxide, water, and brine, dried over, e.g., sodium sulfate and concentrated to obtain the crude product. This crude product is dissolved in ethyl acetate, benzoic anhydride is added, and the mixture is stirred at, e.g., 80° C. for, e.g., 3 hours and 30 min. Once, e.g., LCMS shows complete benzoylation of the intermediate amine, the reaction mixture is cooled down to room temperature, washed with saturated sodium bicarbonate, water, and brine, dried over, e.g., sodium sulfate, concentrated, and purified by, e.g., flash chromatography to afford 91.

A solution of 3-[4-(4-Benzoylamino-5-iodo-2-oxo-2H-pyrimidin-1-yl)-phenyl]-5-(2-tert-butoxycarbonylamino-ethyl)-morpholine-4-carboxylic acid tert-butyl ester (91) and alkyne 93 in, e.g., anhydrous DMF is degassed under high vacuum and purged with argon twice. To this solution is added DIPEA followed by Pd(PPh$_3$)$_4$, and CuI. The mixture is then stirred at, e.g., 70° C. for, e.g., 12 hours. Once, e.g., LCMS shows complete consumption of 91, the reaction mixture is cooled to room temperature, methanol is added, and the mixture is stirred at, e.g., 80° C. for, e.g., 4 hours. Once, e.g., LCMS shows complete consumption of the Sonogashira coupled intermediate and formation of debenzoylated cyclized product 92, the mixture is cooled down to room temperature and concentrated. Water is then added and the aqueous phase is extracted with ethyl acetate. The combined organic phases are washed with water, ammonium hydroxide, water and brine, dried over, e.g., sodium sulfate, concentrated, and purified by flash chromatography to afford 92.

To a stirred solution of 92 in, e.g., dichloromethane is added a 4 N solution of HCl in 1,4-dioxane and the resulting mixture is stirred for, e.g., 50 min. Once, e.g., LCMS shows complete deprotection of the Boc groups, the mixture is concentrated to dryness and the resulting residue is dissolved in anhydrous methanol. To this solution is added N,N'-di-Boc-1H-pyrazole-1-carboxamidine and i-Pr$_2$NEt and the resulting mixture is stirred at room temperature for, e.g., 14 hours. Once, e.g., LCMS shows complete consumption of the intermediate amine, the mixture is concentrated and the resulting residue is dissolved in trifluoroacetic acid. Thioanisole is then added to the solution and the resulting mixture s stirred at room temperature for, e.g., 24 hours. Once, e.g., LCMS shows complete deprotection of the Cbz and Boc groups, the mixture is concentrated and the product is purified by, e.g., HPLC chromatograph. Product fractions are concentrated to dryness, suspended in ethanol and concentrated to dryness. The TFA salt of the product is converted to the HCl salt of the product by using HCl. The reaction mixture is then concentrated and lyophilized to afford compound 357.

4. CHARACTERIZATION OF COMPOUNDS OF THE INVENTION

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, for example, as anti-cancer, anti-bacterial, anti-fungal, anti-parasitic or anti-viral agents. Also, it can be possible to assay how the compounds interact with a ribosome or ribosomal subunit and/or are effective as modulators (for example, inhibitors) of protein synthesis using techniques known in the art. General methodologies for performing high-throughput screening are described, for example, in Devlin (1998) *High Throughput Screening*. Marcel Dekker; and U.S. Pat. No. 5,763,263. High-throughput assays can use one or more different assay techniques including, but not limited to, those described below.

(1) Surface Binding Studies.

A variety of binding assays can be useful in screening new molecules for their binding activity. One approach includes surface plasmon resonance (SPR) that can be used to evaluate the binding properties of molecules of interest with respect to a ribosome, ribosomal subunit or a fragment thereof.

SPR methodologies measure the interaction between two or more macromolecules in real-time through the generation of a quantum-mechanical surface plasmon. One device, (BIAcore Biosensor® from Pharmacia Biosensor, Piscataway, N.J.) provides a focused beam of polychromatic light to the interface between a gold film (provided as a disposable biosensor "chip") and a buffer compartment that can be regulated by the user. A 100 nm thick "hydrogel" composed of carboxylated dextran that provides a matrix for the covalent immobilization of analytes of interest is attached to the gold film. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies that are depleted, the BIAcore establishes an optical interface which accurately reports the behavior of the generated surface plasmon resonance. When designed as above, the plasmon resonance (and thus the depletion spectrum) is sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and sensitive real-time measurement of the molecular interactions without the need to label either component.

(2) Fluorescence Polarization.

Fluorescence polarization (FP) is a measurement technique that can readily be applied to protein-protein, protein-ligand, or RNA-ligand interactions in order to derive $IC_{50}$s and Kds of the association reaction between two molecules. In this technique one of the molecules of interest is conjugated with a fluorophore. This is generally the smaller molecule in the system (in this case, the compound of interest). The sample mixture, containing both the ligand-probe conjugate and the ribosome, ribosomal subunit or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(3) Protein Synthesis.

It is contemplated that, in addition to characterization by the foregoing biochemical assays, the compound of interest can also be characterized as a modulator (for example, an inhibitor of protein synthesis) of the functional activity of the ribosome or ribosomal subunit.

Furthermore, more specific protein synthesis inhibition assays can be performed by administering the compound to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of $^3H$ leucine or $^{35}S$ methionine, or similar experiments can be performed to investigate protein synthesis activity. A change in the amount or the rate of protein synthesis in the cell in the presence of a molecule of interest indicates that the molecule is a modulator of protein synthesis. A decrease in the rate or the amount of protein synthesis indicates that the molecule is an inhibitor of protein synthesis.

(4) Antimicrobial Assays and Other Evaluation.

Furthermore, the compounds can be assayed for anti-proliferative or anti-infective properties on a cellular level. For example, where the target organism is a microorganism, the activity of compounds of interest can be assayed by growing the microorganisms of interest in media either containing or lacking the compound. Growth inhibition can be indicative that the molecule can be acting as a protein synthesis inhibitor. More specifically, the activity of the compounds of interest against bacterial pathogens can be demonstrated by the ability of the compound to inhibit growth of defined strains of human pathogens. For this purpose, a panel of bacterial strains can be assembled to include a variety of target pathogenic species, some containing resistance mechanisms that have been characterized. Use of such a panel of organisms permits the determination of structure-activity relationships not only in regards to potency and spectrum, but also with a view to obviating resistance mechanisms.

The in vitro activity of the compounds of the present invention can be determined. Antimicrobial testing is typically performed to determine the minimum inhibitory concentration (MIC). Minimum inhibitory concentrations (MICs) are determined by the microdilution method in a final volume of 100 µl according to protocols outlined by The Clinical and Laboratory Standards Institute (CLSI). Performance standards for reference strains are assessed within the same experimental design to maintain quality control. See, for example, Clinical Laboratory Standards Institute: Methods for dilution antimicrobial susceptibility tests for bacteria that grow aerobically M7-A8. Approved Standard-Eighth Edition. Wayne, Pa.: CLSI; December 2008; and Clinical Laboratory Standards Institute: Performance Standards for Antimicrobial Susceptibility Testing M100-S20; Approved Standard-Twentieth Edition. Wayne, Pa.: CLSI; June 2010.

The antimicrobial and other drug properties of the compounds can further be evaluated in various in vivo mammalian assays, such as a mouse or rat peritonitis infectious models, skin and soft tissue models (often referred to as the thigh model), or a mouse pneumonia model. There are septicemia or organ infection models known to those skilled in the art. These efficacy models can be used as part of the evaluation process and can be used as a guide of potential efficacy in humans. Endpoints can vary from reduction in bacterial burden to lethality. For the latter endpoint, results are often expressed as a $PD_{50}$ value, or the dose of drug that protects 50% of the animals from mortality.

To further assess a compound's drug-like properties, measurements of inhibition of cytochrome P450 enzymes and phase II metabolizing enzyme activity can also be measured either using recombinant human enzyme systems or more complex systems like human liver microsomes. Further, compounds can be assessed as substrates of these metabolic enzyme activities as well. These activities are useful in determining the potential of a compound to cause drug-drug interactions or generate metabolites that retain or have no useful antimicrobial activity.

To get an estimate of the potential of the compound to be orally bioavailable, one can also perform solubility and Caco-2 assays. The latter is a cell line from human epithelium that allows measurement of drug uptake and passage through a Caco-2 cell monolayer often growing within wells of a 24-well microtiter plate equipped with a 1 micron membrane. Free drug concentrations can be measured on the basolateral side of the monolayer, assessing the amount of drug that can pass through the intestinal monolayer. Appropriate controls to ensure monolayer integrity and tightness of gap junctions are needed. Using this same system one can get an estimate of P-glycoprotein mediated efflux. P-glycoprotein is a pump that localizes to the apical membrane of cells, forming polarized monolayers. This pump can abrogate the active or passive uptake across the Caco-2 cell membrane, resulting in less drug passing through the intestinal epithelial layer. These results are often done in conjunction with solubility measurements and both of these factors are known to contribute to oral bioavailability in mammals. Measurements of oral bioavailability in animals and ultimately in man using traditional pharmacokinetic experiments will determine the absolute oral bioavailability.

Experimental results can also be used to build models that help predict physical-chemical parameters that contribute to drug-like properties. When such a model is verified, experimental methodology can be reduced, with increased reliance on the model predictability.

(5) Animal Pharmacology and Toxicology.

The compounds of the present invention can be evaluated for efficacy in well-known animal models. The following table provides representative animal models for various infection indications.

| Target Infection Indication | Animal Model of Efficacy |
|---|---|
| HAP/VAP | Efficacy in mouse and/or rat pneumoniae model vs. respiratory tract infection pathogens of interest (*Streptococcus pneumoniae*, including multi-drug resistant *Streptococcus pneumoniae*, *H. influenzae*, methicillin resistant *Staphylococcus aureus* (MRSA), and *Pseudomonas. aeruginosa*) |
| cSSSI | Efficacy in mouse model against pathogens of interest (MRSA, *K. pneumoniae*) |
| Sepsis | Efficacy in mouse peritonitis model vs. pathogens of interest (*E. coli*, *K. pneumoniae*, *E. faecalis*, MRSA) |
| cUTI | Efficacy in mouse model against *E. coli*, *K. pneumoniae* and/or MRSA) |
| Febrile neutropenia | Efficacy in mouse peritonitis model against *S. aureus*, *S. epidermidis*, *S. pneumoniae*, *S. pyogenes*, *P. aeruginosa* |

Animal Model for Complicated Skin and Skin Structure Infections (cSSSI): Murine Skin and Soft Tissue Infection Model of *Klebsiella pneumoniae* 1705966 in Thighs of Neutropenic Female CD-1 Mice This model is useful to assess the efficacy of compounds of the present invention in a *Klebsiella pneumoniae* 1705966 neutropenic mouse thigh infection model using female ICR (CD-1) mice.

Study Design:

Species: Female ICR (CD-1) Mice, 8 to 9 weeks old, weighting 25-29 g.

Inoculum: *Klebsiella pneumoniae* 17059663 was streaked from frozen stock onto Blood agar (Tryptic Soy Agar+5% Sheep Blood), BD, #221261) and incubated overnight at 35° C. After overnight incubation, enough bacteria (approx. 1 full loop) to measure $OD_{625}$=0.990 was transferred from plate and diluted into 10 ml pre-warmed Mueller-Hinton broth. This culture was further diluted 1:1000 into pre-warmed MH broth and grown for approximately 2 hours at 35° C. with shaking. Each mouse was given 0.1 mL of 1:1000 dilution culture injected into both caudal thigh muscles under isoflurane inhalation anesthesia.

| Dilution | Initial O.D. | Final O.D. (after ~2 hr. incubation) |
|---|---|---|
| 1:10 | 0.135 | 0.424 |
| 1:100 | 0.014 | 0.215 |
| 1:1000 | 0.001 | 0.035 |

Neutropenia is induced by intraperitoneal (I.P.) administration of Cyclophosphamide monohydrate on Day −4 (150 mg/kg) and Day −1 (100 mg/kg).

Vehicle: 0.9% sodium chloride

Dosing: Each mouse in the treated groups was given the appropriate dose of the compound to be tested in a volume of 0.2 ml, 2 and 8 hrs. post bacterial inoculation.

Time points:

Controls: 0, 2, 6, and 24 hrs.

Treated: 24 hrs.

Sampling: 2 or 3 mice/time point were euthanized via $CO_2$, and their caudal thigh muscles excised and homogenized. The thigh muscles were placed in 5 ml sterile PBS in Stomacher Filter bag and homogenized with Micro-Biomaster80 (Brinkmann) for 60 seconds, normal setting and 1:10 dilutions were made per standard protocol in a 96-well plate. Aliquots of 25 ul for each dilution, as well as the homogenate, were plated on blood agar plates and incubated at 35° C. to determine the CFU/mL over the time course. After overnight incubation, colonies were counted.

Animal Model for Sepsis:

Murine Peritonitis Model (*E. coli*, *K. Pneumoniae*, *E. Faecalis*, MRSA)

This model is used to evaluate the effect of subcutaneous (SC) treatment with compounds of the present invention on growth of *Escherichia coli* ATCC 25922 in a mouse peritonitis model using female Swiss Webster mice.

Controls:

Negative: Inoculum only

Inoculum Vehicle Intraperitoneal

Positive: Ciprofloxacin

Study Design:

Species: Female Swiss Webster Mice

Inoculation: *Escherichia coli* ATCC 25922 is made by adding 1 ml (4/6/07) stock to 9 ml 0.25% Brewer's Yeast to make (1:10), then 1 ml of the (1:10) will be added to 9 ml 0.25% Brewer's Yeast to make (1:100), then 1 ml of the (1:100) will be added to 9 ml 0.25% Brewer's Yeast to make (1:1000), then 2.5 ml of the (1:1000) will be added to 122.5 ml 0.25% Brewer's Yeast to make (1:50,000), 1 ml/mouse will be inoculated intraperitoneally (IP).

Route of Administration: SC

Dosing: Vehicle for compounds of the present invention: Saline or 50 mM Sodium phosphate buffer in 10% Captisol in water, pH=7.2.

Dose Administration: Q3H×3 beginning at 30 min post bacterial inoculation

Study Duration: 24 hrs. 0.25% Brewer's Yeast Extract (BYE): Dilute 2% prepared on Nov. 12, 2009 (Lot. 2158K, MP Biomedicals) 25 ml 2%+175 ml 1×PBS.

Outcome Measures: Colony Forming Unit's from peritoneal wash and spleen homogenate and drug levels from wash, spleen homogenate, and plasma.

Blood is collected via cardiac puncture while mouse is under $CO_2$ narcosis. The whole blood sample is placed in heparinized eppendorf tubes and kept on wet ice until centrifuged (4 min @14,000 rpm). Plasma is transferred to 96 deep-well block on dry ice and stored at −20° C.

Immediately following blood collection, 2 ml of sterile PBS (phosphate buffered saline) was injected into the peritoneal cavity with a 25 G needle. The abdomen was gently massaged, and a small incision was made to allow access to the peritoneal cavity. The peritoneal wash fluid was collected using sterile technique, serially diluted 1:10, plated on blood agar plates, and incubated overnight at 35° C.

Spleens were harvested and placed in 1 ml sterile PBS in Stomacher bag and homogenized with MicroBiomaster80 (Brinkmann) for 60 seconds, normal setting and 1:10 dilutions were made. 25 µl of each dilution, as well as the homogenate, was plated on blood agar plates and incubated at 35° C. to determine the CFU/mL over the time course. After overnight incubation, colonies were counted.

Other Animal Models

Similarly, other animal infection models can be used for hospital acquired pneumonia (HAP)/ventilator acquired pneumonia (VAP), complicated urinary tract infections (cUTI), and febrile neutropenia.

5. FORMULATION AND ADMINISTRATION

The compositions and methods of the present invention can be practiced by delivering the compounds of the present invention using a means for delivery e.g., any suitable carrier. The dose of active compound, mode of administration and use of suitable carrier will depend upon the intended patient or subject and the targeted microorganism, e.g., the target bacterial organism. The formulations, both for human medical use and veterinary use, of compounds according to the present invention typically include such compounds in association with a pharmaceutically acceptable carrier.

The carrier(s) should be "acceptable" in the sense of being compatible with compounds of the present invention and not deleterious to the recipient. Pharmaceutically acceptable carriers, in this regard, are intended to include any and all solvents, dispersion media, coatings, absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the invention and/or known in the art) also can be incorporated into the compositions. The formulations can conveniently be presented in dosage unit form and can be prepared by any of the methods well known in the art of pharmacy/microbiology. In general, some formulations are prepared by bringing the compound into association with a liquid carrier or a finely divided solid carrier or both, and then, if necessary, shaping the product into the desired formulation.

A pharmaceutical composition of the invention should be formulated to be compatible with its intended route of administration. Solutions or suspensions can include the following components: a sterile diluent such as water, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide.

A wide variety of formulations and administration methods, including, e.g., intravenous formulations and administration methods can be found in S. K. Niazi, ed., Handbook of Pharmaceutical Formulations, Vols. 1-6 [Vol. 1 Compressed Solid Products, Vol. 2 Uncompressed Drug Products, Vol. 3 Liquid Products, Vol. 4 Semi-Solid Products, Vol. 5 Over the Counter Products, and Vol. 6 Sterile Products], CRC Press, Apr. 27, 2004.

Useful solutions for oral or parenteral administration can be prepared by any of the methods well known in the pharmaceutical art, described, for example, in *Remington's Pharmaceutical Sciences,* 18th ed. (Mack Publishing Company, 1990). Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, and hydrogenated naphthalenes. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration can be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug can also be administered in the form of a bolus, electuary or paste. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where adhesion to a tissue surface is desired the composition can include the drug dispersed in a fibrinogen-thrombin composition or other bioadhesive. The compound then can be painted, sprayed or otherwise applied to the desired tissue surface. Alternatively, the drugs can be formulated for parenteral or oral administration to humans or other mammals, for example, in effective amounts, e.g., amounts that provide appropriate concentrations of the drug to target tissue for a time sufficient to induce the desired effect.

Where the active compound is to be used as part of a transplant procedure, it can be provided to the living tissue or organ to be transplanted prior to removal of tissue or organ from the donor. The compound can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, either by oral or parenteral administration, using any of the methods and formulations described herein and/or known in the art. Where the drug comprises part of a tissue or organ preservation solution, any commercially available preservation solution can be used to advantage. For example, useful solutions known in the art include Collins solution, Wisconsin solution, Belzer solution, Euro-collins solution and lactated Ringer's solution.

In conjunction with the methods of the present invention, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a drug as well as tailoring the dosage and/or therapeutic regimen of treatment with the drug.

Generally, an effective amount of dosage of active compound will be in the range of from about 0.1 to about 100 mg/kg of body weight/day, more preferably from about 1.0 to about 50 mg/kg of body weight/day. The amount administered will also likely depend on such variables as the type of surgery or invasive medical procedure, the overall health status of the patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum.

Nonlimiting doses of active compound comprise from about 0.1 to about 1500 mg per dose. Nonlimiting examples of doses, which can be formulated as a unit dose for convenient administration to a patient include: about 25 mg, about 50 mg, about 75 mg, about 100 mg, about 125 mg, about 150 mg, about 175 mg, about 200 mg, about 225 mg, about 250 mg, about 275 mg, about 300 mg, about 325, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050, mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, and about 1500 mg. The foregoing doses are useful for administering the compounds of the present invention according to the methods of the present invention.

As is understood by one of ordinary skill in the art, generally, when dosages are described for a pharmaceutical active, the dosage is given on the basis of the parent or active moiety. Therefore, if a salt, hydrate, or another form of the parent or active moiety is used, a corresponding adjustment in the weight of the compound is made, although the dose is still referred to on the basis of the parent or active moiety delivered. As a nonlimiting example, if the parent or active moiety of interest is a monocarboxylic acid having a molecular weight of 250, and if the monosodium salt of the acid is desired to be delivered to be delivered at the same dosage, then an adjustment is made recognizing that the monosodium salt would have a molecular weight of approximately 272 (i.e., minus 1H or 1.008 atomic mass units and plus 1 Na or 22.99 atomic mass units). Therefore, a 250 mg dosage of the parent or active compound would correspond to about 272 mg of the monosodium salt, which would also deliver 250 mg of the parent or active compound. Said another way, about 272 mg of the monosodium salt would be equivalent to a 250 mg dosage of the parent or active compound.

Formulation Examples

I. Formulation for Intravenous Administration

| Ingredients | Amount |
| --- | --- |
| Antimicrobial Compound of the present invention | 0.1-1500 total mg |
| Dextrose, USP | 50 mg/ml |
| Sodium citrate, USP | 1.60-1.75 mg/ml |
| Citric Acid, USP | 0.80-0.90 mg/ml |
| Water, USP | q.s |

This formulation for intravenous administration is formulated by heating water for injection to about 60° C. Next the sodium citrate, citric acid and dextrose are added and stirred until dissolved. A solution or aqueous slurry of the antimicrobial compound is added to the previous mixture and stirred until dissolved. The mixture is cooled to 25° C. with stirring. The pH is measured and adjusted if necessary. Lastly the mixture is brought to the desired volume, if necessary, with water for injection. The mixture is filtered, filled into the desired container (vial, syringe, infusion container, etc.), over wrapped and terminally moist heat sterilized.

This formulation is useful for intravenous administration, either bolus or infusion, to a patient for treating, preventing, reducing the risk of, or delaying the onset of infection.

II. Lyophilisate for Reconstitution

Alternatively, the antimicrobial compound can be provided as a lyophilisate which can be reconstituted before intravenous or intramuscular administration.

| Ingredient | mg per injection vial |
| --- | --- |
| Antimicrobial Compound of the present invention | 0.1-1500 |
| Cyclodextrin | 1500 |

Reconstitution solution for a volume to be administered of 50 ml (infusion): 5% aqueous glucose solution.
Reconstitution solution for a volume to be administered of 15 ml (bolus): 3.3% aqueous glucose solution.
The foregoing lyophilisate is useful for reconstitution and intravenous administration, either bolus or infusion, to a patient for treating, preventing, reducing the risk of, or delaying the onset of infection.

III. Lyophilisate for Reconstitution

| Ingredient | mg per injection vial |
| --- | --- |
| Antimicrobial Compound of the present invention | 0.1-1500 |
| soya lecithin | 2250 |
| Sodium cholate | 1500 |

Reconstitution solution for a volume to be administered of 50 ml (infusion): 4% aqueous glucose solution.

Reconstitution solution for a volume to be administered of 15 ml (bolus): 2% aqueous glucose solution The foregoing lyophilisate is useful for reconstitution and intravenous administration, either bolus or infusion, to a patient for treating, preventing, reducing the risk of, or delaying the onset of infection.

IV. Lyophilisate for Reconstitution

| Ingredient | mg per injection vial |
| --- | --- |
| Antimicrobial Compound of the present invention | 0.1-1500 |
| soya lecithin | 900 |
| Sodium glycocholate | 540 |

Reconstitution solution for a volume to be administered of 15 ml (bolus): 3.3% aqueous glucose solution.

The foregoing lyophilisate is useful for reconstitution and intravenous administration, either bolus or infusion, to a patient for treating, preventing, reducing the risk of, or delaying the onset of infection.

V. Tablet for Oral Administration

| Ingredients | Per Tablet | Per 4000 Tablets |
| --- | --- | --- |
| Antimicrobial Compound of the present invention | 0.1-1500 mg | 0.4-6000 g |
| Anhydrous Lactose, NF | 110.45 mg | 441.8 g |
| Microcrystalline Cellulose NF | 80.0 mg | 320.0 g |
| Magnesium Stearate Impalpable Powder NF | 1.00 mg | 4.0 g |
| Croscarmellose Sodium NF Type A | 2.00 mg | 8.0 g |

The antimicrobial compound (any of the compounds equivalent to the desired delivery strength, e.g., 50 to 1500 mg per tablet) is premixed with ⅓ of the microcrystalline cellulose NF and ½ of the anhydrous lactose NF in a ribbon blender for 5 minutes at 20 RPM. To the premix is added the remaining ⅔ of the microcrystalline cellulose NF and the remaining ½ of the anhydrous lactose NF. This is blended for 10 minutes at 20 RPM. Croscarmellose sodium is added to the blended powders and mixed for 5 minutes at 20 RPM. Finally the magnesium stearate is added to the mixture by passing through a 90 mesh screen and blended for an additional 5 minutes at 20 RPM. The lubricated mixture is compressed to provide tablets of 500 mg active ingredient.

These tablets are useful for oral administration to a patient for treating, prevention, reducing the risk of, or delaying the onset of infection.

6. EXAMPLES

Nuclear magnetic resonance (NMR) spectra were obtained on a Bruker Avance 300 or Avance 500 spectrometer, or in some cases a GE-Nicolet 300 spectrometer. Common reaction solvents were either high performance liquid chromatography (HPLC) grade or American Chemical Society (ACS) grade, and anhydrous as obtained from the manufacturer unless otherwise noted. "Chromatography" or "purified by silica gel" refers to flash column chromatography using silica gel (EM Merck, Silica Gel 60, 230-400 mesh) unless otherwise noted.

The compounds or tautomers thereof, or pharmaceutically acceptable salts, esters or prodrugs of said compounds or tautomers of the present invention can be prepared using known chemical transformations adapted to the particular situation at hand.

Some of the abbreviations used in the following experimental details of the synthesis of the examples are defined below: h or hr=hour(s); min=minute(s); mol=mole(s); mmol=millimole(s); M=molar; M=micromolar; g=gram(s); μg=microgram(s); rt=room temperature; L=liter(s); mL=milliliter(s); $Et_2O$=diethyl ether, THF=tetrahydrofuran; DMSO=dimethyl sulfoxide; EtOAc=ethyl acetate; $Et_3N$=triethylamine; i-$Pr_2NEt$ or DIPEA=diisopropylethylamine; $CH_2Cl_2$=methylene chloride; $CHCl_3$=chloroform; $CDCl_3$=deuterated chloroform; $CCl_4$=carbon tetrachloride; MeOH=methanol; $CD_3OD$=deuterated methanol; EtOH=ethanol; DMF=dimethylformamide; BOC=t-butoxycarbonyl; CBZ=benzyloxycarbonyl; TBS=t-butyldimethylsilyl; TBSCl=t-butyldimethylsilyl chloride; TFA=trifluoroacetic acid; DBU=diazabicycloundecene; TBDPSCl=t-butyldiphenylchlorosilane; Hunig's Base=N,N-diisopropylethylamine; DMAP=4-dimethylaminopyridine; CuI=copper (I) iodide; MsCl=methanesulfonyl chloride; $NaN_3$=sodium azide; $Na_2SO_4$=sodium sulfate; $NaHCO_3$=sodium bicarbonate; NaOH=sodium hydroxide; $MgSO_4$=magnesium sulfate; $K_2CO_3$=potassium carbonate; KOH=potassium hydroxide; $NH_4OH$=ammonium hydroxide; $NH_4Cl$=ammonium chloride; $SiO_2$=silica; Pd—C=palladium on carbon; Pd(dppf)$Cl_2$=dichloro[1,1'-bis(diphenylphosphino)ferrocene]palladium (II).

Exemplary compounds synthesized in accordance with the invention are listed in Table 1. A bolded or dashed bond is shown to indicate a particular stereochemistry at a chiral center, whereas a wavy bond indicates that the substituent can be in either orientation or that the compound is a mixture thereof.

The compounds of the present invention can be prepared, formulated, and delivered as salts, esters, and prodrugs. For convenience, the compounds are generally shown without indicating a particular salt, ester, or prodrug form.

Compounds of the present invention are shown in Table 1 below. ESI-LCMS (electrospray ionization-liquid chromatography mass spectral) data are provided, where available. When data is not available this is indicated by "NA". The LCMS data are provided using the convention for m/z in the format, [M+H]+, except where otherwise indicated.

TABLE 1
| Compound No | Structure | ESI, m/z [M + H]+ |
|---|---|---|
| 1 | 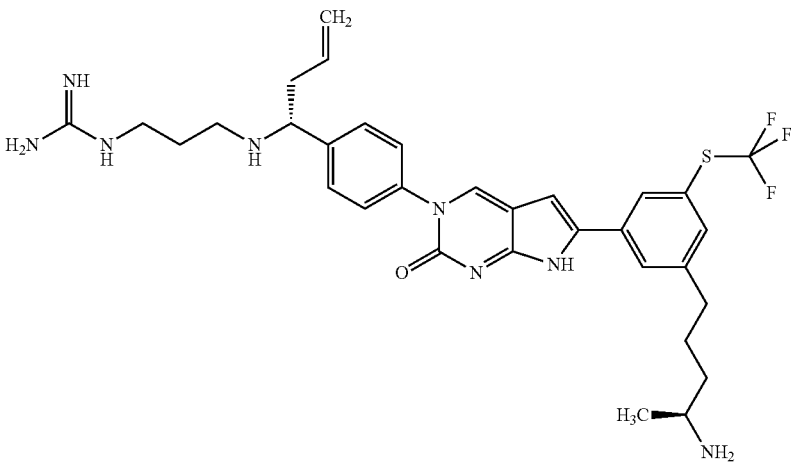 [SMILES: C=CC[C@@H](NCCCNC(=N)N)c1ccc(-n2cc3cc(-c4cc(CCC[C@H](C)N)cc(SC(F)(F)F)c4)[nH]c3nc2=O)cc1] | 641.2 |
| 2 | 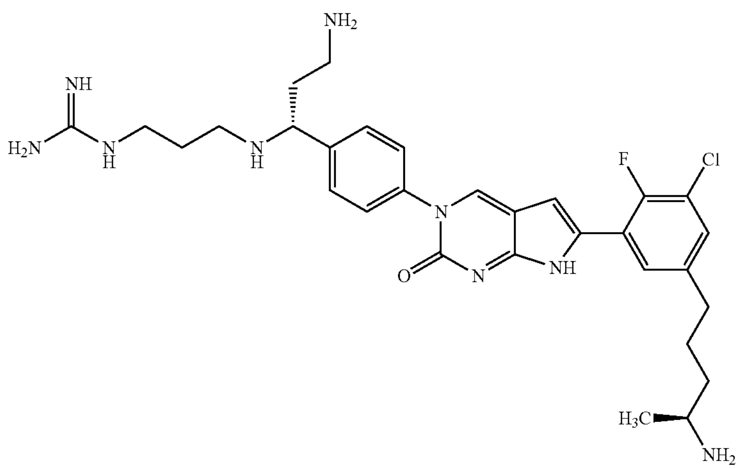 [SMILES: C[C@H](N)CCCc1cc(Cl)c(F)c(-c2cc3cn(-c4ccc([C@@H](CCN)NCCCNC(=N)N)cc4)c(=O)nc3[nH]2)c1] | 596.1 |
| 3 | 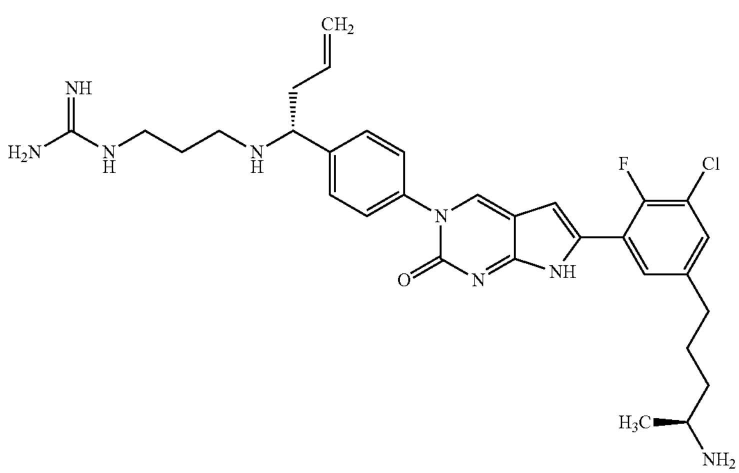 [SMILES: C=CC[C@@H](NCCCNC(=N)N)c1ccc(-n2cc3cc(-c4cc(CCC[C@H](C)N)cc(Cl)c4F)[nH]c3nc2=O)cc1] | 593.2 |

TABLE 1-continued
| Compound No | Structure | ESI, m/z [M + H]+ |
|---|---|---|
| 4 | 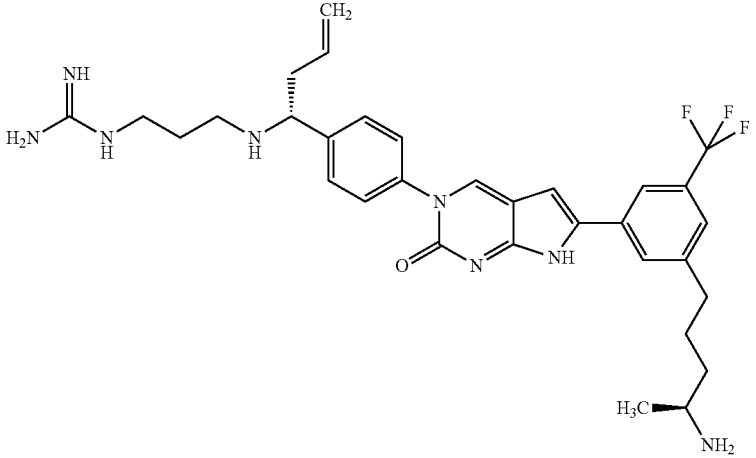 [SMILES: C=CC[C@@H](NCCCNC(=N)N)c1ccc(-n2cc3cc(-c4cc(CCC[C@H](C)N)cc(C(F)(F)F)c4)[nH]c3nc2=O)cc1] | 609.1 |
| 5 | 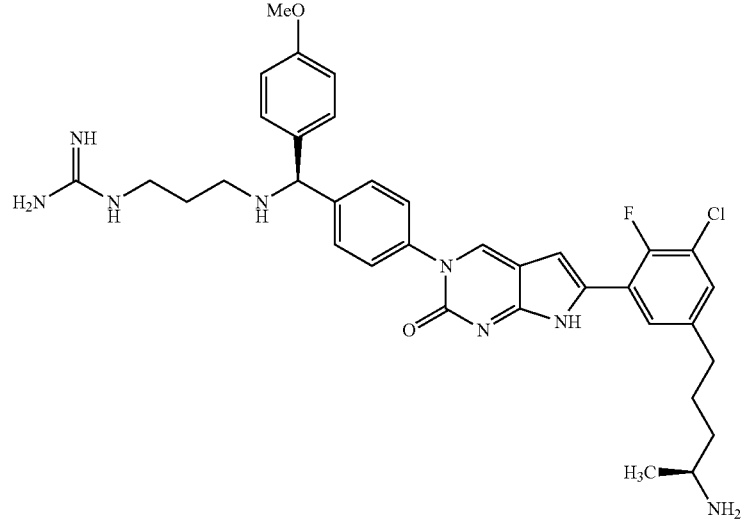 [SMILES: COc1ccc([C@H](NCCCNC(=N)N)c2ccc(-n3cc4cc(-c5cc(CCC[C@H](C)N)cc(Cl)c5F)[nH]c4nc3=O)cc2)cc1] | 659 |
| 6 | 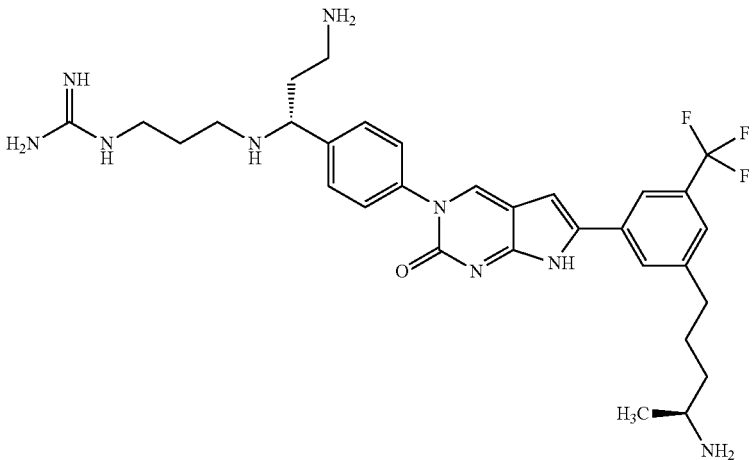 [SMILES: C[C@H](N)CCCc1cc(-c2cc3cn(-c4ccc([C@@H](CCN)NCCCNC(=N)N)cc4)c(=O)nc3[nH]2)cc(C(F)(F)F)c1] | 612.1 |

TABLE 1-continued
| Compound No | Structure | ESI, m/z [M + H]+ |
|---|---|---|
| 7 | 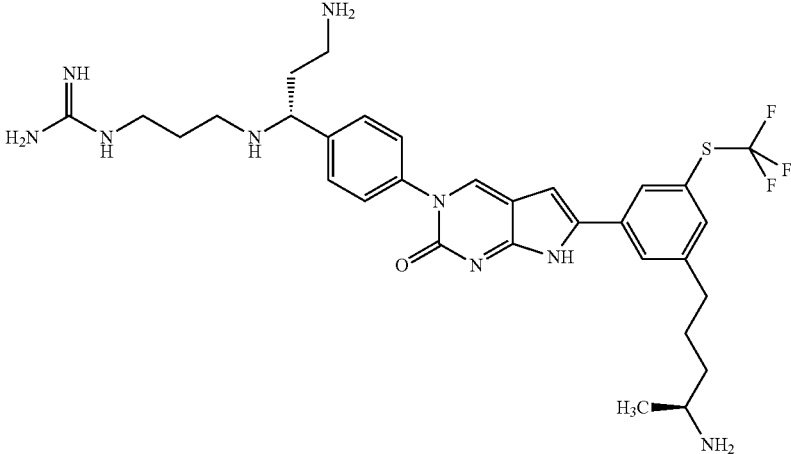 [SMILES: C[C@H](N)CCCc1cc(SC(F)(F)F)cc(-c2cc3cn(-c4ccc([C@@H](CCN)NCCCNC(=N)N)cc4)c(=O)nc3[nH]2)c1] | 644.1 |
| 8 | 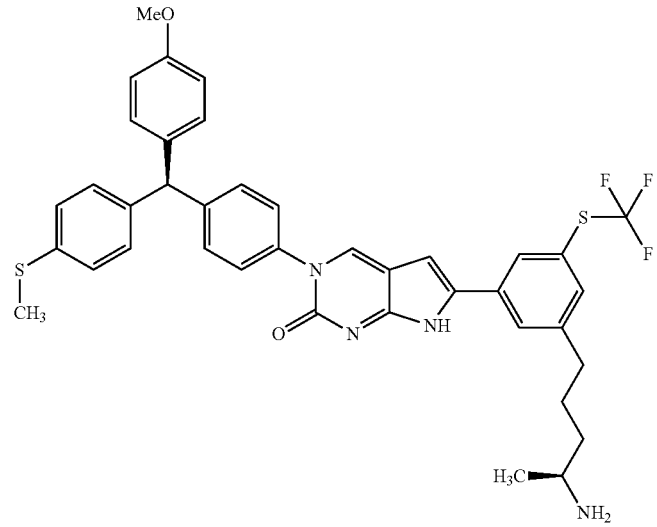 [SMILES: COc1ccc([C@H](c2ccc(SC)cc2)c2ccc(-n3cc4cc(-c5cc(CCC[C@H](C)N)cc(SC(F)(F)F)c5)[nH]c4nc3=O)cc2)cc1] | 715 |
| 9 | 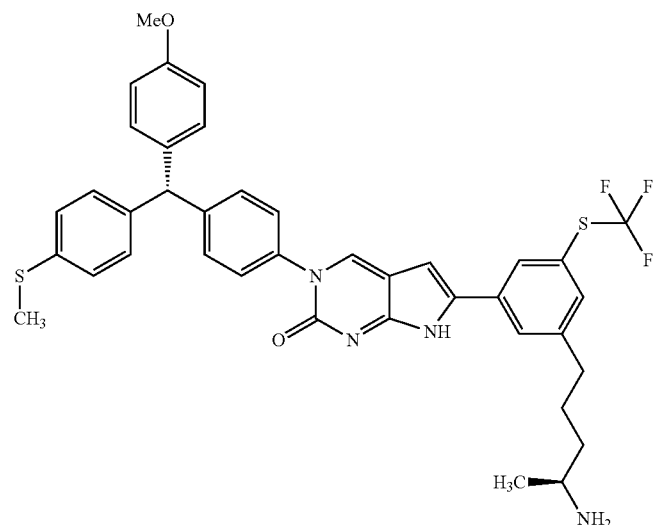 | 715 |

TABLE 1-continued

| Compound No | Structure | ESI, m/z [M + H]+ |
|---|---|---|
| 10 | 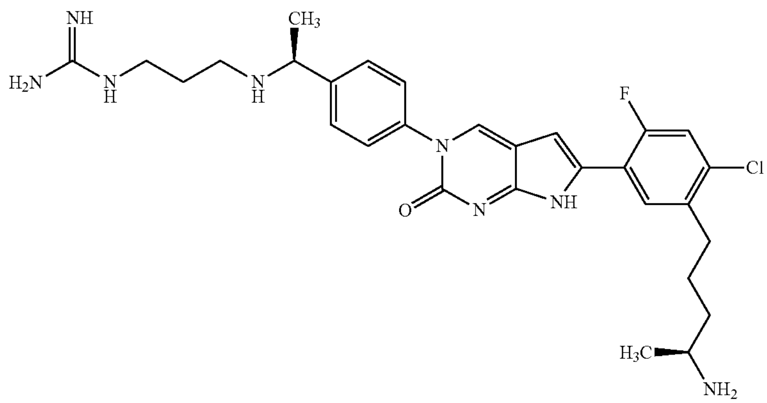 [SMILES: C[C@H](N)CCCc1cc(-c2cc3cn(-c4ccc([C@H](C)NCCCNC(=N)N)cc4)c(=O)nc3[nH]2)c(F)cc1Cl] | 567.1 |
| 11 | 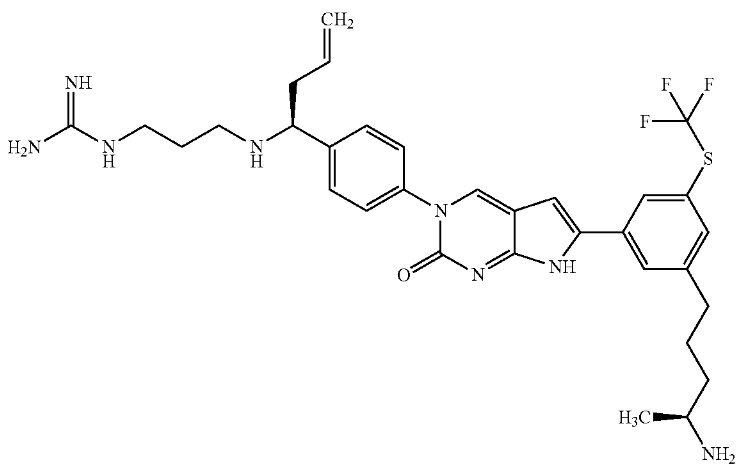 [SMILES: C=CC[C@H](NCCCNC(=N)N)c1ccc(-n2cc3cc(-c4cc(CCC[C@H](C)N)cc(SC(F)(F)F)c4)[nH]c3nc2=O)cc1] | 641.5 |
| 12 | 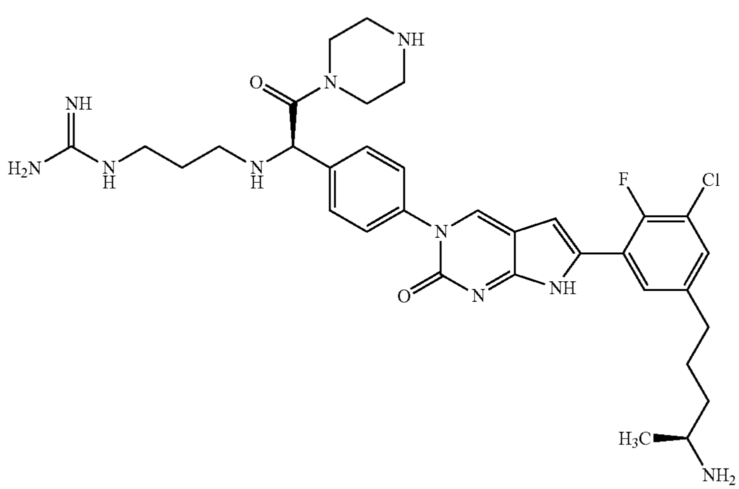 [SMILES: C[C@H](N)CCCc1cc(Cl)c(F)c(-c2cc3cn(-c4ccc([C@@H](NCCCNC(=N)N)C(=O)N5CCNCC5)cc4)c(=O)nc3[nH]2)c1] | 665.2 |

TABLE 1-continued

| Compound No | Structure | ESI, m/z [M + H]+ |
|---|---|---|
| 13 | 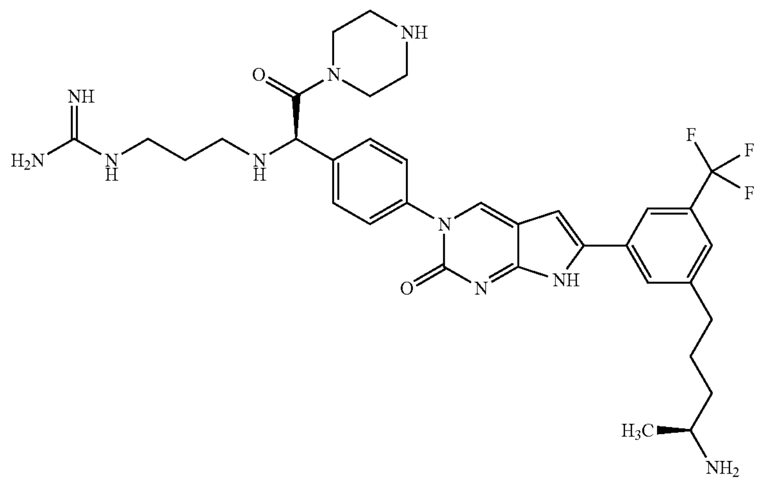 [SMILES: C[C@H](N)CCCc1cc(-c2cc3cn(-c4ccc([C@@H](NCCCNC(=N)N)C(=O)N5CCNCC5)cc4)c(=O)nc3[nH]2)cc(C(F)(F)F)c1] | 681.1 |
| 14 | 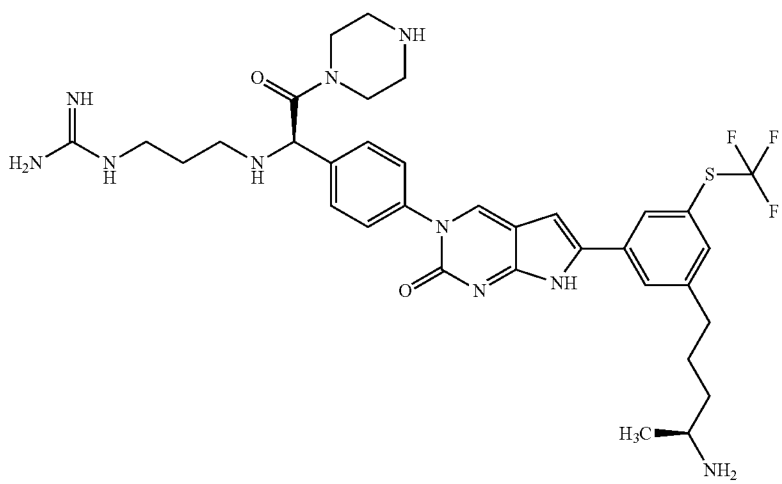 [SMILES: C[C@H](N)CCCc1cc(SC(F)(F)F)cc(-c2cc3cn(-c4ccc([C@@H](NCCCNC(=N)N)C(=O)N5CCNCC5)cc4)c(=O)nc3[nH]2)c1] | 713.2 |
| 15 | 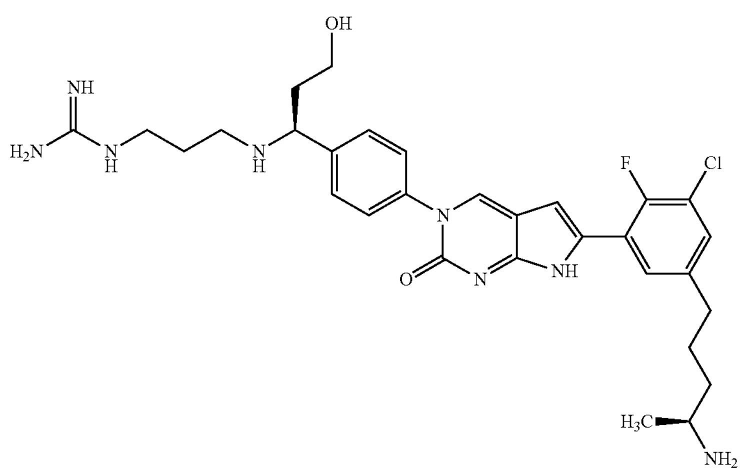 | 597.1 |

TABLE 1-continued
| Compound No | Structure | ESI, m/z [M + H]+ |
|---|---|---|
| 16 | 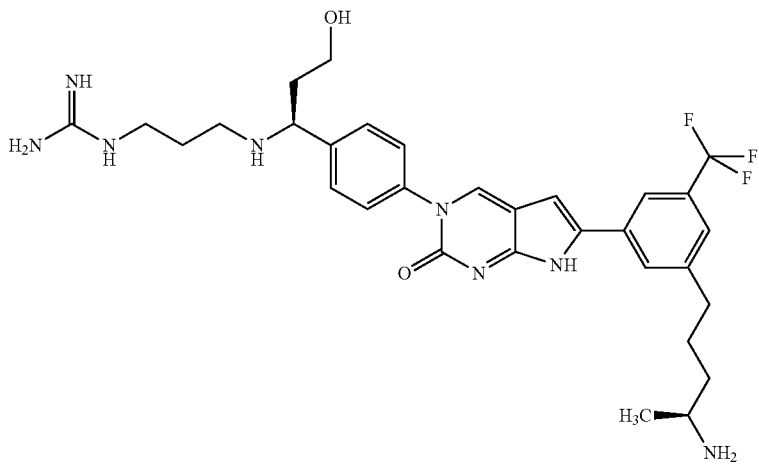 [SMILES: C[C@H](N)CCCc1cc(-c2cc3cn(-c4ccc([C@H](CCO)NCCCNC(=N)N)cc4)c(=O)nc3[nH]2)cc(C(F)(F)F)c1] | 613.2 |
| 17 | 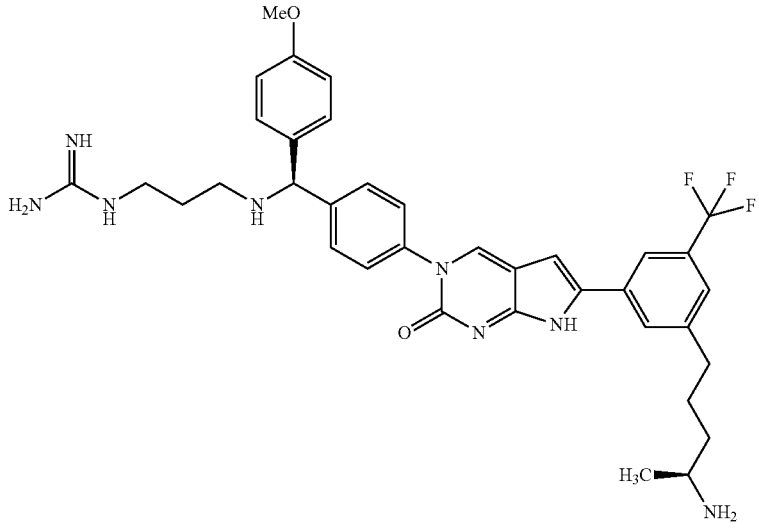 [SMILES: COc1ccc([C@H](NCCCNC(=N)N)c2ccc(-n3cc4cc(-c5cc(CCC[C@H](C)N)cc(C(F)(F)F)c5)[nH]c4nc3=O)cc2)cc1] | 675.2 |
| 18 | 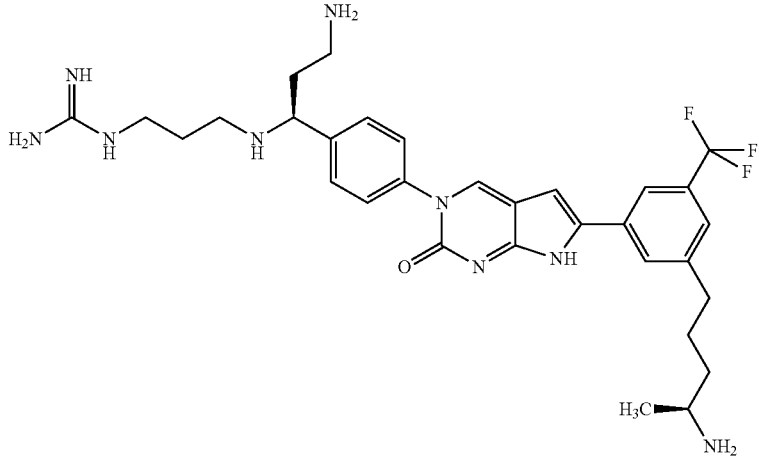 [SMILES: C[C@H](N)CCCc1cc(-c2cc3cn(-c4ccc([C@H](CCN)NCCCNC(=N)N)cc4)c(=O)nc3[nH]2)cc(C(F)(F)F)c1] | 612.2 |

TABLE 1-continued
| Compound No | Structure | ESI, m/z [M + H]+ |
|---|---|---|
| 19 | 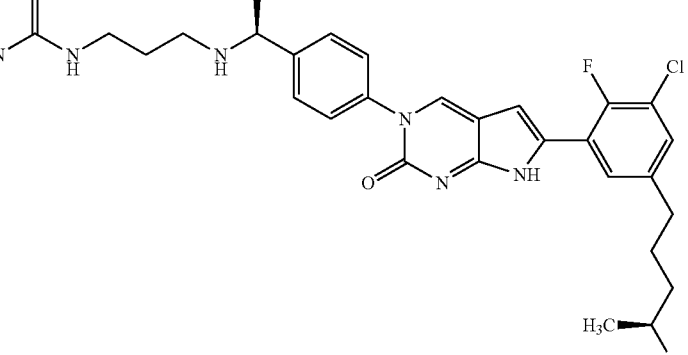 | 596.1 |
| 20 | 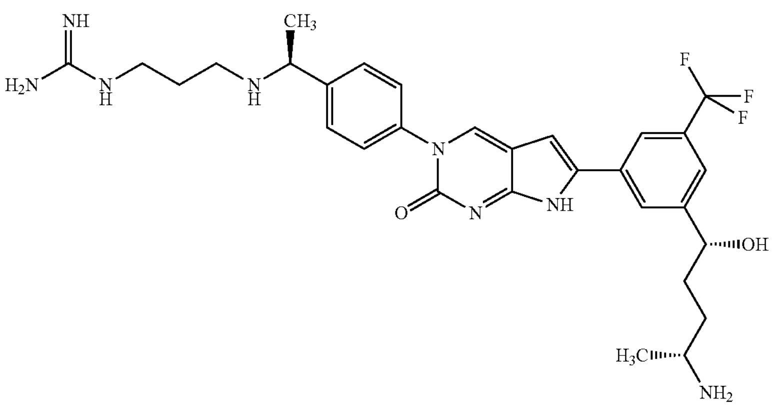 [SMILES: C[C@H](NCCCNC(=N)N)c1ccc(-n2cc3cc(-c4cc([C@H](O)CC[C@@H](C)N)cc(C(F)(F)F)c4)[nH]c3nc2=O)cc1] | 599 |
| 21 | 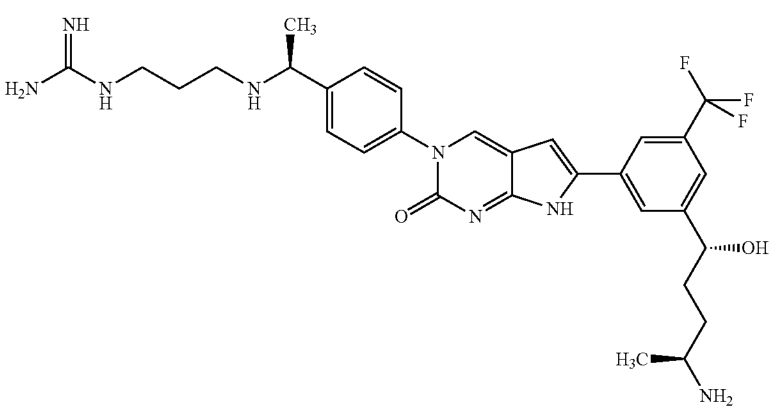 [SMILES: C[C@H](N)CC[C@@H](O)c1cc(-c2cc3cn(-c4ccc([C@H](C)NCCCNC(=N)N)cc4)c(=O)nc3[nH]2)cc(C(F)(F)F)c1] | 599 |

TABLE 1-continued
| Compound No | Structure | ESI, m/z [M + H]+ |
|---|---|---|
| 22 | 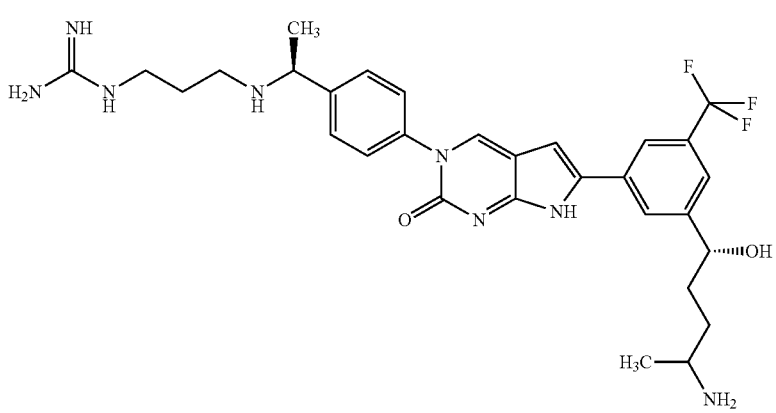 [SMILES: CC(N)CC[C@@H](O)c1cc(-c2cc3cn(-c4ccc([C@H](C)NCCCNC(=N)N)cc4)c(=O)nc3[nH]2)cc(C(F)(F)F)c1] | 599 |
| 23 | 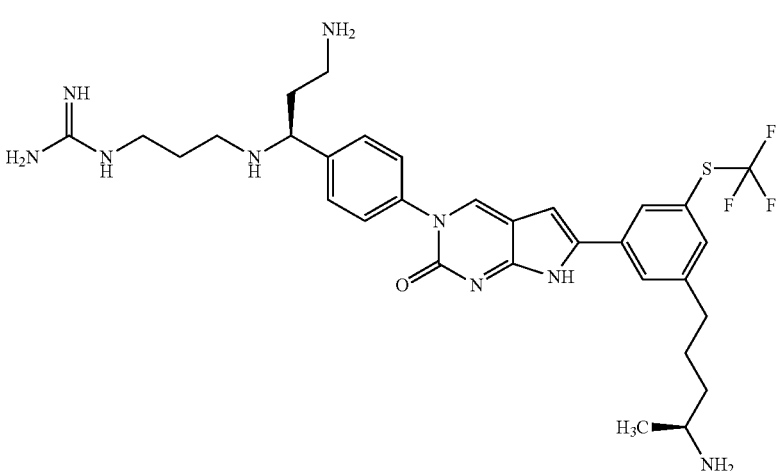 | 644.1 |
| 24 | 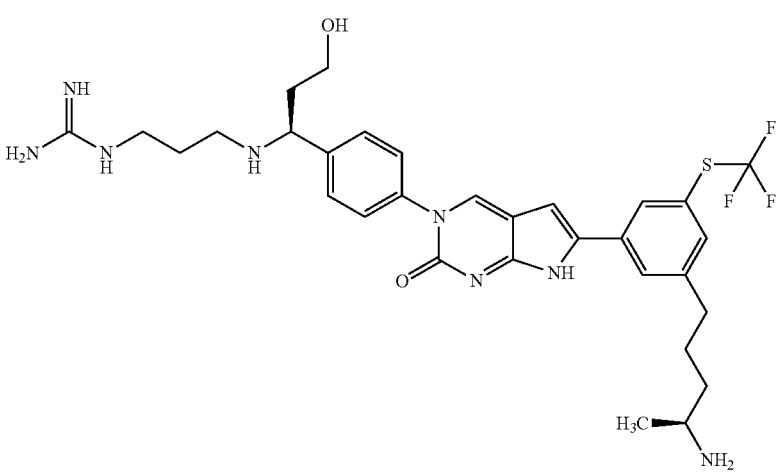 [SMILES: C[C@H](N)CCCc1cc(SC(F)(F)F)cc(-c2cc3cn(-c4ccc([C@H](CCO)NCCCNC(=N)N)cc4)c(=O)nc3[nH]2)c1] | 645.1 |

TABLE 1-continued
| Compound No | Structure | ESI, m/z [M + H]+ |
|---|---|---|
| 25 | 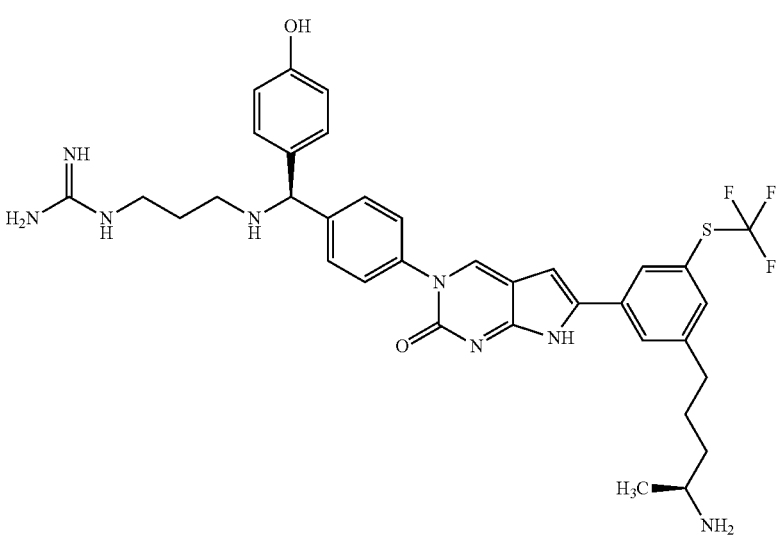 [SMILES: C[C@H](N)CCCc1cc(SC(F)(F)F)cc(-c2cc3cn(-c4ccc([C@@H](NCCCNC(=N)N)c5ccc(O)cc5)cc4)c(=O)nc3[nH]2)c1] | 693.1 |
| 26 | 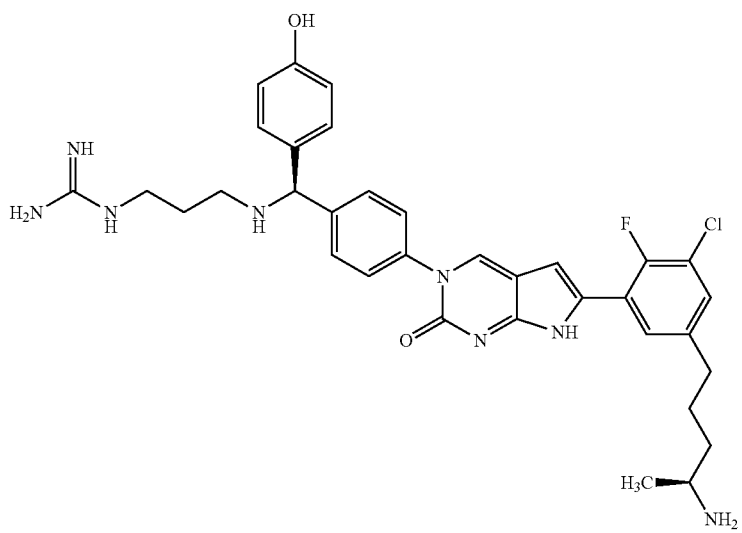 [SMILES: C[C@H](N)CCCc1cc(Cl)c(F)c(-c2cc3cn(-c4ccc([C@@H](NCCCNC(=N)N)c5ccc(O)cc5)cc4)c(=O)nc3[nH]2)c1] | 645.2 |
| 27 | 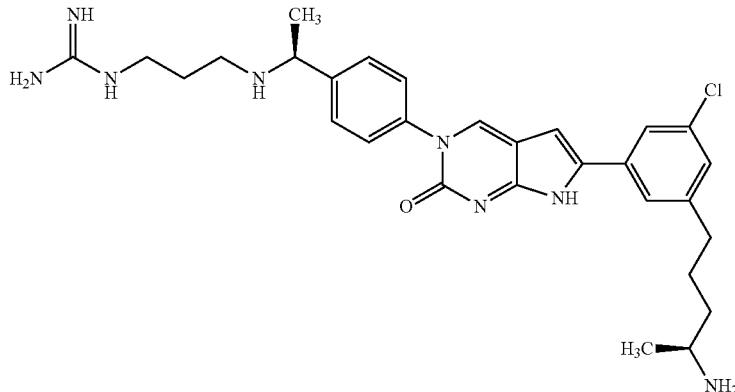 | 549.1 |

TABLE 1-continued

| Compound No | Structure | ESI, m/z [M + H]+ |
|---|---|---|
| 28 | 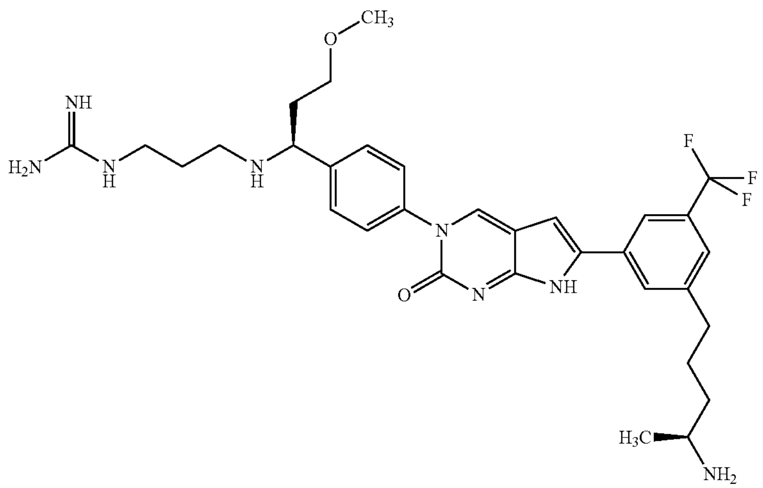 [SMILES: COCC[C@H](NCCCNC(=N)N)c1ccc(-n2cc3cc(-c4cc(CCC[C@H](C)N)cc(C(F)(F)F)c4)[nH]c3nc2=O)cc1] | 627.2 |
| 29 | 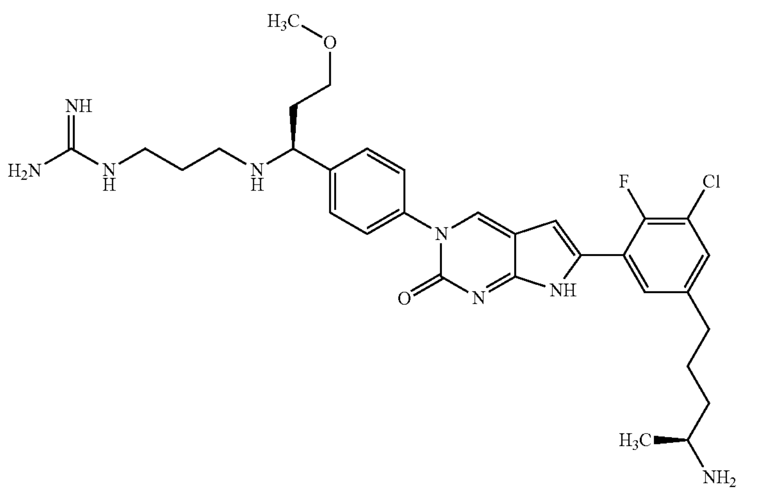 [SMILES: COCC[C@H](NCCCNC(=N)N)c1ccc(-n2cc3cc(-c4cc(CCC[C@H](C)N)cc(Cl)c4F)[nH]c3nc2=O)cc1] | 611.1 |
| 30 | 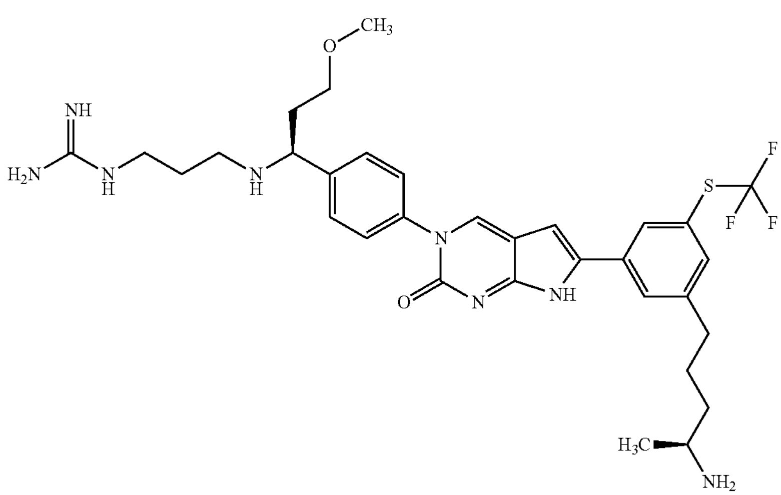 [SMILES: COCC[C@H](NCCCNC(=N)N)c1ccc(-n2cc3cc(-c4cc(CCC[C@H](C)N)cc(SC(F)(F)F)c4)[nH]c3nc2=O)cc1] | 659.2 |

TABLE 1-continued
| Compound No | Structure | ESI, m/z [M + H]+ |
|---|---|---|
| 31 | 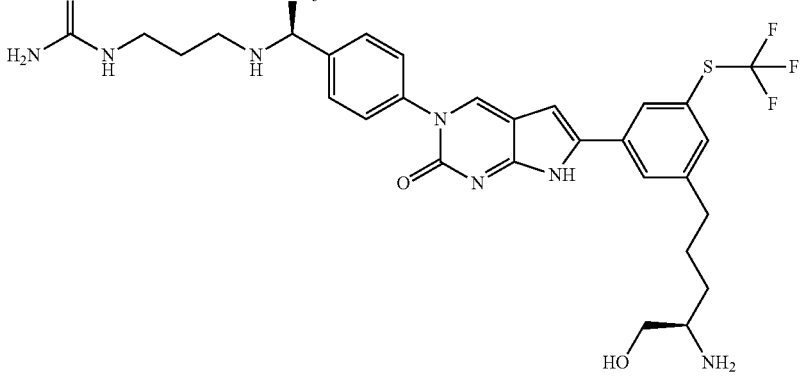 | 631.1 |
| 32 | 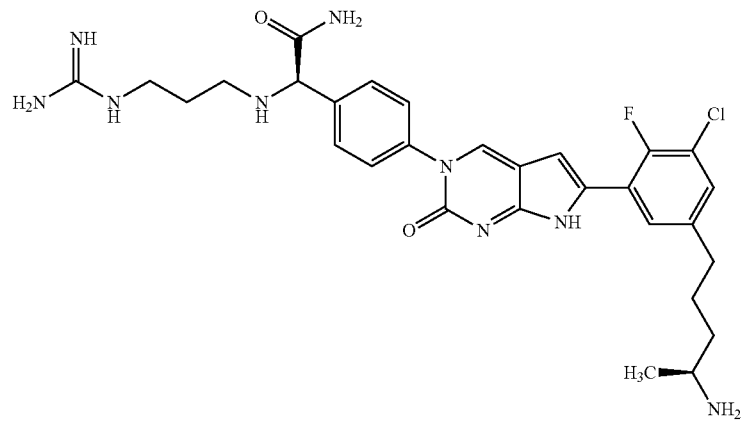 [SMILES: C[C@H](N)CCCc1cc(Cl)c(F)c(-c2cc3cn(-c4ccc([C@@H](NCCCNC(=N)N)C(N)=O)cc4)c(=O)nc3[nH]2)c1] | 596.1 |
| 33 | 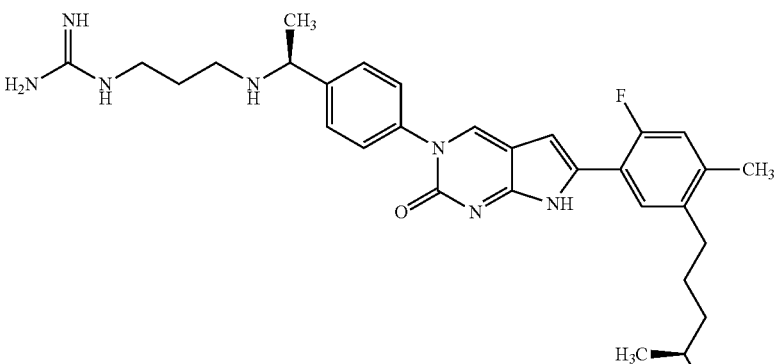 | 547.1 |

TABLE 1-continued

| Compound No | Structure | ESI, m/z [M + H]+ |
|---|---|---|
| 34 | 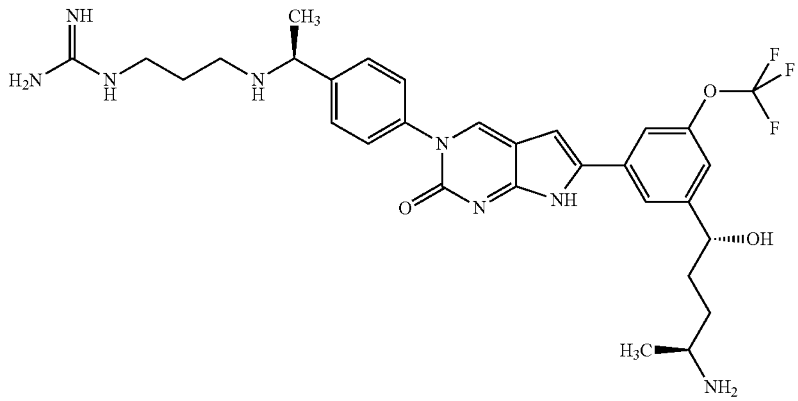 [SMILES: C[C@H](N)CC[C@@H](O)c1cc(OC(F)(F)F)cc(-c2cc3cn(-c4ccc([C@H](C)NCCCNC(=N)N)cc4)c(=O)nc3[nH]2)c1] | 615 |
| 35 | 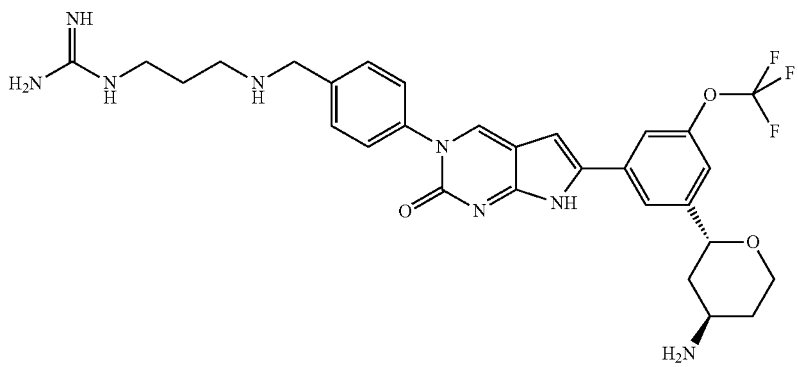 [SMILES: N=C(N)NCCCNCc1ccc(-n2cc3cc(-c4cc(OC(F)(F)F)cc([C@H]5C[C@H](N)CCO5)c4)[nH]c3nc2=O)cc1] | 599 |
| 36 | 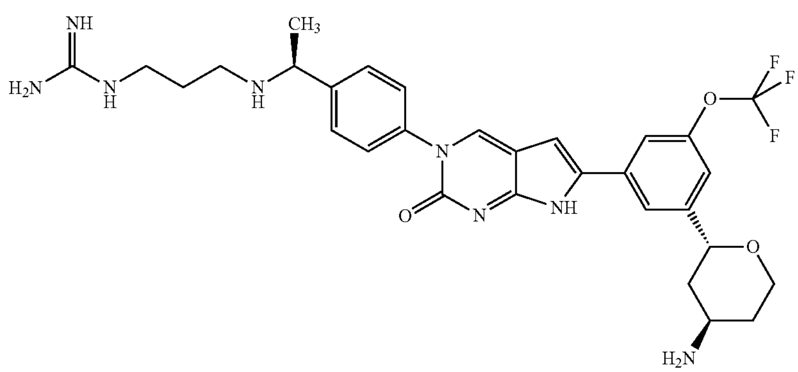 [SMILES: C[C@H](NCCCNC(=N)N)c1ccc(-n2cc3cc(-c4cc(OC(F)(F)F)cc([C@H]5C[C@H](N)CCO5)c4)[nH]c3nc2=O)cc1] | 613 |
| 37 | 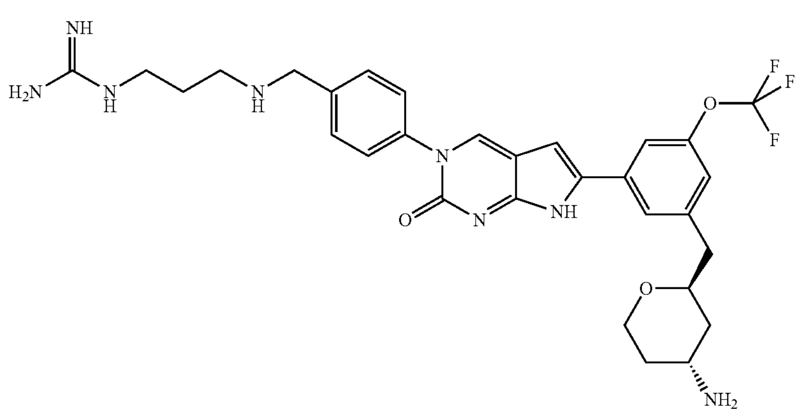 [SMILES: N=C(N)NCCCNCc1ccc(-n2cc3cc(-c4cc(C[C@H]5C[C@H](N)CCO5)cc(OC(F)(F)F)c4)[nH]c3nc2=O)cc1] | 613 |

TABLE 1-continued
| Compound No | Structure | ESI, m/z [M + H]+ |
|---|---|---|
| 38 | 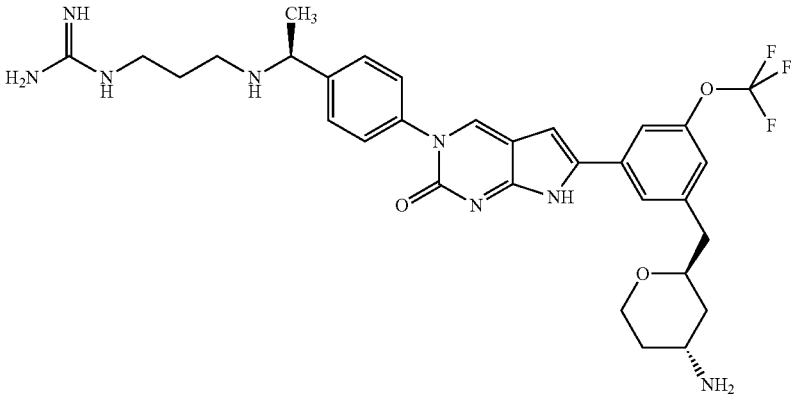 [SMILES: C[C@H](NCCCNC(=N)N)c1ccc(-n2cc3cc(-c4cc(C[C@H]5C[C@H](N)CCO5)cc(OC(F)(F)F)c4)[nH]c3nc2=O)cc1] | 627 |
| 39 | 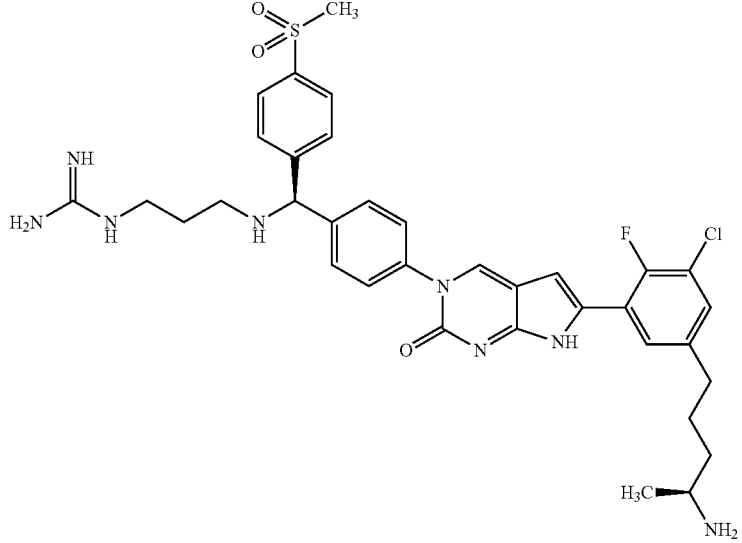 [SMILES: C[C@H](N)CCCc1cc(Cl)c(F)c(-c2cc3cn(-c4ccc([C@@H](NCCCNC(=N)N)c5ccc(S(C)(=O)=O)cc5)cc4)c(=O)nc3[nH]2)c1] | 707.15 |
| 40 | 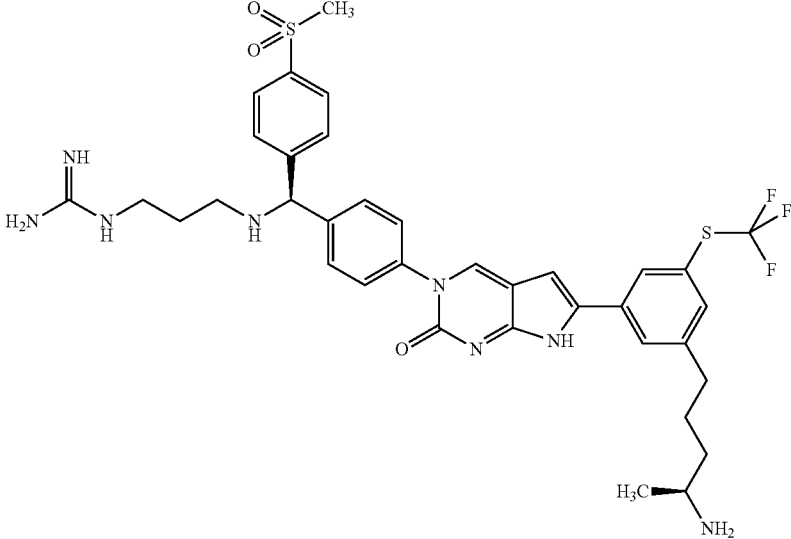 [SMILES: C[C@H](N)CCCc1cc(SC(F)(F)F)cc(-c2cc3cn(-c4ccc([C@@H](NCCCNC(=N)N)c5ccc(S(C)(=O)=O)cc5)cc4)c(=O)nc3[nH]2)c1] | 755.1 |

| Compound No | Structure | ESI, m/z [M + H]+ |
|---|---|---|
| 41 | 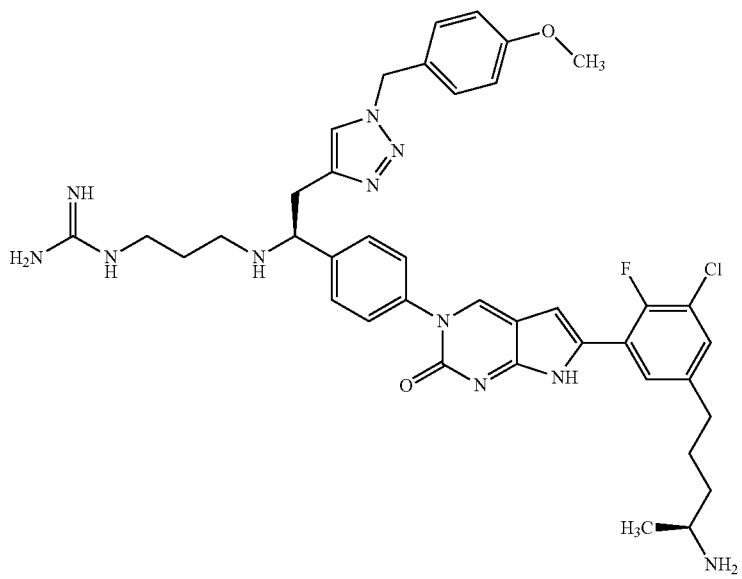 [SMILES: COc1ccc(Cn2cc(C[C@H](NCCCNC(=N)N)c3ccc(-n4cc5cc(-c6cc(CCC[C@H](C)N)cc(Cl)c6F)[nH]c5nc4=O)cc3)nn2)cc1] | 754.6 |
| 42 | 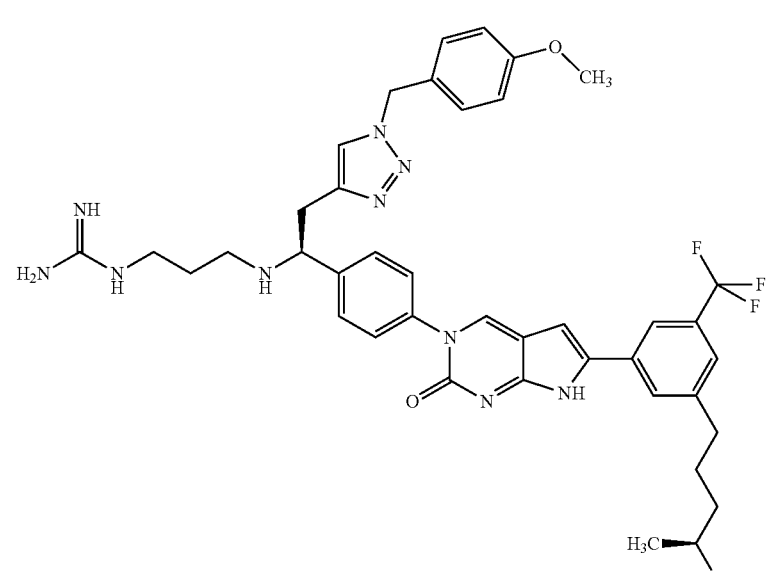 | 770.3 |

TABLE 1-continued

| Compound No | Structure | ESI, m/z [M + H]+ |
|---|---|---|
| 43 | 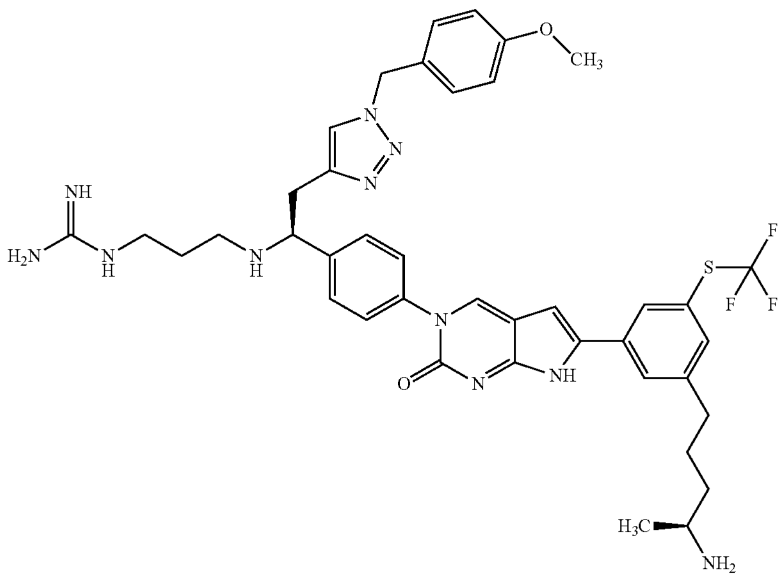 [SMILES: COc1ccc(Cn2cc(C[C@H](NCCCNC(=N)N)c3ccc(-n4cc5cc(-c6cc(CCC[C@H](C)N)cc(SC(F)(F)F)c6)[nH]c5nc4=O)cc3)nn2)cc1] | 802.2 |
| 44 | 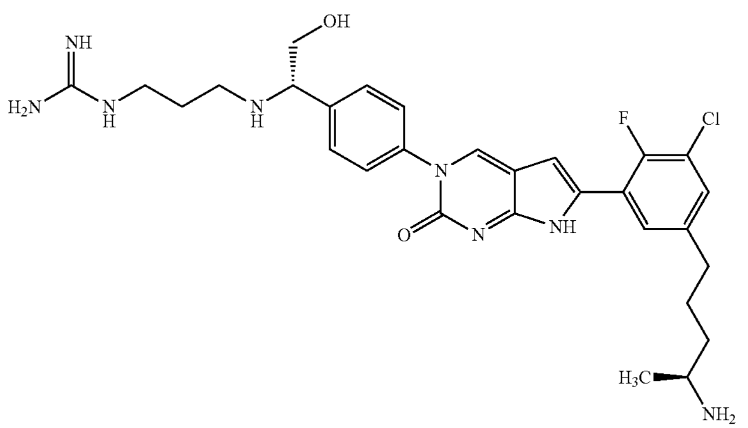 [SMILES: C[C@H](N)CCCc1cc(Cl)c(F)c(-c2cc3cn(-c4ccc([C@@H](CO)NCCCNC(=N)N)cc4)c(=O)nc3[nH]2)c1] | 583.1 |
| 45 | 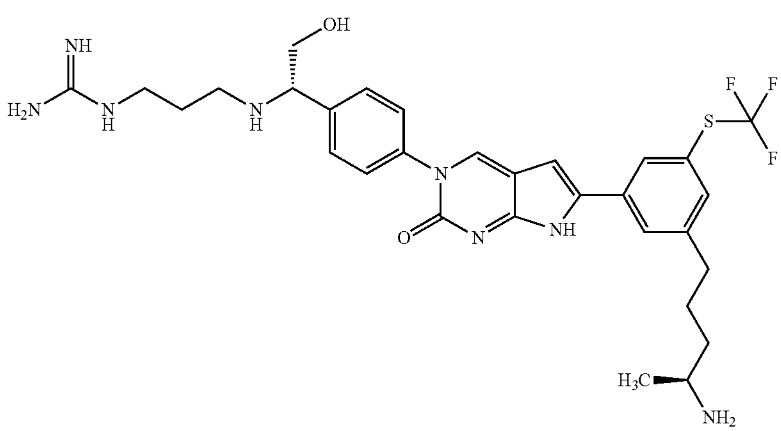 | 631.2 |

TABLE 1-continued
| Compound No | Structure | ESI, m/z [M + H]+ |
|---|---|---|
| 46 | 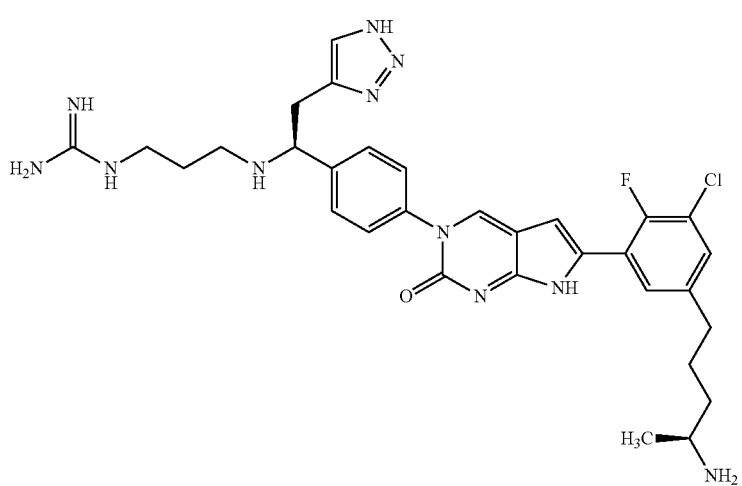 [SMILES: C[C@H](N)CCCc1cc(Cl)c(F)c(-c2cc3cn(-c4ccc([C@H](Cc5c[nH]nn5)NCCCNC(=N)N)cc4)c(=O)nc3[nH]2)c1] | 634.1 |
| 47 | 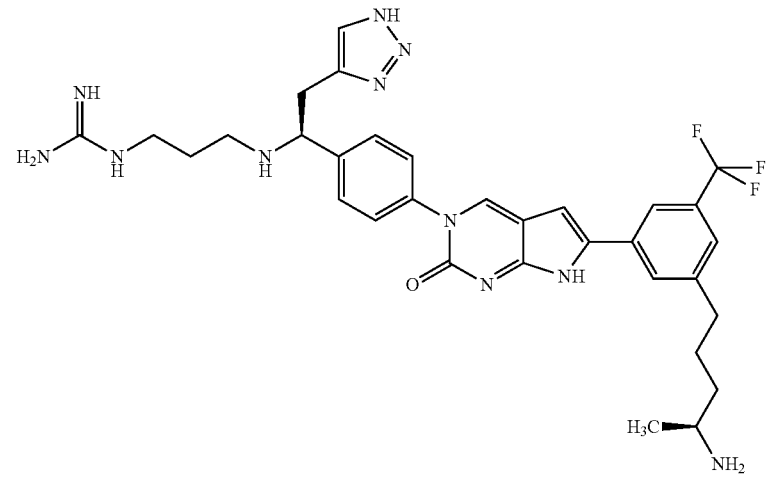 [SMILES: C[C@H](N)CCCc1cc(-c2cc3cn(-c4ccc([C@H](Cc5c[nH]nn5)NCCCNC(=N)N)cc4)c(=O)nc3[nH]2)cc(C(F)(F)F)c1] | 650.2 |
| 48 | 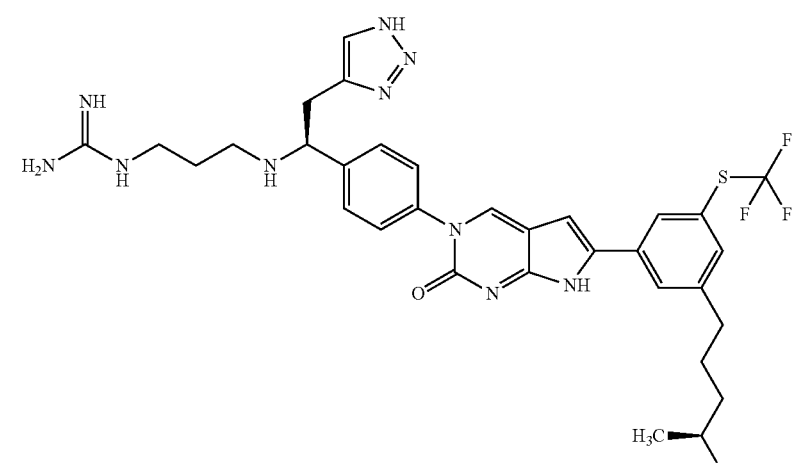 | 682.2 |

TABLE 1-continued
| Compound No | Structure | ESI, m/z [M + H]+ |
|---|---|---|
| 49 | 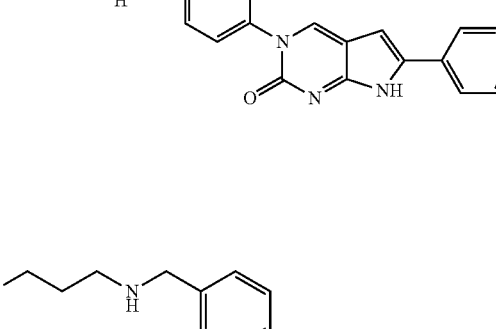 | |
| 50 | 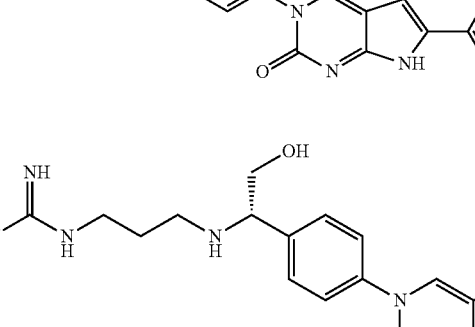 | |
| 51 | 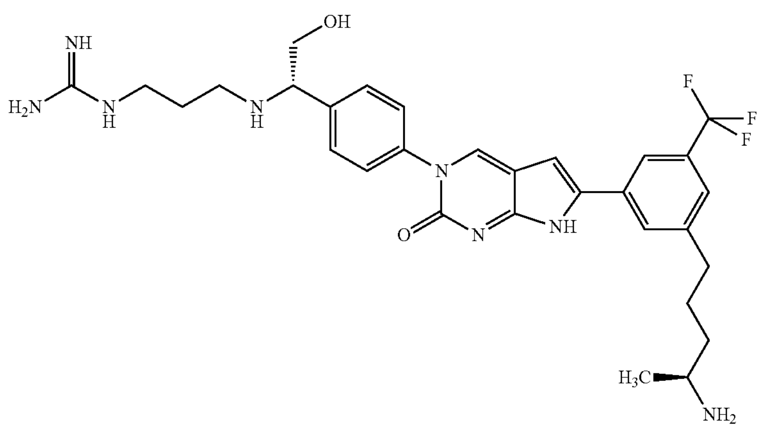 [SMILES: C[C@H](N)CCCc1cc(-c2cc3cn(-c4ccc([C@@H](CO)NCCCNC(=N)N)cc4)c(=O)nc3[nH]2)cc(C(F)(F)F)c1] | 599.1 |
| 52 | 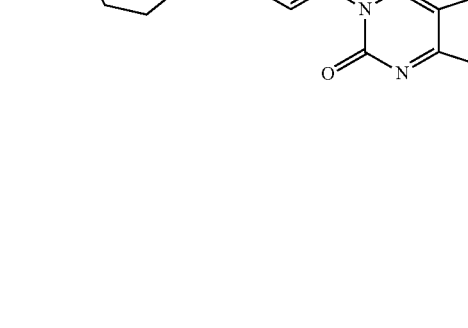 | |
| 53 | 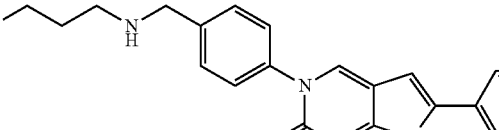 | |

TABLE 1-continued

| Compound No | Structure | ESI, m/z [M + H]+ |
|---|---|---|
| 54 | 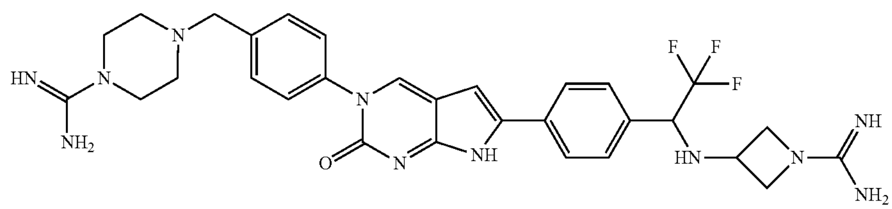 [SMILES: N=C(N)N1CCN(Cc2ccc(-n3cc4cc(-c5ccc(C(NC6CN(C(=N)N)C6)C(F)(F)F)cc5)[nH]c4nc3=O)cc2)CC1] | |
| 55 | 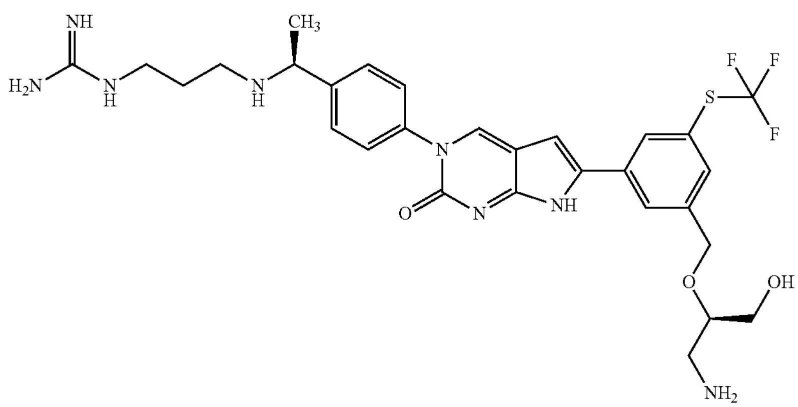 [SMILES: C[C@H](NCCCNC(=N)N)c1ccc(-n2cc3cc(-c4cc(CO[C@H](CN)CO)cc(SC(F)(F)F)c4)[nH]c3nc2=O)cc1] | 633 |
| 56 | 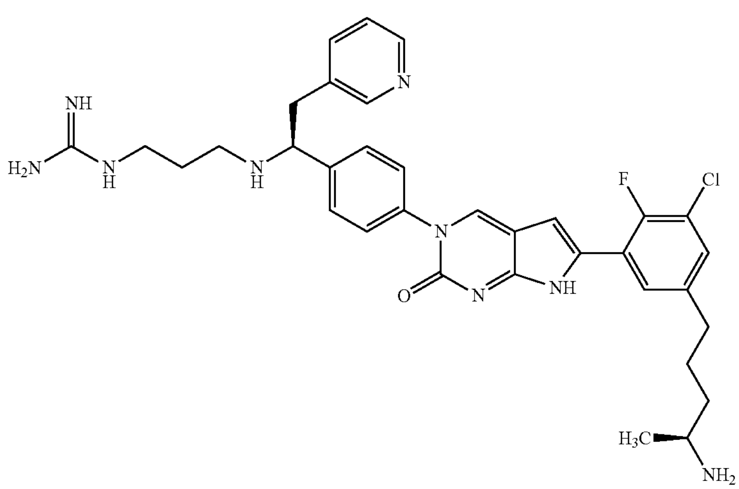 [SMILES: C[C@H](N)CCCc1cc(Cl)c(F)c(-c2cc3cn(-c4ccc([C@H](Cc5cccnc5)NCCCNC(=N)N)cc4)c(=O)nc3[nH]2)c1] | 644.1 |

TABLE 1-continued

| Compound No | Structure | ESI, m/z [M + H]+ |
|---|---|---|
| 57 | 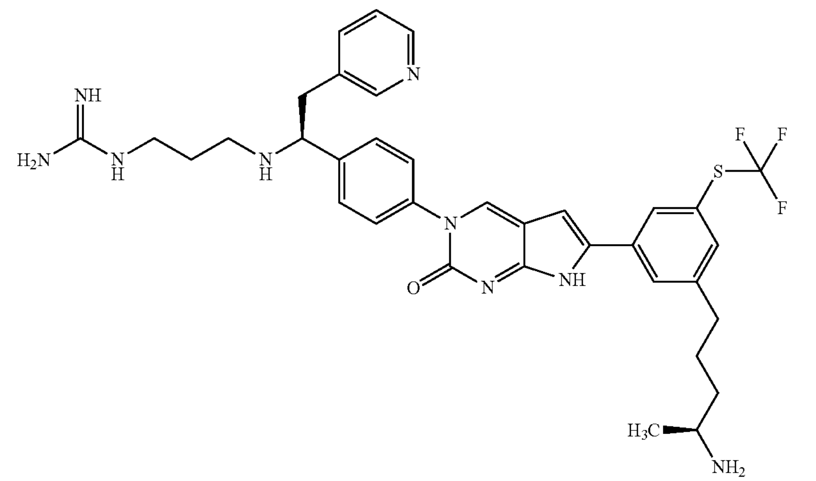 [SMILES: C[C@H](N)CCCc1cc(SC(F)(F)F)cc(-c2cc3cn(-c4ccc([C@H](Cc5cccnc5)NCCCNC(=N)N)cc4)c(=O)nc3[nH]2)c1] | 692.2 |
| 58 | 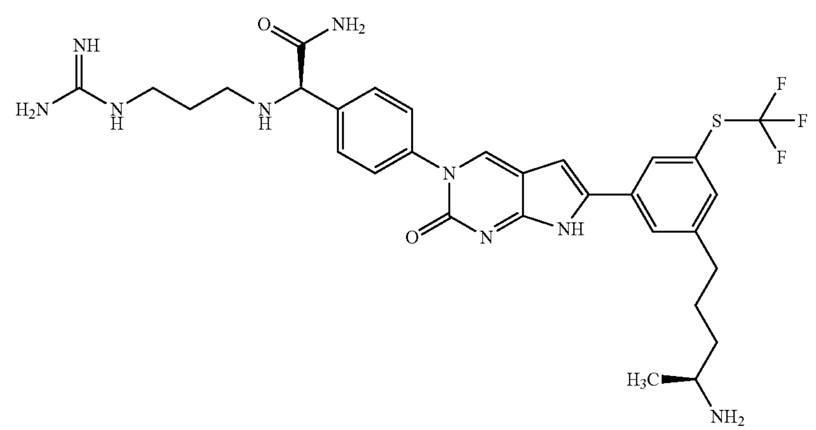 [SMILES: C[C@H](N)CCCc1cc(SC(F)(F)F)cc(-c2cc3cn(-c4ccc([C@@H](NCCCNC(=N)N)C(N)=O)cc4)c(=O)nc3[nH]2)c1] | 644.2 |
| 59 | 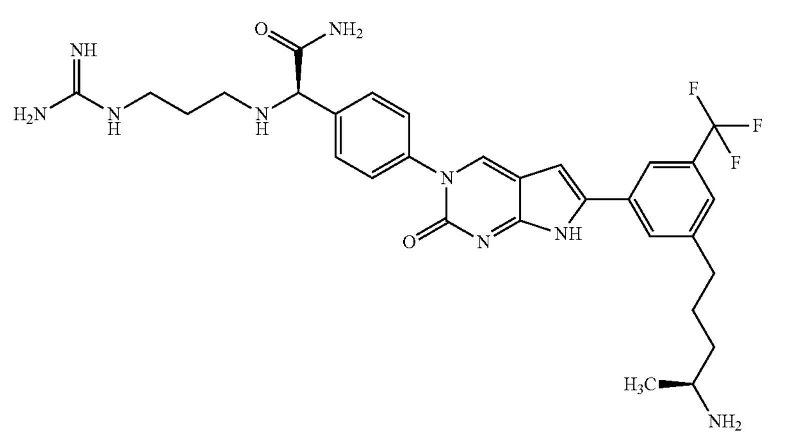 [SMILES: C[C@H](N)CCCc1cc(-c2cc3cn(-c4ccc([C@@H](NCCCNC(=N)N)C(N)=O)cc4)c(=O)nc3[nH]2)cc(C(F)(F)F)c1] | 612.1 |

TABLE 1-continued

| Compound No | Structure | ESI, m/z [M + H]+ |
|---|---|---|
| 60 | 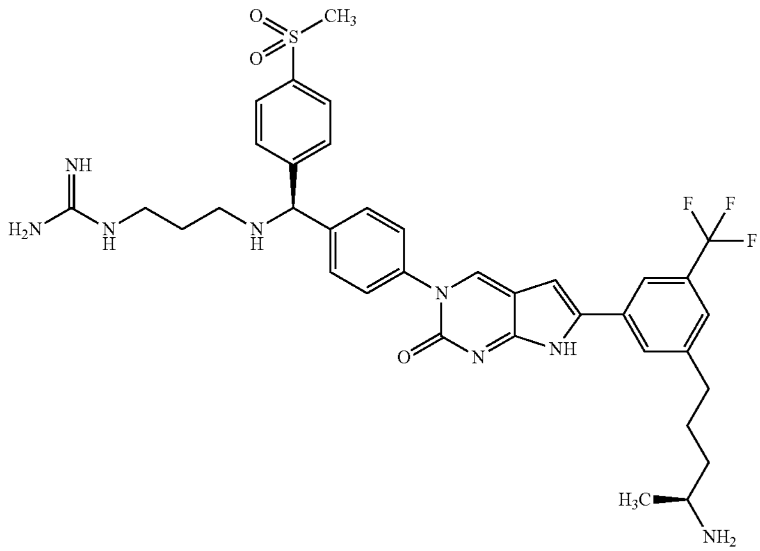 [SMILES: C[C@H](N)CCCc1cc(-c2cc3cn(-c4ccc([C@@H](NCCCNC(=N)N)c5ccc(S(C)(=O)=O)cc5)cc4)c(=O)nc3[nH]2)cc(C(F)(F)F)c1] | 723.1 |
| 61 | 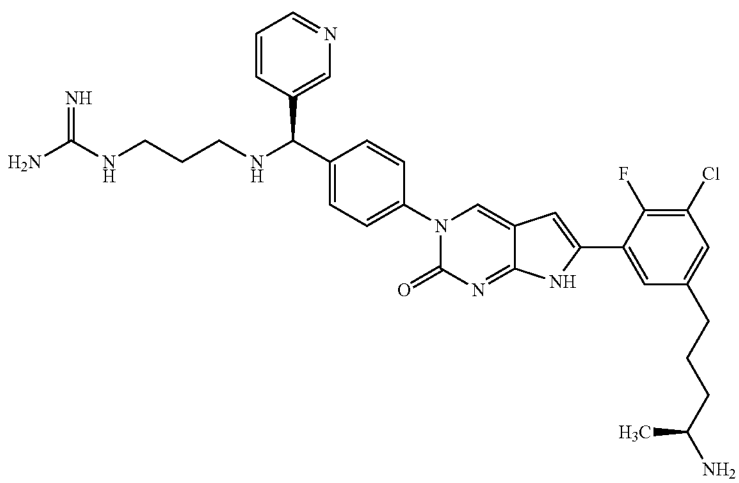 [SMILES: C[C@H](N)CCCc1cc(Cl)c(F)c(-c2cc3cn(-c4ccc([C@@H](NCCCNC(=N)N)c5cccnc5)cc4)c(=O)nc3[nH]2)c1] | 630.1 |
| 62 | 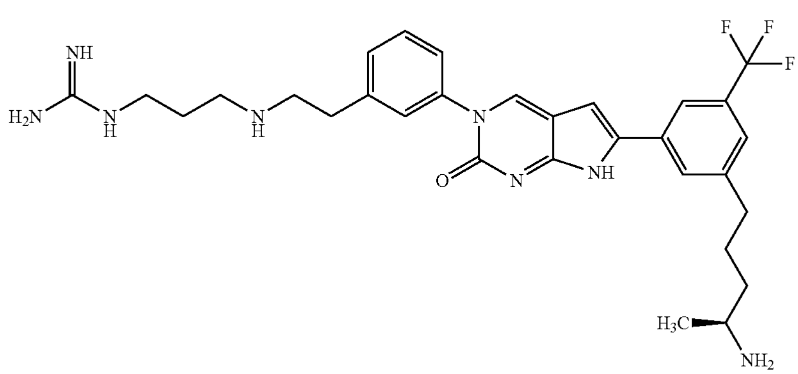 [SMILES: C[C@H](N)CCCc1cc(-c2cc3cn(-c4cccc(CCNCCCNC(=N)N)c4)c(=O)nc3[nH]2)cc(C(F)(F)F)c1] | |

TABLE 1-continued
| Compound No | Structure | ESI, m/z [M + H]+ |
|---|---|---|
| 63 | 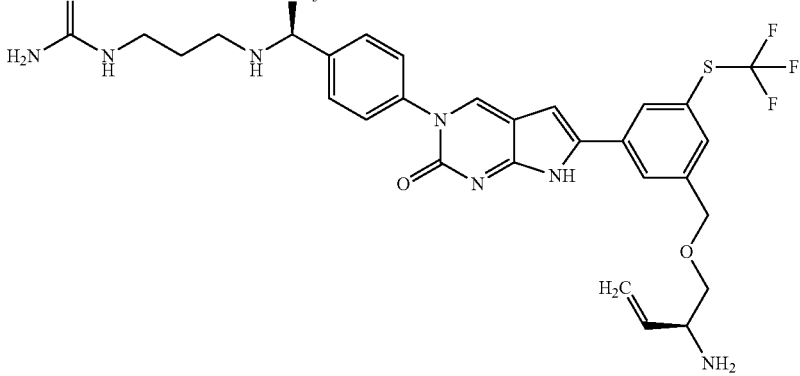 | 629 |
| 64 | 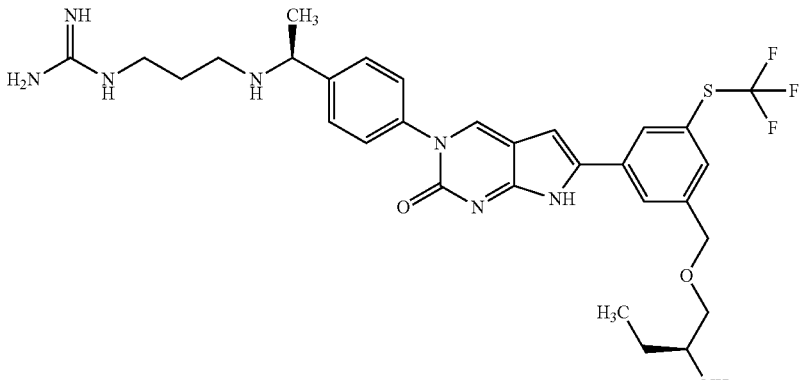 | 631 |
| 65 | 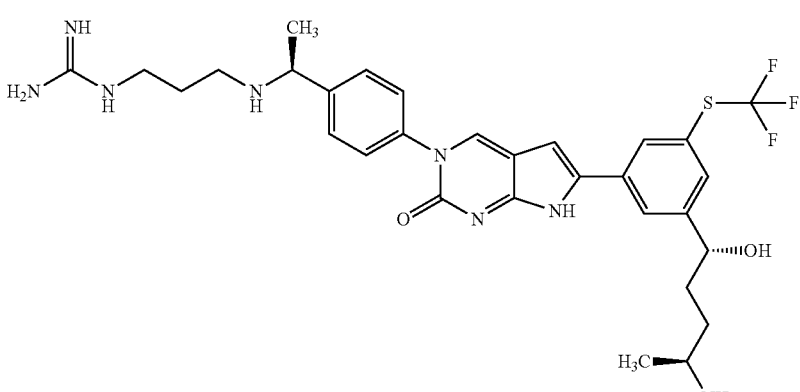 | 631.8 |

TABLE 1-continued

| Compound No | Structure | ESI, m/z [M + H]+ |
|---|---|---|
| 66 | 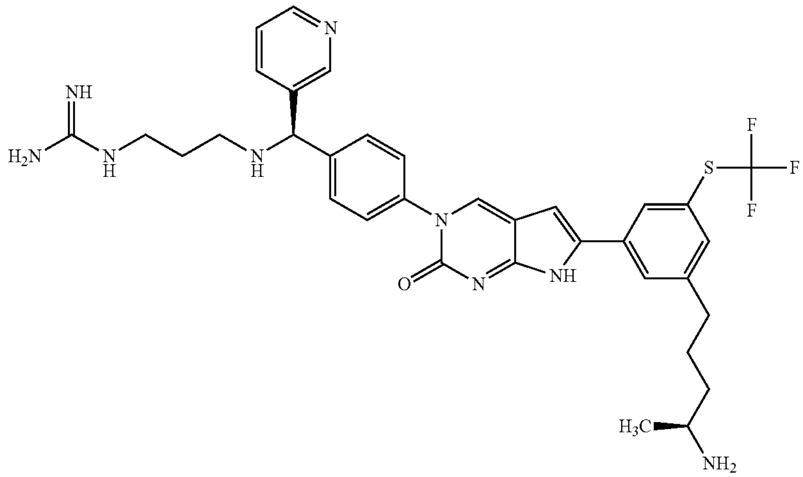 [SMILES: C[C@H](N)CCCc1cc(SC(F)(F)F)cc(-c2cc3cn(-c4ccc([C@@H](NCCCNC(=N)N)c5cccnc5)cc4)c(=O)nc3[nH]2)c1] | 678.2 |
| 67 | 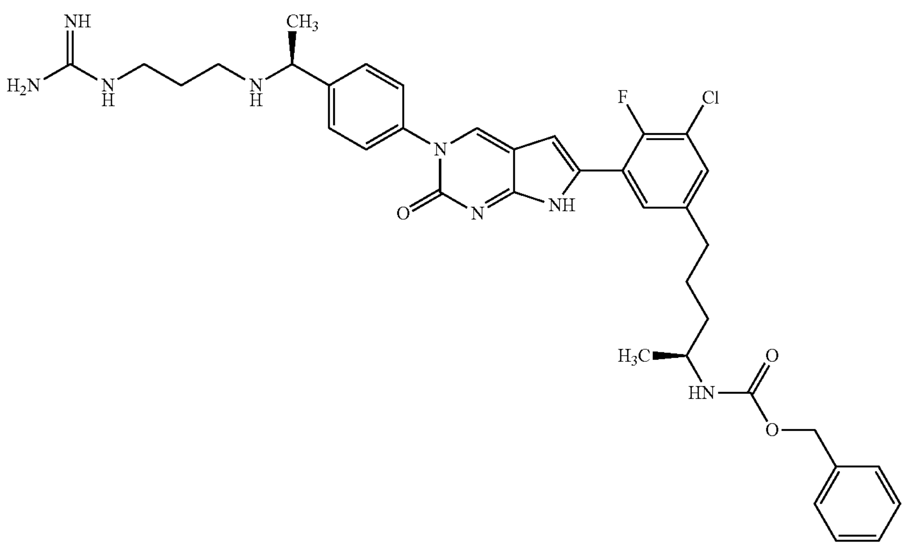 [SMILES: C[C@H](NCCCNC(=N)N)c1ccc(-n2cc3cc(-c4cc(CCC[C@H](C)NC(=O)OCc5ccccc5)cc(Cl)c4F)[nH]c3nc2=O)cc1] | 701.1 |
| 68 | 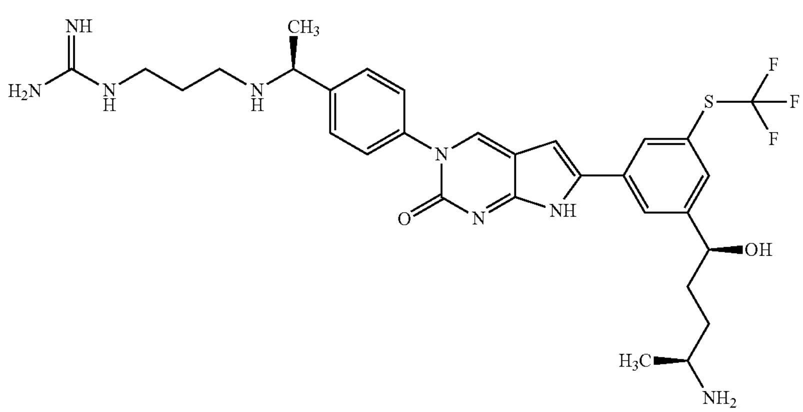 [SMILES: C[C@H](N)CC[C@H](O)c1cc(SC(F)(F)F)cc(-c2cc3cn(-c4ccc([C@H](C)NCCCNC(=N)N)cc4)c(=O)nc3[nH]2)c1] | 631 |

TABLE 1-continued

| Compound No | Structure | ESI, m/z [M + H]+ |
|---|---|---|
| 69 | 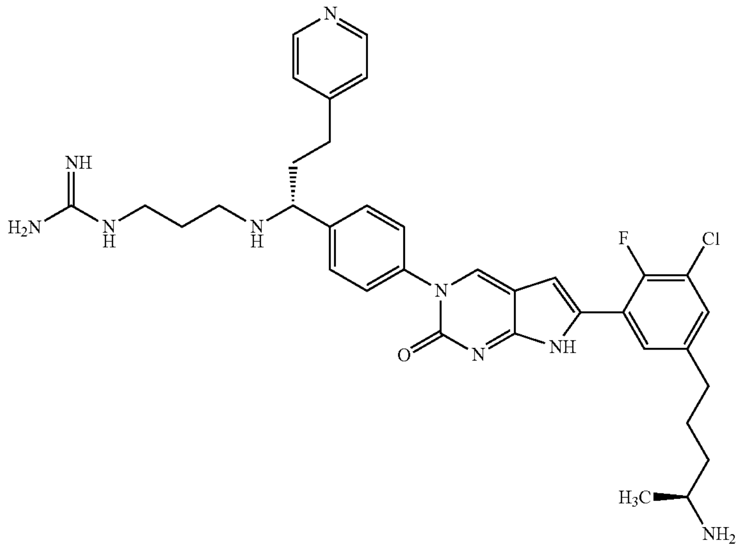 [SMILES: C[C@H](N)CCCc1cc(Cl)c(F)c(-c2cc3cn(-c4ccc([C@@H](CCc5ccncc5)NCCCNC(=N)N)cc4)c(=O)nc3[nH]2)c1] | 658.3 |
| 70 | 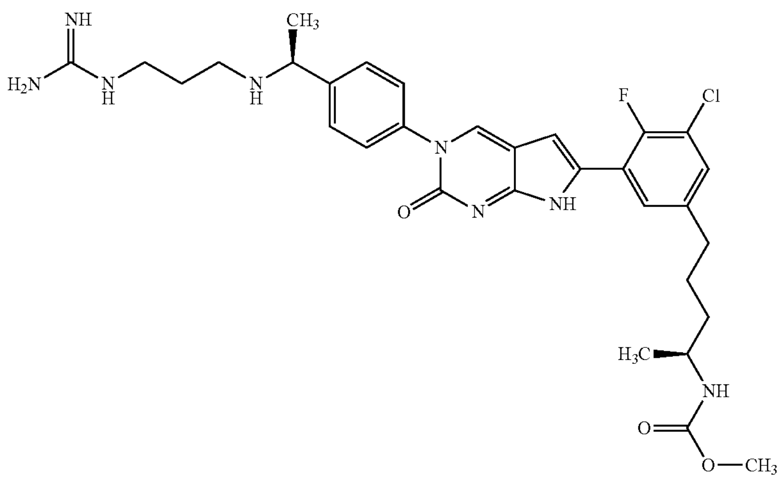 [SMILES: COC(=O)N[C@@H](C)CCCc1cc(Cl)c(F)c(-c2cc3cn(-c4ccc([C@H](C)NCCCNC(=N)N)cc4)c(=O)nc3[nH]2)c1] | 625.1 |
| 71 | 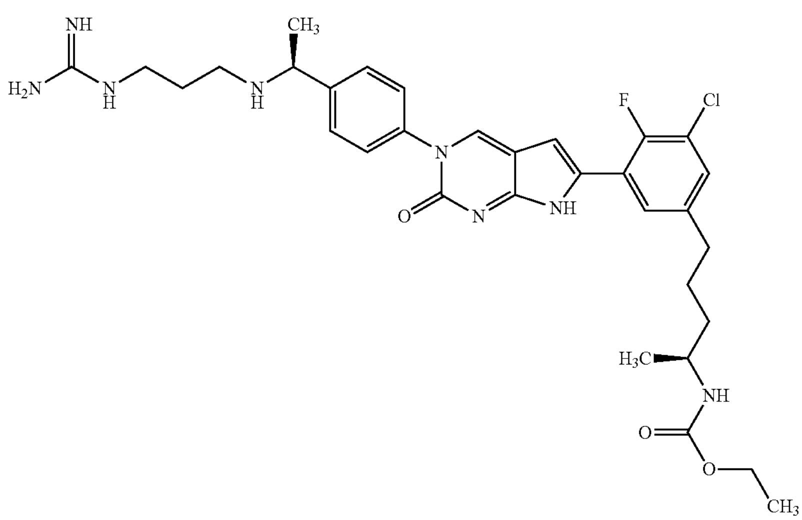 [SMILES: CCOC(=O)N[C@@H](C)CCCc1cc(Cl)c(F)c(-c2cc3cn(-c4ccc([C@H](C)NCCCNC(=N)N)cc4)c(=O)nc3[nH]2)c1] | 639.1 |

TABLE 1-continued
| Compound No | Structure | ESI, m/z [M + H]+ |
|---|---|---|
| 72 | 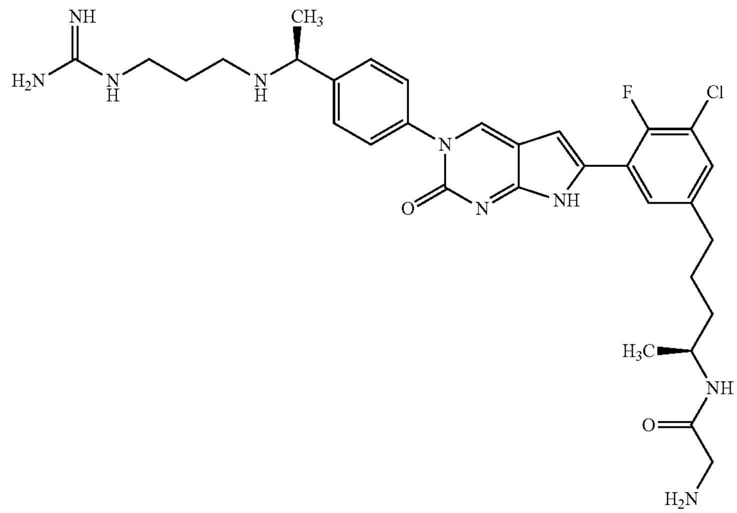 [SMILES: C[C@H](NCCCNC(=N)N)c1ccc(-n2cc3cc(-c4cc(CCC[C@H](C)NC(=O)CN)cc(Cl)c4F)[nH]c3nc2=O)cc1] | 624.2 |
| 73 | 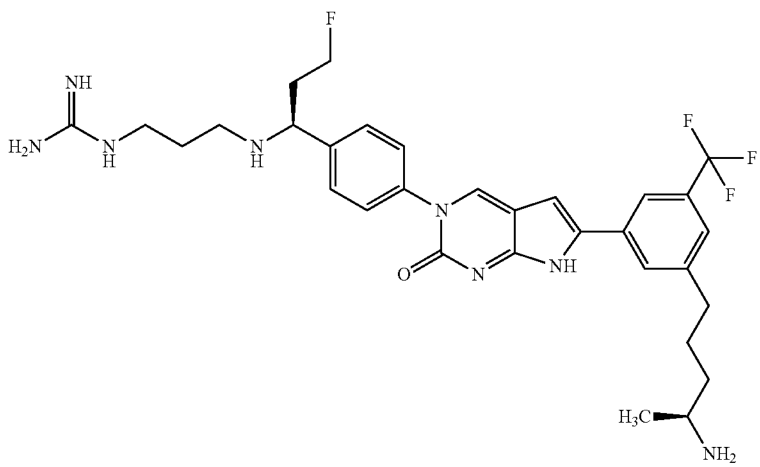 [SMILES: C[C@H](N)CCCc1cc(-c2cc3cn(-c4ccc([C@H](CCF)NCCCNC(=N)N)cc4)c(=O)nc3[nH]2)cc(C(F)(F)F)c1] | 615.1 |
| 74 | 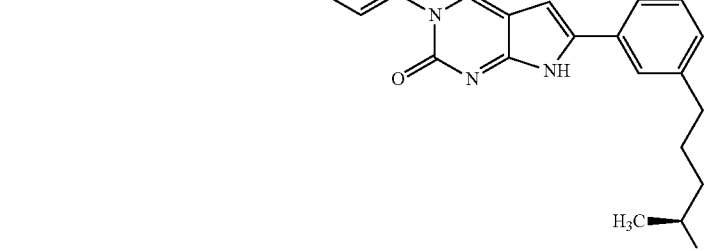 | 599 |

TABLE 1-continued

| Compound No | Structure | ESI, m/z [M + H]+ |
|---|---|---|
| 75 | 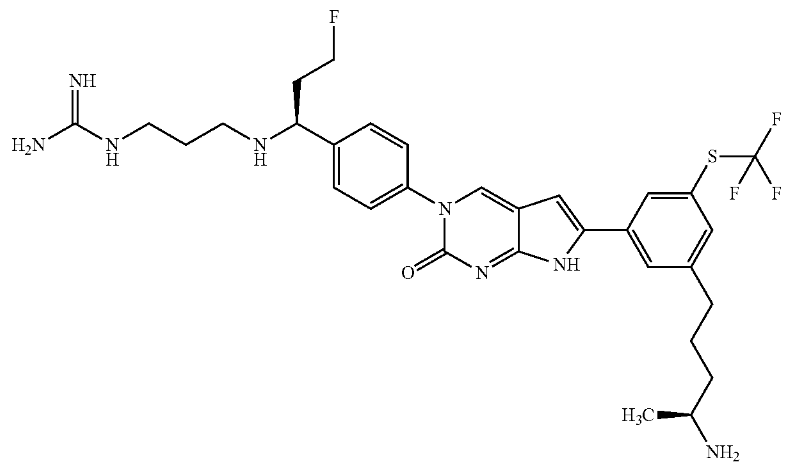 [SMILES: C[C@H](N)CCCc1cc(SC(F)(F)F)cc(-c2cc3cn(-c4ccc([C@H](CCF)NCCCNC(=N)N)cc4)c(=O)nc3[nH]2)c1] | 647.2 |
| 76 | 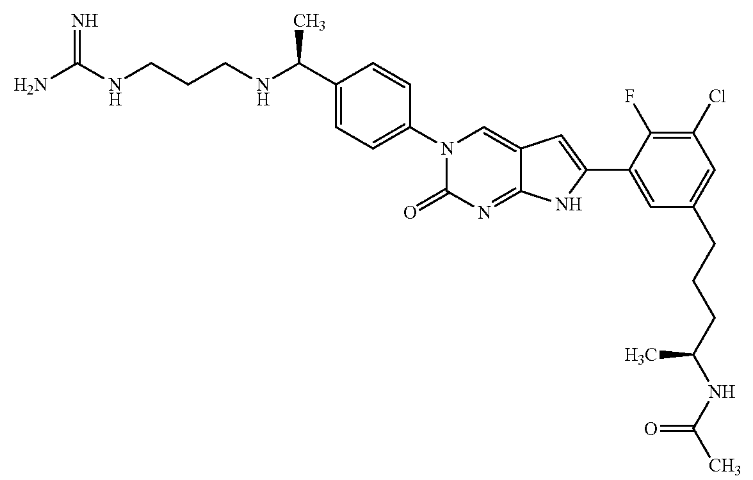 [SMILES: CC(=O)N[C@@H](C)CCCc1cc(Cl)c(F)c(-c2cc3cn(-c4ccc([C@H](C)NCCCNC(=N)N)cc4)c(=O)nc3[nH]2)c1] | 609.1 |
| 77 | 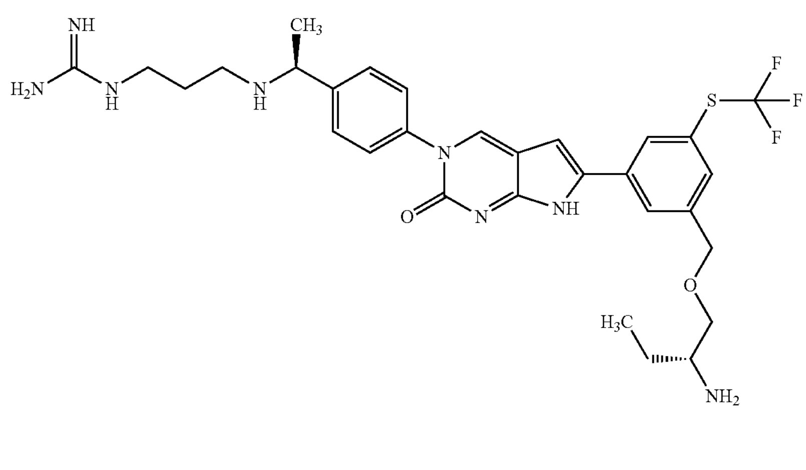 [SMILES: CC[C@@H](N)COCc1cc(SC(F)(F)F)cc(-c2cc3cn(-c4ccc([C@H](C)NCCCNC(=N)N)cc4)c(=O)nc3[nH]2)c1] | 631 |

TABLE 1-continued
| Compound No | Structure | ESI, m/z [M + H]+ |
|---|---|---|
| 78 | 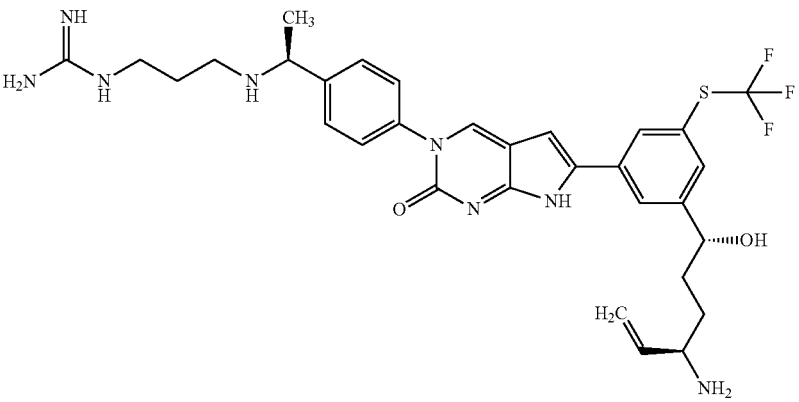 [SMILES: C=C[C@H](N)CC[C@@H](O)c1cc(SC(F)(F)F)cc(-c2cc3cn(-c4ccc([C@H](C)NCCCNC(=N)N)cc4)c(=O)nc3[nH]2)c1] | 643 |
| 79 | 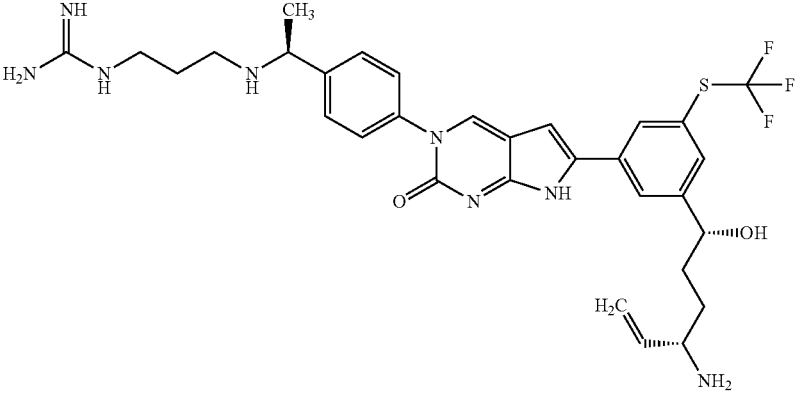 [SMILES: C=C[C@@H](N)CC[C@@H](O)c1cc(SC(F)(F)F)cc(-c2cc3cn(-c4ccc([C@H](C)NCCCNC(=N)N)cc4)c(=O)nc3[nH]2)c1] | 643 |
| 80 | 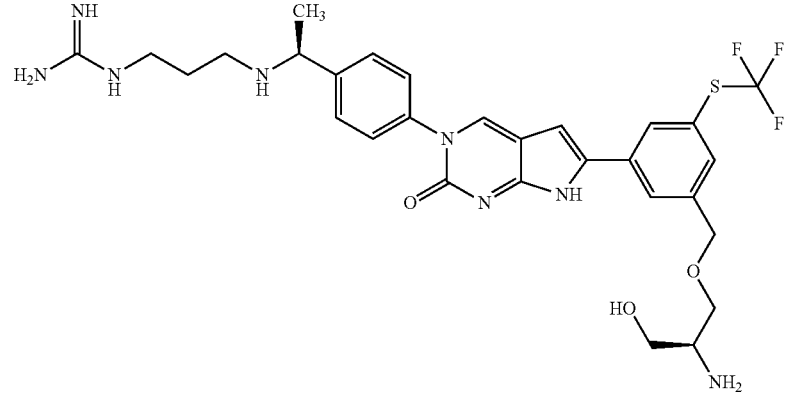 [SMILES: C[C@H](NCCCNC(=N)N)c1ccc(-n2cc3cc(-c4cc(COC[C@@H](N)CO)cc(SC(F)(F)F)c4)[nH]c3nc2=O)cc1] | 633.2 |

TABLE 1-continued
| Compound No | Structure | ESI, m/z [M + H]+ |
|---|---|---|
| 81 | 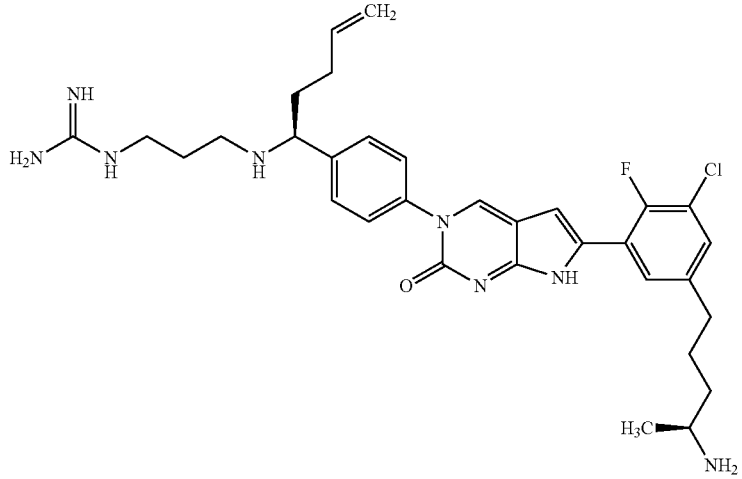 [SMILES: C=CCC[C@H](NCCCNC(=N)N)c1ccc(-n2cc3cc(-c4cc(CCC[C@H](C)N)cc(Cl)c4F)[nH]c3nc2=O)cc1] | 607.1 |
| 82 | 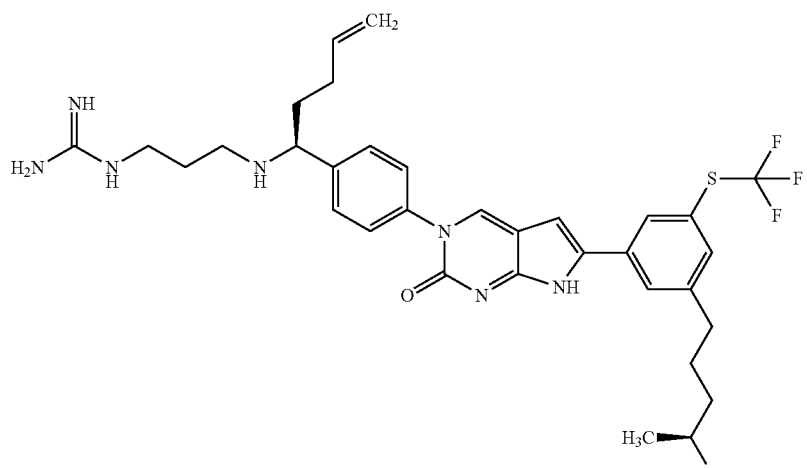 | 655.1 |
| 83 | 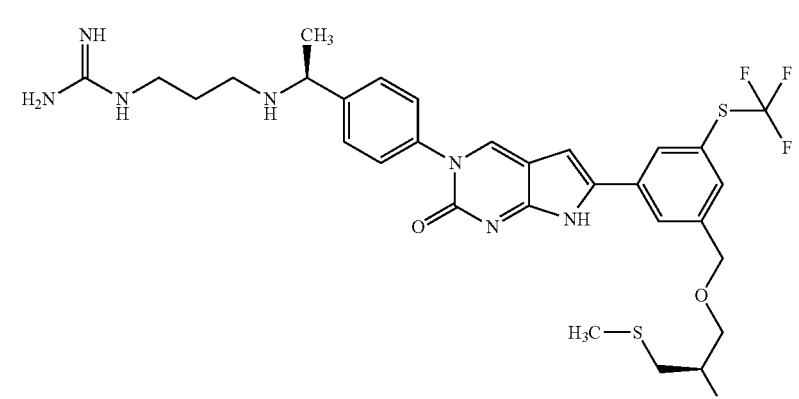 | 663.1 |

TABLE 1-continued
| Compound No | Structure | ESI, m/z [M + H]+ |
|---|---|---|
| 84 | 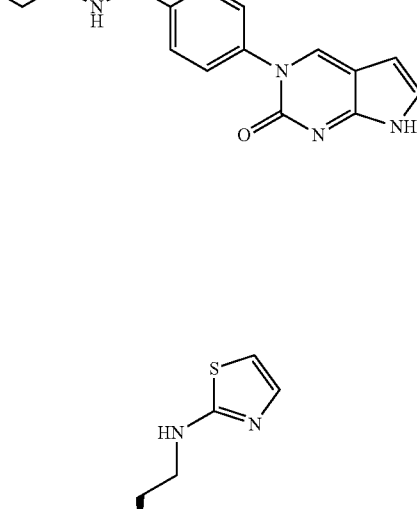 | 646.2 |
| 85 | 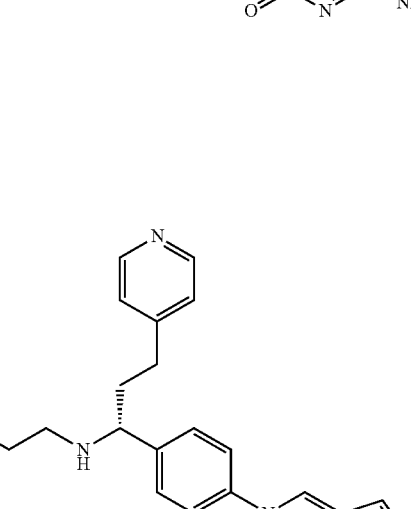 | [M + 2H]²⁺ 340.1 |
| 86 | 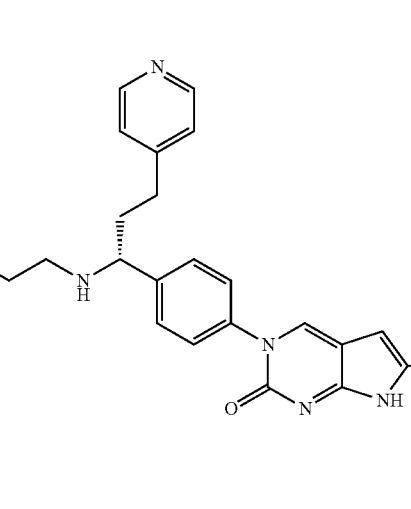 | 706.2 |

TABLE 1-continued

| Compound No | Structure | ESI, m/z [M + H]+ |
|---|---|---|
| 87 | 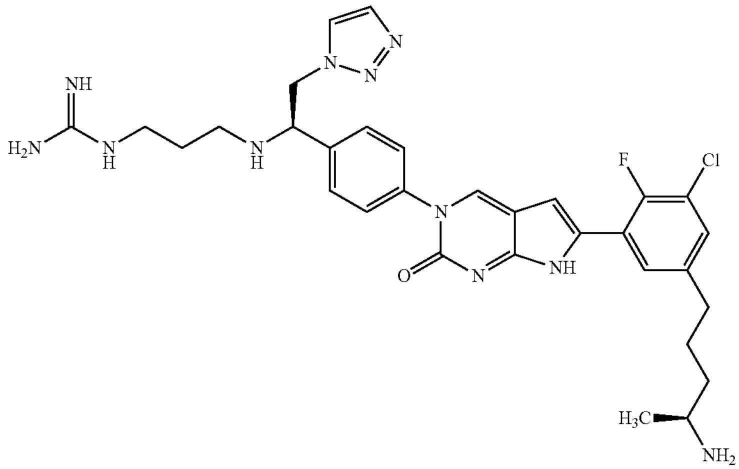 [SMILES: C[C@H](N)CCCc1cc(Cl)c(F)c(-c2cc3cn(-c4ccc([C@H](Cn5ccnn5)NCCCNC(=N)N)cc4)c(=O)nc3[nH]2)c1] | 634.2 |
| 88 | 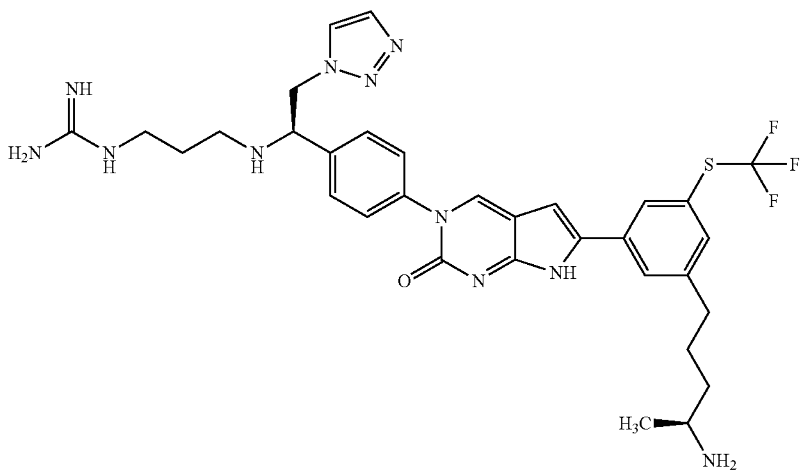 [SMILES: C[C@H](N)CCCc1cc(SC(F)(F)F)cc(-c2cc3cn(-c4ccc([C@H](Cn5ccnn5)NCCCNC(=N)N)cc4)c(=O)nc3[nH]2)c1] | 682.2 |
| 89 | 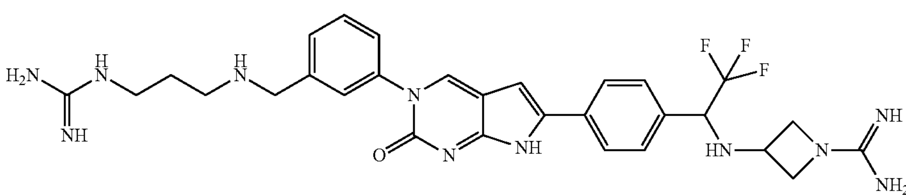 [SMILES: N=C(N)NCCCNCc1cccc(-n2cc3cc(-c4ccc(C(NC5CN(C(=N)N)C5)C(F)(F)F)cc4)[nH]c3nc2=O)c1] | |
| 90 | 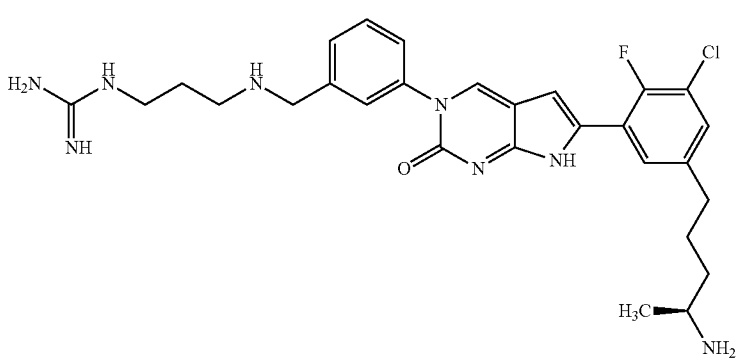 [SMILES: C[C@H](N)CCCc1cc(Cl)c(F)c(-c2cc3cn(-c4cccc(CNCCCNC(=N)N)c4)c(=O)nc3[nH]2)c1] | |

TABLE 1-continued

| Compound No | Structure | ESI, m/z [M + H]+ |
|---|---|---|
| 91 | 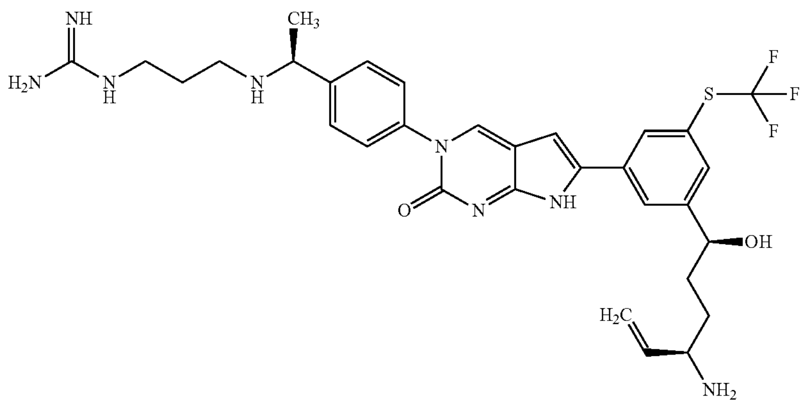 [SMILES: C=C[C@H](N)CC[C@H](O)c1cc(SC(F)(F)F)cc(-c2cc3cn(-c4ccc([C@H](C)NCCCNC(=N)N)cc4)c(=O)nc3[nH]2)c1] | 643 |
| 92 | 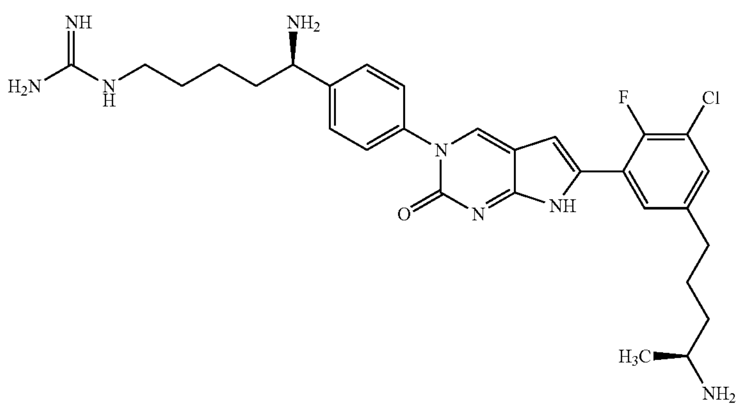 [SMILES: C[C@H](N)CCCc1cc(Cl)c(F)c(-c2cc3cn(-c4ccc([C@H](N)CCCCNC(=N)N)cc4)c(=O)nc3[nH]2)c1] | 567.1 |
| 93 | 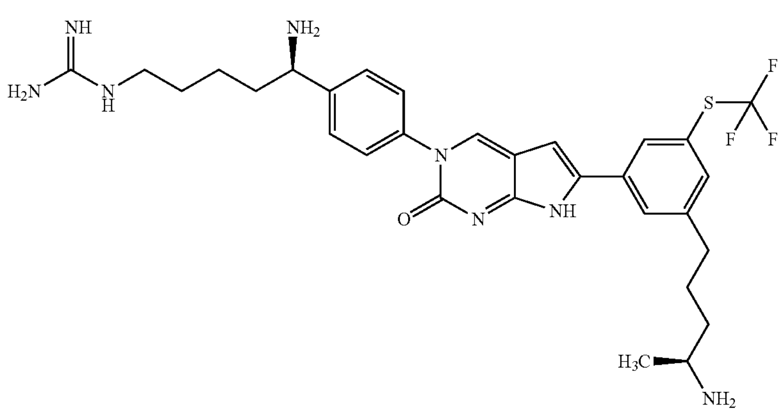 [SMILES: C[C@H](N)CCCc1cc(SC(F)(F)F)cc(-c2cc3cn(-c4ccc([C@H](N)CCCCNC(=N)N)cc4)c(=O)nc3[nH]2)c1] | 615.2 |

TABLE 1-continued

| Compound No | Structure | ESI, m/z [M + H]+ |
|---|---|---|
| 94 | 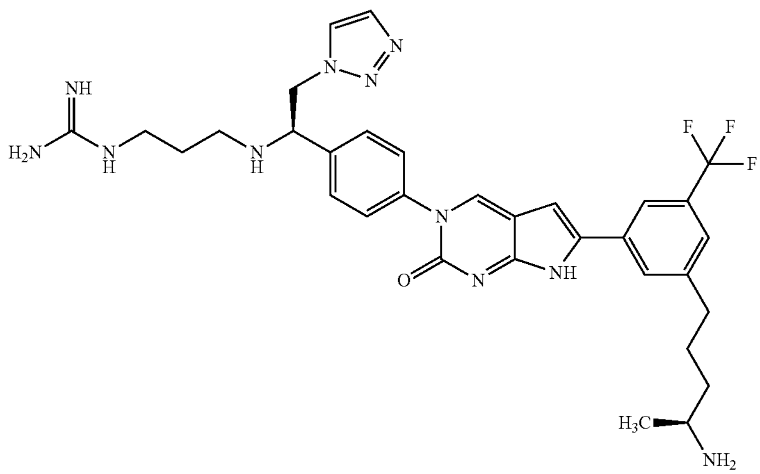 [SMILES: C[C@H](N)CCCc1cc(-c2cc3cn(-c4ccc([C@H](Cn5ccnn5)NCCCNC(=N)N)cc4)c(=O)nc3[nH]2)cc(C(F)(F)F)c1] | 650.3 |
| 95 | 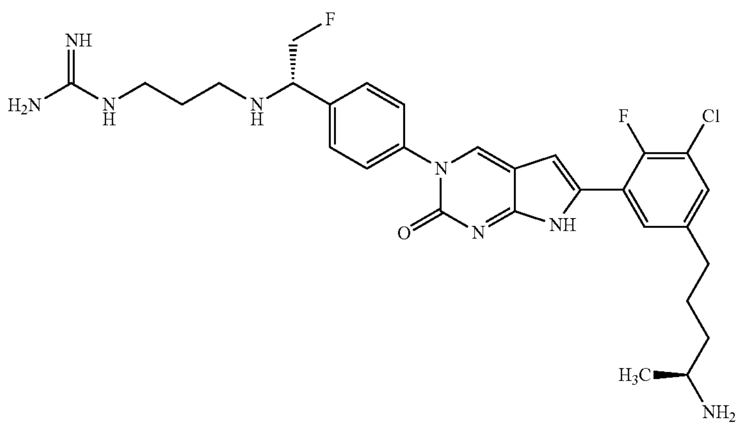 [SMILES: C[C@H](N)CCCc1cc(Cl)c(F)c(-c2cc3cn(-c4ccc([C@@H](CF)NCCCNC(=N)N)cc4)c(=O)nc3[nH]2)c1] | 585.1 |
| 96 | 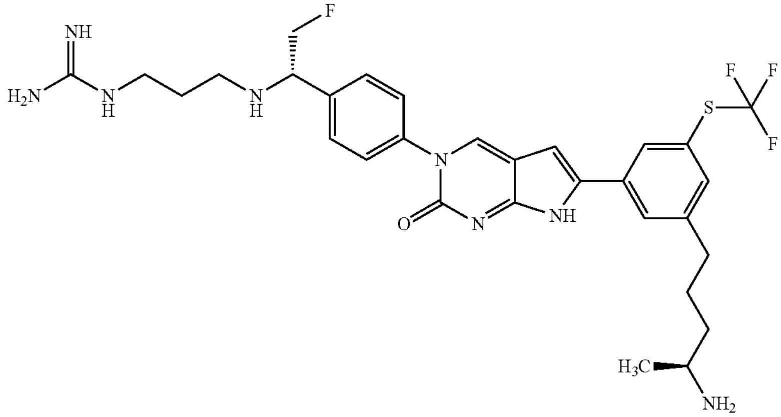 [SMILES: C[C@H](N)CCCc1cc(SC(F)(F)F)cc(-c2cc3cn(-c4ccc([C@@H](CF)NCCCNC(=N)N)cc4)c(=O)nc3[nH]2)c1] | 633.1 |

TABLE 1-continued

| Compound No | Structure | ESI, m/z [M + H]+ |
|---|---|---|
| 97 | 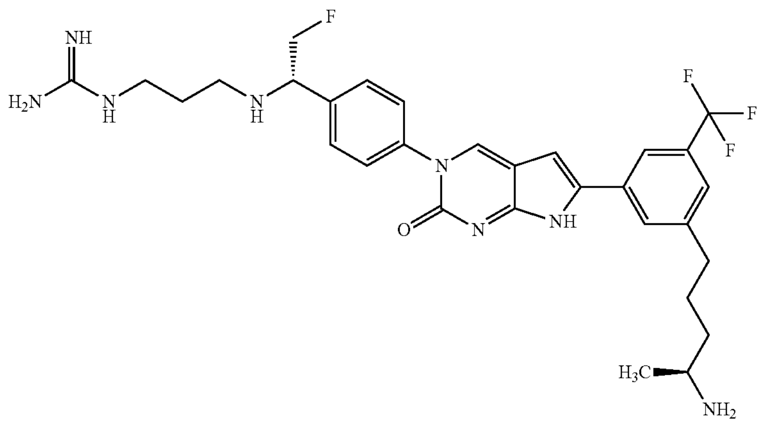 [SMILES: C[C@H](N)CCCc1cc(-c2cc3cn(-c4ccc([C@@H](CF)NCCCNC(=N)N)cc4)c(=O)nc3[nH]2)cc(C(F)(F)F)c1] | 601.2 |
| 98 | 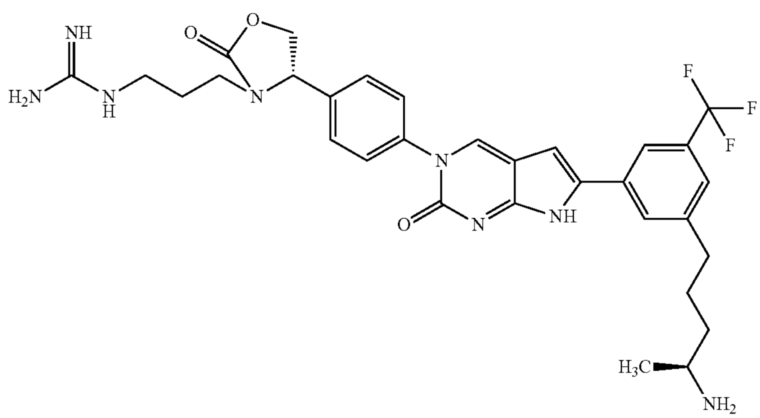 [SMILES: C[C@H](N)CCCc1cc(-c2cc3cn(-c4ccc([C@H]5COC(=O)N5CCCNC(=N)N)cc4)c(=O)nc3[nH]2)cc(C(F)(F)F)c1] | 625.2 |
| 99 | 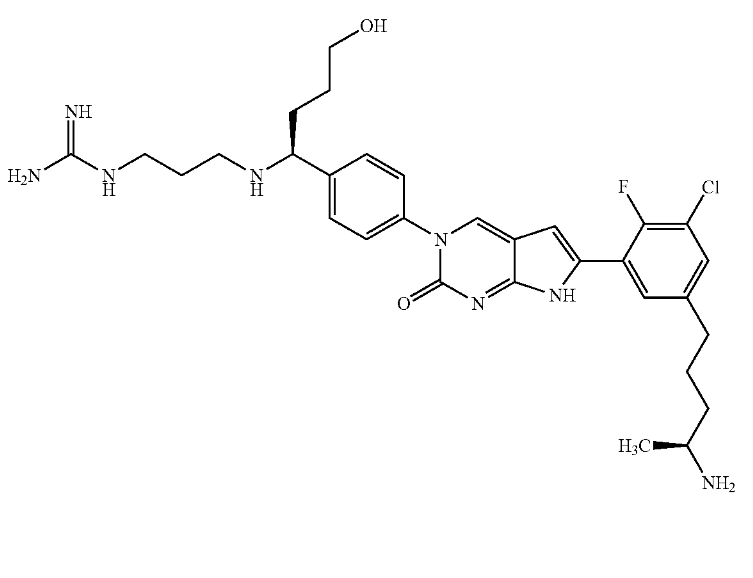 [SMILES: C[C@H](N)CCCc1cc(Cl)c(F)c(-c2cc3cn(-c4ccc([C@H](CCCO)NCCCNC(=N)N)cc4)c(=O)nc3[nH]2)c1] | 611.1 |

TABLE 1-continued
| Compound No | Structure | ESI, m/z [M + H]+ |
|---|---|---|
| 100 | 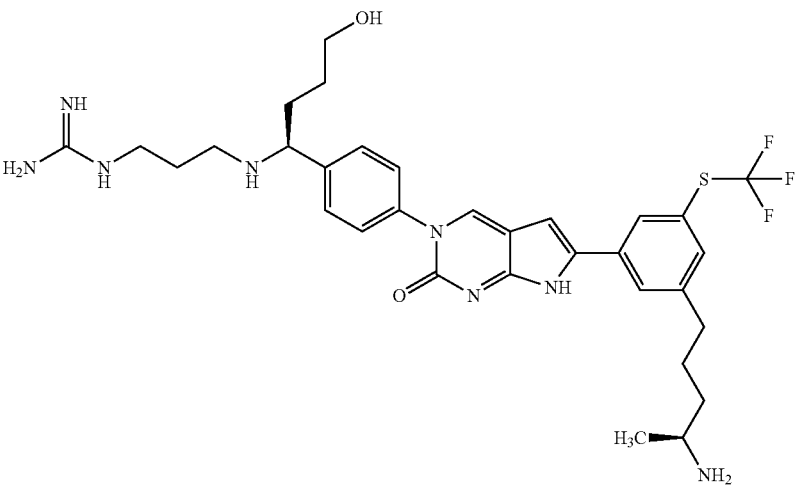 [SMILES: C[C@H](N)CCCc1cc(SC(F)(F)F)cc(-c2cc3cn(-c4ccc([C@H](CCCO)NCCCNC(=N)N)cc4)c(=O)nc3[nH]2)c1] | 659.2 |
| 101 | 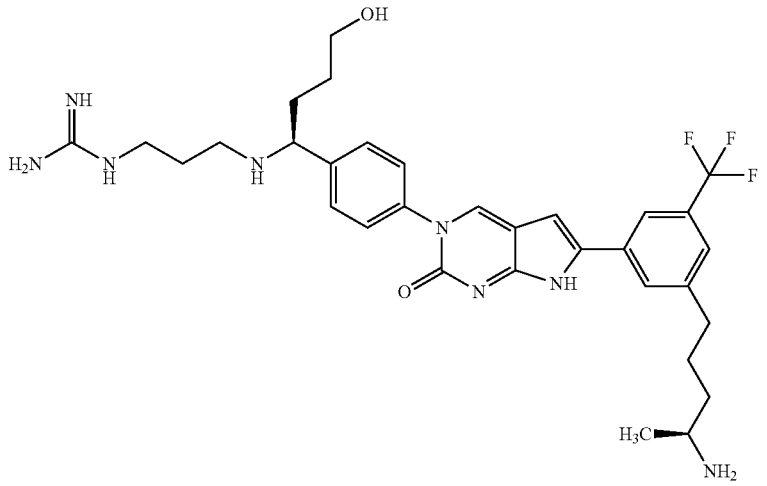 [SMILES: C[C@H](N)CCCc1cc(-c2cc3cn(-c4ccc([C@H](CCCO)NCCCNC(=N)N)cc4)c(=O)nc3[nH]2)cc(C(F)(F)F)c1] | 627.3 |
| 102 | 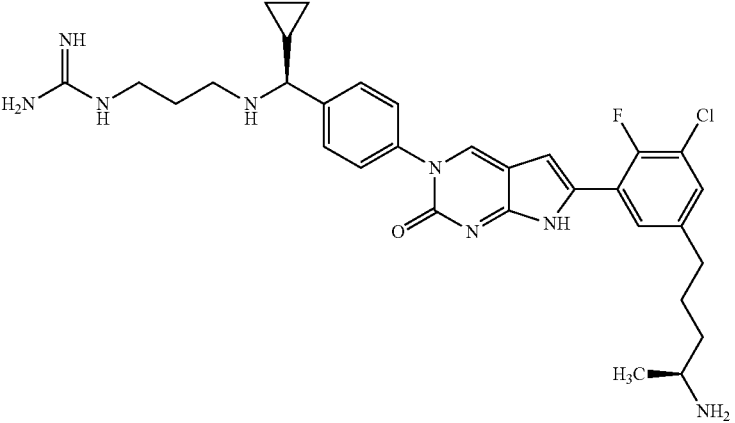 [SMILES: C[C@H](N)CCCc1cc(Cl)c(F)c(-c2cc3cn(-c4ccc([C@@H](NCCCNC(=N)N)C5CC5)cc4)c(=O)nc3[nH]2)c1] | 593.1 |

TABLE 1-continued
| Compound No | Structure | ESI, m/z [M + H]+ |
|---|---|---|
| 103 | 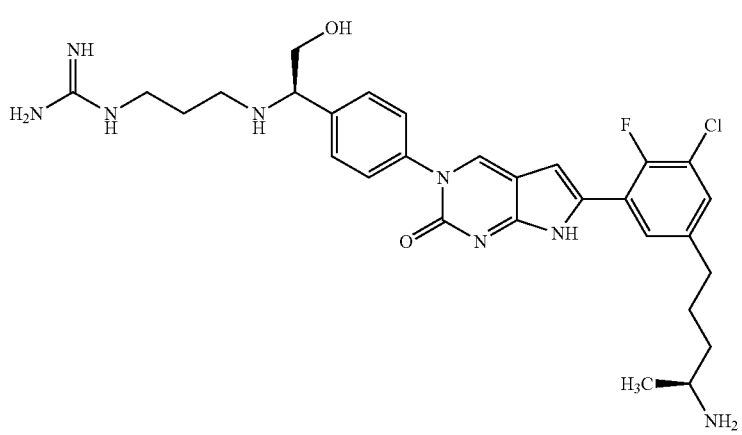 [SMILES: C[C@H](N)CCCc1cc(Cl)c(F)c(-c2cc3cn(-c4ccc([C@H](CO)NCCCNC(=N)N)cc4)c(=O)nc3[nH]2)c1] | 583.1 |
| 104 | 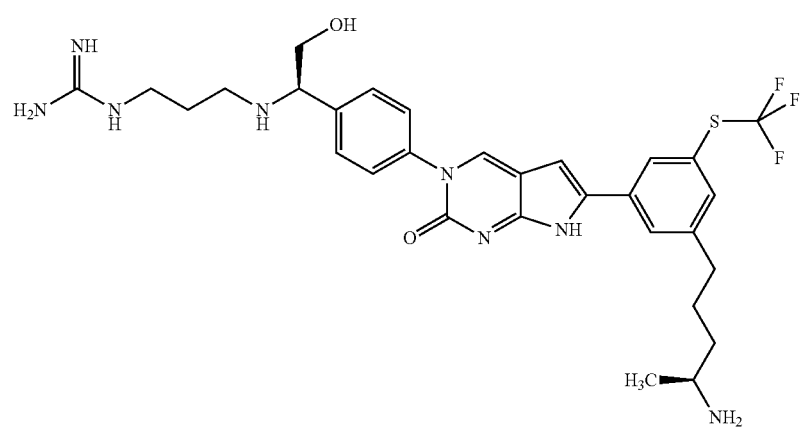 [SMILES: C[C@H](N)CCCc1cc(SC(F)(F)F)cc(-c2cc3cn(-c4ccc([C@H](CO)NCCCNC(=N)N)cc4)c(=O)nc3[nH]2)c1] | 631.2 |
| 105 | 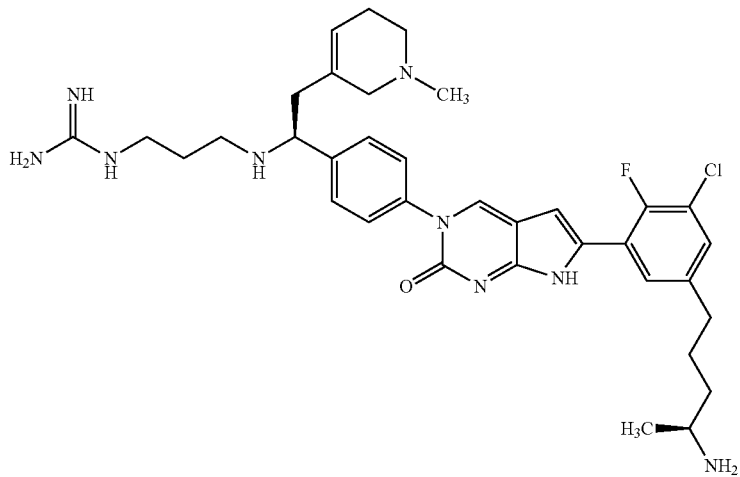 [SMILES: C[C@H](N)CCCc1cc(Cl)c(F)c(-c2cc3cn(-c4ccc([C@H](CC5=CCCN(C)C5)NCCCNC(=N)N)cc4)c(=O)nc3[nH]2)c1] | 662.1 |

TABLE 1-continued
| Compound No | Structure | ESI, m/z [M + H]+ |
|---|---|---|
| 106 | 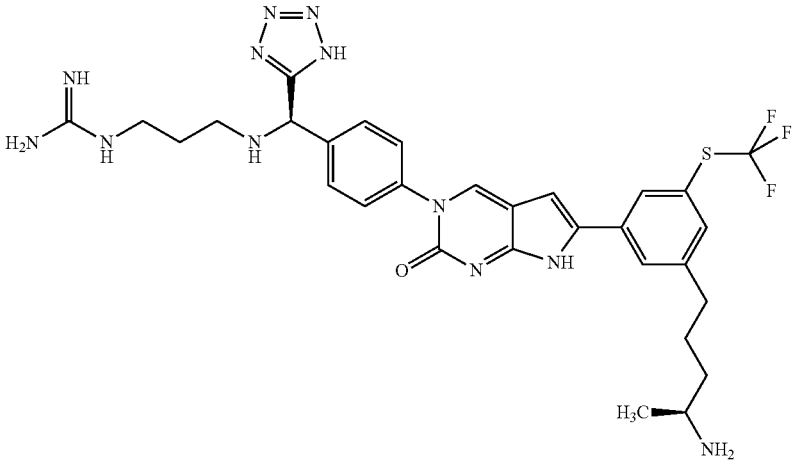 [SMILES: C[C@H](N)CCCc1cc(SC(F)(F)F)cc(-c2cc3cn(-c4ccc([C@@H](NCCCNC(=N)N)c5nnn[nH]5)cc4)c(=O)nc3[nH]2)c1] | 669.3 |
| 107 | 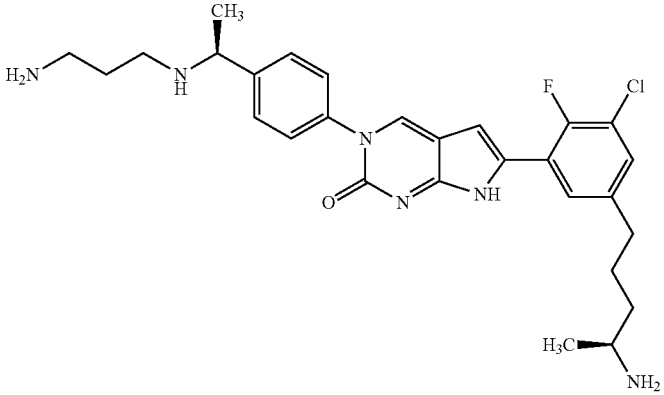 | 525.1 |
| 108 | 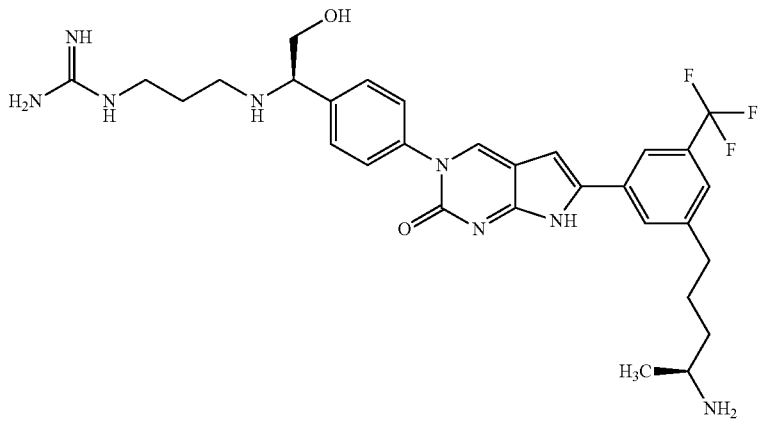 [SMILES: C[C@H](N)CCCc1cc(-c2cc3cn(-c4ccc([C@H](CO)NCCCNC(=N)N)cc4)c(=O)nc3[nH]2)cc(C(F)(F)F)c1] | 599.3 |
| 109 | 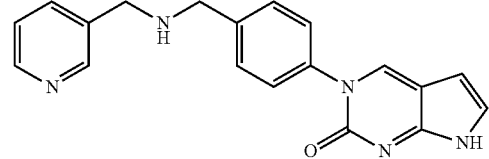 [SMILES: O=c1nc2[nH]ccc2cn1-c1ccc(CNCc2cccnc2)cc1] | 331.9 |

TABLE 1-continued

| Compound No | Structure | ESI, m/z [M + H]+ |
|---|---|---|
| 110 | 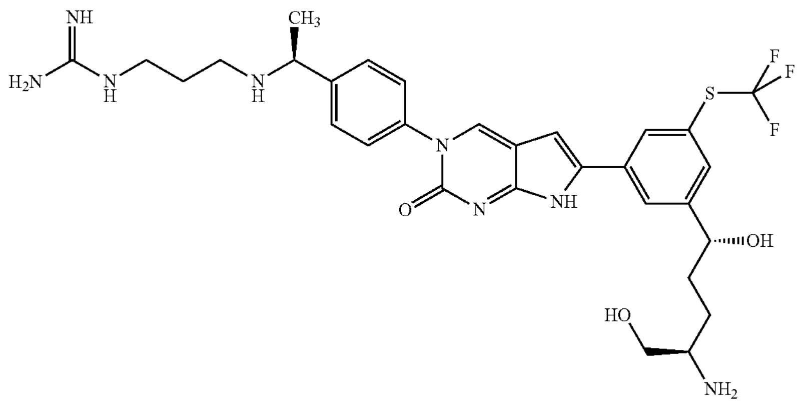 [SMILES: C[C@H](NCCCNC(=N)N)c1ccc(-n2cc3cc(-c4cc(SC(F)(F)F)cc([C@H](O)CC[C@@H](N)CO)c4)[nH]c3nc2=O)cc1] | 647 |
| 111 | 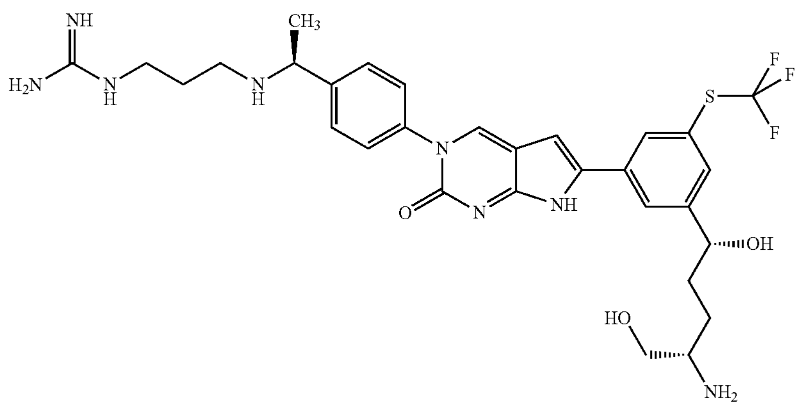 [SMILES: C[C@H](NCCCNC(=N)N)c1ccc(-n2cc3cc(-c4cc(SC(F)(F)F)cc([C@H](O)CC[C@H](N)CO)c4)[nH]c3nc2=O)cc1] | 647 |
| 112 | 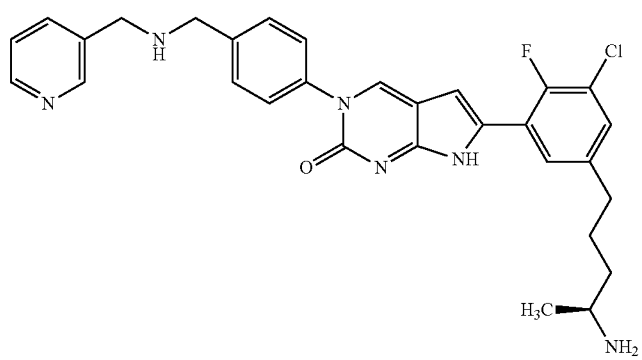 [SMILES: C[C@H](N)CCCc1cc(Cl)c(F)c(-c2cc3cn(-c4ccc(CNCc5cccnc5)cc4)c(=O)nc3[nH]2)c1] | 545.1 |
| 113 | 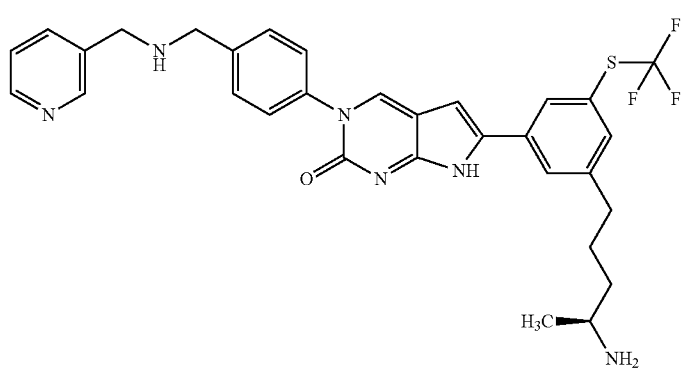 [SMILES: C[C@H](N)CCCc1cc(SC(F)(F)F)cc(-c2cc3cn(-c4ccc(CNCc5cccnc5)cc4)c(=O)nc3[nH]2)c1] | 593.1 |

TABLE 1-continued
| Compound No | Structure | ESI, m/z [M + H]+ |
|---|---|---|
| 114 | 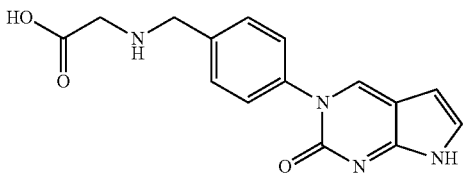 [SMILES: O=C(O)CNCc1ccc(-n2cc3cc[nH]c3nc2=O)cc1] | 299.1 |
| 115 | 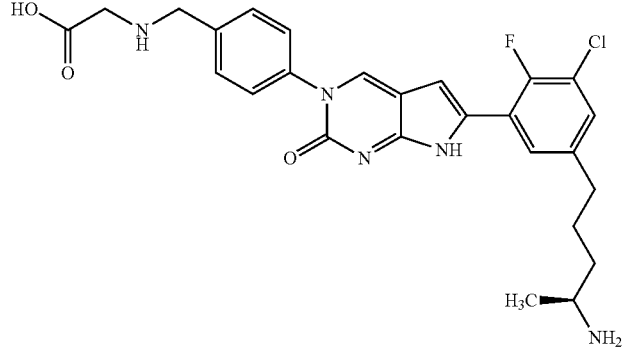 [SMILES: C[C@H](N)CCCc1cc(Cl)c(F)c(-c2cc3cn(-c4ccc(CNCC(=O)O)cc4)c(=O)nc3[nH]2)c1] | 512 |
| 116 | 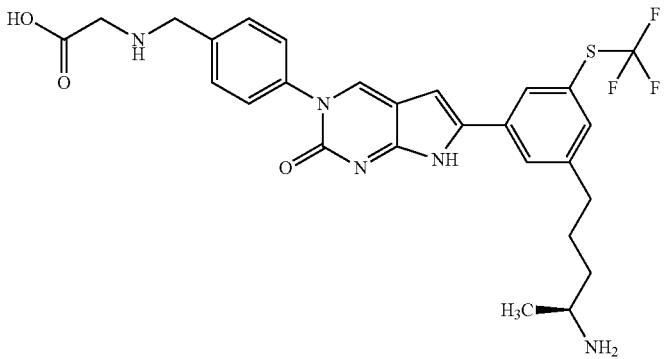 [SMILES: C[C@H](N)CCCc1cc(SC(F)(F)F)cc(-c2cc3cn(-c4ccc(CNCC(=O)O)cc4)c(=O)nc3[nH]2)c1] | 560.1 |
| 117 | 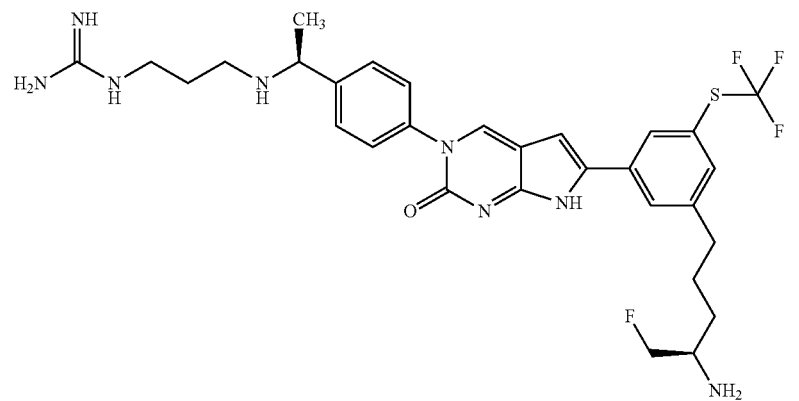 [SMILES: C[C@H](NCCCNC(=N)N)c1ccc(-n2cc3cc(-c4cc(CCC[C@@H](N)CF)cc(SC(F)(F)F)c4)[nH]c3nc2=O)cc1] | 633.2 |

TABLE 1-continued
| Compound No | Structure | ESI, m/z [M + H]+ |
|---|---|---|
| 118 | 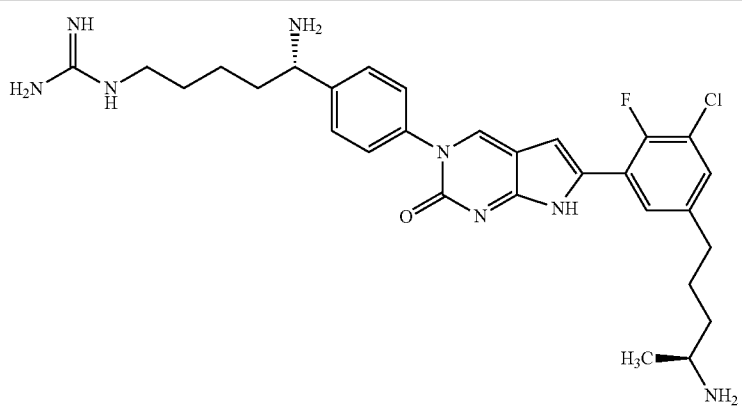 [SMILES: C[C@H](N)CCCc1cc(Cl)c(F)c(-c2cc3cn(-c4ccc([C@@H](N)CCCCNC(=N)N)cc4)c(=O)nc3[nH]2)c1] | 567.2 |
| 119 | 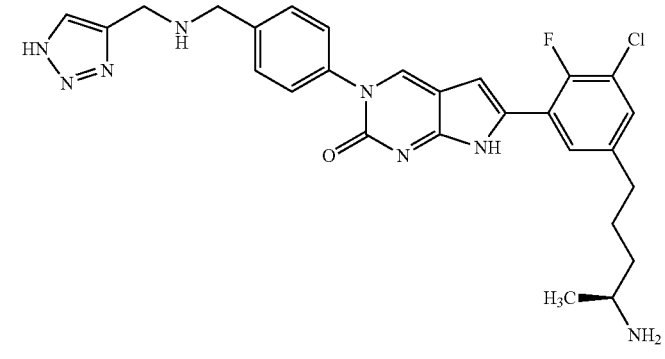 [SMILES: C[C@H](N)CCCc1cc(Cl)c(F)c(-c2cc3cn(-c4ccc(CNCc5c[nH]nn5)cc4)c(=O)nc3[nH]2)c1] | 535.1 |
| 120 | 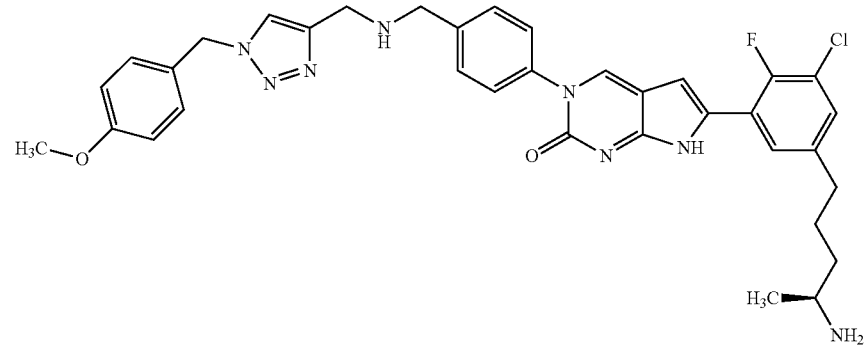 [SMILES: COc1ccc(Cn2cc(CNCc3ccc(-n4cc5cc(-c6cc(CCC[C@H](C)N)cc(Cl)c6F)[nH]c5nc4=O)cc3)nn2)cc1] | 655.4 |
| 121 | 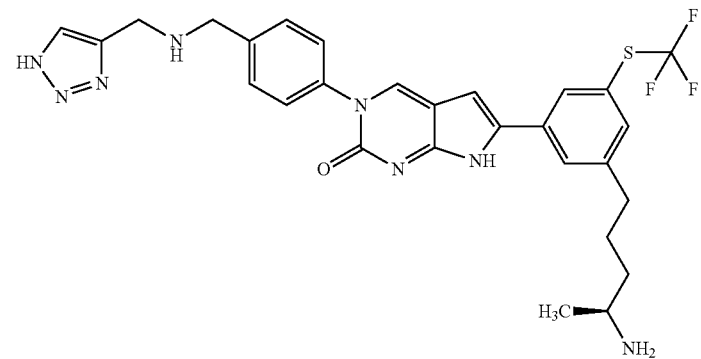 [SMILES: C[C@H](N)CCCc1cc(SC(F)(F)F)cc(-c2cc3cn(-c4ccc(CNCc5c[nH]nn5)cc4)c(=O)nc3[nH]2)c1] | 583.3 |

TABLE 1-continued
| Compound No | Structure | ESI, m/z [M + H]+ |
|---|---|---|
| 122 | 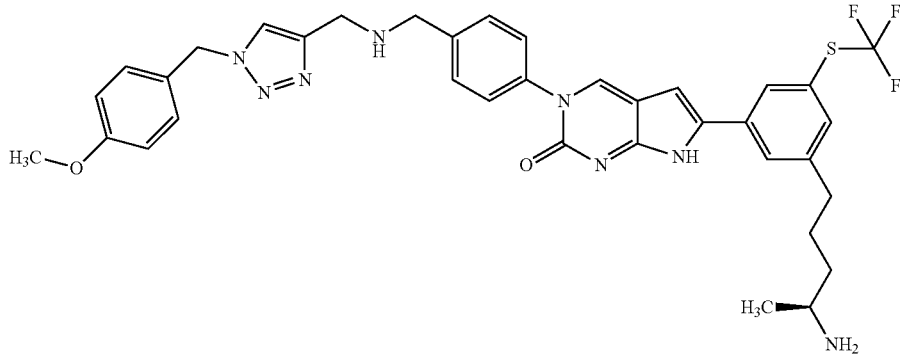 [SMILES: COc1ccc(Cn2cc(CNCc3ccc(-n4cc5cc(-c6cc(CCC[C@H](C)N)cc(SC(F)(F)F)c6)[nH]c5nc4=O)cc3)nn2)cc1] | 703.3 |
| 123 | 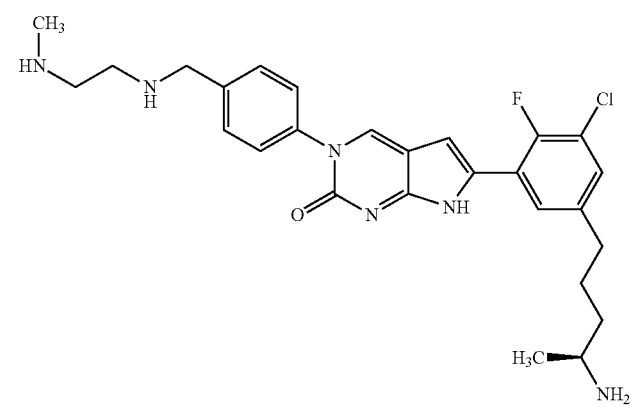 [SMILES: CNCCNCc1ccc(-n2cc3cc(-c4cc(CCC[C@H](C)N)cc(Cl)c4F)[nH]c3nc2=O)cc1] | 511.3 |
| 124 | 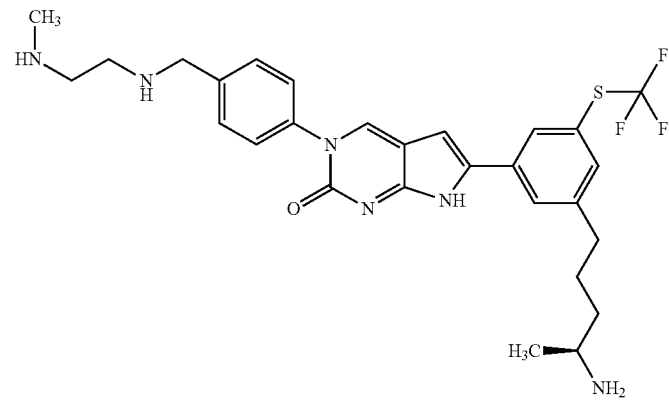 [SMILES: CNCCNCc1ccc(-n2cc3cc(-c4cc(CCC[C@H](C)N)cc(SC(F)(F)F)c4)[nH]c3nc2=O)cc1] | 559.1 |

TABLE 1-continued

| Compound No | Structure | ESI, m/z [M + H]+ |
|---|---|---|
| 125 | 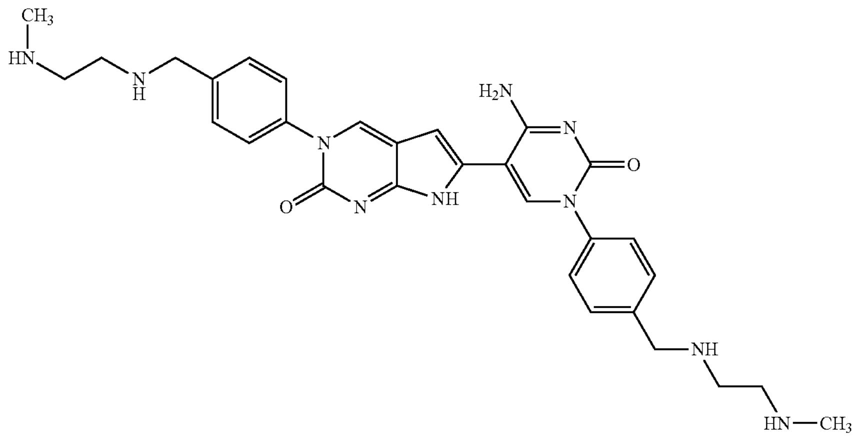 [SMILES: CNCCNCc1ccc(-n2cc(-c3cc4cn(-c5ccc(CNCCNC)cc5)c(=O)nc4[nH]3)c(N)nc2=O)cc1] | 570.1 |
| 126 | 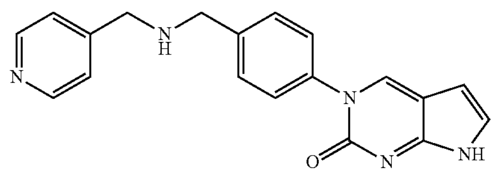 [SMILES: O=c1nc2[nH]ccc2cn1-c1ccc(CNCc2ccncc2)cc1] | [M + 23] = 354 |
| 127 | 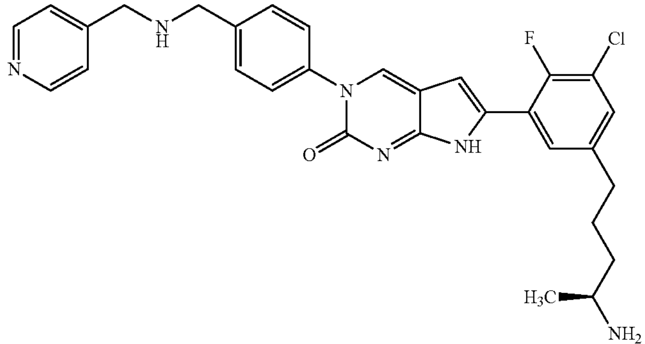 [SMILES: C[C@H](N)CCCc1cc(Cl)c(F)c(-c2cc3cn(-c4ccc(CNCc5ccncc5)cc4)c(=O)nc3[nH]2)c1] | 545.1 |
| 128 | 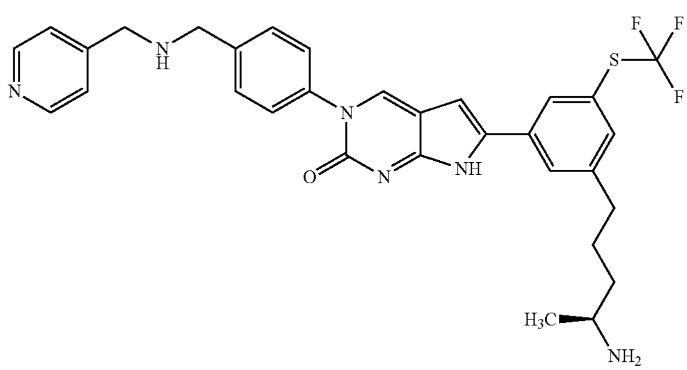 [SMILES: C[C@H](N)CCCc1cc(SC(F)(F)F)cc(-c2cc3cn(-c4ccc(CNCc5ccncc5)cc4)c(=O)nc3[nH]2)c1] | 593.2 |
| 129 | 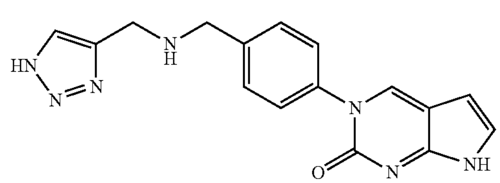 [SMILES: O=c1nc2[nH]ccc2cn1-c1ccc(CNCc2c[nH]nn2)cc1] | 321.9 |

TABLE 1-continued

| Compound No | Structure | ESI, m/z [M + H]+ |
|---|---|---|
| 130 | 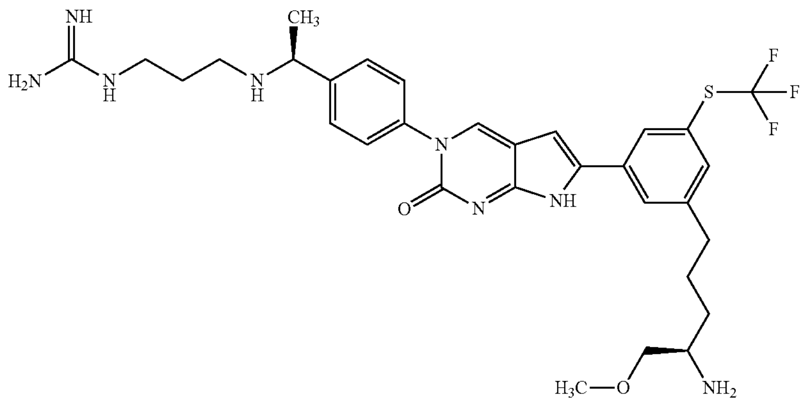 [SMILES: COC[C@H](N)CCCc1cc(SC(F)(F)F)cc(-c2cc3cn(-c4ccc([C@H](C)NCCCNC(=N)N)cc4)c(=O)nc3[nH]2)c1] | 645.3 |
| 131 | 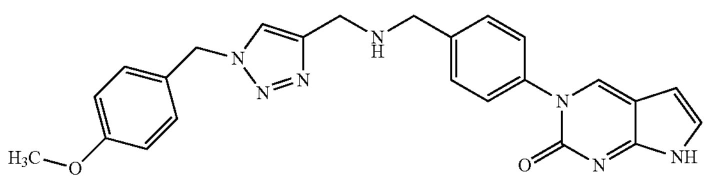 [SMILES: COc1ccc(Cn2cc(CNCc3ccc(-n4cc5cc[nH]c5nc4=O)cc3)nn2)cc1] | 442.8 |
| 132 | 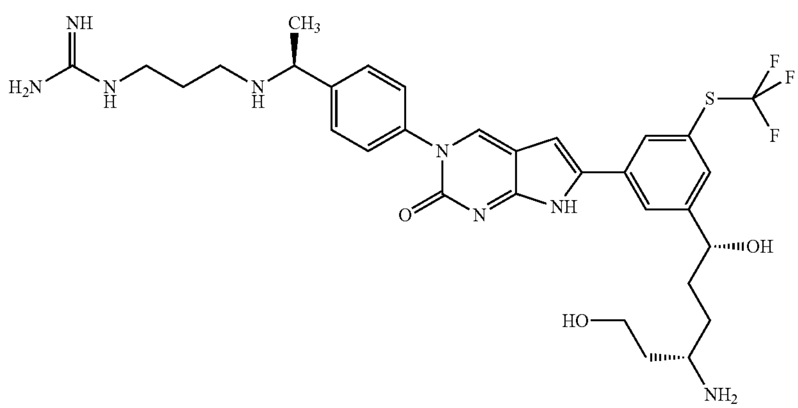 [SMILES: C[C@H](NCCCNC(=N)N)c1ccc(-n2cc3cc(-c4cc(SC(F)(F)F)cc([C@H](O)CC[C@H](N)CCO)c4)[nH]c3nc2=O)cc1] | 661 |
| 133 | 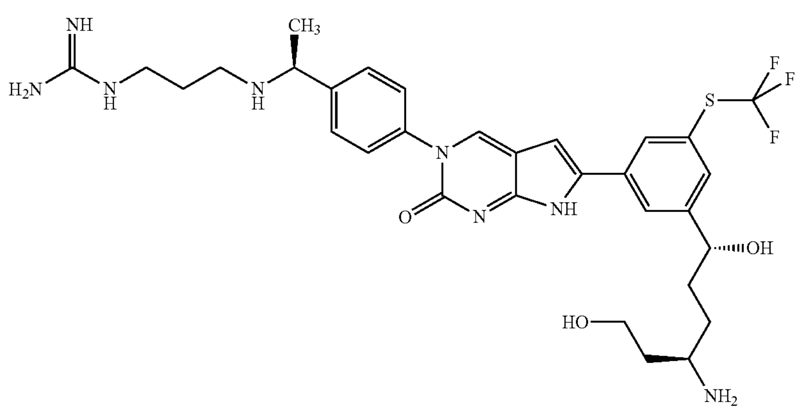 [SMILES: C[C@H](NCCCNC(=N)N)c1ccc(-n2cc3cc(-c4cc(SC(F)(F)F)cc([C@H](O)CC[C@@H](N)CCO)c4)[nH]c3nc2=O)cc1] | 661 |

TABLE 1-continued

| Compound No | Structure | ESI, m/z [M + H]+ |
|---|---|---|
| 134 | 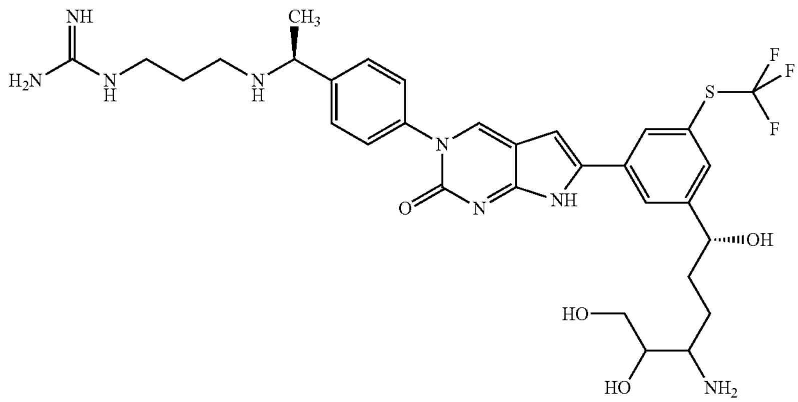 [SMILES: C[C@H](NCCCNC(=N)N)c1ccc(-n2cc3cc(-c4cc(SC(F)(F)F)cc([C@H](O)CCC(N)C(O)CO)c4)[nH]c3nc2=O)cc1] | 677 |
| 135 | 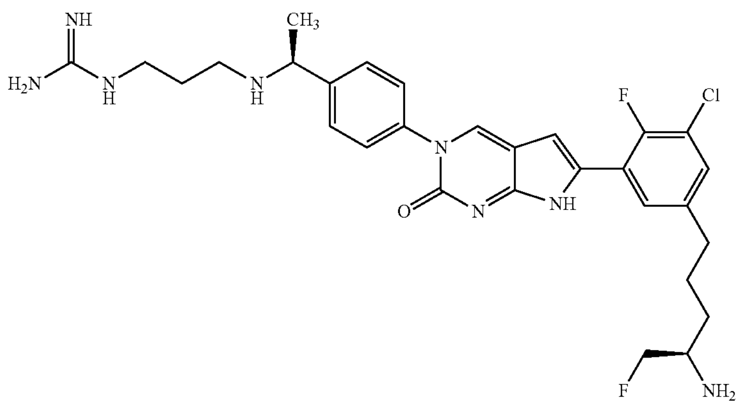 [SMILES: C[C@H](NCCCNC(=N)N)c1ccc(-n2cc3cc(-c4cc(CCC[C@@H](N)CF)cc(Cl)c4F)[nH]c3nc2=O)cc1] | 585.1 |
| 136 | 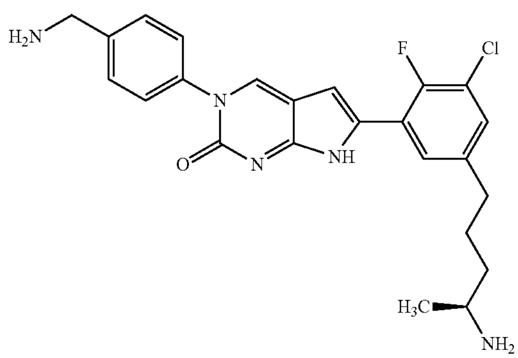 [SMILES: C[C@H](N)CCCc1cc(Cl)c(F)c(-c2cc3cn(-c4ccc(CN)cc4)c(=O)nc3[nH]2)c1] | 454 |
| 137 | 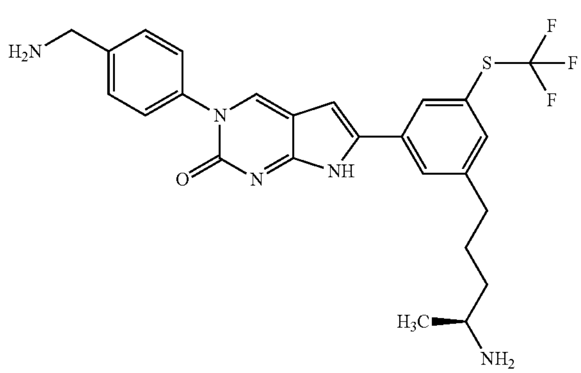 [SMILES: C[C@H](N)CCCc1cc(SC(F)(F)F)cc(-c2cc3cn(-c4ccc(CN)cc4)c(=O)nc3[nH]2)c1] | 502 |

TABLE 1-continued

| Compound No | Structure | ESI, m/z [M + H]+ |
|---|---|---|
| 138 | 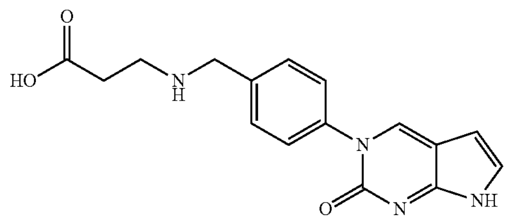 [SMILES: O=C(O)CCNCc1ccc(-n2cc3cc[nH]c3nc2=O)cc1] | 312.9 |
| 139 | 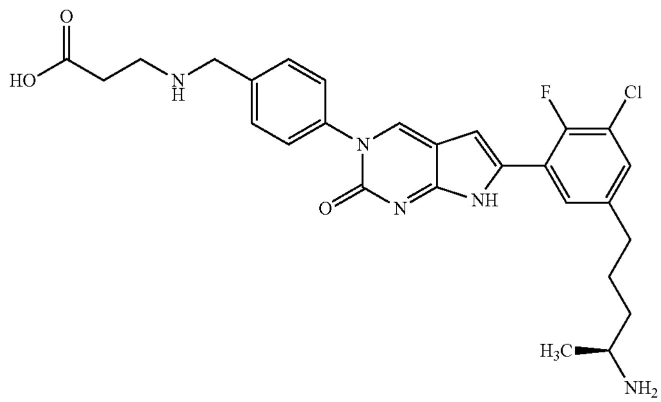 [SMILES: C[C@H](N)CCCc1cc(Cl)c(F)c(-c2cc3cn(-c4ccc(CNCCC(=O)O)cc4)c(=O)nc3[nH]2)c1] | 526.1 |
| 140 | 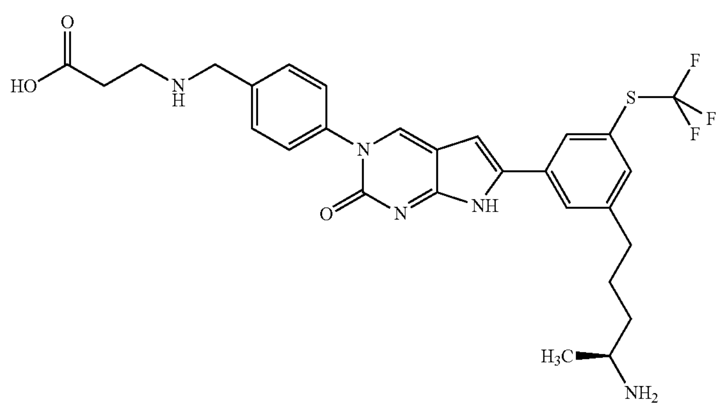 [SMILES: C[C@H](N)CCCc1cc(SC(F)(F)F)cc(-c2cc3cn(-c4ccc(CNCCC(=O)O)cc4)c(=O)nc3[nH]2)c1] | 573.7 |
| 141 | 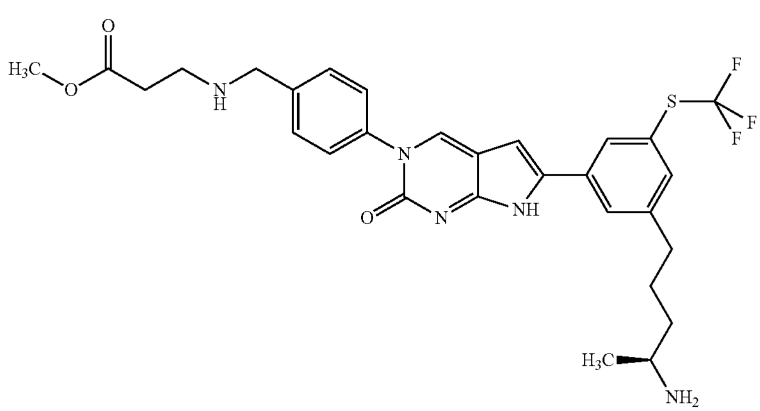 [SMILES: COC(=O)CCNCc1ccc(-n2cc3cc(-c4cc(CCC[C@H](C)N)cc(SC(F)(F)F)c4)[nH]c3nc2=O)cc1] | 588.1 |

TABLE 1-continued

| Compound No | Structure | ESI, m/z [M + H]+ |
|---|---|---|
| 142 | 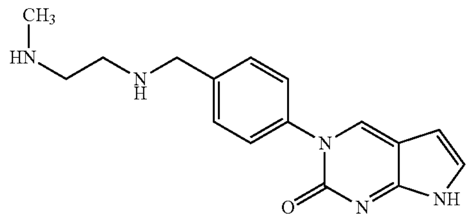 [SMILES: CNCCNCc1ccc(-n2cc3cc[nH]c3nc2=O)cc1] | 298 |
| 143 | 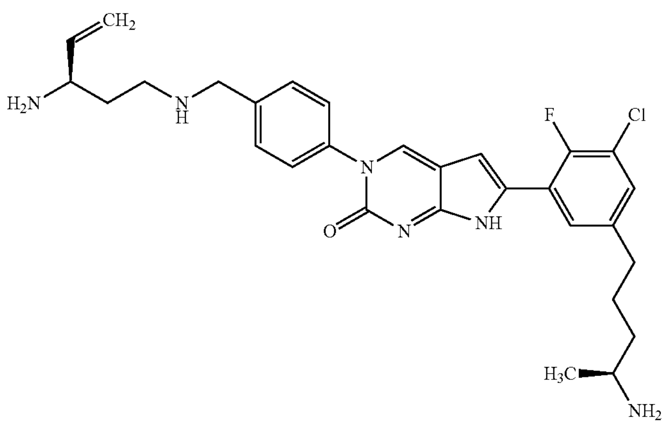 [SMILES: C=C[C@H](N)CCNCc1ccc(-n2cc3cc(-c4cc(CCC[C@H](C)N)cc(Cl)c4F)[nH]c3nc2=O)cc1] | 537.03 |
| 144 | 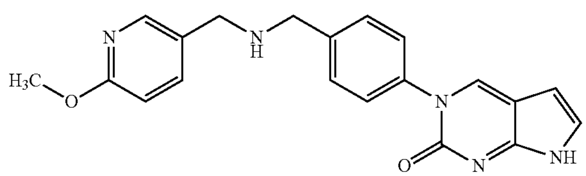 [SMILES: COc1ccc(CNCc2ccc(-n3cc4cc[nH]c4nc3=O)cc2)cn1] | 361.9 |
| 145 | 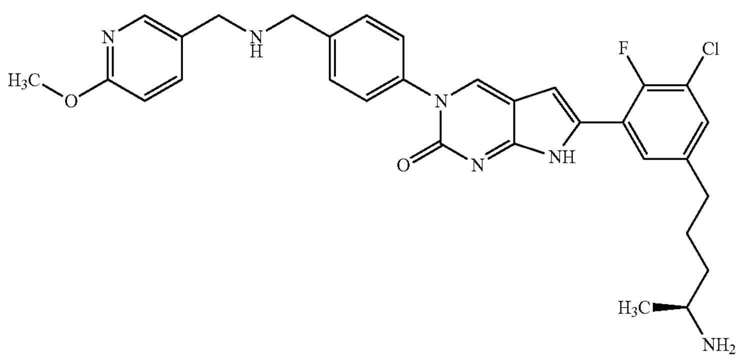 [SMILES: COc1ccc(CNCc2ccc(-n3cc4cc(-c5cc(CCC[C@H](C)N)cc(Cl)c5F)[nH]c4nc3=O)cc2)cn1] | 575.1 |
| 146 | 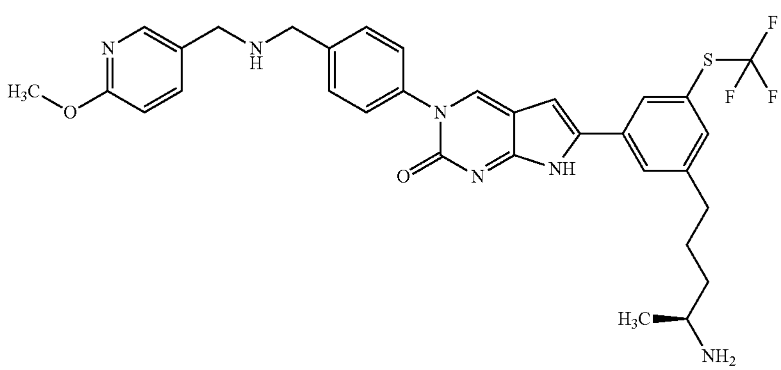 [SMILES: COc1ccc(CNCc2ccc(-n3cc4cc(-c5cc(CCC[C@H](C)N)cc(SC(F)(F)F)c5)[nH]c4nc3=O)cc2)cn1] | 623.1 |

TABLE 1-continued

| Compound No | Structure | ESI, m/z [M + H]+ |
|---|---|---|
| 147 | 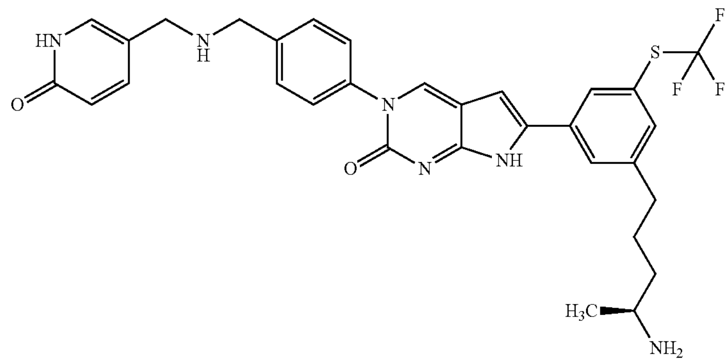 [SMILES: C[C@H](N)CCCc1cc(SC(F)(F)F)cc(-c2cc3cn(-c4ccc(CNCc5ccc(=O)[nH]c5)cc4)c(=O)nc3[nH]2)c1] | 609.3 |
| 148 | 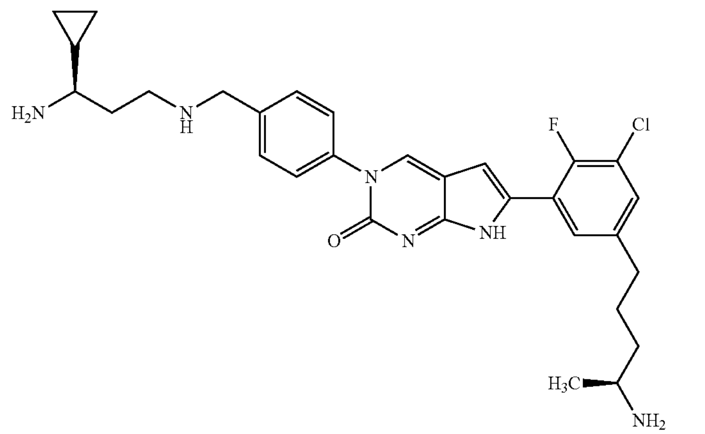 [SMILES: C[C@H](N)CCCc1cc(Cl)c(F)c(-c2cc3cn(-c4ccc(CNCC[C@@H](N)C5CC5)cc4)c(=O)nc3[nH]2)c1] | 551.1 |
| 149 | 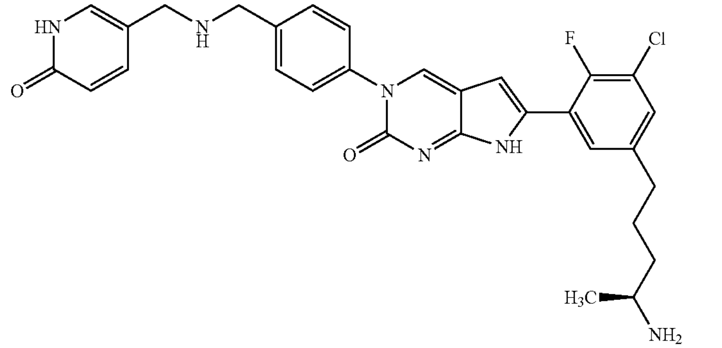 [SMILES: C[C@H](N)CCCc1cc(Cl)c(F)c(-c2cc3cn(-c4ccc(CNCc5ccc(=O)[nH]c5)cc4)c(=O)nc3[nH]2)c1] | 561.1 |
| 150 | 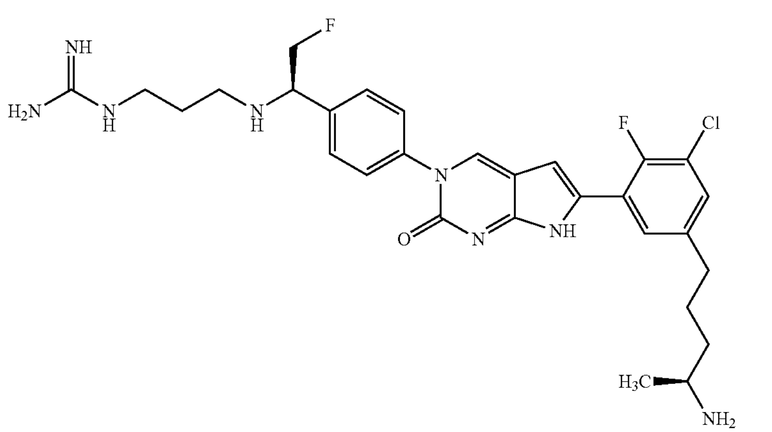 [SMILES: C[C@H](N)CCCc1cc(Cl)c(F)c(-c2cc3cn(-c4ccc([C@H](CF)NCCCNC(=N)N)cc4)c(=O)nc3[nH]2)c1] | 585.1 |

TABLE 1-continued
| Compound No | Structure | ESI, m/z [M + H]+ |
|---|---|---|
| 151 | 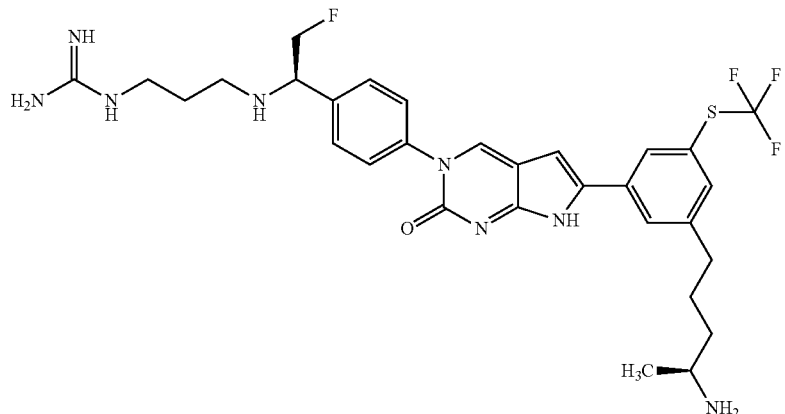 | 633.2 |
| 152 | 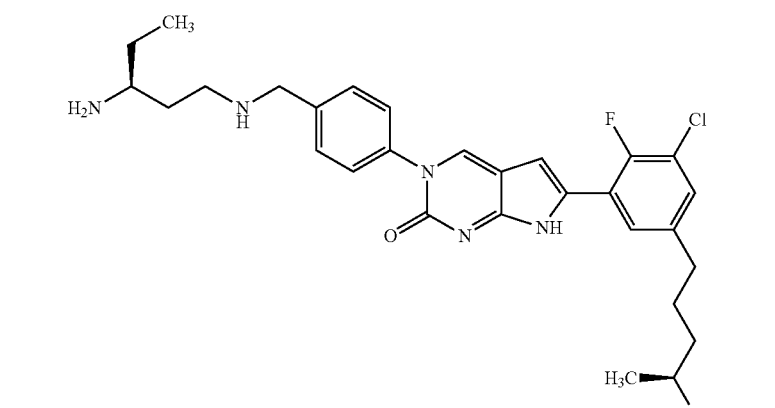 | 539.3 |
| 153 | 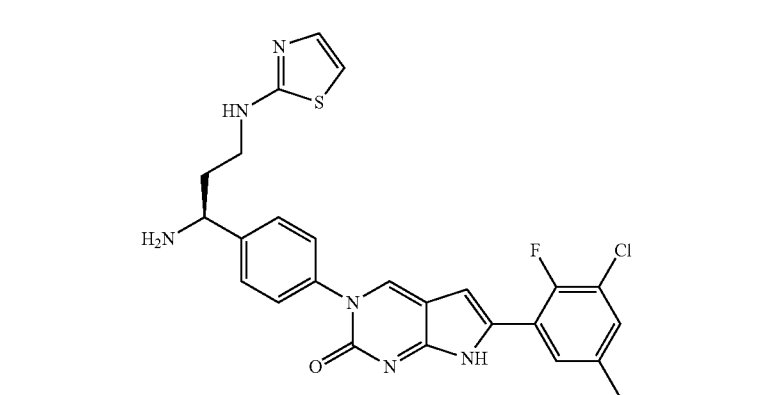 | 579.9 |

TABLE 1-continued

| Compound No | Structure | ESI, m/z [M + H]+ |
|---|---|---|
| 154 | 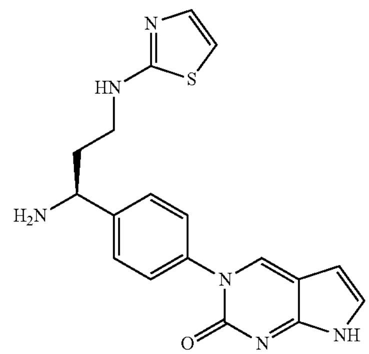 [SMILES: N[C@@H](CCNc1nccs1)c1ccc(-n2cc3cc[nH]c3nc2=O)cc1] | 388.8 |
| 155 | 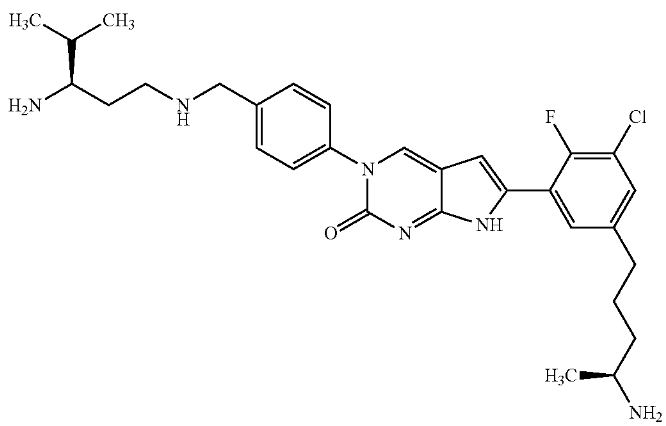 [SMILES: CC(C)[C@H](N)CCNCc1ccc(-n2cc3cc(-c4cc(CCC[C@H](C)N)cc(Cl)c4F)[nH]c3nc2=O)cc1] | 554 |
| 156 | 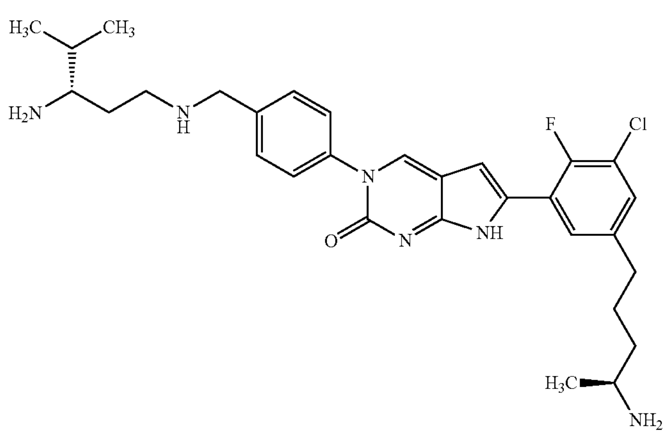 [SMILES: CC(C)[C@@H](N)CCNCc1ccc(-n2cc3cc(-c4cc(CCC[C@H](C)N)cc(Cl)c4F)[nH]c3nc2=O)cc1] | 553 |

TABLE 1-continued

| Compound No | Structure | ESI, m/z [M + H]+ |
|---|---|---|
| 157 | 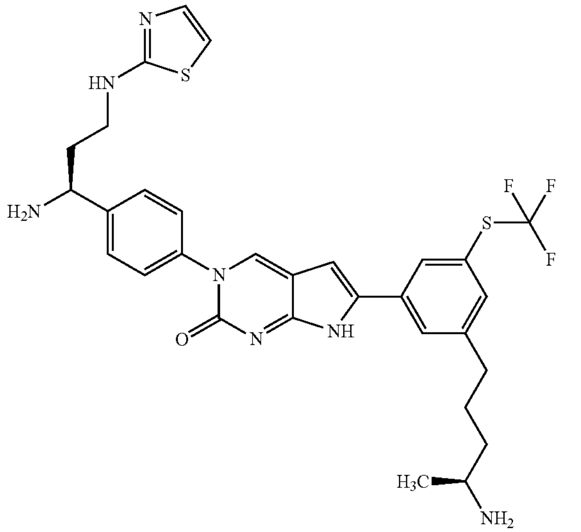 [SMILES: C[C@H](N)CCCc1cc(SC(F)(F)F)cc(-c2cc3cn(-c4ccc([C@@H](N)CCNc5nccs5)cc4)c(=O)nc3[nH]2)c1] | 628.2 |
| 158 | 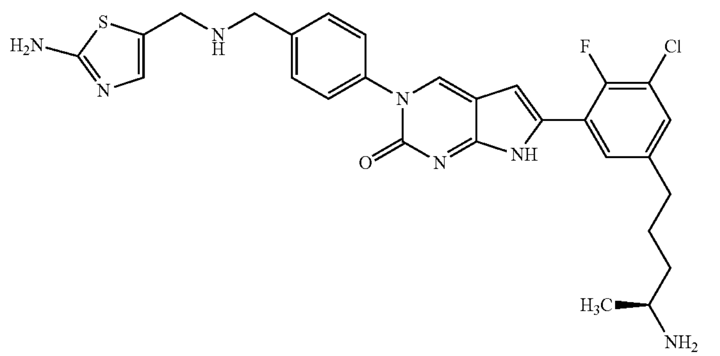 [SMILES: C[C@H](N)CCCc1cc(Cl)c(F)c(-c2cc3cn(-c4ccc(CNCc5cnc(N)s5)cc4)c(=O)nc3[nH]2)c1] | 566.1 |
| 159 | 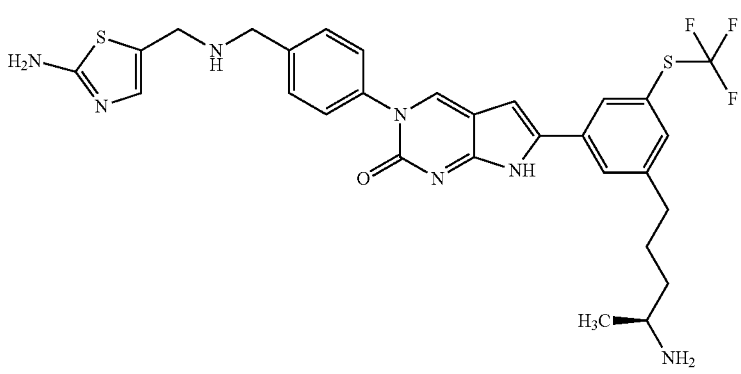 [SMILES: C[C@H](N)CCCc1cc(SC(F)(F)F)cc(-c2cc3cn(-c4ccc(CNCc5cnc(N)s5)cc4)c(=O)nc3[nH]2)c1] | 614.3 |

TABLE 1-continued

| Compound No | Structure | ESI, m/z [M + H]+ |
|---|---|---|
| 160 | 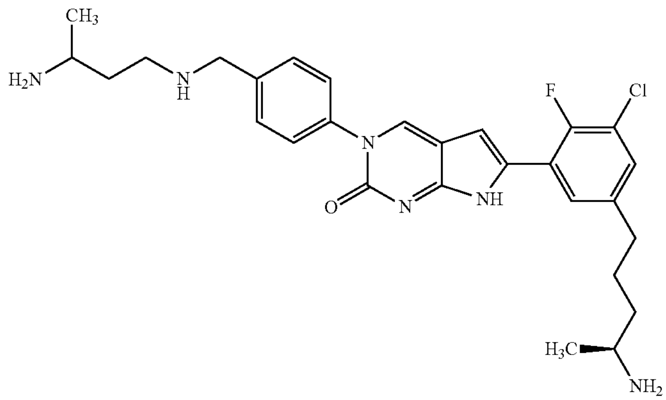 [SMILES: CC(N)CCNCc1ccc(-n2cc3cc(-c4cc(CCC[C@H](C)N)cc(Cl)c4F)[nH]c3nc2=O)cc1] | 525.2 |
| 161 | 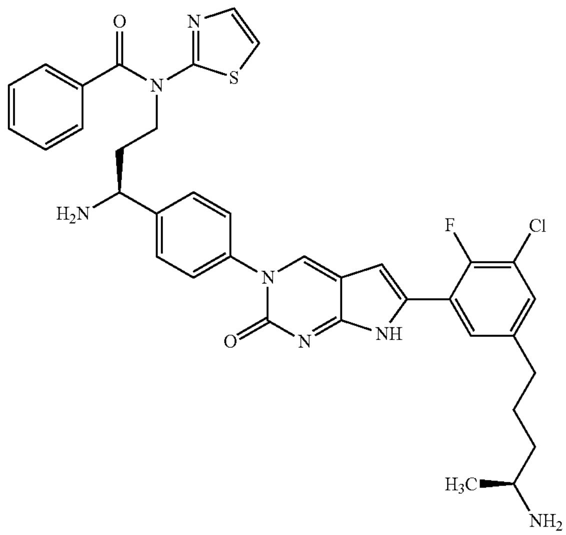 [SMILES: C[C@H](N)CCCc1cc(Cl)c(F)c(-c2cc3cn(-c4ccc([C@@H](N)CCN(C(=O)c5ccccc5)c5nccs5)cc4)c(=O)nc3[nH]2)c1] | 684 |
| 162 | 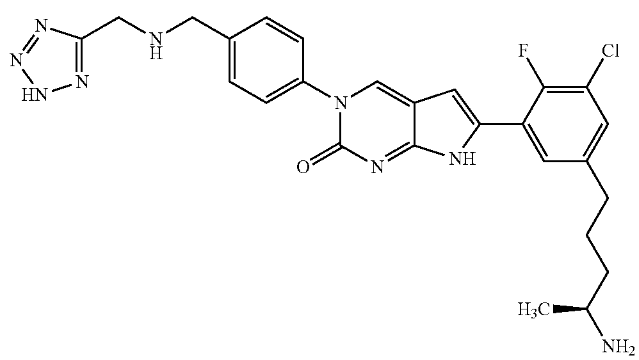 [SMILES: C[C@H](N)CCCc1cc(Cl)c(F)c(-c2cc3cn(-c4ccc(CNCc5nn[nH]n5)cc4)c(=O)nc3[nH]2)c1] | 536 |

TABLE 1-continued

| Compound No | Structure | ESI, m/z [M + H]+ |
|---|---|---|
| 163 | 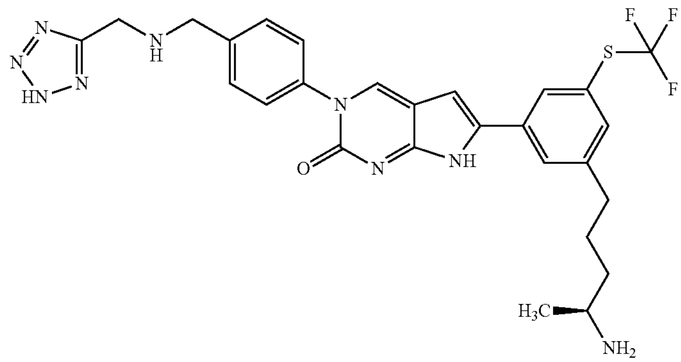 [SMILES: C[C@H](N)CCCc1cc(SC(F)(F)F)cc(-c2cc3cn(-c4ccc(CNCc5nn[nH]n5)cc4)c(=O)nc3[nH]2)c1] | 584.1 |
| 164 | 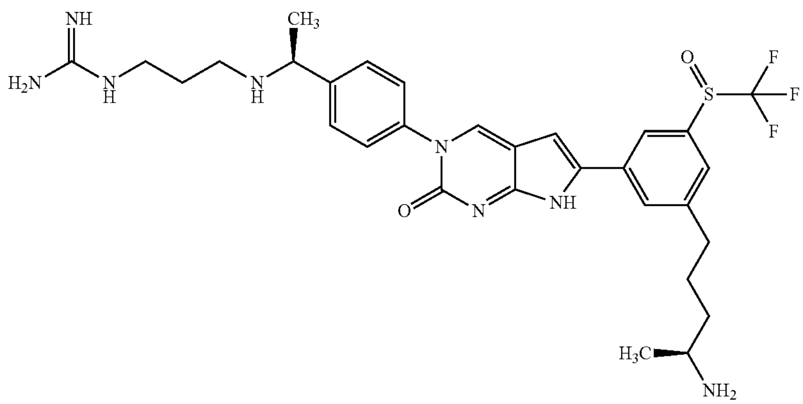 [SMILES: C[C@H](N)CCCc1cc(-c2cc3cn(-c4ccc([C@H](C)NCCCNC(=N)N)cc4)c(=O)nc3[nH]2)cc(S(=O)C(F)(F)F)c1] | 631.2 |
| 165 | 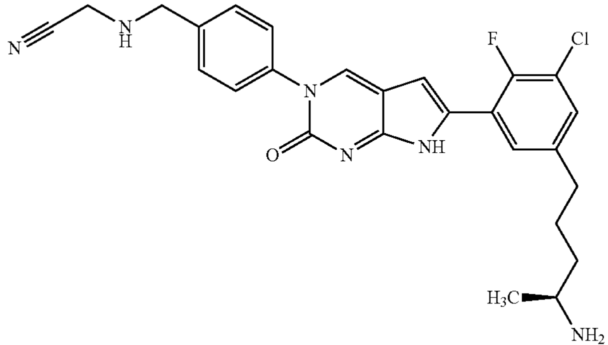 [SMILES: C[C@H](N)CCCc1cc(Cl)c(F)c(-c2cc3cn(-c4ccc(CNCC#N)cc4)c(=O)nc3[nH]2)c1] | 493.1 |
| 166 | 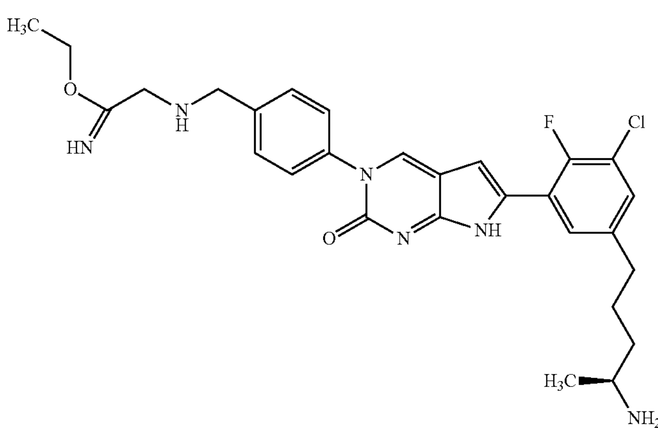 [SMILES: CCOC(=N)CNCc1ccc(-n2cc3cc(-c4cc(CCC[C@H](C)N)cc(Cl)c4F)[nH]c3nc2=O)cc1] | 540.1 |

TABLE 1-continued
| Compound No | Structure | ESI, m/z [M + H]+ |
|---|---|---|
| 167 | 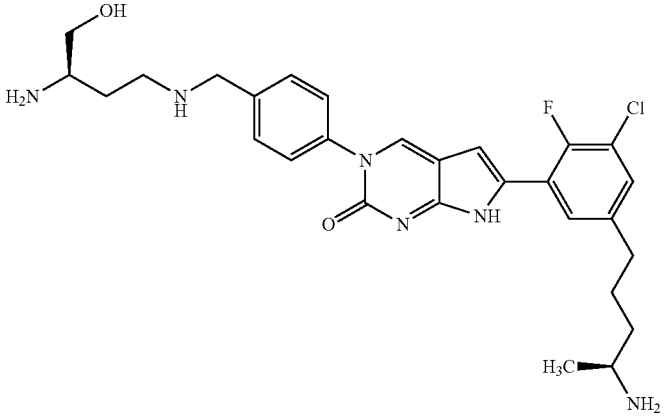 [SMILES: C[C@H](N)CCCc1cc(Cl)c(F)c(-c2cc3cn(-c4ccc(CNCC[C@@H](N)CO)cc4)c(=O)nc3[nH]2)c1] | 541 |
| 168 | 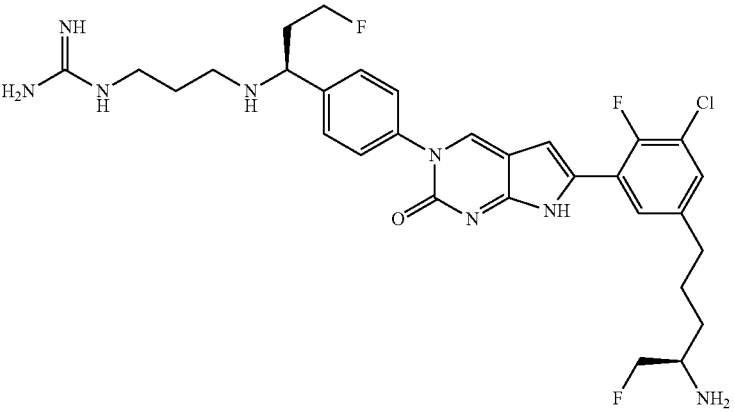 [SMILES: N=C(N)NCCCN[C@@H](CCF)c1ccc(-n2cc3cc(-c4cc(CCC[C@@H](N)CF)cc(Cl)c4F)[nH]c3nc2=O)cc1] | 617.2 |
| 169 | 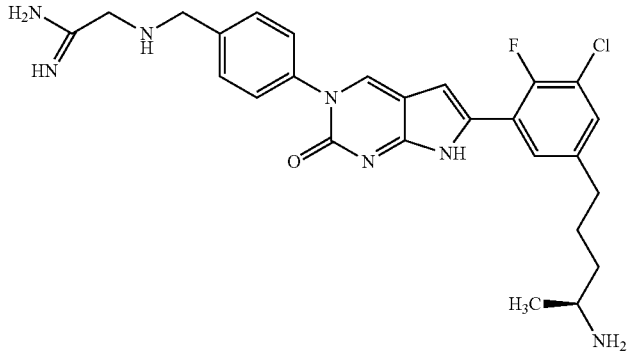 [SMILES: C[C@H](N)CCCc1cc(Cl)c(F)c(-c2cc3cn(-c4ccc(CNCC(=N)N)cc4)c(=O)nc3[nH]2)c1] | 511 |
| 170 | 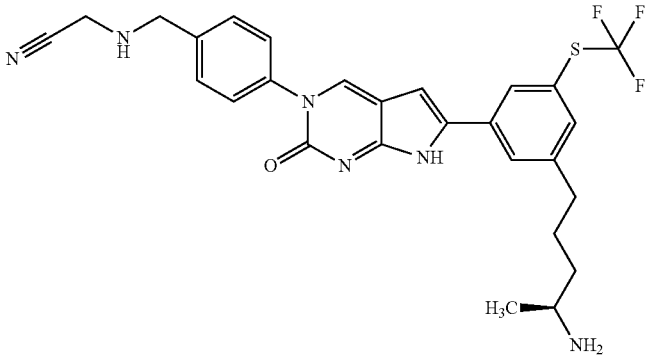 [SMILES: C[C@H](N)CCCc1cc(SC(F)(F)F)cc(-c2cc3cn(-c4ccc(CNCC#N)cc4)c(=O)nc3[nH]2)c1] | 541.1 |

TABLE 1-continued
| Compound No | Structure | ESI, m/z [M + H]+ |
|---|---|---|
| 171 | 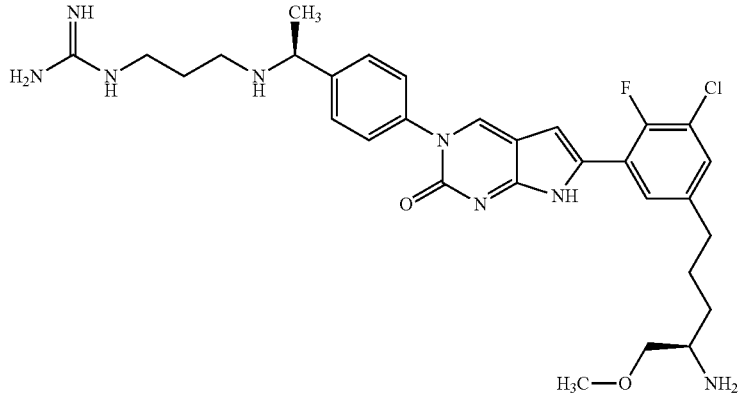 [SMILES: COC[C@H](N)CCCc1cc(Cl)c(F)c(-c2cc3cn(-c4ccc([C@H](C)NCCCNC(=N)N)cc4)c(=O)nc3[nH]2)c1] | 597.2 |
| 172 | 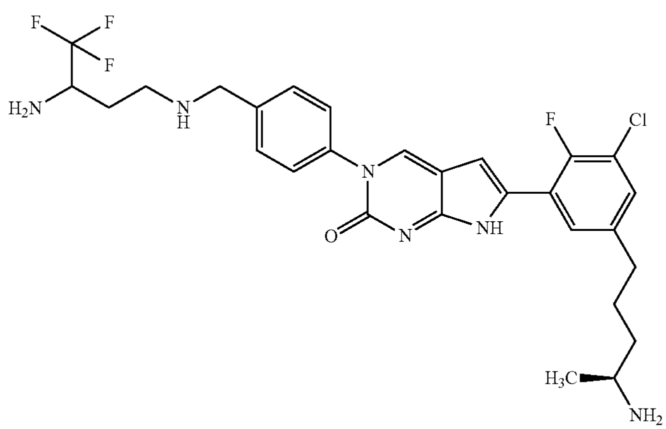 [SMILES: C[C@H](N)CCCc1cc(Cl)c(F)c(-c2cc3cn(-c4ccc(CNCCC(N)C(F)(F)F)cc4)c(=O)nc3[nH]2)c1] | 579 |
| 173 | 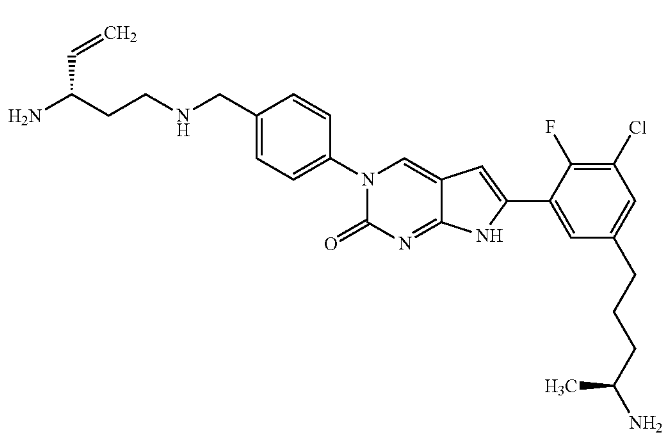 [SMILES: C=C[C@@H](N)CCNCc1ccc(-n2cc3cc(-c4cc(CCC[C@H](C)N)cc(Cl)c4F)[nH]c3nc2=O)cc1] | 537 |

TABLE 1-continued

| Compound No | Structure | ESI, m/z [M + H]+ |
|---|---|---|
| 174 | 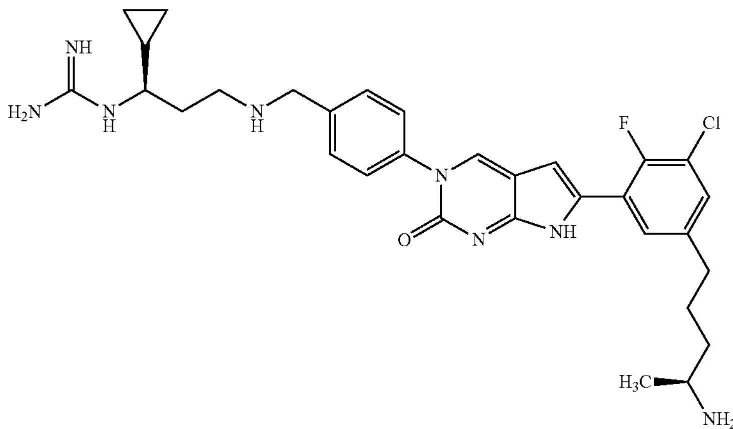 [SMILES: C[C@H](N)CCCc1cc(Cl)c(F)c(-c2cc3cn(-c4ccc(CNCC[C@@H](NC(=N)N)C5CC5)cc4)c(=O)nc3[nH]2)c1] | 593.3 |
| 175 | 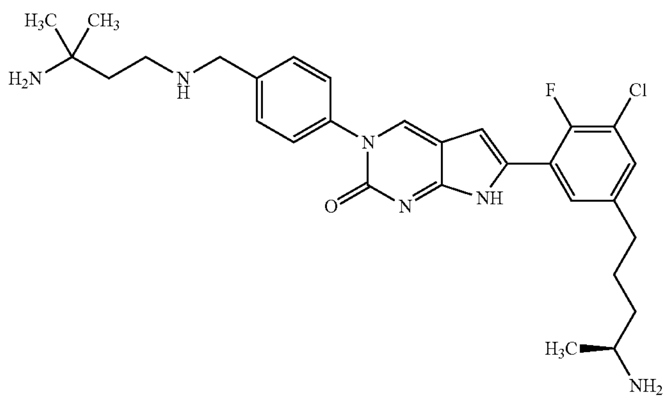 [SMILES: C[C@H](N)CCCc1cc(Cl)c(F)c(-c2cc3cn(-c4ccc(CNCCC(C)(C)N)cc4)c(=O)nc3[nH]2)c1] | 539.6 |
| 176 | 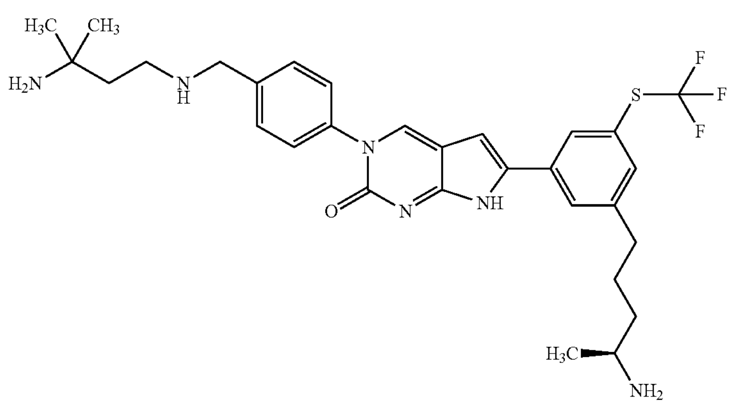 [SMILES: C[C@H](N)CCCc1cc(SC(F)(F)F)cc(-c2cc3cn(-c4ccc(CNCCC(C)(C)N)cc4)c(=O)nc3[nH]2)c1] | 586.9 |

TABLE 1-continued

| Compound No | Structure | ESI, m/z [M + H]+ |
|---|---|---|
| 177 | 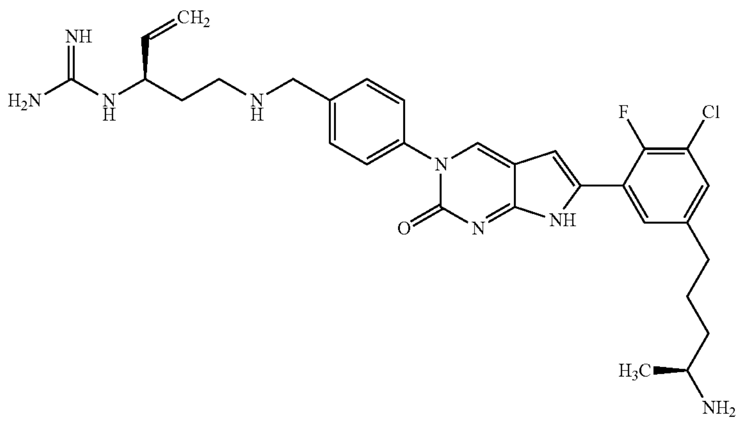 [SMILES: C=C[C@@H](CCNCc1ccc(-n2cc3cc(-c4cc(CCC[C@H](C)N)cc(Cl)c4F)[nH]c3nc2=O)cc1)NC(=N)N] | 579 |
| 178 | 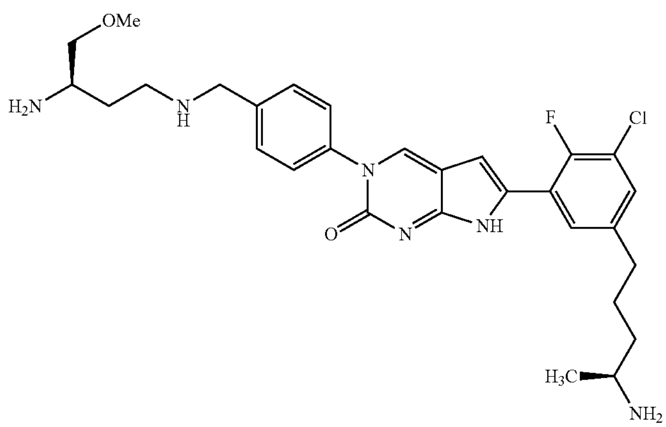 [SMILES: COC[C@H](N)CCNCc1ccc(-n2cc3cc(-c4cc(CCC[C@H](C)N)cc(Cl)c4F)[nH]c3nc2=O)cc1] | 555 |
| 179 | 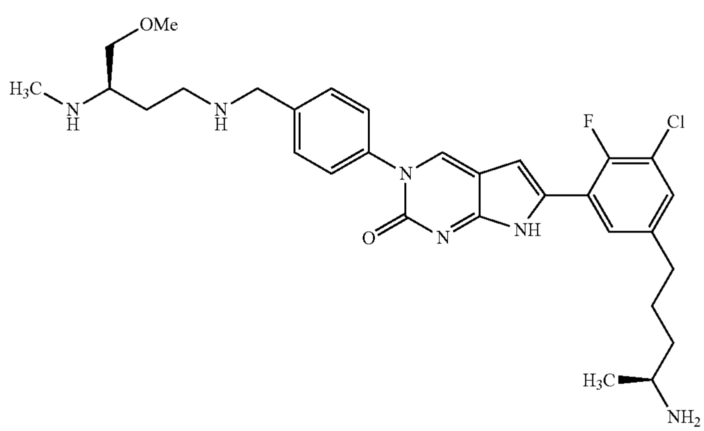 [SMILES: CN[C@H](CCNCc1ccc(-n2cc3cc(-c4cc(CCC[C@H](C)N)cc(Cl)c4F)[nH]c3nc2=O)cc1)COC] | 569 |

TABLE 1-continued

| Compound No | Structure | ESI, m/z [M + H]+ |
|---|---|---|
| 180 | 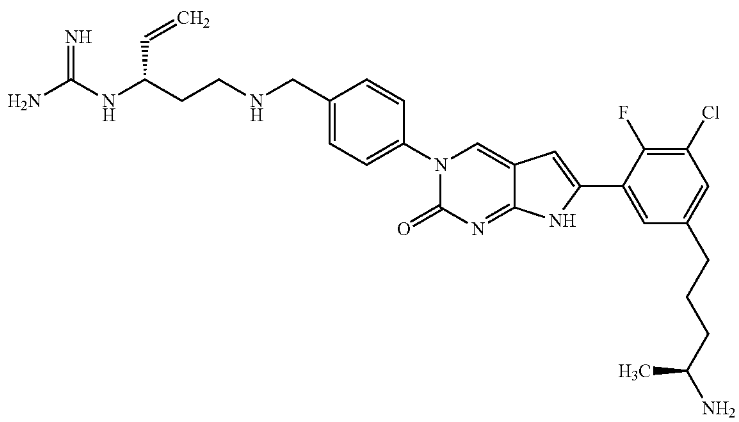 [SMILES: C=C[C@H](CCNCc1ccc(-n2cc3cc(-c4cc(CCC[C@H](C)N)cc(Cl)c4F)[nH]c3nc2=O)cc1)NC(=N)N] | 580 |
| 181 | 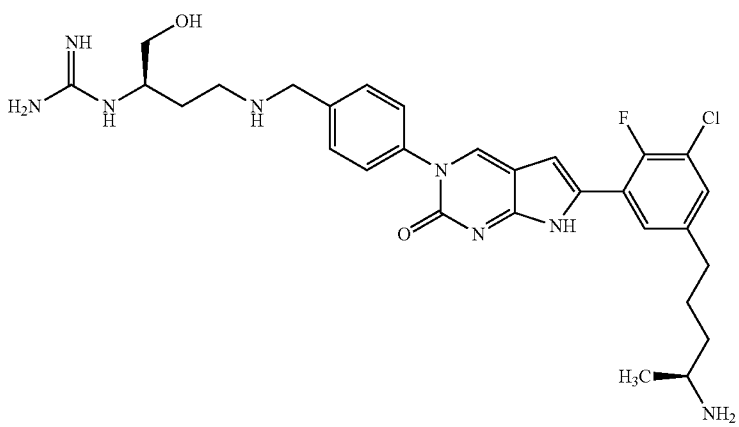 [SMILES: C[C@H](N)CCCc1cc(Cl)c(F)c(-c2cc3cn(-c4ccc(CNCC[C@H](CO)NC(=N)N)cc4)c(=O)nc3[nH]2)c1] | 584 |
| 182 | 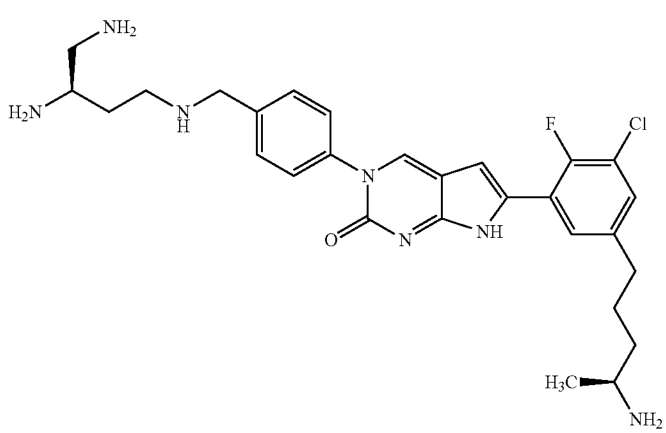 | 540.6 |

TABLE 1-continued
| Compound No | Structure | ESI, m/z [M + H]+ |
|---|---|---|
| 183 | 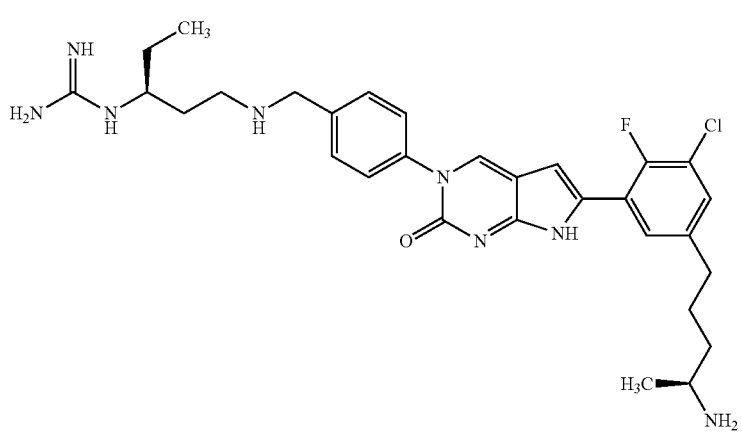 [SMILES: CC[C@@H](CCNCc1ccc(-n2cc3cc(-c4cc(CCC[C@H](C)N)cc(Cl)c4F)[nH]c3nc2=O)cc1)NC(=N)N] | 581.3 |
| 184 | 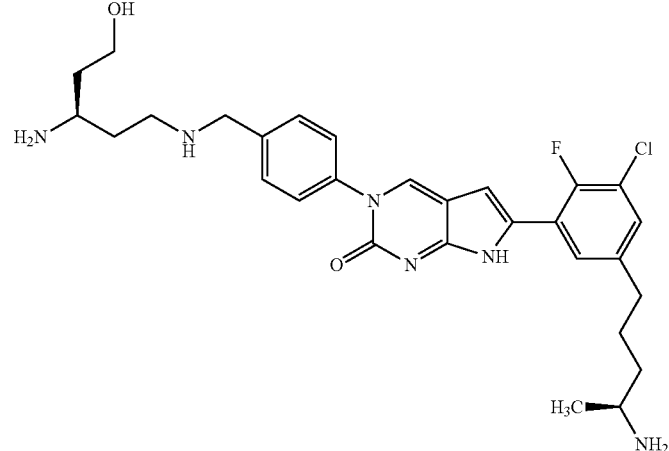 [SMILES: C[C@H](N)CCCc1cc(Cl)c(F)c(-c2cc3cn(-c4ccc(CNCC[C@@H](N)CCO)cc4)c(=O)nc3[nH]2)c1] | 555.1 |
| 185 | 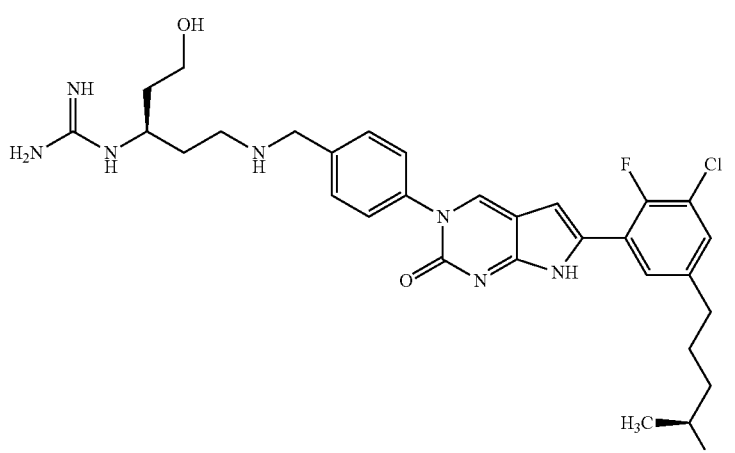 | 597.2 |

TABLE 1-continued
| Compound No | Structure | ESI, m/z [M + H]+ |
|---|---|---|
| 186 | 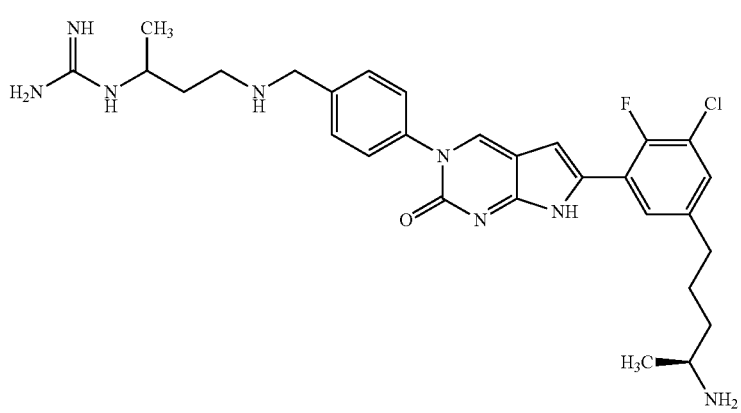 | 567.1 |
| 187 | 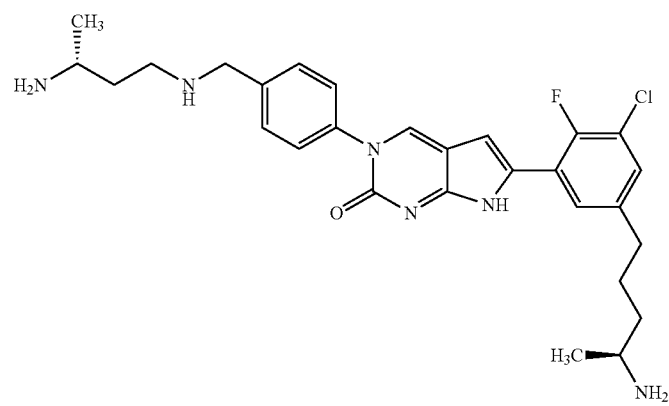 | 525.2 |
| 188 | 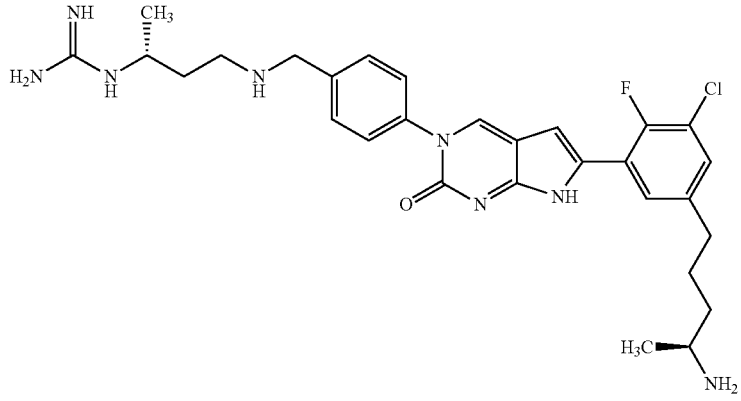 [SMILES: CC(CCNCc1ccc(-n2cc3cc(-c4cc(CCC[C@H](C)N)cc(Cl)c4F)[nH]c3nc2=O)cc1)NC(=N)N] | 567.1 |

TABLE 1-continued
| Compound No | Structure | ESI, m/z [M + H]+ |
|---|---|---|
| 189 | 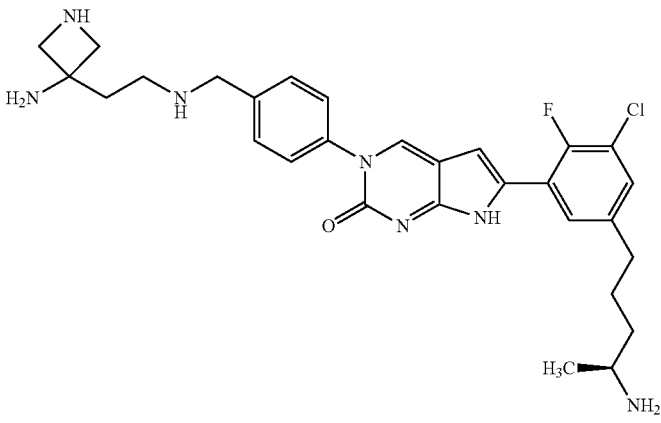 [SMILES: C[C@H](N)CCCc1cc(Cl)c(F)c(-c2cc3cn(-c4ccc(CNCCC5(N)CNC5)cc4)c(=O)nc3[nH]2)c1] | 552.2 |
| 190 | 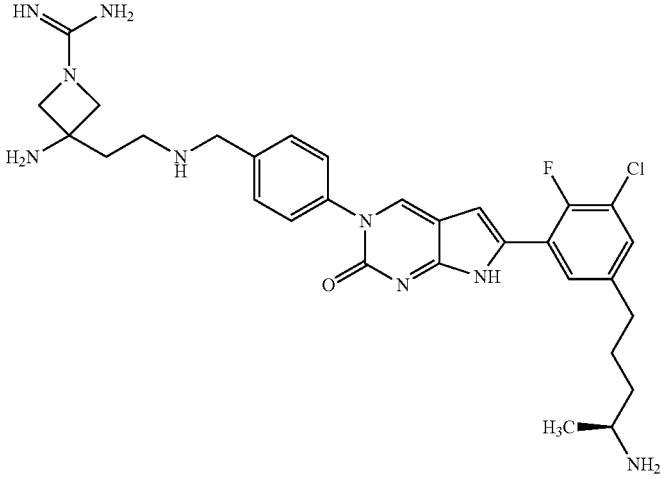 [SMILES: C[C@H](N)CCCc1cc(Cl)c(F)c(-c2cc3cn(-c4ccc(CNCCC5(N)CN(C(=N)N)C5)cc4)c(=O)nc3[nH]2)c1] | 594.1 |
| 191 | 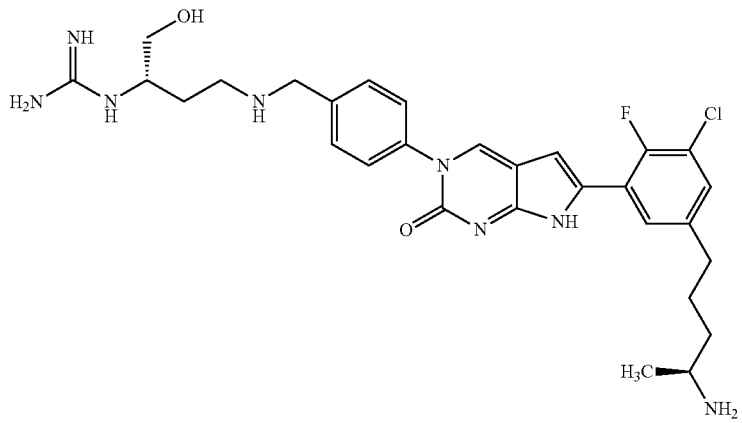 | 583 |

TABLE 1-continued

| Compound No | Structure | ESI, m/z [M + H]+ |
|---|---|---|
| 192 | 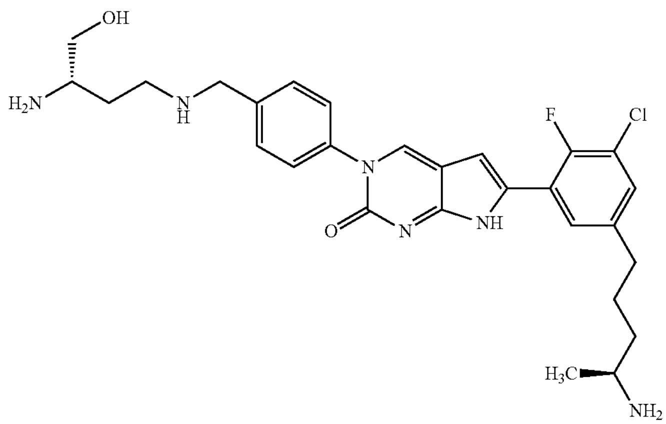 [SMILES: C[C@H](N)CCCc1cc(Cl)c(F)c(-c2cc3cn(-c4ccc(CNCC[C@H](N)CO)cc4)c(=O)nc3[nH]2)c1] | 541 |
| 193 | 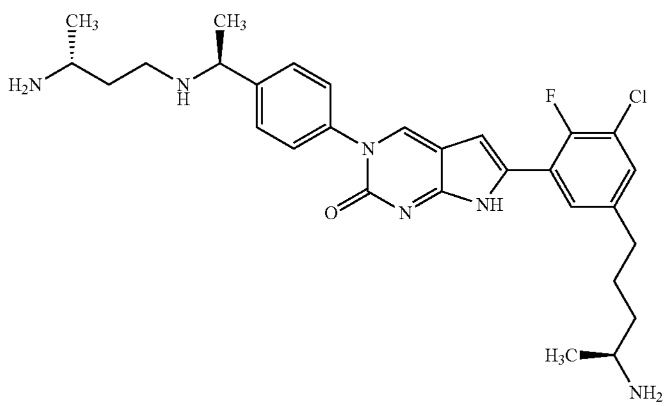 [SMILES: C[C@H](N)CCCc1cc(Cl)c(F)c(-c2cc3cn(-c4ccc([C@H](C)NCC[C@@H](C)N)cc4)c(=O)nc3[nH]2)c1] | 539 |
| 194 | 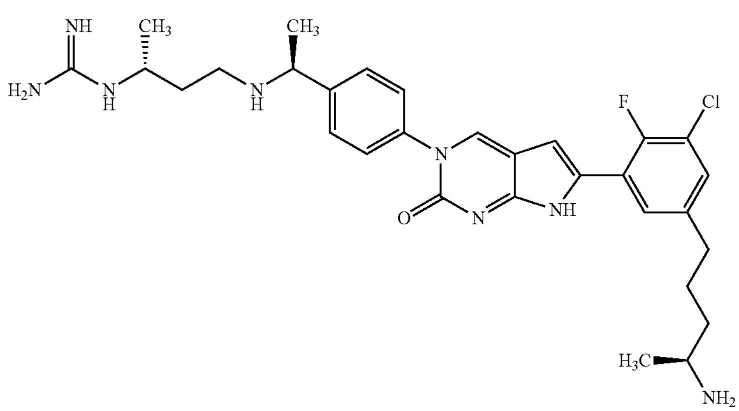 [SMILES: C[C@H](N)CCCc1cc(Cl)c(F)c(-c2cc3cn(-c4ccc([C@H](C)NCC[C@@H](C)NC(=N)N)cc4)c(=O)nc3[nH]2)c1] | 581 |

TABLE 1-continued

| Compound No | Structure | ESI, m/z [M + H]+ |
|---|---|---|
| 195 | 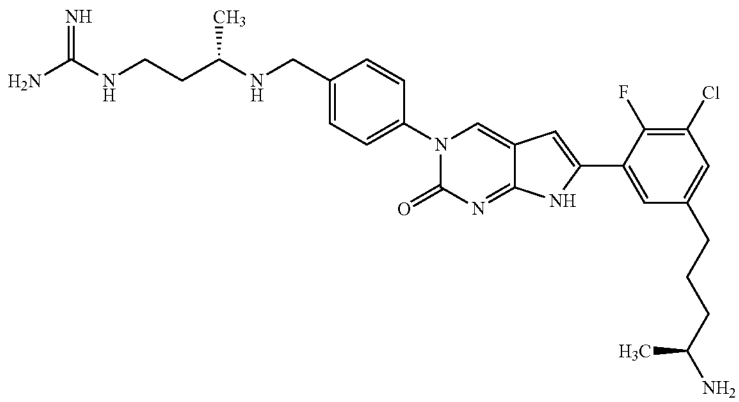 [SMILES: C[C@H](N)CCCc1cc(Cl)c(F)c(-c2cc3cn(-c4ccc(CN[C@@H](C)CCNC(=N)N)cc4)c(=O)nc3[nH]2)c1] | 567.1 |
| 196 | 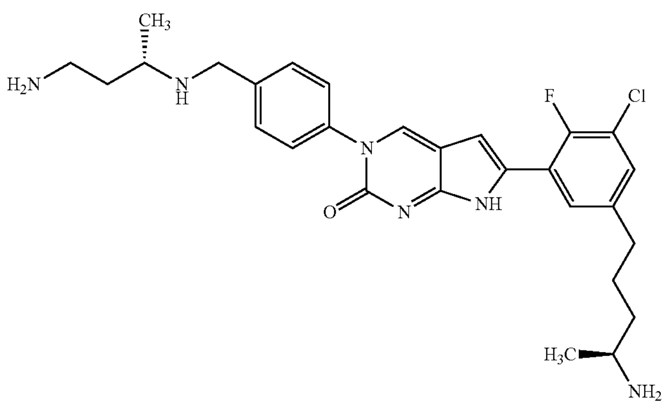 [SMILES: C[C@H](N)CCCc1cc(Cl)c(F)c(-c2cc3cn(-c4ccc(CN[C@@H](C)CCN)cc4)c(=O)nc3[nH]2)c1] | 525.1 |
| 197 | 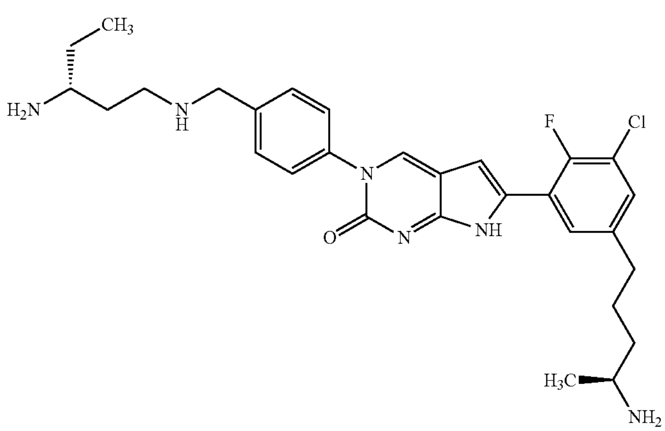 [SMILES: CC[C@@H](N)CCNCc1ccc(-n2cc3cc(-c4cc(CCC[C@H](C)N)cc(Cl)c4F)[nH]c3nc2=O)cc1] | 539.1 |

TABLE 1-continued

| Compound No | Structure | ESI, m/z [M + H]+ |
|---|---|---|
| 198 | 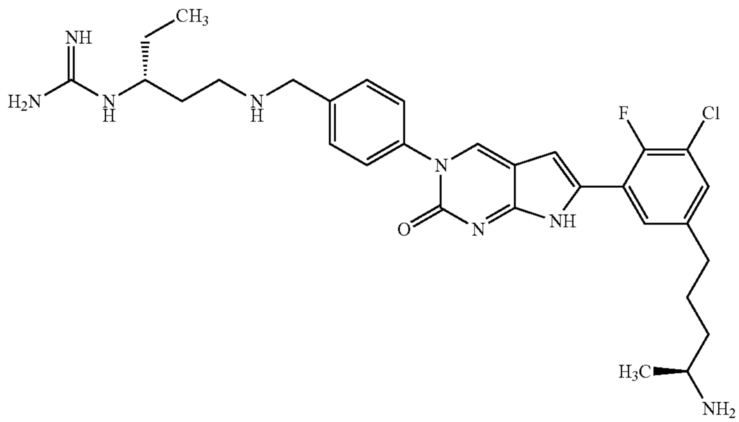 [SMILES: CC[C@H](CCNCc1ccc(-n2cc3cc(-c4cc(CCC[C@H](C)N)cc(Cl)c4F)[nH]c3nc2=O)cc1)NC(=N)N] | 581.1 |
| 199 | 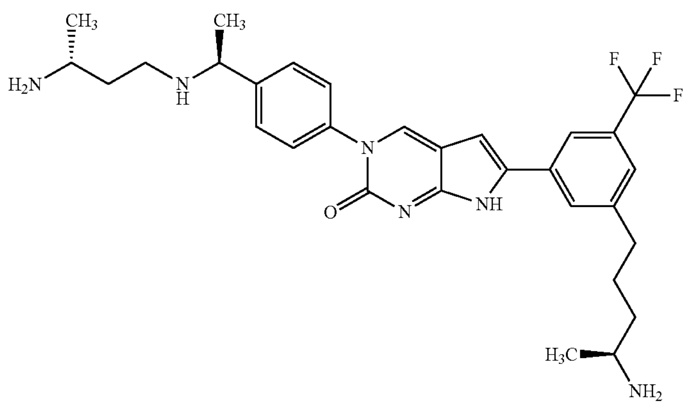 [SMILES: C[C@H](N)CCCc1cc(-c2cc3cn(-c4ccc([C@H](C)NCC[C@@H](C)N)cc4)c(=O)nc3[nH]2)cc(C(F)(F)F)c1] | 555.3 |
| 200 | 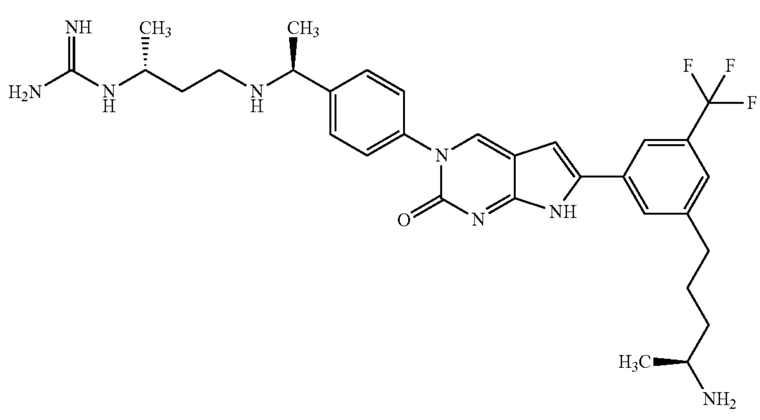 [SMILES: C[C@H](N)CCCc1cc(-c2cc3cn(-c4ccc([C@H](C)NCC[C@@H](C)NC(=N)N)cc4)c(=O)nc3[nH]2)cc(C(F)(F)F)c1] | 597.2 |

TABLE 1-continued
| Compound No | Structure | ESI, m/z [M + H]+ |
|---|---|---|
| 201 | 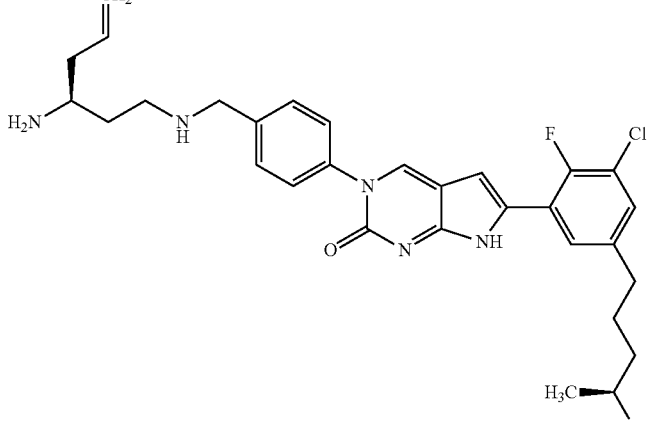 | 551.1 |
| 202 | 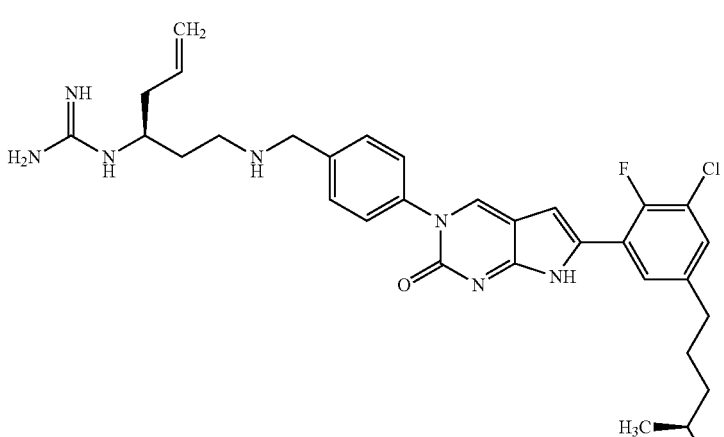 | 593.1 |
| 203 | 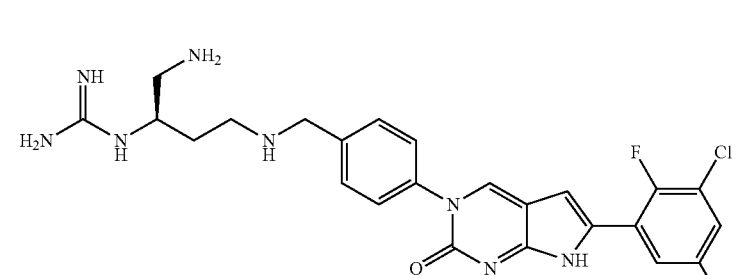 | 582.8 |

TABLE 1-continued

| Compound No | Structure | ESI, m/z [M + H]+ |
|---|---|---|
| 204 | 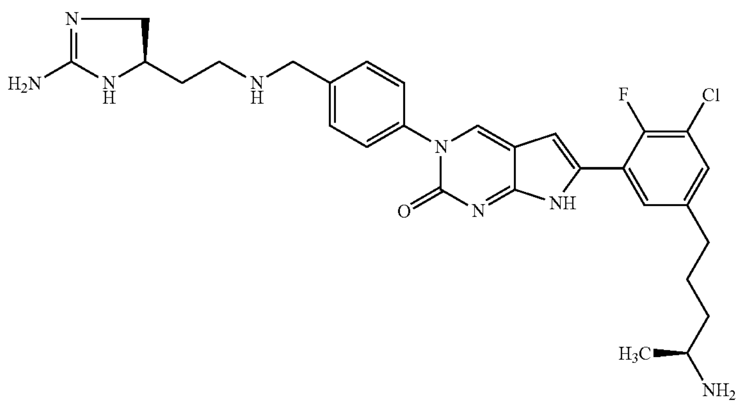 [SMILES: C[C@H](N)CCCc1cc(Cl)c(F)c(-c2cc3cn(-c4ccc(CNCC[C@@H]5CN=C(N)N5)cc4)c(=O)nc3[nH]2)c1] | 565.2 |
| 205 | 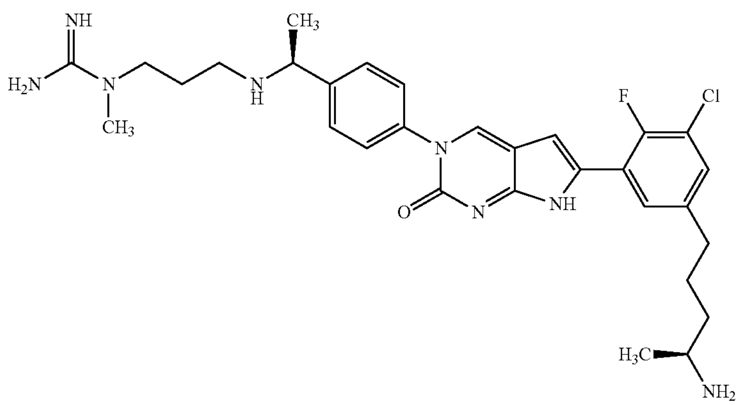 [SMILES: C[C@H](N)CCCc1cc(Cl)c(F)c(-c2cc3cn(-c4ccc([C@H](C)NCCCN(C)C(=N)N)cc4)c(=O)nc3[nH]2)c1] | 581.3 |
| 206 | 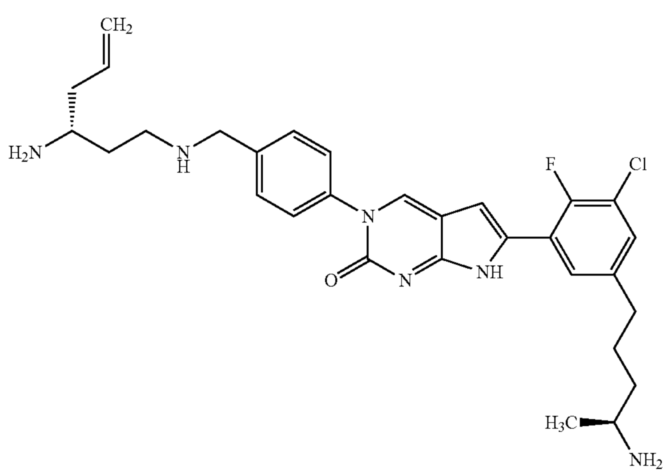 [SMILES: C=CC[C@@H](N)CCNCc1ccc(-n2cc3cc(-c4cc(CCC[C@H](C)N)cc(Cl)c4F)[nH]c3nc2=O)cc1] | 551.3 |

TABLE 1-continued
| Compound No | Structure | ESI, m/z [M + H]+ |
|---|---|---|
| 207 | 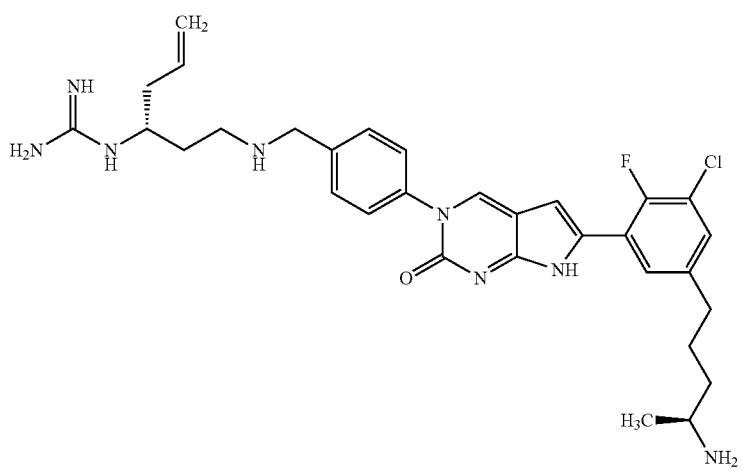 [SMILES: C=CC[C@H](CCNCc1ccc(-n2cc3cc(-c4cc(CCC[C@H](C)N)cc(Cl)c4F)[nH]c3nc2=O)cc1)NC(=N)N] | 593.1 |
| 208 | 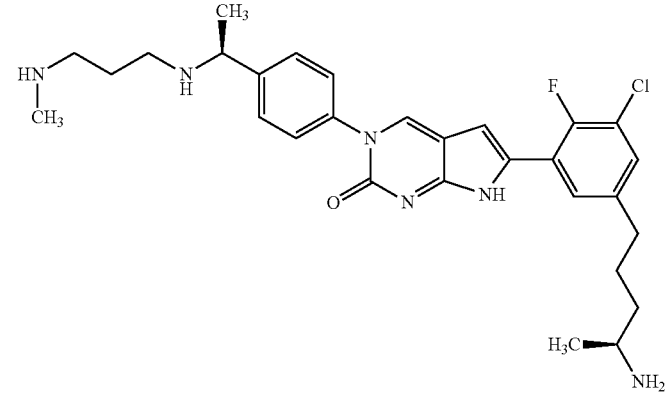 [SMILES: CNCCCN[C@@H](C)c1ccc(-n2cc3cc(-c4cc(CCC[C@H](C)N)cc(Cl)c4F)[nH]c3nc2=O)cc1] | 539.2 |
| 209 | 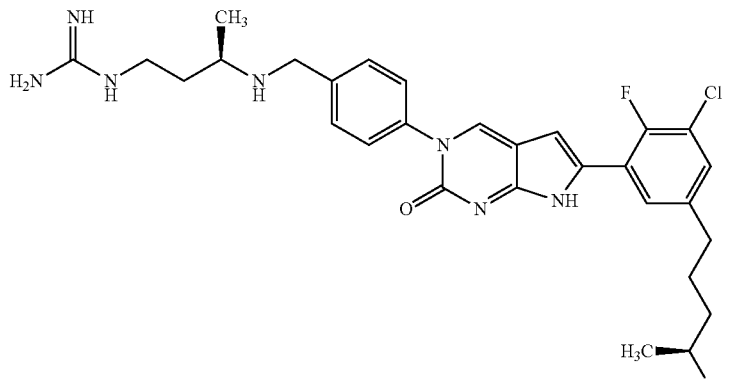 | 567.1 |

TABLE 1-continued

| Compound No | Structure | ESI, m/z [M + H]+ |
|---|---|---|
| 210 | 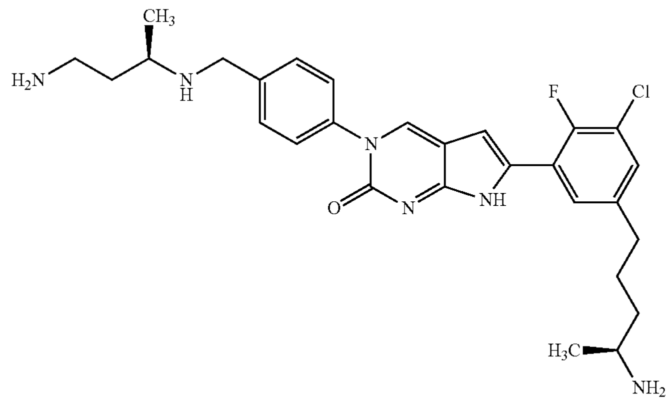 [SMILES: C[C@H](N)CCCc1cc(Cl)c(F)c(-c2cc3cn(-c4ccc(CN[C@H](C)CCN)cc4)c(=O)nc3[nH]2)c1] | 525.2 |
| 211 | 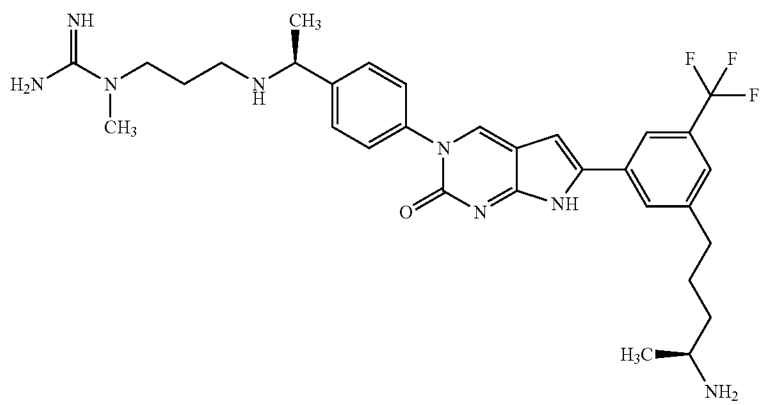 [SMILES: C[C@H](N)CCCc1cc(-c2cc3cn(-c4ccc([C@H](C)NCCCN(C)C(=N)N)cc4)c(=O)nc3[nH]2)cc(C(F)(F)F)c1] | 597.2 |
| 212 | 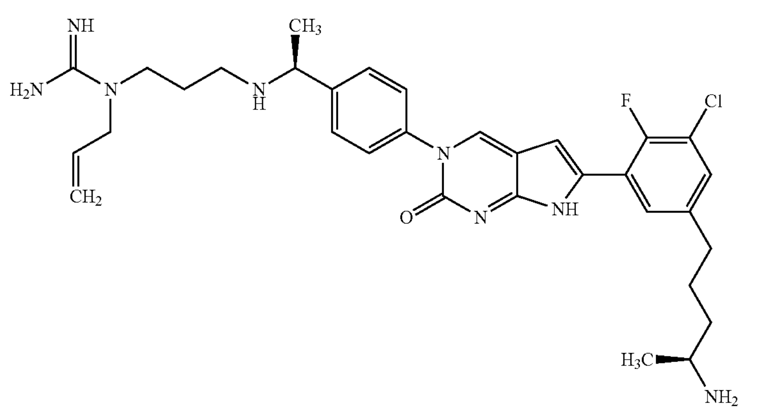 [SMILES: C=CCN(CCCN[C@@H](C)c1ccc(-n2cc3cc(-c4cc(CCC[C@H](C)N)cc(Cl)c4F)[nH]c3nc2=O)cc1)C(=N)N] | 607.2 |

TABLE 1-continued
| Compound No | Structure | ESI, m/z [M + H]+ |
|---|---|---|
| 213 | 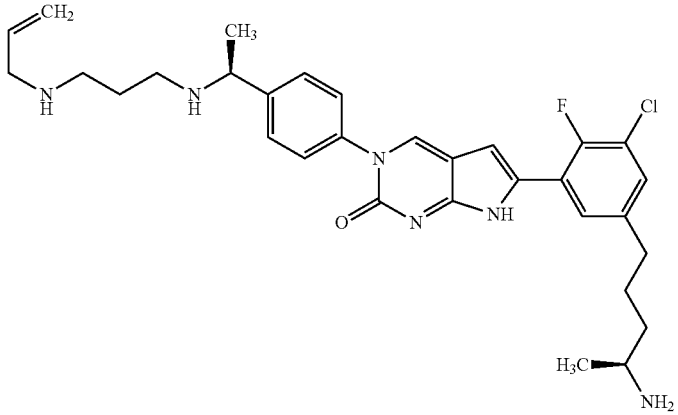 [SMILES: C=CCNCCCN[C@@H](C)c1ccc(-n2cc3cc(-c4cc(CCC[C@H](C)N)cc(Cl)c4F)[nH]c3nc2=O)cc1] | 565.1 |
| 214 | 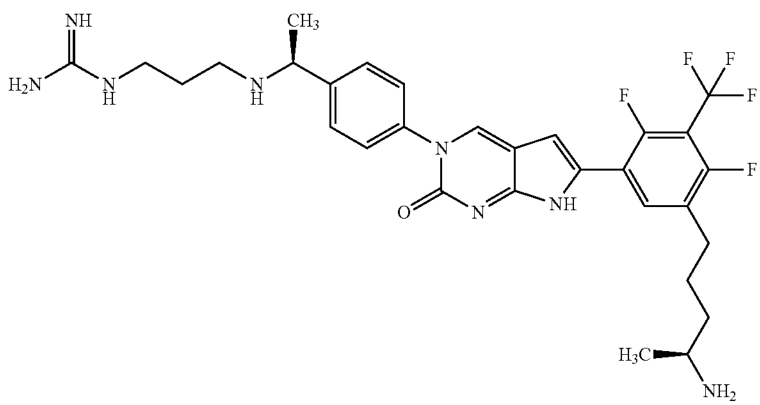 [SMILES: C[C@H](N)CCCc1cc(-c2cc3cn(-c4ccc([C@H](C)NCCCNC(=N)N)cc4)c(=O)nc3[nH]2)c(F)c(C(F)(F)F)c1F] | 619.2 |
| 215 | 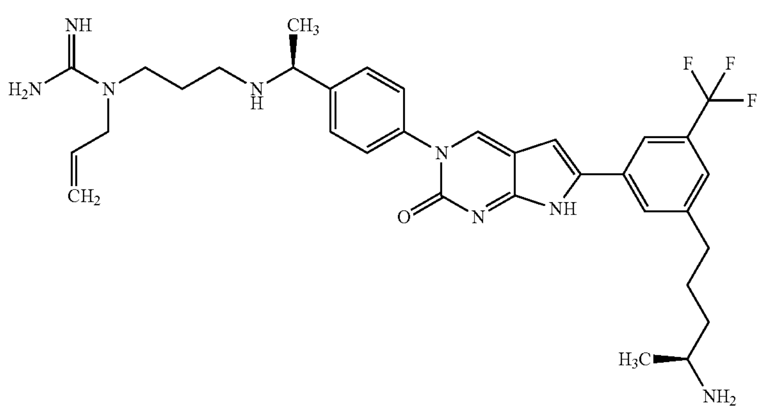 [SMILES: C=CCN(CCCN[C@@H](C)c1ccc(-n2cc3cc(-c4cc(CCC[C@H](C)N)cc(C(F)(F)F)c4)[nH]c3nc2=O)cc1)C(=N)N] | 623.2 |

TABLE 1-continued
| Compound No | Structure | ESI, m/z [M + H]+ |
|---|---|---|
| 216 | 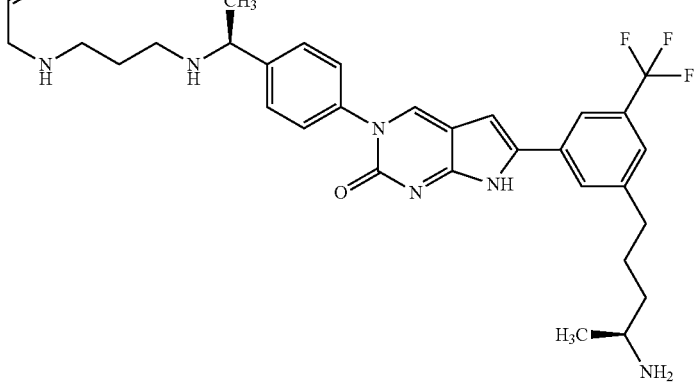 | 581.1 |
| 217 | 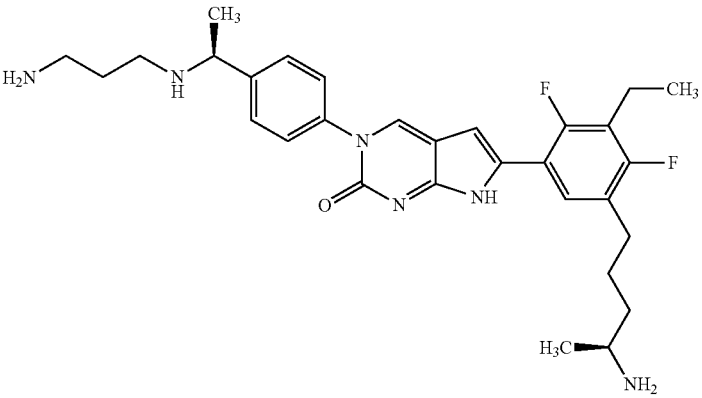 [SMILES: CCc1c(F)c(CCC[C@H](C)N)cc(-c2cc3cn(-c4ccc([C@H](C)NCCCN)cc4)c(=O)nc3[nH]2)c1F] | 537.1 |
| 218 | 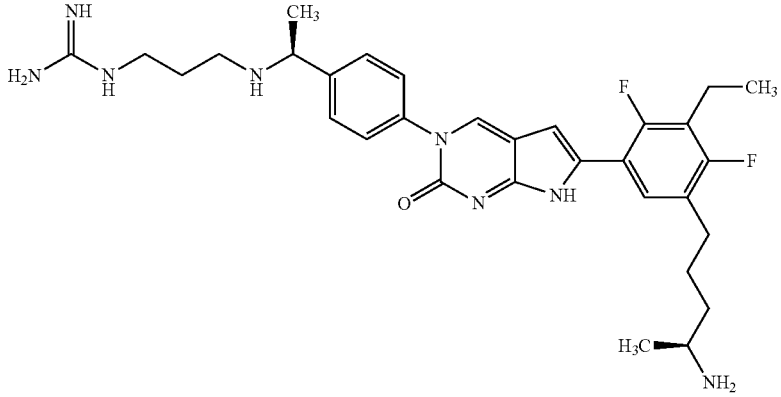 [SMILES: CCc1c(F)c(CCC[C@H](C)N)cc(-c2cc3cn(-c4ccc([C@H](C)NCCCNC(=N)N)cc4)c(=O)nc3[nH]2)c1F] | 579.2 |

TABLE 1-continued
| Compound No | Structure | ESI, m/z [M + H]+ |
|---|---|---|
| 219 | 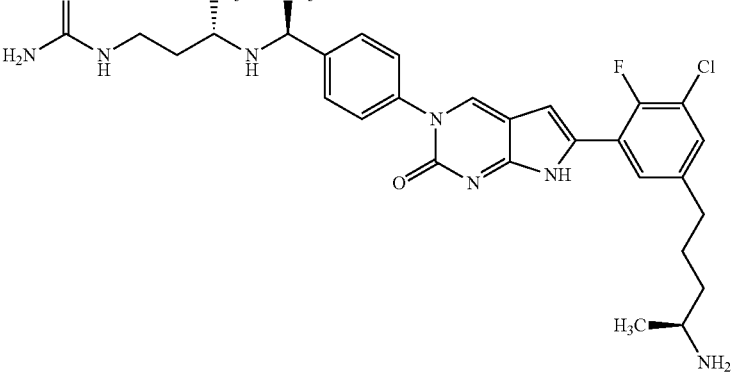 | 581.1 |
| 220 | 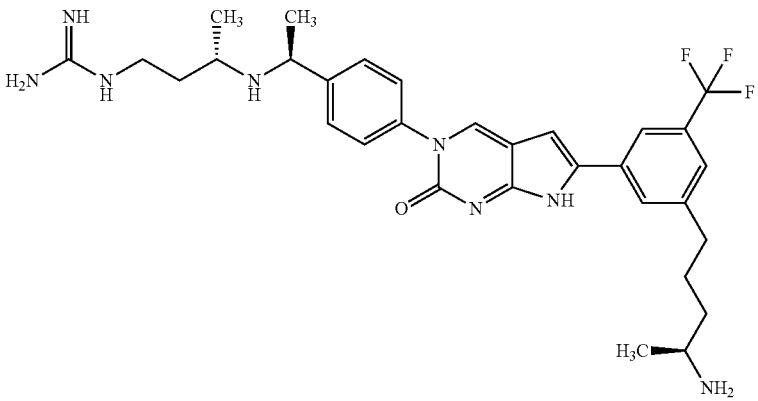 [SMILES: C[C@H](N)CCCc1cc(-c2cc3cn(-c4ccc([C@H](C)N[C@@H](C)CCNC(=N)N)cc4)c(=O)nc3[nH]2)cc(C(F)(F)F)c1] | 597.1 |
| 221 | 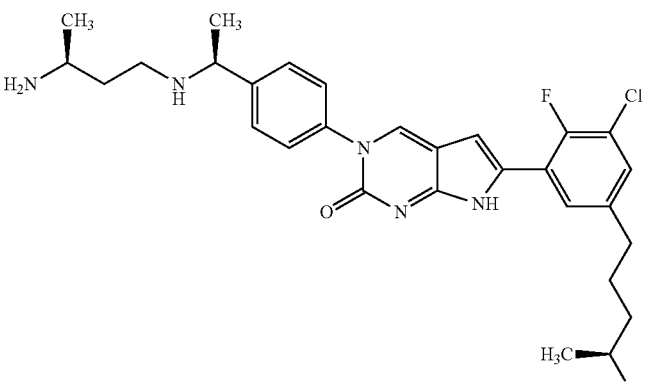 | 539.6 |

TABLE 1-continued
| Compound No | Structure | ESI, m/z [M + H]+ |
|---|---|---|
| 222 | 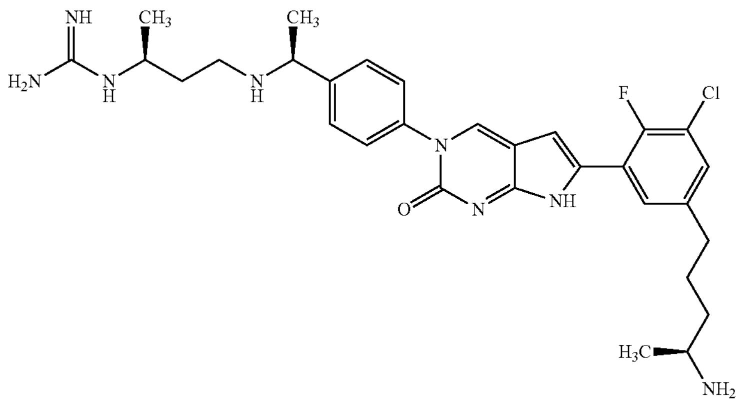 [SMILES: C[C@H](N)CCCc1cc(Cl)c(F)c(-c2cc3cn(-c4ccc([C@H](C)NCC[C@H](C)NC(=N)N)cc4)c(=O)nc3[nH]2)c1] | 581.1 |
| 223 | 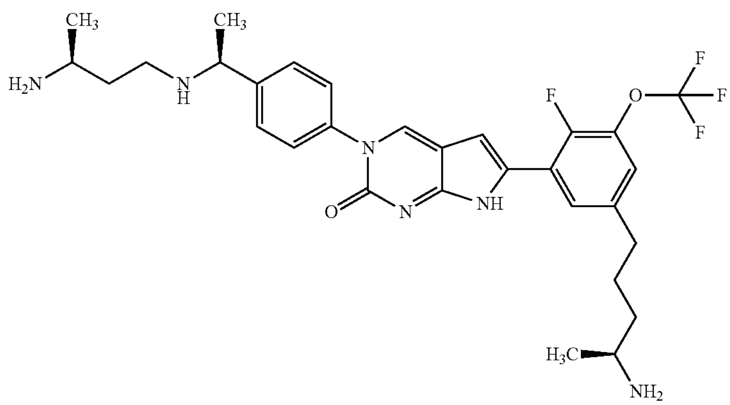 [SMILES: C[C@H](N)CCCc1cc(OC(F)(F)F)c(F)c(-c2cc3cn(-c4ccc([C@H](C)NCC[C@H](C)N)cc4)c(=O)nc3[nH]2)c1] | 589.1 |
| 224 | 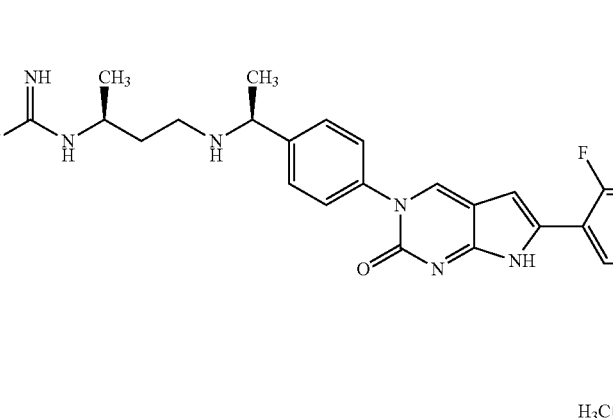 | 631.3 |

TABLE 1-continued

| Compound No | Structure | ESI, m/z [M + H]+ |
|---|---|---|
| 225 | 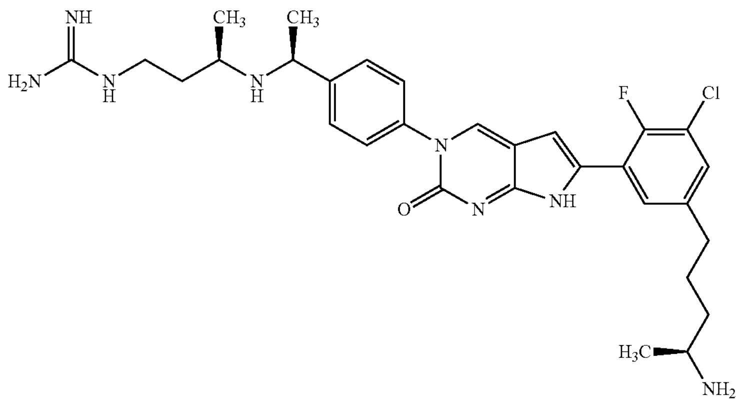 [SMILES: C[C@H](N)CCCc1cc(Cl)c(F)c(-c2cc3cn(-c4ccc([C@H](C)N[C@H](C)CCNC(=N)N)cc4)c(=O)nc3[nH]2)c1] | 581.2 |
| 226 | 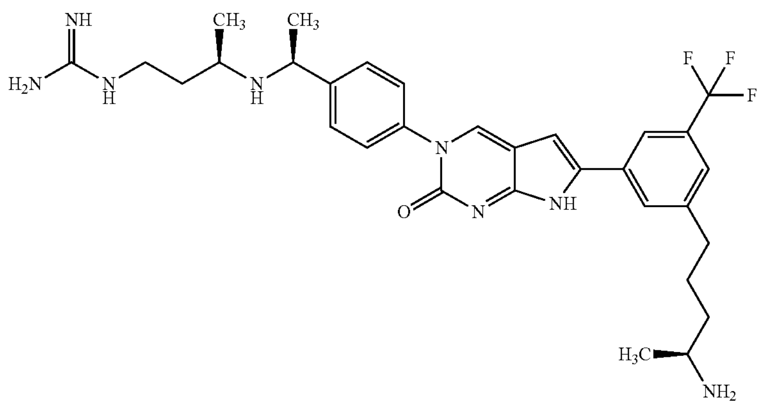 [SMILES: C[C@H](N)CCCc1cc(-c2cc3cn(-c4ccc([C@H](C)N[C@H](C)CCNC(=N)N)cc4)c(=O)nc3[nH]2)cc(C(F)(F)F)c1] | 597 |
| 227 | 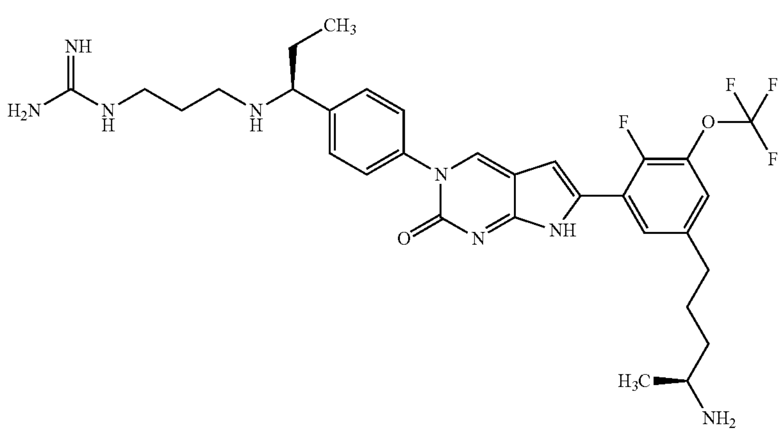 [SMILES: CC[C@H](NCCCNC(=N)N)c1ccc(-n2cc3cc(-c4cc(CCC[C@H](C)N)cc(OC(F)(F)F)c4F)[nH]c3nc2=O)cc1] | 631.2 |

TABLE 1-continued
| Compound No | Structure | ESI, m/z [M + H]+ |
|---|---|---|
| 228 | 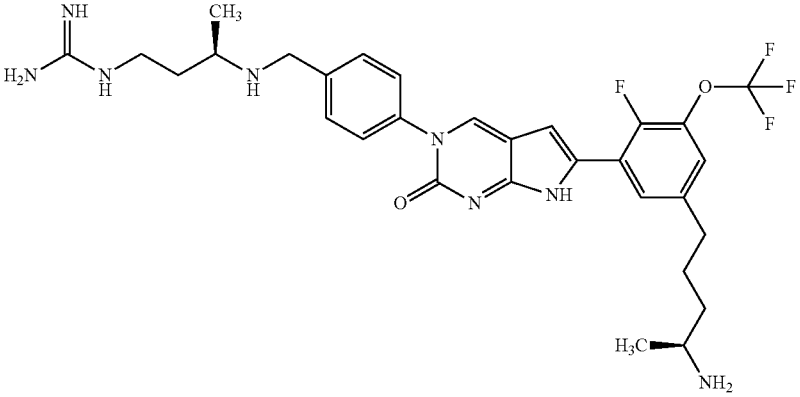 [SMILES: C[C@H](N)CCCc1cc(OC(F)(F)F)c(F)c(-c2cc3cn(-c4ccc(CN[C@H](C)CCNC(=N)N)cc4)c(=O)nc3[nH]2)c1] | 617.2 |
| 229 | 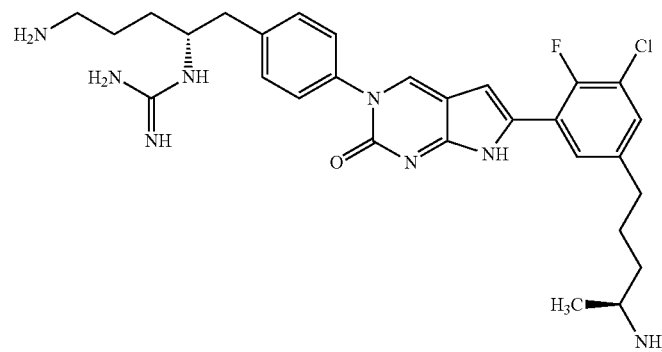 | 567 |
| 230 | 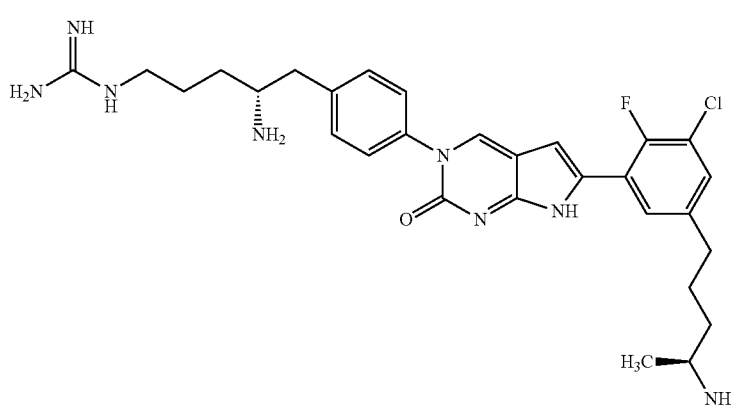 | 567.1 |
| 231 | 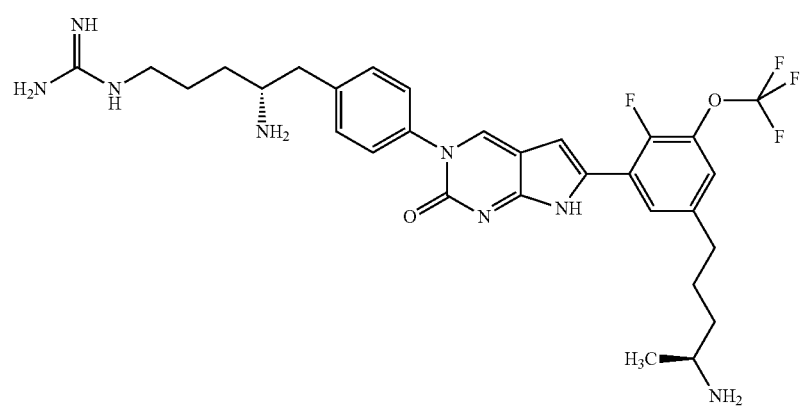 [SMILES: C[C@H](N)CCCc1cc(OC(F)(F)F)c(F)c(-c2cc3cn(-c4ccc(C[C@H](N)CCCNC(=N)N)cc4)c(=O)nc3[nH]2)c1] | 617.3 |

TABLE 1-continued
| Compound No | Structure | ESI, m/z [M + H]+ |
|---|---|---|
| 232 | 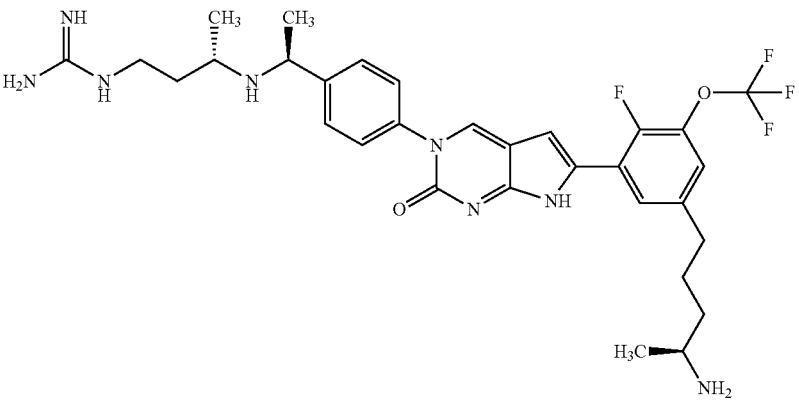 [SMILES: C[C@H](N)CCCc1cc(OC(F)(F)F)c(F)c(-c2cc3cn(-c4ccc([C@H](C)N[C@@H](C)CCNC(=N)N)cc4)c(=O)nc3[nH]2)c1] | 631.2 |
| 233 | 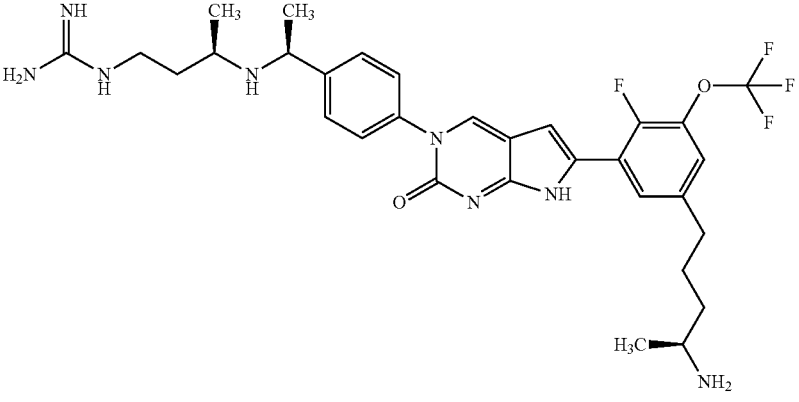 [SMILES: C[C@H](N)CCCc1cc(OC(F)(F)F)c(F)c(-c2cc3cn(-c4ccc([C@H](C)N[C@H](C)CCNC(=N)N)cc4)c(=O)nc3[nH]2)c1] | 631.1 |
| 234 | 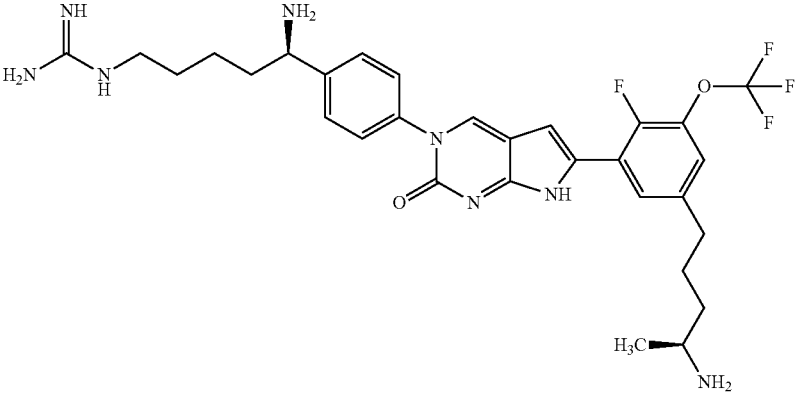 [SMILES: C[C@H](N)CCCc1cc(OC(F)(F)F)c(F)c(-c2cc3cn(-c4ccc([C@H](N)CCCCNC(=N)N)cc4)c(=O)nc3[nH]2)c1] | 617.1 |

TABLE 1-continued
| Compound No | Structure | ESI, m/z [M + H]+ |
|---|---|---|
| 235 | 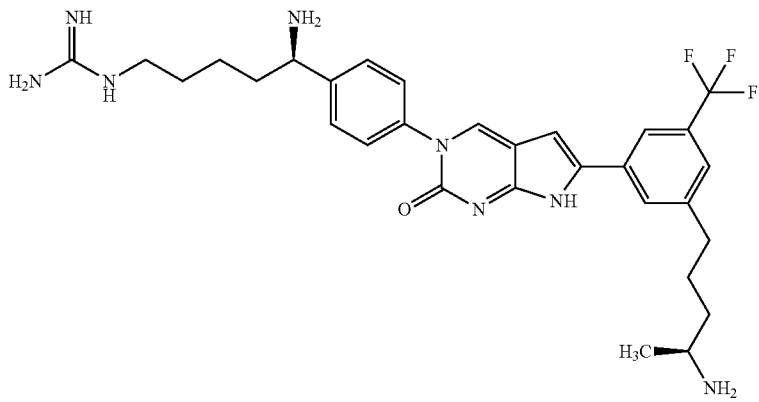 [SMILES: C[C@H](N)CCCc1cc(-c2cc3cn(-c4ccc([C@H](N)CCCCNC(=N)N)cc4)c(=O)nc3[nH]2)cc(C(F)(F)F)c1] | 583.1 |
| 236 | 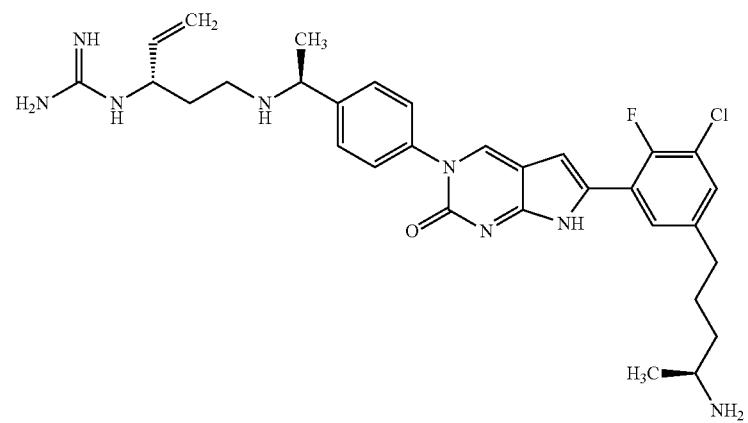 | 593.1 |
| 237 | 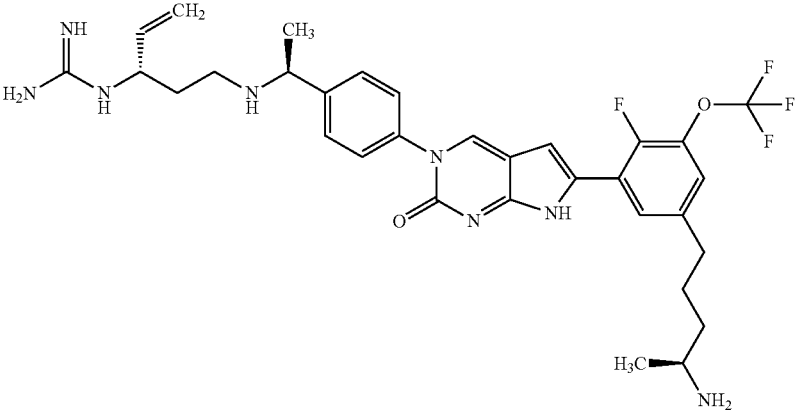 [SMILES: C=C[C@H](CCN[C@@H](C)c1ccc(-n2cc3cc(-c4cc(CCC[C@H](C)N)cc(OC(F)(F)F)c4F)[nH]c3nc2=O)cc1)NC(=N)N] | 643.2 |

TABLE 1-continued

| Compound No | Structure | ESI, m/z [M + H]+ |
|---|---|---|
| 238 | 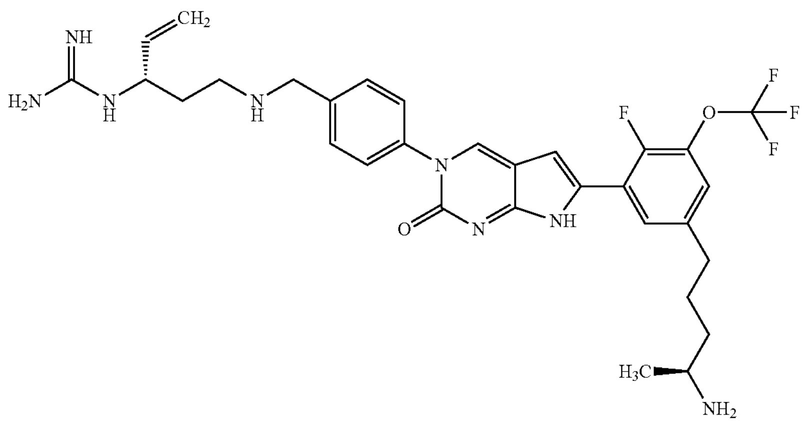 | 629.5 |
| 239 | 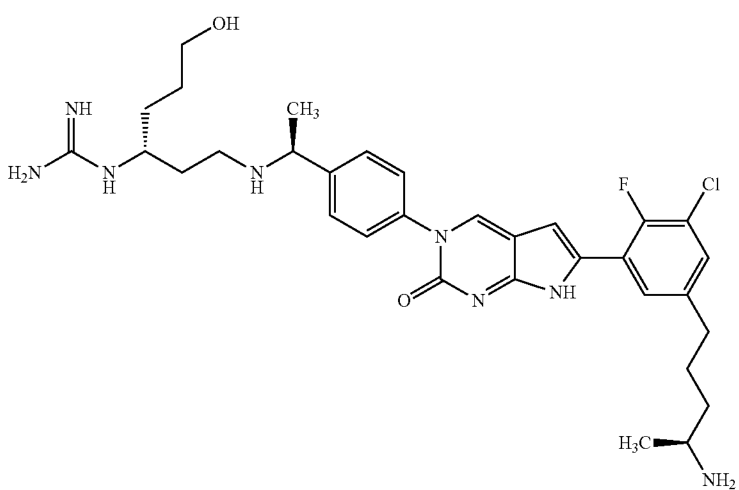 | 625 |
| 240 | 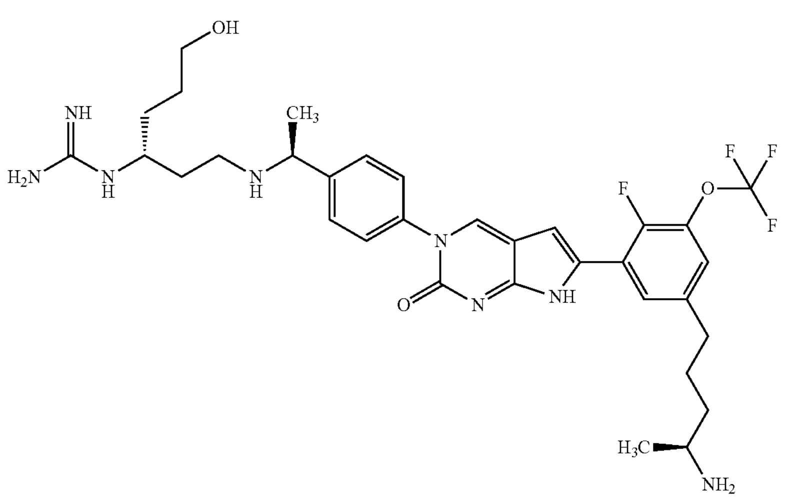 [SMILES: C[C@H](N)CCCc1cc(OC(F)(F)F)c(F)c(-c2cc3cn(-c4ccc([C@H](C)NCC[C@@H](CCCO)NC(=N)N)cc4)c(=O)nc3[nH]2)c1] | 675.1 |

TABLE 1-continued
| Compound No | Structure | ESI, m/z [M + H]+ |
|---|---|---|
| 241 | 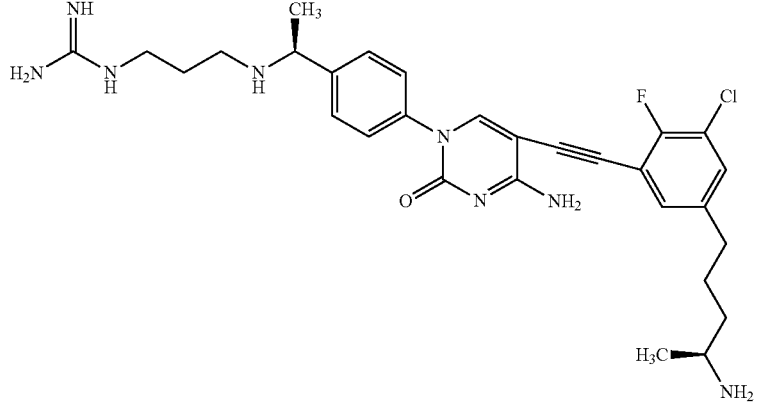 [SMILES: C[C@H](N)CCCc1cc(Cl)c(F)c(C#Cc2cn(-c3ccc([C@H](C)NCCCNC(=N)N)cc3)c(=O)nc2N)c1] | 567.1 |
| 242 | 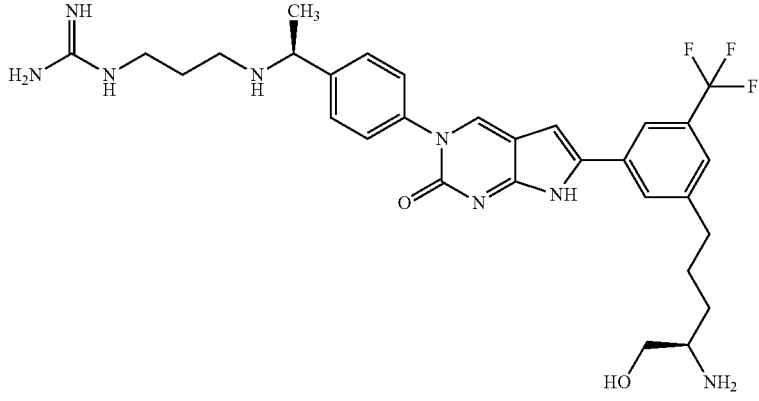 [SMILES: C[C@H](NCCCNC(=N)N)c1ccc(-n2cc3cc(-c4cc(CCC[C@@H](N)CO)cc(C(F)(F)F)c4)[nH]c3nc2=O)cc1] | 599.3 |
| 243 | 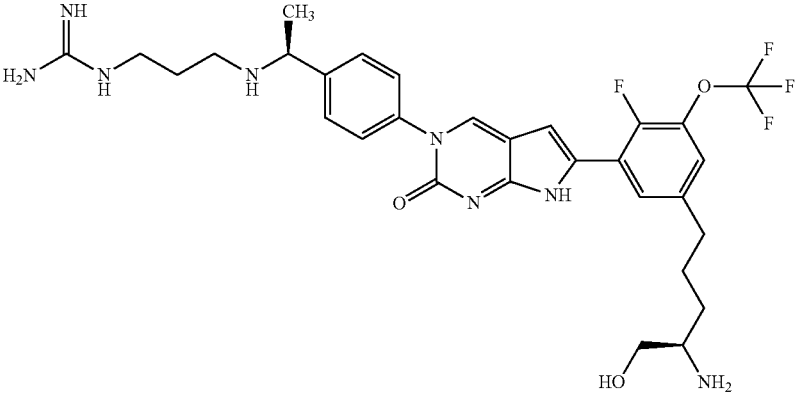 [SMILES: C[C@H](NCCCNC(=N)N)c1ccc(-n2cc3cc(-c4cc(CCC[C@@H](N)CO)cc(OC(F)(F)F)c4F)[nH]c3nc2=O)cc1] | 633.2 |

| Compound No | Structure | ESI, m/z [M + H]+ |
|---|---|---|
| 244 | 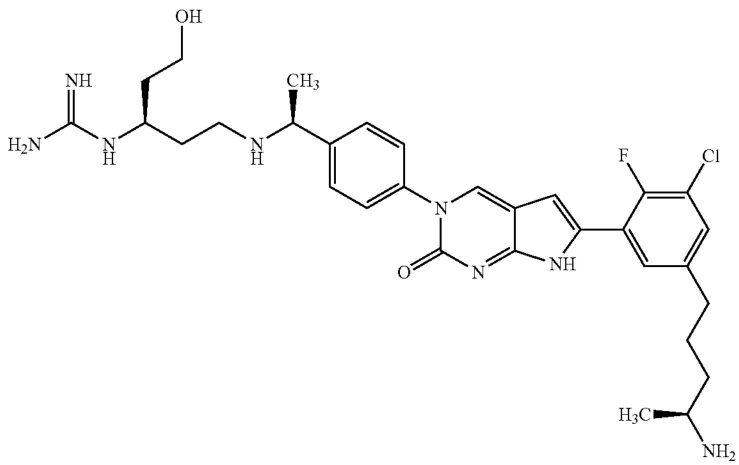 [SMILES: C[C@H](N)CCCc1cc(Cl)c(F)c(-c2cc3cn(-c4ccc([C@H](C)NCC[C@H](CCO)NC(=N)N)cc4)c(=O)nc3[nH]2)c1] | 611.6 |
| 245 | 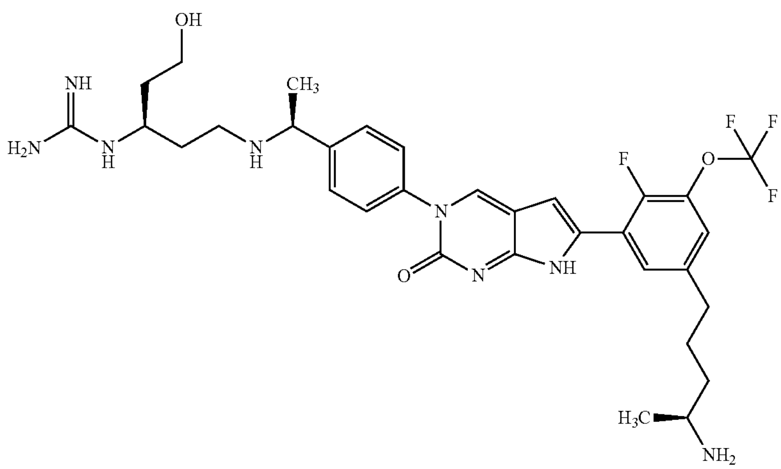 [SMILES: C[C@H](N)CCCc1cc(OC(F)(F)F)c(F)c(-c2cc3cn(-c4ccc([C@H](C)NCC[C@H](CCO)NC(=N)N)cc4)c(=O)nc3[nH]2)c1] | 661.3 |
| 246 | 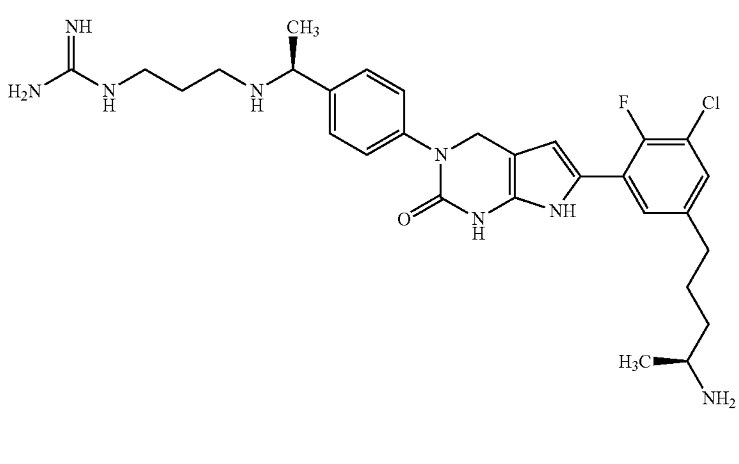 [SMILES: C[C@H](N)CCCc1cc(Cl)c(F)c(-c2cc3c([nH]2)NC(=O)N(c2ccc([C@H](C)NCCCNC(=N)N)cc2)C3)c1] | 569.4 |

TABLE 1-continued

| Compound No | Structure | ESI, m/z [M + H]+ |
|---|---|---|
| 247 | 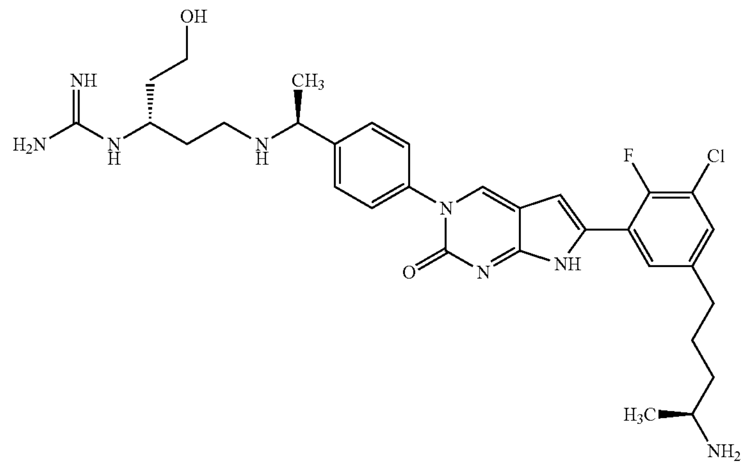 [SMILES: C[C@H](N)CCCc1cc(Cl)c(F)c(-c2cc3cn(-c4ccc([C@H](C)NCC[C@@H](CCO)NC(=N)N)cc4)c(=O)nc3[nH]2)c1] | 611.1 |
| 248 | 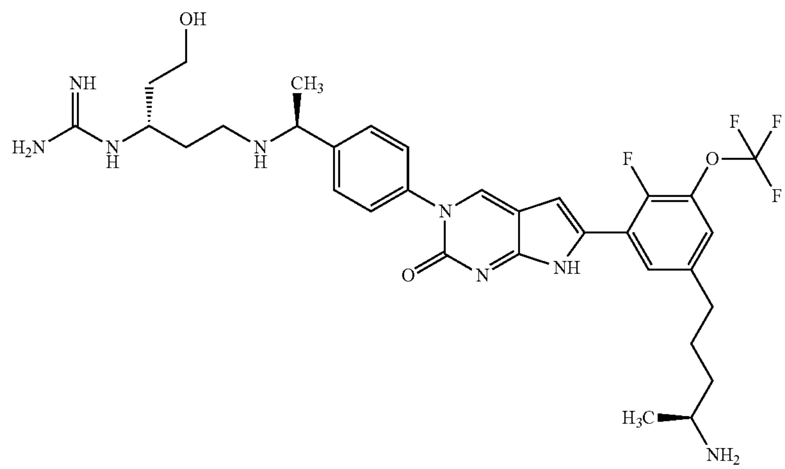 [SMILES: C[C@H](N)CCCc1cc(OC(F)(F)F)c(F)c(-c2cc3cn(-c4ccc([C@H](C)NCC[C@@H](CCO)NC(=N)N)cc4)c(=O)nc3[nH]2)c1] | 661.2 |
| 249 | 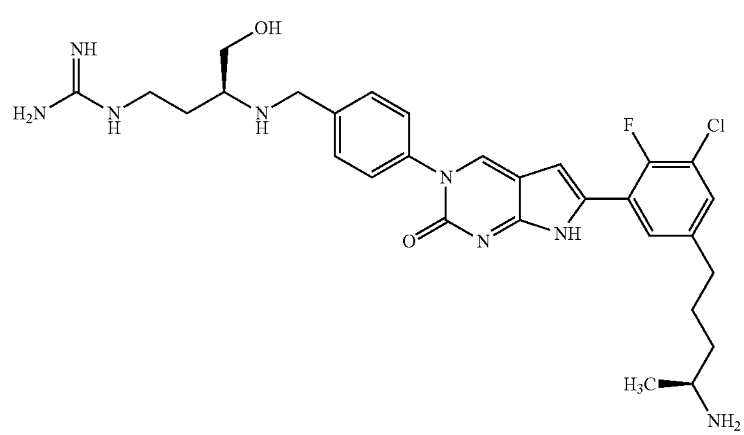 [SMILES: C[C@H](N)CCCc1cc(Cl)c(F)c(-c2cc3cn(-c4ccc(CN[C@H](CO)CCNC(=N)N)cc4)c(=O)nc3[nH]2)c1] | 583 |

TABLE 1-continued

| Compound No | Structure | ESI, m/z [M + H]+ |
|---|---|---|
| 250 | 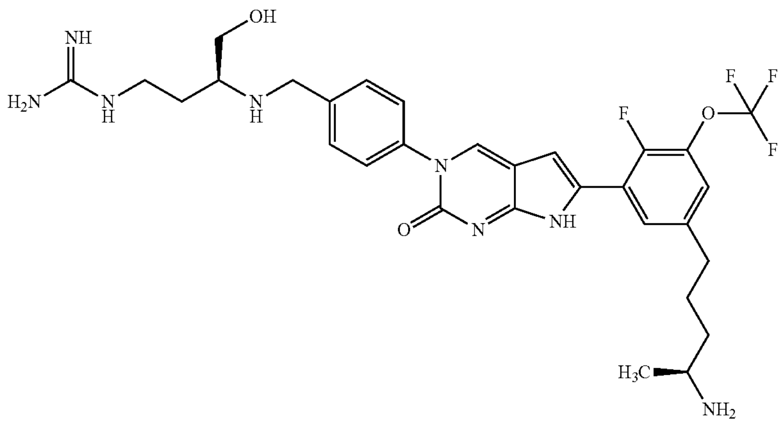 [SMILES: C[C@H](N)CCCc1cc(OC(F)(F)F)c(F)c(-c2cc3cn(-c4ccc(CN[C@H](CO)CCNC(=N)N)cc4)c(=O)nc3[nH]2)c1] | 633.6 |
| 251 | 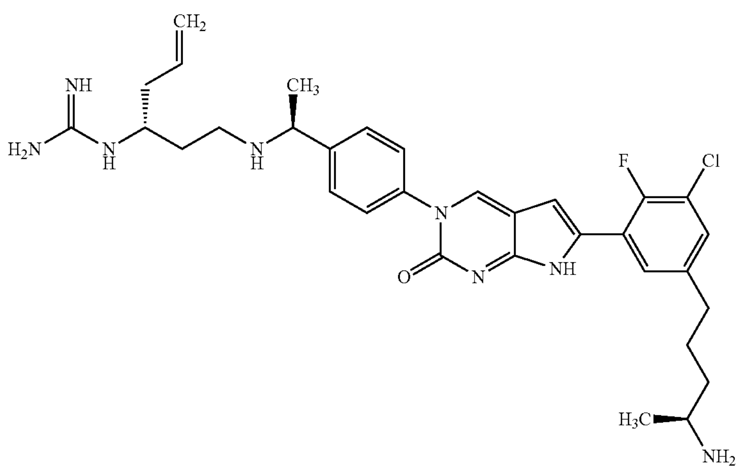 [SMILES: C=CC[C@H](CCN[C@@H](C)c1ccc(-n2cc3cc(-c4cc(CCC[C@H](C)N)cc(Cl)c4F)[nH]c3nc2=O)cc1)NC(=N)N] | 607.1 |
| 252 | 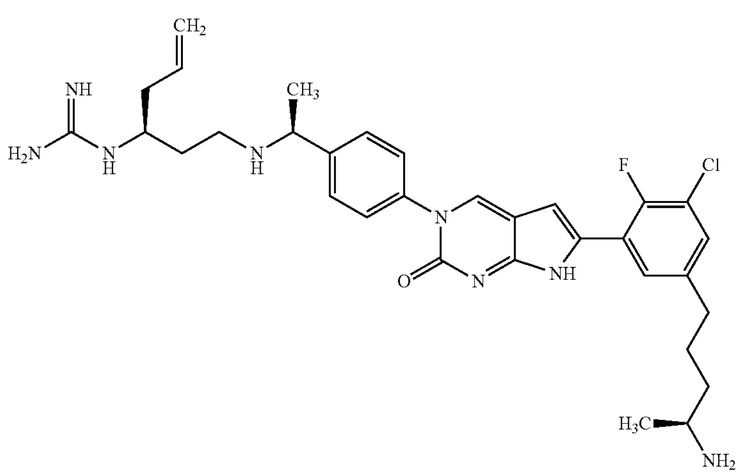 [SMILES: C=CC[C@@H](CCN[C@@H](C)c1ccc(-n2cc3cc(-c4cc(CCC[C@H](C)N)cc(Cl)c4F)[nH]c3nc2=O)cc1)NC(=N)N] | 607.1 |

TABLE 1-continued

| Compound No | Structure | ESI, m/z [M + H]+ |
|---|---|---|
| 253 | 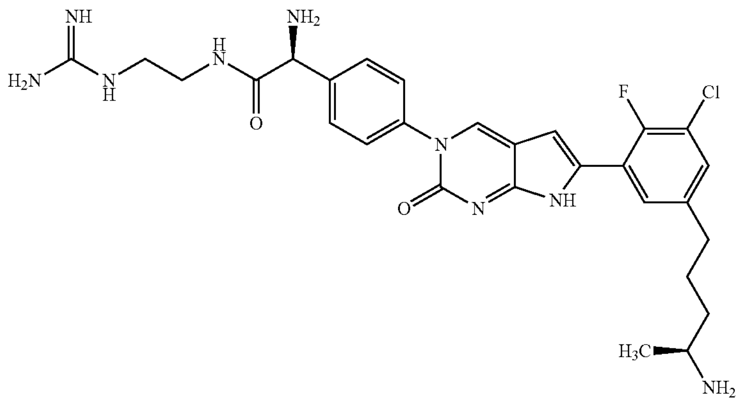 [SMILES: C[C@H](N)CCCc1cc(Cl)c(F)c(-c2cc3cn(-c4ccc([C@H](N)C(=O)NCCNC(=N)N)cc4)c(=O)nc3[nH]2)c1] | 582.1 |
| 254 | 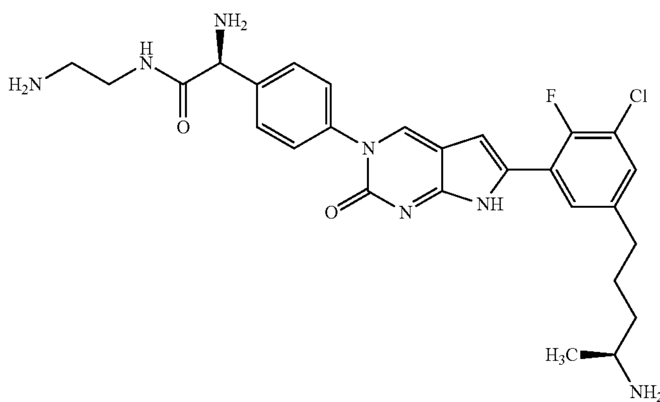 [SMILES: C[C@H](N)CCCc1cc(Cl)c(F)c(-c2cc3cn(-c4ccc([C@H](N)C(=O)NCCN)cc4)c(=O)nc3[nH]2)c1] | 540.1 |
| 255 | 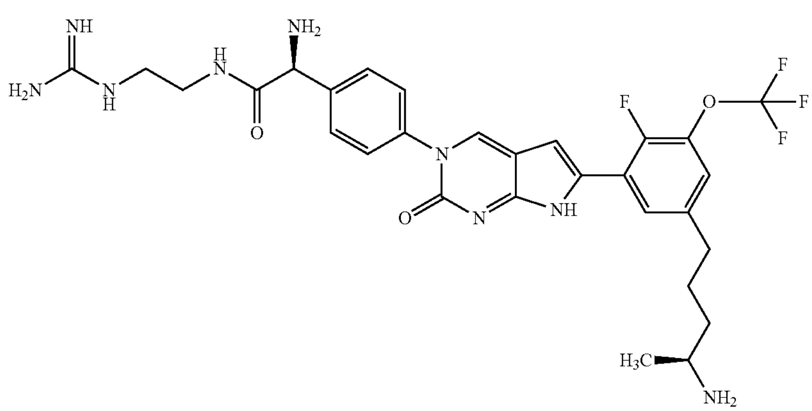 [SMILES: C[C@H](N)CCCc1cc(OC(F)(F)F)c(F)c(-c2cc3cn(-c4ccc([C@H](N)C(=O)NCCNC(=N)N)cc4)c(=O)nc3[nH]2)c1] | 632.2 |

TABLE 1-continued

| Compound No | Structure | ESI, m/z [M + H]+ |
|---|---|---|
| 256 | 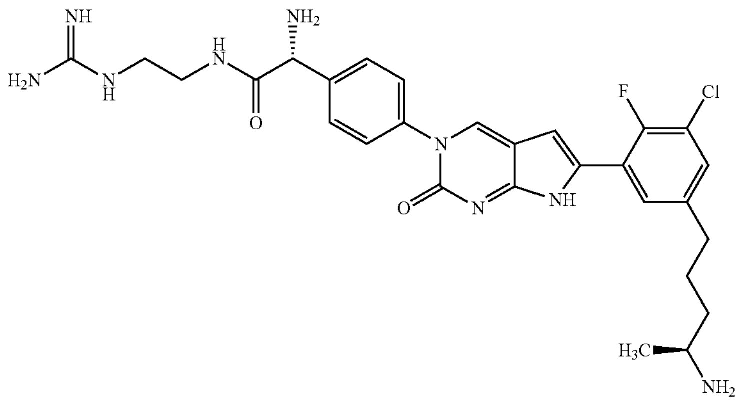 [SMILES: C[C@H](N)CCCc1cc(Cl)c(F)c(-c2cc3cn(-c4ccc([C@@H](N)C(=O)NCCNC(=N)N)cc4)c(=O)nc3[nH]2)c1] | 582.1 |
| 257 | 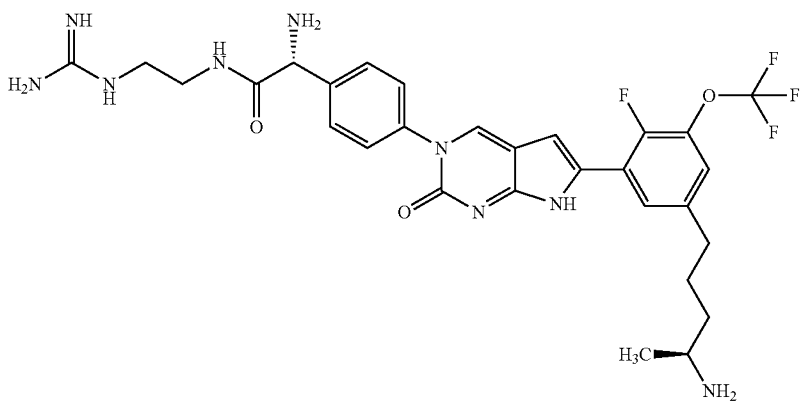 [SMILES: C[C@H](N)CCCc1cc(OC(F)(F)F)c(F)c(-c2cc3cn(-c4ccc([C@@H](N)C(=O)NCCNC(=N)N)cc4)c(=O)nc3[nH]2)c1] | 632.2 |
| 258 | 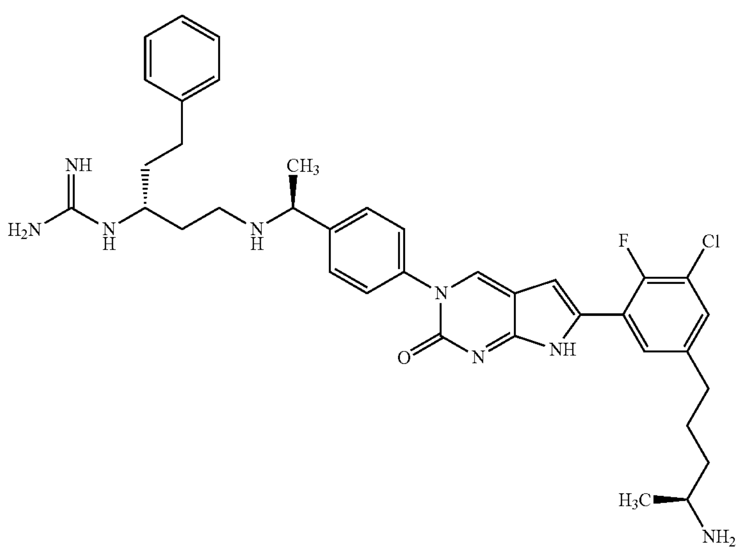 [SMILES: C[C@H](N)CCCc1cc(Cl)c(F)c(-c2cc3cn(-c4ccc([C@H](C)NCC[C@@H](CCc5ccccc5)NC(=N)N)cc4)c(=O)nc3[nH]2)c1] | 671.2 |

TABLE 1-continued

| Compound No | Structure | ESI, m/z [M + H]+ |
|---|---|---|
| 259 | 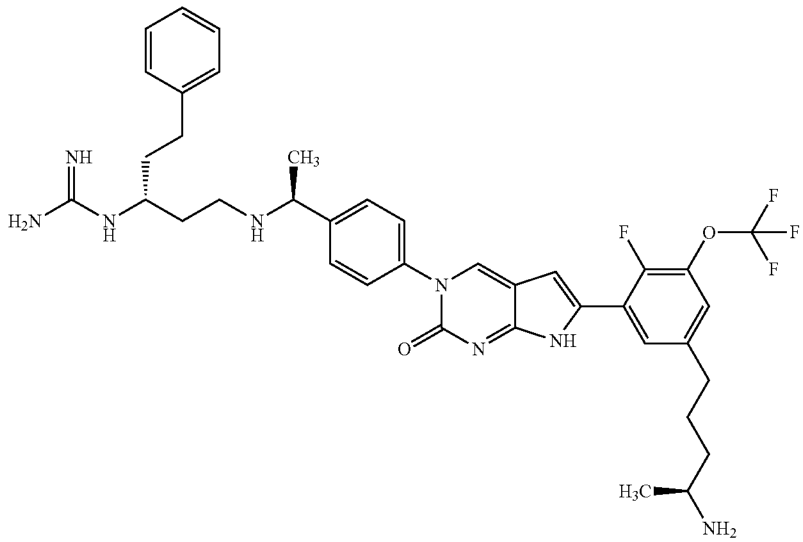 [SMILES: C[C@H](N)CCCc1cc(OC(F)(F)F)c(F)c(-c2cc3cn(-c4ccc([C@H](C)NCC[C@@H](CCc5ccccc5)NC(=N)N)cc4)c(=O)nc3[nH]2)c1] | 721.2 |
| 260 | 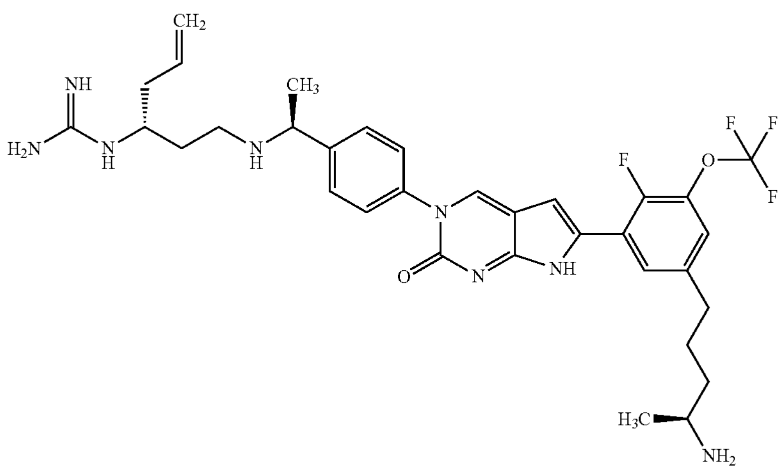 | 657.2 |
| 261 | 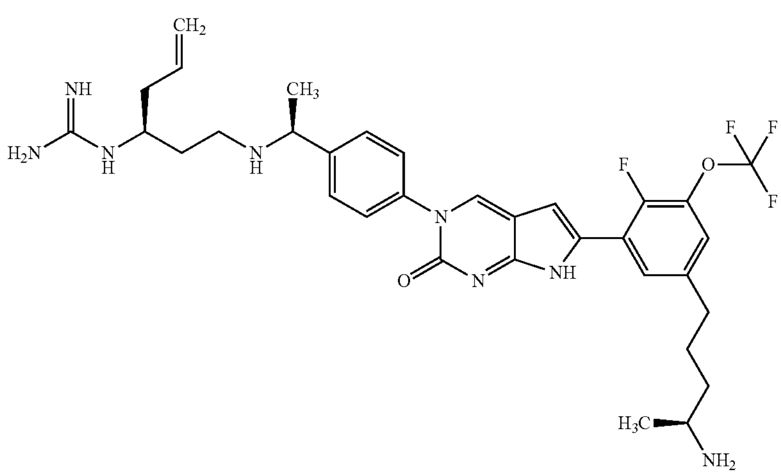 | 657.2 |

TABLE 1-continued
| Compound No | Structure | ESI, m/z [M + H]+ |
|---|---|---|
| 262 | 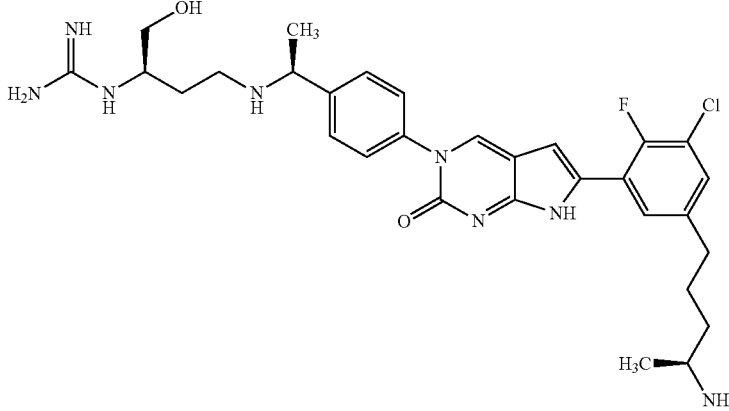 | 597.1 |
| 263 | 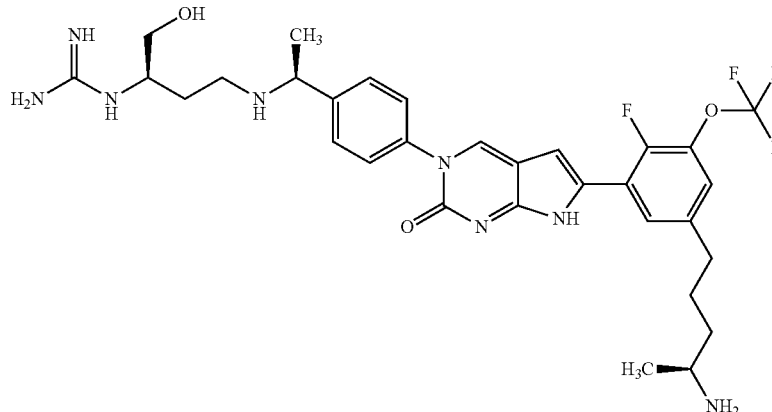 | 647.2 |
| 264 | 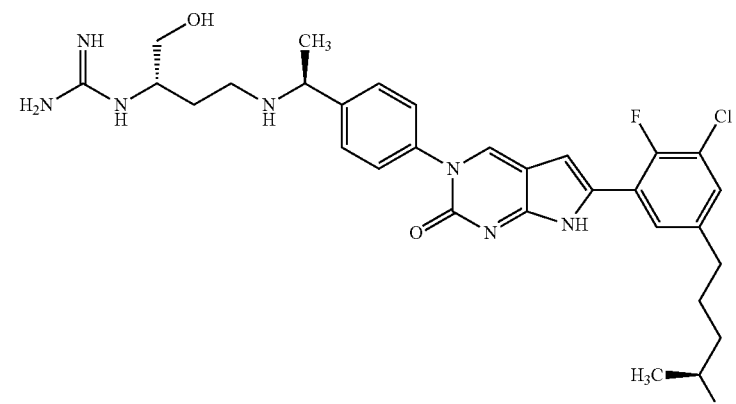 | 597.1 |

TABLE 1-continued

| Compound No | Structure | ESI, m/z [M + H]+ |
|---|---|---|
| 265 | 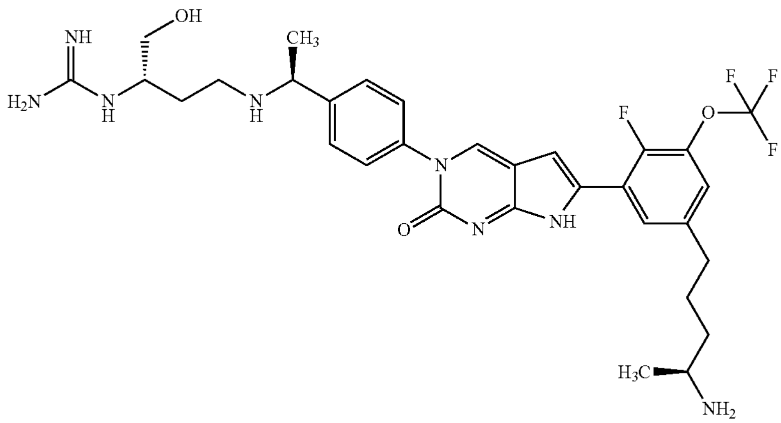 [SMILES: C[C@H](N)CCCc1cc(OC(F)(F)F)c(F)c(-c2cc3cn(-c4ccc([C@H](C)NCC[C@@H](CO)NC(=N)N)cc4)c(=O)nc3[nH]2)c1] | 647.1 |
| 266 | 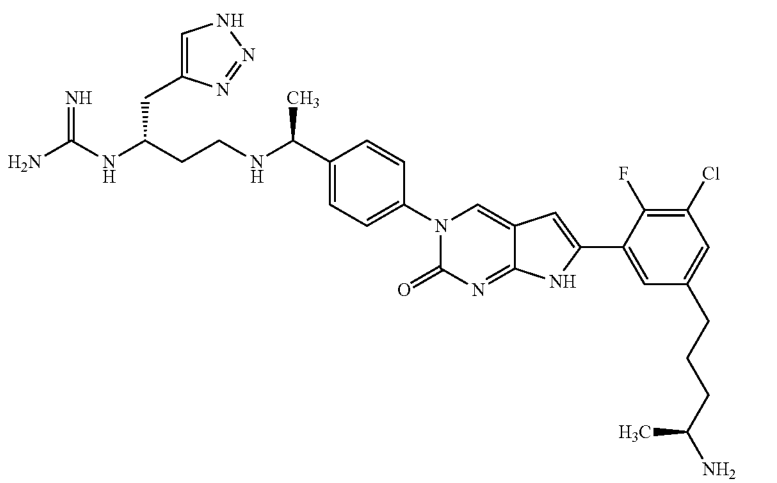 [SMILES: C[C@H](N)CCCc1cc(Cl)c(F)c(-c2cc3cn(-c4ccc([C@H](C)NCC[C@@H](Cc5c[nH]nn5)NC(=N)N)cc4)c(=O)nc3[nH]2)c1] | 648.2 |
| 267 | 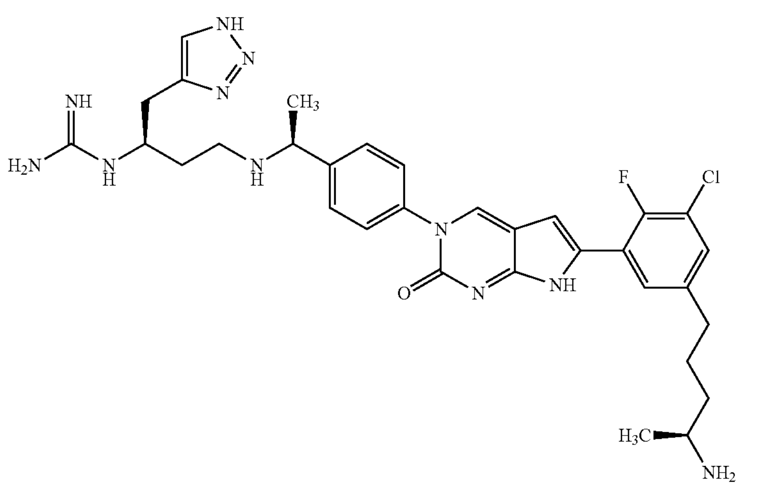 [SMILES: C[C@H](N)CCCc1cc(Cl)c(F)c(-c2cc3cn(-c4ccc([C@H](C)NCC[C@H](Cc5c[nH]nn5)NC(=N)N)cc4)c(=O)nc3[nH]2)c1] | 648.2 |

TABLE 1-continued

| Compound No | Structure | ESI, m/z [M + H]+ |
|---|---|---|
| 268 | 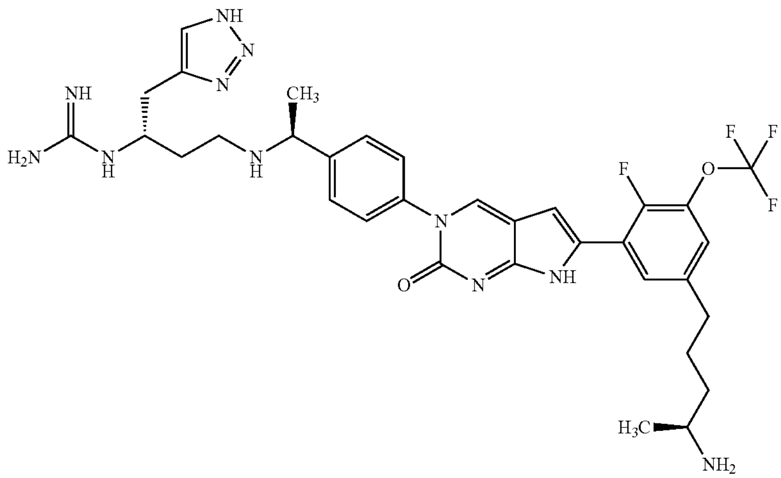 [SMILES: C[C@H](N)CCCc1cc(OC(F)(F)F)c(F)c(-c2cc3cn(-c4ccc([C@H](C)NCC[C@@H](Cc5c[nH]nn5)NC(=N)N)cc4)c(=O)nc3[nH]2)c1] | 698.1 |
| 269 | 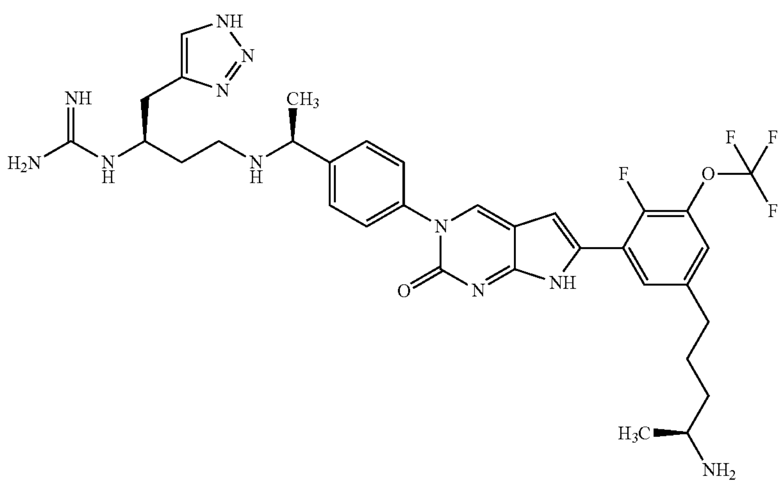 [SMILES: C[C@H](N)CCCc1cc(OC(F)(F)F)c(F)c(-c2cc3cn(-c4ccc([C@H](C)NCC[C@H](Cc5c[nH]nn5)NC(=N)N)cc4)c(=O)nc3[nH]2)c1] | 698.1 |
| 270 | 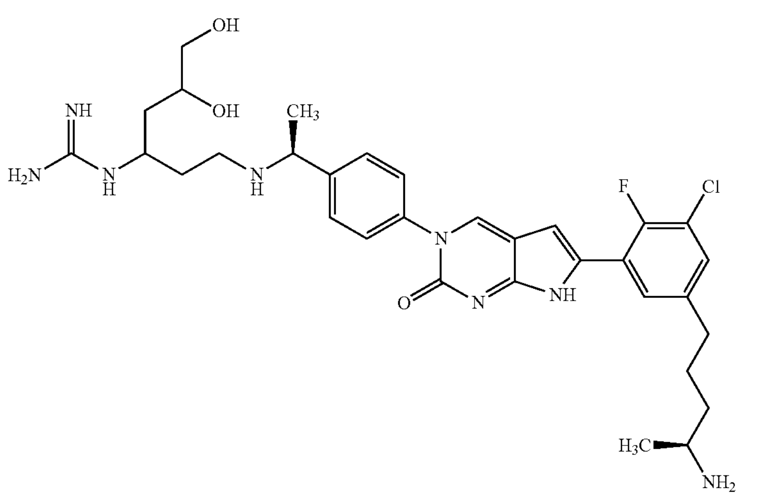 [SMILES: C[C@H](N)CCCc1cc(Cl)c(F)c(-c2cc3cn(-c4ccc([C@H](C)NCCC(CC(O)CO)NC(=N)N)cc4)c(=O)nc3[nH]2)c1] | 641.2 |

TABLE 1-continued

| Compound No | Structure | ESI, m/z [M + H]+ |
|---|---|---|
| 271 | 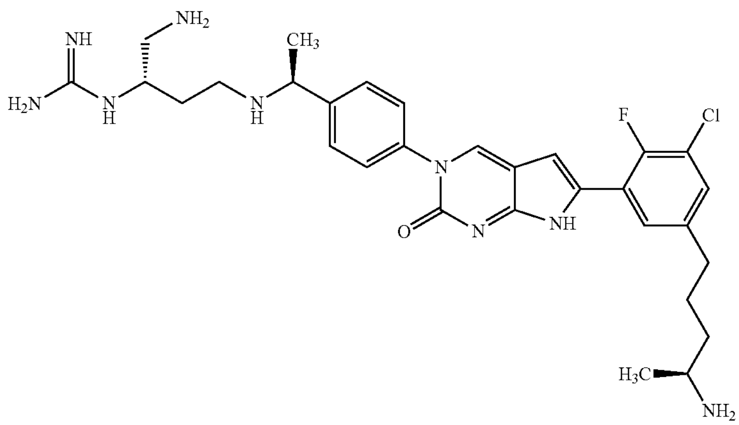 [SMILES: C[C@H](N)CCCc1cc(Cl)c(F)c(-c2cc3cn(-c4ccc([C@H](C)NCC[C@@H](CN)NC(=N)N)cc4)c(=O)nc3[nH]2)c1] | |
| 272 | 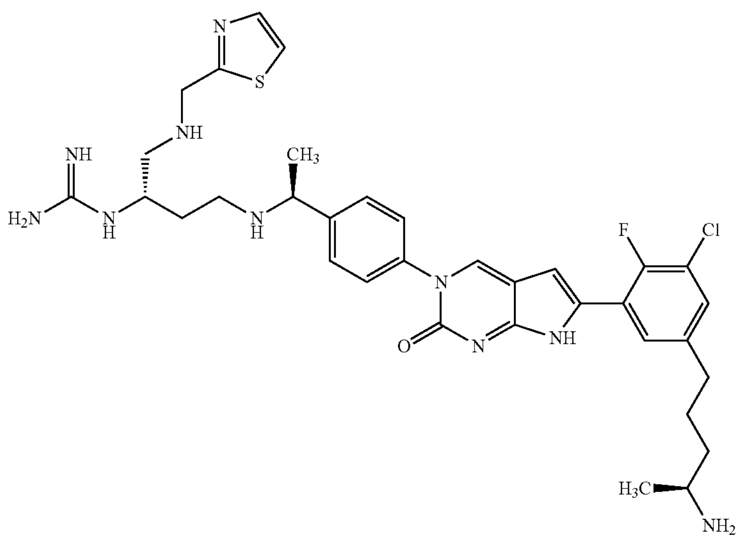 [SMILES: C[C@H](N)CCCc1cc(Cl)c(F)c(-c2cc3cn(-c4ccc([C@H](C)NCC[C@@H](CNCc5nccs5)NC(=N)N)cc4)c(=O)nc3[nH]2)c1] | |
| 273 | 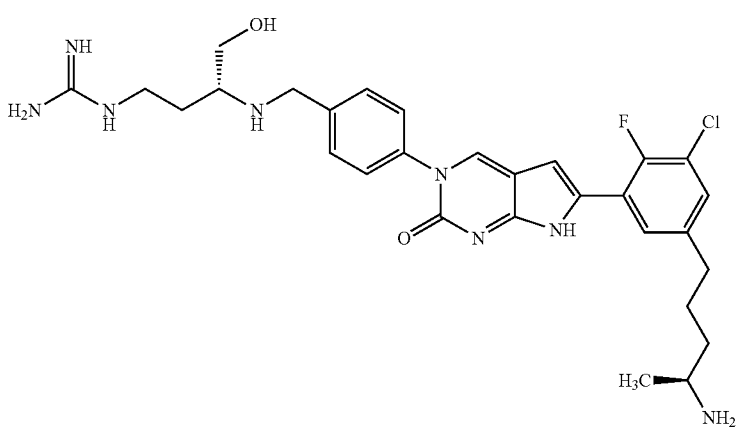 [SMILES: C[C@H](N)CCCc1cc(Cl)c(F)c(-c2cc3cn(-c4ccc(CN[C@@H](CO)CCNC(=N)N)cc4)c(=O)nc3[nH]2)c1] | 584 |

TABLE 1-continued
| Compound No | Structure | ESI, m/z [M + H]+ |
|---|---|---|
| 274 | 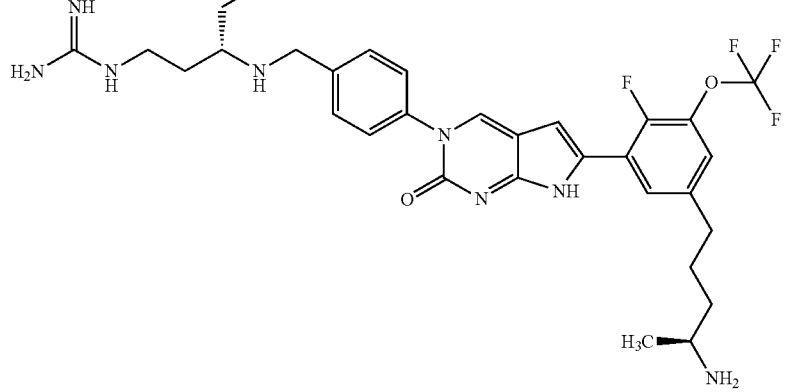 | 634 |
| 275 | 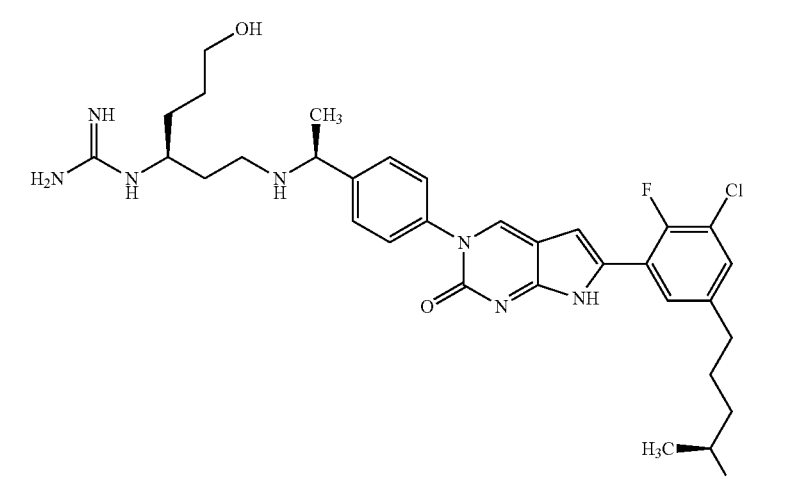 | |
| 276 | 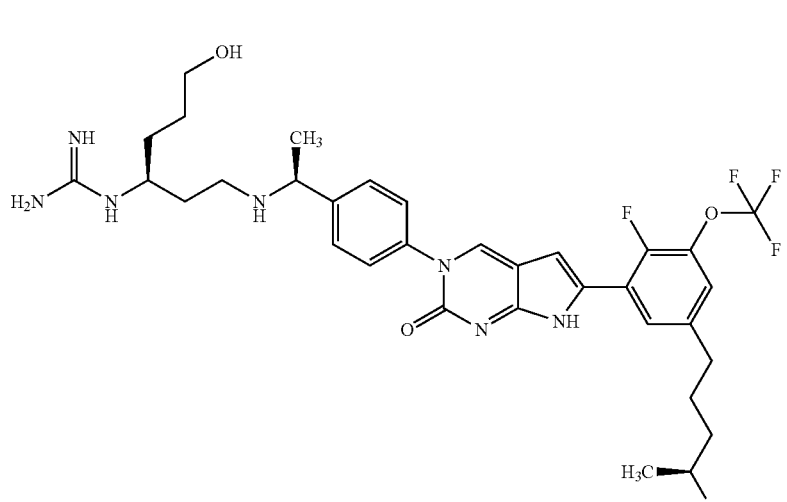 | |

TABLE 1-continued

| Compound No | Structure | ESI, m/z [M + H]+ |
|---|---|---|
| 277 | 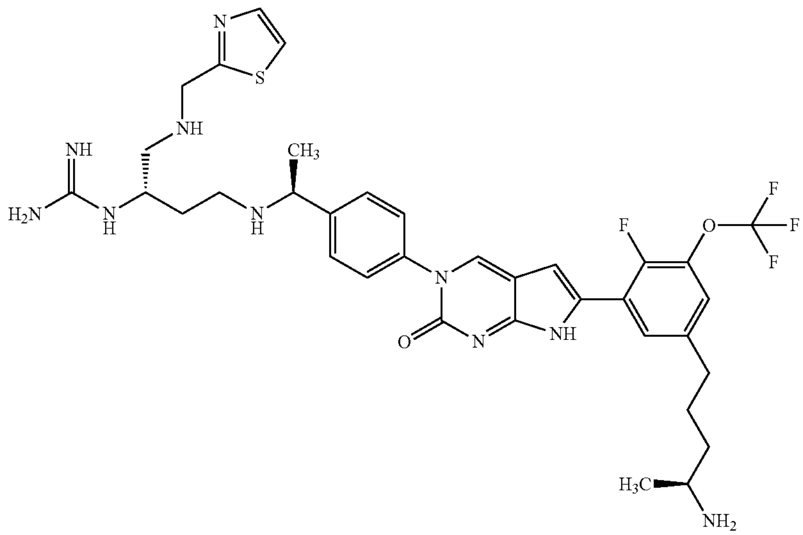 [SMILES: C[C@H](N)CCCc1cc(OC(F)(F)F)c(F)c(-c2cc3cn(-c4ccc([C@H](C)NCC[C@@H](CNCc5nccs5)NC(=N)N)cc4)c(=O)nc3[nH]2)c1] | |
| 278 | 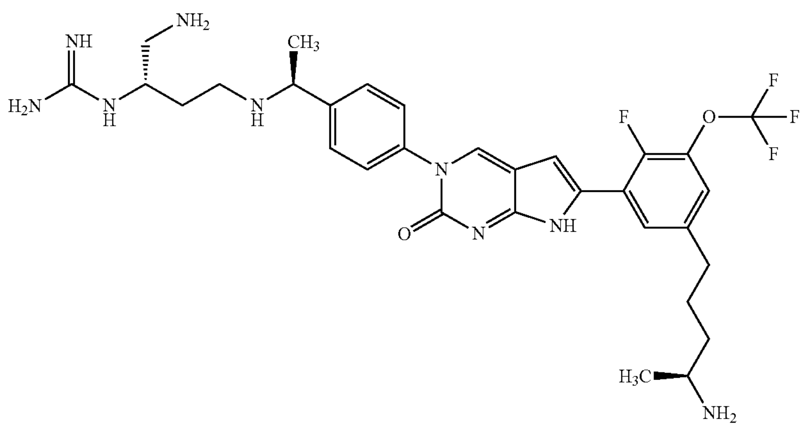 [SMILES: C[C@H](N)CCCc1cc(OC(F)(F)F)c(F)c(-c2cc3cn(-c4ccc([C@H](C)NCC[C@@H](CN)NC(=N)N)cc4)c(=O)nc3[nH]2)c1] | |
| 279 | 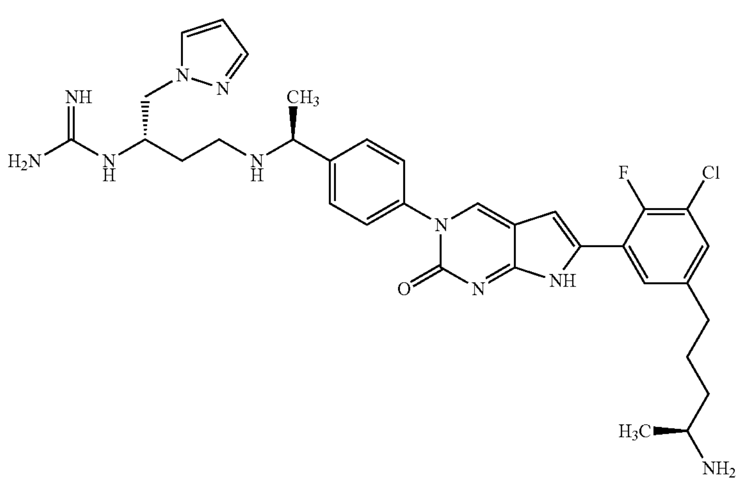 [SMILES: C[C@H](N)CCCc1cc(Cl)c(F)c(-c2cc3cn(-c4ccc([C@H](C)NCC[C@@H](Cn5cccn5)NC(=N)N)cc4)c(=O)nc3[nH]2)c1] | |

TABLE 1-continued

| Compound No | Structure | ESI, m/z [M + H]+ |
|---|---|---|
| 280 | 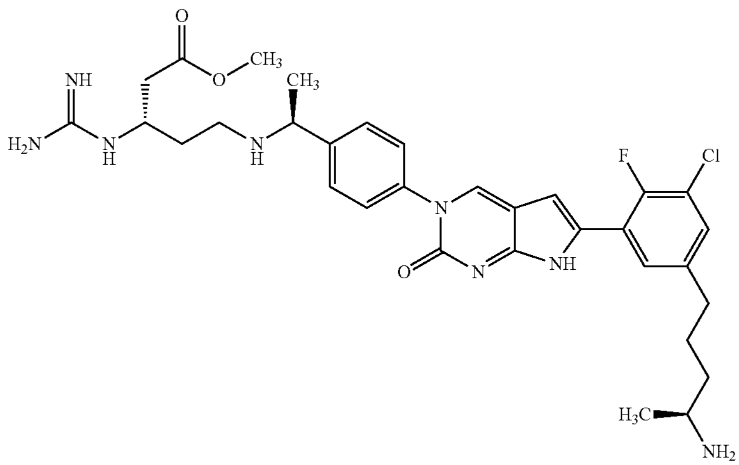 [SMILES: COC(=O)C[C@H](CCN[C@@H](C)c1ccc(-n2cc3cc(-c4cc(CCC[C@H](C)N)cc(Cl)c4F)[nH]c3nc2=O)cc1)NC(=N)N] | |
| 281 | 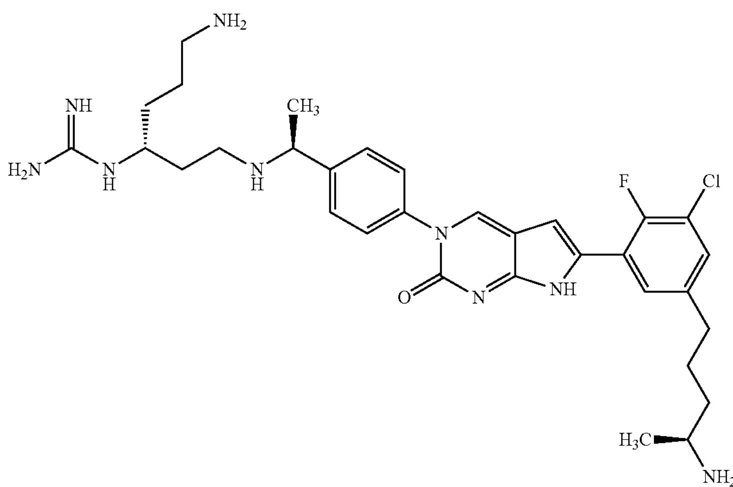 [SMILES: C[C@H](N)CCCc1cc(Cl)c(F)c(-c2cc3cn(-c4ccc([C@H](C)NCC[C@@H](CCCN)NC(=N)N)cc4)c(=O)nc3[nH]2)c1] | 624.5 |
| 282 | 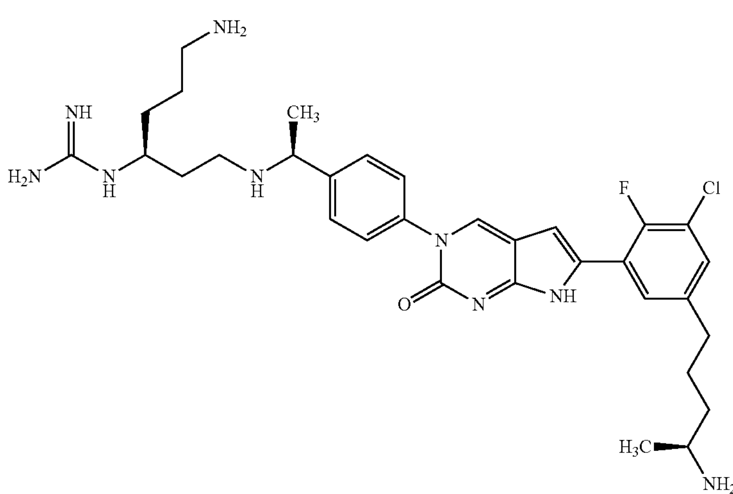 [SMILES: C[C@H](N)CCCc1cc(Cl)c(F)c(-c2cc3cn(-c4ccc([C@H](C)NCC[C@H](CCCN)NC(=N)N)cc4)c(=O)nc3[nH]2)c1] | 624.5 |

TABLE 1-continued
| Compound No | Structure | ESI, m/z [M + H]+ |
|---|---|---|
| 283 | 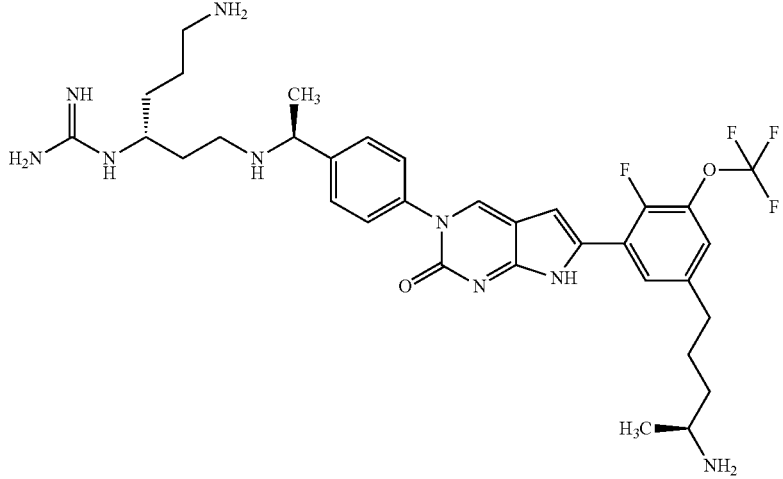 [SMILES: C[C@H](N)CCCc1cc(OC(F)(F)F)c(F)c(-c2cc3cn(-c4ccc([C@H](C)NCC[C@@H](CCCN)NC(=N)N)cc4)c(=O)nc3[nH]2)c1] | 674.6 |
| 284 | 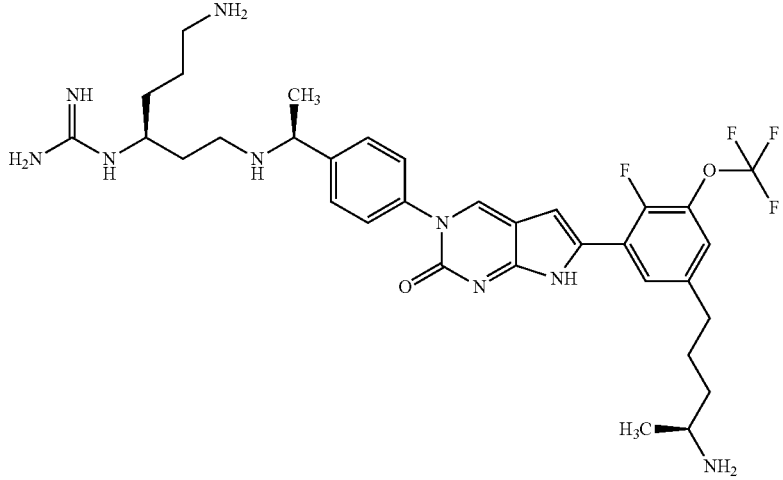 | 674.6 |
| 285 | 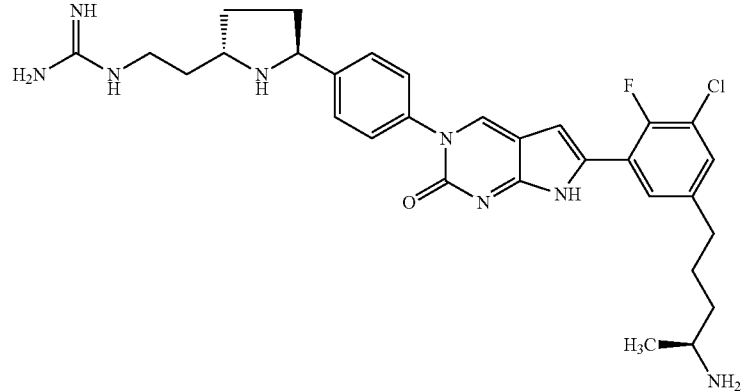 [SMILES: C[C@H](N)CCCc1cc(Cl)c(F)c(-c2cc3cn(-c4ccc([C@@H]5CC[C@@H](CCNC(=N)N)N5)cc4)c(=O)nc3[nH]2)c1] | 579.3 |

TABLE 1-continued

| Compound No | Structure | ESI, m/z [M + H]+ |
|---|---|---|
| 286 | 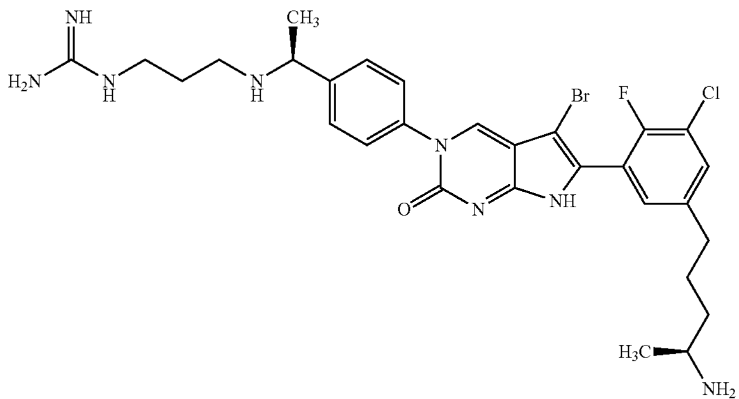 [SMILES: C[C@H](N)CCCc1cc(Cl)c(F)c(-c2[nH]c3nc(=O)n(-c4ccc([C@H](C)NCCCNC(=N)N)cc4)cc3c2Br)c1] | 647.2 |
| 287 | 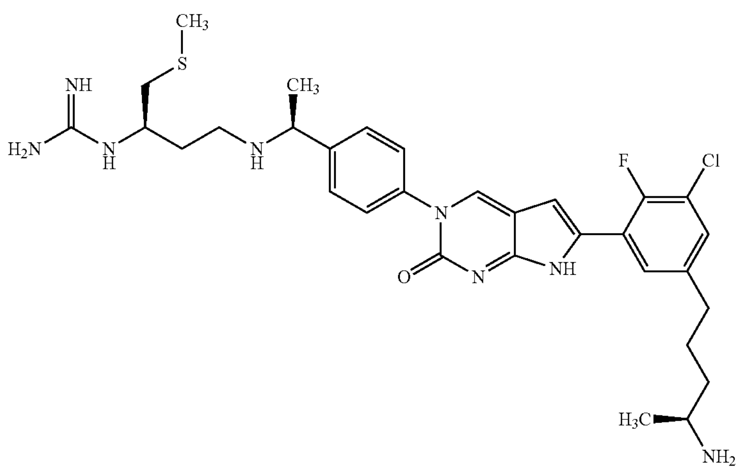 | 627.9 |
| 288 | 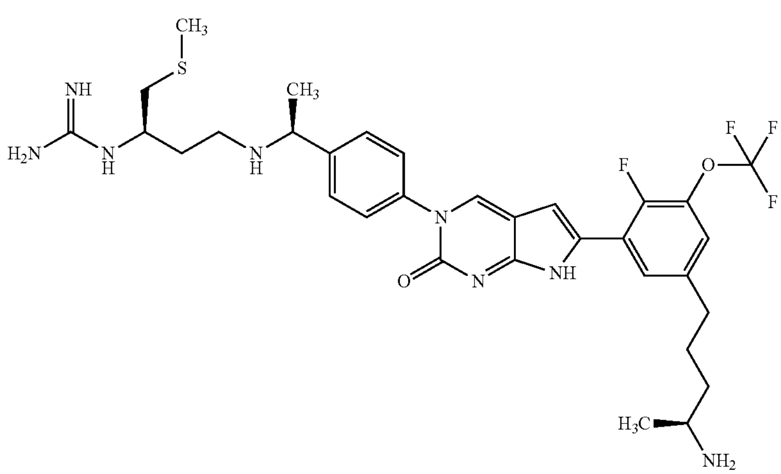 | 677.5 |

TABLE 1-continued
| Compound No | Structure | ESI, m/z [M + H]+ |
|---|---|---|
| 289 | 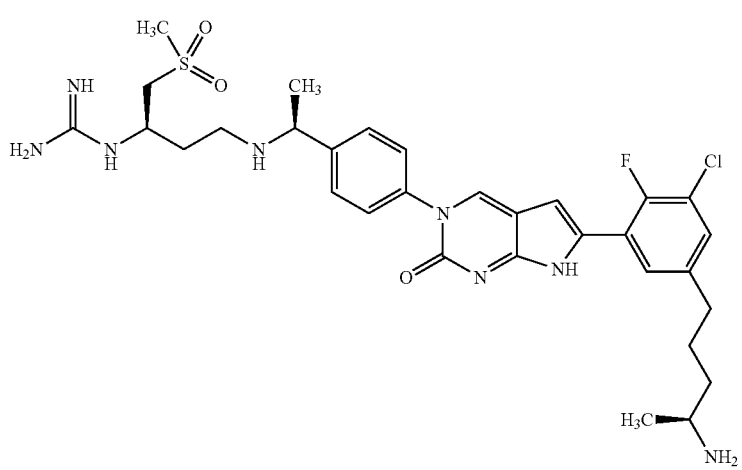 [SMILES: C[C@H](N)CCCc1cc(Cl)c(F)c(-c2cc3cn(-c4ccc([C@H](C)NCC[C@H](CS(C)(=O)=O)NC(=N)N)cc4)c(=O)nc3[nH]2)c1] | 659.7 |
| 290 | 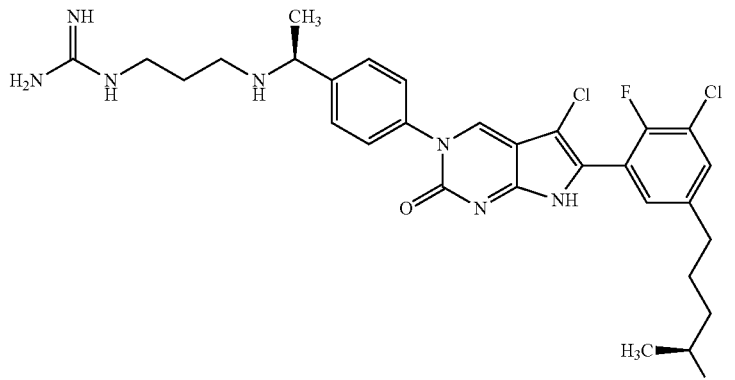 | 601.6 |
| 291 | 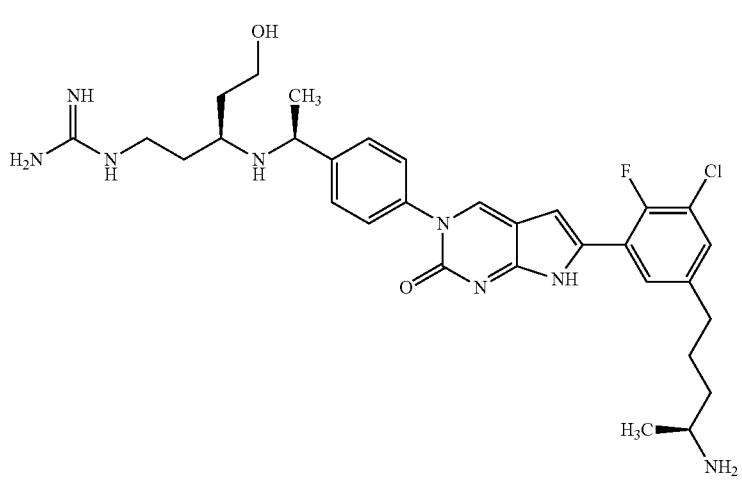 | 611.7 |

TABLE 1-continued
| Compound No | Structure | ESI, m/z [M + H]+ |
|---|---|---|
| 292 | 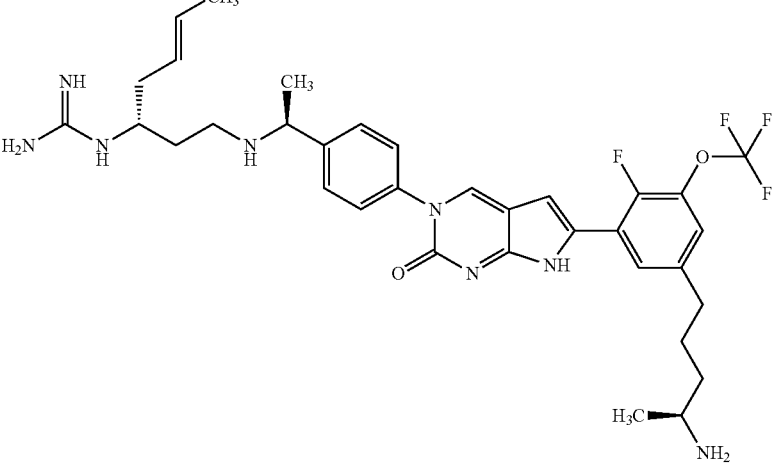 | 671.8 |
| 293 | 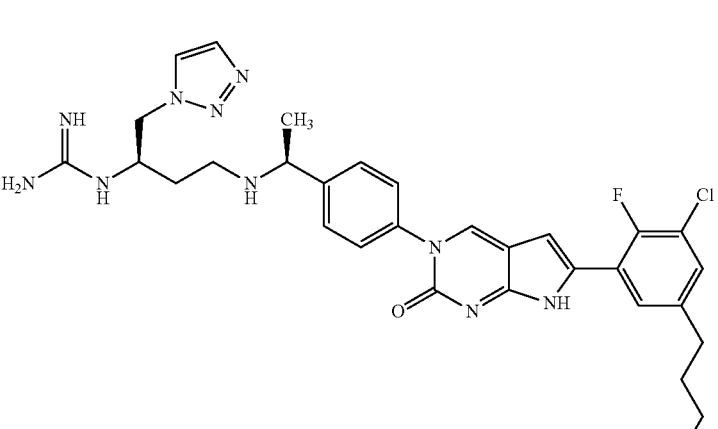 | 648.8 |
| 294 | 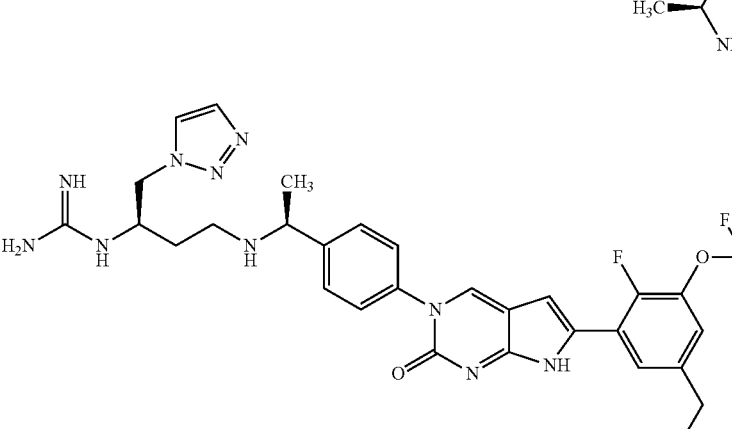 | 698.8 |

TABLE 1-continued

| Compound No | Structure | ESI, m/z [M + H]+ |
| --- | --- | --- |
| 295 | 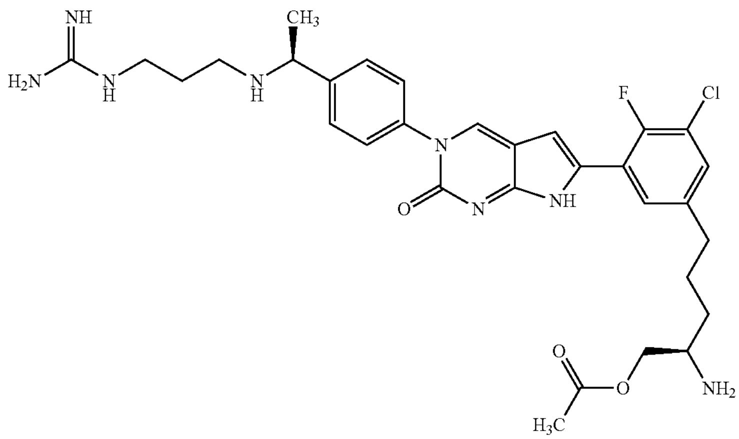 [SMILES: CC(=O)OC[C@H](N)CCCc1cc(Cl)c(F)c(-c2cc3cn(-c4ccc([C@H](C)NCCCNC(=N)N)cc4)c(=O)nc3[nH]2)c1] | 625.7 |
| 296 | 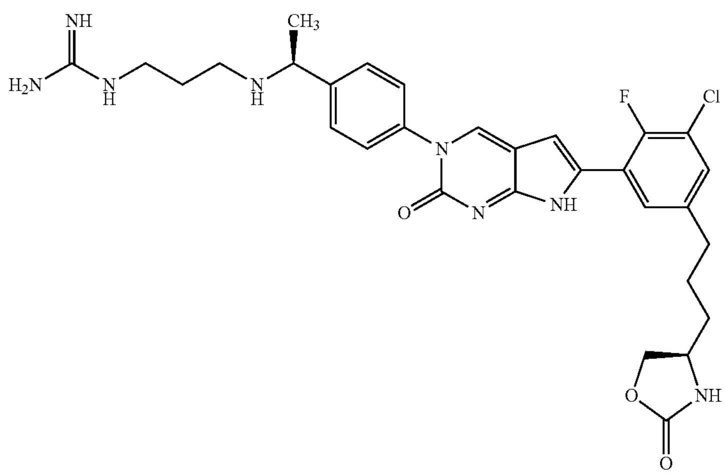 [SMILES: C[C@H](NCCCNC(=N)N)c1ccc(-n2cc3cc(-c4cc(CCC[C@@H]5COC(=O)N5)cc(Cl)c4F)[nH]c3nc2=O)cc1] | 609.7 |
| 297 | 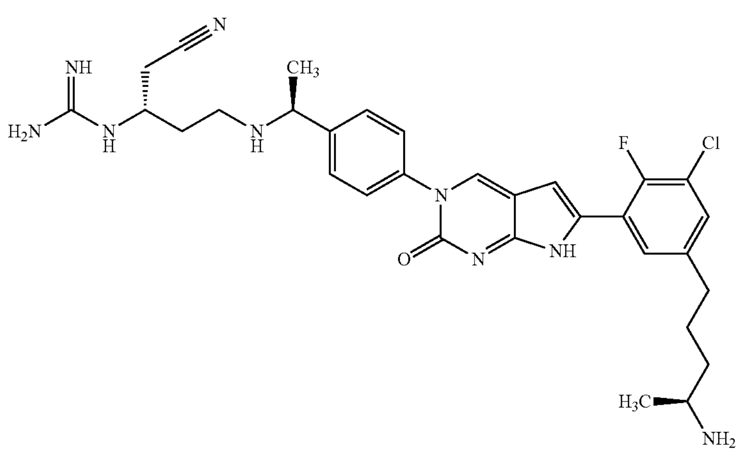 [SMILES: C[C@H](N)CCCc1cc(Cl)c(F)c(-c2cc3cn(-c4ccc([C@H](C)NCC[C@@H](CC#N)NC(=N)N)cc4)c(=O)nc3[nH]2)c1] | 606.7 |

TABLE 1-continued

| Compound No | Structure | ESI, m/z [M + H]+ |
|---|---|---|
| 298 | 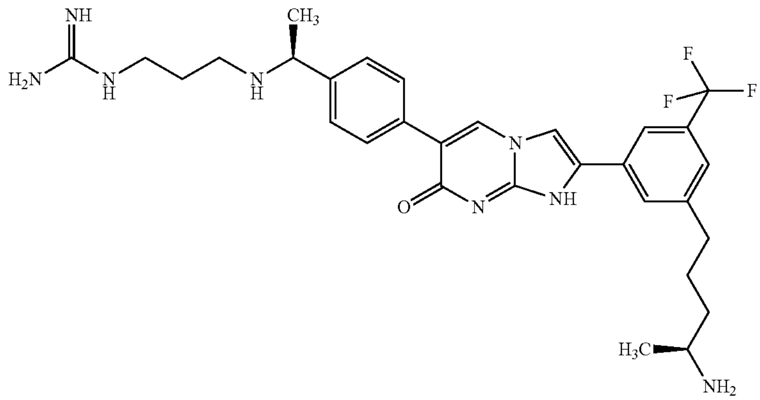 [SMILES: C[C@H](N)CCCc1cc(-c2cn3cc(-c4ccc([C@H](C)NCCCNC(=N)N)cc4)c(=O)nc3[nH]2)cc(C(F)(F)F)c1] | 583.8 |
| 299 | 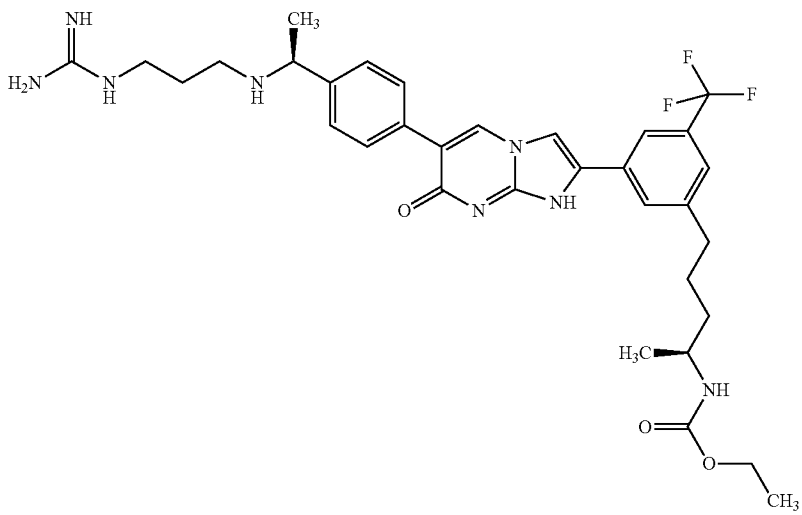 [SMILES: CCOC(=O)N[C@@H](C)CCCc1cc(-c2cn3cc(-c4ccc([C@H](C)NCCCNC(=N)N)cc4)c(=O)nc3[nH]2)cc(C(F)(F)F)c1] | 655.8 |
| 300 | 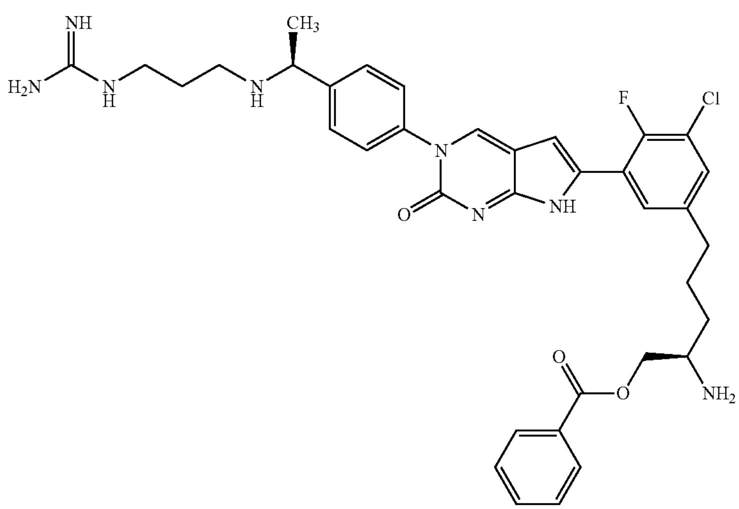 [SMILES: C[C@H](NCCCNC(=N)N)c1ccc(-n2cc3cc(-c4cc(CCC[C@@H](N)COC(=O)c5ccccc5)cc(Cl)c4F)[nH]c3nc2=O)cc1] | 687.8 |

TABLE 1-continued

| Compound No | Structure | ESI, m/z [M + H]+ |
| --- | --- | --- |
| 301 | 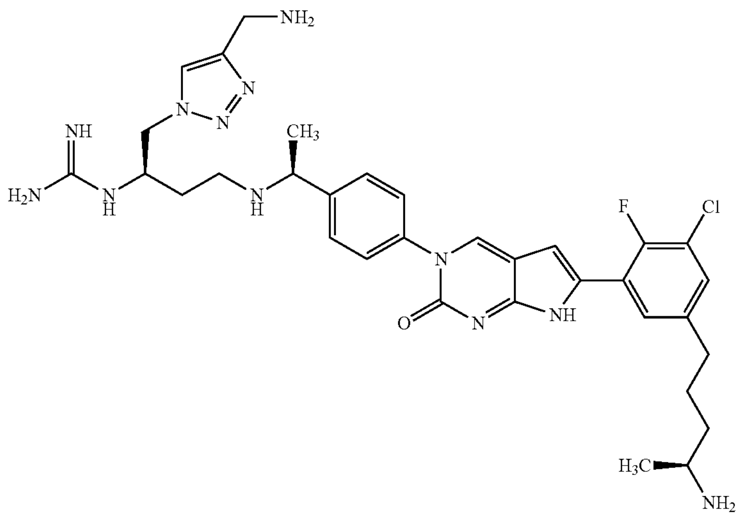 [SMILES: C[C@H](N)CCCc1cc(Cl)c(F)c(-c2cc3cn(-c4ccc([C@H](C)NCC[C@H](Cn5cc(CN)nn5)NC(=N)N)cc4)c(=O)nc3[nH]2)c1] | 677.8 |
| 302 | 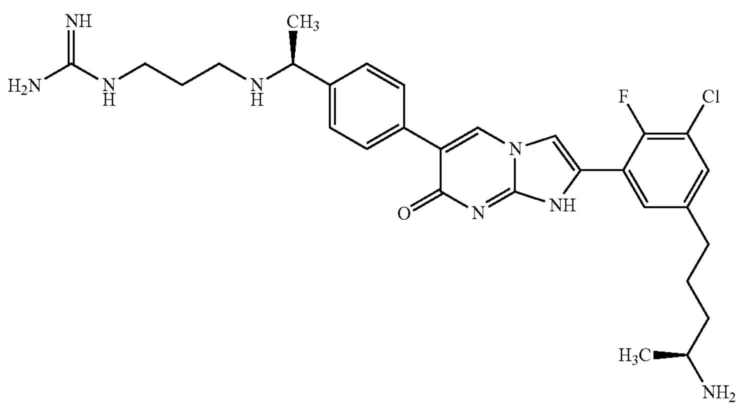 [SMILES: C[C@H](N)CCCc1cc(Cl)c(F)c(-c2cn3cc(-c4ccc([C@H](C)NCCCNC(=N)N)cc4)c(=O)nc3[nH]2)c1] | 567.7 |
| 303 | 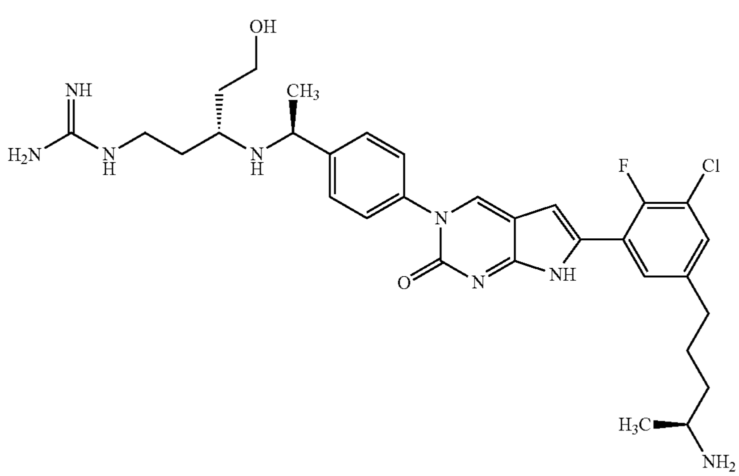 [SMILES: C[C@H](N)CCCc1cc(Cl)c(F)c(-c2cc3cn(-c4ccc([C@H](C)N[C@@H](CCO)CCNC(=N)N)cc4)c(=O)nc3[nH]2)c1] | 611.8 |

TABLE 1-continued

| Compound No | Structure | ESI, m/z [M + H]+ |
|---|---|---|
| 304 | 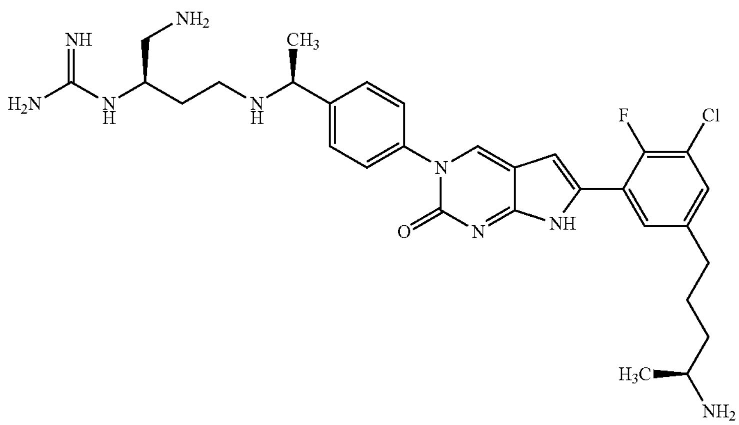 | 596.8 |
| 305 | 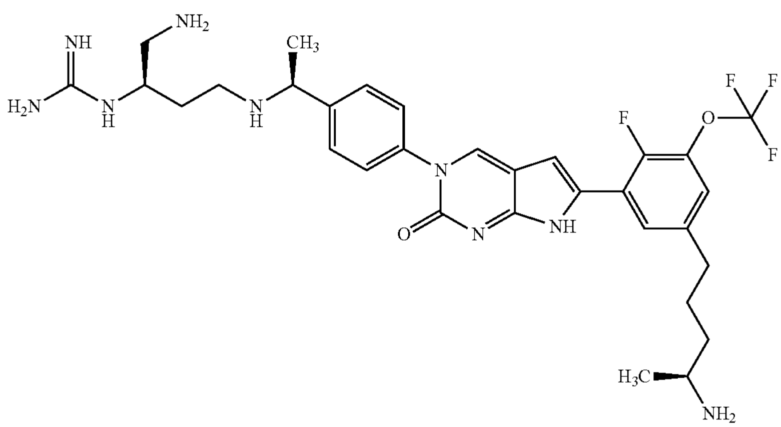 | 646.8 |
| 306 | 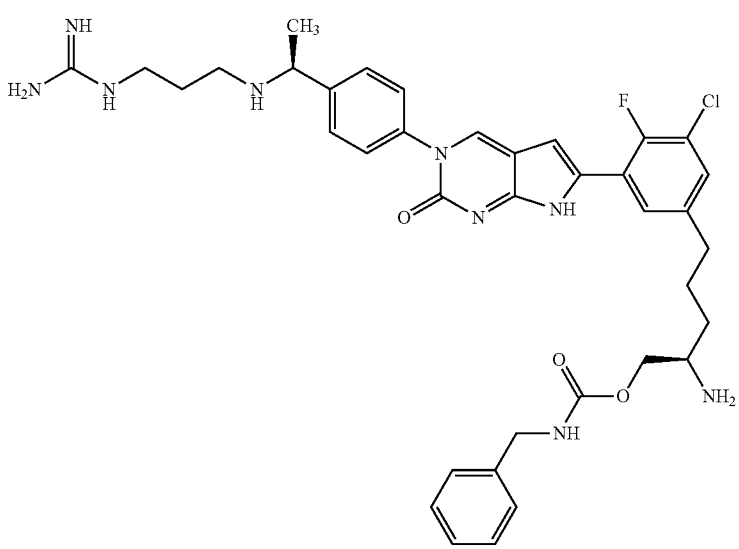 [SMILES: C[C@H](NCCCNC(=N)N)c1ccc(-n2cc3cc(-c4cc(CCC[C@@H](N)COC(=O)NCc5ccccc5)cc(Cl)c4F)[nH]c3nc2=O)cc1] | 716.8 |

TABLE 1-continued
| Compound No | Structure | ESI, m/z [M + H]+ |
|---|---|---|
| 307 | 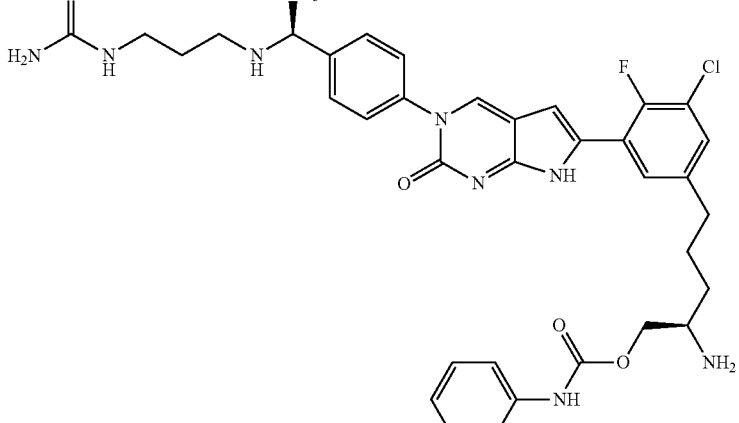 | 702.8 |
| 308 | 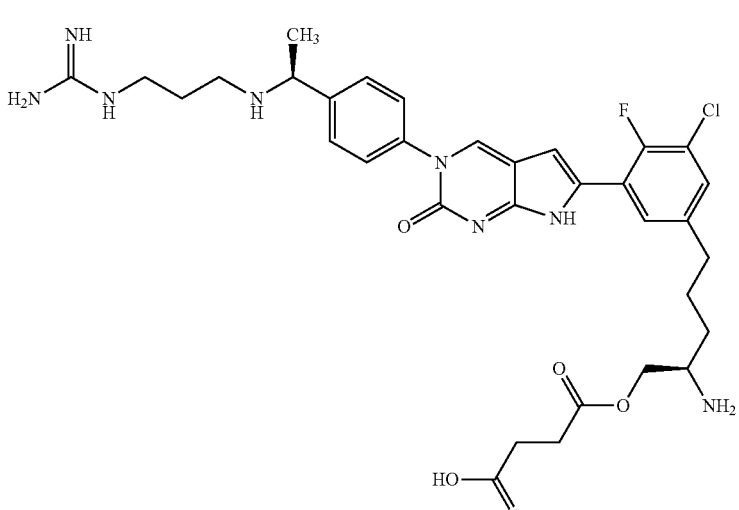 | 683.8 |
| 309 | 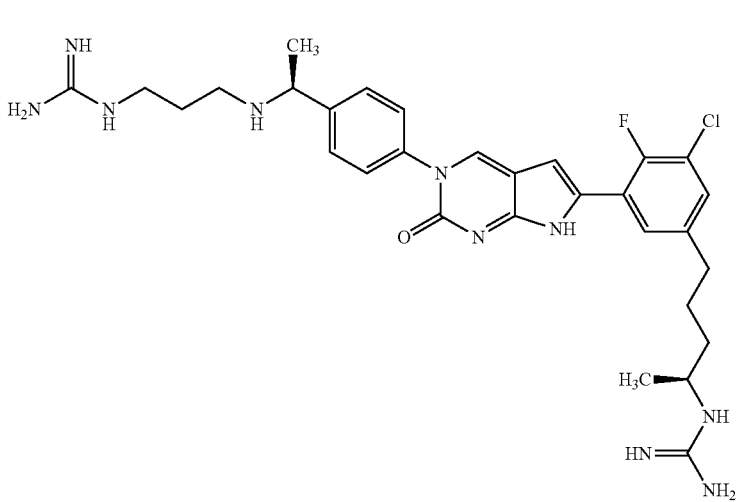 [SMILES: C[C@H](NCCCNC(=N)N)c1ccc(-n2cc3cc(-c4cc(CCC[C@H](C)NC(=N)N)cc(Cl)c4F)[nH]c3nc2=O)cc1] | 609.8 |

TABLE 1-continued
| Compound No | Structure | ESI, m/z [M + H]+ |
|---|---|---|
| 310 | 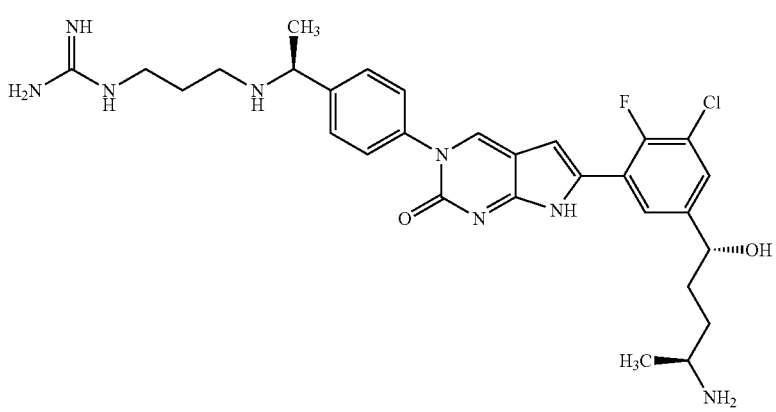 [SMILES: C[C@H](N)CC[C@@H](O)c1cc(Cl)c(F)c(-c2cc3cn(-c4ccc([C@H](C)NCCCNC(=N)N)cc4)c(=O)nc3[nH]2)c1] | 583.8 |
| 311 | 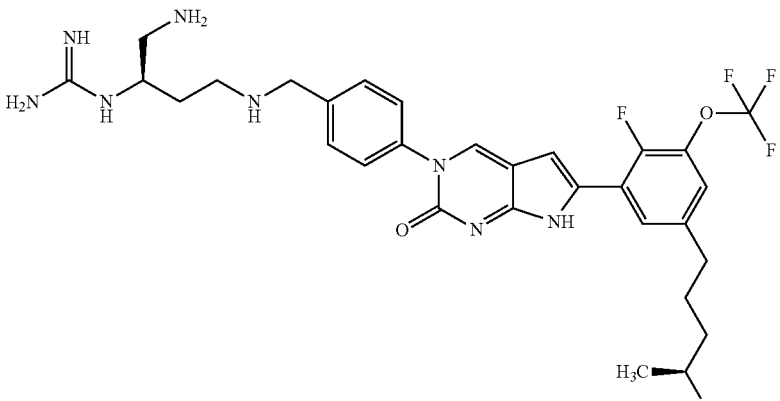 | 632.8 |
| 312 | 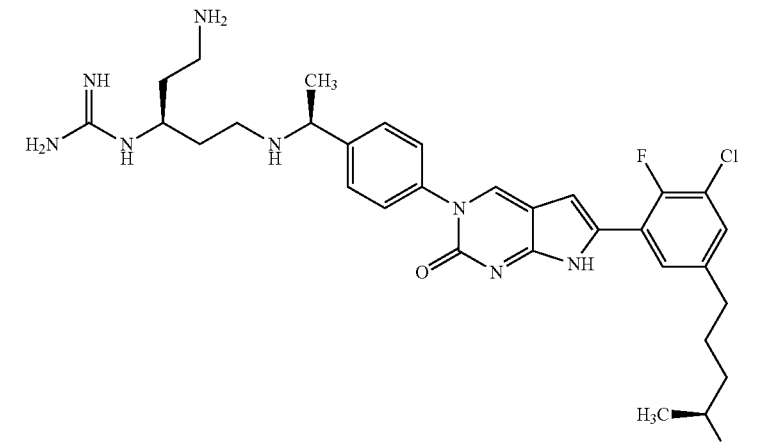 | 610.8 |

TABLE 1-continued

| Compound No | Structure | ESI, m/z [M + H]+ |
|---|---|---|
| 313 | 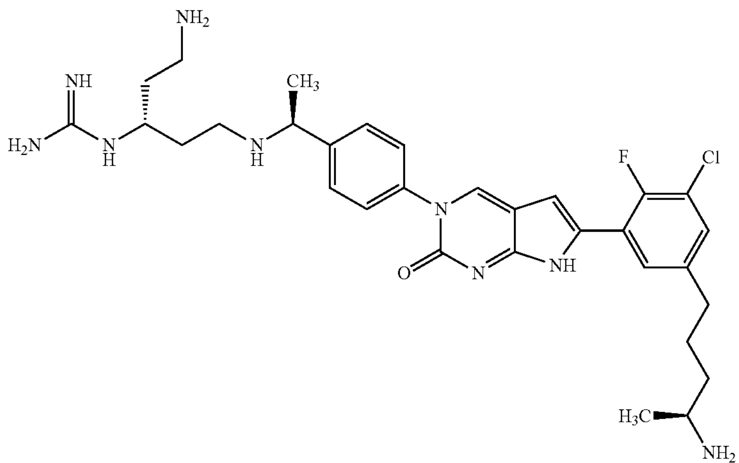 [SMILES: C[C@H](N)CCCc1cc(Cl)c(F)c(-c2cc3cn(-c4ccc([C@H](C)NCC[C@@H](CCN)NC(=N)N)cc4)c(=O)nc3[nH]2)c1] | 610.8 |
| 314 | 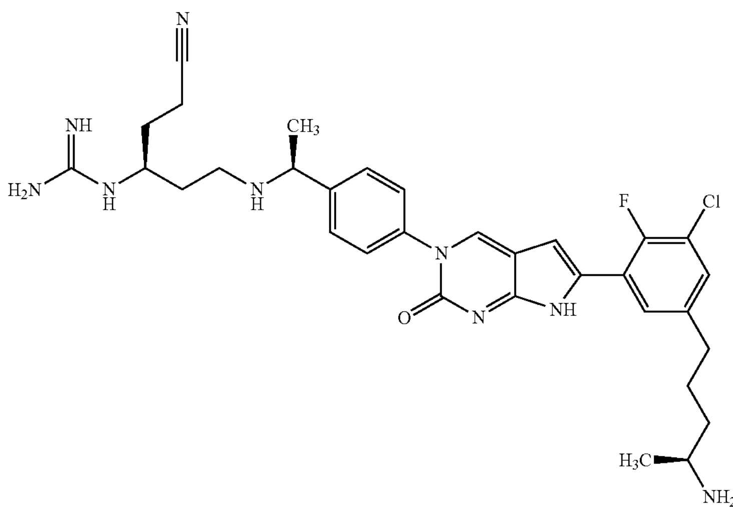 [SMILES: C[C@H](N)CCCc1cc(Cl)c(F)c(-c2cc3cn(-c4ccc([C@H](C)NCC[C@H](CCC#N)NC(=N)N)cc4)c(=O)nc3[nH]2)c1] | 621 |
| 315 | 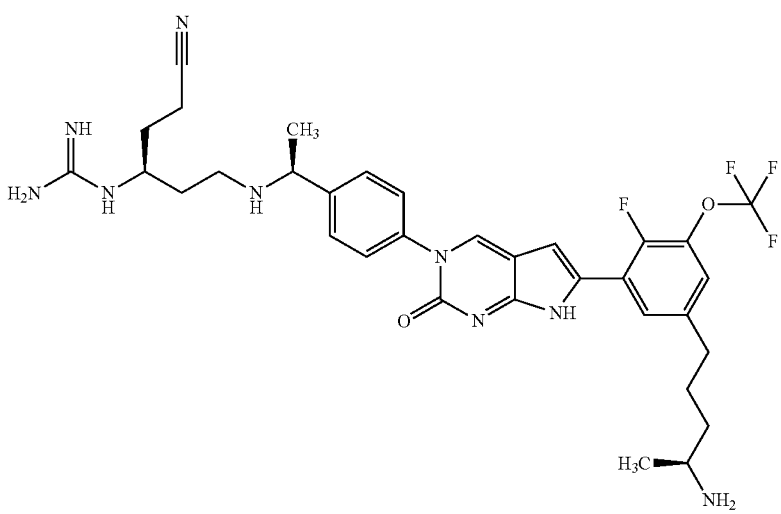 [SMILES: C[C@H](N)CCCc1cc(OC(F)(F)F)c(F)c(-c2cc3cn(-c4ccc([C@H](C)NCC[C@H](CCC#N)NC(=N)N)cc4)c(=O)nc3[nH]2)c1] | 670.8 |

TABLE 1-continued

| Compound No | Structure | ESI, m/z [M + H]+ |
|---|---|---|
| 316 | 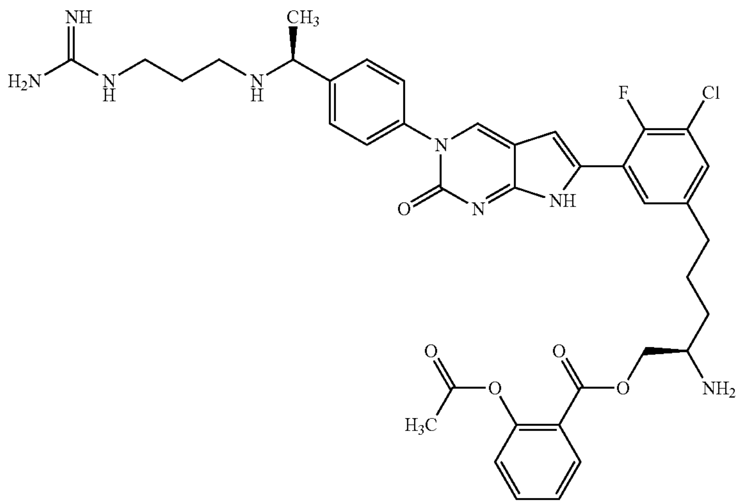 [SMILES: CC(=O)Oc1ccccc1C(=O)OC[C@H](N)CCCc1cc(Cl)c(F)c(-c2cc3cn(-c4ccc([C@H](C)NCCCNC(=N)N)cc4)c(=O)nc3[nH]2)c1] | 745.8 |
| 317 | 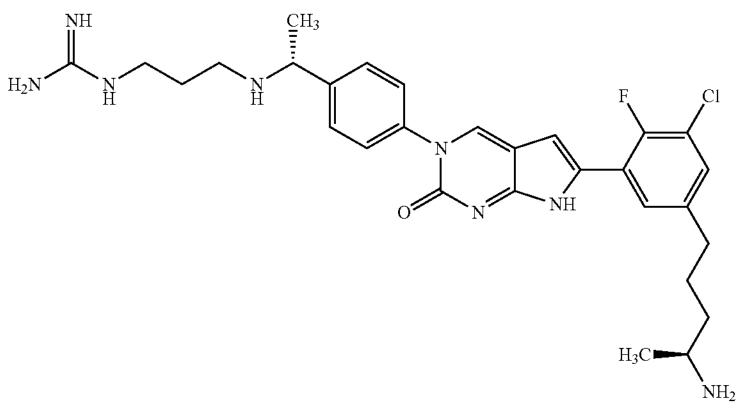 [SMILES: C[C@H](N)CCCc1cc(Cl)c(F)c(-c2cc3cn(-c4ccc([C@@H](C)NCCCNC(=N)N)cc4)c(=O)nc3[nH]2)c1] | 567.7 |
| 318 | 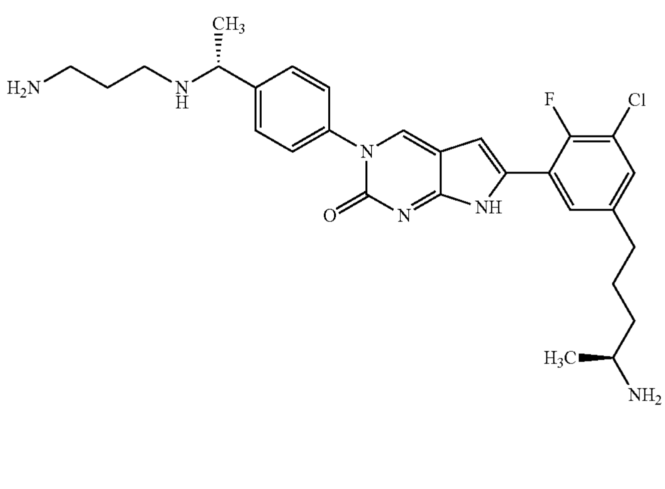 [SMILES: C[C@H](N)CCCc1cc(Cl)c(F)c(-c2cc3cn(-c4ccc([C@@H](C)NCCCN)cc4)c(=O)nc3[nH]2)c1] | 525.8 |

TABLE 1-continued
| Compound No | Structure | ESI, m/z [M + H]+ |
|---|---|---|
| 319 | 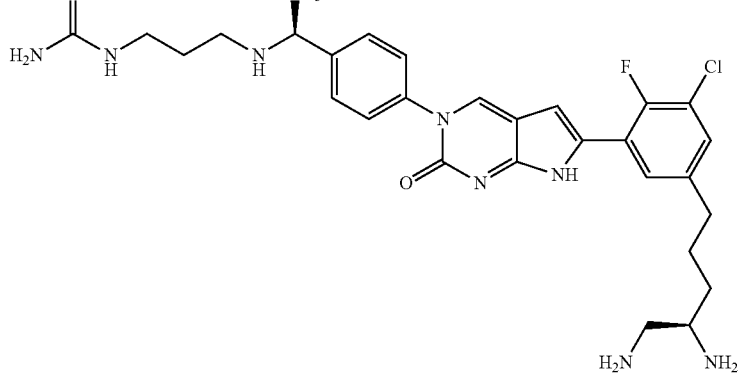 | 582.8 |
| 320 | 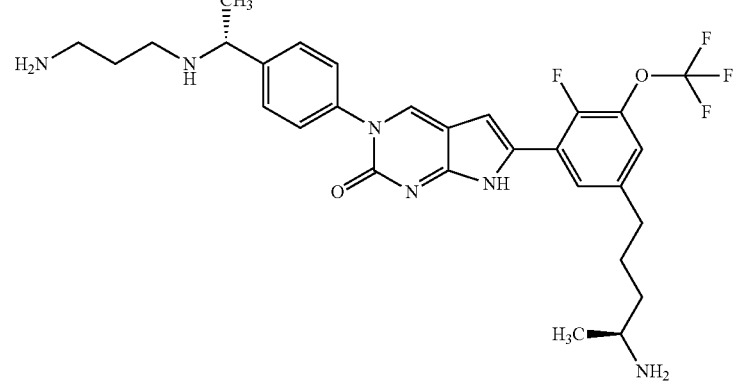 | 575.8 |
| 321 | 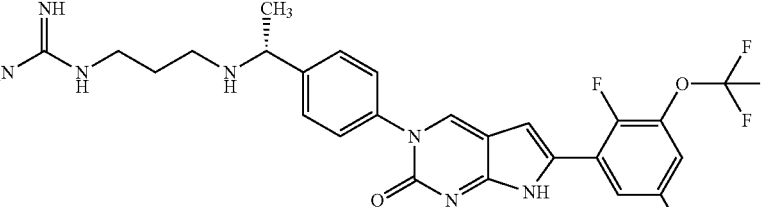 | 617.8 |

TABLE 1-continued

| Compound No | Structure | ESI, m/z [M + H]+ |
|---|---|---|
| 322 | 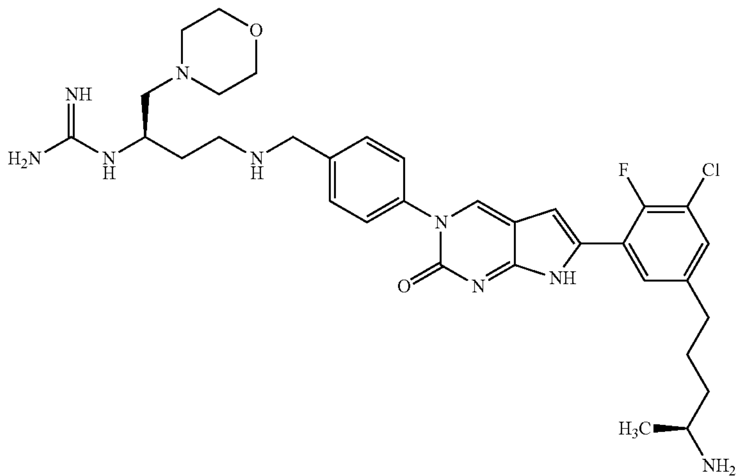 [SMILES: C[C@H](N)CCCc1cc(Cl)c(F)c(-c2cc3cn(-c4ccc(CNCC[C@H](CN5CCOCC5)NC(=N)N)cc4)c(=O)nc3[nH]2)c1] | 652.9 |
| 323 | 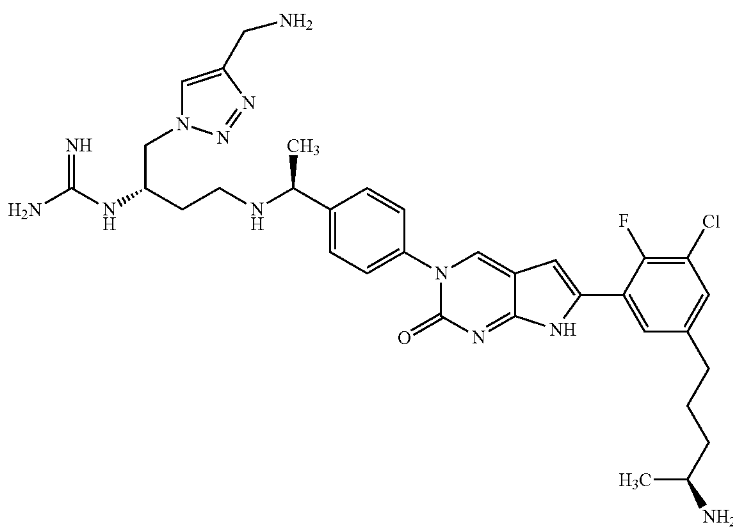 [SMILES: C[C@H](N)CCCc1cc(Cl)c(F)c(-c2cc3cn(-c4ccc([C@H](C)NCC[C@@H](Cn5cc(CN)nn5)NC(=N)N)cc4)c(=O)nc3[nH]2)c1] | 677.8 |
| 324 | 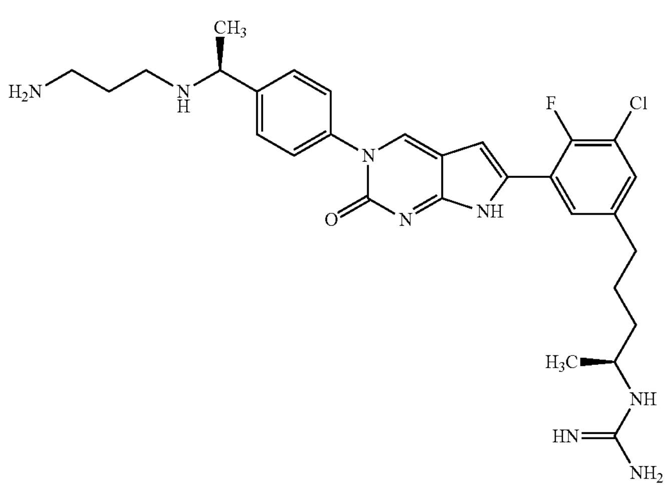 [SMILES: C[C@H](NCCCN)c1ccc(-n2cc3cc(-c4cc(CCC[C@H](C)NC(=N)N)cc(Cl)c4F)[nH]c3nc2=O)cc1] | 567.8 |

TABLE 1-continued
| Compound No | Structure | ESI, m/z [M + H]+ |
|---|---|---|
| 325 | 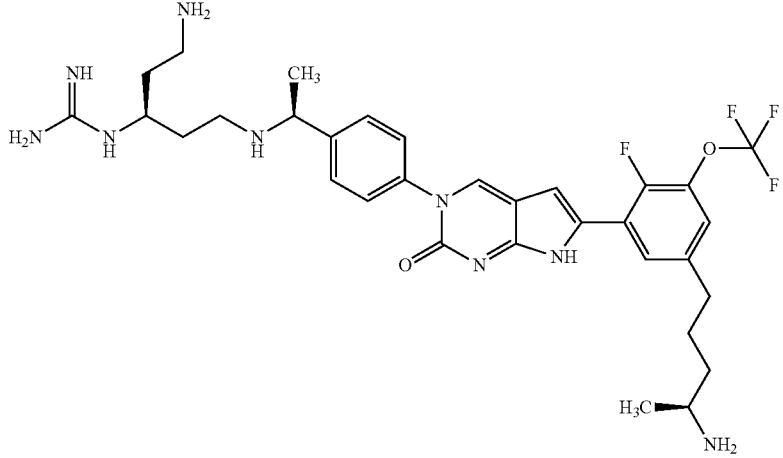 | 660.8 |
| 326 | 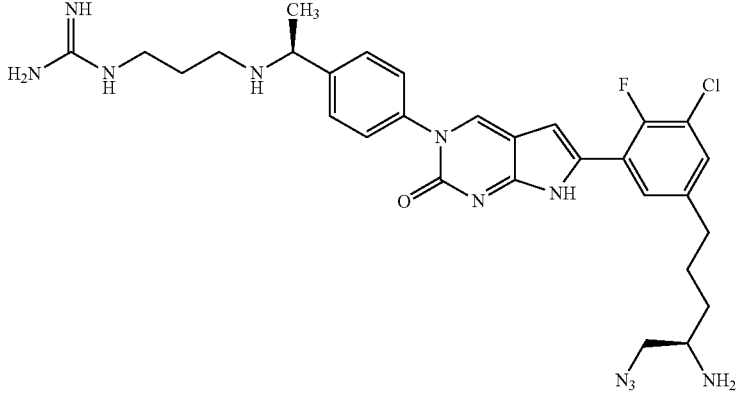 [SMILES: C[C@H](NCCCNC(=N)N)c1ccc(-n2cc3cc(-c4cc(CCC[C@@H](N)CN=[N+]=[N-])cc(Cl)c4F)[nH]c3nc2=O)cc1] | 608.8 |
| 327 | 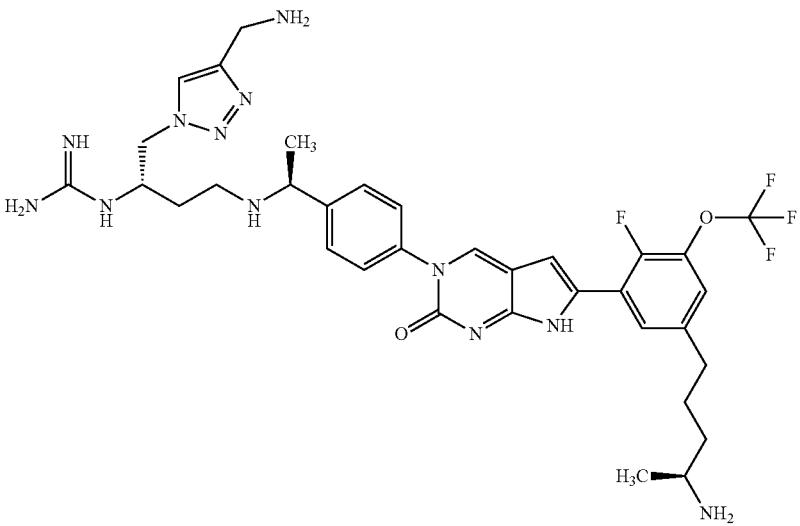 [SMILES: C[C@H](N)CCCc1cc(OC(F)(F)F)c(F)c(-c2cc3cn(-c4ccc([C@H](C)NCC[C@@H](Cn5cc(CN)nn5)NC(=N)N)cc4)c(=O)nc3[nH]2)c1] | 727.36 |

TABLE 1-continued

| Compound No | Structure | ESI, m/z [M + H]+ |
|---|---|---|
| 328 | 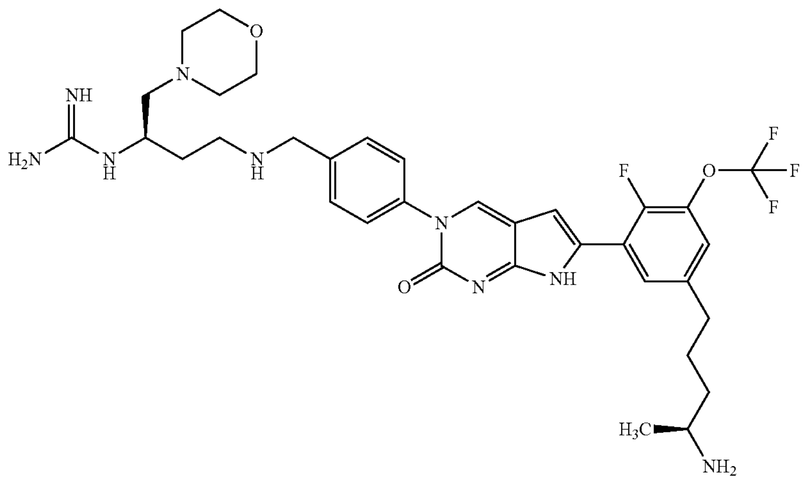 [SMILES: C[C@H](N)CCCc1cc(OC(F)(F)F)c(F)c(-c2cc3cn(-c4ccc(CNCC[C@H](CN5CCOCC5)NC(=N)N)cc4)c(=O)nc3[nH]2)c1] | 702.8 |
| 329 | 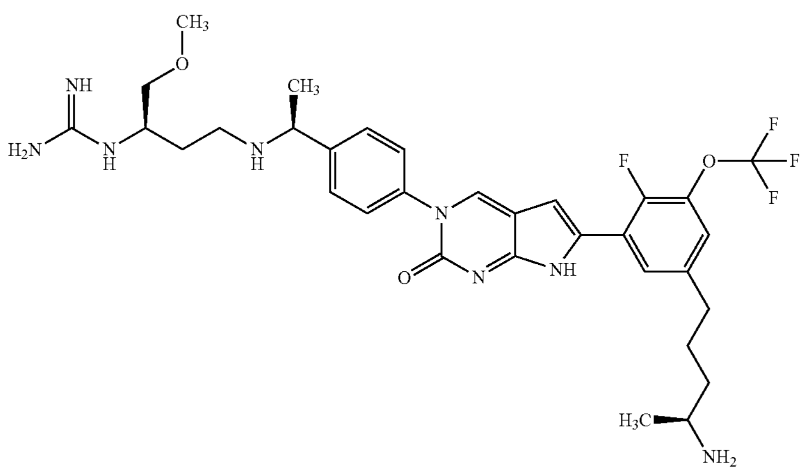 [SMILES: COC[C@@H](CCN[C@@H](C)c1ccc(-n2cc3cc(-c4cc(CCC[C@H](C)N)cc(OC(F)(F)F)c4F)[nH]c3nc2=O)cc1)NC(=N)N] | 661.8 |
| 330 | 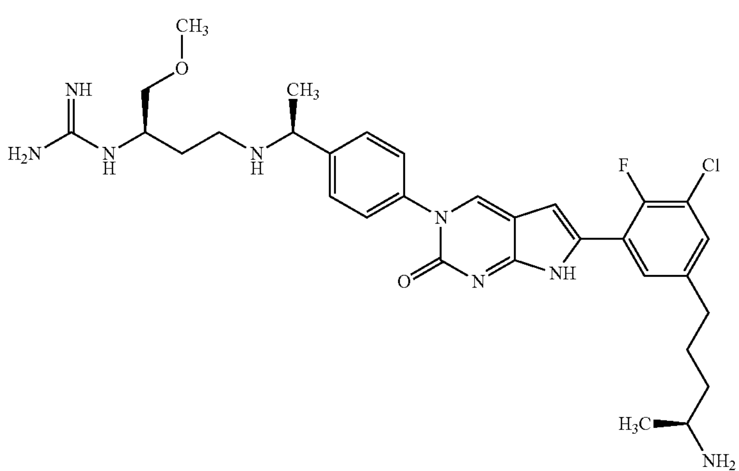 | 611.8 |

TABLE 1-continued
| Compound No | Structure | ESI, m/z [M + H]+ |
|---|---|---|
| 331 | 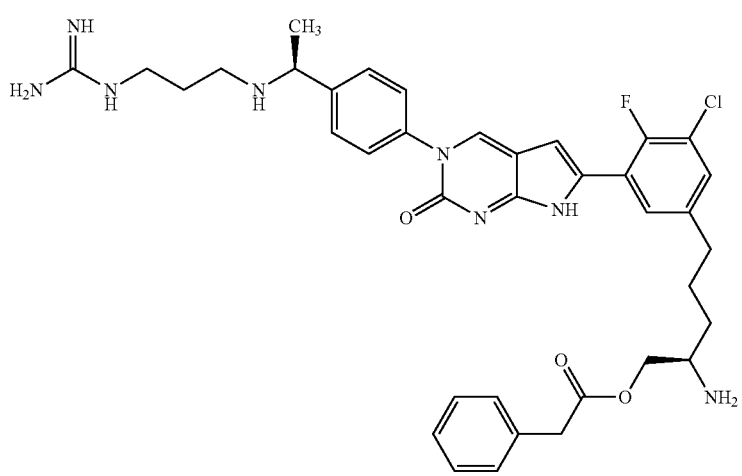 [SMILES: C[C@H](NCCCNC(=N)N)c1ccc(-n2cc3cc(-c4cc(CCC[C@@H](N)COC(=O)Cc5ccccc5)cc(Cl)c4F)[nH]c3nc2=O)cc1] | 701.9 |
| 332 | 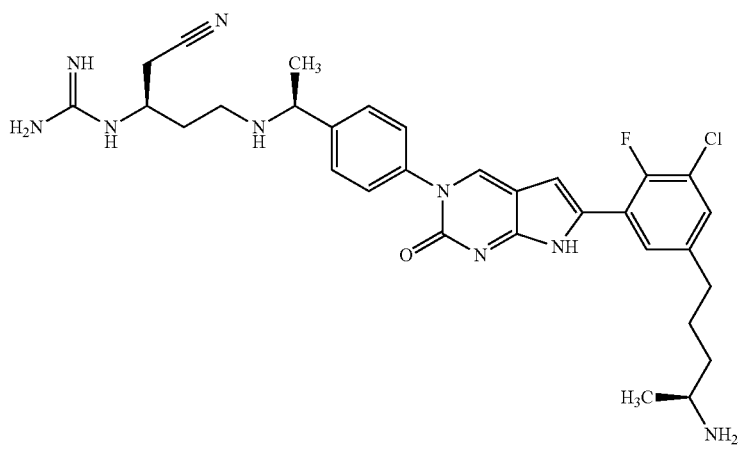 [SMILES: C[C@H](N)CCCc1cc(Cl)c(F)c(-c2cc3cn(-c4ccc([C@H](C)NCC[C@H](CC#N)NC(=N)N)cc4)c(=O)nc3[nH]2)c1] | 606.8 |
| 333 | 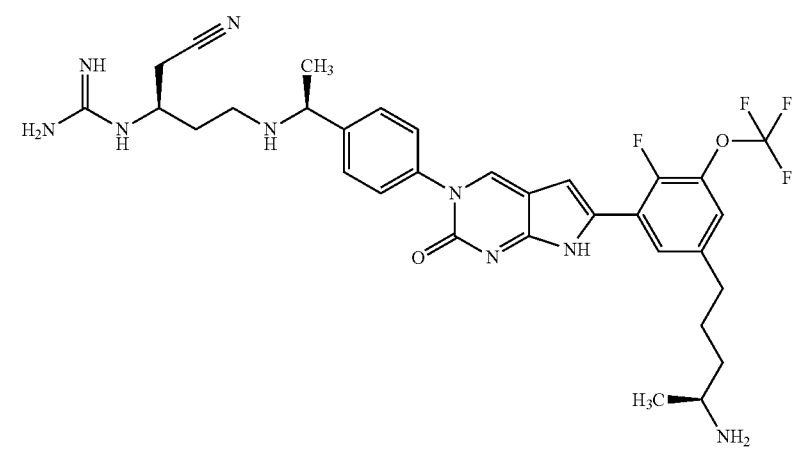 [SMILES: C[C@H](N)CCCc1cc(OC(F)(F)F)c(F)c(-c2cc3cn(-c4ccc([C@H](C)NCC[C@H](CC#N)NC(=N)N)cc4)c(=O)nc3[nH]2)c1] | 656.8 |

TABLE 1-continued

| Compound No | Structure | ESI, m/z [M + H]+ |
|---|---|---|
| 334 | 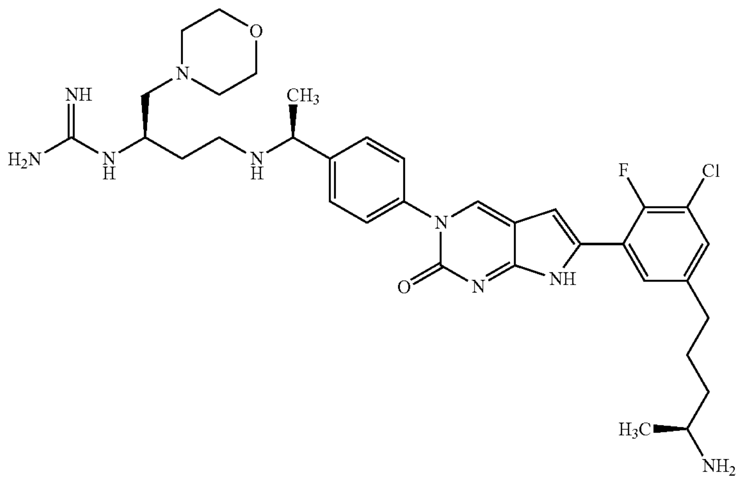 [SMILES: C[C@H](N)CCCc1cc(Cl)c(F)c(-c2cc3cn(-c4ccc([C@H](C)NCC[C@H](CN5CCOCC5)NC(=N)N)cc4)c(=O)nc3[nH]2)c1] | 668.8 |
| 335 | 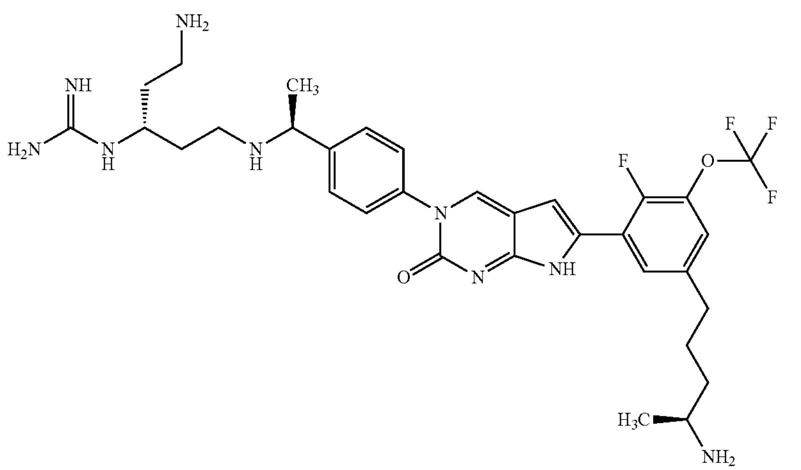 [SMILES: C[C@H](N)CCCc1cc(OC(F)(F)F)c(F)c(-c2cc3cn(-c4ccc([C@H](C)NCC[C@@H](CCN)NC(=N)N)cc4)c(=O)nc3[nH]2)c1] | 660.8 |
| 336 | 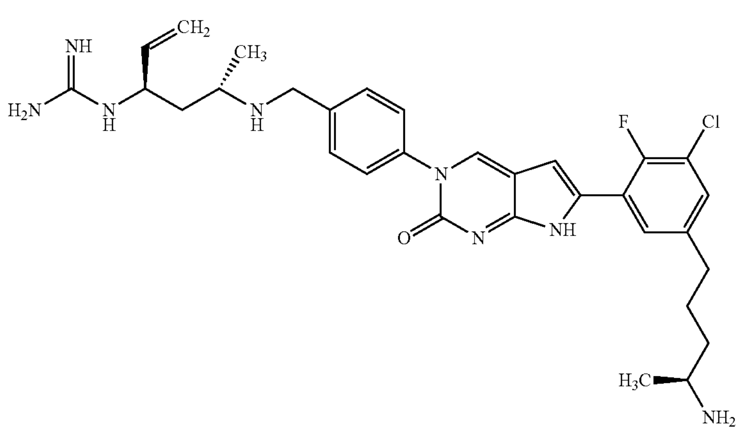 [SMILES: C=C[C@@H](C[C@H](C)NCc1ccc(-n2cc3cc(-c4cc(CCC[C@H](C)N)cc(Cl)c4F)[nH]c3nc2=O)cc1)NC(=N)N] | 593.8 |

//
TABLE 1-continued
| Compound No | Structure | ESI, m/z [M + H]+ |
|---|---|---|
| 337 | 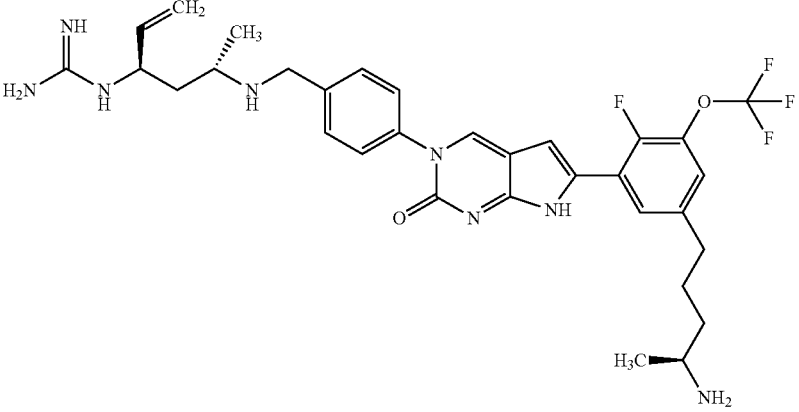 [SMILES: C=C[C@@H](C[C@H](C)NCc1ccc(-n2cc3cc(-c4cc(CCC[C@H](C)N)cc(OC(F)(F)F)c4F)[nH]c3nc2=O)cc1)NC(=N)N] | 643.8 |
| 338 | 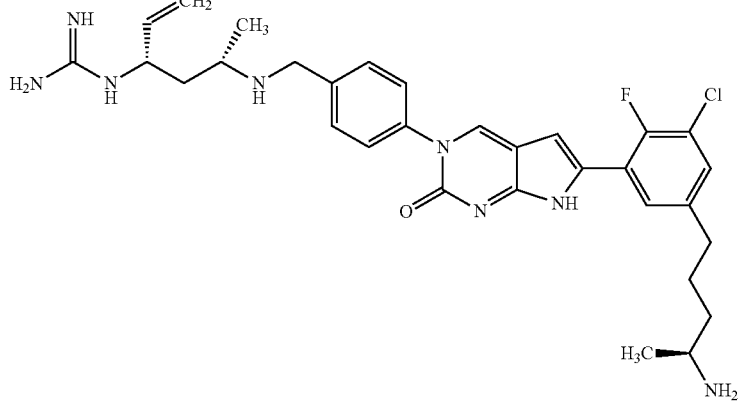 | 593.8 |
| 339 | 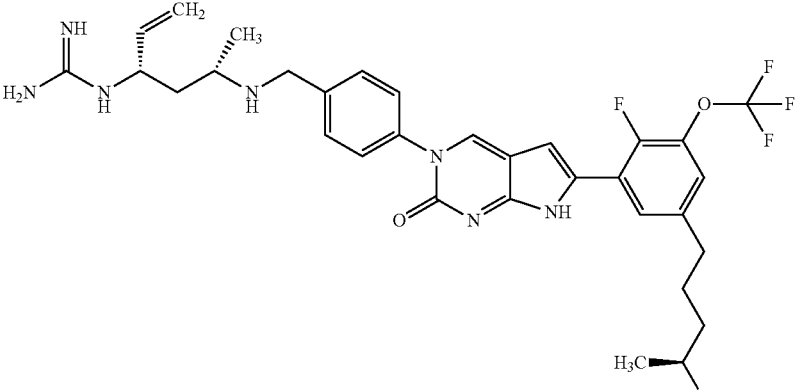 | 643.8 |

TABLE 1-continued

| Compound No | Structure | ESI, m/z [M + H]+ |
|---|---|---|
| 340 | 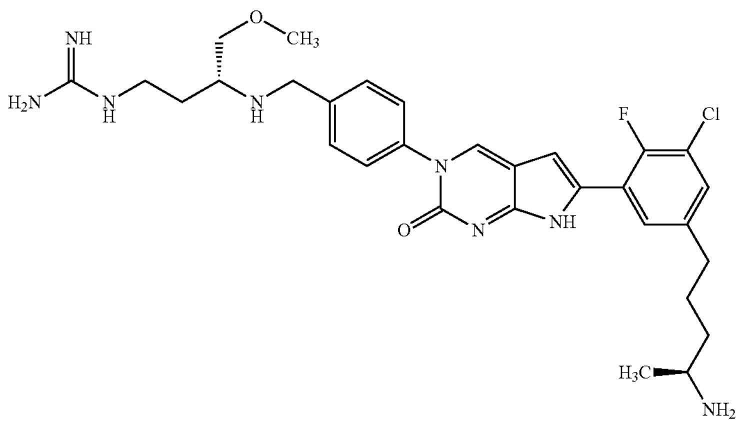 [SMILES: COC[C@@H](CCNC(=N)N)NCc1ccc(-n2cc3cc(-c4cc(CCC[C@H](C)N)cc(Cl)c4F)[nH]c3nc2=O)cc1] | 597.8 |
| 341 | 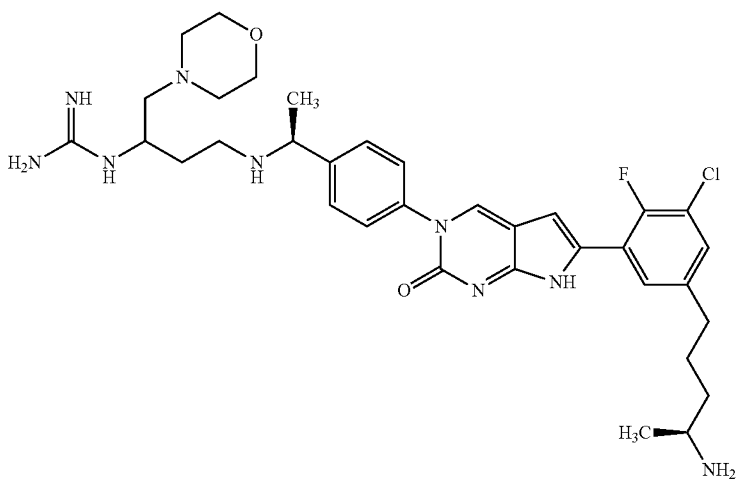 [SMILES: C[C@H](N)CCCc1cc(Cl)c(F)c(-c2cc3cn(-c4ccc([C@H](C)NCCC(CN5CCOCC5)NC(=N)N)cc4)c(=O)nc3[nH]2)c1] | 666.23 |
| 342 | 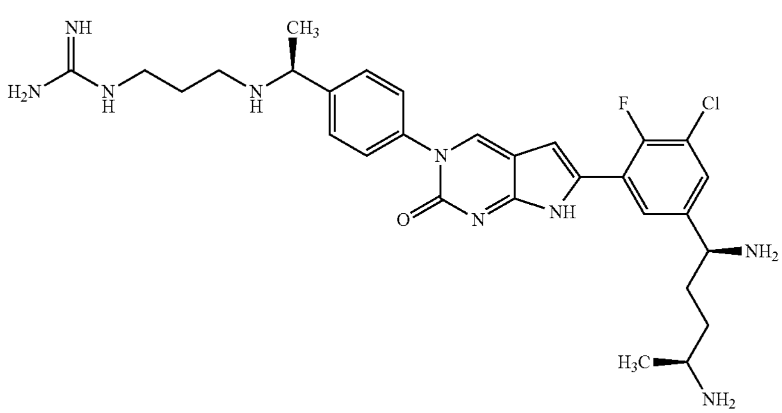 [SMILES: C[C@H](N)CC[C@H](N)c1cc(Cl)c(F)c(-c2cc3cn(-c4ccc([C@H](C)NCCCNC(=N)N)cc4)c(=O)nc3[nH]2)c1] | 582.8 |

TABLE 1-continued
| Compound No | Structure | ESI, m/z [M + H]+ |
|---|---|---|
| 343 | 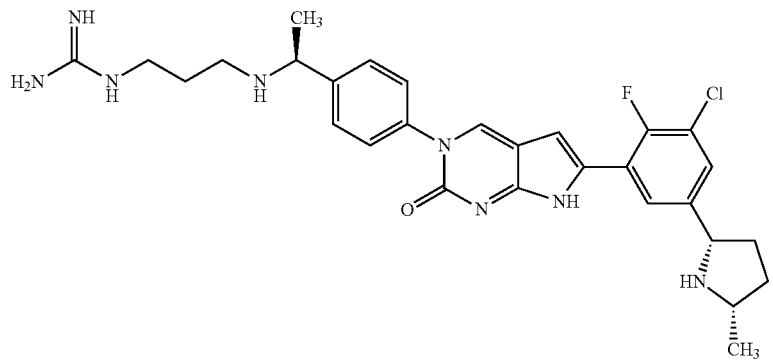 [SMILES: C[C@H](NCCCNC(=N)N)c1ccc(-n2cc3cc(-c4cc([C@@H]5CC[C@H](C)N5)cc(Cl)c4F)[nH]c3nc2=O)cc1] | 565.8 |
| 344 | 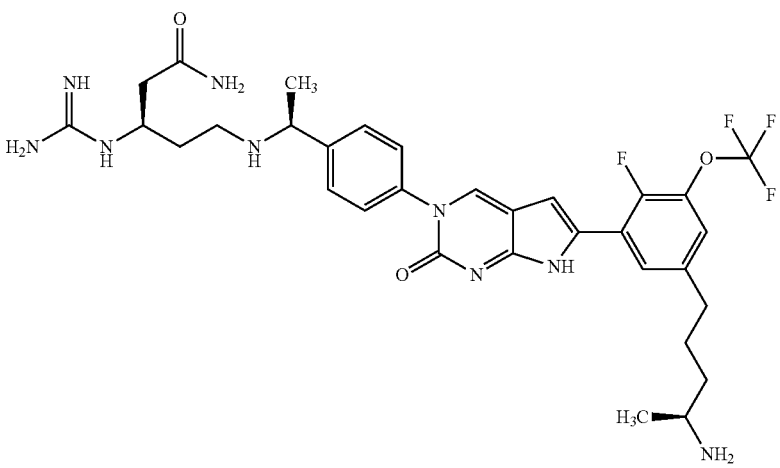 [SMILES: C[C@H](N)CCCc1cc(OC(F)(F)F)c(F)c(-c2cc3cn(-c4ccc([C@H](C)NCC[C@H](CC(N)=O)NC(=N)N)cc4)c(=O)nc3[nH]2)c1] | 674.1 |
| 345 | 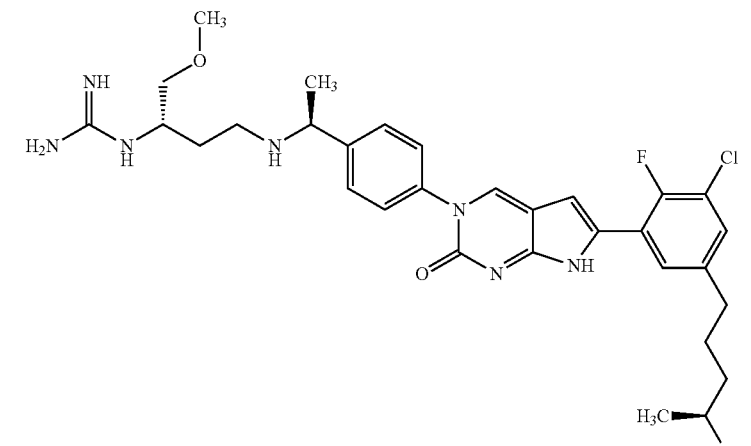 | 611.15 |

TABLE 1-continued

| Compound No | Structure | ESI, m/z [M + H]+ |
|---|---|---|
| 346 | 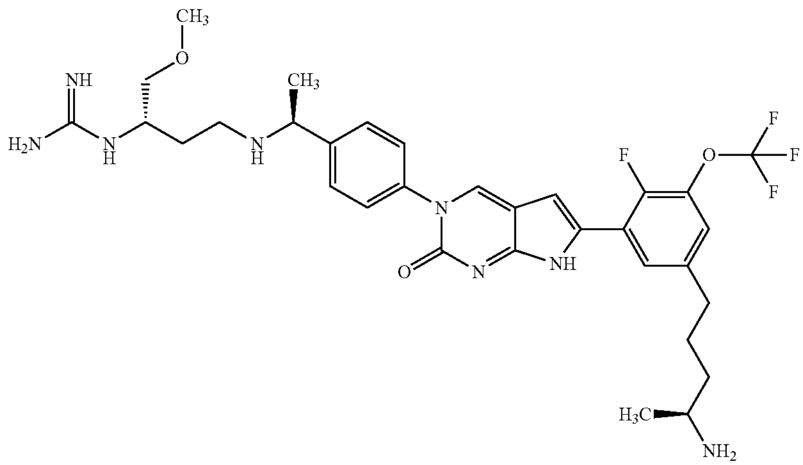 [SMILES: COC[C@H](CCN[C@@H](C)c1ccc(-n2cc3cc(-c4cc(CCC[C@H](C)N)cc(OC(F)(F)F)c4F)[nH]c3nc2=O)cc1)NC(=N)N] | 661.71 |
| 347 | 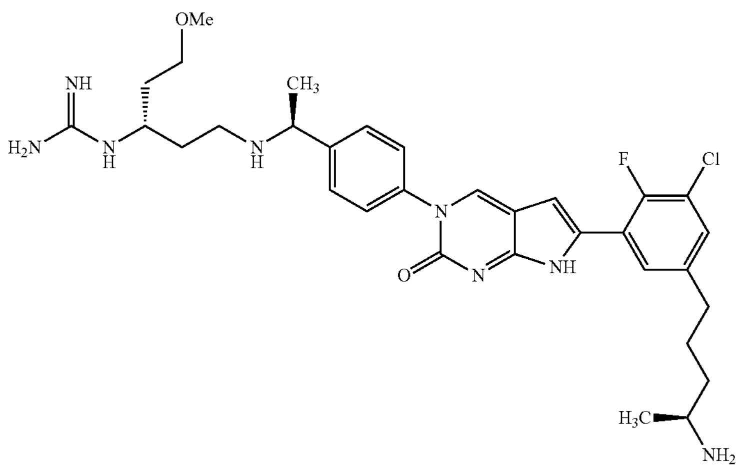 | 625.8 |
| 348 | 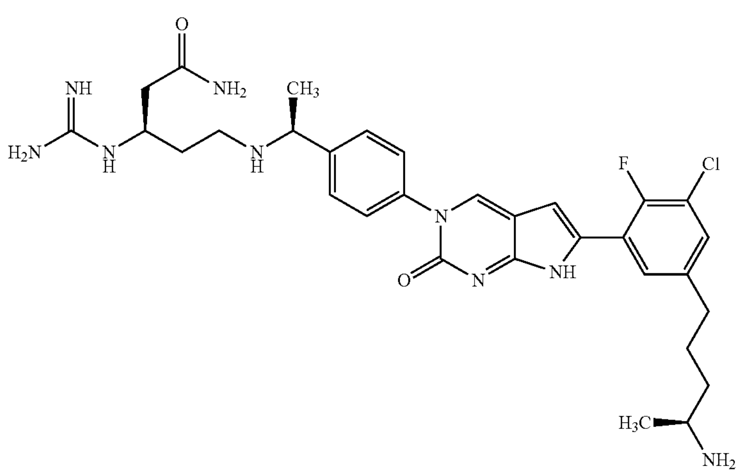 [SMILES: C[C@H](N)CCCc1cc(Cl)c(F)c(-c2cc3cn(-c4ccc([C@H](C)NCC[C@H](CC(N)=O)NC(=N)N)cc4)c(=O)nc3[nH]2)c1] | 624.8 |

TABLE 1-continued

| Compound No | Structure | ESI, m/z [M + H]+ |
|---|---|---|
| 349 | 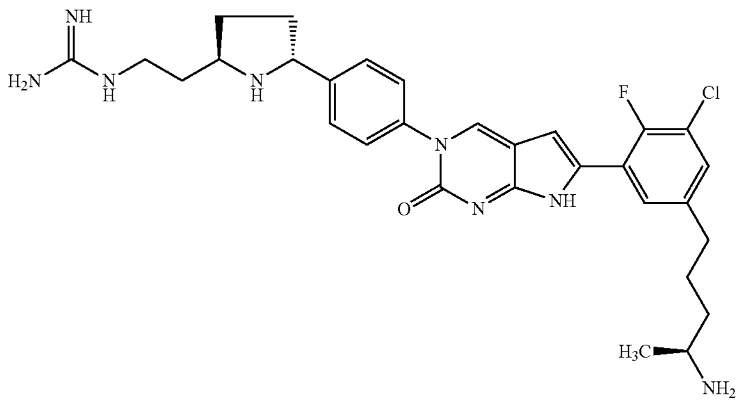 [SMILES: C[C@H](N)CCCc1cc(Cl)c(F)c(-c2cc3cn(-c4ccc([C@H]5CC[C@H](CCNC(=N)N)N5)cc4)c(=O)nc3[nH]2)c1] | 579.7 |
| 350 | 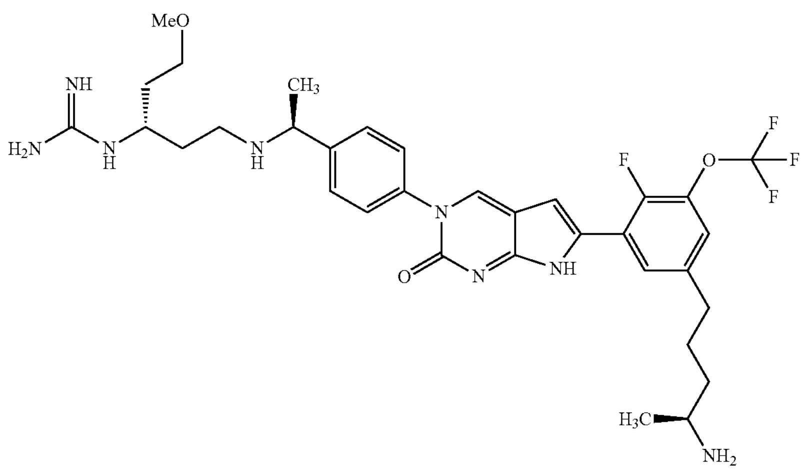 [SMILES: COCC[C@H](CCN[C@@H](C)c1ccc(-n2cc3cc(-c4cc(CCC[C@H](C)N)cc(OC(F)(F)F)c4F)[nH]c3nc2=O)cc1)NC(=N)N] | 675.8 |
| 351 | 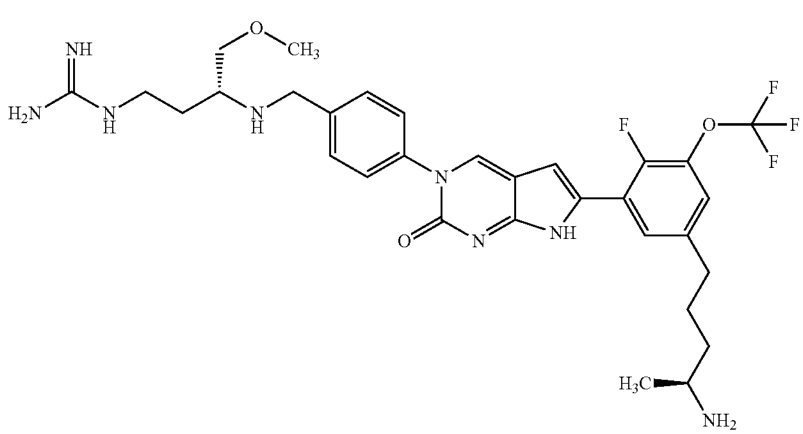 [SMILES: COC[C@@H](CCNC(=N)N)NCc1ccc(-n2cc3cc(-c4cc(CCC[C@H](C)N)cc(OC(F)(F)F)c4F)[nH]c3nc2=O)cc1] | 647.7 |

TABLE 1-continued

| Compound No | Structure | ESI, m/z [M + H]+ |
|---|---|---|
| 352 | 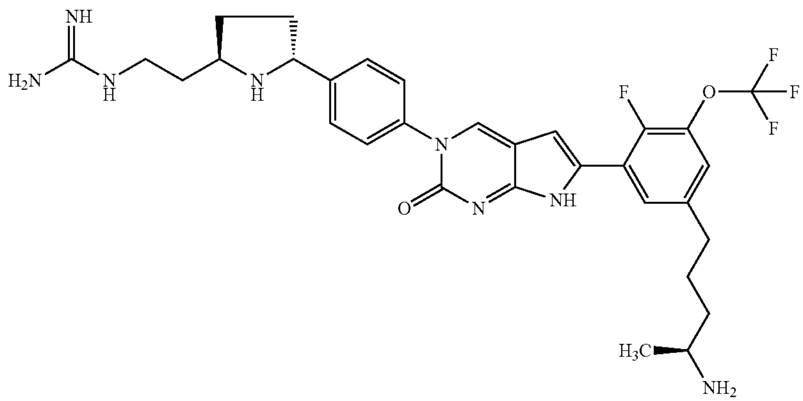 [SMILES: C[C@H](N)CCCc1cc(OC(F)(F)F)c(F)c(-c2cc3cn(-c4ccc([C@H]5CC[C@H](CCNC(=N)N)N5)cc4)c(=O)nc3[nH]2)c1] | 629.7 |
| 353 | 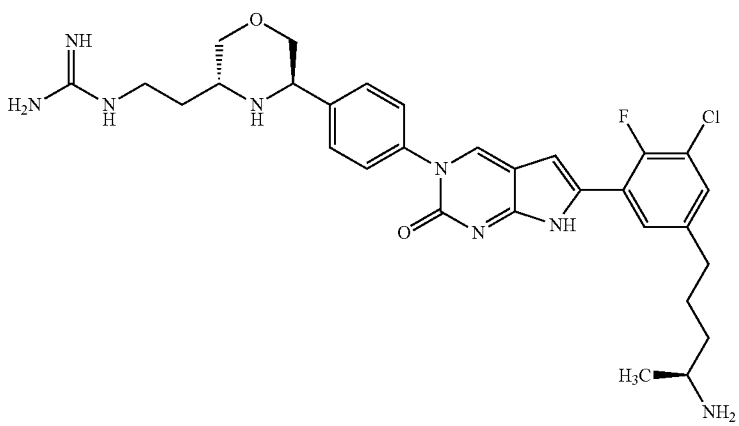 [SMILES: C[C@H](N)CCCc1cc(Cl)c(F)c(-c2cc3cn(-c4ccc([C@@H]5COC[C@@H](CCNC(=N)N)N5)cc4)c(=O)nc3[nH]2)c1] | 595.7 |
| 354 | 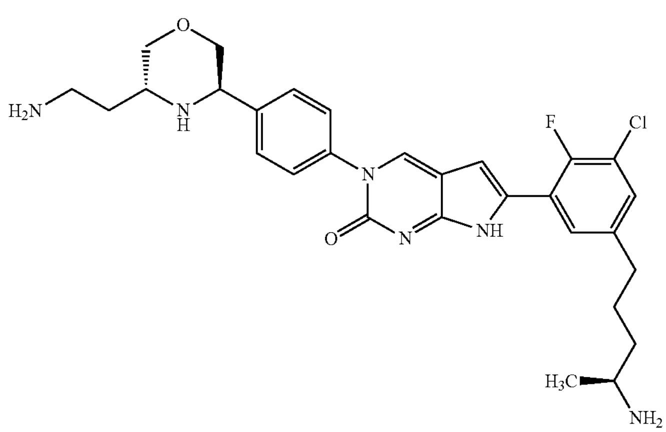 [SMILES: C[C@H](N)CCCc1cc(Cl)c(F)c(-c2cc3cn(-c4ccc([C@@H]5COC[C@@H](CCN)N5)cc4)c(=O)nc3[nH]2)c1] | 553.6 |

TABLE 1-continued
| Compound No | Structure | ESI, m/z [M + H]+ |
|---|---|---|
| 355 | 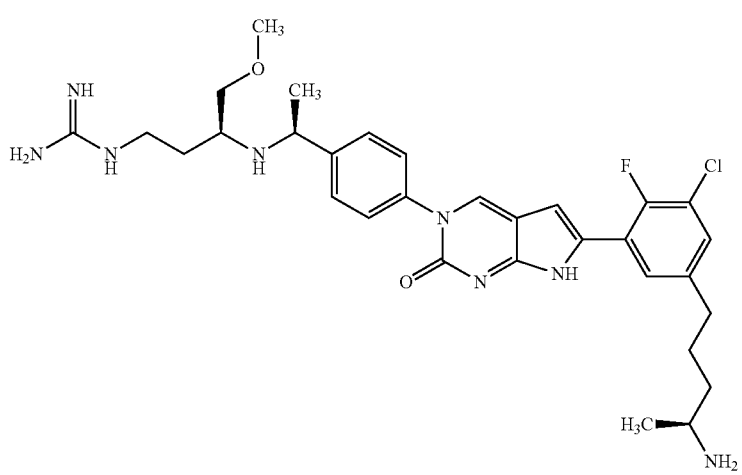 [SMILES: COC[C@H](CCNC(=N)N)N[C@@H](C)c1ccc(-n2cc3cc(-c4cc(CCC[C@H](C)N)cc(Cl)c4F)[nH]c3nc2=O)cc1] | 611.7 |
| 356 | 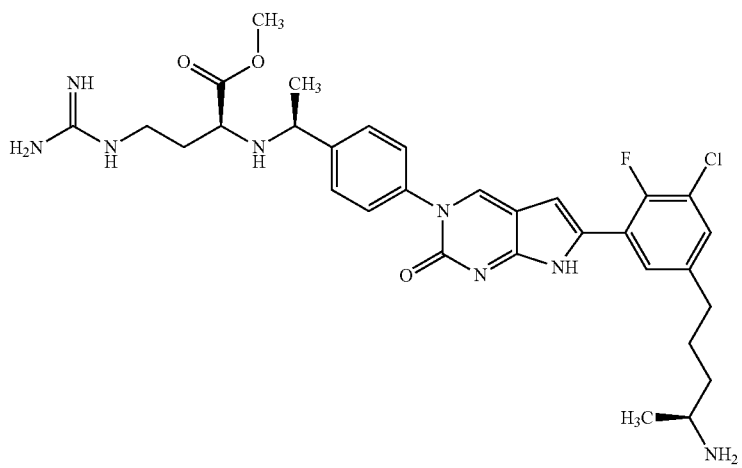 [SMILES: COC(=O)[C@H](CCNC(=N)N)N[C@@H](C)c1ccc(-n2cc3cc(-c4cc(CCC[C@H](C)N)cc(Cl)c4F)[nH]c3nc2=O)cc1] | 625.7 |
| 357 | 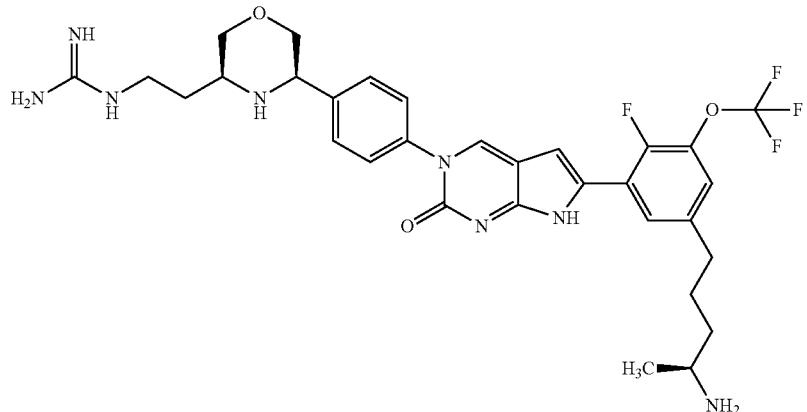 | 645.7 |

TABLE 1-continued

| Compound No | Structure | ESI, m/z [M + H]+ |
|---|---|---|
| 358 | 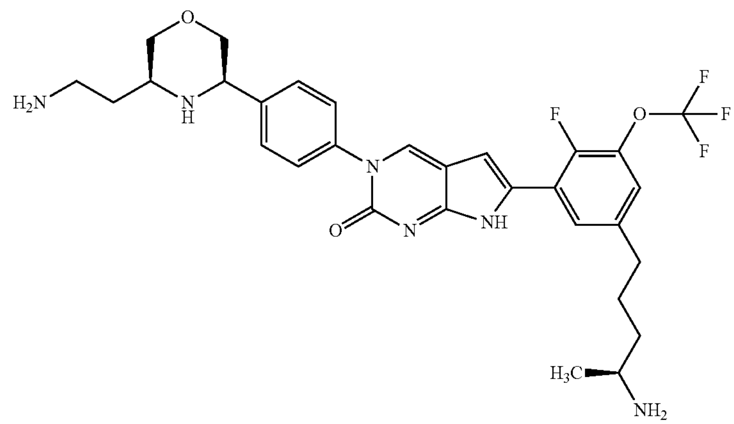 [SMILES: C[C@H](N)CCCc1cc(OC(F)(F)F)c(F)c(-c2cc3cn(-c4ccc([C@@H]5COC[C@H](CCN)N5)cc4)c(=O)nc3[nH]2)c1] | 603.6 |
| 359 | 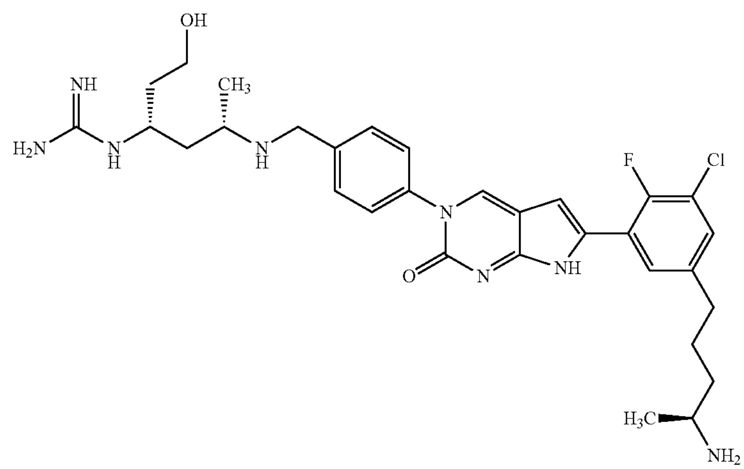 [SMILES: C[C@H](N)CCCc1cc(Cl)c(F)c(-c2cc3cn(-c4ccc(CN[C@@H](C)C[C@@H](CCO)NC(=N)N)cc4)c(=O)nc3[nH]2)c1] | 611.7 |
| 360 | 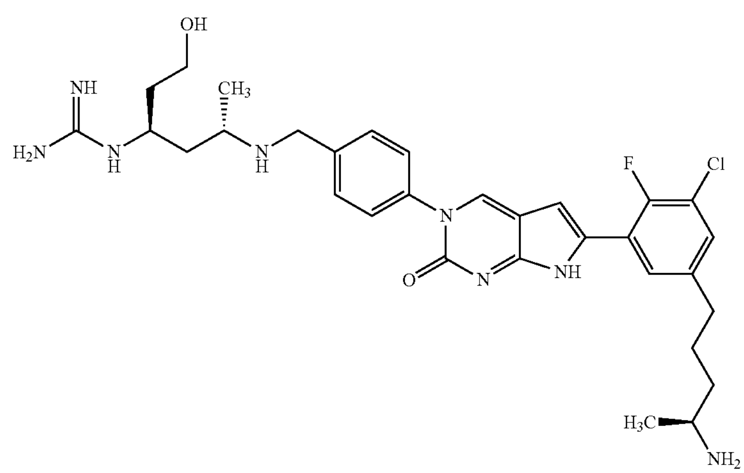 [SMILES: C[C@H](N)CCCc1cc(Cl)c(F)c(-c2cc3cn(-c4ccc(CN[C@@H](C)C[C@H](CCO)NC(=N)N)cc4)c(=O)nc3[nH]2)c1] | 611.7 |

TABLE 1-continued

| Compound No | Structure | ESI, m/z [M + H]+ |
|---|---|---|
| 361 | 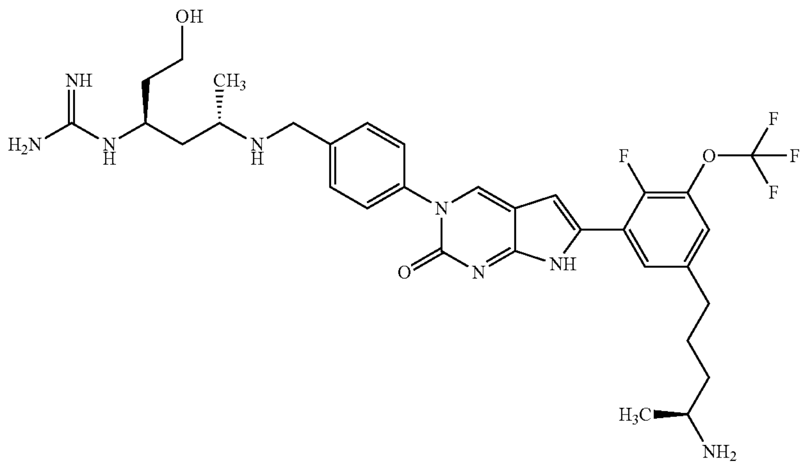 [SMILES: C[C@H](N)CCCc1cc(OC(F)(F)F)c(F)c(-c2cc3cn(-c4ccc(CN[C@@H](C)C[C@H](CCO)NC(=N)N)cc4)c(=O)nc3[nH]2)c1] | 661.7 |
| 362 | 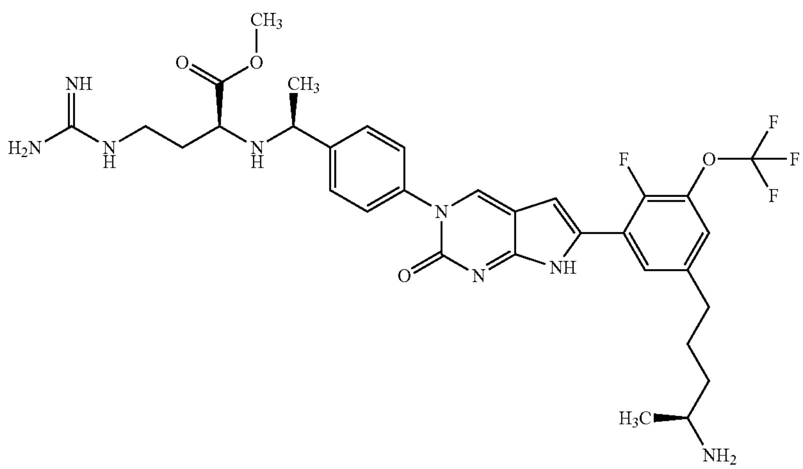 [SMILES: COC(=O)[C@H](CCNC(=N)N)N[C@@H](C)c1ccc(-n2cc3cc(-c4cc(CCC[C@H](C)N)cc(OC(F)(F)F)c4F)[nH]c3nc2=O)cc1] | 675.7 |
| 363 | 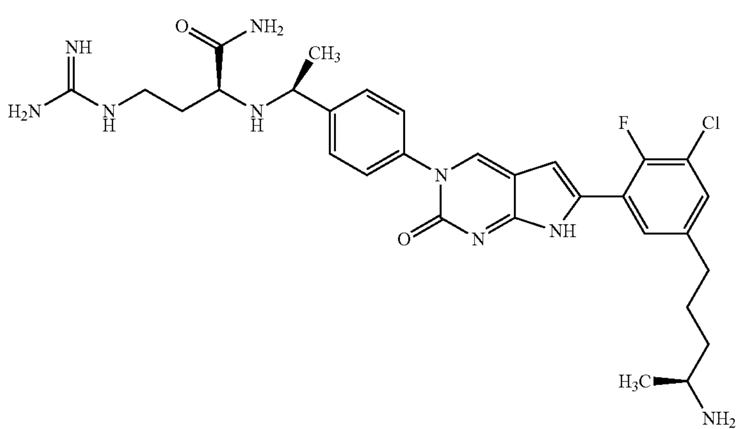 [SMILES: C[C@H](N)CCCc1cc(Cl)c(F)c(-c2cc3cn(-c4ccc([C@H](C)N[C@@H](CCNC(=N)N)C(N)=O)cc4)c(=O)nc3[nH]2)c1] | 610.7 |

TABLE 1-continued

| Compound No | Structure | ESI, m/z [M + H]+ |
|---|---|---|
| 364 | 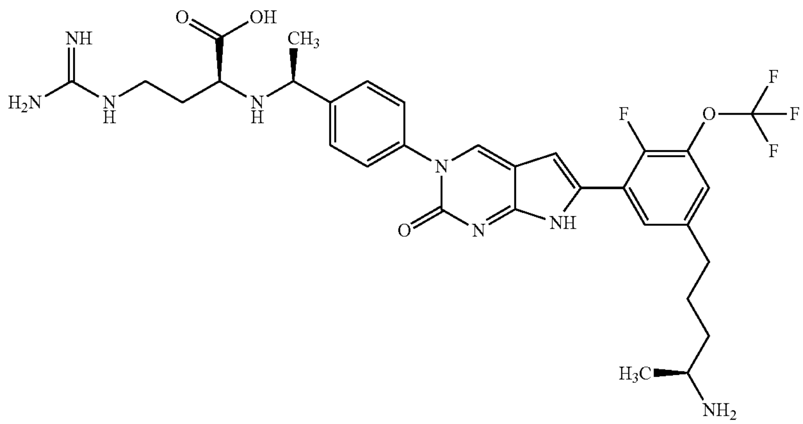 [SMILES: C[C@H](N)CCCc1cc(OC(F)(F)F)c(F)c(-c2cc3cn(-c4ccc([C@H](C)N[C@@H](CCNC(=N)N)C(=O)O)cc4)c(=O)nc3[nH]2)c1] | 661.7 |
| 365 | 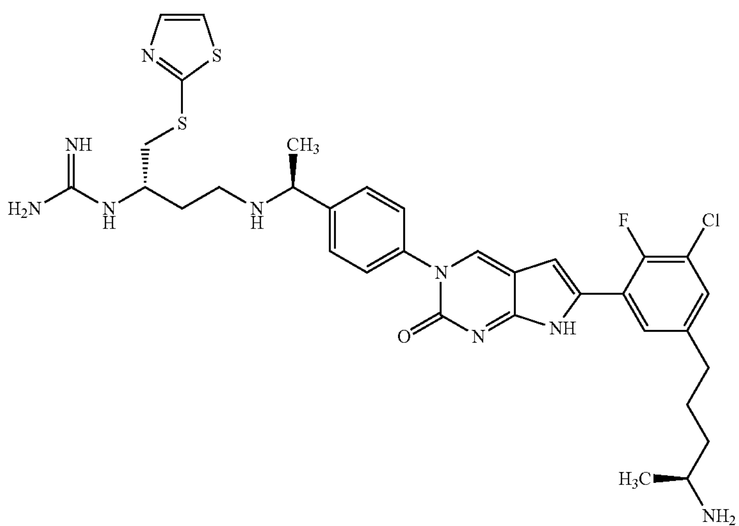 [SMILES: C[C@H](N)CCCc1cc(Cl)c(F)c(-c2cc3cn(-c4ccc([C@H](C)NCC[C@@H](CSc5nccs5)NC(=N)N)cc4)c(=O)nc3[nH]2)c1] | 697.31 |
| 366 | 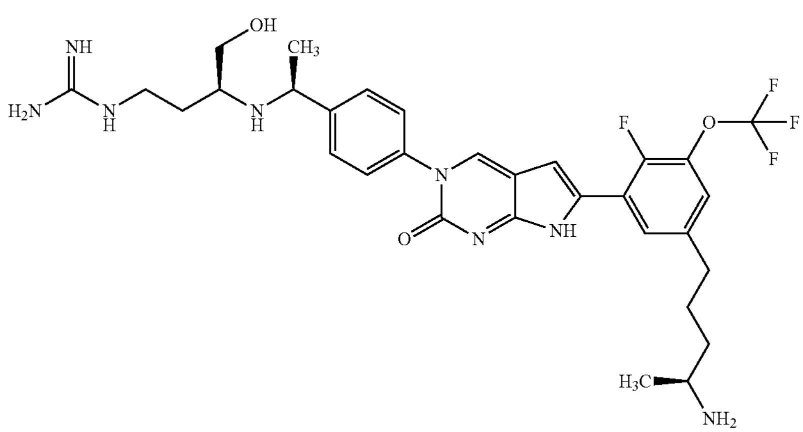 [SMILES: C[C@H](N)CCCc1cc(OC(F)(F)F)c(F)c(-c2cc3cn(-c4ccc([C@H](C)N[C@H](CO)CCNC(=N)N)cc4)c(=O)nc3[nH]2)c1] | 647.7 |

TABLE 1-continued
| Compound No | Structure | ESI, m/z [M + H]+ |
|---|---|---|
| 367 | 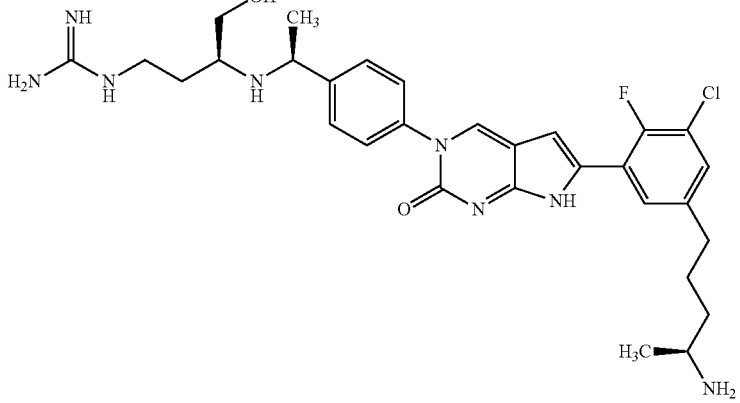 | 597.7 |
| 368 | 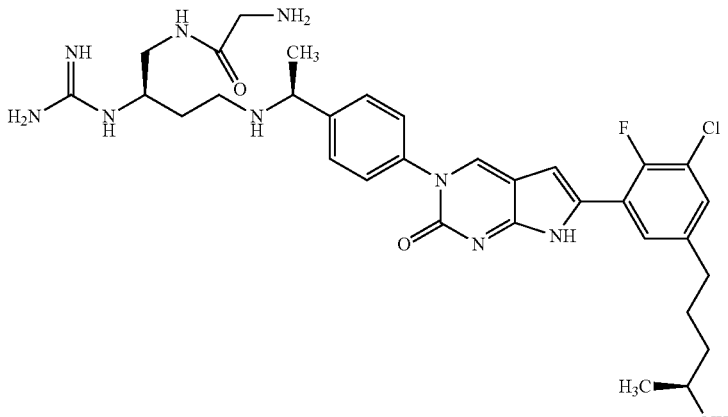 | 653.7 |
| 369 | 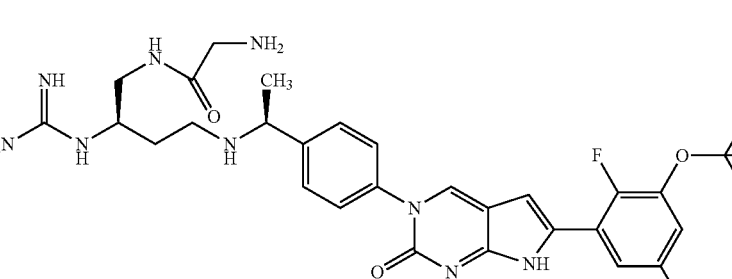 | 703.8 |

TABLE 1-continued
| Compound No | Structure | ESI, m/z [M + H]+ |
|---|---|---|
| 370 | 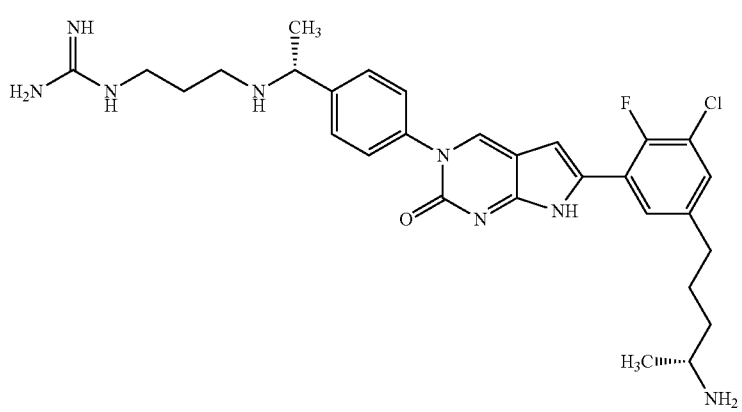 [SMILES: C[C@@H](N)CCCc1cc(Cl)c(F)c(-c2cc3cn(-c4ccc([C@@H](C)NCCCNC(=N)N)cc4)c(=O)nc3[nH]2)c1] | 567.7 |
| 371 | 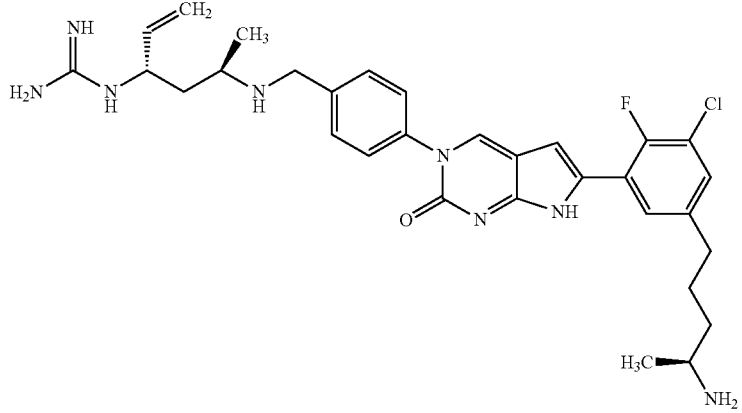 [SMILES: C=C[C@H](C[C@@H](C)NCc1ccc(-n2cc3cc(-c4cc(CCC[C@H](C)N)cc(Cl)c4F)[nH]c3nc2=O)cc1)NC(=N)N] | 593.7 |
| 372 | 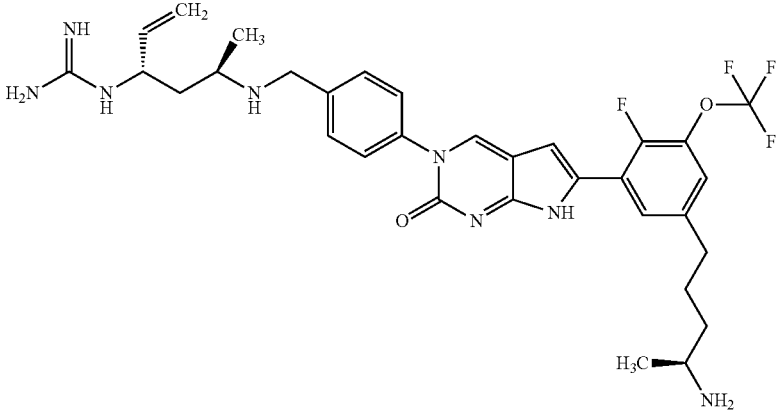 [SMILES: C=C[C@H](C[C@@H](C)NCc1ccc(-n2cc3cc(-c4cc(CCC[C@H](C)N)cc(OC(F)(F)F)c4F)[nH]c3nc2=O)cc1)NC(=N)N] | 643.7 |

TABLE 1-continued
| Compound No | Structure | ESI, m/z [M + H]+ |
|---|---|---|
| 373 | 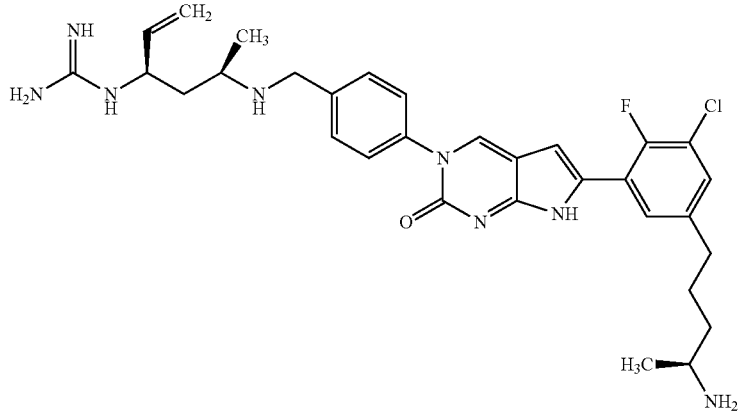 | 593.7 |
| 374 | 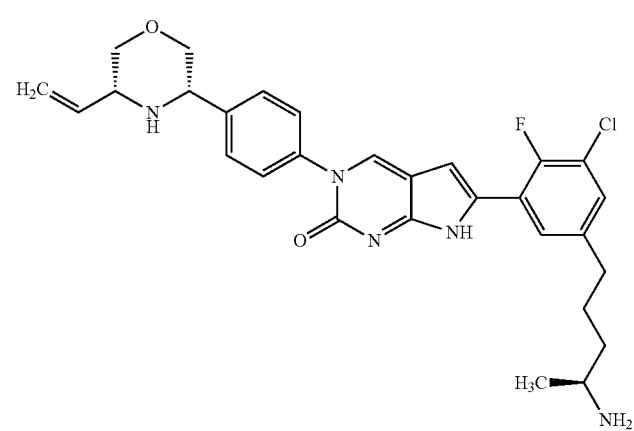 [SMILES: C=C[C@@H]1COC[C@H](c2ccc(-n3cc4cc(-c5cc(CCC[C@H](C)N)cc(Cl)c5F)[nH]c4nc3=O)cc2)N1] | 536.6 |
| 375 | 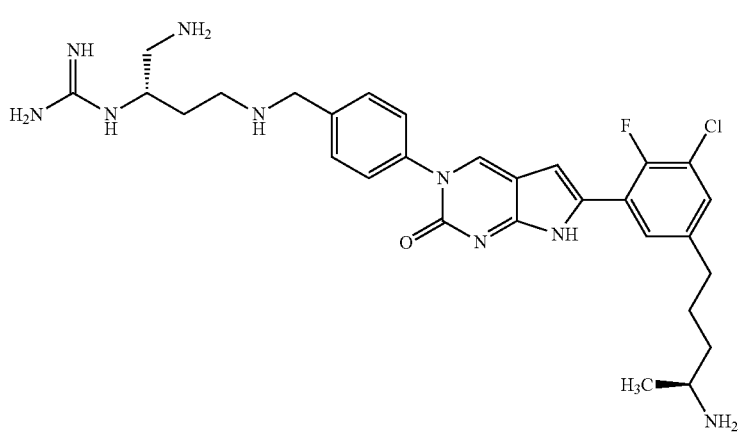 | 582.7 |

TABLE 1-continued
| Compound No | Structure | ESI, m/z [M + H]+ |
|---|---|---|
| 376 | 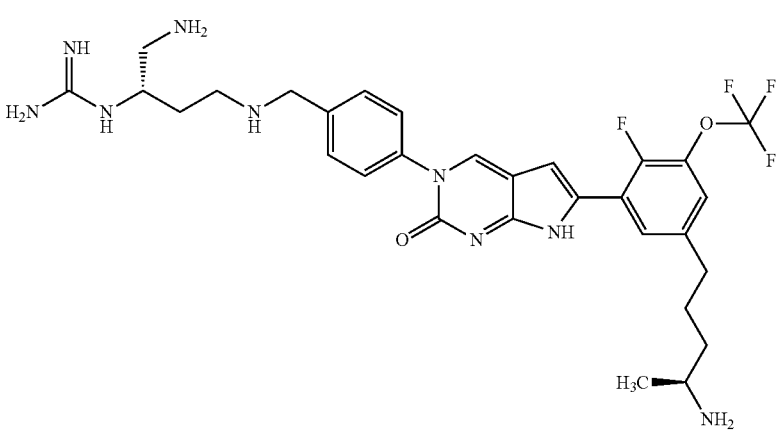 [SMILES: C[C@H](N)CCCc1cc(OC(F)(F)F)c(F)c(-c2cc3cn(-c4ccc(CNCC[C@@H](CN)NC(=N)N)cc4)c(=O)nc3[nH]2)c1] | 632.8 |
| 377 | 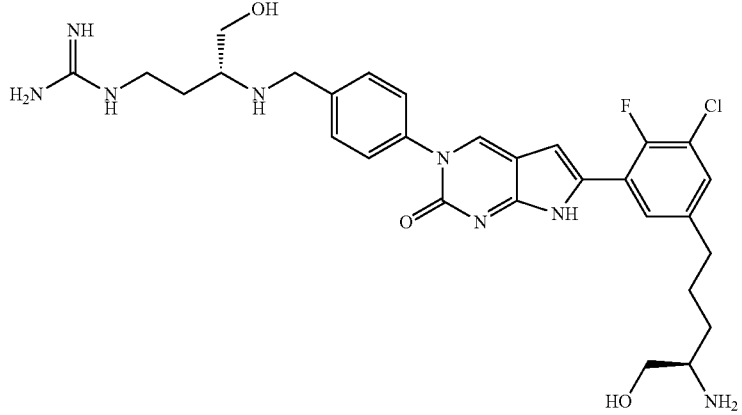 | 599.7 |
| 378 | 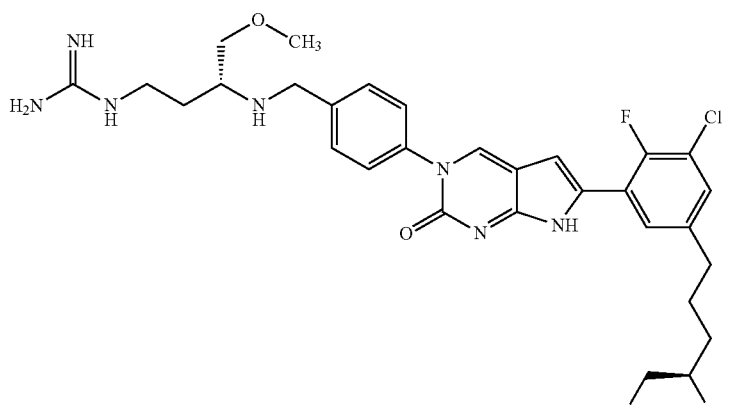 | 613.7 |

TABLE 1-continued

| Compound No | Structure | ESI, m/z [M + H]+ |
|---|---|---|
| 379 | 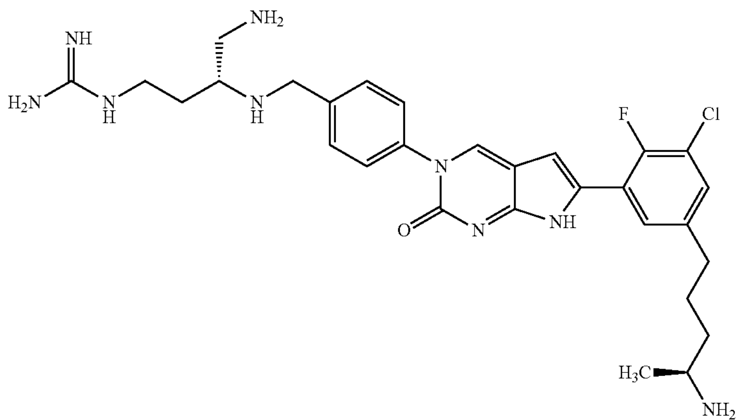 [SMILES: C[C@H](N)CCCc1cc(Cl)c(F)c(-c2cc3cn(-c4ccc(CN[C@@H](CN)CCNC(=N)N)cc4)c(=O)nc3[nH]2)c1] | 582.7 |
| 380 | 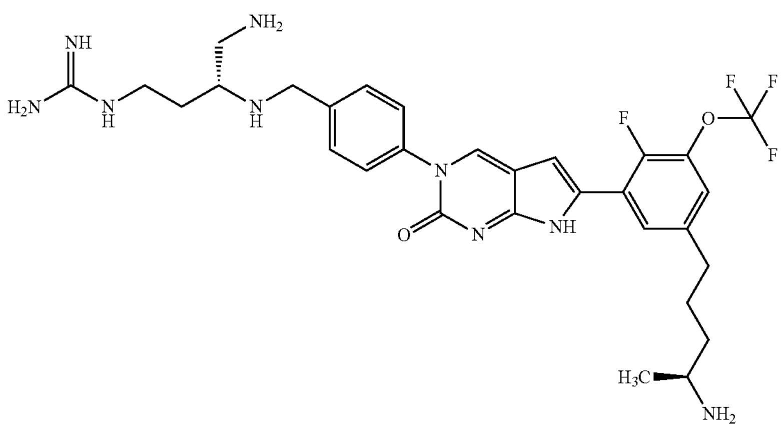 | 632.7 |
| 381 | 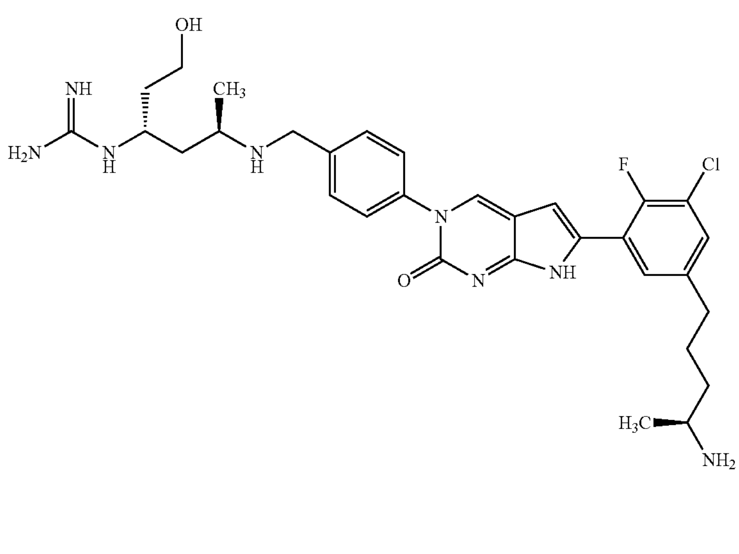 [SMILES: C[C@H](N)CCCc1cc(Cl)c(F)c(-c2cc3cn(-c4ccc(CN[C@H](C)C[C@@H](CCO)NC(=N)N)cc4)c(=O)nc3[nH]2)c1] | 611.7 |

TABLE 1-continued
| Compound No | Structure | ESI, m/z [M + H]+ |
|---|---|---|
| 382 | 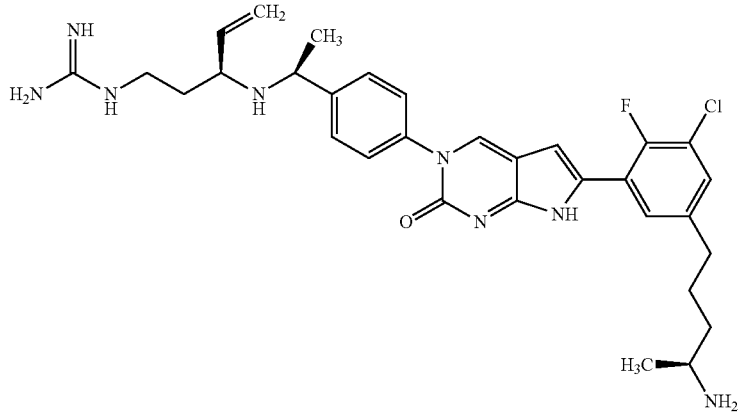 [SMILES: C=C[C@H](CCNC(=N)N)N[C@@H](C)c1ccc(-n2cc3cc(-c4cc(CCC[C@H](C)N)cc(Cl)c4F)[nH]c3nc2=O)cc1] | 593.7 |
| 383 | 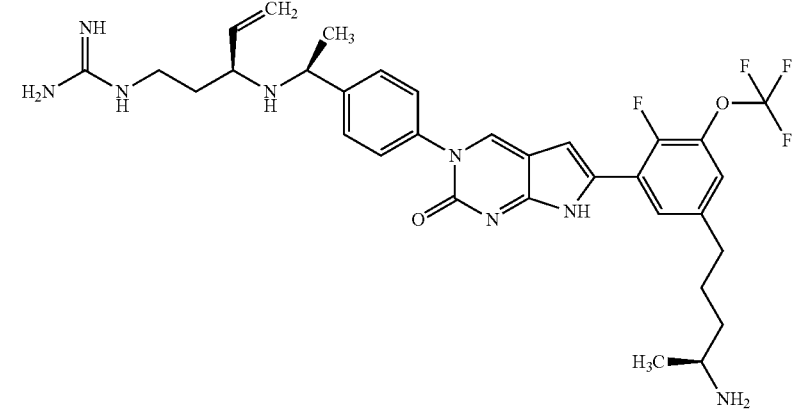 [SMILES: C=C[C@H](CCNC(=N)N)N[C@@H](C)c1ccc(-n2cc3cc(-c4cc(CCC[C@H](C)N)cc(OC(F)(F)F)c4F)[nH]c3nc2=O)cc1] | 643.7 |
| 384 | 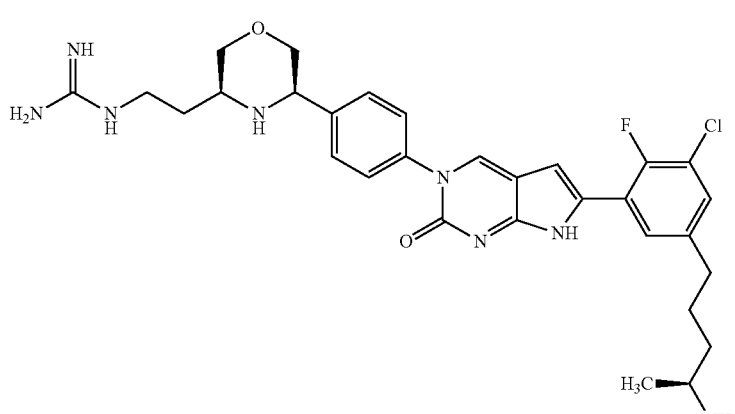 | 595.7 |

TABLE 1-continued

| Compound No | Structure | ESI, m/z [M + H]+ |
|---|---|---|
| 385 | 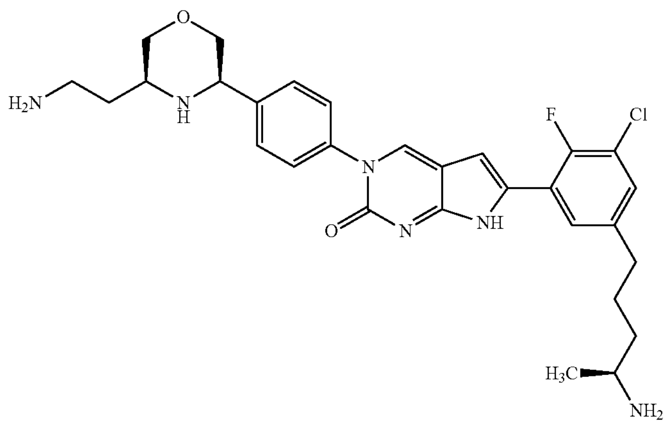 [SMILES: C[C@H](N)CCCc1cc(Cl)c(F)c(-c2cc3cn(-c4ccc([C@@H]5COC[C@H](CCN)N5)cc4)c(=O)nc3[nH]2)c1] | 553.6 |
| 386 | 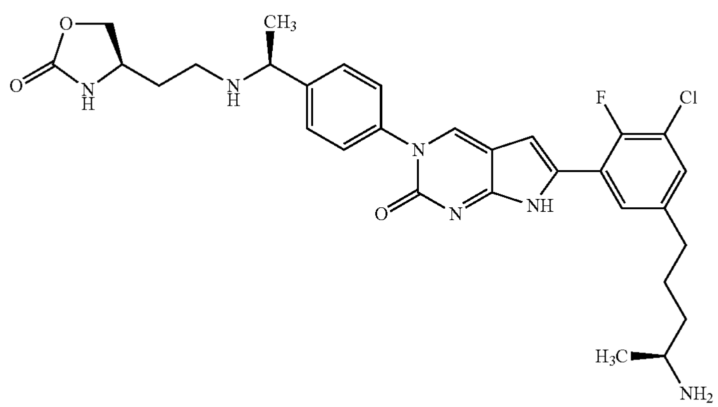 [SMILES: C[C@H](N)CCCc1cc(Cl)c(F)c(-c2cc3cn(-c4ccc([C@H](C)NCC[C@@H]5COC(=O)N5)cc4)c(=O)nc3[nH]2)c1] | 581.7 |
| 387 | 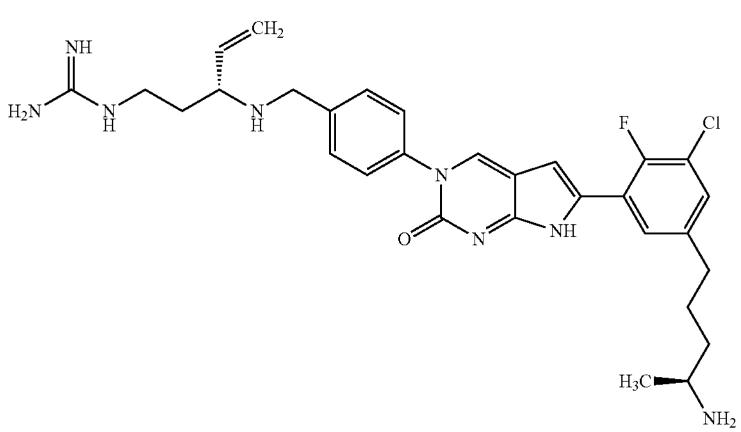 [SMILES: C=C[C@@H](CCNC(=N)N)NCc1ccc(-n2cc3cc(-c4cc(CCC[C@H](C)N)cc(Cl)c4F)[nH]c3nc2=O)cc1] | 579.7 |

TABLE 1-continued
| Compound No | Structure | ESI, m/z [M + H]+ |
|---|---|---|
| 388 | 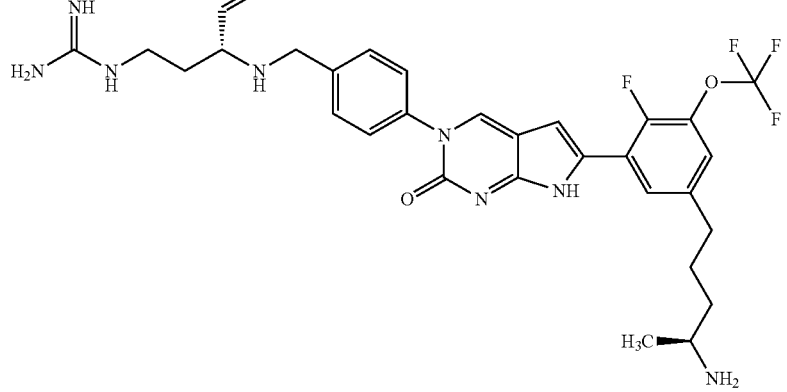 | 629.7 |
| 389 | 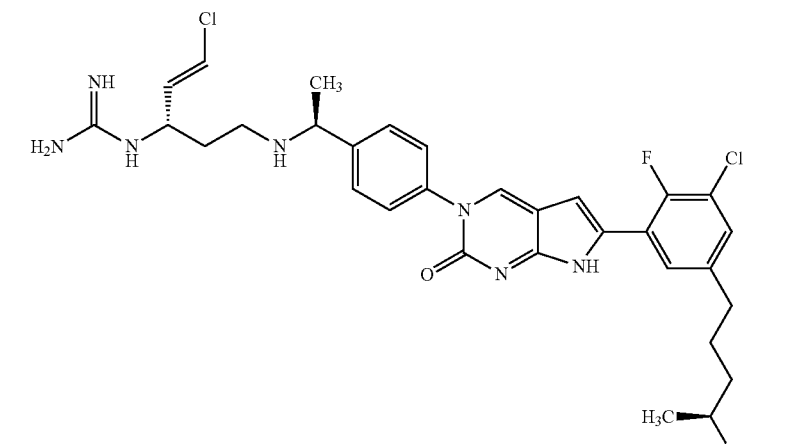 | 628.59 |
| 390 | 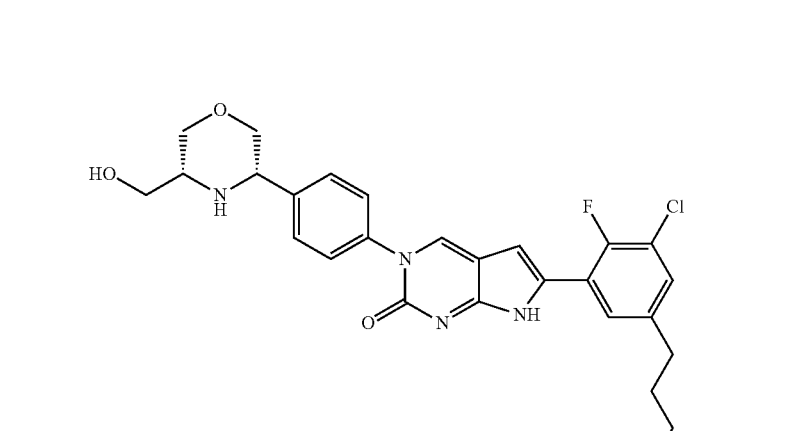 | 540.6 |

TABLE 1-continued

| Compound No | Structure | ESI, m/z [M + H]+ |
| --- | --- | --- |
| 391 | 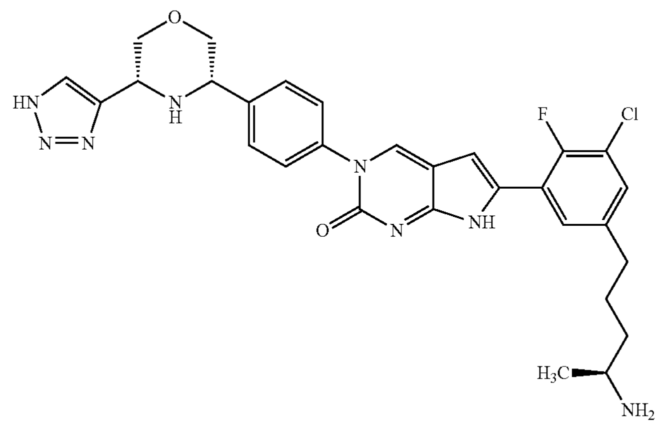 [SMILES: C[C@H](N)CCCc1cc(Cl)c(F)c(-c2cc3cn(-c4ccc([C@H]5COC[C@@H](c6c[nH]nn6)N5)cc4)c(=O)nc3[nH]2)c1] | 577.6 |
| 392 | 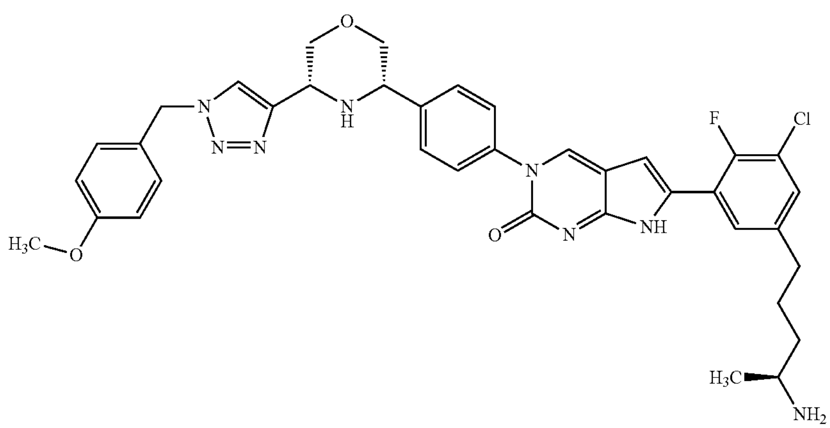 [SMILES: COc1ccc(Cn2cc([C@@H]3COC[C@H](c4ccc(-n5cc6cc(-c7cc(CCC[C@H](C)N)cc(Cl)c7F)[nH]c6nc5=O)cc4)N3)nn2)cc1] | 697.8 |
| 393 | 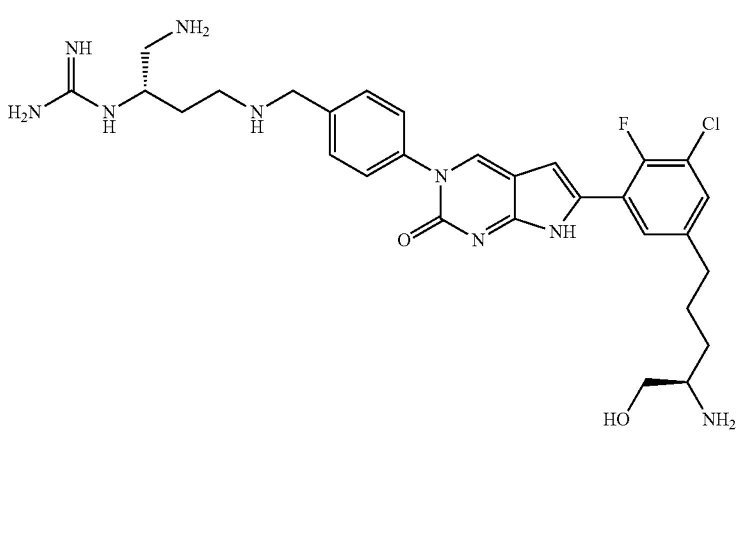 [SMILES: N=C(N)N[C@H](CN)CCNCc1ccc(-n2cc3cc(-c4cc(CCC[C@@H](N)CO)cc(Cl)c4F)[nH]c3nc2=O)cc1] | 598.7 |

TABLE 1-continued

| Compound No | Structure | ESI, m/z [M + H]+ |
|---|---|---|
| 394 | 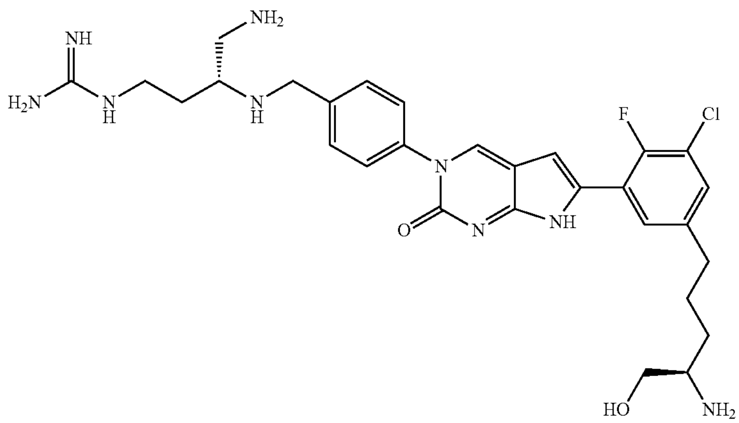 [SMILES: N=C(N)NCC[C@H](CN)NCc1ccc(-n2cc3cc(-c4cc(CCC[C@@H](N)CO)cc(Cl)c4F)[nH]c3nc2=O)cc1] | 598.7 |
| 395 | 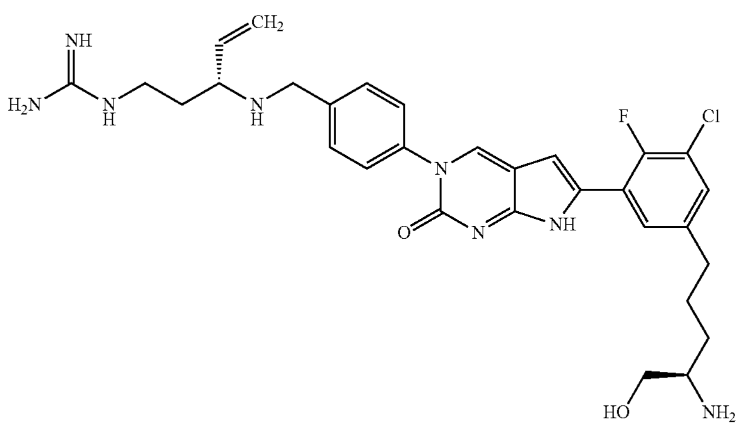 [SMILES: C=C[C@@H](CCNC(=N)N)NCc1ccc(-n2cc3cc(-c4cc(CCC[C@@H](N)CO)cc(Cl)c4F)[nH]c3nc2=O)cc1] | 595.7 |
| 396 | 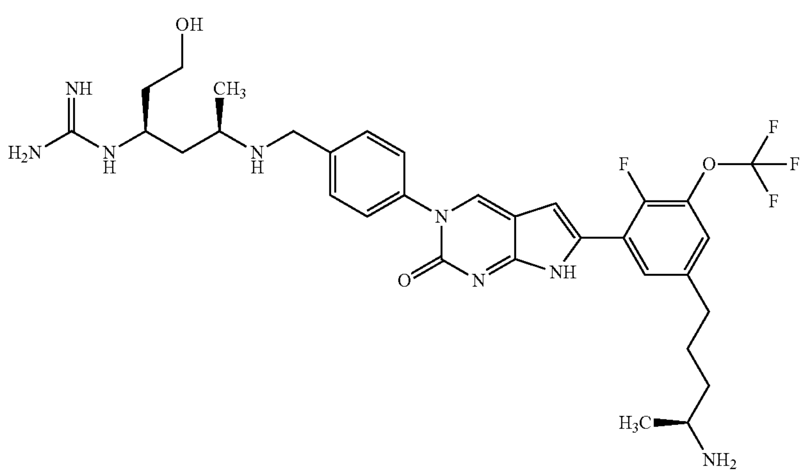 [SMILES: C[C@H](N)CCCc1cc(OC(F)(F)F)c(F)c(-c2cc3cn(-c4ccc(CN[C@H](C)C[C@H](CCO)NC(=N)N)cc4)c(=O)nc3[nH]2)c1] | 661.7 |

TABLE 1-continued

| Compound No | Structure | ESI, m/z [M + H]+ |
|---|---|---|
| 397 | 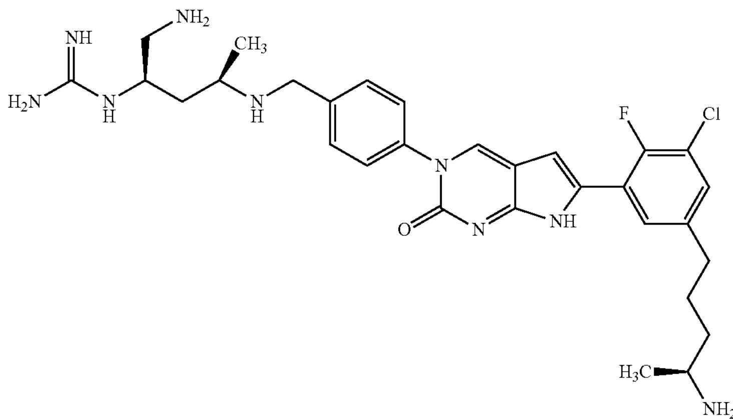 [SMILES: C[C@H](N)CCCc1cc(Cl)c(F)c(-c2cc3cn(-c4ccc(CN[C@H](C)C[C@H](CN)NC(=N)N)cc4)c(=O)nc3[nH]2)c1] | 596.7 |
| 398 | 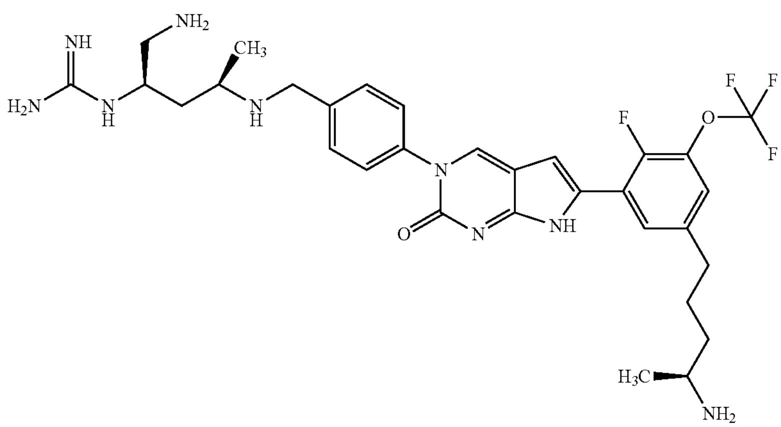 [SMILES: C[C@H](N)CCCc1cc(OC(F)(F)F)c(F)c(-c2cc3cn(-c4ccc(CN[C@H](C)C[C@H](CN)NC(=N)N)cc4)c(=O)nc3[nH]2)c1] | 646.7 |
| 399 | 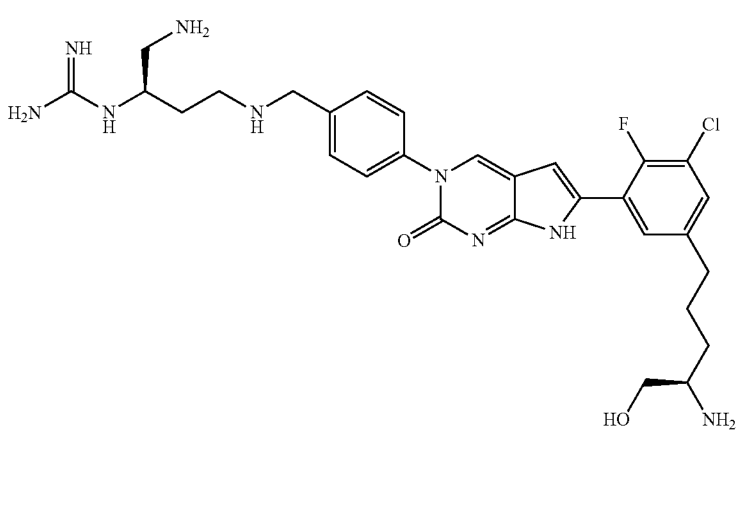 [SMILES: N=C(N)N[C@@H](CN)CCNCc1ccc(-n2cc3cc(-c4cc(CCC[C@@H](N)CO)cc(Cl)c4F)[nH]c3nc2=O)cc1] | 598.7 |

TABLE 1-continued

| Compound No | Structure | ESI, m/z [M + H]+ |
|---|---|---|
| 400 | 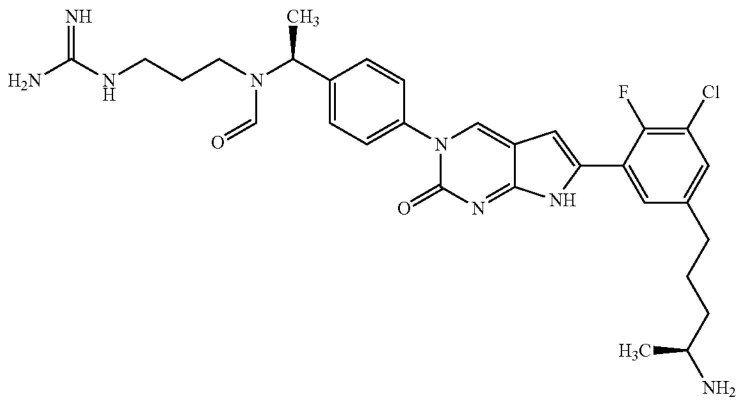 [SMILES: C[C@H](N)CCCc1cc(Cl)c(F)c(-c2cc3cn(-c4ccc([C@H](C)N(C=O)CCCNC(=N)N)cc4)c(=O)nc3[nH]2)c1] | 595.7 |
| 401 | 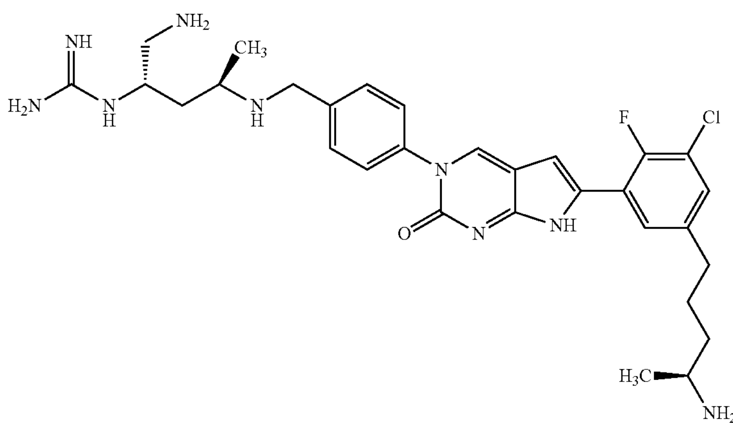 [SMILES: C[C@H](N)CCCc1cc(Cl)c(F)c(-c2cc3cn(-c4ccc(CN[C@H](C)C[C@@H](CN)NC(=N)N)cc4)c(=O)nc3[nH]2)c1] | 596.7 |
| 402 | 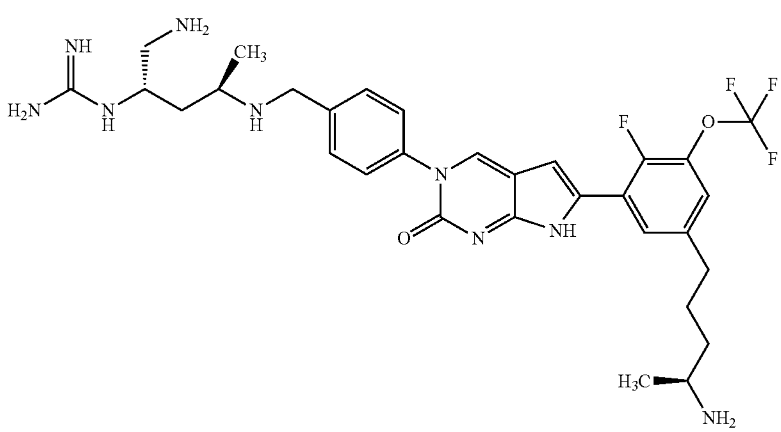 [SMILES: C[C@H](N)CCCc1cc(OC(F)(F)F)c(F)c(-c2cc3cn(-c4ccc(CN[C@H](C)C[C@@H](CN)NC(=N)N)cc4)c(=O)nc3[nH]2)c1] | 646.8 |

TABLE 1-continued
| Compound No | Structure | ESI, m/z [M + H]+ |
|---|---|---|
| 403 | 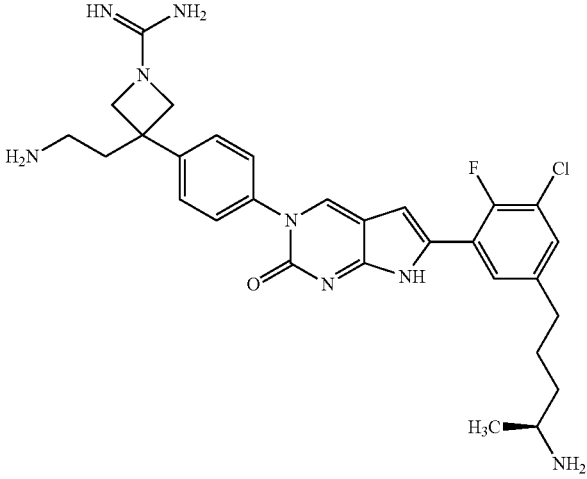 [SMILES: C[C@H](N)CCCc1cc(Cl)c(F)c(-c2cc3cn(-c4ccc(C5(CCN)CN(C(=N)N)C5)cc4)c(=O)nc3[nH]2)c1] | 566.09 |
| 404 | 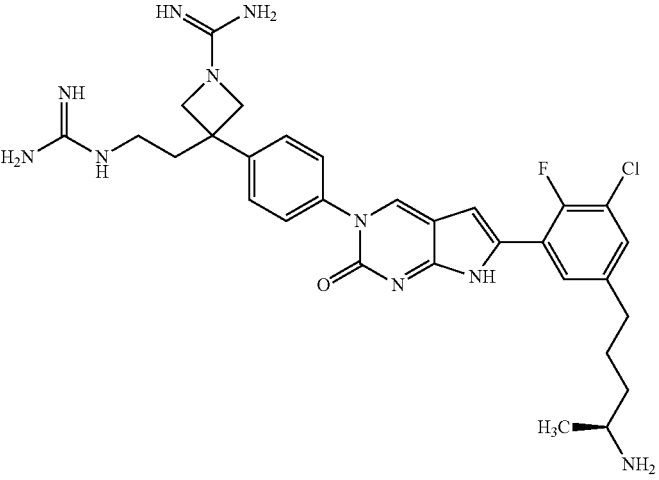 [SMILES: C[C@H](N)CCCc1cc(Cl)c(F)c(-c2cc3cn(-c4ccc(C5(CCNC(=N)N)CN(C(=N)N)C5)cc4)c(=O)nc3[nH]2)c1] | 608.13 |
| 405 | 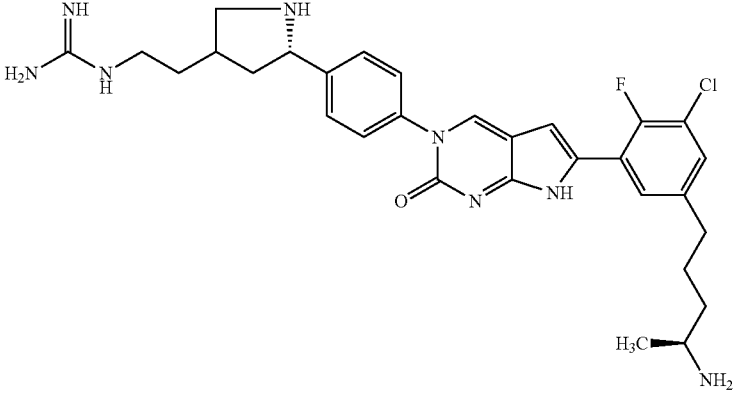 | 579.7 |

TABLE 1-continued

| Compound No | Structure | ESI, m/z [M + H]+ |
| --- | --- | --- |
| 406 | 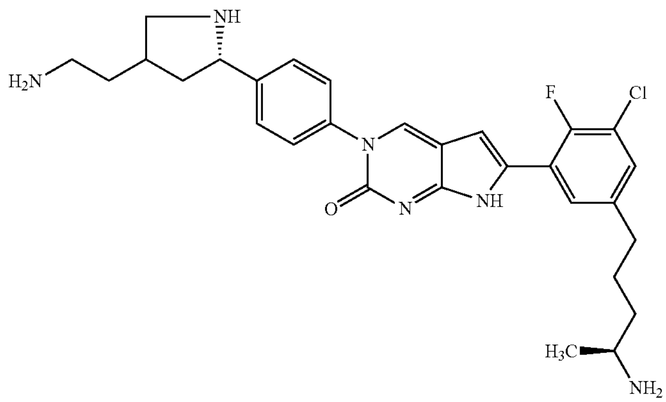 | 537.7 |
| 407 | 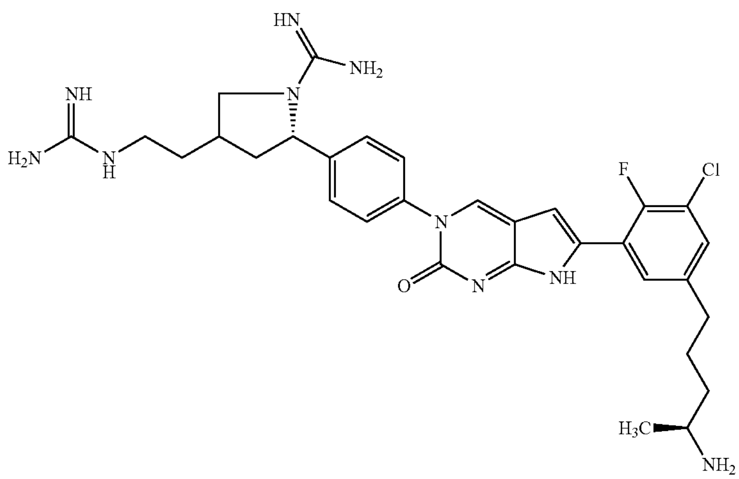 | 621.6 |
| 408 | 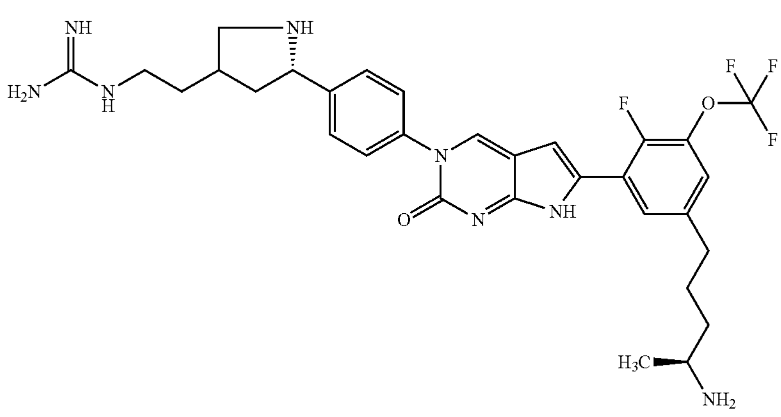 | 629.7 |

TABLE 1-continued
| Compound No | Structure | ESI, m/z [M + H]+ |
|---|---|---|
| 409 | 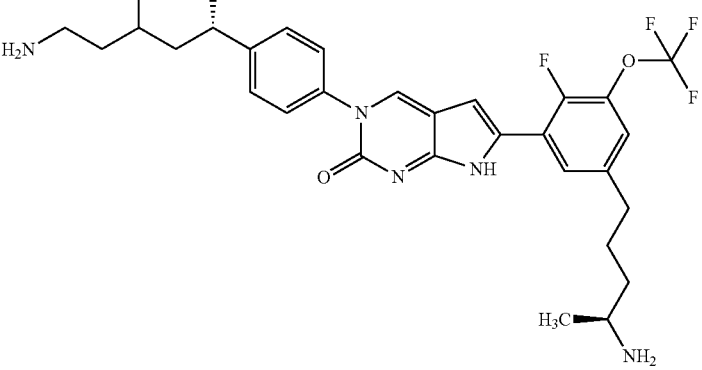 | 587.7 |
| 410 | 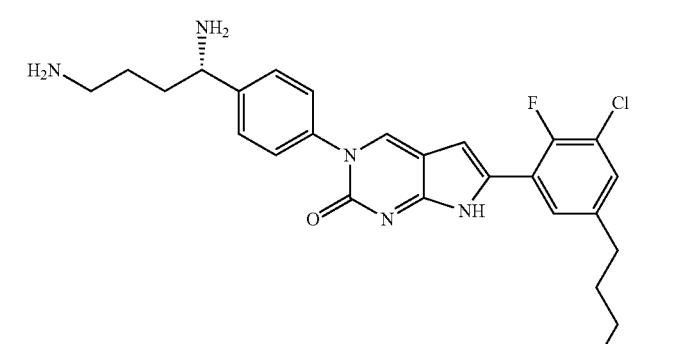 | 511.7 |
| 411 | 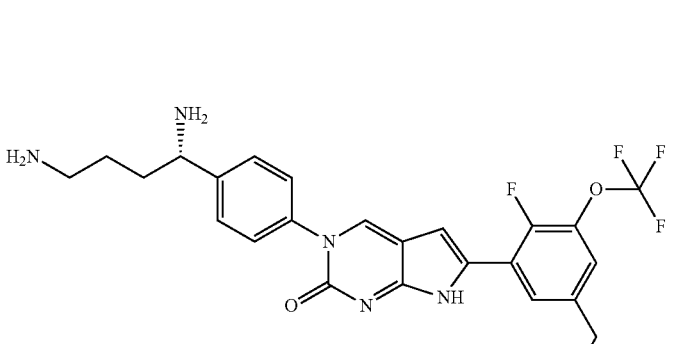 | 561.7 |

TABLE 1-continued
| Compound No | Structure | ESI, m/z [M + H]+ |
|---|---|---|
| 412 | 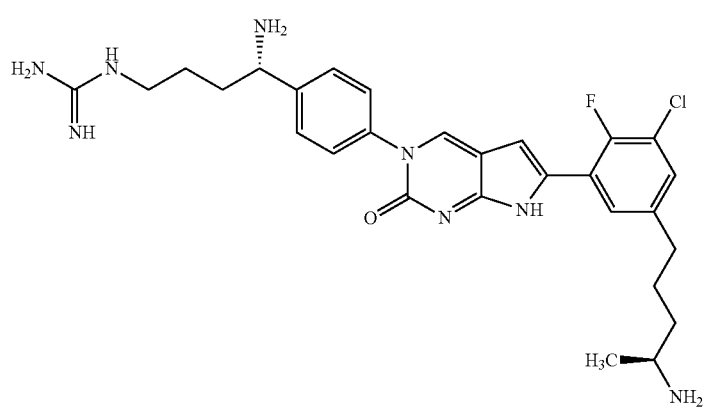 [SMILES: C[C@H](N)CCCc1cc(Cl)c(F)c(-c2cc3cn(-c4ccc([C@@H](N)CCCNC(=N)N)cc4)c(=O)nc3[nH]2)c1] | 553.7 |
| 413 | 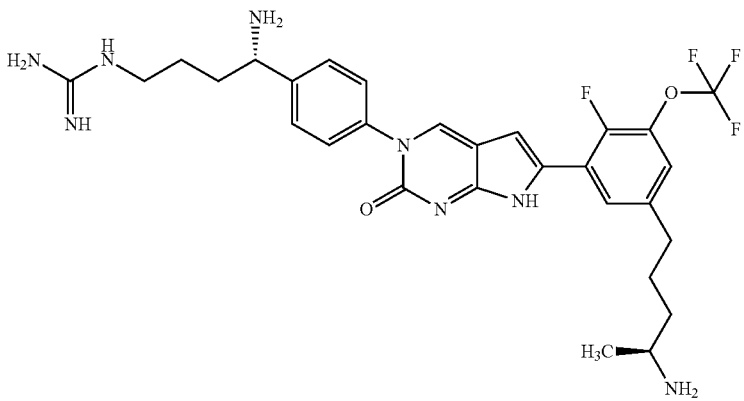 [SMILES: C[C@H](N)CCCc1cc(OC(F)(F)F)c(F)c(-c2cc3cn(-c4ccc([C@@H](N)CCCNC(=N)N)cc4)c(=O)nc3[nH]2)c1] | 603.8 |
| 414 | 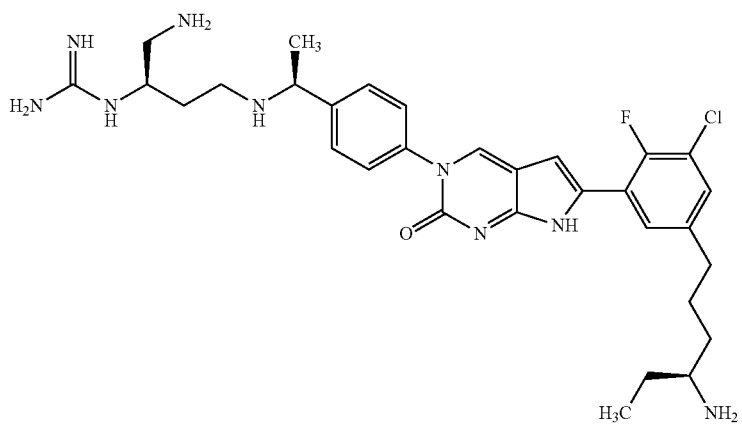 [SMILES: CC[C@H](N)CCCc1cc(Cl)c(F)c(-c2cc3cn(-c4ccc([C@H](C)NCC[C@H](CN)NC(=N)N)cc4)c(=O)nc3[nH]2)c1] | 610.7 |

TABLE 1-continued

| Compound No | Structure | ESI, m/z [M + H]+ |
|---|---|---|
| 415 | 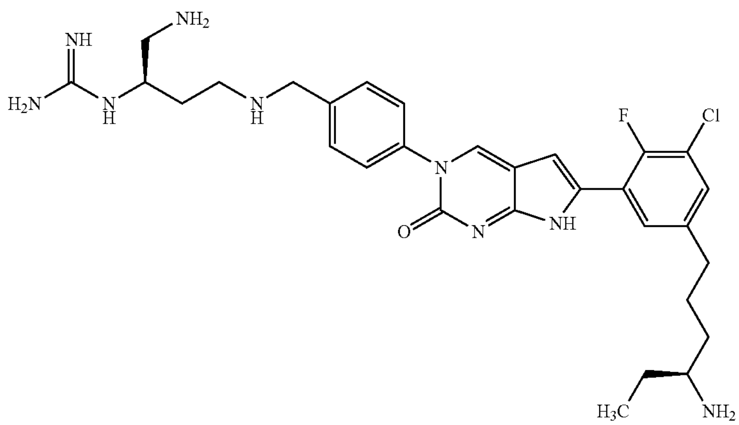 | 596.7 |
| 416 | 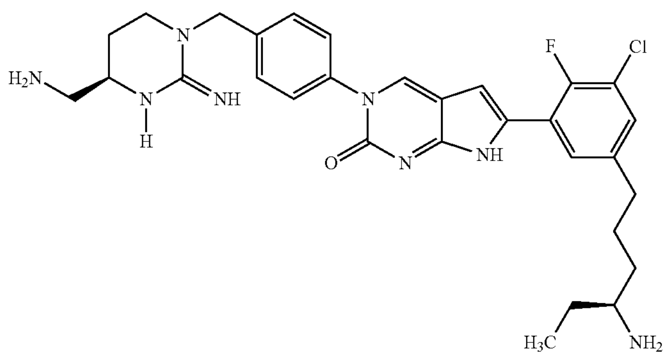 [SMILES: CC[C@H](N)CCCc1cc(Cl)c(F)c(-c2cc3cn(-c4ccc(CN5CC[C@H](CN)NC5=N)cc4)c(=O)nc3[nH]2)c1] | 579.7 |
| 417 | 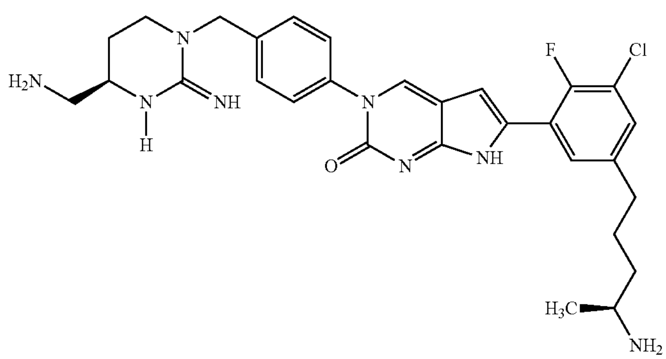 [SMILES: C[C@H](N)CCCc1cc(Cl)c(F)c(-c2cc3cn(-c4ccc(CN5CC[C@H](CN)NC5=N)cc4)c(=O)nc3[nH]2)c1] | 565.7 |
| 418 | 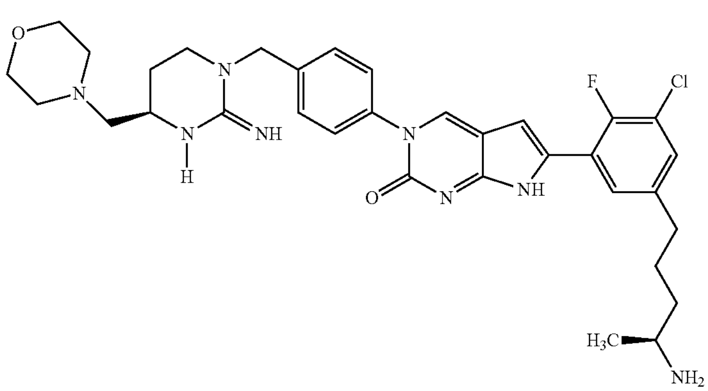 [SMILES: C[C@H](N)CCCc1cc(Cl)c(F)c(-c2cc3cn(-c4ccc(CN5CC[C@H](CN6CCOCC6)NC5=N)cc4)c(=O)nc3[nH]2)c1] | 635.9 |

TABLE 1-continued

| Compound No | Structure | ESI, m/z [M + H]+ |
|---|---|---|
| 419 | 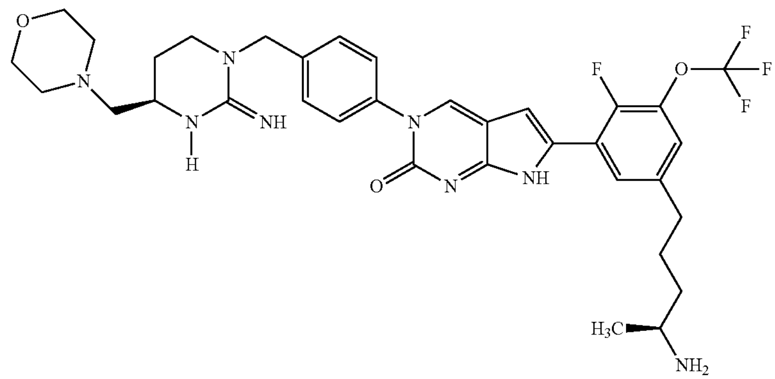 [SMILES: C[C@H](N)CCCc1cc(OC(F)(F)F)c(F)c(-c2cc3cn(-c4ccc(CN5CC[C@H](CN6CCOCC6)NC5=N)cc4)c(=O)nc3[nH]2)c1] | 685.8 |
| 420 | 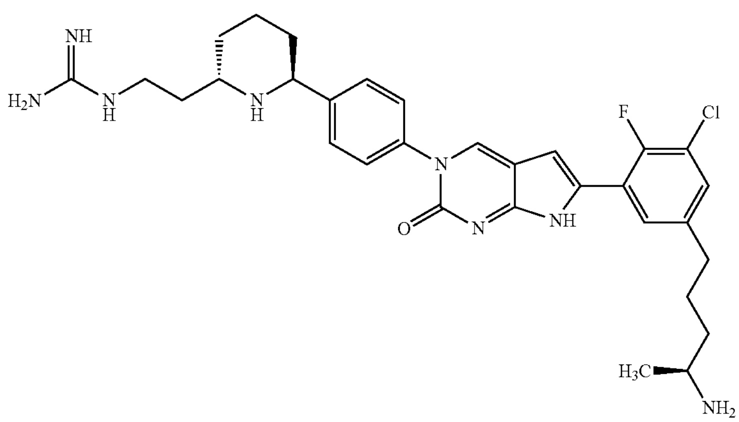 [SMILES: C[C@H](N)CCCc1cc(Cl)c(F)c(-c2cc3cn(-c4ccc([C@@H]5CCC[C@@H](CCNC(=N)N)N5)cc4)c(=O)nc3[nH]2)c1] | 593.7 |
| 421 | 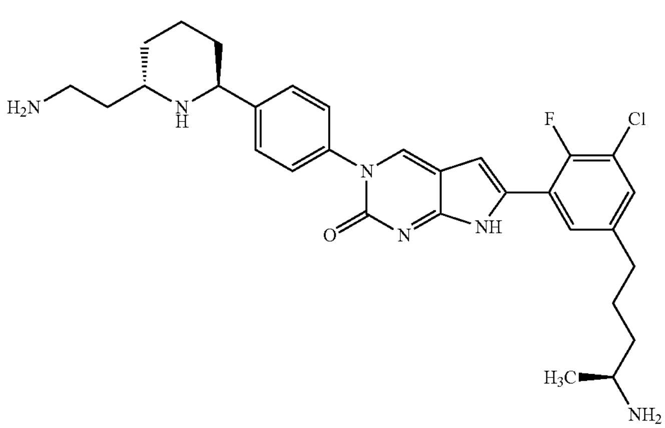 [SMILES: C[C@H](N)CCCc1cc(Cl)c(F)c(-c2cc3cn(-c4ccc([C@@H]5CCC[C@@H](CCN)N5)cc4)c(=O)nc3[nH]2)c1] | 551.7 |

TABLE 1-continued

| Compound No | Structure | ESI, m/z [M + H]+ |
|---|---|---|
| 422 | 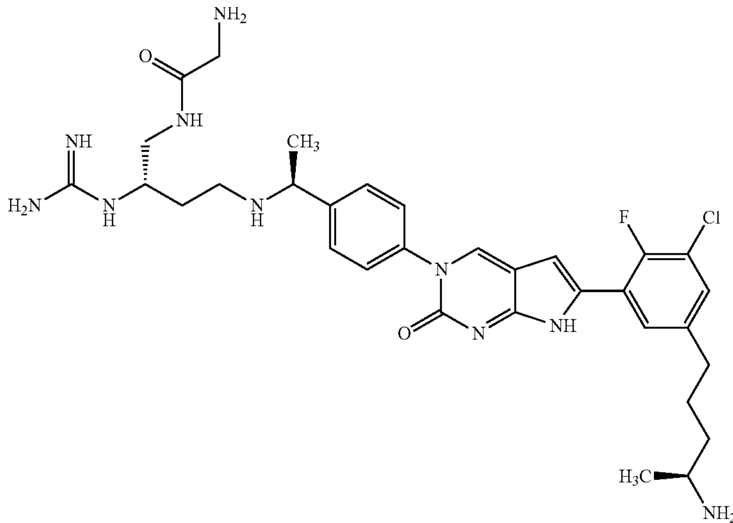 [SMILES: C[C@H](N)CCCc1cc(Cl)c(F)c(-c2cc3cn(-c4ccc([C@H](C)NCC[C@@H](CNC(=O)CN)NC(=N)N)cc4)c(=O)nc3[nH]2)c1] | 653.8 |
| 423 | 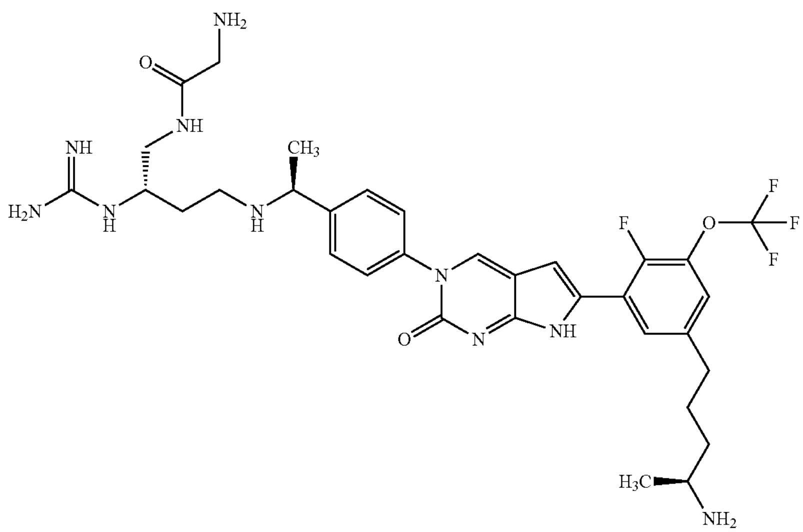 [SMILES: C[C@H](N)CCCc1cc(OC(F)(F)F)c(F)c(-c2cc3cn(-c4ccc([C@H](C)NCC[C@@H](CNC(=O)CN)NC(=N)N)cc4)c(=O)nc3[nH]2)c1] | 703.7 |
| 424 | 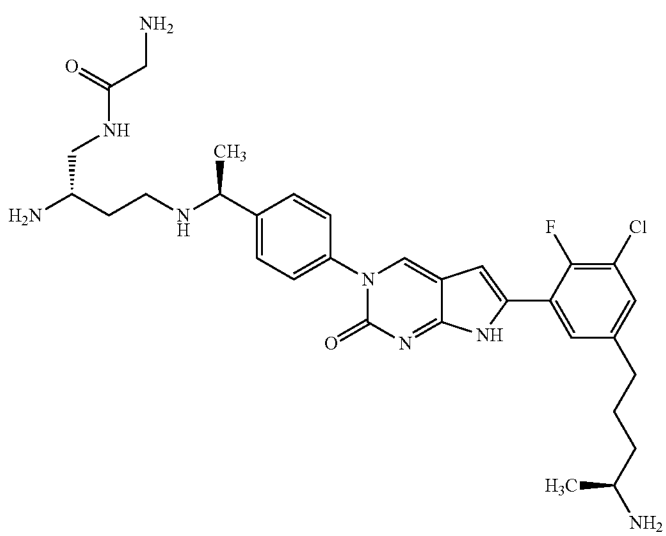 [SMILES: C[C@H](N)CCCc1cc(Cl)c(F)c(-c2cc3cn(-c4ccc([C@H](C)NCC[C@H](N)CNC(=O)CN)cc4)c(=O)nc3[nH]2)c1] | 611.7 |

TABLE 1-continued

| Compound No | Structure | ESI, m/z [M + H]+ |
|---|---|---|
| 425 | 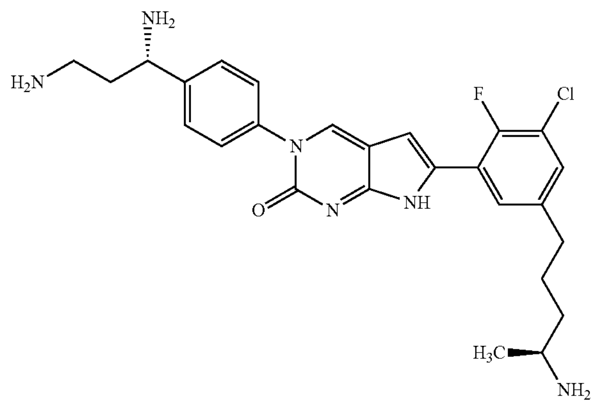 [SMILES: C[C@H](N)CCCc1cc(Cl)c(F)c(-c2cc3cn(-c4ccc([C@@H](N)CCN)cc4)c(=O)nc3[nH]2)c1] | 497.6 |
| 426 | 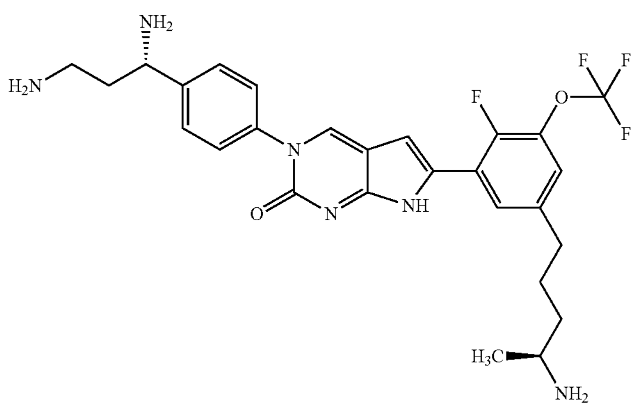 [SMILES: C[C@H](N)CCCc1cc(OC(F)(F)F)c(F)c(-c2cc3cn(-c4ccc([C@@H](N)CCN)cc4)c(=O)nc3[nH]2)c1] | 547.6 |
| 427 | 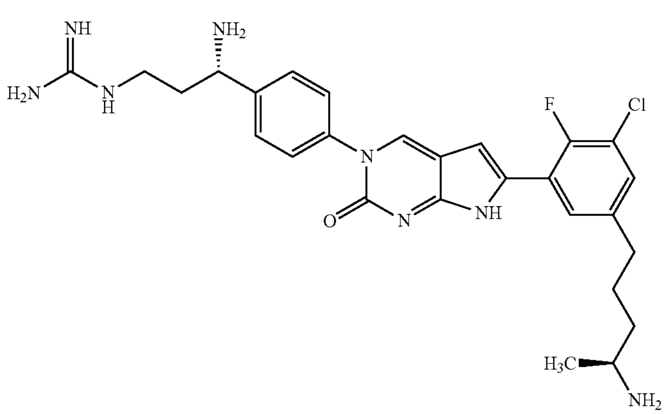 [SMILES: C[C@H](N)CCCc1cc(Cl)c(F)c(-c2cc3cn(-c4ccc([C@@H](N)CCNC(=N)N)cc4)c(=O)nc3[nH]2)c1] | 539.6 |

TABLE 1-continued
| Compound No | Structure | ESI, m/z [M + H]+ |
|---|---|---|
| 428 | 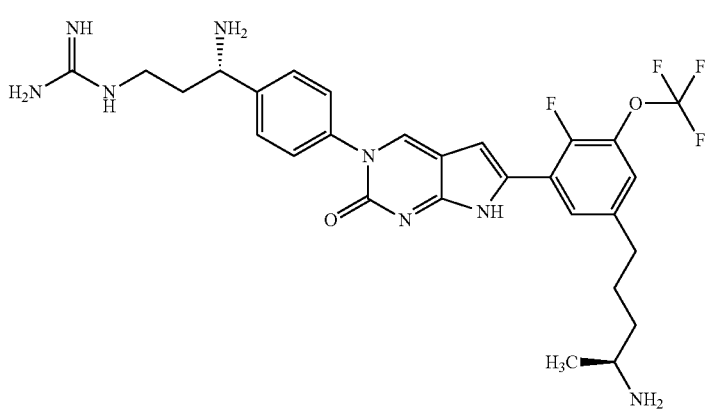 [SMILES: C[C@H](N)CCCc1cc(OC(F)(F)F)c(F)c(-c2cc3cn(-c4ccc([C@@H](N)CCNC(=N)N)cc4)c(=O)nc3[nH]2)c1] | 589.7 |
| 429 | 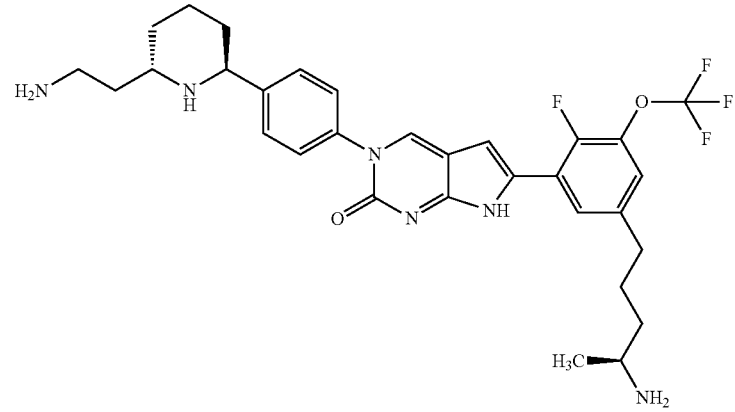 [SMILES: C[C@H](N)CCCc1cc(OC(F)(F)F)c(F)c(-c2cc3cn(-c4ccc([C@@H]5CCC[C@@H](CCN)N5)cc4)c(=O)nc3[nH]2)c1] | 601.7 |
| 430 | 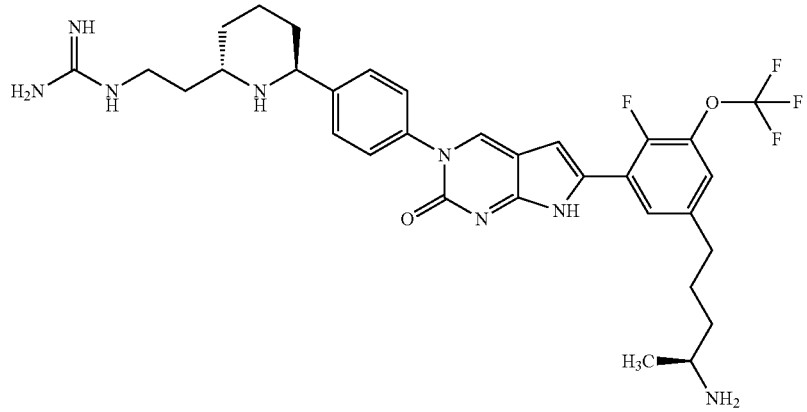 [SMILES: C[C@H](N)CCCc1cc(OC(F)(F)F)c(F)c(-c2cc3cn(-c4ccc([C@@H]5CCC[C@@H](CCNC(=N)N)N5)cc4)c(=O)nc3[nH]2)c1] | 643.7 |

TABLE 1-continued
| Compound No | Structure | ESI, m/z [M + H]+ |
|---|---|---|
| 431 | 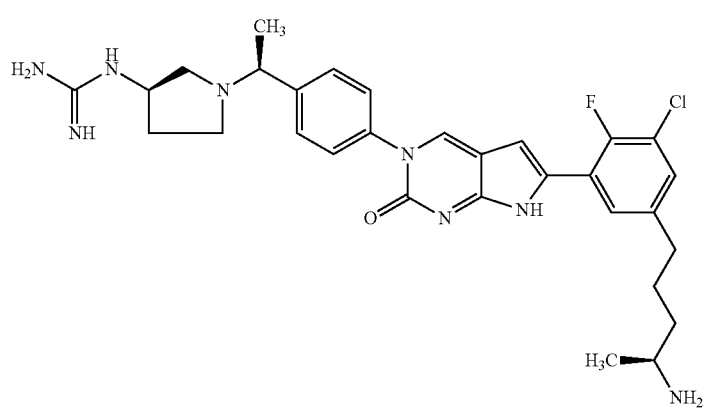 [SMILES: C[C@H](N)CCCc1cc(Cl)c(F)c(-c2cc3cn(-c4ccc([C@H](C)N5CC[C@@H](NC(=N)N)C5)cc4)c(=O)nc3[nH]2)c1] | 579.7 |
| 432 | 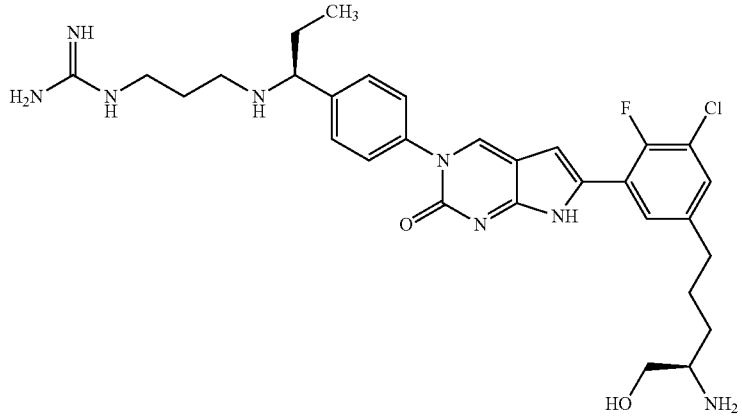 [SMILES: CC[C@H](NCCCNC(=N)N)c1ccc(-n2cc3cc(-c4cc(CCC[C@@H](N)CO)cc(Cl)c4F)[nH]c3nc2=O)cc1] | 597.7 |
| 433 | 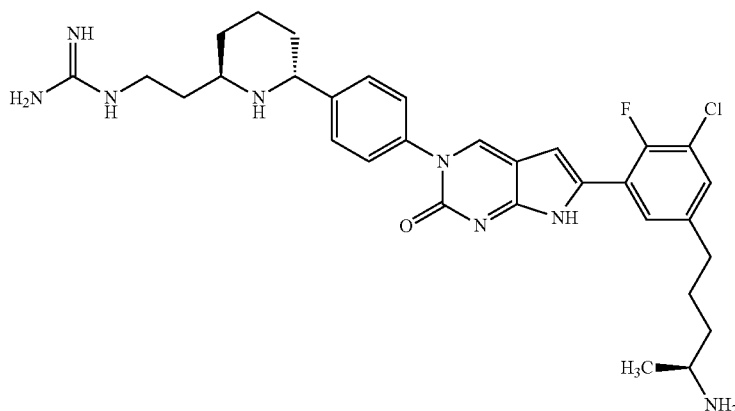 | 593.7 |

TABLE 1-continued

| Compound No | Structure | ESI, m/z [M + H]+ |
|---|---|---|
| 434 | 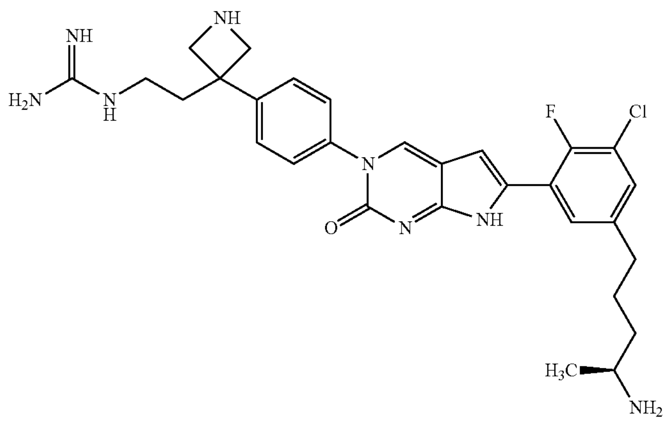 [SMILES: C[C@H](N)CCCc1cc(Cl)c(F)c(-c2cc3cn(-c4ccc(C5(CCNC(=N)N)CNC5)cc4)c(=O)nc3[nH]2)c1] | 566.09 |
| 435 | 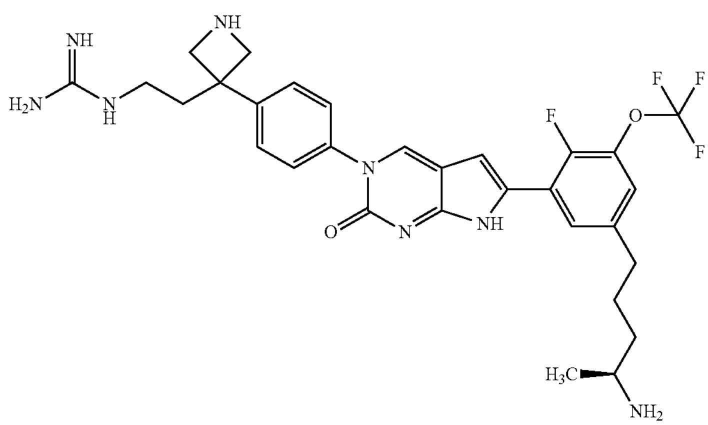 [SMILES: C[C@H](N)CCCc1cc(OC(F)(F)F)c(F)c(-c2cc3cn(-c4ccc(C5(CCNC(=N)N)CNC5)cc4)c(=O)nc3[nH]2)c1] | 615.64 |
| 436 | 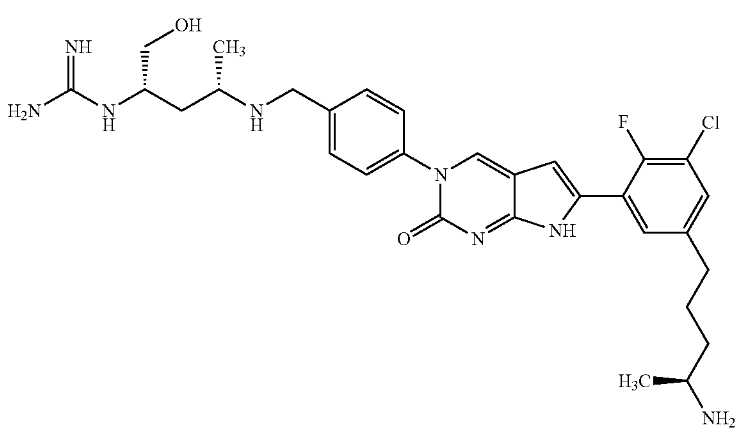 | 597.7 |

TABLE 1-continued
| Compound No | Structure | ESI, m/z [M + H]+ |
|---|---|---|
| 437 | 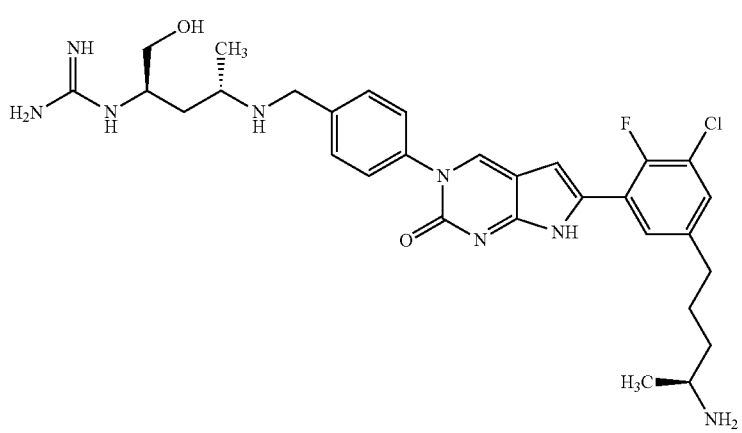 [SMILES: C[C@H](N)CCCc1cc(Cl)c(F)c(-c2cc3cn(-c4ccc(CN[C@@H](C)C[C@H](CO)NC(=N)N)cc4)c(=O)nc3[nH]2)c1] | 597.7 |
| 438 | 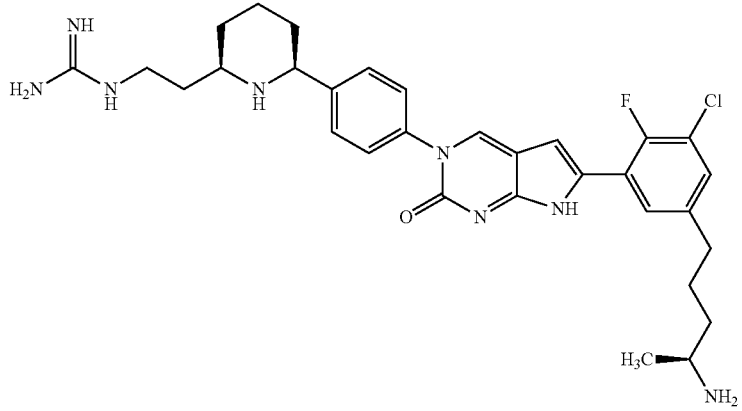 [SMILES: C[C@H](N)CCCc1cc(Cl)c(F)c(-c2cc3cn(-c4ccc([C@@H]5CCC[C@H](CCNC(=N)N)N5)cc4)c(=O)nc3[nH]2)c1] | 593.7 |
| 439 | 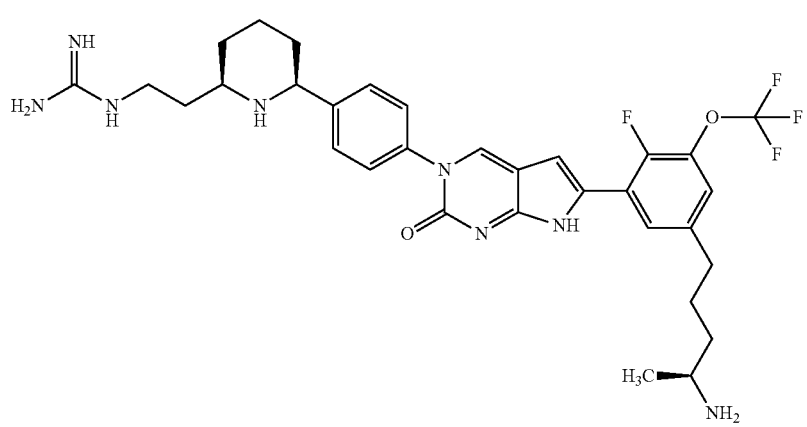 [SMILES: C[C@H](N)CCCc1cc(OC(F)(F)F)c(F)c(-c2cc3cn(-c4ccc([C@@H]5CCC[C@H](CCNC(=N)N)N5)cc4)c(=O)nc3[nH]2)c1] | 643.7 |

TABLE 1-continued

| Compound No | Structure | ESI, m/z [M + H]+ |
|---|---|---|
| 440 | 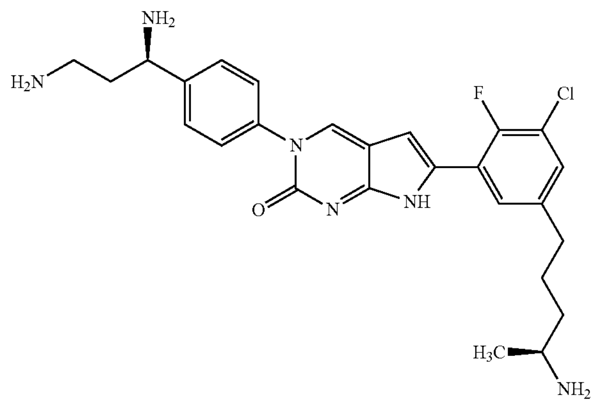 [SMILES: C[C@H](N)CCCc1cc(Cl)c(F)c(-c2cc3cn(-c4ccc([C@H](N)CCN)cc4)c(=O)nc3[nH]2)c1] | 497.6 |
| 441 | 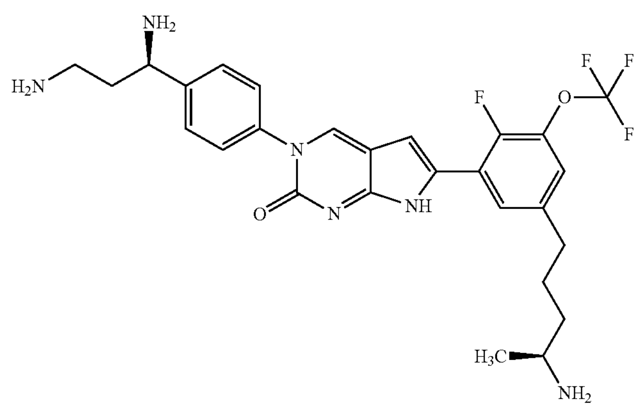 [SMILES: C[C@H](N)CCCc1cc(OC(F)(F)F)c(F)c(-c2cc3cn(-c4ccc([C@H](N)CCN)cc4)c(=O)nc3[nH]2)c1] | 547.7 |
| 442 | 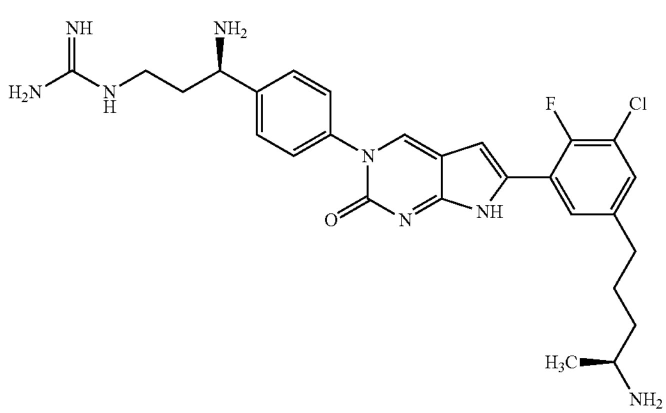 [SMILES: C[C@H](N)CCCc1cc(Cl)c(F)c(-c2cc3cn(-c4ccc([C@H](N)CCNC(=N)N)cc4)c(=O)nc3[nH]2)c1] | 539.7 |

TABLE 1-continued

| Compound No | Structure | ESI, m/z [M + H]+ |
|---|---|---|
| 443 | 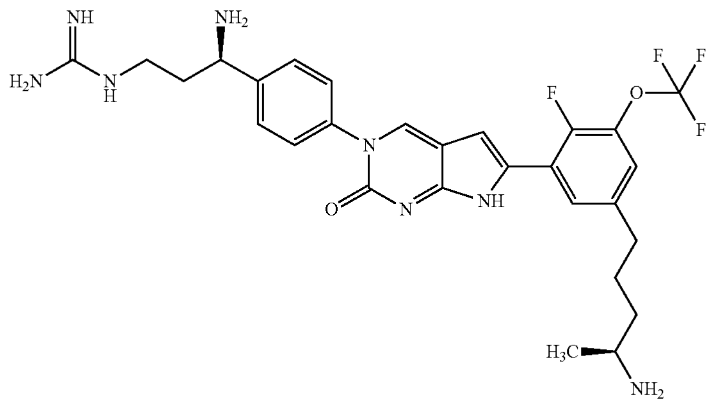 [SMILES: C[C@H](N)CCCc1cc(OC(F)(F)F)c(F)c(-c2cc3cn(-c4ccc([C@H](N)CCNC(=N)N)cc4)c(=O)nc3[nH]2)c1] | 589.7 |
| 444 | 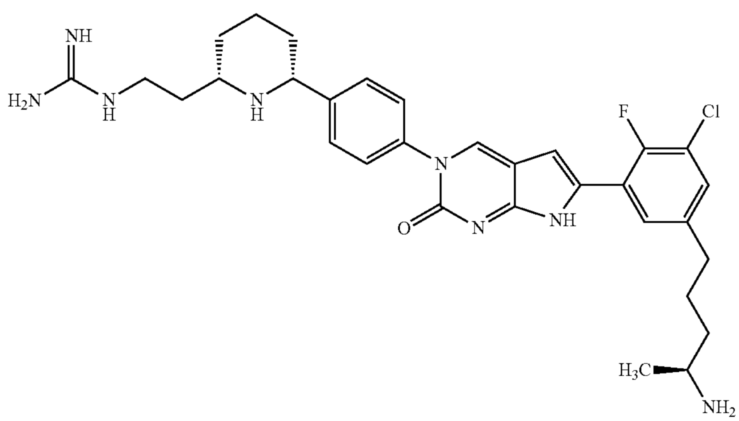 [SMILES: C[C@H](N)CCCc1cc(Cl)c(F)c(-c2cc3cn(-c4ccc([C@H]5CCC[C@@H](CCNC(=N)N)N5)cc4)c(=O)nc3[nH]2)c1] | 593.6 |
| 445 | 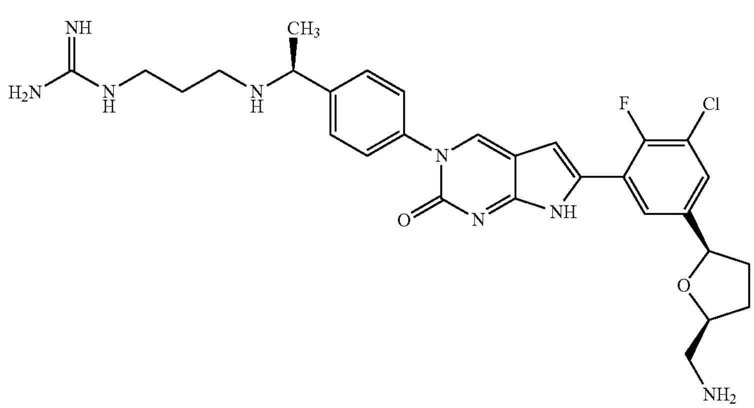 [SMILES: C[C@H](NCCCNC(=N)N)c1ccc(-n2cc3cc(-c4cc([C@H]5CC[C@@H](CN)O5)cc(Cl)c4F)[nH]c3nc2=O)cc1] | 581.6 |

TABLE 1-continued
| Compound No | Structure | ESI, m/z [M + H]+ |
|---|---|---|
| 446 | 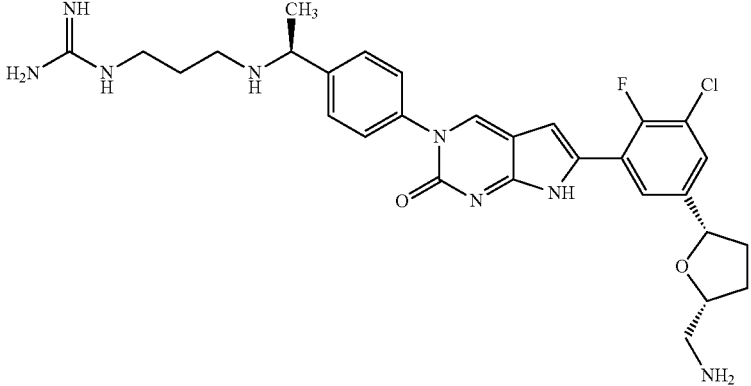 [SMILES: C[C@H](NCCCNC(=N)N)c1ccc(-n2cc3cc(-c4cc([C@@H]5CC[C@H](CN)O5)cc(Cl)c4F)[nH]c3nc2=O)cc1] | 581.6 |
| 447 | 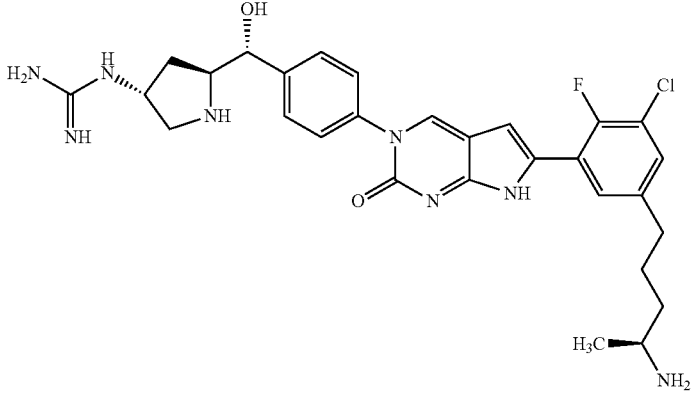 [SMILES: C[C@H](N)CCCc1cc(Cl)c(F)c(-c2cc3cn(-c4ccc([C@@H](O)[C@@H]5C[C@@H](NC(=N)N)CN5)cc4)c(=O)nc3[nH]2)c1] | 581.6 |
| 448 | 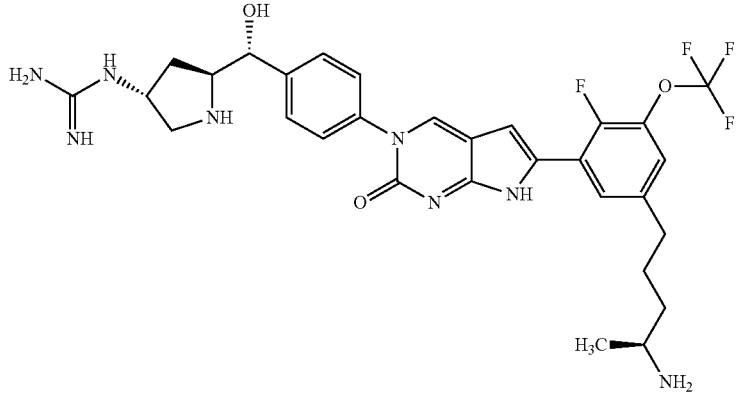 [SMILES: C[C@H](N)CCCc1cc(OC(F)(F)F)c(F)c(-c2cc3cn(-c4ccc([C@@H](O)[C@@H]5C[C@@H](NC(=N)N)CN5)cc4)c(=O)nc3[nH]2)c1] | 631.7 |

TABLE 1-continued
| Compound No | Structure | ESI, m/z [M + H]+ |
|---|---|---|
| 449 | 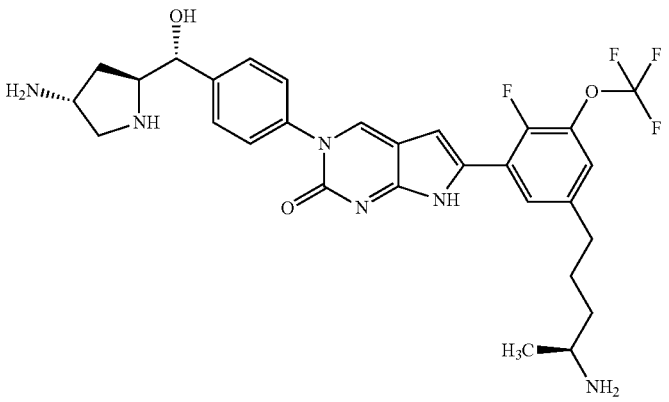 [SMILES: C[C@H](N)CCCc1cc(OC(F)(F)F)c(F)c(-c2cc3cn(-c4ccc([C@@H](O)[C@@H]5C[C@@H](N)CN5)cc4)c(=O)nc3[nH]2)c1] | 589.6 |
| 450 | 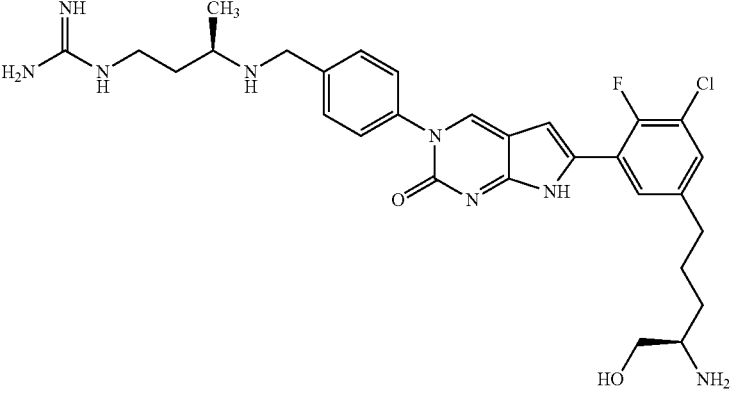 [SMILES: C[C@H](CCNC(=N)N)NCc1ccc(-n2cc3cc(-c4cc(CCC[C@@H](N)CO)cc(Cl)c4F)[nH]c3nc2=O)cc1] | 583.6 |
| 451 | 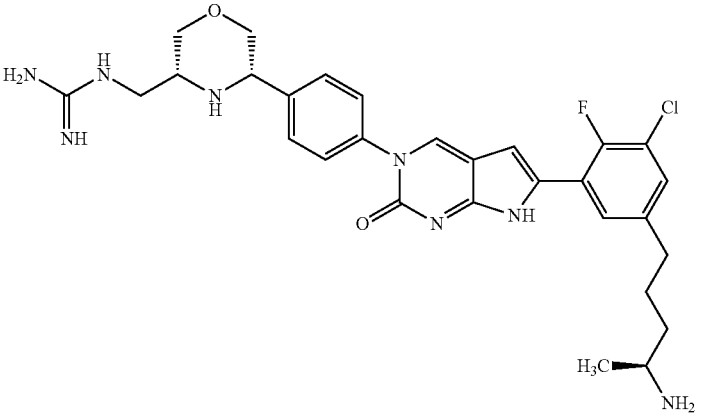 [SMILES: C[C@H](N)CCCc1cc(Cl)c(F)c(-c2cc3cn(-c4ccc([C@H]5COC[C@@H](CNC(=N)N)N5)cc4)c(=O)nc3[nH]2)c1] | 581.6 |

TABLE 1-continued

| Compound No | Structure | ESI, m/z [M + H]+ |
|---|---|---|
| 452 | 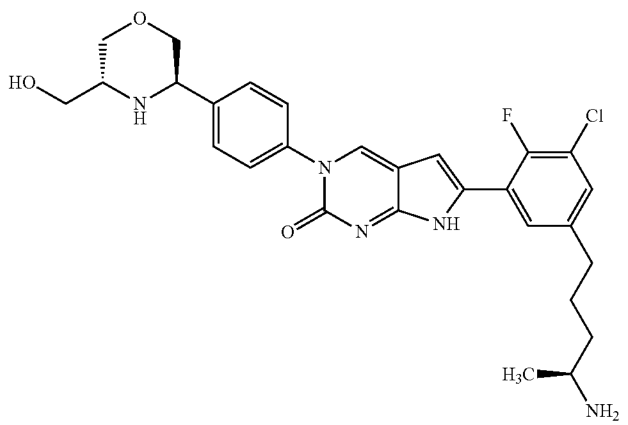 [SMILES: C[C@H](N)CCCc1cc(Cl)c(F)c(-c2cc3cn(-c4ccc([C@@H]5COC[C@@H](CO)N5)cc4)c(=O)nc3[nH]2)c1] | 540.6 |
| 453 | 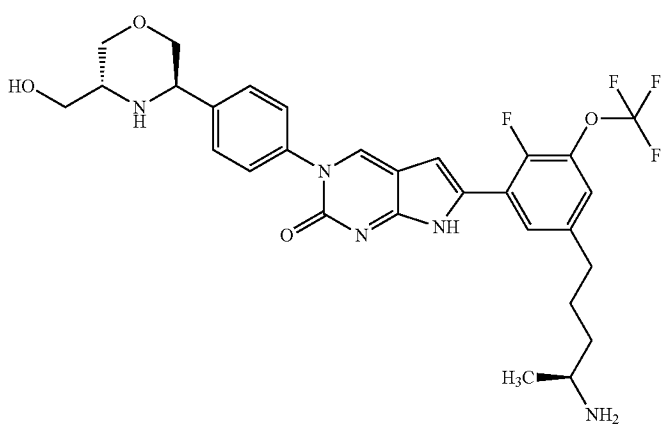 [SMILES: C[C@H](N)CCCc1cc(OC(F)(F)F)c(F)c(-c2cc3cn(-c4ccc([C@@H]5COC[C@@H](CO)N5)cc4)c(=O)nc3[nH]2)c1] | 590.6 |
| 454 | 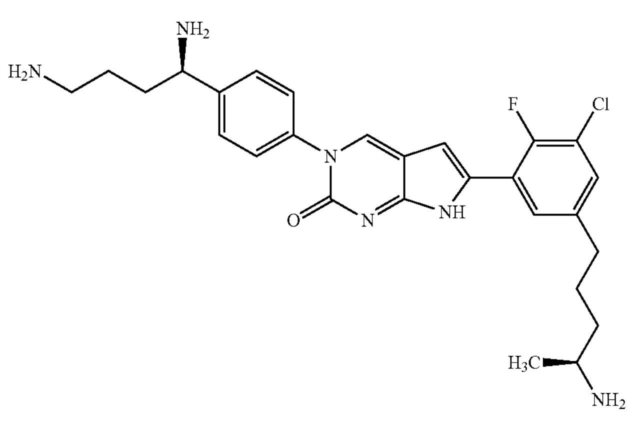 [SMILES: C[C@H](N)CCCc1cc(Cl)c(F)c(-c2cc3cn(-c4ccc([C@H](N)CCCN)cc4)c(=O)nc3[nH]2)c1] | 511.6 |

TABLE 1-continued

| Compound No | Structure | ESI, m/z [M + H]+ |
|---|---|---|
| 455 | 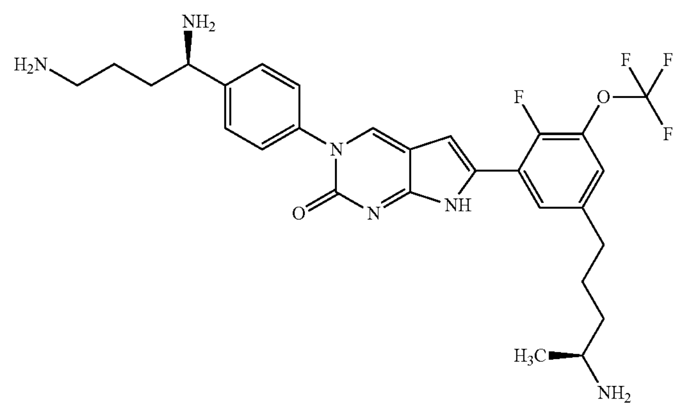 [SMILES: C[C@H](N)CCCc1cc(OC(F)(F)F)c(F)c(-c2cc3cn(-c4ccc([C@H](N)CCCN)cc4)c(=O)nc3[nH]2)c1] | 561.6 |
| 456 | 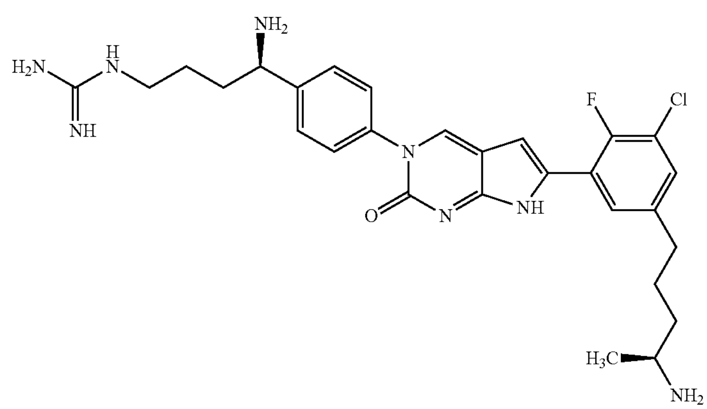 [SMILES: C[C@H](N)CCCc1cc(Cl)c(F)c(-c2cc3cn(-c4ccc([C@H](N)CCCNC(=N)N)cc4)c(=O)nc3[nH]2)c1] | 553.6 |
| 457 | 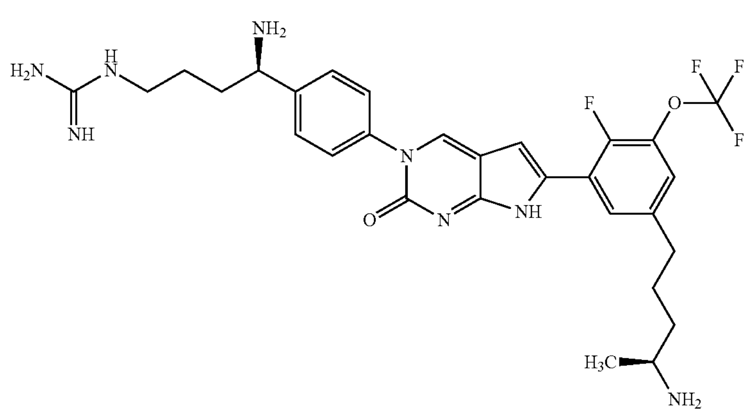 [SMILES: C[C@H](N)CCCc1cc(OC(F)(F)F)c(F)c(-c2cc3cn(-c4ccc([C@H](N)CCCNC(=N)N)cc4)c(=O)nc3[nH]2)c1] | 603.6 |

TABLE 1-continued

| Compound No | Structure | ESI, m/z [M + H]+ |
|---|---|---|
| 458 | 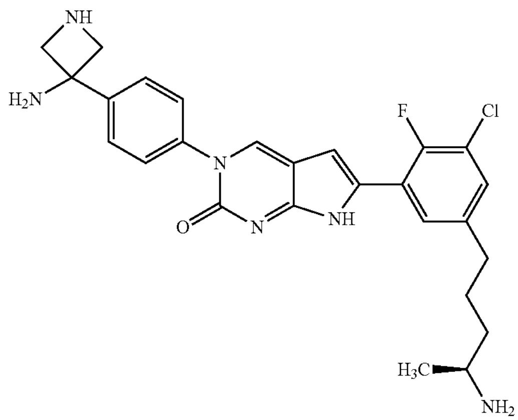 [SMILES: C[C@H](N)CCCc1cc(Cl)c(F)c(-c2cc3cn(-c4ccc(C5(N)CNC5)cc4)c(=O)nc3[nH]2)c1] | 496 |
| 459 | 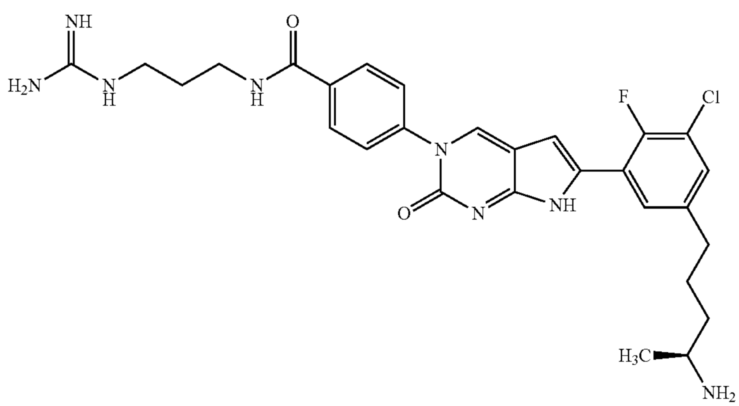 [SMILES: C[C@H](N)CCCc1cc(Cl)c(F)c(-c2cc3cn(-c4ccc(C(=O)NCCCNC(=N)N)cc4)c(=O)nc3[nH]2)c1] | 567.6 |
| 460 | 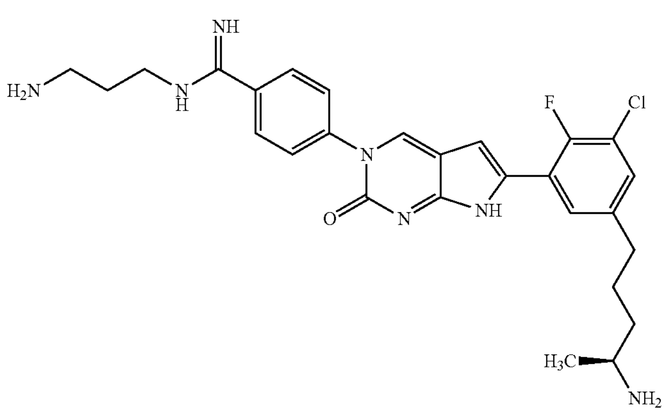 [SMILES: C[C@H](N)CCCc1cc(Cl)c(F)c(-c2cc3cn(-c4ccc(C(=N)NCCCN)cc4)c(=O)nc3[nH]2)c1] | 524.6 |

TABLE 1-continued

| Compound No | Structure | ESI, m/z [M + H]+ |
|---|---|---|
| 461 | 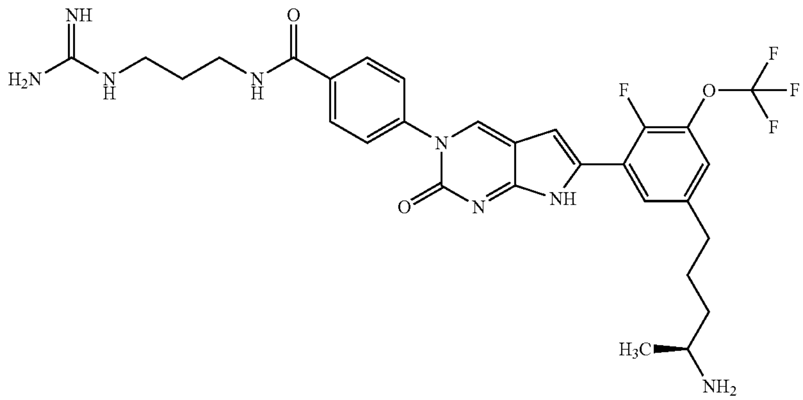 [SMILES: C[C@H](N)CCCc1cc(OC(F)(F)F)c(F)c(-c2cc3cn(-c4ccc(C(=O)NCCCNC(=N)N)cc4)c(=O)nc3[nH]2)c1] | 617.6 |
| 462 | 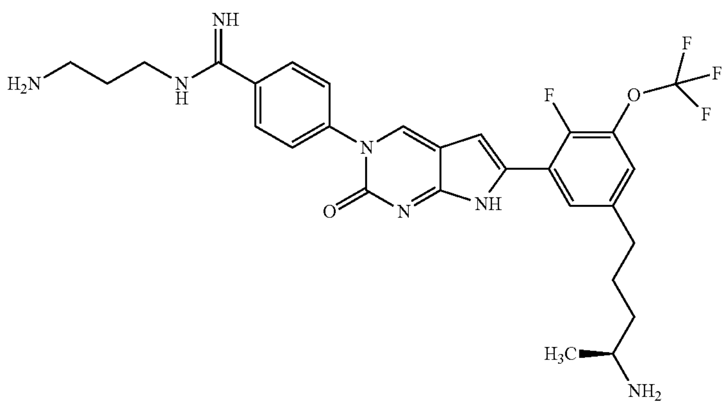 [SMILES: C[C@H](N)CCCc1cc(OC(F)(F)F)c(F)c(-c2cc3cn(-c4ccc(C(=N)NCCCN)cc4)c(=O)nc3[nH]2)c1] | 574.6 |
| 463 | 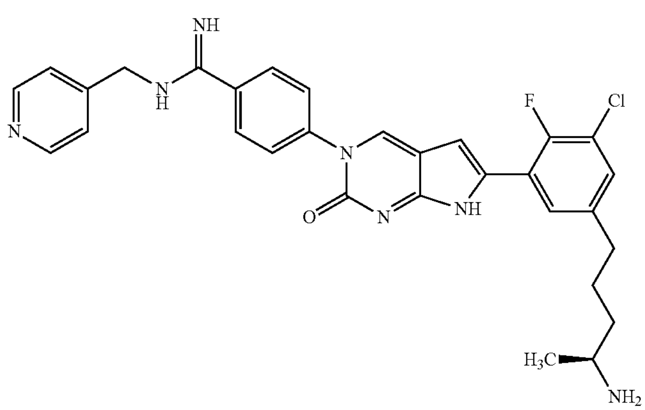 [SMILES: C[C@H](N)CCCc1cc(Cl)c(F)c(-c2cc3cn(-c4ccc(C(=N)NCc5ccncc5)cc4)c(=O)nc3[nH]2)c1] | 576.6 |

TABLE 1-continued

| Compound No | Structure | ESI, m/z [M + H]+ |
|---|---|---|
| 464 | 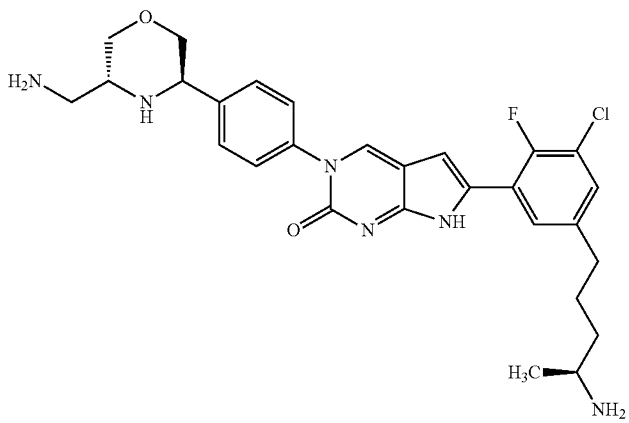 [SMILES: C[C@H](N)CCCc1cc(Cl)c(F)c(-c2cc3cn(-c4ccc([C@@H]5COC[C@@H](CN)N5)cc4)c(=O)nc3[nH]2)c1] | 539.6 |
| 465 | 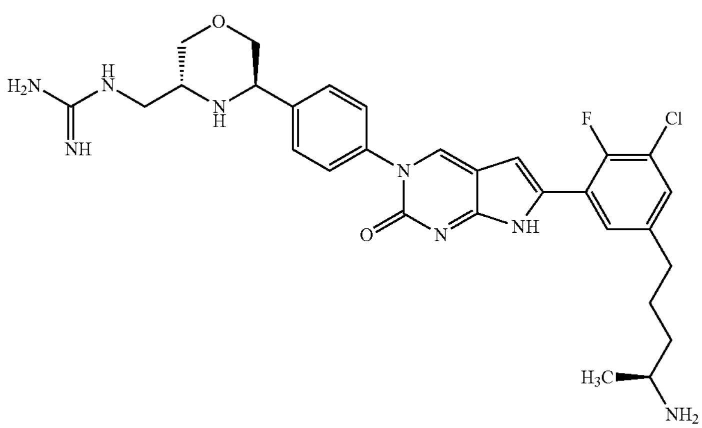 [SMILES: C[C@H](N)CCCc1cc(Cl)c(F)c(-c2cc3cn(-c4ccc([C@@H]5COC[C@@H](CNC(=N)N)N5)cc4)c(=O)nc3[nH]2)c1] | 581.6 |
| 466 | 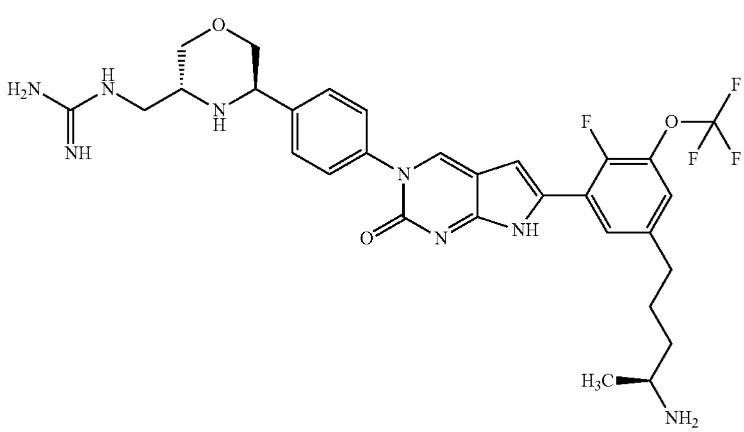 [SMILES: C[C@H](N)CCCc1cc(OC(F)(F)F)c(F)c(-c2cc3cn(-c4ccc([C@@H]5COC[C@@H](CNC(=N)N)N5)cc4)c(=O)nc3[nH]2)c1] | 631.6 |

TABLE 1-continued
| Compound No | Structure | ESI, m/z [M + H]+ |
|---|---|---|
| 467 | 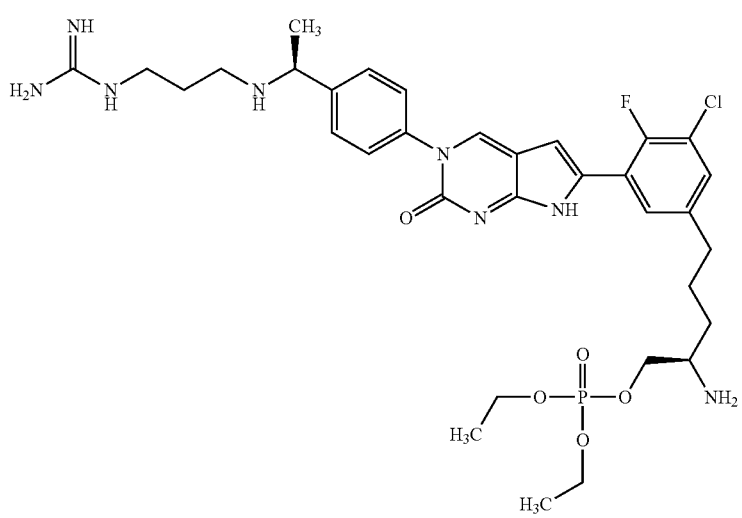 [SMILES: CCOP(=O)(OCC)OC[C@H](N)CCCc1cc(Cl)c(F)c(-c2cc3cn(-c4ccc([C@H](C)NCCCNC(=N)N)cc4)c(=O)nc3[nH]2)c1] | 719.7 |
| 468 | 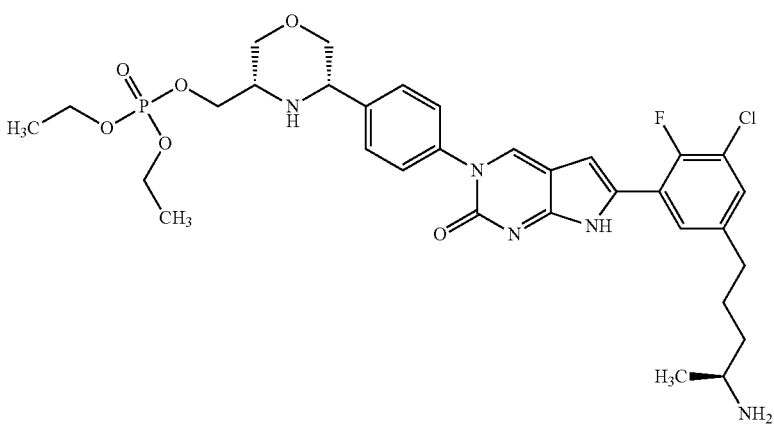 [SMILES: CCOP(=O)(OCC)OC[C@@H]1COC[C@H](c2ccc(-n3cc4cc(-c5cc(CCC[C@H](C)N)cc(Cl)c5F)[nH]c4nc3=O)cc2)N1] | 677.6 |
| 469 | 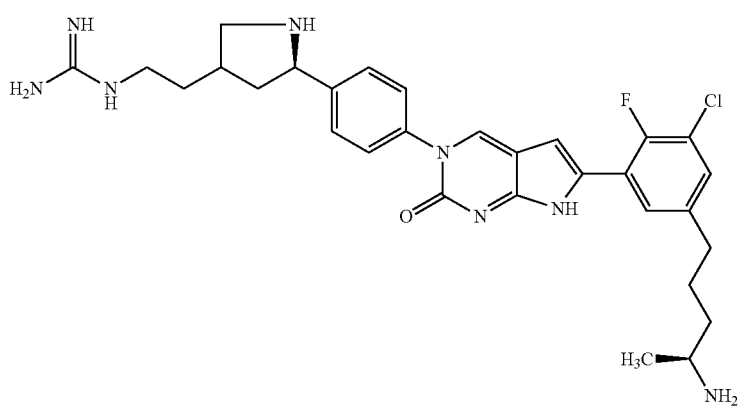 | 579.6 |

TABLE 1-continued
| Compound No | Structure | ESI, m/z [M + H]+ |
|---|---|---|
| 470 | 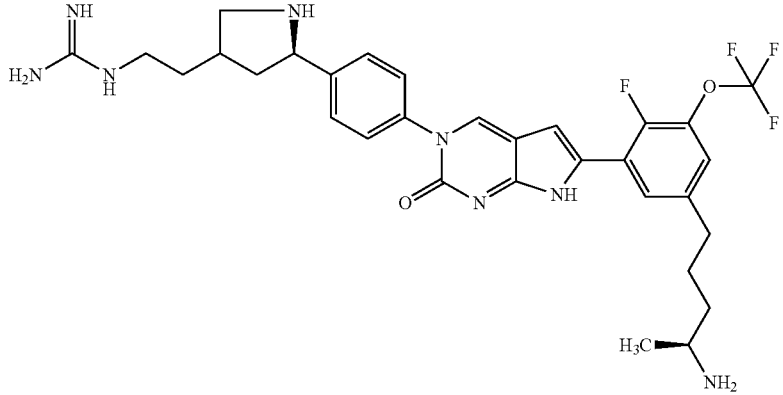 | 629.6 |
| 471 | 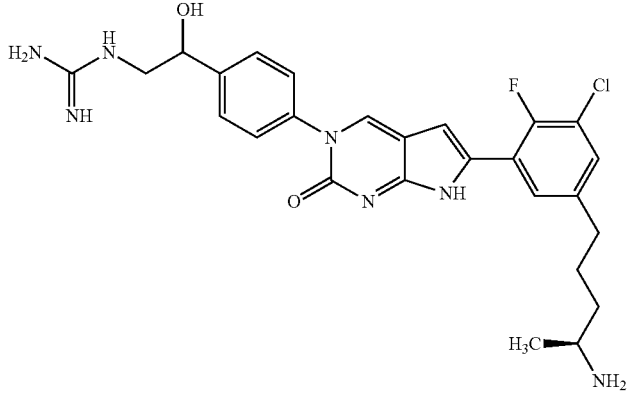 [SMILES: C[C@H](N)CCCc1cc(Cl)c(F)c(-c2cc3cn(-c4ccc(C(O)CNC(=N)N)cc4)c(=O)nc3[nH]2)c1] | 527.01 |
| 472 | 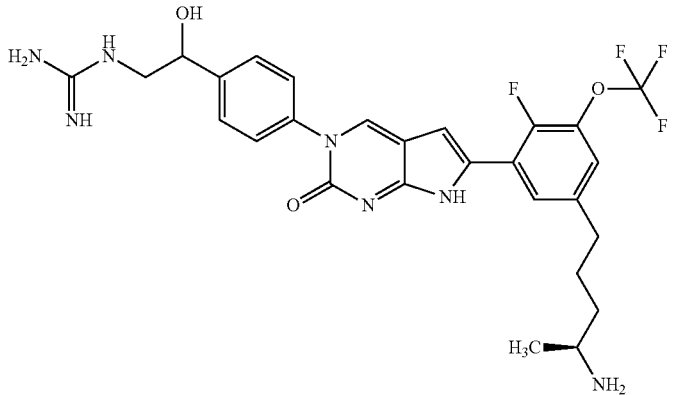 [SMILES: C[C@H](N)CCCc1cc(OC(F)(F)F)c(F)c(-c2cc3cn(-c4ccc(C(O)CNC(=N)N)cc4)c(=O)nc3[nH]2)c1] | 576.57 |

TABLE 1-continued
| Compound No | Structure | ESI, m/z [M + H]+ |
|---|---|---|
| 473 | 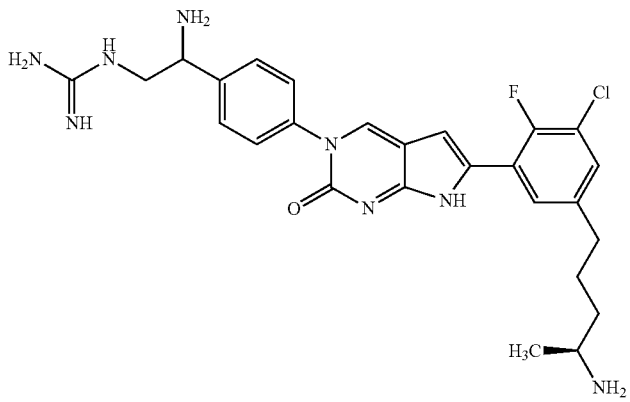 | 526.03 |
| 474 | 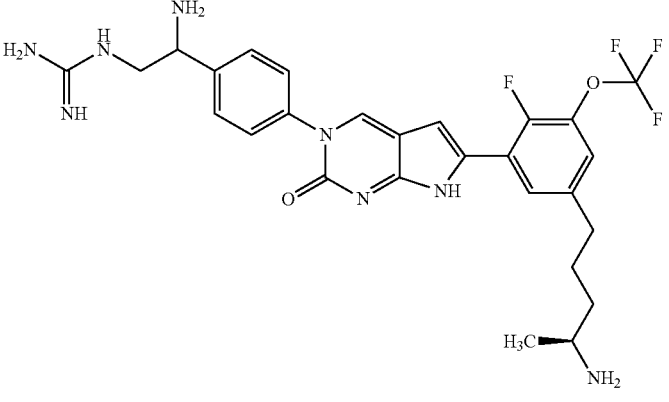 [SMILES: C[C@H](N)CCCc1cc(OC(F)(F)F)c(F)c(-c2cc3cn(-c4ccc(C(N)CNC(=N)N)cc4)c(=O)nc3[nH]2)c1] | 575.58 |
| 475 | 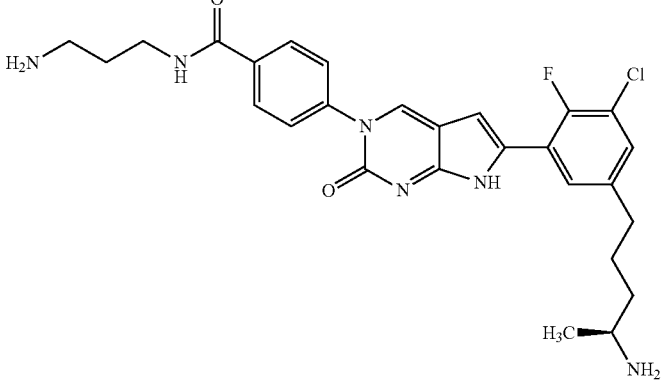 | 525.6 |

TABLE 1-continued
| Compound No | Structure | ESI, m/z [M + H]+ |
|---|---|---|
| 476 | 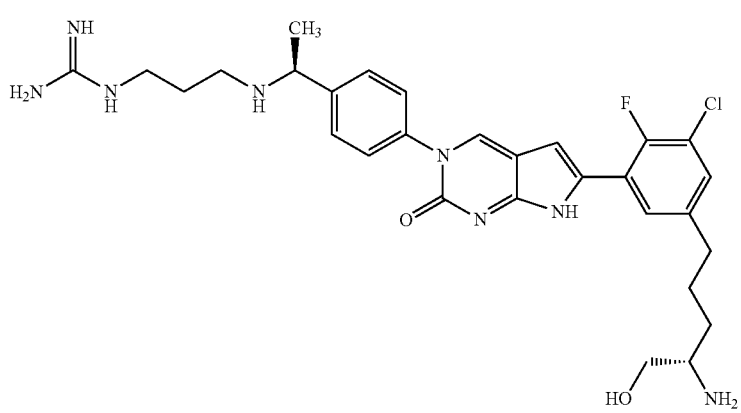 [SMILES: C[C@H](NCCCNC(=N)N)c1ccc(-n2cc3cc(-c4cc(CCC[C@H](N)CO)cc(Cl)c4F)[nH]c3nc2=O)cc1] | 583.6 |
| 477 | 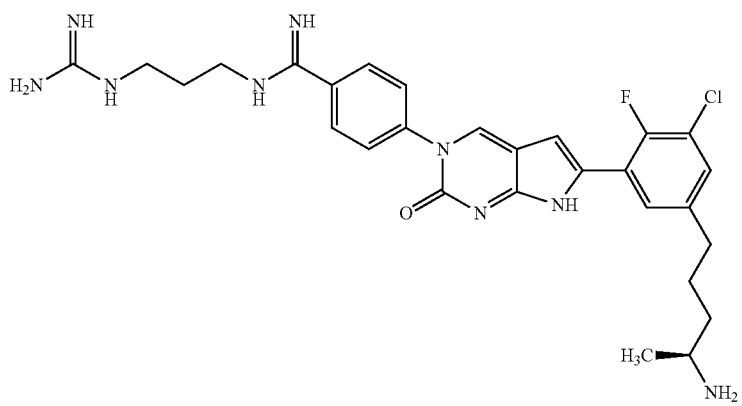 | 566.6 |
| 478 | 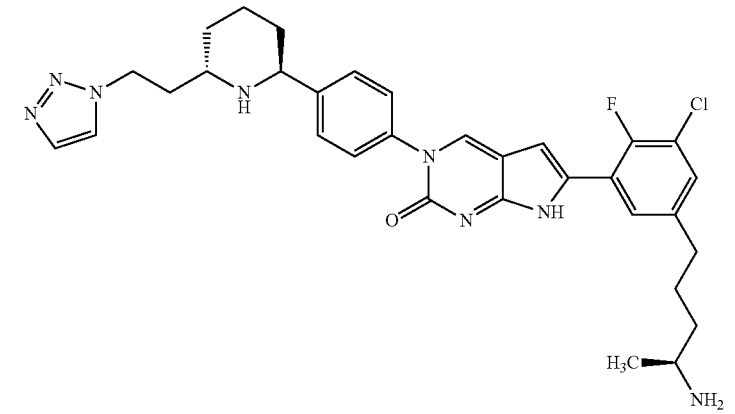 [SMILES: C[C@H](N)CCCc1cc(Cl)c(F)c(-c2cc3cn(-c4ccc([C@@H]5CCC[C@@H](CCn6ccnn6)N5)cc4)c(=O)nc3[nH]2)c1] | 603.7 |

TABLE 1-continued

| Compound No | Structure | ESI, m/z [M + H]+ |
|---|---|---|
| 479 | 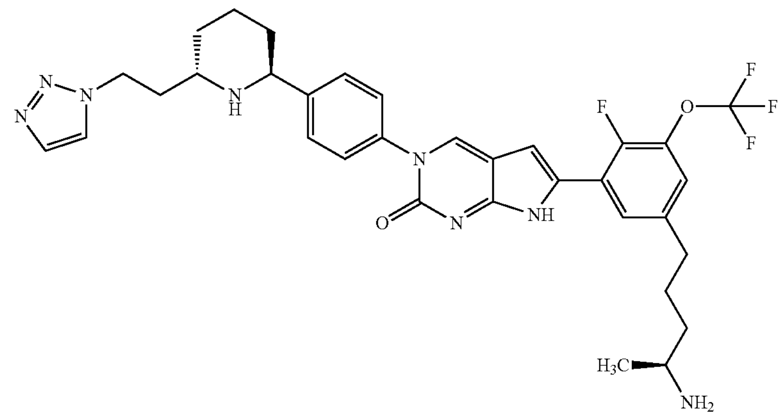 [SMILES: C[C@H](N)CCCc1cc(OC(F)(F)F)c(F)c(-c2cc3cn(-c4ccc([C@@H]5CCC[C@@H](CCn6ccnn6)N5)cc4)c(=O)nc3[nH]2)c1] | 653.8 |
| 480 | 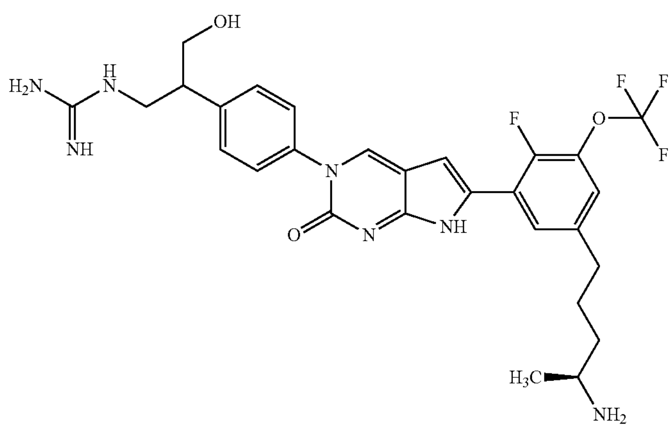 [SMILES: C[C@H](N)CCCc1cc(OC(F)(F)F)c(F)c(-c2cc3cn(-c4ccc(C(CO)CNC(=N)N)cc4)c(=O)nc3[nH]2)c1] | 590.59 |
| 481 | 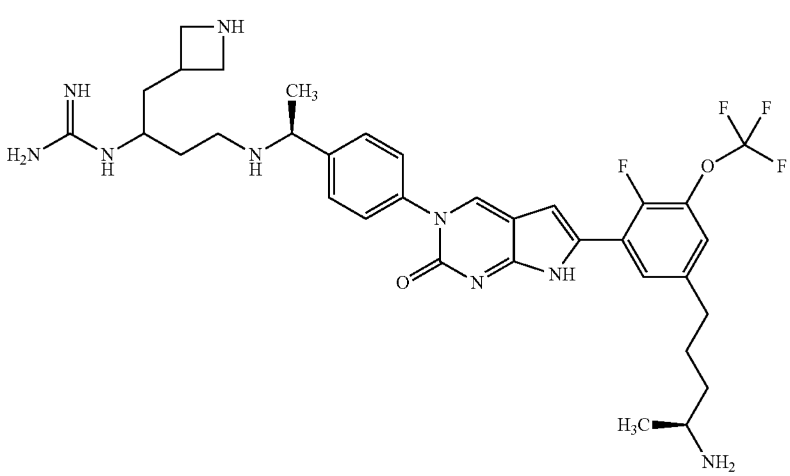 [SMILES: C[C@H](N)CCCc1cc(OC(F)(F)F)c(F)c(-c2cc3cn(-c4ccc([C@H](C)NCCC(CC5CNC5)NC(=N)N)cc4)c(=O)nc3[nH]2)c1] | 686.77 |

TABLE 1-continued
| Compound No | Structure | ESI, m/z [M + H]+ |
|---|---|---|
| 482 | 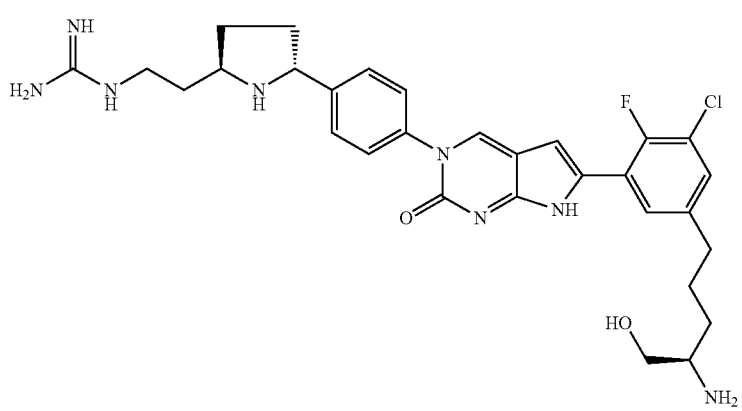 [SMILES: N=C(N)NCC[C@H]1CC[C@H](c2ccc(-n3cc4cc(-c5cc(CCC[C@@H](N)CO)cc(Cl)c5F)[nH]c4nc3=O)cc2)N1] | 595.6 |
| 483 | 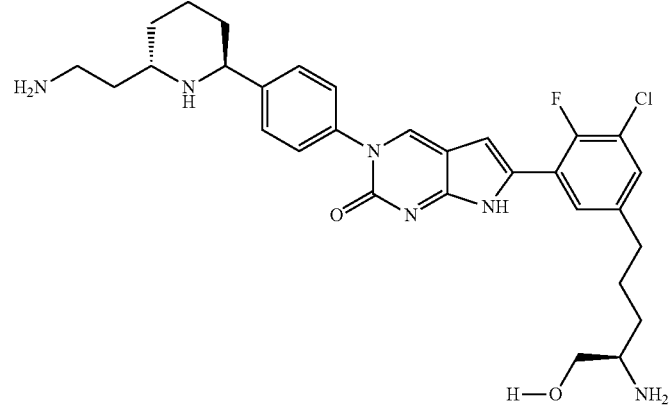 [SMILES: NCC[C@@H]1CCC[C@@H](c2ccc(-n3cc4cc(-c5cc(CCC[C@@H](N)CO)cc(Cl)c5F)[nH]c4nc3=O)cc2)N1] | 567.6 |
| 484 | 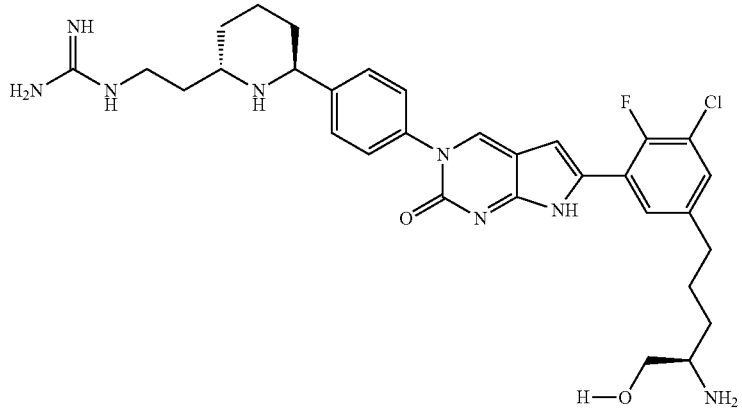 [SMILES: N=C(N)NCC[C@@H]1CCC[C@@H](c2ccc(-n3cc4cc(-c5cc(CCC[C@@H](N)CO)cc(Cl)c5F)[nH]c4nc3=O)cc2)N1] | 609.6 |

TABLE 1-continued

| Compound No | Structure | ESI, m/z [M + H]+ |
|---|---|---|
| 485 | 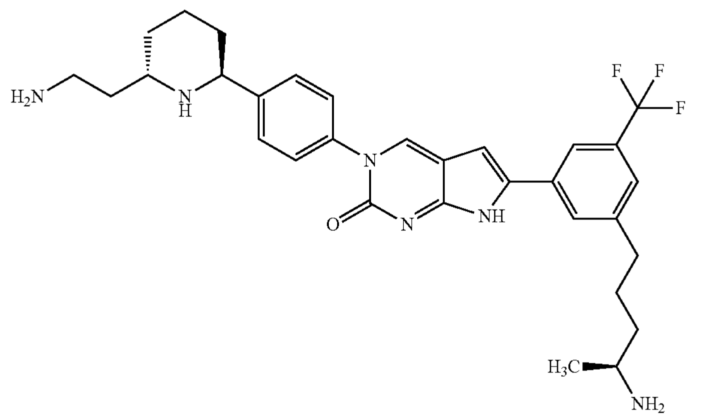 [SMILES: C[C@H](N)CCCc1cc(-c2cc3cn(-c4ccc([C@@H]5CCC[C@@H](CCN)N5)cc4)c(=O)nc3[nH]2)cc(C(F)(F)F)c1] | 567.7 |
| 486 | 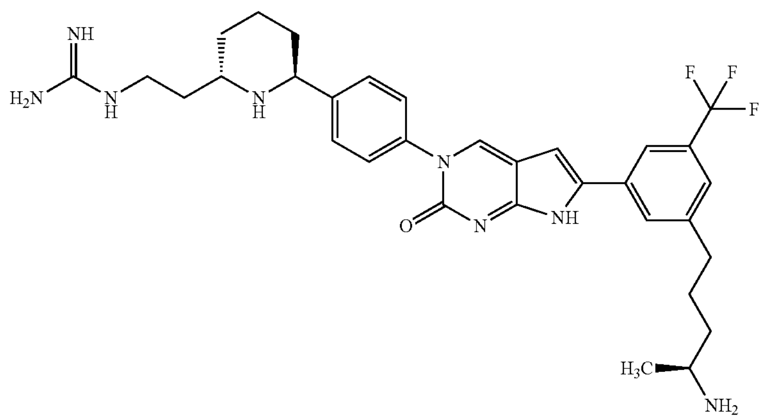 [SMILES: C[C@H](N)CCCc1cc(-c2cc3cn(-c4ccc([C@@H]5CCC[C@@H](CCNC(=N)N)N5)cc4)c(=O)nc3[nH]2)cc(C(F)(F)F)c1] | 609.7 |
| 487 | 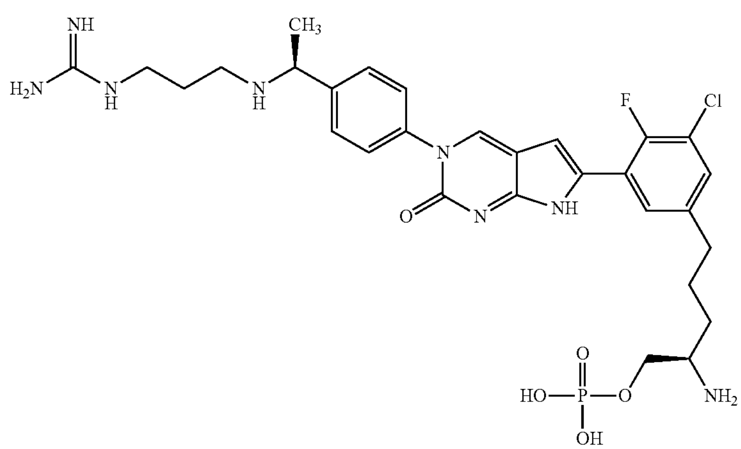 [SMILES: C[C@H](NCCCNC(=N)N)c1ccc(-n2cc3cc(-c4cc(CCC[C@@H](N)COP(=O)(O)O)cc(Cl)c4F)[nH]c3nc2=O)cc1] | 663.6 |

TABLE 1-continued

| Compound No | Structure | ESI, m/z [M + H]+ |
|---|---|---|
| 488 | 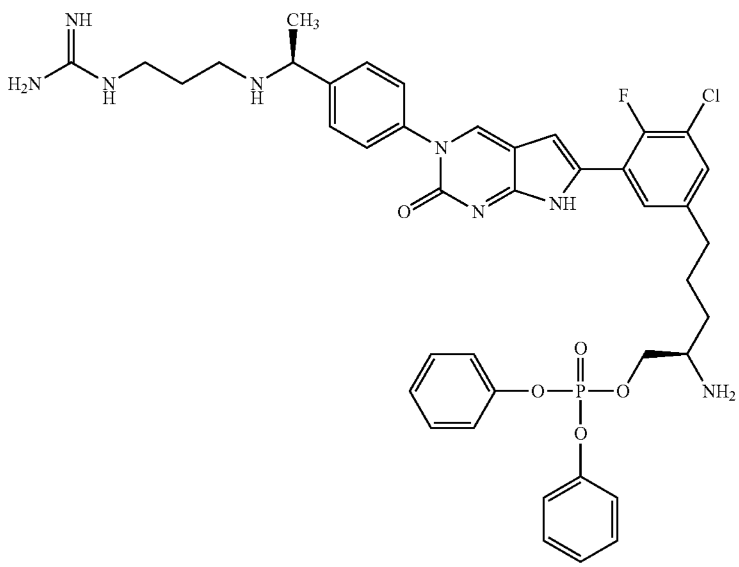 [SMILES: C[C@H](NCCCNC(=N)N)c1ccc(-n2cc3cc(-c4cc(CCC[C@@H](N)COP(=O)(Oc5ccccc5)Oc5ccccc5)cc(Cl)c4F)[nH]c3nc2=O)cc1] | 815.7 |
| 489 | 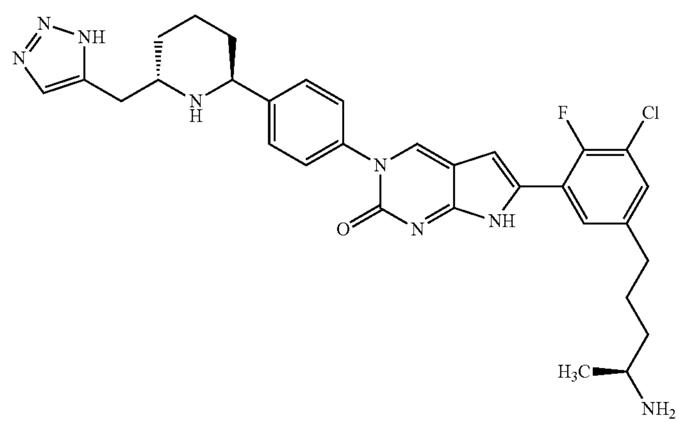 [SMILES: C[C@H](N)CCCc1cc(Cl)c(F)c(-c2cc3cn(-c4ccc([C@@H]5CCC[C@@H](Cc6cnn[nH]6)N5)cc4)c(=O)nc3[nH]2)c1] | 589 |
| 490 | 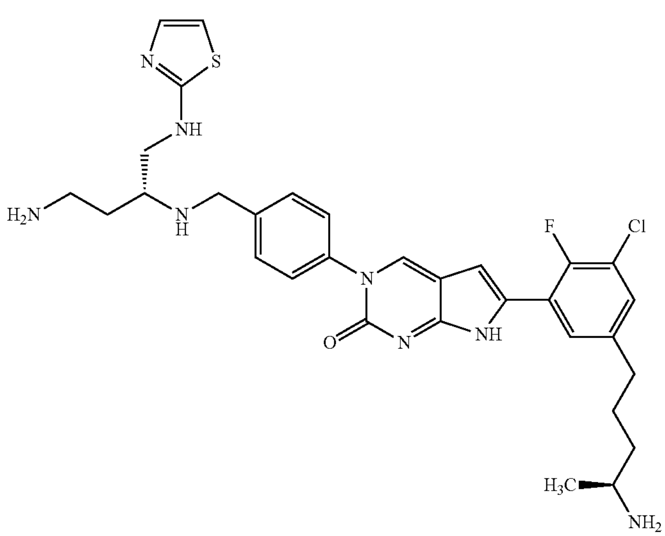 [SMILES: C[C@H](N)CCCc1cc(Cl)c(F)c(-c2cc3cn(-c4ccc(CN[C@H](CCN)CNc5nccs5)cc4)c(=O)nc3[nH]2)c1] | 624.19 |

TABLE 1-continued
| Compound No | Structure | ESI, m/z [M + H]+ |
|---|---|---|
| 491 | 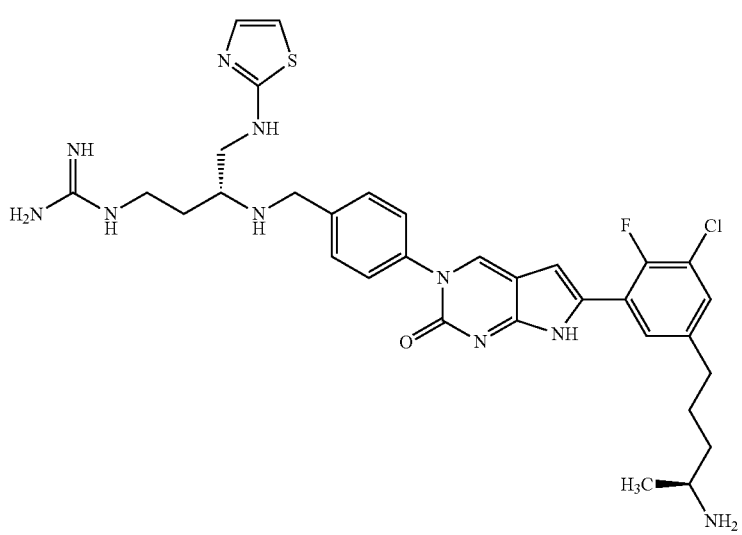 [SMILES: C[C@H](N)CCCc1cc(Cl)c(F)c(-c2cc3cn(-c4ccc(CN[C@H](CCNC(=N)N)CNc5nccs5)cc4)c(=O)nc3[nH]2)c1] | 666.23 |
| 492 | 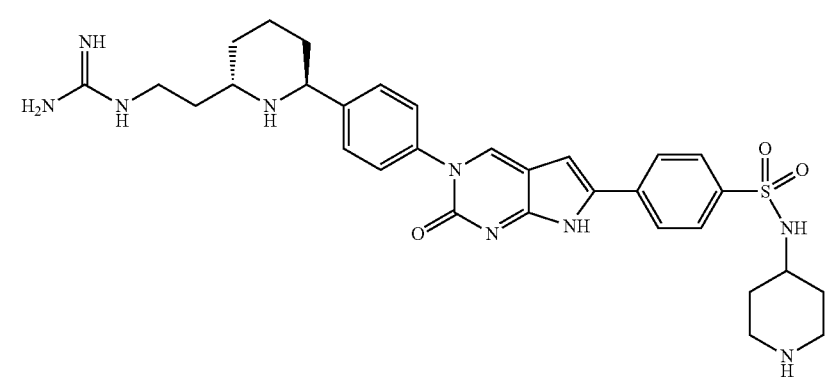 [SMILES: N=C(N)NCC[C@@H]1CCC[C@@H](c2ccc(-n3cc4cc(-c5ccc(S(=O)(=O)NC6CCNCC6)cc5)[nH]c4nc3=O)cc2)N1] | 618.7 |
| 493 | 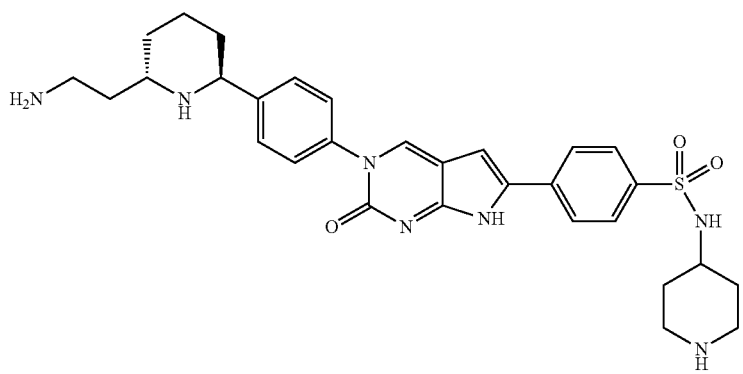 [SMILES: NCC[C@@H]1CCC[C@@H](c2ccc(-n3cc4cc(-c5ccc(S(=O)(=O)NC6CCNCC6)cc5)[nH]c4nc3=O)cc2)N1] | 576.7 |

TABLE 1-continued
| Compound No | Structure | ESI, m/z [M + H]+ |
|---|---|---|
| 494 | 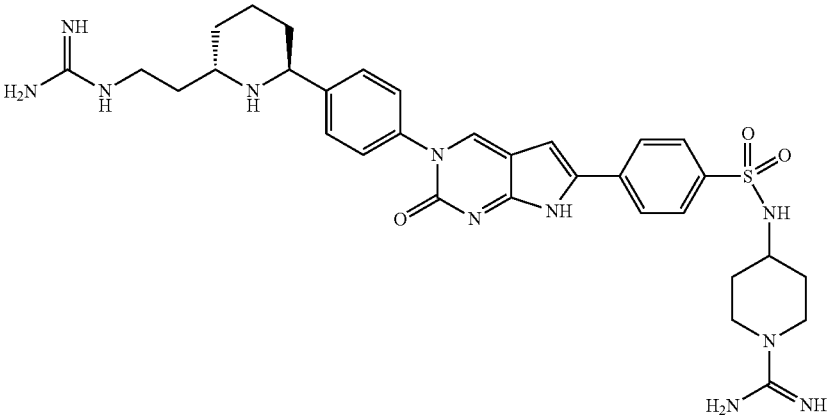 [SMILES: N=C(N)NCC[C@@H]1CCC[C@@H](c2ccc(-n3cc4cc(-c5ccc(S(=O)(=O)NC6CCN(C(=N)N)CC6)cc5)[nH]c4nc3=O)cc2)N1] | 660.7 |
| 495 | 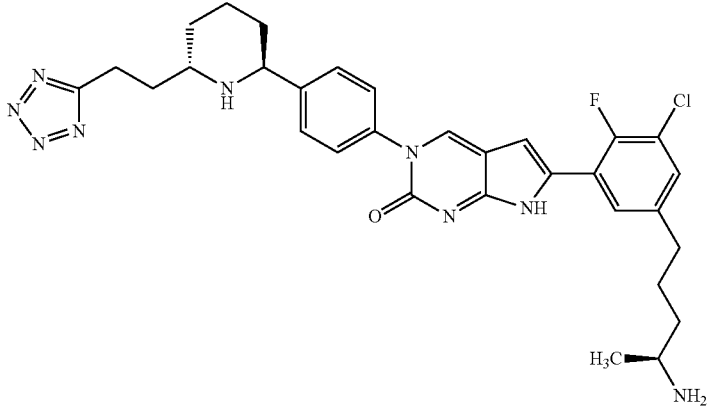 | 604 |
| 496 | 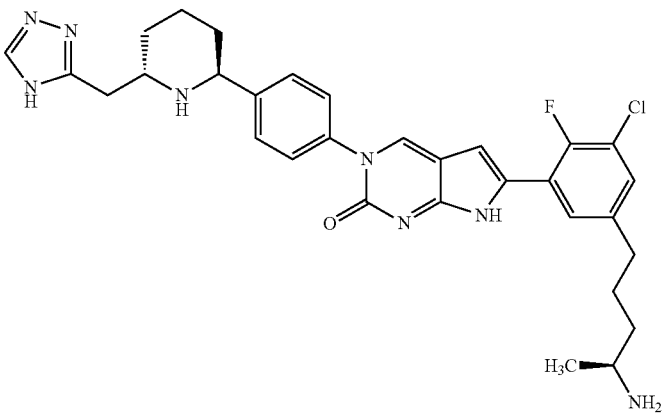 [SMILES: C[C@H](N)CCCc1cc(Cl)c(F)c(-c2cc3cn(-c4ccc([C@@H]5CCC[C@@H](Cc6nnc[nH]6)N5)cc4)c(=O)nc3[nH]2)c1] | 589 |

TABLE 1-continued
| Compound No | Structure | ESI, m/z [M + H]+ |
|---|---|---|
| 497 | 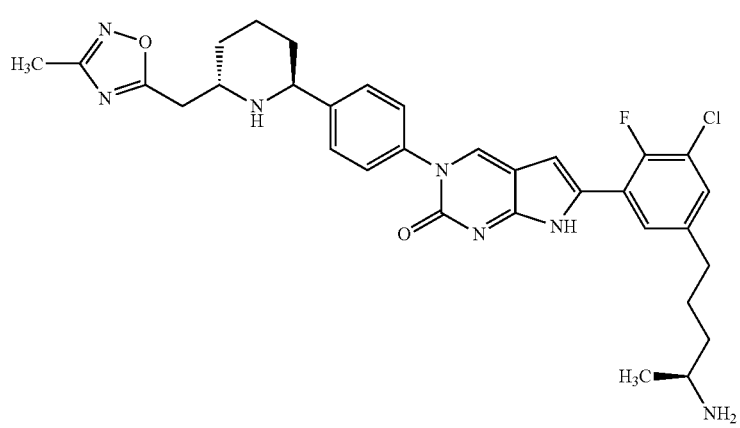 [SMILES: Cc1noc(C[C@@H]2CCC[C@@H](c3ccc(-n4cc5cc(-c6cc(CCC[C@H](C)N)cc(Cl)c6F)[nH]c5nc4=O)cc3)N2)n1] | 604 |
| 498 | 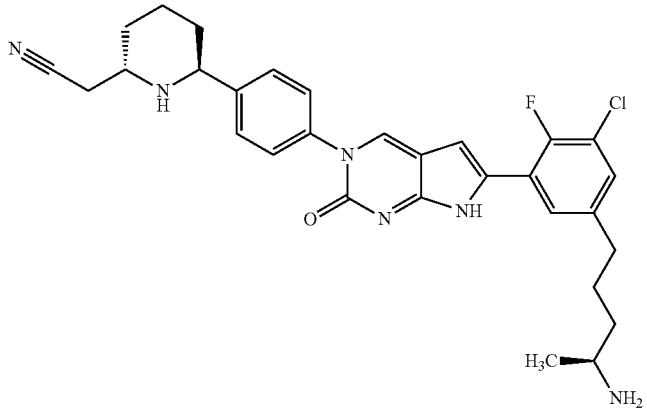 [SMILES: C[C@H](N)CCCc1cc(Cl)c(F)c(-c2cc3cn(-c4ccc([C@@H]5CCC[C@@H](CC#N)N5)cc4)c(=O)nc3[nH]2)c1] | 547 |
| 499 | 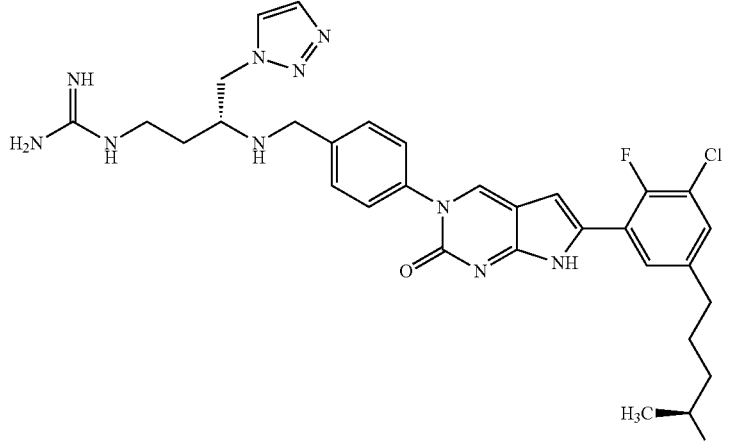 | 635.16 |

TABLE 1-continued
| Compound No | Structure | ESI, m/z [M + H]+ |
|---|---|---|
| 500 | 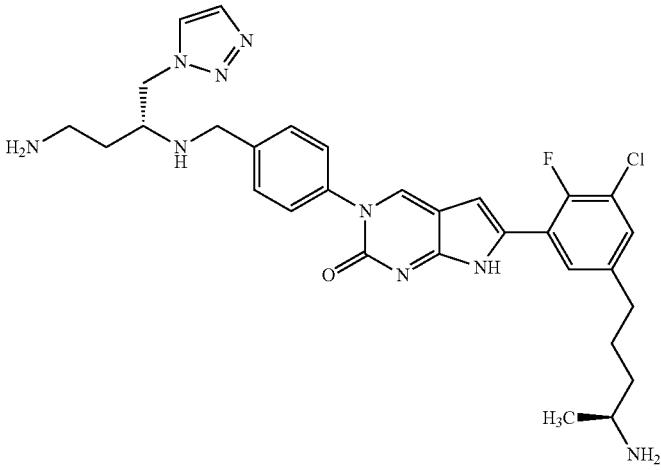 [SMILES: C[C@H](N)CCCc1cc(Cl)c(F)c(-c2cc3cn(-c4ccc(CN[C@H](CCN)Cn5ccnn5)cc4)c(=O)nc3[nH]2)c1] | 593.12 |
| 501 | 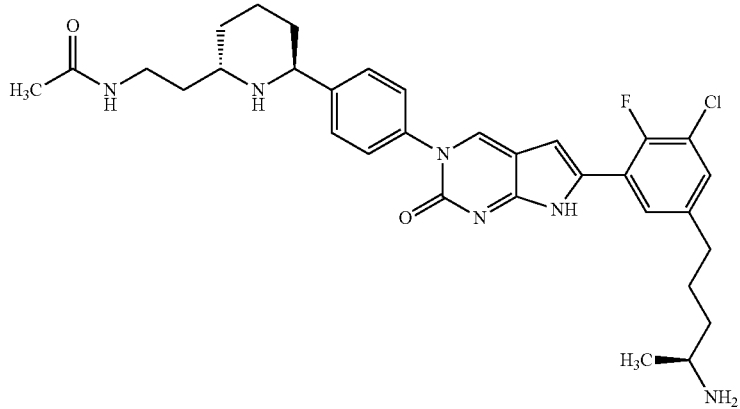 [SMILES: CC(=O)NCC[C@@H]1CCC[C@@H](c2ccc(-n3cc4cc(-c5cc(CCC[C@H](C)N)cc(Cl)c5F)[nH]c4nc3=O)cc2)N1] | 593 |
| 502 | 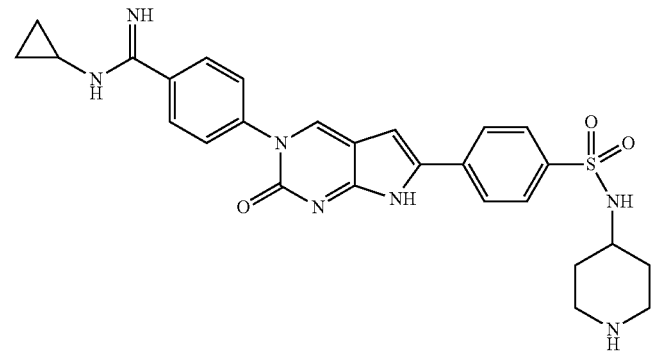 [SMILES: N=C(NC1CC1)c1ccc(-n2cc3cc(-c4ccc(S(=O)(=O)NC5CCNCC5)cc4)[nH]c3nc2=O)cc1] | 532.5 |

TABLE 1-continued
| Compound No | Structure | ESI, m/z [M + H]+ |
|---|---|---|
| 503 | 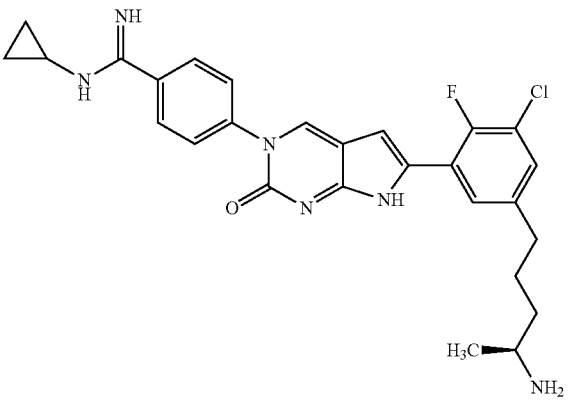 [SMILES: C[C@H](N)CCCc1cc(Cl)c(F)c(-c2cc3cn(-c4ccc(C(=N)NC5CC5)cc4)c(=O)nc3[nH]2)c1] | 507.4 |
| 504 | 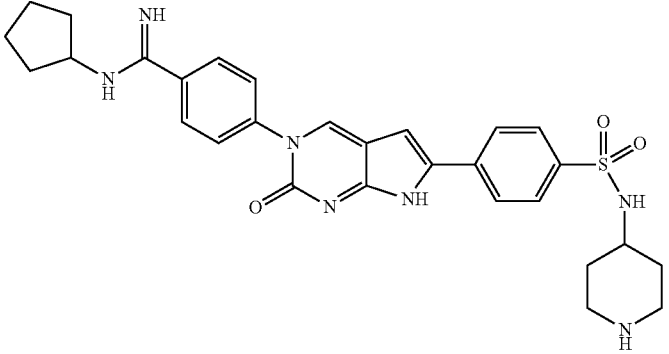 [SMILES: N=C(NC1CCCC1)c1ccc(-n2cc3cc(-c4ccc(S(=O)(=O)NC5CCNCC5)cc4)[nH]c3nc2=O)cc1] | 560.6 |
| 505 | 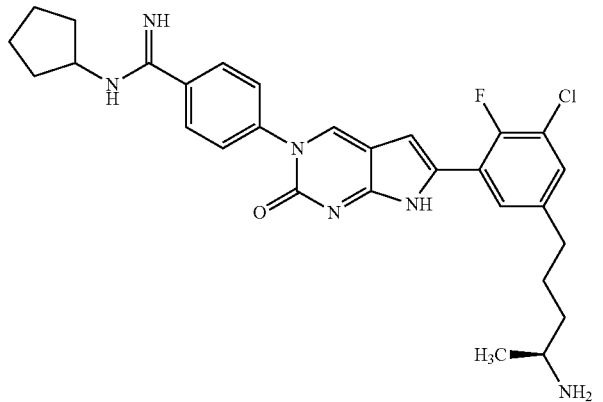 [SMILES: C[C@H](N)CCCc1cc(Cl)c(F)c(-c2cc3cn(-c4ccc(C(=N)NC5CCCC5)cc4)c(=O)nc3[nH]2)c1] | 535.4 |

TABLE 1-continued
| Compound No | Structure | ESI, m/z [M + H]+ |
|---|---|---|
| 506 | 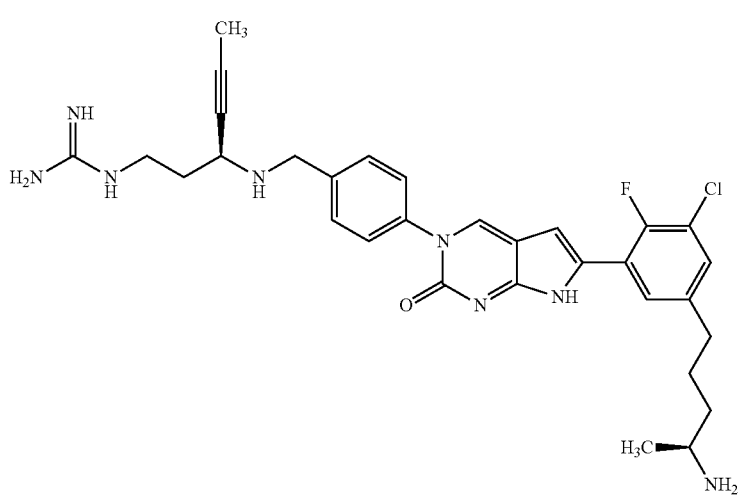 [SMILES: CC#C[C@H](CCNC(=N)N)NCc1ccc(-n2cc3cc(-c4cc(CCC[C@H](C)N)cc(Cl)c4F)[nH]c3nc2=O)cc1] | 591.6 |
| 507 | 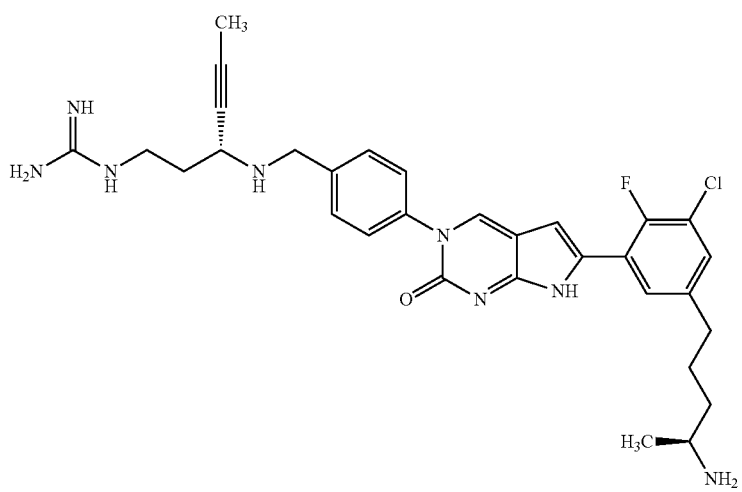 [SMILES: CC#C[C@@H](CCNC(=N)N)NCc1ccc(-n2cc3cc(-c4cc(CCC[C@H](C)N)cc(Cl)c4F)[nH]c3nc2=O)cc1] | 591.6 |
| 508 | 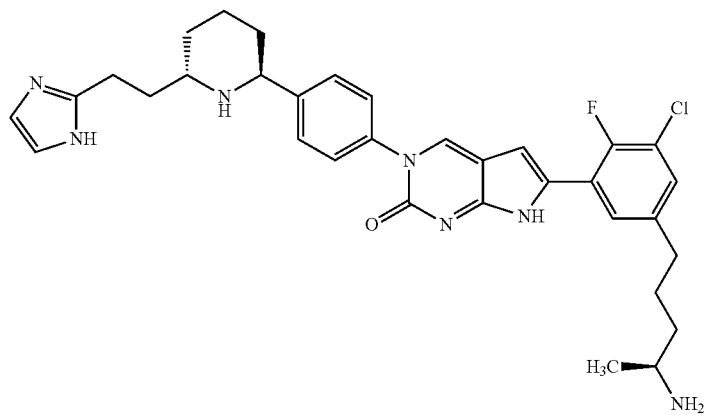 | 602 |

TABLE 1-continued

| Compound No | Structure | ESI, m/z [M + H]+ |
|---|---|---|
| 509 | 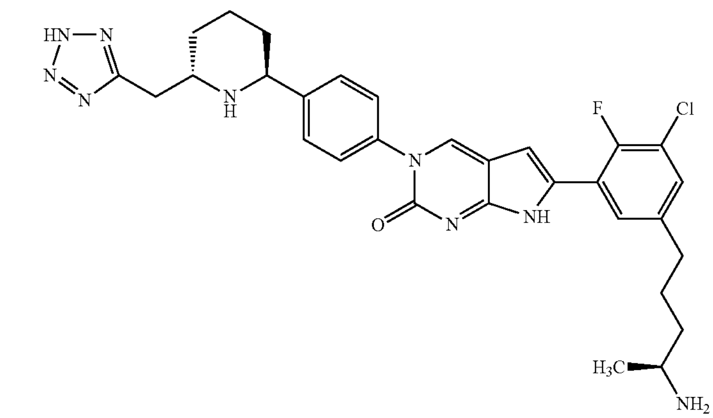 [SMILES: C[C@H](N)CCCc1cc(Cl)c(F)c(-c2cc3cn(-c4ccc([C@@H]5CCC[C@@H](Cc6nn[nH]n6)N5)cc4)c(=O)nc3[nH]2)c1] | 591 |
| 510 | 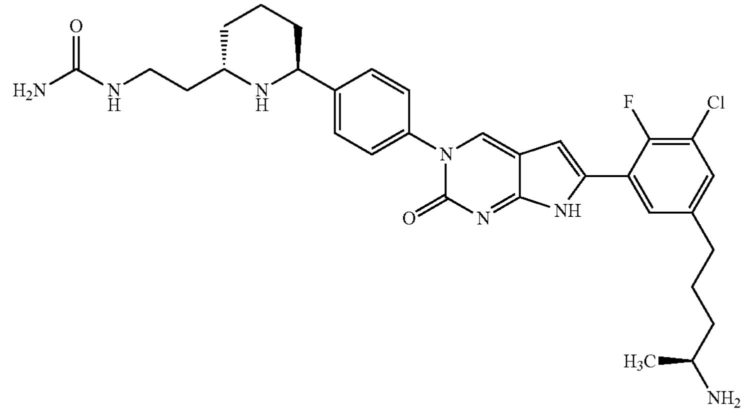 [SMILES: C[C@H](N)CCCc1cc(Cl)c(F)c(-c2cc3cn(-c4ccc([C@@H]5CCC[C@@H](CCNC(N)=O)N5)cc4)c(=O)nc3[nH]2)c1] | 594 |
| 511 | 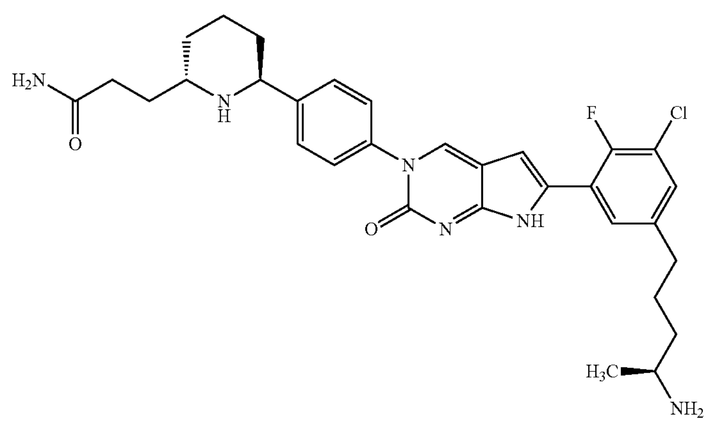 [SMILES: C[C@H](N)CCCc1cc(Cl)c(F)c(-c2cc3cn(-c4ccc([C@@H]5CCC[C@@H](CCC(N)=O)N5)cc4)c(=O)nc3[nH]2)c1] | 579 |

TABLE 1-continued

| Compound No | Structure | ESI, m/z [M + H]+ |
|---|---|---|
| 512 | 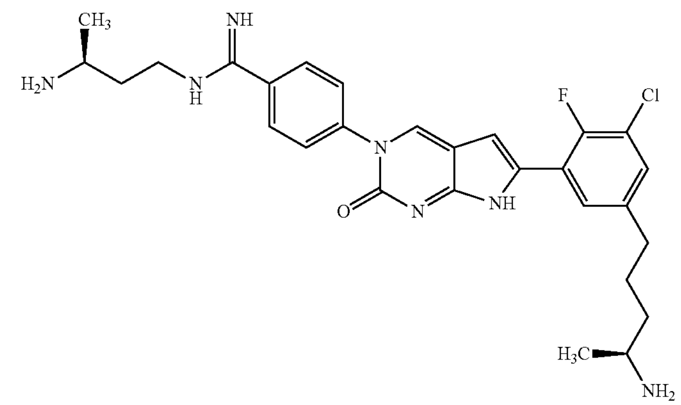 [SMILES: C[C@H](N)CCCc1cc(Cl)c(F)c(-c2cc3cn(-c4ccc(C(=N)NCC[C@H](C)N)cc4)c(=O)nc3[nH]2)c1] | 538.6 |
| 513 | 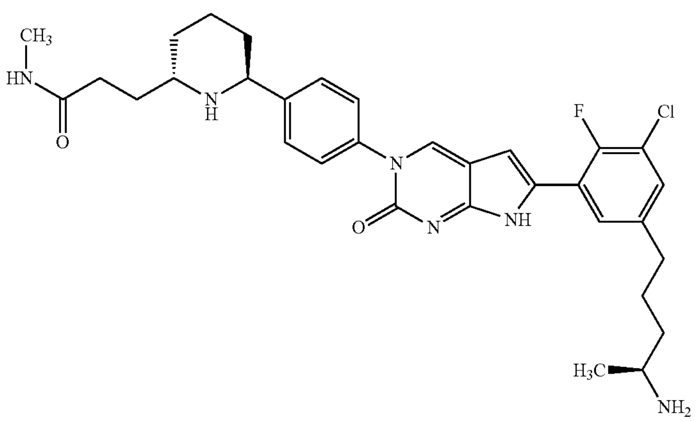 [SMILES: CNC(=O)CC[C@@H]1CCC[C@@H](c2ccc(-n3cc4cc(-c5cc(CCC[C@H](C)N)cc(Cl)c5F)[nH]c4nc3=O)cc2)N1] | 593 |
| 514 | 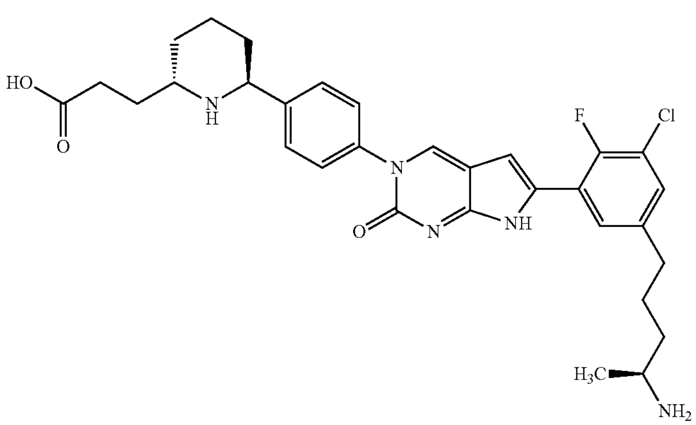 [SMILES: C[C@H](N)CCCc1cc(Cl)c(F)c(-c2cc3cn(-c4ccc([C@@H]5CCC[C@@H](CCC(=O)O)N5)cc4)c(=O)nc3[nH]2)c1] | 580 |

TABLE 1-continued
| Compound No | Structure | ESI, m/z [M + H]+ |
|---|---|---|
| 515 | 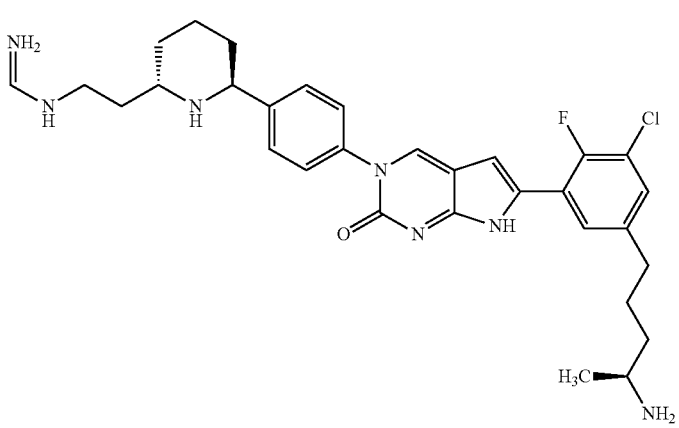 [SMILES: C[C@H](N)CCCc1cc(Cl)c(F)c(-c2cc3cn(-c4ccc([C@@H]5CCC[C@@H](CCNC=N)N5)cc4)c(=O)nc3[nH]2)c1] | 578.6 |
| 516 | 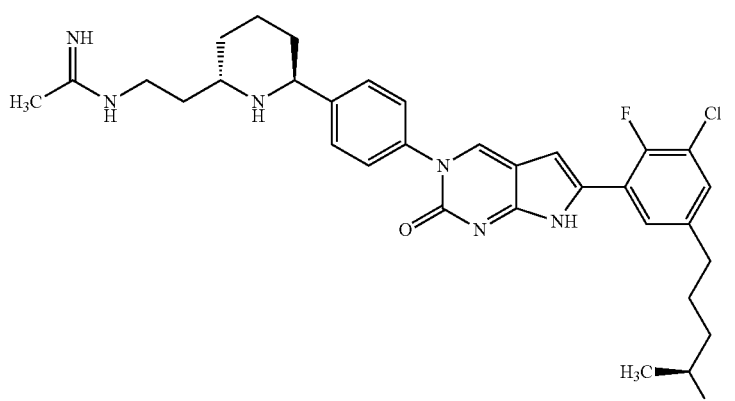 | 592.5 |
| 517 | 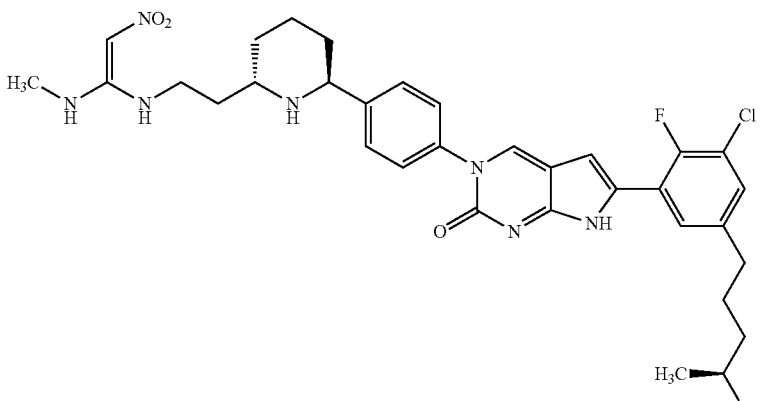 | 651.7 |

TABLE 1-continued

| Compound No | Structure | ESI, m/z [M + H]+ |
|---|---|---|
| 518 | 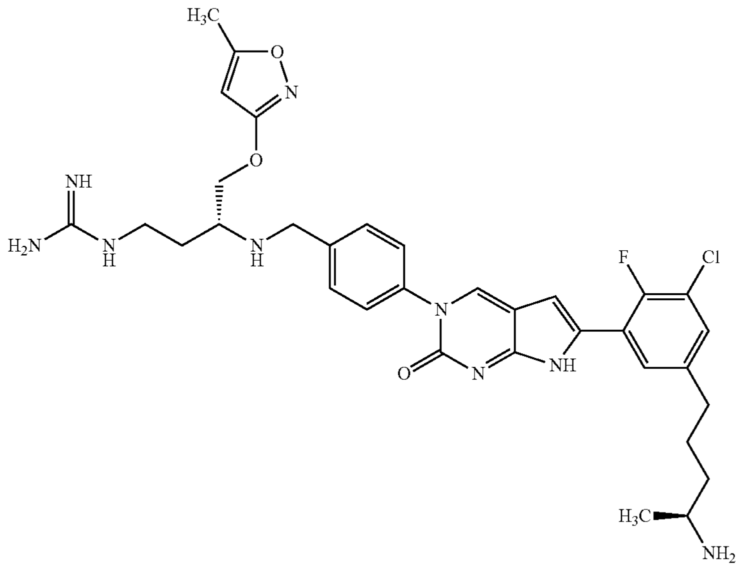 [SMILES: Cc1cc(OC[C@@H](CCNC(=N)N)NCc2ccc(-n3cc4cc(-c5cc(CCC[C@H](C)N)cc(Cl)c5F)[nH]c4nc3=O)cc2)no1] | 664.6 |
| 519 | 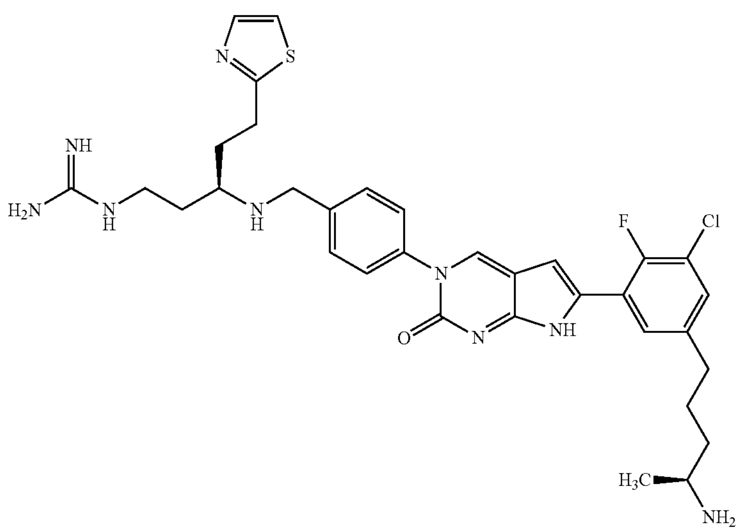 [SMILES: C[C@H](N)CCCc1cc(Cl)c(F)c(-c2cc3cn(-c4ccc(CN[C@@H](CCNC(=N)N)CCc5nccs5)cc4)c(=O)nc3[nH]2)c1] | 664.7 |
| 520 | 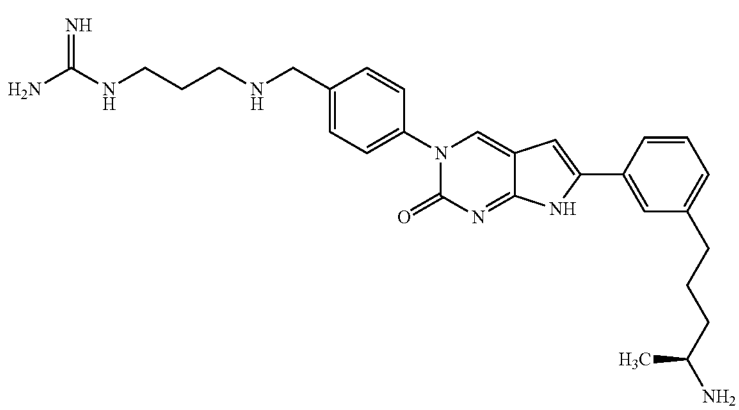 [SMILES: C[C@H](N)CCCc1cccc(-c2cc3cn(-c4ccc(CNCCCNC(=N)N)cc4)c(=O)nc3[nH]2)c1] | 501.6 |

TABLE 1-continued

| Compound No | Structure | ESI, m/z [M + H]+ |
|---|---|---|
| 521 | 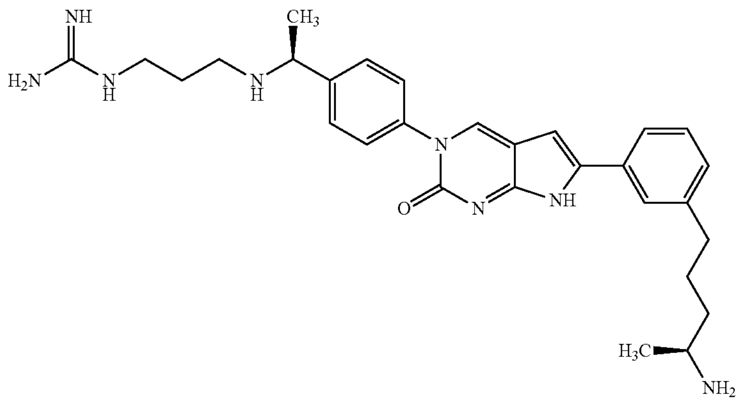 [SMILES: C[C@H](N)CCCc1cccc(-c2cc3cn(-c4ccc([C@H](C)NCCCNC(=N)N)cc4)c(=O)nc3[nH]2)c1] | 515.6 |
| 522 | 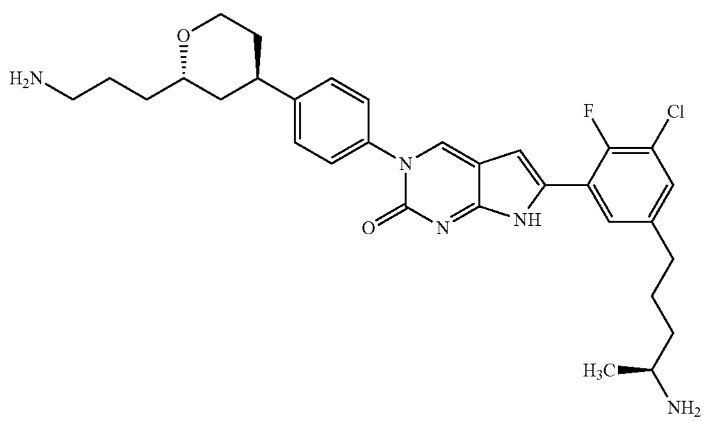 [SMILES: C[C@H](N)CCCc1cc(Cl)c(F)c(-c2cc3cn(-c4ccc([C@@H]5CCO[C@@H](CCCN)C5)cc4)c(=O)nc3[nH]2)c1] | 567.12 |
| 523 | 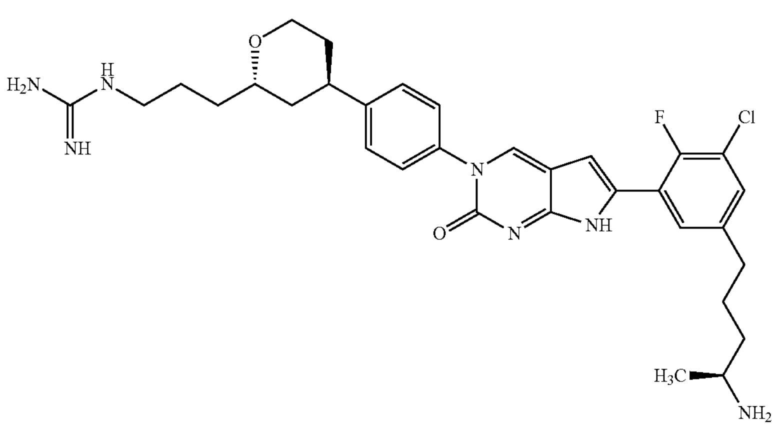 [SMILES: C[C@H](N)CCCc1cc(Cl)c(F)c(-c2cc3cn(-c4ccc([C@@H]5CCO[C@@H](CCCNC(=N)N)C5)cc4)c(=O)nc3[nH]2)c1] | 609.16 |

TABLE 1-continued
| Compound No | Structure | ESI, m/z [M + H]+ |
|---|---|---|
| 524 | 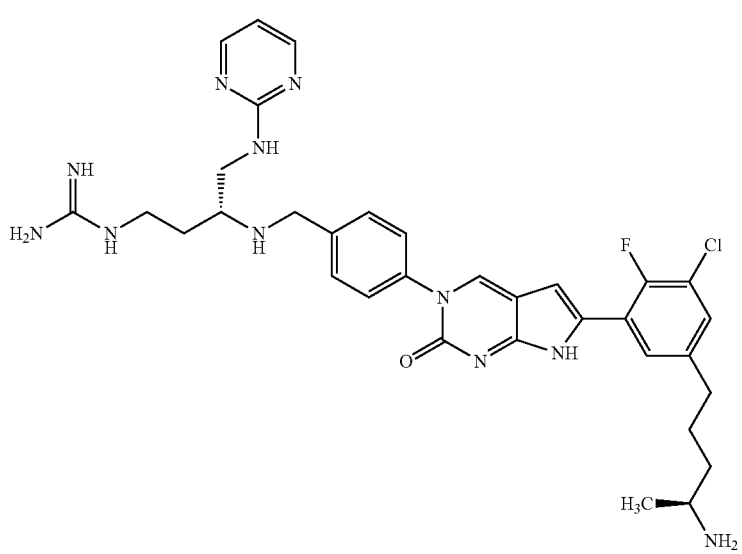 [SMILES: C[C@H](N)CCCc1cc(Cl)c(F)c(-c2cc3cn(-c4ccc(CN[C@H](CCNC(=N)N)CNc5ncccn5)cc4)c(=O)nc3[nH]2)c1] | 660.7 |
| 525 | 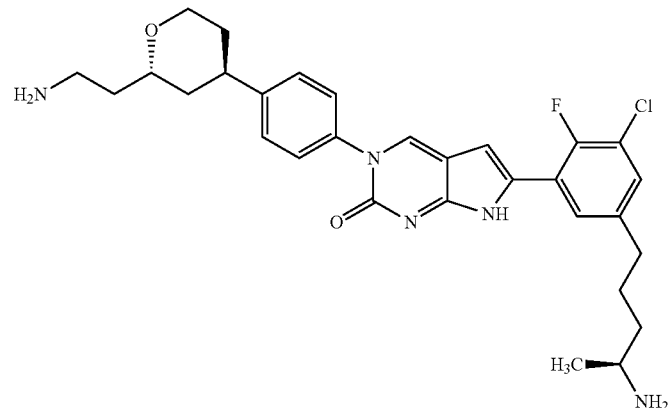 | 553.09 |
| 526 | 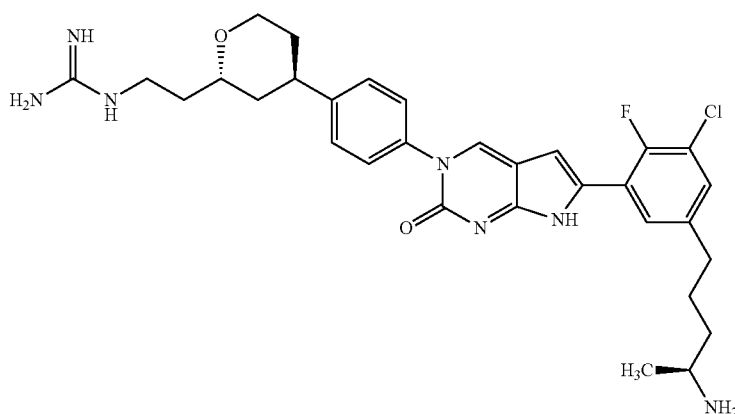 | 595.13 |

TABLE 1-continued
| Compound No | Structure | ESI, m/z [M + H]+ |
|---|---|---|
| 527 | 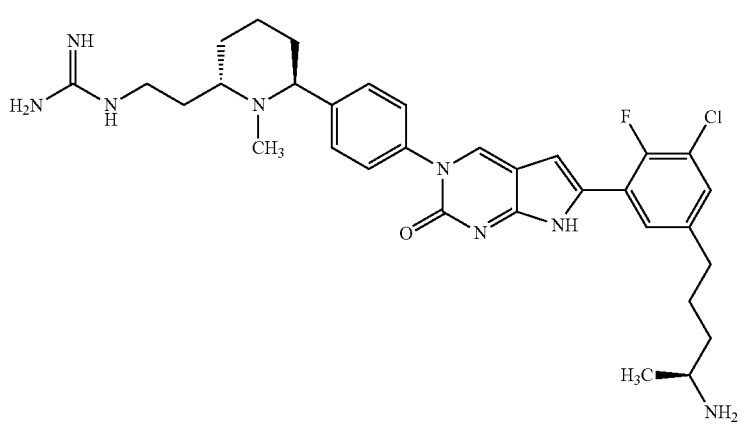 [SMILES: C[C@H](N)CCCc1cc(Cl)c(F)c(-c2cc3cn(-c4ccc([C@@H]5CCC[C@@H](CCNC(=N)N)N5C)cc4)c(=O)nc3[nH]2)c1] | 607.7 |
| 528 | 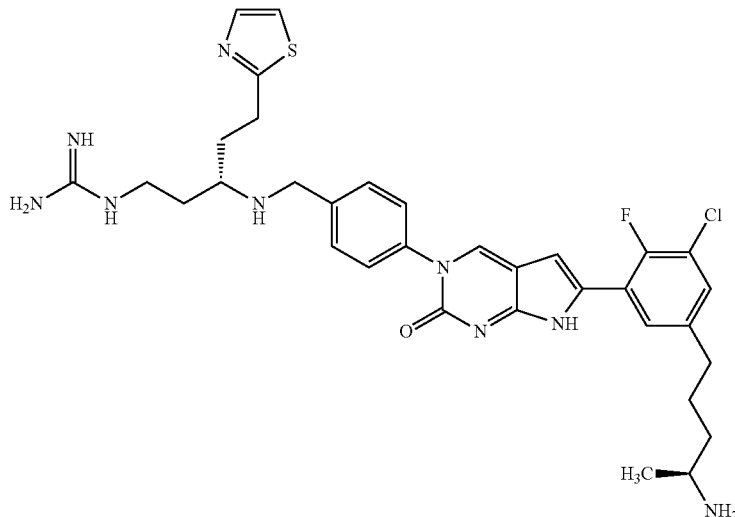 | 664.6 |
| 529 | 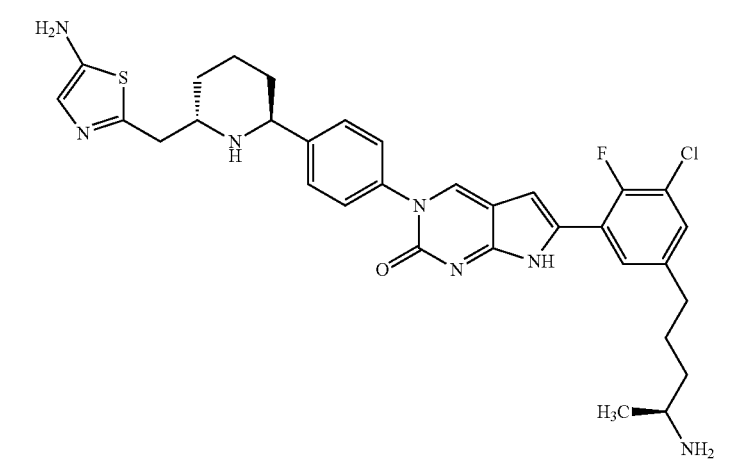 [SMILES: C[C@H](N)CCCc1cc(Cl)c(F)c(-c2cc3cn(-c4ccc([C@@H]5CCC[C@@H](Cc6ncc(N)s6)N5)cc4)c(=O)nc3[nH]2)c1] | 620 |

TABLE 1-continued

| Compound No | Structure | ESI, m/z [M + H]+ |
|---|---|---|
| 530 | 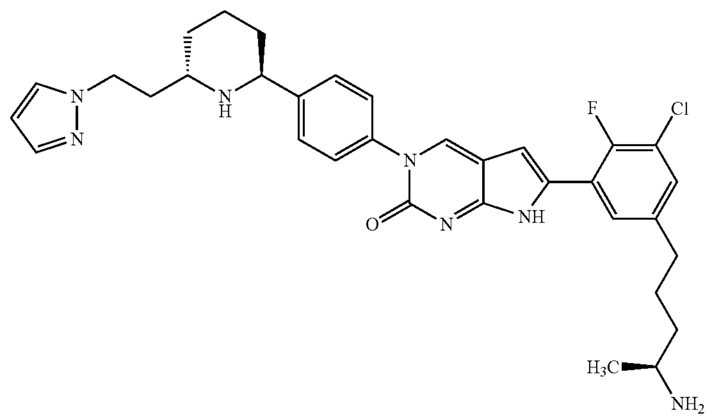 [SMILES: C[C@H](N)CCCc1cc(Cl)c(F)c(-c2cc3cn(-c4ccc([C@@H]5CCC[C@@H](CCn6cccn6)N5)cc4)c(=O)nc3[nH]2)c1] | 602 |
| 531 | 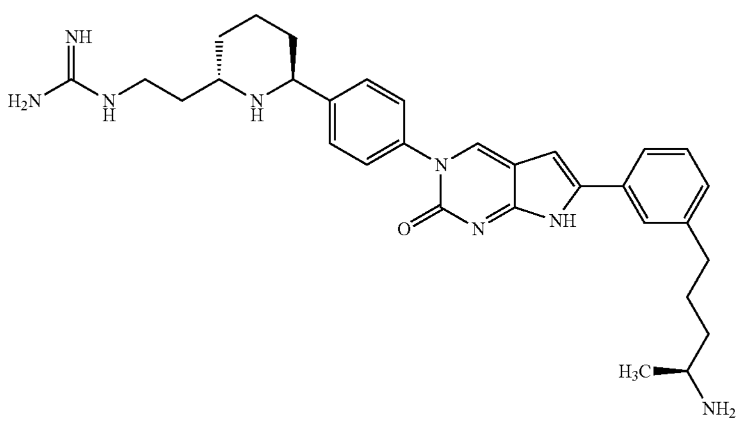 [SMILES: C[C@H](N)CCCc1cccc(-c2cc3cn(-c4ccc([C@@H]5CCC[C@@H](CCNC(=N)N)N5)cc4)c(=O)nc3[nH]2)c1] | 541.7 |
| 532 | 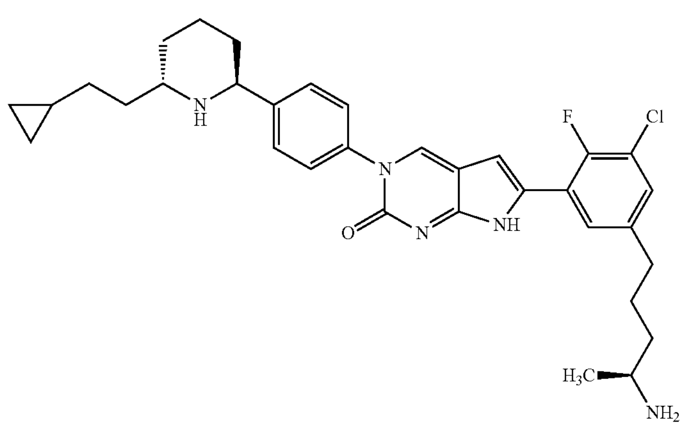 [SMILES: C[C@H](N)CCCc1cc(Cl)c(F)c(-c2cc3cn(-c4ccc([C@@H]5CCC[C@@H](CCC6CC6)N5)cc4)c(=O)nc3[nH]2)c1] | 576 |

TABLE 1-continued

| Compound No | Structure | ESI, m/z [M + H]+ |
|---|---|---|
| 533 | 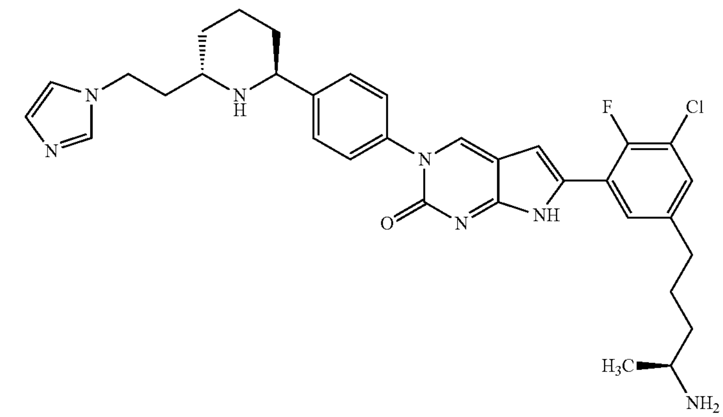 [SMILES: C[C@H](N)CCCc1cc(Cl)c(F)c(-c2cc3cn(-c4ccc([C@@H]5CCC[C@@H](CCn6ccnc6)N5)cc4)c(=O)nc3[nH]2)c1] | 602 |
| 534 | 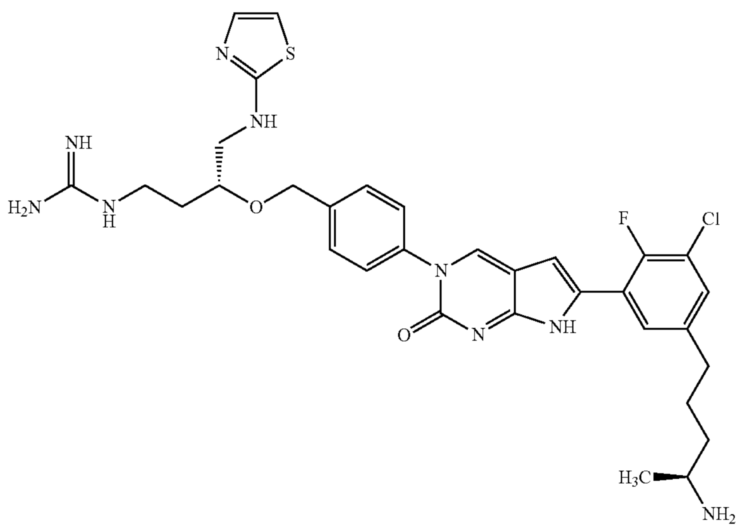 [SMILES: C[C@H](N)CCCc1cc(Cl)c(F)c(-c2cc3cn(-c4ccc(CO[C@H](CCNC(=N)N)CNc5nccs5)cc4)c(=O)nc3[nH]2)c1] | 666.7 |
| 535 | 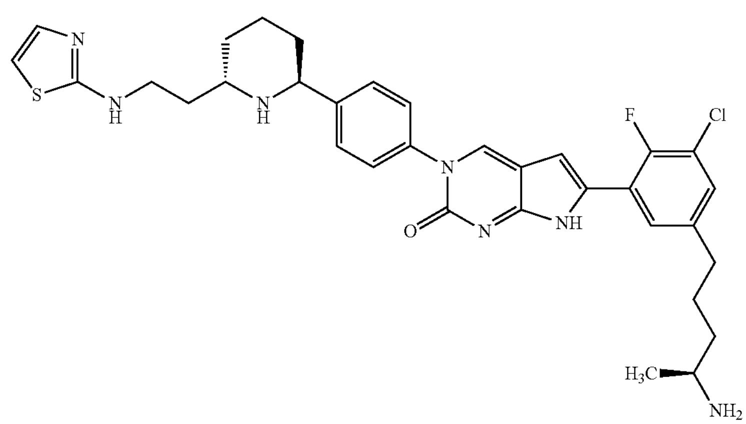 [SMILES: C[C@H](N)CCCc1cc(Cl)c(F)c(-c2cc3cn(-c4ccc([C@@H]5CCC[C@@H](CCNc6nccs6)N5)cc4)c(=O)nc3[nH]2)c1] | 634.6 |

TABLE 1-continued

| Compound No | Structure | ESI, m/z [M + H]+ |
|---|---|---|
| 536 | 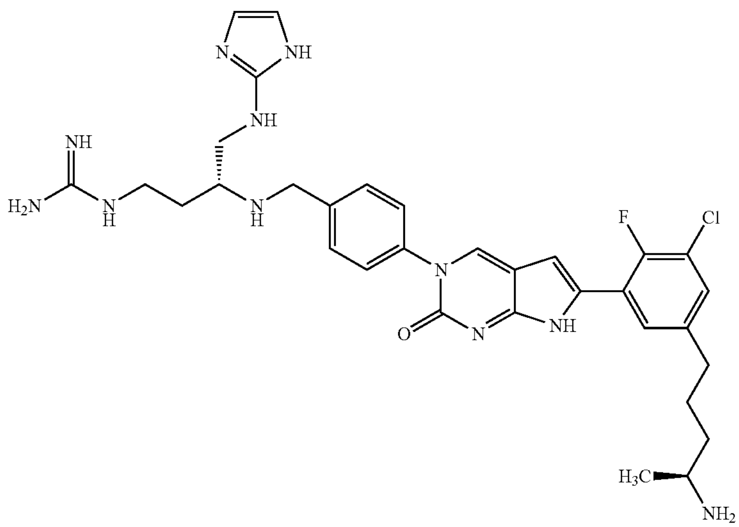 [SMILES: C[C@H](N)CCCc1cc(Cl)c(F)c(-c2cc3cn(-c4ccc(CN[C@H](CCNC(=N)N)CNc5ncc[nH]5)cc4)c(=O)nc3[nH]2)c1] | 648.7 |
| 537 | 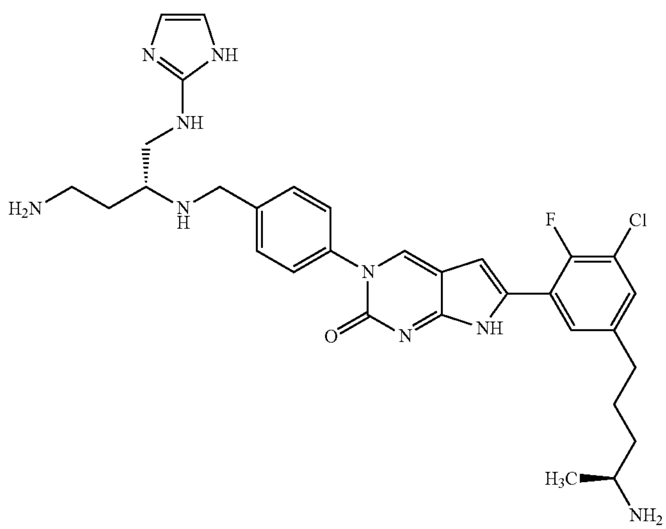 [SMILES: C[C@H](N)CCCc1cc(Cl)c(F)c(-c2cc3cn(-c4ccc(CN[C@H](CCN)CNc5ncc[nH]5)cc4)c(=O)nc3[nH]2)c1] | 606.6 |
| 538 | 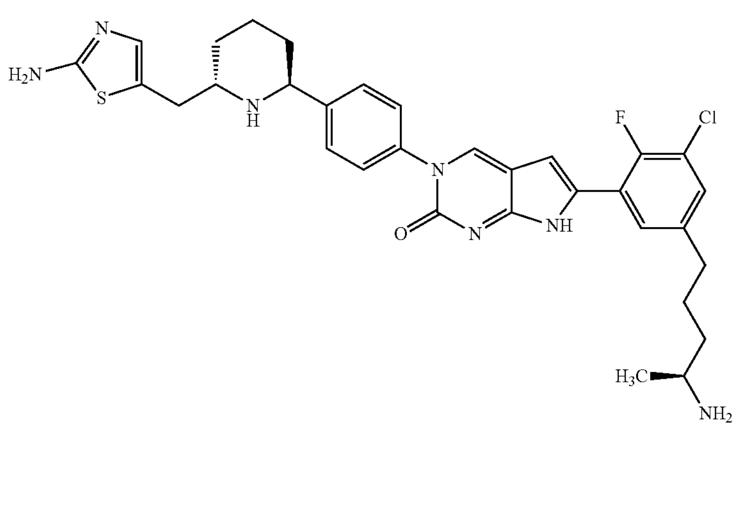 [SMILES: C[C@H](N)CCCc1cc(Cl)c(F)c(-c2cc3cn(-c4ccc([C@@H]5CCC[C@@H](Cc6cnc(N)s6)N5)cc4)c(=O)nc3[nH]2)c1] | 620 |

TABLE 1-continued

| Compound No | Structure | ESI, m/z [M + H]+ |
|---|---|---|
| 539 | 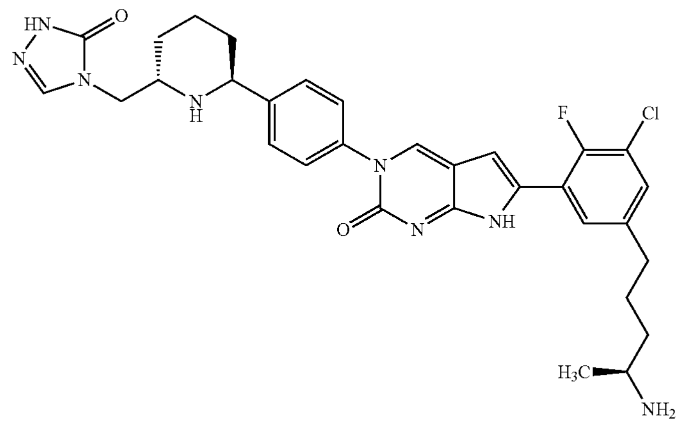 [SMILES: C[C@H](N)CCCc1cc(Cl)c(F)c(-c2cc3cn(-c4ccc([C@@H]5CCC[C@@H](Cn6cn[nH]c6=O)N5)cc4)c(=O)nc3[nH]2)c1] | 605 |
| 540 | 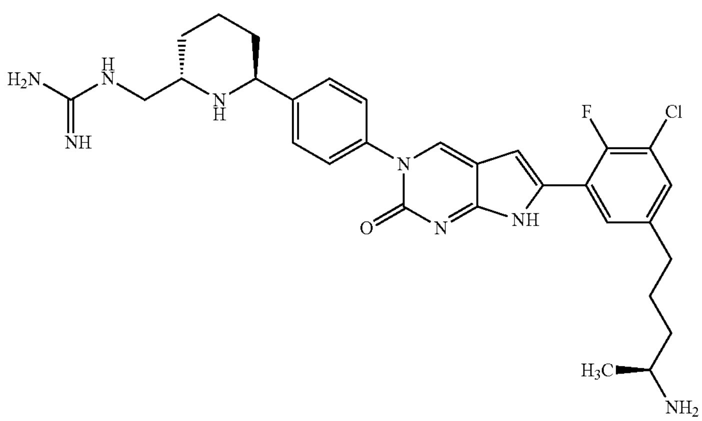 [SMILES: C[C@H](N)CCCc1cc(Cl)c(F)c(-c2cc3cn(-c4ccc([C@@H]5CCC[C@@H](CNC(=N)N)N5)cc4)c(=O)nc3[nH]2)c1] | 579 |
| 541 | 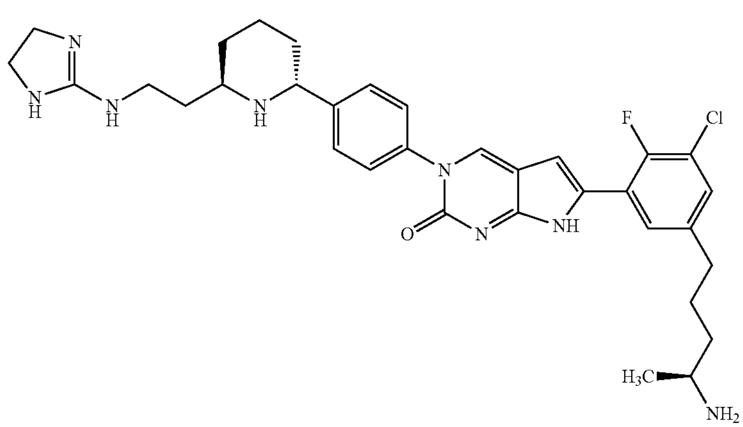 [SMILES: C[C@H](N)CCCc1cc(Cl)c(F)c(-c2cc3cn(-c4ccc([C@H]5CCC[C@H](CCNC6=NCCN6)N5)cc4)c(=O)nc3[nH]2)c1] | 619.7 |

TABLE 1-continued

| Compound No | Structure | ESI, m/z [M + H]+ |
|---|---|---|
| 542 | 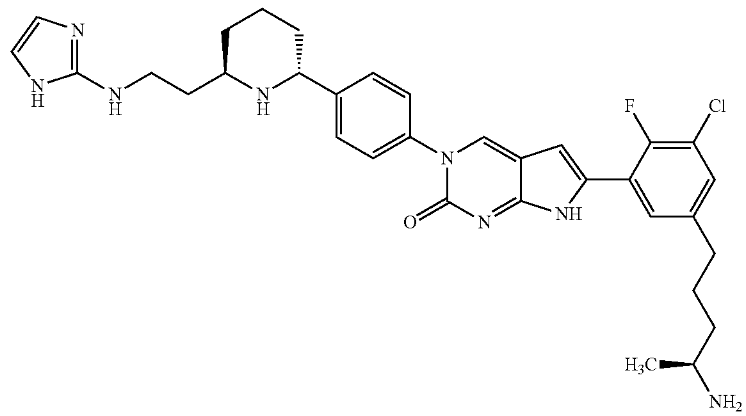 [SMILES: C[C@H](N)CCCc1cc(Cl)c(F)c(-c2cc3cn(-c4ccc([C@H]5CCC[C@H](CCNc6ncc[nH]6)N5)cc4)c(=O)nc3[nH]2)c1] | 617.7 |
| 543 | 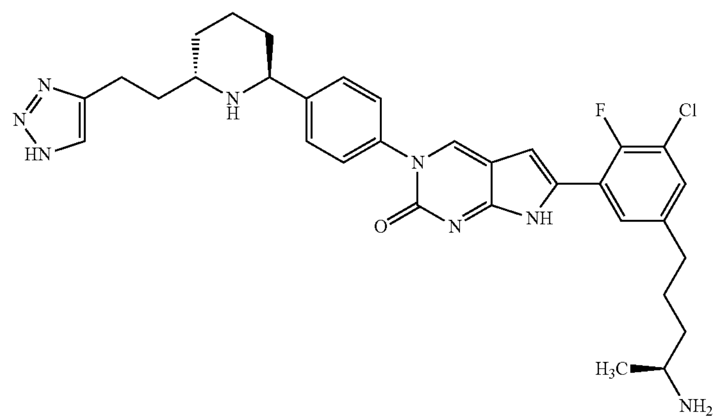 [SMILES: C[C@H](N)CCCc1cc(Cl)c(F)c(-c2cc3cn(-c4ccc([C@@H]5CCC[C@@H](CCc6c[nH]nn6)N5)cc4)c(=O)nc3[nH]2)c1] | 603 |
| 544 | 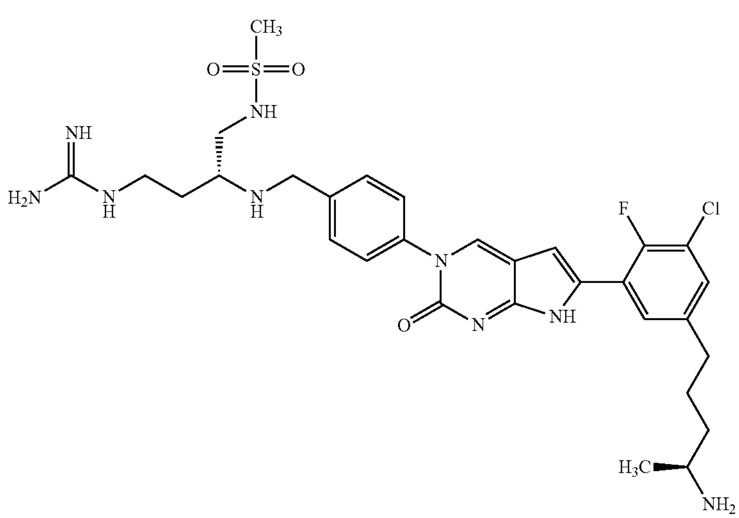 [SMILES: C[C@H](N)CCCc1cc(Cl)c(F)c(-c2cc3cn(-c4ccc(CN[C@H](CCNC(=N)N)CNS(C)(=O)=O)cc4)c(=O)nc3[nH]2)c1] | 660 |

TABLE 1-continued

| Compound No | Structure | ESI, m/z [M + H]+ |
|---|---|---|
| 545 | 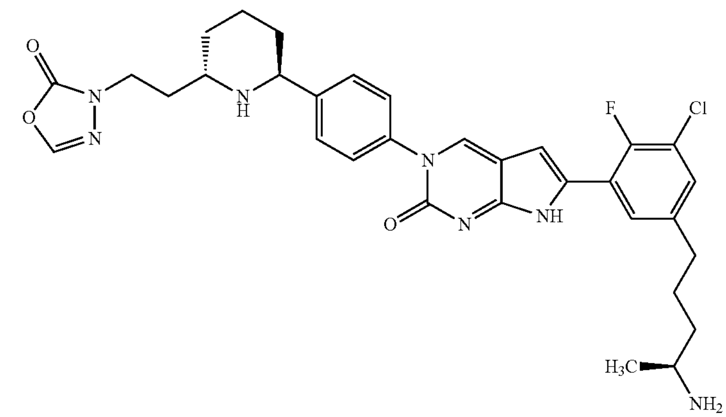 [SMILES: C[C@H](N)CCCc1cc(Cl)c(F)c(-c2cc3cn(-c4ccc([C@@H]5CCC[C@@H](CCn6ncoc6=O)N5)cc4)c(=O)nc3[nH]2)c1] | 620 |
| 546 | 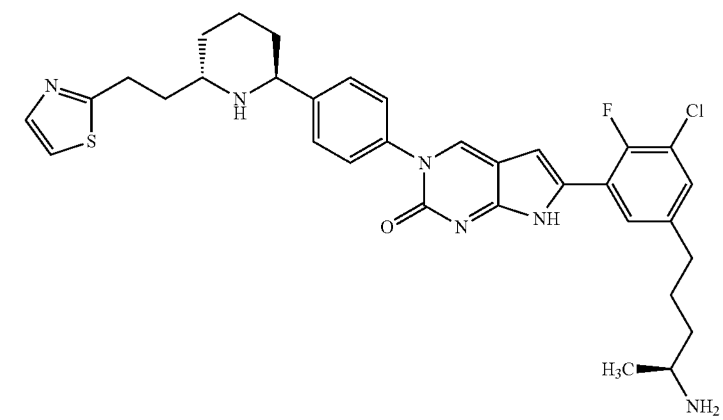 [SMILES: C[C@H](N)CCCc1cc(Cl)c(F)c(-c2cc3cn(-c4ccc([C@@H]5CCC[C@@H](CCc6nccs6)N5)cc4)c(=O)nc3[nH]2)c1] | 619 |
| 547 | 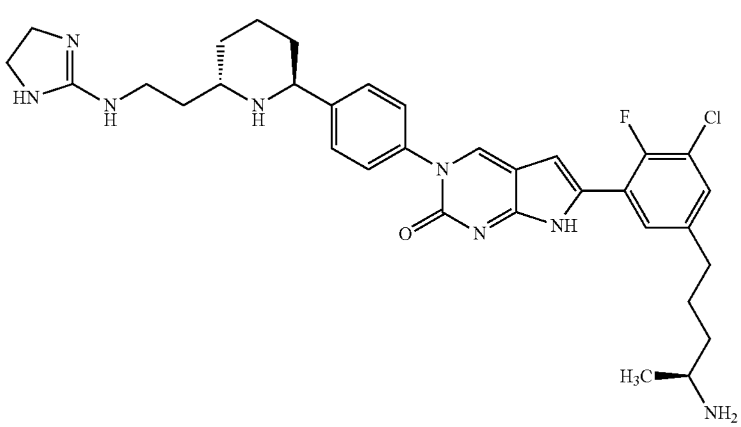 [SMILES: C[C@H](N)CCCc1cc(Cl)c(F)c(-c2cc3cn(-c4ccc([C@@H]5CCC[C@@H](CCNC6=NCCN6)N5)cc4)c(=O)nc3[nH]2)c1] | 619.7 |

TABLE 1-continued

| Compound No | Structure | ESI, m/z [M + H]+ |
|---|---|---|
| 548 | 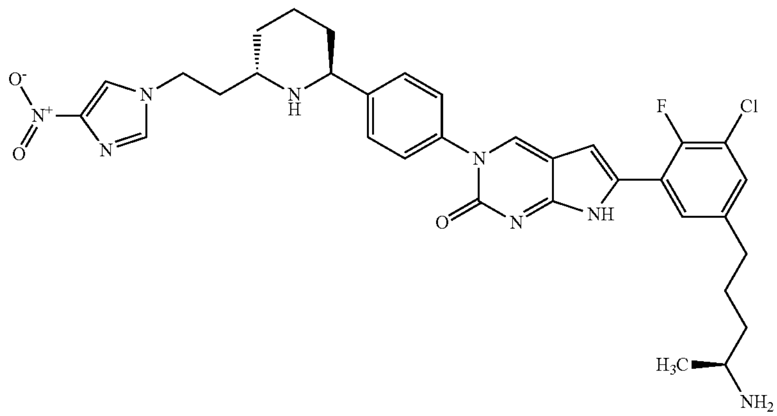 [SMILES: C[C@H](N)CCCc1cc(Cl)c(F)c(-c2cc3cn(-c4ccc([C@@H]5CCC[C@@H](CCn6cnc([N+](=O)[O-])c6)N5)cc4)c(=O)nc3[nH]2)c1] | 647 |
| 549 | 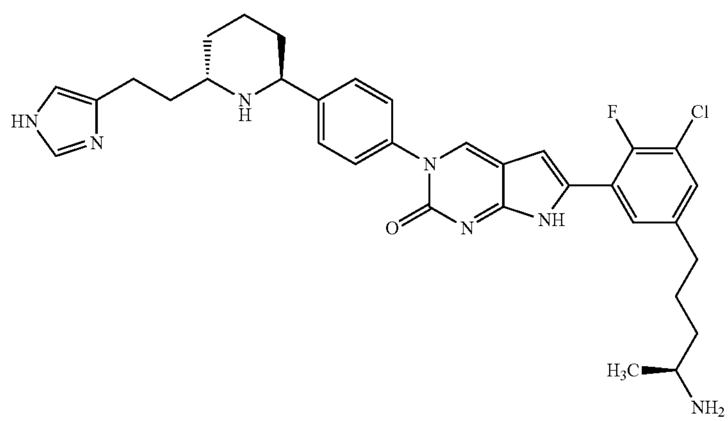 [SMILES: C[C@H](N)CCCc1cc(Cl)c(F)c(-c2cc3cn(-c4ccc([C@@H]5CCC[C@@H](CCc6c[nH]cn6)N5)cc4)c(=O)nc3[nH]2)c1] | 602 |
| 550 | 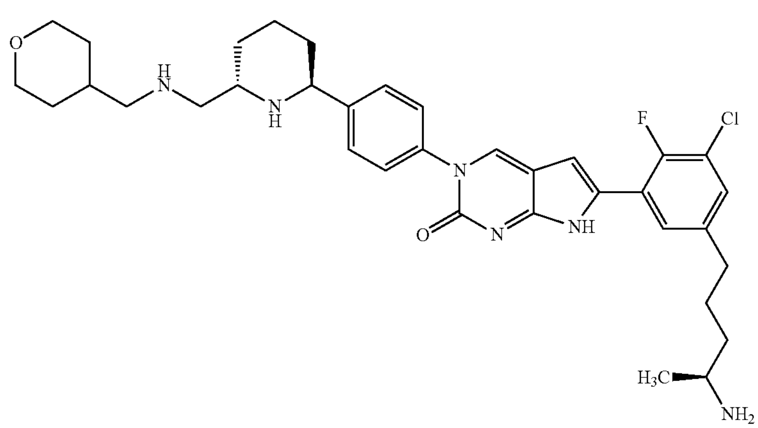 [SMILES: C[C@H](N)CCCc1cc(Cl)c(F)c(-c2cc3cn(-c4ccc([C@@H]5CCC[C@@H](CNCC6CCOCC6)N5)cc4)c(=O)nc3[nH]2)c1] | 635 |

TABLE 1-continued

| Compound No | Structure | ESI, m/z [M + H]+ |
|---|---|---|
| 551 | 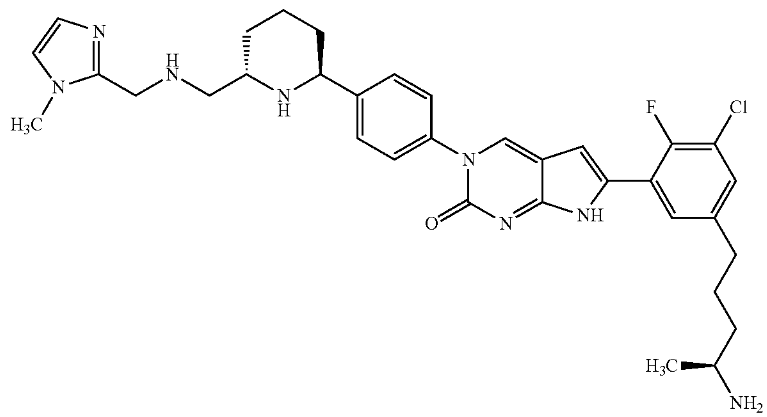 [SMILES: C[C@H](N)CCCc1cc(Cl)c(F)c(-c2cc3cn(-c4ccc([C@@H]5CCC[C@@H](CNCc6nccn6C)N5)cc4)c(=O)nc3[nH]2)c1] | 631 |
| 552 | 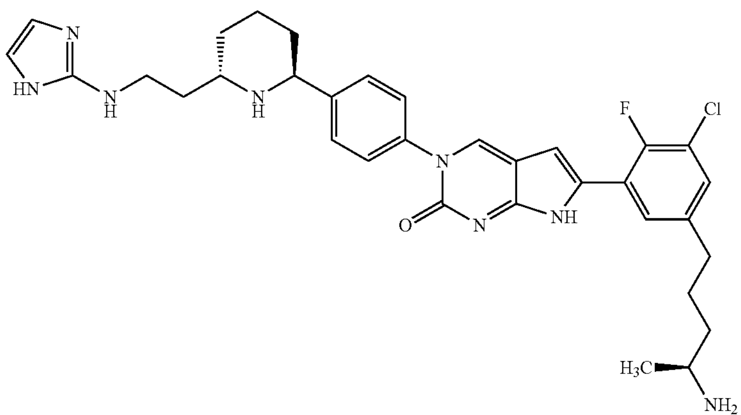 [SMILES: C[C@H](N)CCCc1cc(Cl)c(F)c(-c2cc3cn(-c4ccc([C@@H]5CCC[C@@H](CCNc6ncc[nH]6)N5)cc4)c(=O)nc3[nH]2)c1] | 617.7 |
| 553 | 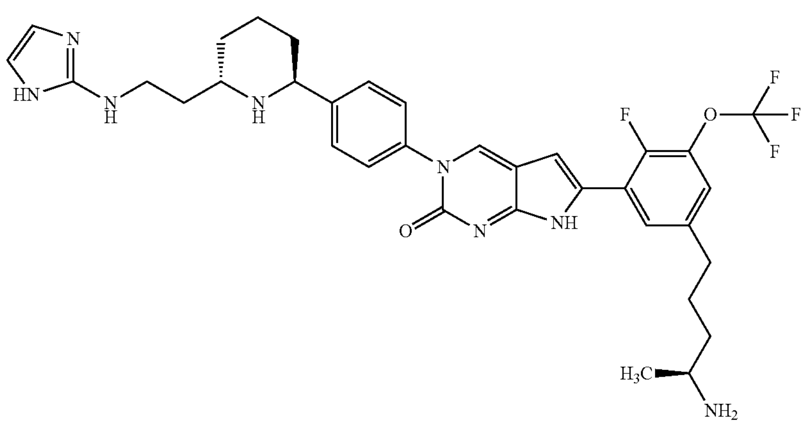 [SMILES: C[C@H](N)CCCc1cc(OC(F)(F)F)c(F)c(-c2cc3cn(-c4ccc([C@@H]5CCC[C@@H](CCNc6ncc[nH]6)N5)cc4)c(=O)nc3[nH]2)c1] | 667.7 |

TABLE 1-continued
| Compound No | Structure | ESI, m/z [M + H]+ |
|---|---|---|
| 554 | 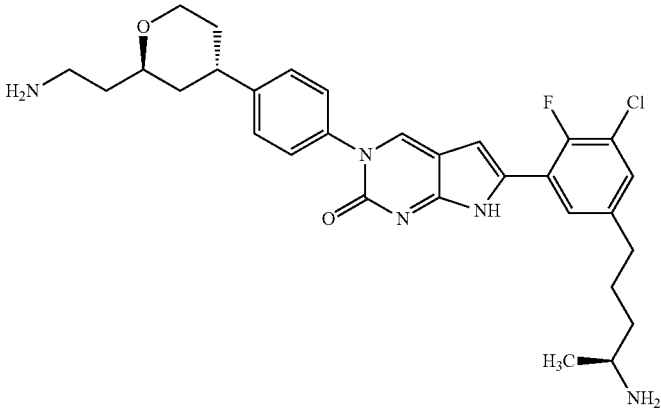 [SMILES: C[C@H](N)CCCc1cc(Cl)c(F)c(-c2cc3cn(-c4ccc([C@H]5CCO[C@H](CCN)C5)cc4)c(=O)nc3[nH]2)c1] | 553.09 |
| 555 | 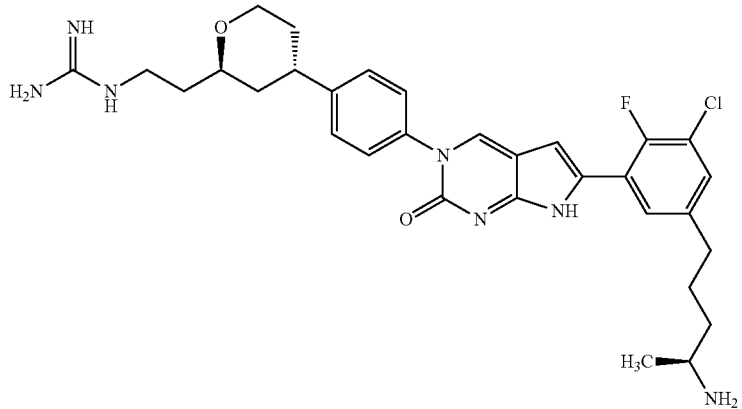 [SMILES: C[C@H](N)CCCc1cc(Cl)c(F)c(-c2cc3cn(-c4ccc([C@H]5CCO[C@H](CCNC(=N)N)C5)cc4)c(=O)nc3[nH]2)c1] | 595.13 |
| 556 | 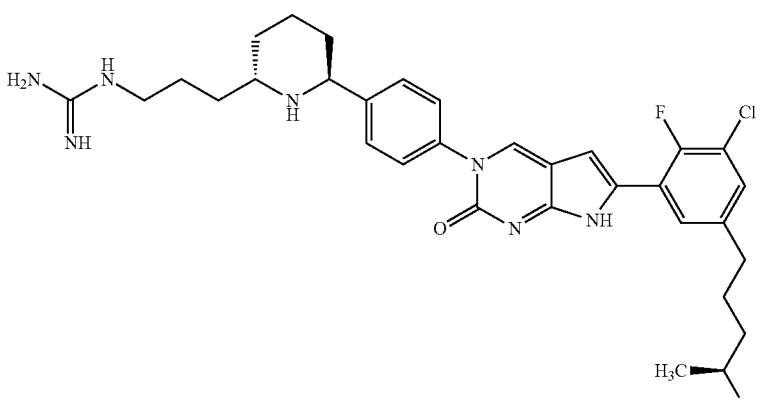 | 607 |

TABLE 1-continued

| Compound No | Structure | ESI, m/z [M + H]+ |
|---|---|---|
| 557 | 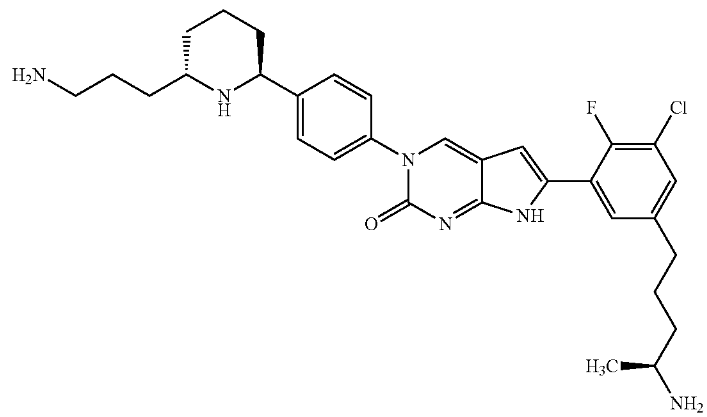 [SMILES: C[C@H](N)CCCc1cc(Cl)c(F)c(-c2cc3cn(-c4ccc([C@@H]5CCC[C@@H](CCCN)N5)cc4)c(=O)nc3[nH]2)c1] | 565 |
| 558 | 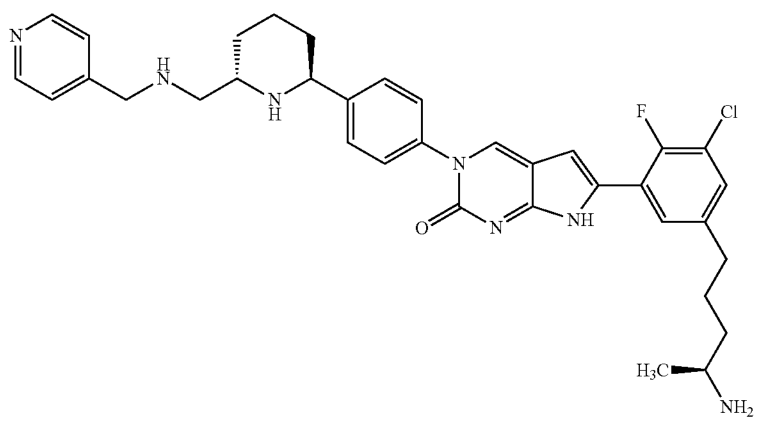 [SMILES: C[C@H](N)CCCc1cc(Cl)c(F)c(-c2cc3cn(-c4ccc([C@@H]5CCC[C@@H](CNCc6ccncc6)N5)cc4)c(=O)nc3[nH]2)c1] | 628 |
| 559 | 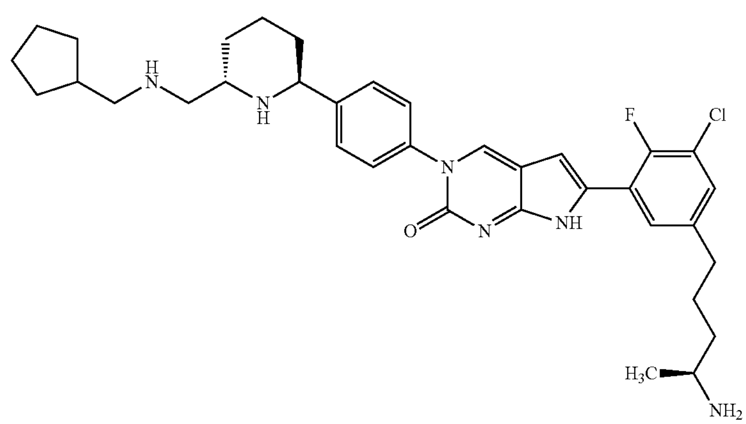 [SMILES: C[C@H](N)CCCc1cc(Cl)c(F)c(-c2cc3cn(-c4ccc([C@@H]5CCC[C@@H](CNCC6CCCC6)N5)cc4)c(=O)nc3[nH]2)c1] | 619 |

TABLE 1-continued

| Compound No | Structure | ESI, m/z [M + H]+ |
|---|---|---|
| 560 | 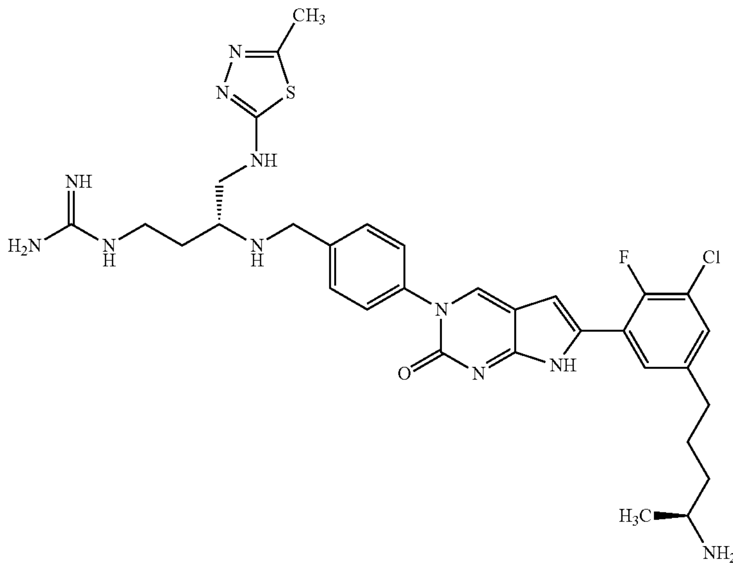 [SMILES: Cc1nnc(NC[C@@H](CCNC(=N)N)NCc2ccc(-n3cc4cc(-c5cc(CCC[C@H](C)N)cc(Cl)c5F)[nH]c4nc3=O)cc2)s1] | 680 |
| 561 | 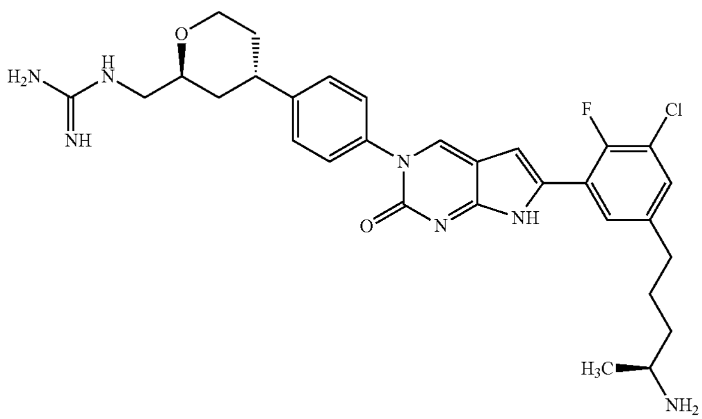 [SMILES: C[C@H](N)CCCc1cc(Cl)c(F)c(-c2cc3cn(-c4ccc([C@H]5CCO[C@H](CNC(=N)N)C5)cc4)c(=O)nc3[nH]2)c1] | 581.1 |
| 562 | 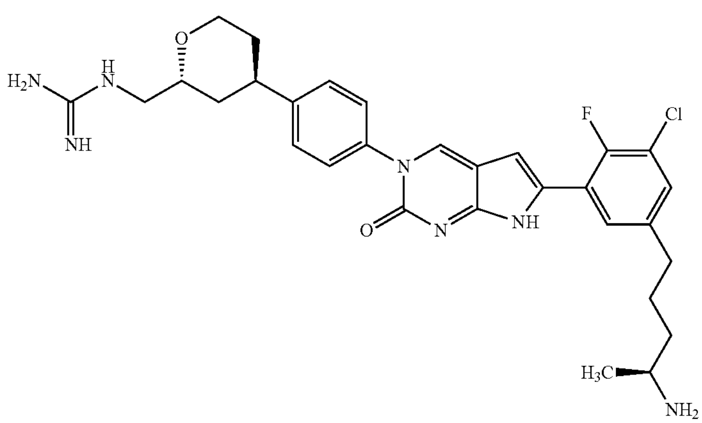 | 581.1 |

TABLE 1-continued
| Compound No | Structure | ESI, m/z [M + H]+ |
|---|---|---|
| 563 | 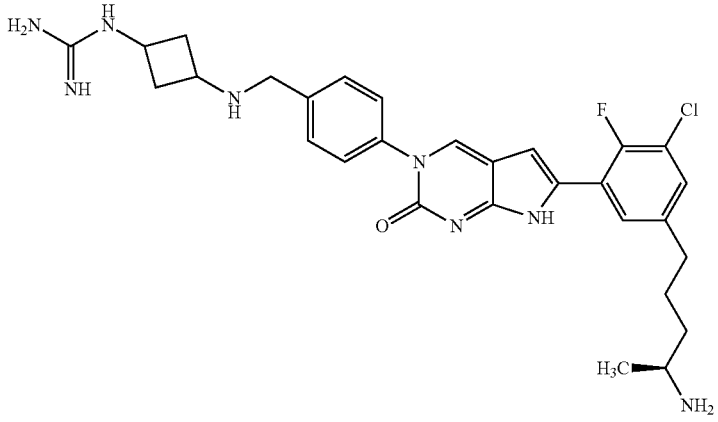 [SMILES: C[C@H](N)CCCc1cc(Cl)c(F)c(-c2cc3cn(-c4ccc(CNC5CC(NC(=N)N)C5)cc4)c(=O)nc3[nH]2)c1] | 565.6 |
| 564 | 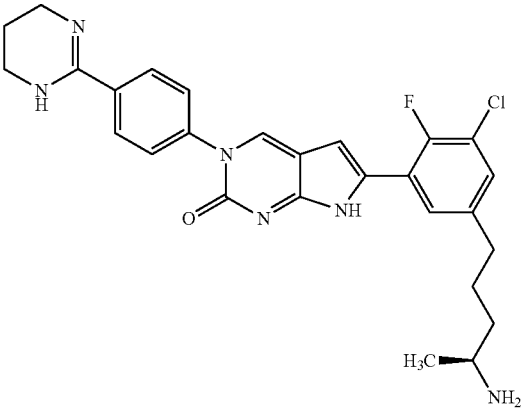 [SMILES: C[C@H](N)CCCc1cc(Cl)c(F)c(-c2cc3cn(-c4ccc(C5=NCCCN5)cc4)c(=O)nc3[nH]2)c1] | 507.6 |
| 565 | 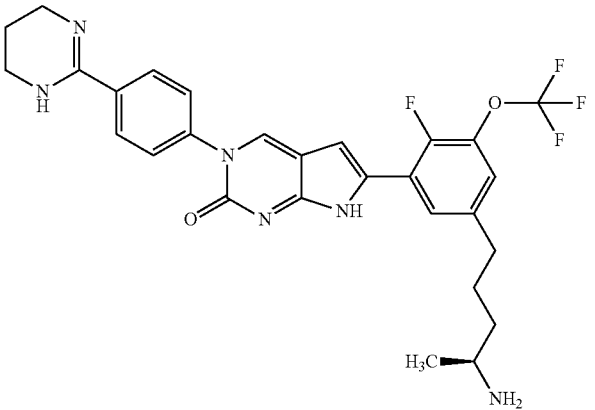 [SMILES: C[C@H](N)CCCc1cc(OC(F)(F)F)c(F)c(-c2cc3cn(-c4ccc(C5=NCCCN5)cc4)c(=O)nc3[nH]2)c1] | 557.5 |

TABLE 1-continued

| Compound No | Structure | ESI, m/z [M + H]+ |
|---|---|---|
| 566 | 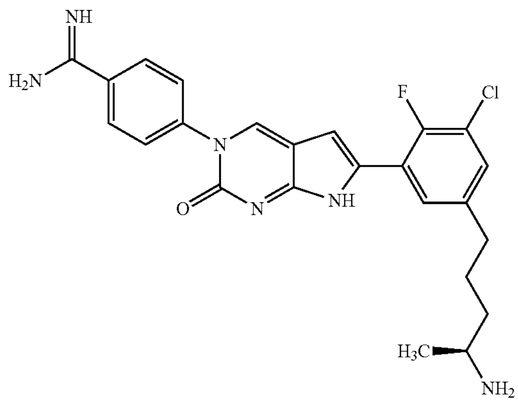 [SMILES: C[C@H](N)CCCc1cc(Cl)c(F)c(-c2cc3cn(-c4ccc(C(=N)N)cc4)c(=O)nc3[nH]2)c1] | 467.5 |
| 567 | 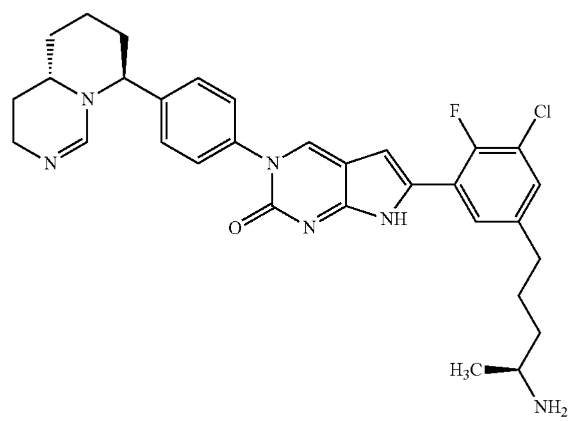 [SMILES: C[C@H](N)CCCc1cc(Cl)c(F)c(-c2cc3cn(-c4ccc([C@@H]5CCC[C@H]6CCN=CN65)cc4)c(=O)nc3[nH]2)c1] | 561.4 |
| 568 | 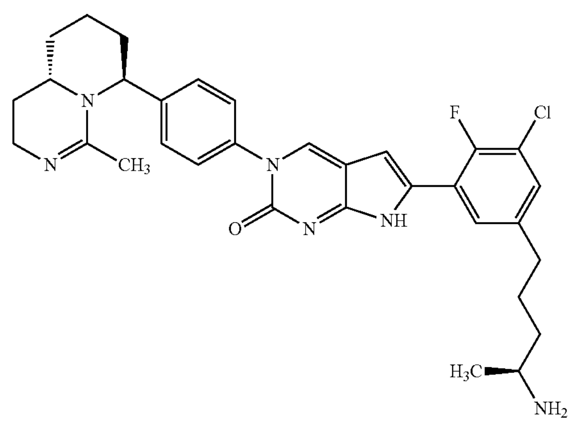 [SMILES: CC1=NCC[C@@H]2CCC[C@@H](c3ccc(-n4cc5cc(-c6cc(CCC[C@H](C)N)cc(Cl)c6F)[nH]c5nc4=O)cc3)N12] | 575.5 |
| 569 | 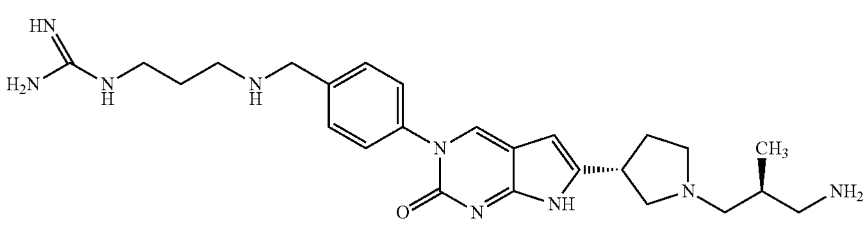 [SMILES: C[C@@H](CN)CN1CC[C@@H](c2cc3cn(-c4ccc(CNCCCNC(=N)N)cc4)c(=O)nc3[nH]2)C1] | 480.6 |

TABLE 1-continued

| Compound No | Structure | ESI, m/z [M + H]+ |
|---|---|---|
| 570 | 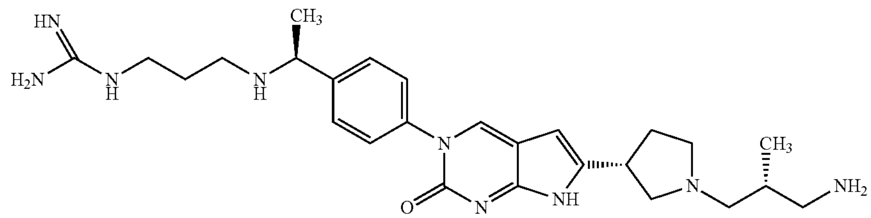 [SMILES: C[C@H](CN)CN1CC[C@@H](c2cc3cn(-c4ccc([C@H](C)NCCCNC(=N)N)cc4)c(=O)nc3[nH]2)C1] | 494.7 |
| 571 | 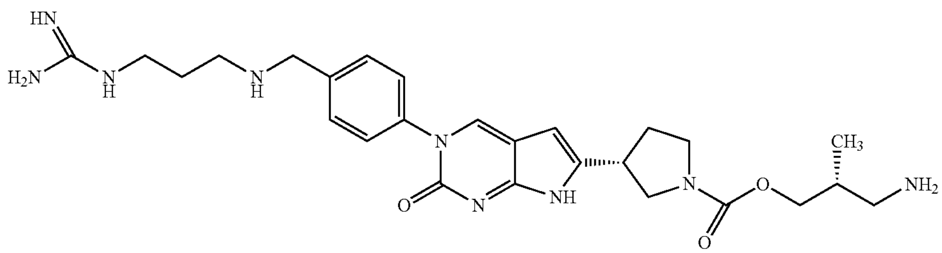 [SMILES: C[C@H](CN)COC(=O)N1CC[C@@H](c2cc3cn(-c4ccc(CNCCCNC(=N)N)cc4)c(=O)nc3[nH]2)C1] | 524.6 |
| 572 | 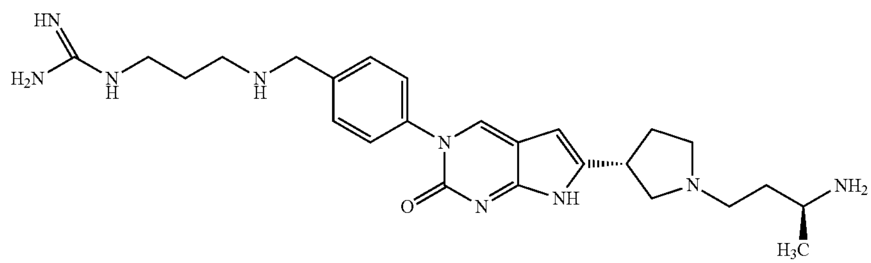 [SMILES: C[C@H](N)CCN1CC[C@@H](c2cc3cn(-c4ccc(CNCCCNC(=N)N)cc4)c(=O)nc3[nH]2)C1] | 480.6 |
| 573 | 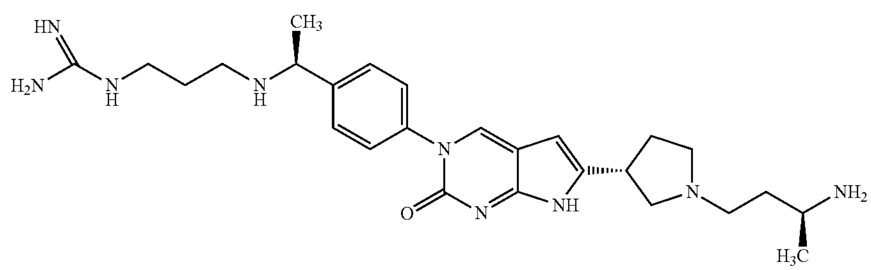 [SMILES: C[C@H](N)CCN1CC[C@@H](c2cc3cn(-c4ccc([C@H](C)NCCCNC(=N)N)cc4)c(=O)nc3[nH]2)C1] | 494.7 |
| 574 | 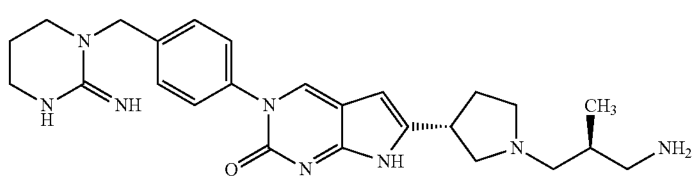 [SMILES: C[C@@H](CN)CN1CC[C@@H](c2cc3cn(-c4ccc(CN5CCCNC5=N)cc4)c(=O)nc3[nH]2)C1] | 463.7 |
| 575 | 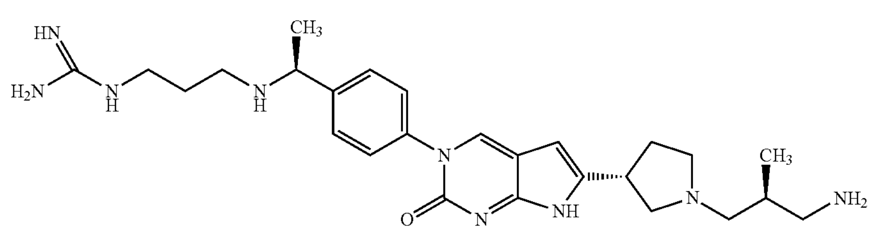 [SMILES: C[C@@H](CN)CN1CC[C@@H](c2cc3cn(-c4ccc([C@H](C)NCCCNC(=N)N)cc4)c(=O)nc3[nH]2)C1] | 494.7 |

TABLE 1-continued
| Compound No | Structure | ESI, m/z [M + H]+ |
|---|---|---|
| 576 | 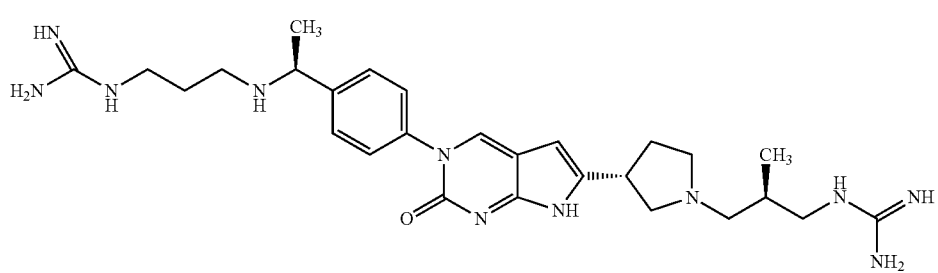 [SMILES: C[C@@H](CNC(=N)N)CN1CC[C@@H](c2cc3cn(-c4ccc([C@H](C)NCCCNC(=N)N)cc4)c(=O)nc3[nH]2)C1] | 536.7 |
| 577 | 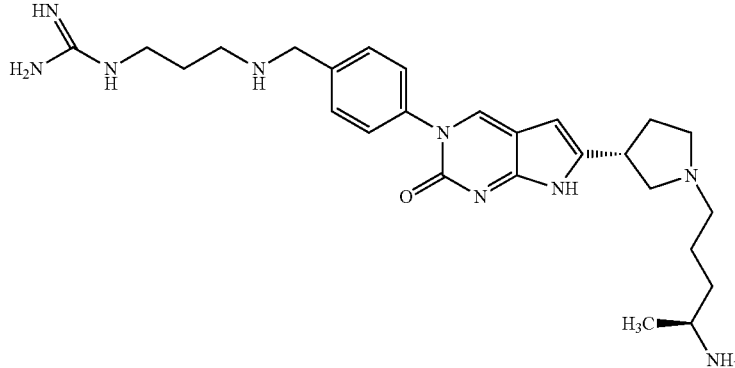 | 494.7 |
| 578 | 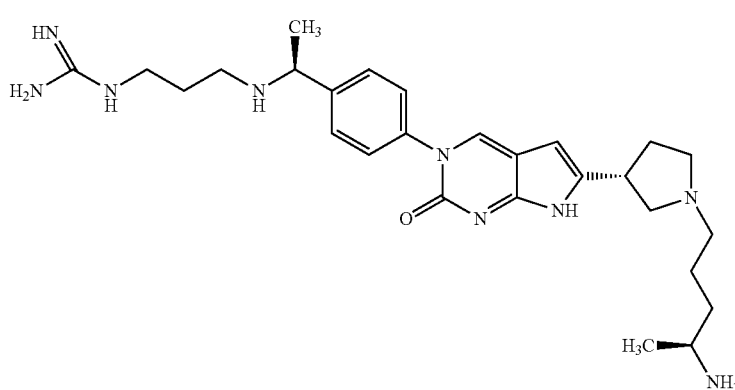 | 508.6 |
| 579 | 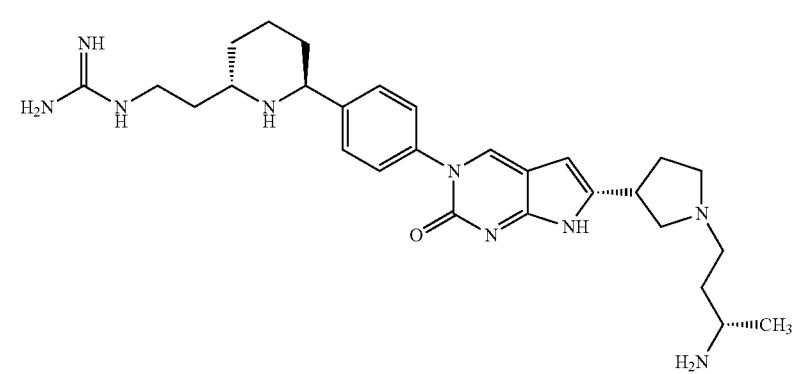 | 520.7 |

TABLE 1-continued

| Compound No | Structure | ESI, m/z [M + H]+ |
|---|---|---|
| 580 | 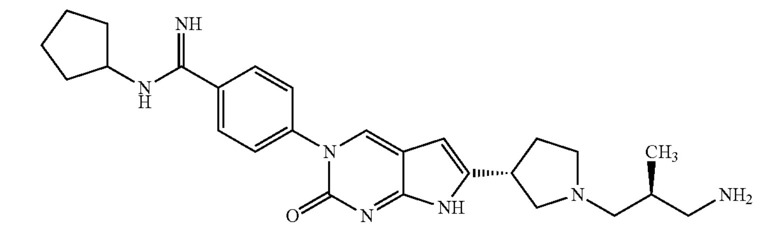 [SMILES: C[C@@H](CN)CN1CC[C@@H](c2cc3cn(-c4ccc(C(=N)NC5CCCC5)cc4)c(=O)nc3[nH]2)C1] | 462.2 |
| 581 | 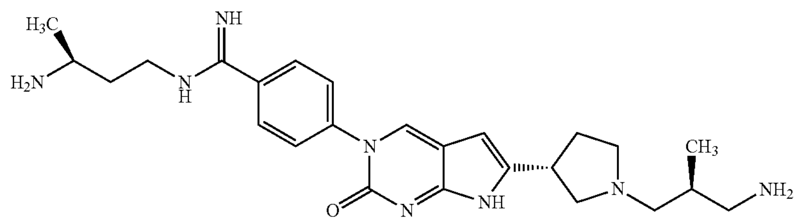 [SMILES: C[C@@H](CN)CN1CC[C@@H](c2cc3cn(-c4ccc(C(=N)NCC[C@H](C)N)cc4)c(=O)nc3[nH]2)C1] | 465.6 |
| 582 | 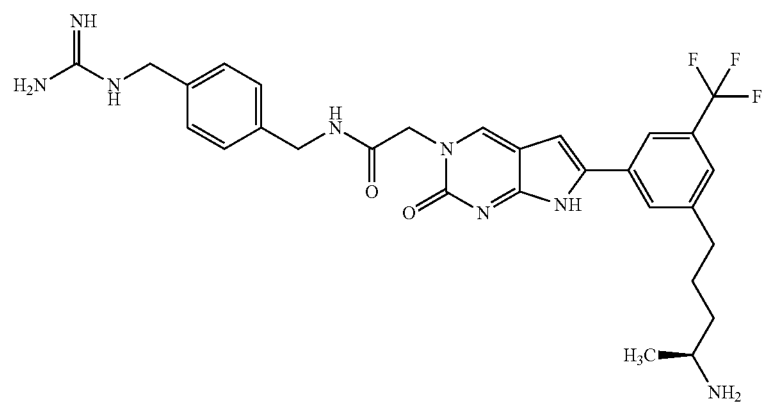 [SMILES: C[C@H](N)CCCc1cc(-c2cc3cn(CC(=O)NCc4ccc(CNC(=N)N)cc4)c(=O)nc3[nH]2)cc(C(F)(F)F)c1] | 583.7 |

The compounds of the present invention can be made using synthetic chemical techniques well known to those of skill in the art.

EXAMPLES

Example 1: Syntheses of Compounds 1-582

Compounds 1-582 were synthesized according to the methods described in WO 2012/173689 and in Schemes 1-10. Compounds 81, 85, 92, 135, 336, 340, 349, 353 and 357 were synthesized according to the methods described below.

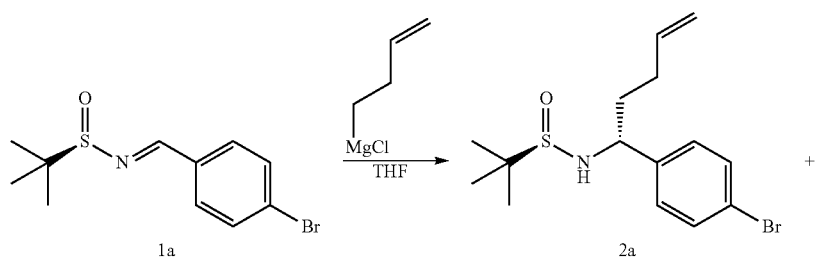

Synthetic scheme for Compound 81

-continued
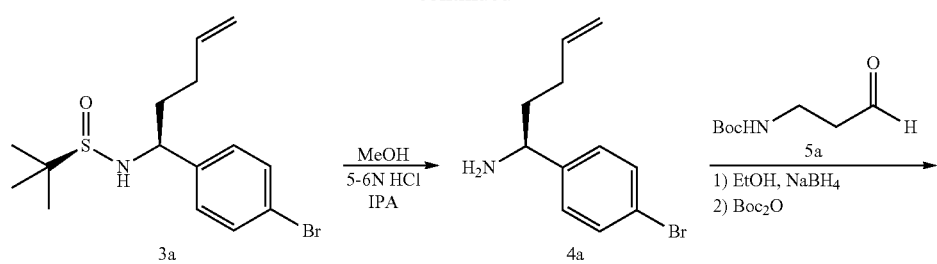
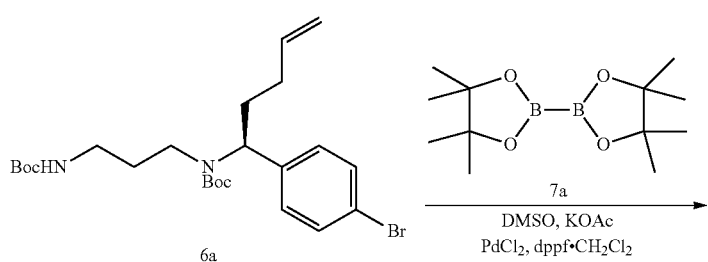
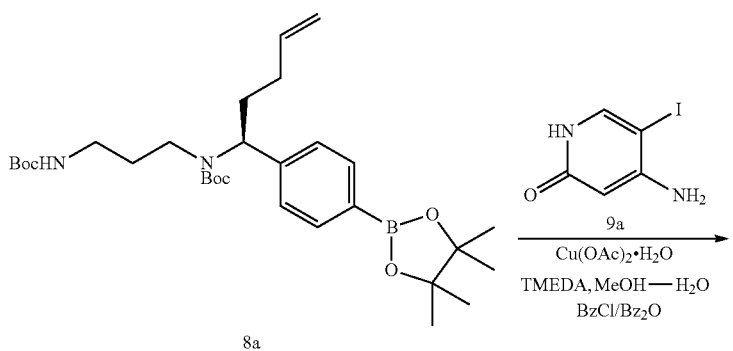
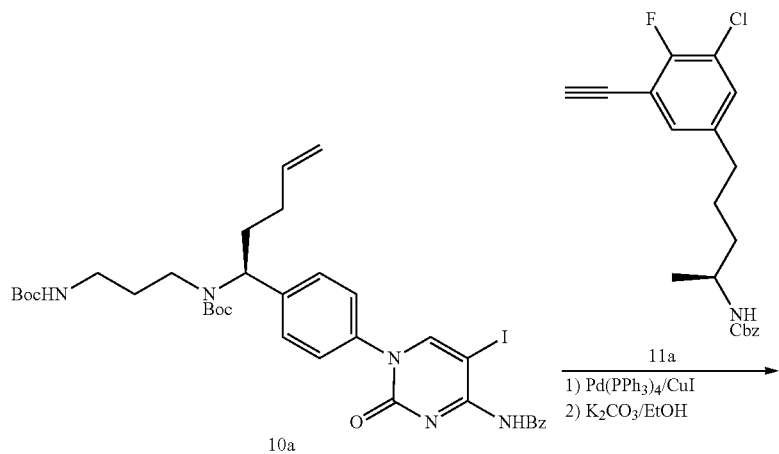

-continued

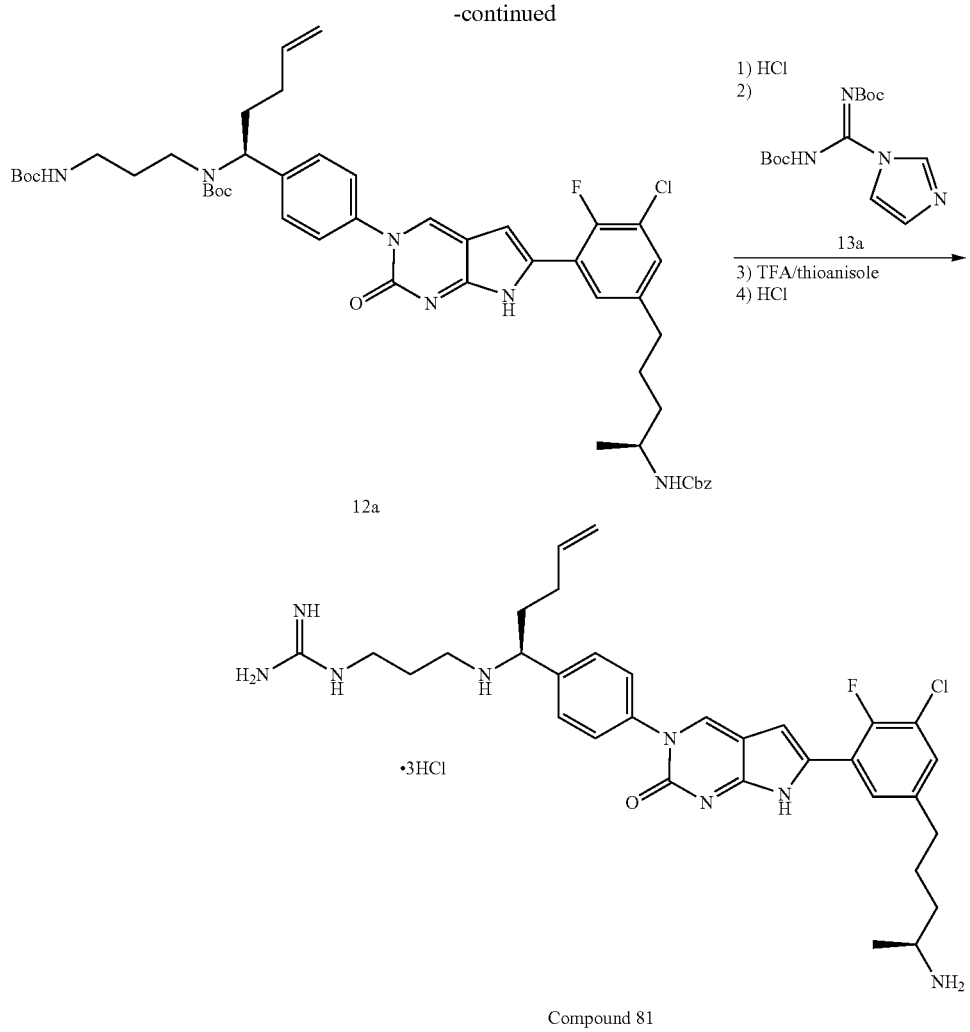

Pyridine para-toluenesulfonate (2.6 g) and magnesium sulfate (124 g) were added to a solution of (R)-(+)-2-methyl-2-propanesulfinamide (25 g) and 4-bromobenzaldehyde (42 g) in dichloromethane (300 mL). The resulting mixture was stirred overnight at ambient temperature. The resulting solution was then filtered, concentrated and purified by flash chromatography over silica gel (5% ethyl acetate in dichloromethane) to yield 48.8 g of compound 1a. A solution of compound 1a (10.1 g) in tetrahydrofuran (THF, 100 mL) was then treated with 3-butenyl magnesium bromide (200 mL, 0.5 M in THF) at −75° C. The mixture was slowly warmed up to ambient temperature and stirred overnight. The reaction was quenched with saturated ammonium chloride solution, extracted with ethyl acetate (3×100 mL). The combined organic layer was dried (with anhydrous sodium sulfate), concentrated and purified by flash chromatography over silica gel (40% ethyl acetate in heptane) to yield 2a and 3a. Compound 3a (2 g) in methanol (15 mL) was treated with 5-6 N HCl in isopropanol (5 mL) to afford amine 4a (1.2 g) as a hydrochloride salt. Compound 4a was converted to Compound 81 (ESI, m/z 607.1 [M+H]$^+$) as shown in the scheme above using a method similar to those described in WO 2012173689. Synthesis of compound 11a was described in WO2012173689.

Synthetic scheme for Compound 85

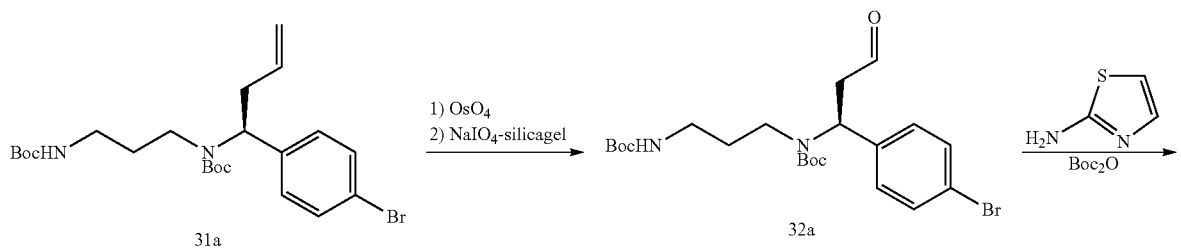

-continued
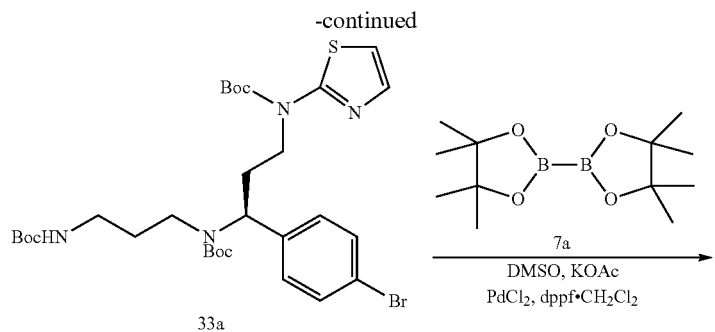
33a
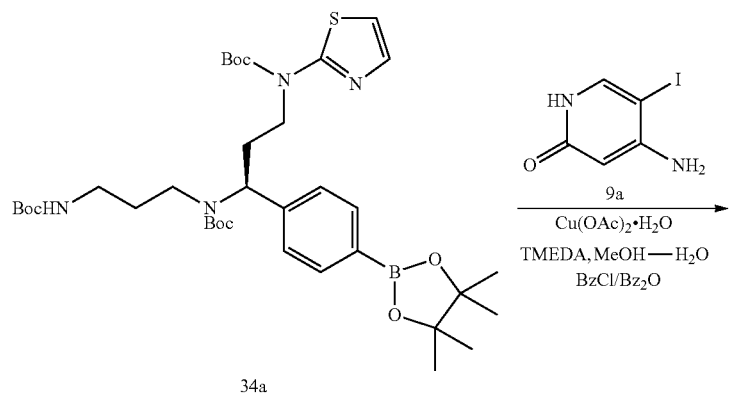
34a
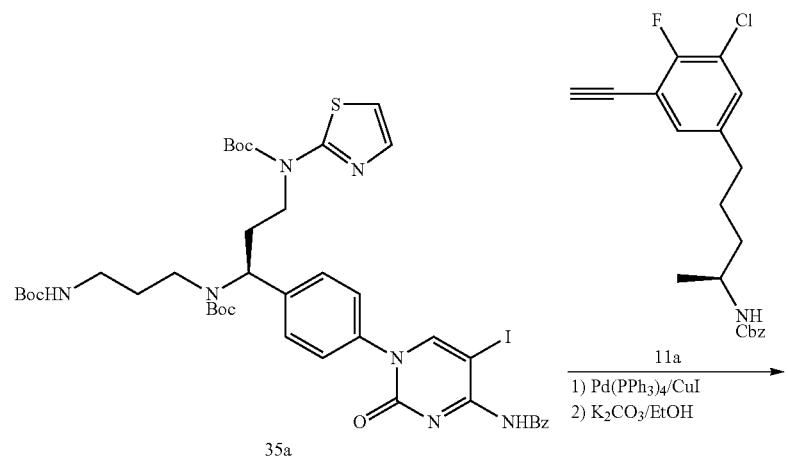
35a
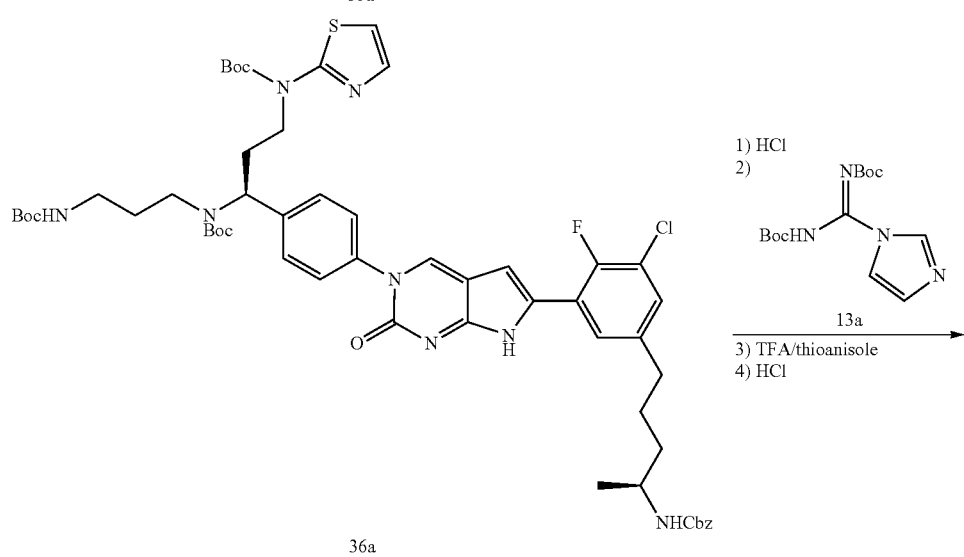
36a

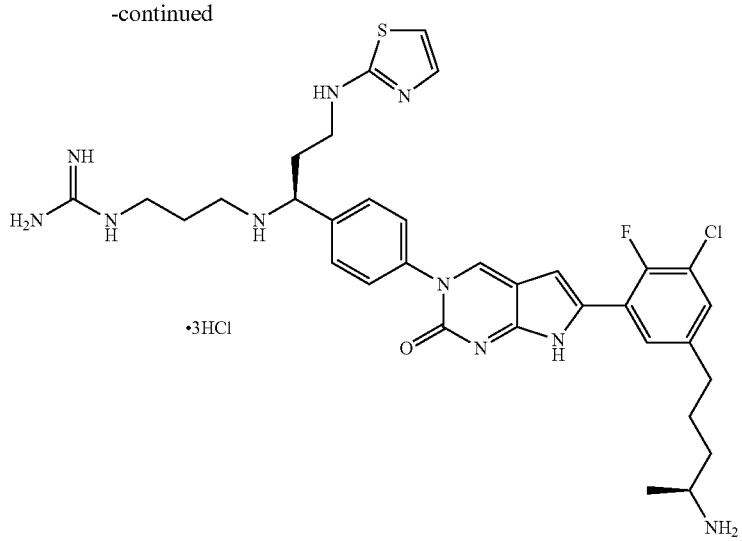

Compound 85

Compound 31a was synthesized using a method similar to that for compound 6a as shown in the synthetic scheme for Compound 81 above. It was then converted to aldehyde 32a by oxidation with Osmium tetroxide and Sodium periodate-silica gel combination. Then the aldehyde 32a underwent reductive amination with 2-amino thiazole followed by protection to yield 33a. This intermediate was converted to Compound 85 (ESI, m/z 340.1 [M+H]$^{+2}$) using a method similar to those as described in WO 2012173689.

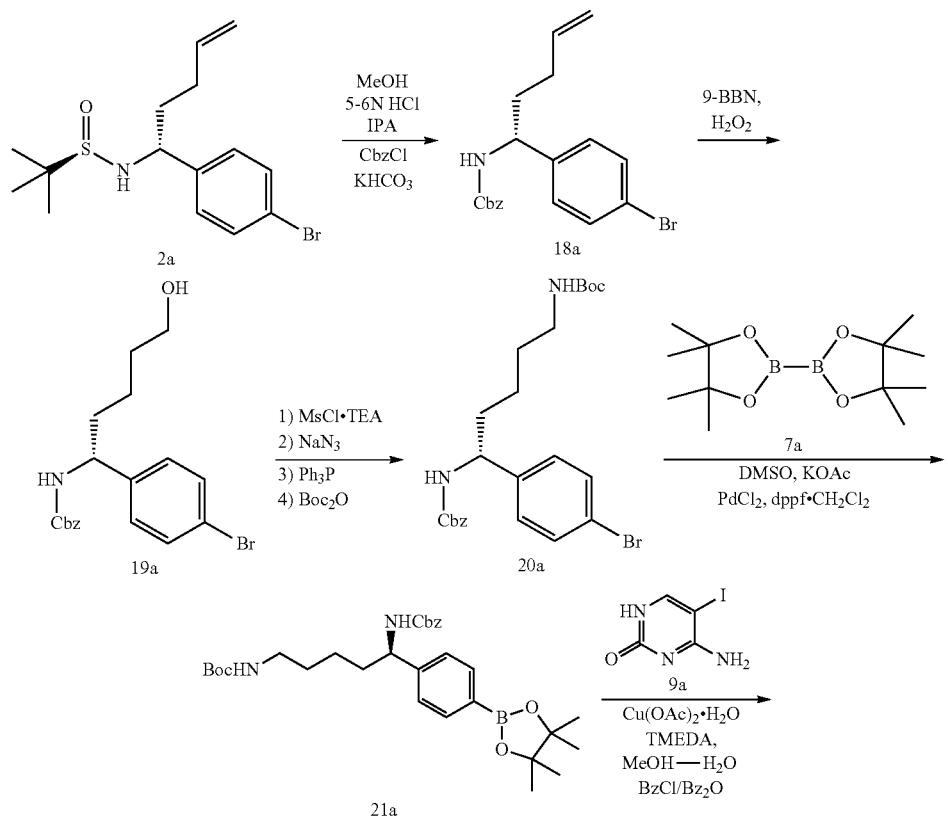

-continued

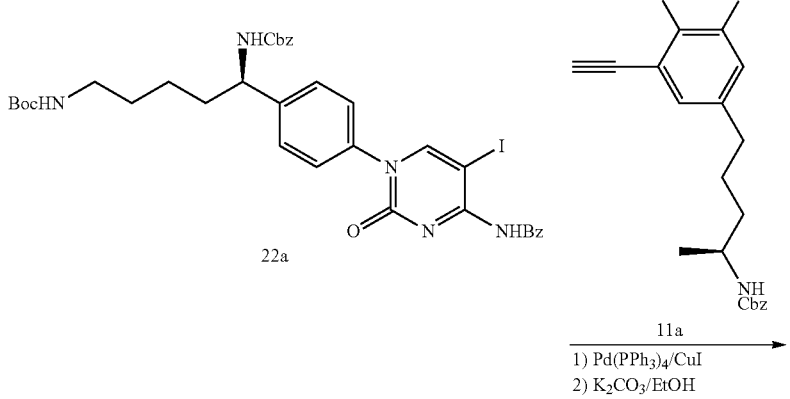

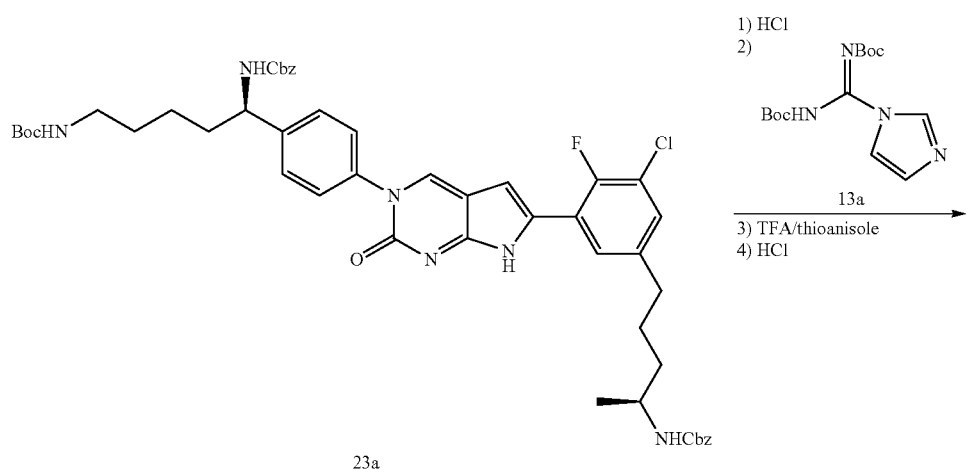

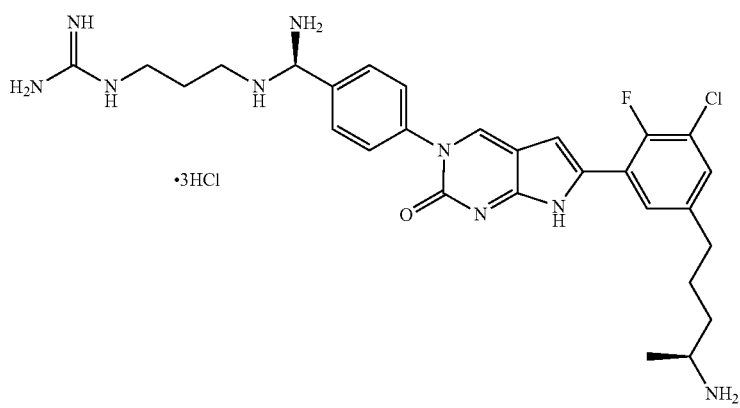

Compound 92

Compound 2a was treated with 5-6 N HCl in isopropanol, to afford corresponding amine which was isolated as protected amine 18a. To a solution of 18a (2.27 g) in THF was added 9-BBN (24.2 ml, 0.5 M in THF) and stirred overnight at ambient temperature. The solution was quenched with hydrogen peroxide and worked up to afford 19a (2.3 g). The alcohol 19a was converted to 20a (0.9 g) using standard synthetic protocol as shown in the scheme above. Compound 20a was converted to Compound 92 (ESI, m/z 567.1 [M+H]$^+$) as shown in the scheme above using a method similar to those described in WO 2012173689.

Synthetic scheme for Compound 135
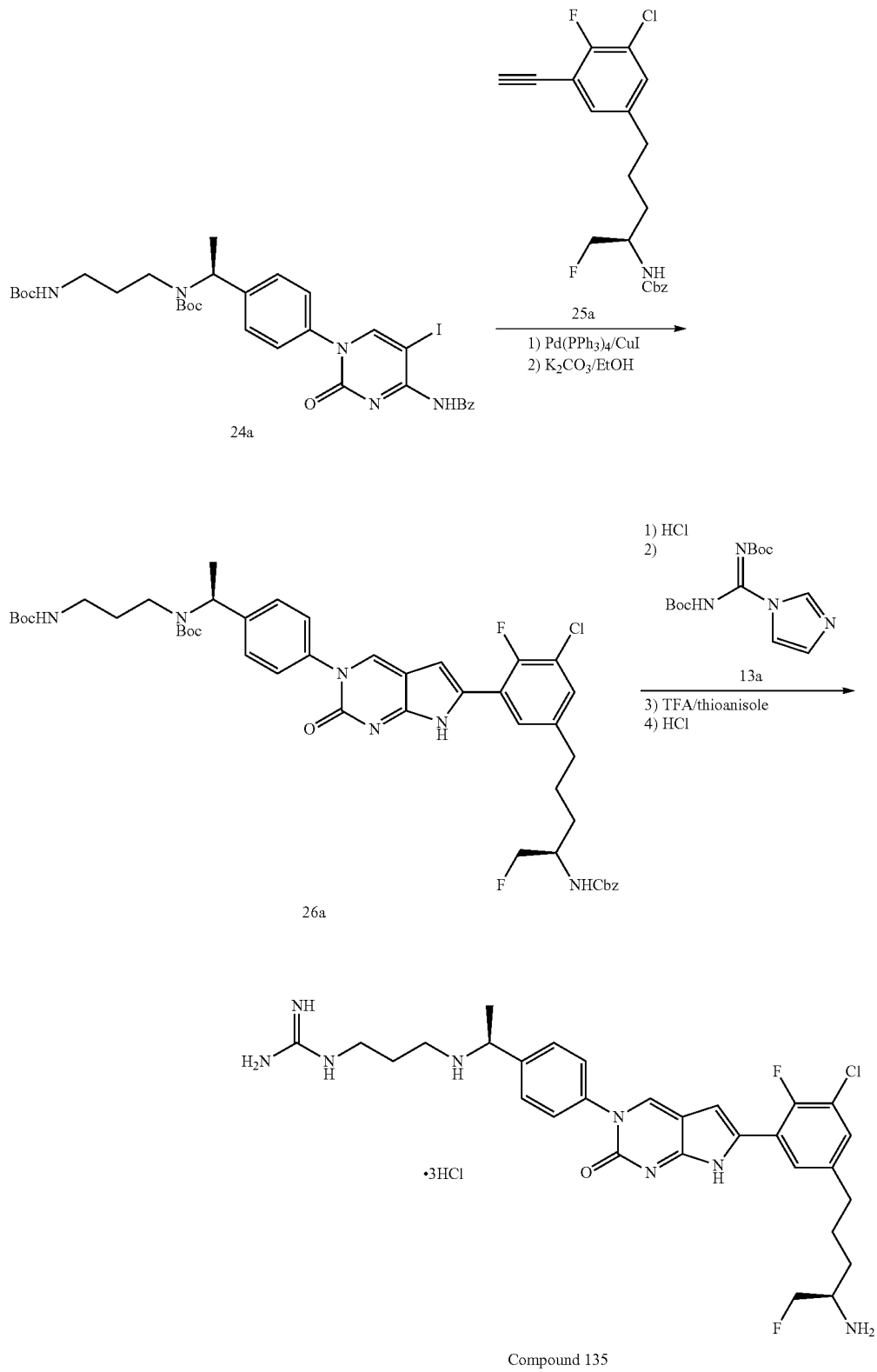
Compound 135
The intermediate 24a (synthesis of which is described in WO 2012173689) was converted to Compound 135 (ESI, m/z 585.1 [M+H]$^+$) as shown in the scheme above using a method similar to those described in WO 2012173689. The alkyne derivative 25a was made using the procedure as shown in the scheme below.

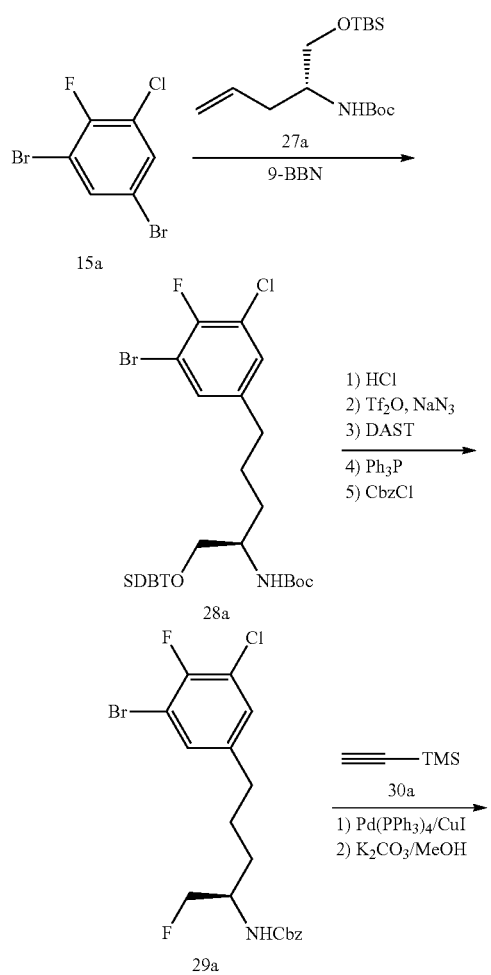

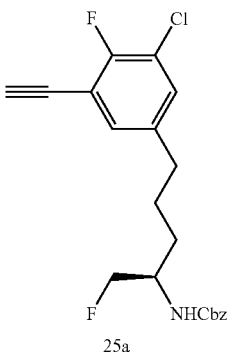

9-BBN (2.1 g) was added to a solution of 27a (4 g) in toluene (15 mL) and THF (15 mL) and the resulting mixture was stirred overnight at ambient temperature. The resulting solution was concentrated and 15a in toluene (40 mL) and 1N NaOH (30 mL) was added followed by Pd(PPh$_3$)$_4$. The resulting mixture was heated at 60° C. for 24 h. After standard work up and purification procedures, 4.7 g of 28a was obtained. The intermediated was then treated with 6N HCl to form corresponding amino alcohol (2.4 g) which was treated with trifluoromethyl sulfonic anhydride and sodium azide to afford corresponding azide (2.4 g). This azide (1.7 g) was treated with DAST followed by triphenyl phosphine and benzyl chloroformate (CbzCl) to afford 29a (0.8 g) as a pure material after chromatography. The polyhalogenated derivative 29a was coupled with 30a as shown above to yield pure 25a (0.5 g) after work up and purification.

Synthetic scheme for Compound 340

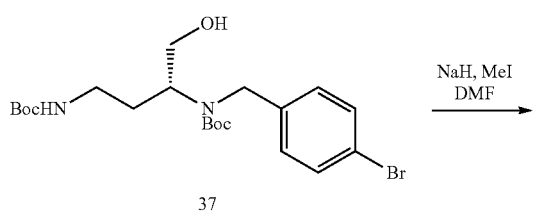

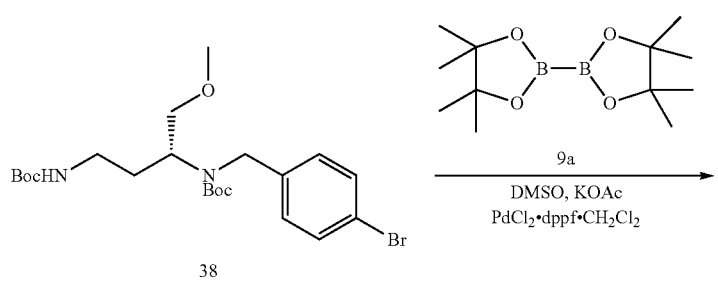

-continued
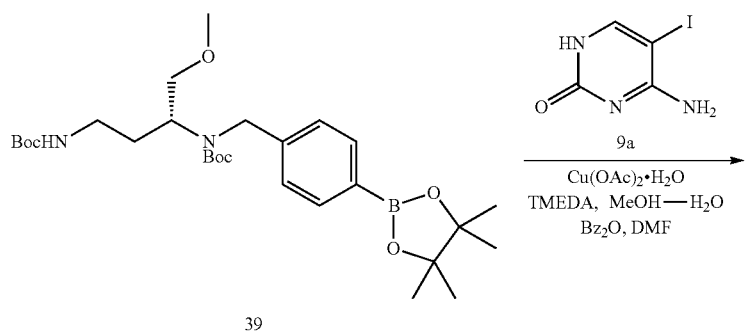
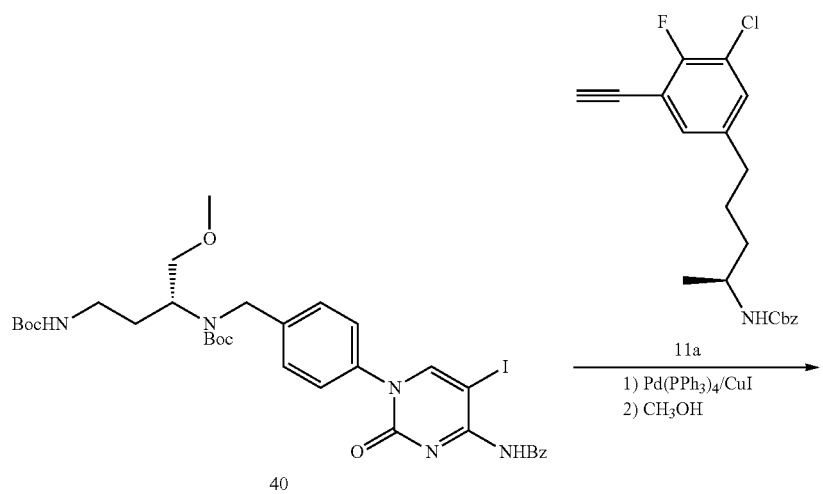
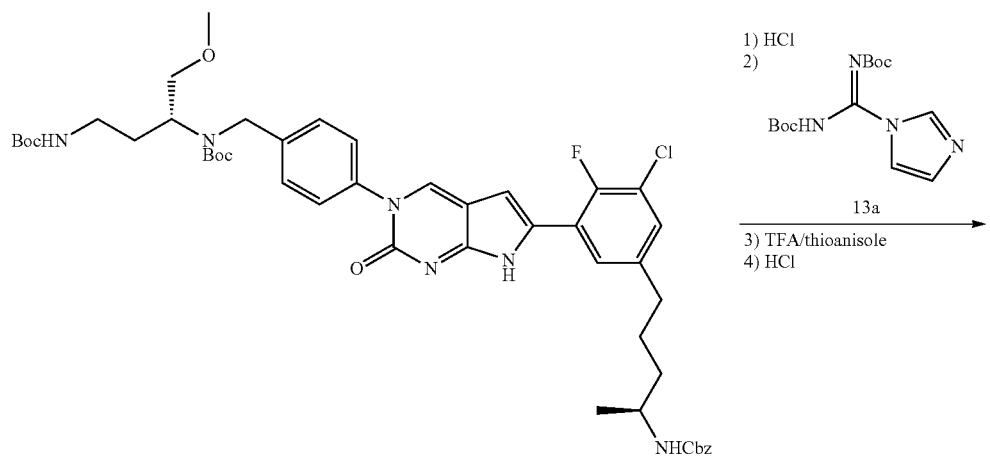

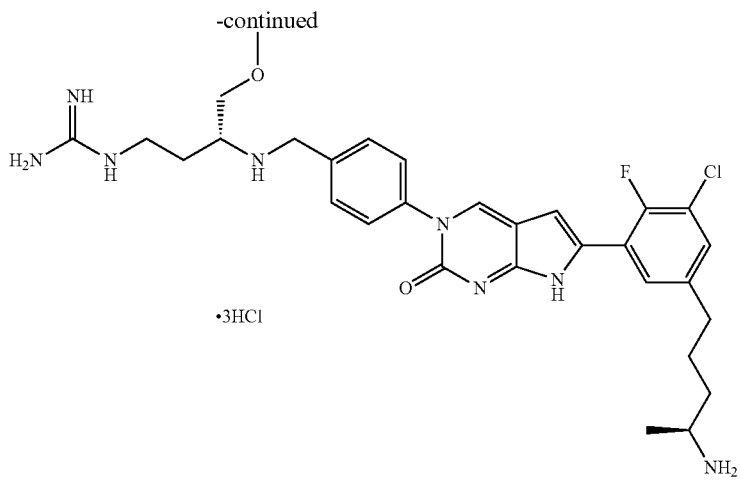

Compound 340

To a solution of 37 (2.5 g, 5.3 mmol) in DMF (20 mL) was added CH$_3$I (0.37 mL, 5.8 mmol) at 0° C. followed by NaH (60% suspension in mineral oil, 0.53 g, 13.2 mmol) and stirred for 1.5 hours at that temperature. The mixture was then warmed up to room temperature (1 hour) after which the reaction was slowly quenched with cold water (50 mL) and brine (50 mL). The solution was extracted with EtOAc (3×50 mL) and the combined organic layers were washed with brine (3×50 mL), dried, concentrated and purified by flash chromatography over silica gel (25% EtOAc/Heptane) to yield 38 (2.3 g). A mixture of 38 (2.3 g, 4.7 mmol), bis(pinacolato)diborane 9a (1.5 g, 5.7 mmol), Pd(dppf)Cl$_2$.CH$_2$Cl$_2$ (0.207 g, 0.3 mmol), and potassium acetate (KOAc) (1.4 g, 14.1 mmol) in DMF (25 mL) was degassed and heated at 85° C. under an atmosphere of argon overnight. The mixture was then diluted with EtOAc (50 mL), washed with water (3×50 mL), dried over MgSO$_4$, filtered and concentrated. The crude product was purified by flash chromatography over silica gel (25% EtOAc/Heptane) to afford 39 (2.2 g). Cu(OAc)$_2$ (0.906 g, 4.9 mmol) was added to a mixture of 39 (2.2 g, 4.1 mmol), 4-amino-5-iodo-1H-pyrimidin-2-one 9a (1.07 g, 4.5 mmol), MeOH (40 mL) and H$_2$O (10 mL), followed by N,N,N'N'-tetramethyl-ethane-1,2-diamine (2.3 mL, 10.2 mmol). The mixture was then stirred at room temperature under air for 48 hours before concentrated to a volume of ca. 130 mL. The residue was partitioned between EtOAc (100 mL) and 20% NH$_4$OH in saturated NH$_4$Cl solution (100 mL). The organic layer was separated and the aqueous layer was extracted with EtOAc (3×25 mL). The combined organics were washed with brine (3×100 mL), dried and concentrated. This material (2.5 g, 3.9 mmol) was dissolved in EtOAc (20 mL) and treated with benzoic anhydride (1.43 g, 6.2 mmol), Et$_3$N (1.6 mL, 9.7 mmol) and stirred for 24 hours. The reaction mixture was partitioned between EtOAc (100 mL) and saturated Na$_2$CO$_3$ solution (100 mL). The organic layer was separated, dried, concentrated and purified by flash chromatography over silica gel (20-40% EtOAc/Heptane) to afford 40 (1.55 g). Compound 40 (0.5 g, 0.7 mmol) and compound 11a (0.275 g, 0.73 mmol) were dissolved in anhydrous DMF (6 mL). The solution was then purged with argon, and CuI (0.018 g, 0.09 mmol), Pd(PPh$_3$)$_4$ (0.05 g, 0.04 mmol), and Et$_3$N (0.27 mL, 2.6 mmol) were added and stirred at 80-85° C. overnight. The solution was then cooled to room temperature, CH$_3$OH (10 mL) and Et$_3$N (1 mL) were added and the resulting mixture was stirred at 80° C. for 6 hours. After cooling to ambient temperature, the mixture was partitioned between EtOAc (50 ml) and 20% NH$_4$OH in saturated NH$_4$Cl solution (50 mL). The organic layer was separated, dried, concentrated and purified by preparative Thin Layer Chromatography (90% EtOAc/Heptane) to yield 41 (0.62 g).

Intermediate 41 was dissolved in CH$_3$OH (20 mL) and 6N HCl (12 mL) and heated to 40° C. for 5 hours. It was then concentrated to dryness, re-dissolved in CH$_3$OH (15 mL) and Hunig's base (0.5 mL, 3.0 mmol) was added followed by 13a (0.208 g, 0.66 mmol) and the resulting mixture was stirred for 24 hours at room temperature. The solution was then partitioned between EtOAc (75 mL) and brine (100 mL) and the organic layer was separated, washed with water (2×25 mL), dried, concentrated and purified by flash chromatography over silica gel (EtOAc/Heptane). This material thus obtained was treated with thioanisole (0.1 mL) and TFA (10 mL) and heated to 50° C. until the starting material disappeared. The reaction mixture was then concentrated and purified by a Shimadzu 10A-VP HPLC instrument using a Varian L4002 column (50 mm I.D.×300 mm) packed with 8 micron irregular C-18 coated silica. Mobile phases (A, water) and (B, methanol) contained 0.15 volume (vol) % of TFA as the buffer (Flow rate: 58 ml/min; a gradient of 20% to 100% of MeOH in water for 40 min was followed by isocratic 100% MeOH for 5 min). Detection was carried out at 220 nm. The product eluted at a R$_f$=ca. 40-45 min. The pure fractions (by LCMS and/or HPLC assay) were concentrated in vacuo. The residue was then treated with 1.0 N HCl/H$_2$O (5 mL) and concentrated almost to dryness. The latter step was repeated and the residue was dissolved in H$_2$O (3 mL). MeCN (1 mL) was then added, and the mixture was lyophilized overnight (vacuum: 2-5 Pa), affording desired compound 340 as the hydrochloride salt (3 HCl). (240 mg, ESI, m/z 597.8 [M+H]$^+$).

Synthetic scheme for Compound 349
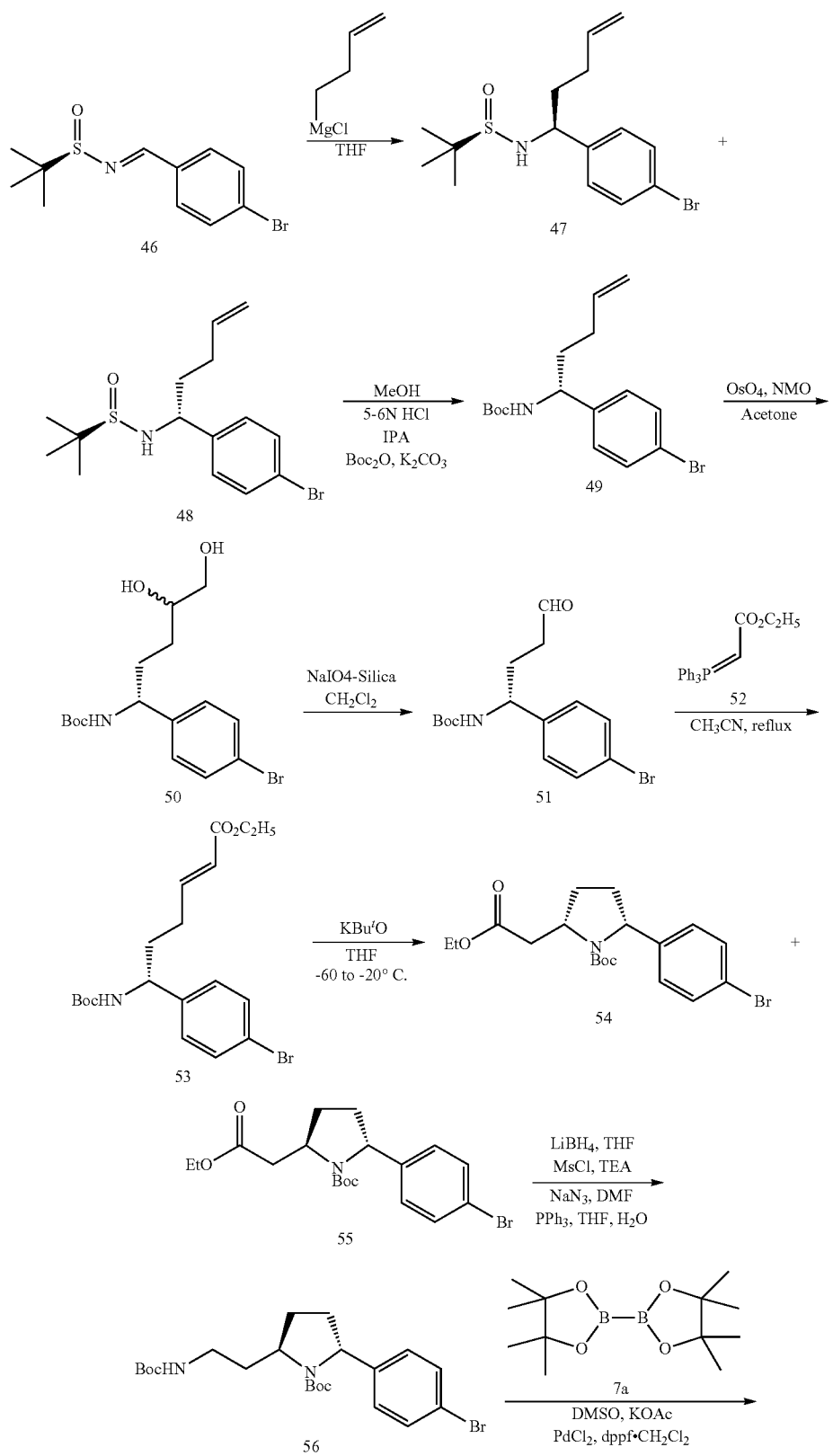

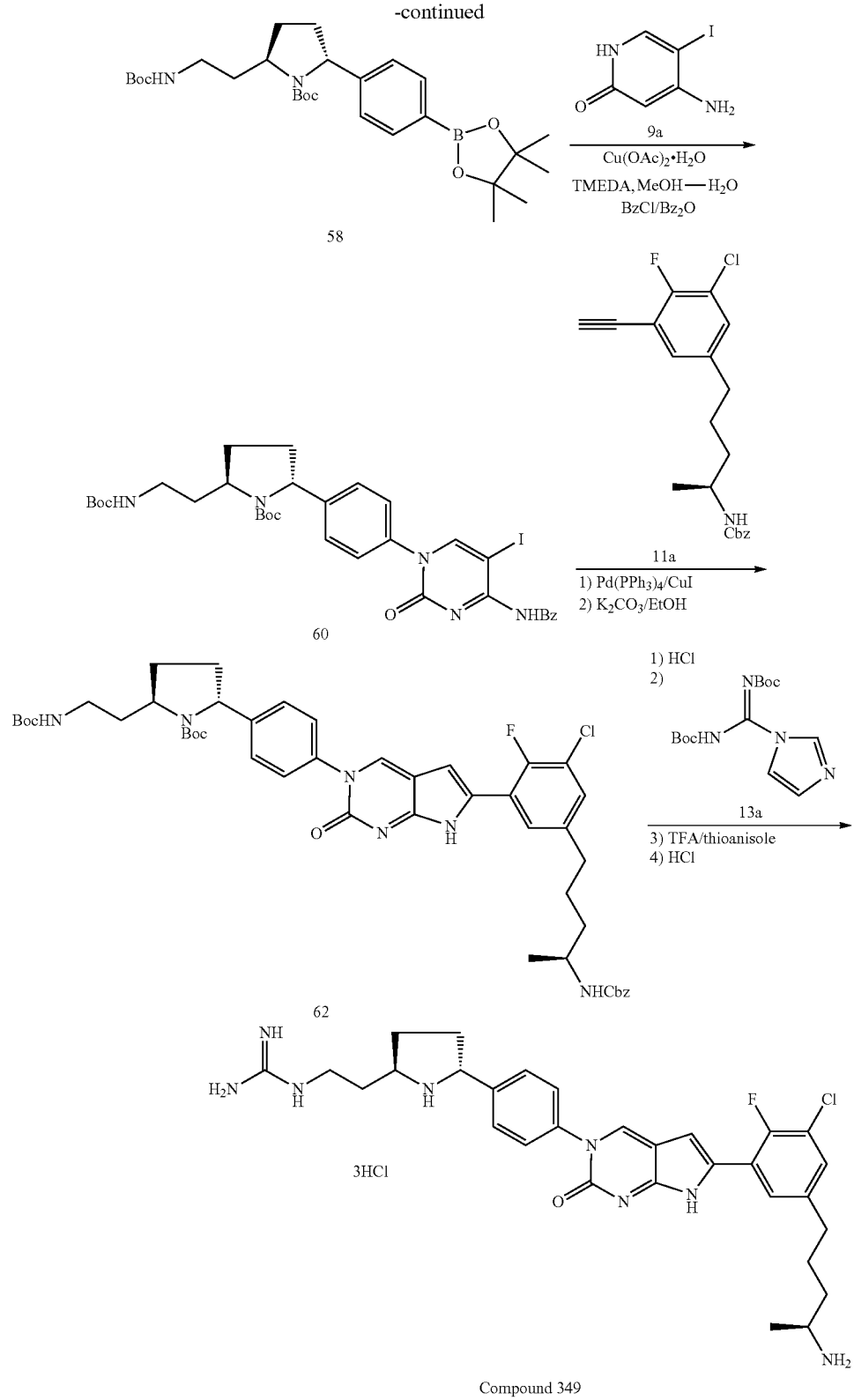

Compound 349

To a solution of (R)-(+)-2-Methyl-2-propanesulfinamide (25 g) and 4-bromobenzaldehyde (42 g) in dichloromethane (300 mL) was added pyridine para-toluenesulfonate (2.6 g) and magnesium sulfate (124 g) and the resulting mixture was stirred overnight at ambient temperature. The mixture was then filtered, concentrated and purified by flash chromatography over silica gel (5% ethyl acetate in dichloromethane) to afford 48.8 g of compound 46. A solution of compound 46 (10.1 g) in tetrahydrofuran (THF, 100 mL) was then treated with 3-butenyl magnesium bromide (200 mL, 0.5 M in THF) at −75° C. The mixture was slowly warmed up to ambient temperature and stirred overnight. The reaction was then quenched with saturated ammonium chloride solution, extracted with ethyl acetate (3×100 mL) and the combined organic layers were dried (with anhydrous sodium sulfate), concentrated and purified by flash chromatography over silica gel (40% ethyl acetate in heptanes) to yield 47 (4.1 g) and 48 (5.6 g). $^1$H NMR (300 MHz, CDCl$_3$): δ 7.47 (d, J=9 Hz, 2H), 7.19 (d, J=9 Hz, 2H), 5.75 (m, 1H), 4.97 (dd, 2H), 4.32 (m, 1H), 3.36 (d, J=3 Hz, 1H), 2.07 (m, 1H), 1.94 (m, 2H), 1.81 (m, 1H), 1.22 (s, 9H).

Compound 48 (5.6 g) in methanol (30 mL) was treated with 5-6 N HCl in isopropanol (15 mL) to afford the intermediate amine which was then treated with saturated solution of K$_2$CO$_3$ (100 mL) and with di-tert-butyl dicarbonate ((Boc)$_2$O. 6 g) and stirred for 72 hours. The resulting solution was then concentrated and extracted with EtOAc (2×100 mL). The combined organic layers were washed with brine (2×100 mL), dried, concentrated and purified by flash chromatography over silica gel (CH$_2$Cl$_2$) to yield 49 (7.3 g). $^1$H NMR (300 MHz, CDCl$_3$): δ 7.45 (d, J=8.3 Hz, 2H), 7.14 (d, J=8.3 Hz, 2H), 5.78 (m, 1H), 5.00 (dd, 2H), 4.77 (br d, 1H), 4.57 (br d, 1H), 2.04 (m, 2H), 1.78 (m, 2H), 1.35 (s, 9H).

To a mixture of 49 (7.3 g, 21.5 mmol) and NMO (5.8 g, 43.0 mmol) was added acetone (100 mL) followed by osmium tetroxide (OsO$_4$) (5-6 mL, 1% in water, 0.215 mmol) and the resulting mixture was stirred overnight at ambient temperature. The reaction mixture was then quenched with saturated of sodium thiosulphate solution (100 mL), extracted with ethyl acetate (3×75 mL), washed with brine (1×100 mL), dried, concentrated and purified by flash chromatography over silica gel (MeOH:CH$_2$Cl$_2$, 1:9) to afford 50 quantitatively. A mixture of 50 and NaIO$_4$-silica gel (43 g, 1.02 mmol/g) in CH$_2$Cl$_2$ (150 mL) was stirred for 5 hours, filtered, and concentrated to afford 51 which was used in the next step without further purification. A mixture of 51 and Wittig salt 52 (10 g, 43 mmol) was placed in a sealed tube with CH$_3$CN (70 mL) and heated to reflux for 72 hours. The solution was then concentrated, extracted with EtOAc (3×75 mL), washed with brine (3×75 mL), dried, and purified by flash chromatography over silica gel (30% Heptane in EtOAc) to afford 4.3 g of 53. $^1$H NMR (300 MHz, CDCl$_3$): δ 7.46 (d, J=8.3 Hz, 2H), 7.14 (d, J=8.3 Hz, 2H), 6.90 (dt, J=15.6, 6.8, 1H), 5.79 (d, J=15.6, 2H), 4.8 (d, J=7.8, 1H), 4.58 (br s, 1H), 4.15 (q, 2H), 2.19 (m, 2H), 1.87 (m, 2H), 1.40 (s, 9H), 1.28 (t, 3H).

To a solution of 53 (2.04 g, 4.95 mmol) in THF (25.0 ml) cooled in an acetone-dry ice bath (−60° C.) was added potassium tert-butoxide (0.433 g, 3.96 mmol, 0.8 equivalents) in one portion and the resulting mixture was stirred at, e.g., −60° C. The acetone-dry ice bath temperature was allowed to warm to ∼−20° C. and it was maintained at ∼−20° C. by addition of dry ice as required. After 2 hours of stirring at that temperature, the reaction was quenched by the addition of water (10.0 ml) and the resulting solution was allowed to warm to room temperature. The reaction mixture was then diluted with ether, the layers were separated and the aqueous layer was extracted with ethyl acetate. The combined organic layers were then dried over anhydrous Na$_2$SO$_4$ and concentrated to afford ∼2.13 g of pale yellow crude viscous liquid which was purified using Combiflash chromatography (80 gm silicycle column, 0-20-40% EtOAc in heptane as an eluent) to afford 54, 0.378 g (19%, minor, cis-isomer) and 55, 0.593 g (29%, major, trans-isomer).

To a solution of 55 (1.30 g, 3.16 mmol) in THF (15.0 ml) cooled in ice bath was added LiBH$_4$ in one portion and the resulting solution was allowed to warm to room temperature and stir under an atmosphere of argon. After stirring at RT overnight (17 hr), LC/MS still showed the presence of starting material therefore an additional ∼0.5 g (22.7 mmol) of LiBH$_4$ was added to push the reaction to completion. After 21 hr stirring at RT, reaction was cooled in ice bath and slowly quenched by the slow addition of ice and 1 N HCl solution (*caution: add HCl very slowly as there is exothermic reaction with vigorous effervescences). The reaction mixture was then extracted with EtOAc and the combined organic layers were dried over anhydrous Na$_2$SO$_4$, filtered and concentrated to afford a pale yellow viscous liquid ∼1.17 g (the alcohol) which was used in next step without any further purification.

1.17 g (∼3.16 mmol) of the primary alcohol was dissolved in CH$_2$Cl$_2$ and Et$_3$N (0.66 ml, 4.74 mmol, 1.5 equivalents) was added. The mixture was cooled in ice bath (0° C.) and MsCl (0.27 ml, 3.5 mmol, 1.1 equivalent) was added. The resulting solution was allowed to warm to room temperature and stirred for 24 hours under argon (additional equivalents of MsCl and Et$_3$N was added if necessary to push the reaction to completion, monitored by LC/MS and TLC). The reaction was then quenched with cold water, the layers were separated and the aqueous layer was extracted with CH$_2$Cl$_2$. The combined organic layers were then dried over anhydrous Na$_2$SO$_4$ and concentrated on to afford viscous oily mesylate (∼1.51 g) which was used for next step without any further purification.

A solution of the mesylate (crude, 3.16 mmol) obtained in the prior step and NaN$_3$ (0.62 g, 9.48 mmol, 3 equivalents) in DMF (10.0 ml) was heated to 70-75° C. in an oil bath under an atmosphere of argon. After 15 hours. LC/MS showed complete conversion of starting material and the reaction mixture was cooled to room temperature, diluted with water (20.0 ml) and extracted with EtOAc. The combined organic layers were then dried (Na$_2$SO$_4$) and concentrated to afford a viscous liquid (the azide) which was used in next step without any further purification.

To solution of the crude azide (3.16 mmol) in THF (10.0 ml) and water (2.0 ml) at room temperature was added triphenylphosphine (1.66, 6.32 mmol, 2 equivalents) and the resulting mixture was heated to 60-65° C. in an oil bath for 16 hours (monitored by LC/MS for conversion of starting material). After 16 hours, the heating was stopped and the reaction mixture was cooled to room temperature. Saturated NaHCO$_3$ solution (10.0 ml) and EtN$^i$Pr$_2$ (∼1.0 ml, 2 equivalents) was added followed by di-tert-butyl dicarbonate ((Boc)$_2$O, 1.1 g, 5.06 mmol, 1.6 equivalents) and the resulting mixture was heated to 45-50° C. in oil bath for 46 hours. The reaction mixture was then cooled to room temperature, diluted with water and EtOAc, and the layers were separated. The aqueous layer was extracted with EtOAc and the combined organic layers were dried (Na$_2$SO$_4$) and concentrated to afford a viscous liquid which was purified using Combiflash chromatography (40 g column, gradient −0 to 40 to 60% EtOAc in heptane as eluent) to afford 0.521 g of 56 (yield 35% for 5 steps).

To a solution of 56 (0.55 g, 1.2 mmol) in DMSO (6.0 ml) under an atmosphere of argon was added bispinacalatodiborane 7a (0.36 g, 1.4 mmol, 1.2 equivalents) and potassium acetate (0.35 g, 3.6 mmol, 3.0 equivalents) followed by PdCl$_2$(dppt)CH$_2$Cl$_2$ (0.05 g, 0.06 mmol, 5 mol %). The resulting mixture was heated with stirring under an atmosphere of argon at 80-85° C. for 20 hours. Once LC/MS showed reaction completion, the reaction mixture was cooled to room temperature, diluted with water (15.0 ml) and 60-70% EtOAc in heptane. The layers were then separated and the aqueous layer was extracted with 60% EtOAc in heptane. The combined organic layers were dried ($Na_2SO_4$) and concentrated to provide a dark brown viscous liquid which was purified using Combiflash chromatography (40 g column, 0-40% EtOAc in heptane as eluent) to afford 0.497 g (80%) of 58.

To a solution of 58 (0.497 g, 0.96 mmol) in MeOH:$H_2O$ (4:1, 25.0 ml) was added iodocytosine, 9a (0.251 g, 1.06 mmol, 1.1 equivalents) followed by $Cu(OAc)_2$, $H_2O$ (0.18 g, 0.96 mmol, 1.0 equivalent) and TMEDA (0.3 ml, 1.92 mmol, 2.0 equivalent). The resulting solution was stirred at room temperature and air was bubbled very slowly through reaction mixture. After stirring for 19 hours at room temperature, the reaction mixture was concentrated to remove any MeOH and diluted with water. The $CH_2Cl_2$ layers were separated and the aqueous later was extracted two more times with $CH_2Cl_2$. The combined organic layers were then dried (anhydrous $Na_2SO_4$) and concentrated afford the coupled product which was used in next step without any further purification.

To a solution in EtOAc (15.0 ml) was added $Bz_2O$ (0.26 g, 1.15 mmol, 1.2 equivalents) and the resulting solution was heated in an oil bath to 70-75° C. under argon atmosphere for 3 hours. Once LC/MS showed reaction completion, the reaction mixture was cooled to room temperature and diluted with saturated $NaHCO_3$ solution. The layers were separated and the aqueous layer was extracted with EtOAc. The combined organics were then dried ($Na_2SO_4$) and concentrated to provide a viscous liquid which was purified using Combiflash chromatography (40 g column, 0 to 40 to 60% EtOAc in heptane as eluent) to afford 0.45 g (64% for 2 steps) of 60 as white solid.

To a degassed solution of 60 (0.252 g, 0.35 mmol) in DMF (6.0 ml) under an atmosphere of argon was added alkyne 11a (0.131 g, 0.35 mmol, 1.0 equivalent) and $EtN^iPr_2$ (0.18 ml, 1.05 mmol, 3.0 equivalents) followed by Pd($PPh_3)_4$ (0-2 g, 0.018 mmol, 5 mol %) and CuI (0.007 g, 0.036 mmol, 10 mol %). The resulting solution was flushed with argon and heated to 70-75° C. with stirring under an atmosphere of argon for 16 hours. Once LC/MS showed complete conversion of 60, the reaction mixture was cooled to room temperature and MeOH (~8.0 ml) was added. The resulting solution was then heated under argon to 75-80° C. for 9 hours (checked by LC/MS for complete conversion of intermediate). The reaction mixture was cooled to room temperature, concentrated to remove MeOH, and diluted with water (15.0 ml). The EtOAc (20 ml) layer was separated and the organic layer was extracted once with EtOAc. The combined organic layers were washed with $NH_4OH$, water and brine, dried ($Na_2SO_4$), and concentrated to provide a dark brown viscous liquid which was purified by using prep TLC (100% EtOAc as eluent) to afford protected intermediate 62 (0.274 g, 90%) as viscous liquid.

To a solution of 62 (0.27 g, 0.31 mmol) in $CH_2Cl_2$ (6.0 ml) was added a 4N solution of HCl in dioxane (1.5 ml) and the resulting solution was stirred at room temperature for 2 hours. Once LC/MS showed complete conversion of starting material, the reaction mixture was concentrated and dried under vacuum to provide the deprotected amine intermediate as a foam which was used in next step without any further purification.

To a solution of the deprotected amine intermediate in MeOH (6.0 ml) at room temperature was added $EtN^iPr_2$ (0.54 ml, 3.1 mmol, 10.0 equivalents) and Bis-boc-guanylpyrazole 13a (0.12 g, 0.37 mmol, 1.32 equivalents) and the resulting reaction mixture was stirred at room temperature. After stirring overnight (16 hours) LC/MS showed complete conversion of starting material. The reaction mixture was then concentrated to afford a viscous liquid which was used in next step without any further purification.

To a solution of the above compound (0.31 mmol) in trifluoroacetic acid (6.0 ml) was added thioanisole (3-4 drops) and the resulting mixture was stirred with heating to 45° C. in an oil bath for 3 hours. Once LC/MS showed reaction completion, the reaction mixture was cooled to room temperature, concentrated, and purified using Varian prep HPLC (method 35-65% B 50 min). HPLC fractions were concentrated and the obtained TFA salt was converted to the HCl salt by treatment with 6 N HCl (2×). The resulting solid was lyophilized to afford 0.102 g of 349 as bright yellow colored solid.

Synthetic scheme for Compound 336

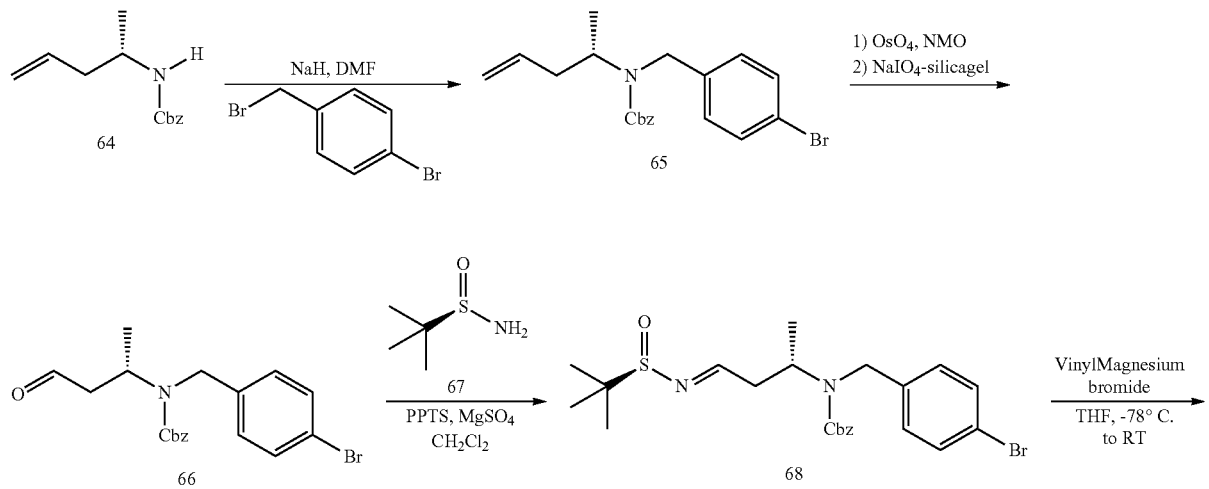

-continued
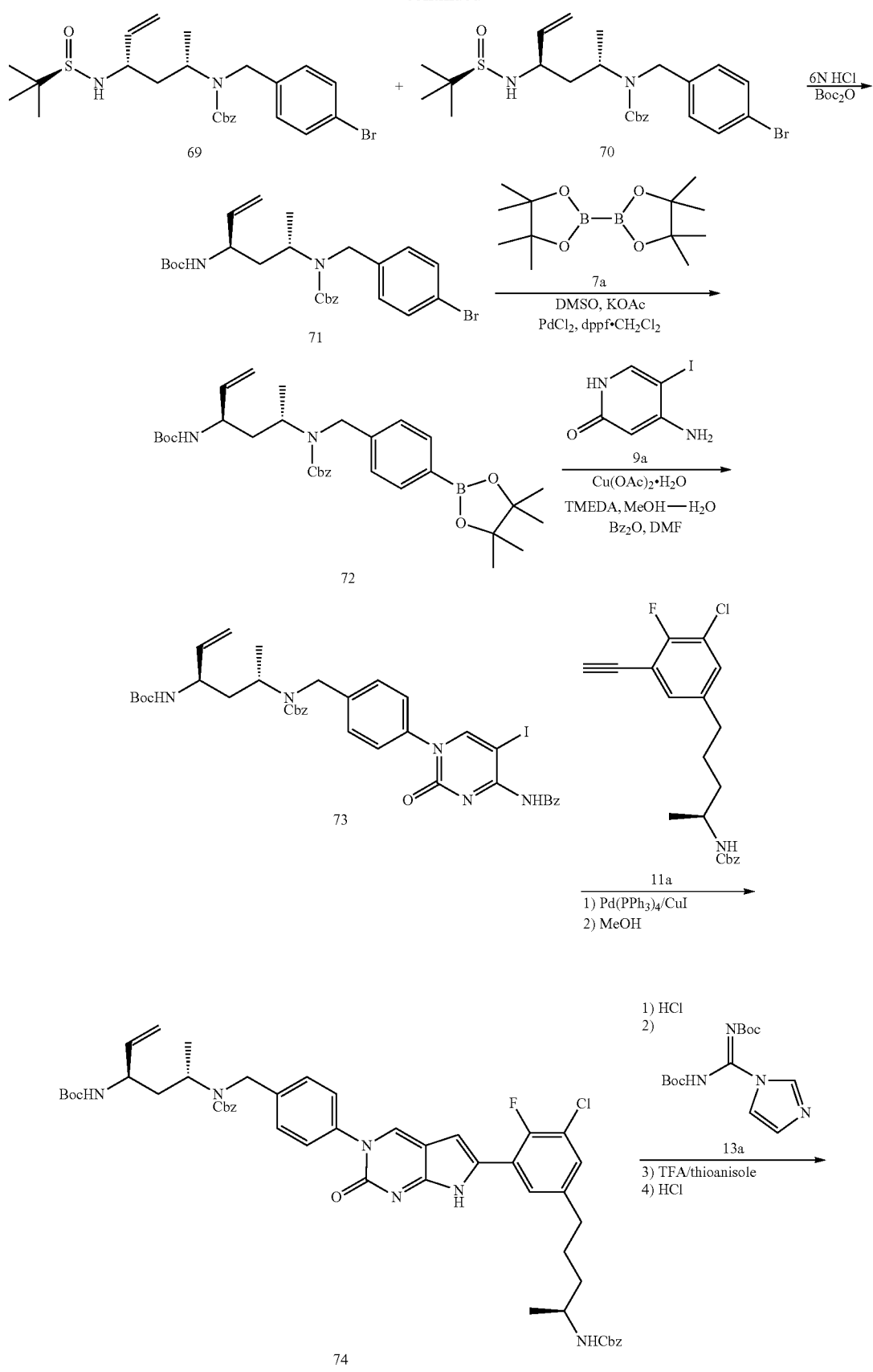

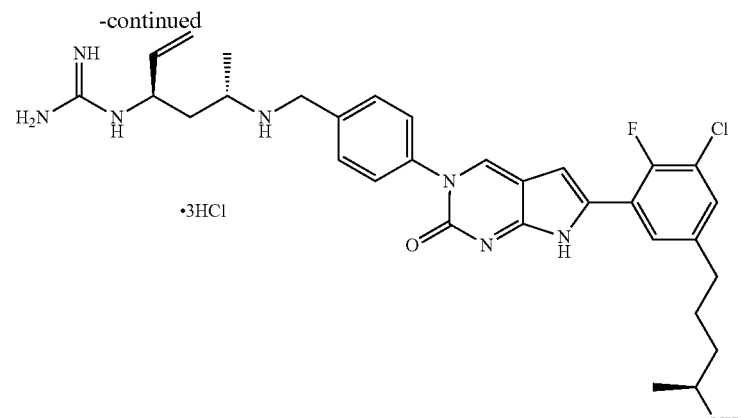

Compound 336

To a solution of (1-methyl-but-3-enyl)-carbamic acid benzyl ester 64 (6.0 g, 27.4 mmol) in DMF (75 mL) was added NaH (1.64 g, 41.1 mmol, 60% dispersion in mineral oil) at 0° C. and the resulting mixture was stirred for 30 minutes. The solution was then slowly warmed up to ambient temperature after which 4-bromo benzyl amide (7.53 g, 30.1 mmol) was added and the mixture was stirred overnight under an inert atmosphere. The mixture was then partitioned between EtOAc (100 mL) and brine (100 mL) and the organic layer was separated. The aqueous layer was extracted with EtOAc (3×20 mL) and the combined organic layers were dried with anhydrous $Na_2SO_4$, concentrated under reduced pressure and purified by flash chromatography over silica gel (0-50% ethyl EtOAc/heptane) to yield 7.2 g of (4-bromo-benzyl)-(1-methyl-but-3-enyl)-carbamic acid benzyl ester 65 (ESI, m/z 388.6 [M+H]$^+$). A solution of 65 (7.2 g, 18.5 mmol) in acetone (50 mL) was then treated with $OsO_4$ (1% in water, 14.2 mL, 0.6 mmol) followed by N-methyl morpholine N-oxide (5.1 g, 37.1 mmol) and stirred at ambient temperature overnight. The reaction was quenched with saturated $Na_2S_2O_3$ solution in water and extracted with EtOAc (3×50 mL). The combined organic layers were washed with water (2×50 mL), dried with anhydrous $Na_2SO_4$, evaporated to dryness and purified by flash chromatography over silica gel ($CH_2Cl_2$:$CH_3OH$, 14:1). This material was dissolved in $CH_2Cl_2$ (100 mL) and treated with $NaIO_4$-silica gel reagent (36.4 g, 1.0 mmol/g). After 2 hours, the resulting solution was filtered and concentrated to provide a clear oil, 66, (4-bromo-benzyl)-(1-methyl-3-oxo-propyl)-carbamic acid benzyl ester, (6.58 g, ESI, m/z 390.5 [M+H]$^+$) which was used in the next step without further purification.

A mixture of 66 (6.58 g, 16.7 mmol), (R)-(+)-2-methyl-2-propanesulfinamide (67, 2.24 g, 18.6 mmol), pyridine para-toluene sulfonate (0.424 g, 1.7 mmol) and $MgSO_4$ (2.23 g, 18.6 mmol) was stirred vigorously in $CH_2Cl_2$ (100 mL) at ambient temperature overnight. The reaction mixture was then partitioned between $CH_2Cl_2$ (50 mL) and water (50 mL) and the organic layer was separated. The aqueous layer was then extracted with $CH_2Cl_2$ (2×50 mL) and the combined organic layers were washed with brine (2×100 mL), dried with anhydrous $Na_2SO_4$, and evaporated to afford 68, (4-bromobenzyl)-[1-methyl-3-(2-methyl-propane-2-sulfinylimino)-propyl]-carbamic acid benzyl ester, (9.43 g) as a clear oil. ESI, m/z 495.6 [M+H]$^+$.

Vinyl magnesium bromide (38.2 mL, 1 M in THF) was added drop wise to solution of 68 (9.43 g, 19.1 mmol) in THF (1×00 mL) at −78° C. and stirred at that temperature until starting material disappeared. The solution was then warmed up to 0° C. and quenched with $NH_4Cl$ solution. The resulting mixture was extracted with EtOAc (3×50 mL), dried with anhydrous $Na_2SO_4$, concentrated under reduced pressure, and purified by flash chromatography over silica gel (20-35% EtOAc/Heptane) to afford 69, (4-bromobenzyl)-[1-methyl-3-(2-methyl-propane-2-sulfinylimino)-pent-4-enyl]-carbamic acid benzyl ester, (3.4 g, ESI, m/z 521.6 [M+H]$^+$) and isomeric 70 (3.8 g). The isomer 70 (3.83 g, 7.9 mmol) was dissolved in $CH_3OH$ (50 mL) and stirred with 5-6 N HCl (in 2-propanol, 20 mL) at ambient temperature. After 4 hours, the solution was concentrated and re-dissolved in THF (50 mL) and water (30 mL). To this solution was added $K_2CO_3$ (3.3 g, 23.6 mmol) and di-tert-butyl dicarbonate (($Boc)_2O$, 2.6 g, 11.8 mmol) and the resulting mixture was stirred at ambient temperature overnight. The reaction mixture was then concentrated and partitioned between EtOAc (100 mL) and water (100 mL). The organic layer was separated, washed with brine (3×100 mL), dried and concentrated to afford 71 (5.32 g) as yellow oil. A mixture of 71 (5.32 g, 10.3 mmol), bis(pinacolato)diborane 7a (3.13 g, 12.3 mmol), Pd(dppf)$Cl_2CH_2Cl_2$ (0.42 g, 0.5 mmol), potassium acetate (KOAc) (3.03 g, 30.8 mmol) in DMSO (25 mL) was degassed and heated to 85° C. under an atmosphere of argon overnight. The mixture was diluted with EtOAc (100 mL), washed with water (3×100 mL), dried over $MgSO_4$, filtered and concentrated. The crude product was then purified by flash chromatography over silica gel (0-50% EtOAc/Heptane) to afford 72 (3.28 g, ESI, m/z 465.7 [M+H]$^+$).

Cu(OAc)$_2$ (1.74 g, 8.7 mmol) was added to a mixture of 72 (3.28 g, 5.8 mmol), 4-amino-5-iodo-1H-pyrimidin-2-one 9a (1.38 g, 5.8 mmol), $CH_3OH$ (100 mL) and $H_2O$ (25 mL) followed by N,N,N',N'-tetramethyl-ethane-1,2-diamine (1.05 mL, 7.0 mmol) and the resulting mixture was stirred at room temperature under air for 48 hours before it was concentrated to a volume of ca. 130 mL. The residue was then partitioned between EtOAc (100 mL) and 20% $NH_4OH$ in saturated $NH_4Cl$ solution (100 mL), the organic layer was separated, and aqueous layer was extracted with EtOAc (3×25 mL). All of the organic layers were combined and washed with brine (3×100 mL), dried, and concentrated. This material (3.4 g, 5.1 mmol) was then dissolved in DMF (30 mL) and treated with benzoic anhydride (1.7 g, 7.6 mmol) and stirred for 72 hours at room temperature. The reaction mixture was then partitioned between EtOAc (100 mL) and saturated Na$_2$CO$_3$ solution (100 mL). The organic layer was separated, dried, concentrated and purified by flash chromatography over silica gel (0-50% EtOAc/Heptane) to afford 73 (2.29 g, ESI, m/z 778.8 [M+H]$^+$) as a desired product. Compound 73 (0.8 g, 1.0 mmol) and compound 11a (0.385 g, 1.0 mmol) were dissolved in anhydrous DMF (10 mL). The solution was purged with argon, and then CuI (0.049 g, 0.3 mmol), Pd(PPh$_3$)$_4$ (0.119 g, 0.1 mmol), and Et$_3$N (1.15 mL, 8.2 mmol) were added and the resulting mixture was stirred at 80-85° C. overnight. The solution then cooled to room temperature, CH$_3$OH (10 mL) was added and the mixture was stirred again at 85° C. for 3 hours. After cooling to ambient temperature, the mixture was partitioned between EtOAc (50 ml) and 20% NH$_4$OH in saturated NH$_4$Cl solution (50 mL). The organic layer was separated, dried, concentrated and purified by flash chromatography over silica gel (2N NH$_3$—CH$_3$OH in CH$_2$Cl$_2$) to yield 74 (0.69 g, ESI, m/z 919.9 [M+H]$^+$).

74 was dissolved in ethanol (30 mL) and 6N HCl (10 mL) and heated to 65° C. for 1 hour. The reaction mixture was then concentrated to dryness, re-dissolved in CH$_3$OH (30 mL) and Hunig's base (1.05 mL, 6.0 mmol) after which 13a (0.256 g, 0.8 mmol) was added and the resulting mixture was stirred for 96 hours at room temperature. The solution was then partitioned between EtOAc (75 mL) and brine (100 mL). The organic layer was separated, washed with water (2×25 mL), dried, concentrated and purified by flash chromatography over silica gel (2N NH$_3$—CH$_3$OH in CH$_2$Cl$_2$). This material thus obtained was treated with thioanisole (0.1 mL) and TFA (10 mL) and heated at 50° C. until the starting material disappeared. The reaction mixture was then concentrated and purified by a Shimadzu 10A-VP HPLC instrument, using a Varian L4002 column (50 mm I.D.×300 mm) packed with 8 micron irregular C-18 coated silica. Mobile phases (A, water) and (B, methanol) contained 0.15 vol % of TFA as the buffer. Flow rate: 58 ml/min; a gradient of 20% to 100% of CH$_3$OH in water for 40 minutes was followed by isocratic 100% CH$_3$OH for 5 minutes. Detection was carried out at 220 nm. The product eluted at R$_1$=ca. 40-45 min. The pure fractions (LCMS and/or HPLC assay) were concentrated in vacuo and the residue was treated with 1.0 N HCl/H$_2$O (5 mL) and concentrated almost to dryness. The latter step was repeated. The residue was then dissolved in H$_2$O (3 mL), CH$_3$CN (1 mL) was added, and the mixture was lyophilized overnight (vacuum: 2-5 Pa), affording desired compound 336×3 HCl salt. (177 mg, ESI, m/z 593.8 [M+H]$^+$).

Synthetic scheme for Compound 353

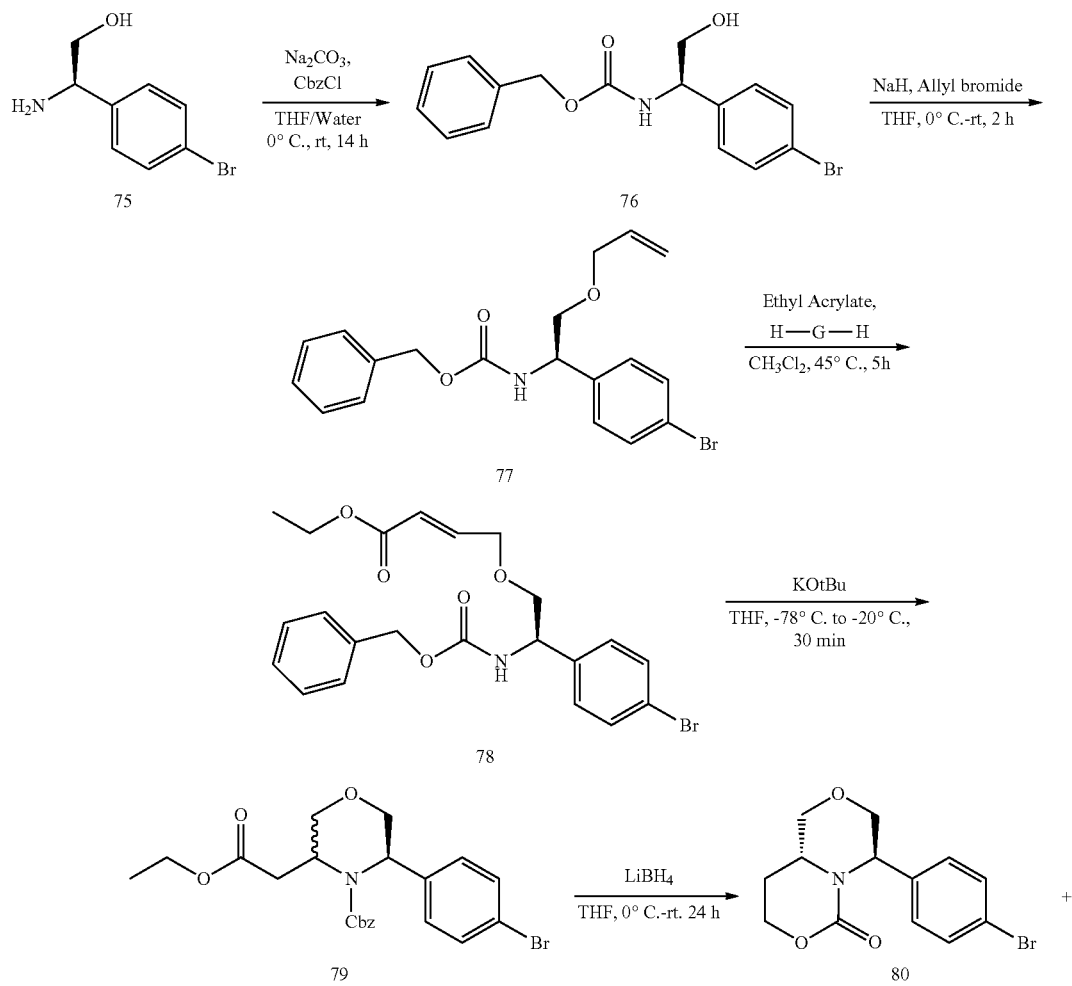

-continued
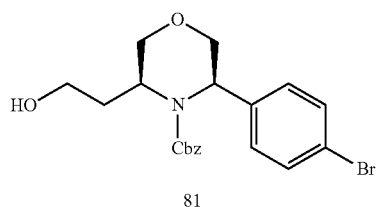
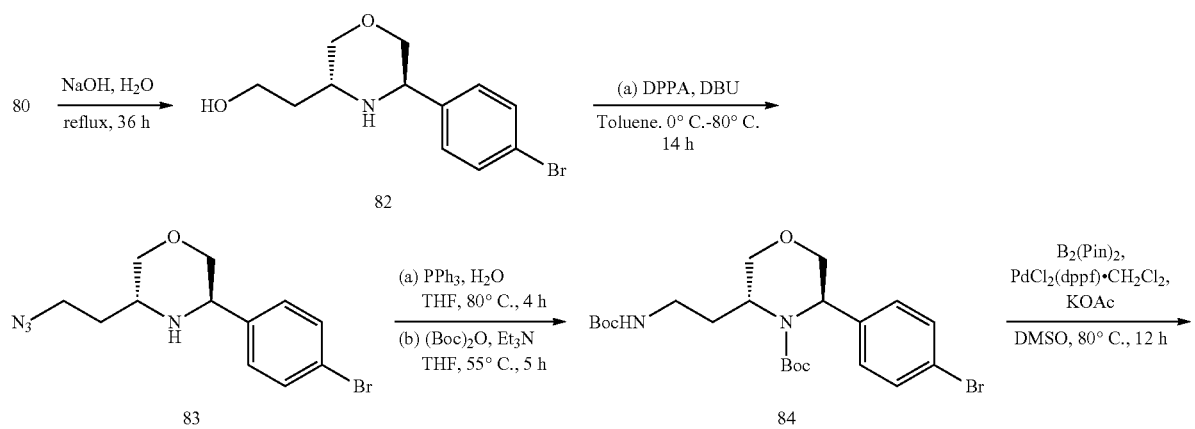
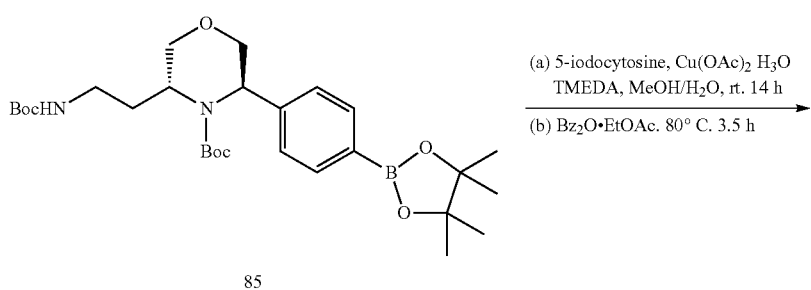
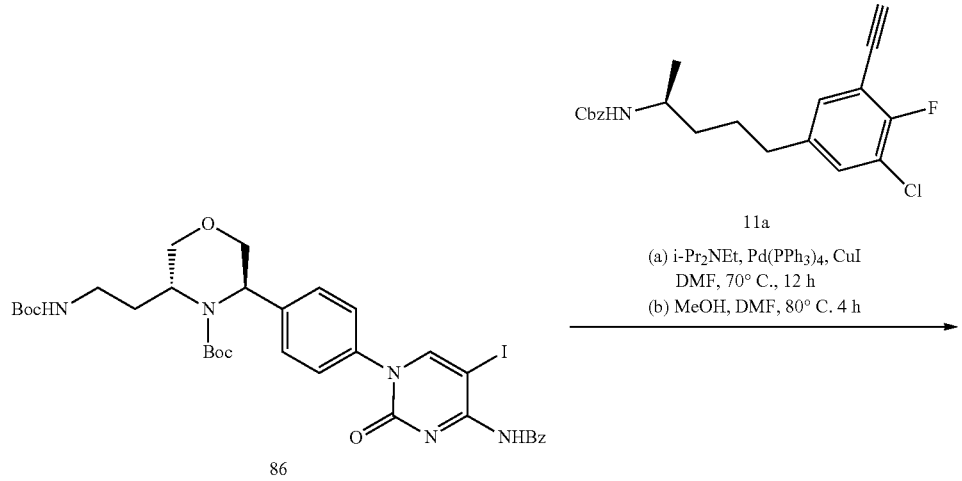

-continued

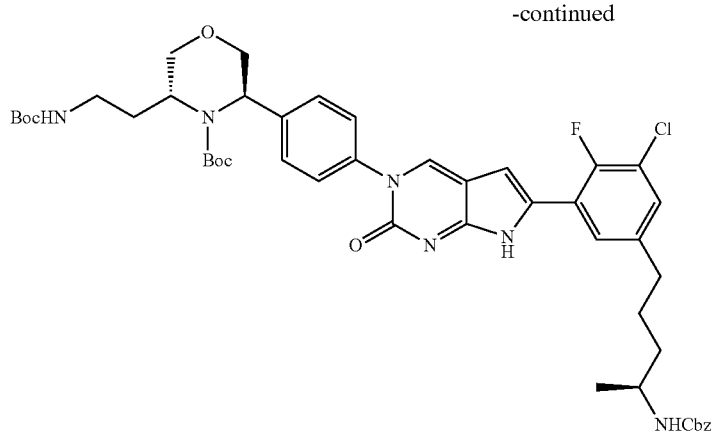

87

(a) HCl, CH₂Cl₂/1.4-dioxane, rt, 1 h
(b) N,N-bispyrazolecarboxamidine, i-Pr₂NEt, MeOH, rt
(c) TFA, thioanisole
(d) HCl

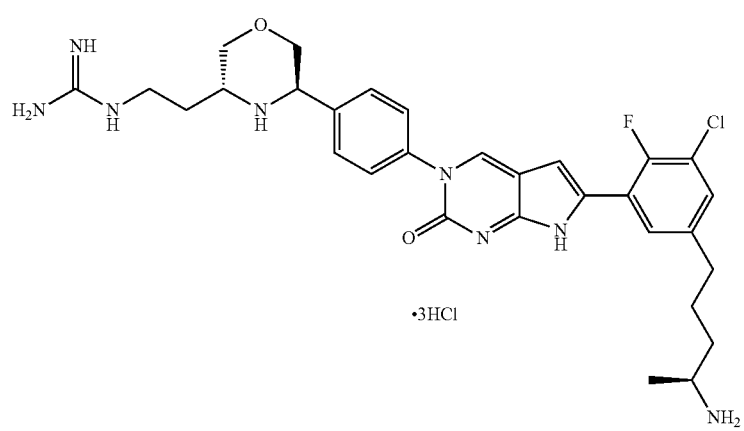

·3HCl

Compound 353

To the solution of 2-Amino-2-(4-bromo-phenyl)-ethanol (5.17 g, 23.92 mmol) in 150 ml of THF was 100 ml of saturated sodium bicarbonate solution followed by benzyl chloroformate (CbzCl) (3.47 ml, 23.92 mmol). The reaction mixture was stirred at room temperature for 14 hours, 200 ml of ethyl acetate was then added and the organic layer was separated, washed with brine, dried over MgSO₄ and concentrated to afford 7.5 g (yield=89%) of 76 as a white solid. $^1$H NMR (300 MHz. CDCl₃): δ 7.49 (d, J=9 Hz, 2H), 7.35-7.30 (m, 5H), 7.16 (d, J=6 Hz, 2H) 5.21 (d, J=6 Hz, 1H), 5.04 (m, 2H), 4.79 (s, br, 1H), 3.88-3.82 (m, 2H), 1.91 (s br, 1H).

To a stirring solution of [1-(4-Bromo-phenyl)-2-hydroxy-ethyl]-carbamic acid benzyl ester (76) (2.59 g, 7.4 mmol) in anhydrous DMF at 0° C. under an atmosphere of argon was added allyl bromide (3.58 g, 29.6 mmol) and the resulting mixture was stirred for 15 min. Sodium tert-butoxide (0.91 g, 8.14 mmol) was then added in 5 portions over a 2 min interval. The mixture was then stirred for 2 hours at 0° C. 100 g of ice was then added to the reaction mixture. The cooling bath was removed and the mixture was extracted with ethyl acetate (100 ml×2). The combined organic layers were then washed with brine, dried over Na₂SO₄, concentrated, and purified by flash column chromatography (80 g silica column, gradient elution of ethyl acetate in heptane from 0-60% in 16 column volumes; product was eluted at 30-31% EtOAc). Fractions were combined and concentrated to obtain 1.7 g (yield=41%) of 77 as a white solid. $^1$H NMR (300 MHz, CDCl₃): δ 7.43 (d, J=9 Hz, 2H), 7.33 (s, br, 5H), 7.19 (d, J=9 Hz, 2H) 5.88-5.77 (m, 1H), 5.56 (s, br, 1H), 5.23-5.01 (m, 3H), 4.82 (s, br, 1H), 3.99-3.90 (m, 2H), 3.70-3.54 (m, 2H).

To stirred solution of 4-[2-Benzyloxycarbonylamino-2-(4-bromo-phenyl)-ethoxy]-but-2-enoic acid ethyl ester (77) (1.17 g, 3 mmol) in anhydrous dichloromethane (10 ml) under an atmosphere of argon was added ethyl acrylate (0.9 g, 9 mmol) and the resulting mixture was stirred for 15 minutes. Hoveyda-Grubbs-II catalyst (0.025 g, 0.06 mmol) was then added and the mixture was stirred at 45° C. for 3 hours. Another additional amount of Hoveyda-Grubbs-II catalyst (0.025 g, 0.06 mmol) was added and the reaction was stirred for another 2 hours at 45° C. Once LCMS showed complete consumption of starting material 77 and formation of 78, the mixture was cooled down, the solvent was evaporated and the product was purified by flash chromatography (80 g silica column, gradient of ethyl acetate in heptane from 0 to 60% in 14 column volumes; product was eluted at 40% gradient). The fractions were combined and concentrated to obtain 1.02 g (yield=73%) of 78 as a colorless sticky solid. $^1$H NMR (300 MHz, CDCl₃): δ 7.44 (d, J=9 Hz, 2H), 7.34 (s, br, 5H), 7.19 (d, J=9 Hz, 2H), 6.90-6.81 (m, 1H), 5.89 (d, J=21 Hz, 1H), 5.52 (s, br 1H), 5.14-5.07 (m, 2H), 4.85 (s, br, 1H), 4.23-4.16 (q, J=21 Hz, 2H), 4.12-4.08 (m, 2H), 3.75-3.64 (m, 2H).

To a solution of 4-[2-Benzyloxycarbonylamino-2-(4-bromo-phenyl)-ethoxy]-but-2-enoic acid ethyl ester (78) (3.37 g, 7.3 mmol) in anhydrous THF (185 ml) at −78° C. under an atmosphere of argon was added potassium tert-butoxide (KO^tBu) (0.65 g, 5.84 mmol) and the resulting mixture was stirred for 30 min. The cooling bath was then removed and the reaction mixture was allowed to warm up to −20° C. (over 30 min). Once LCMS showed complete consumption of 78 and formation of the product 79, 100 g of ice was added followed by 100 ml of water. The aqueous phase was extracted with ethyl acetate (100 ml×2) and the combined organic phases were washed with brine, dried over sodium sulfate, concentrated, and purified by flash chromatography (80 g silica column; ethyl acetate gradient in heptane from 0 to 60% in 14 column volume: product was eluted at 30% of gradient). Upon concentration of the fractions, 1.98 g (yield=66%) of 79 as a yellowish viscous liquid was obtained. $^1$H NMR (300 MHz, CDCl$_3$): δ 7.44-7.34 (m, 11H), 7.29-7.28 (m, 3H) 7.11-7.05 (m, 4H), 5.25-4.90 (m, 5H), 4.89-4.53 (m, 4H), 4.14-3.48 (m, 10H), 3.45-2.89 (m, 1H), 2.97-2.89 (m, 1H), 2.48-2.39 (m, 2H), 2.12-2.03 (dd, 1H), 1.55-1.14 (m, 7H).

To the solution of 3-(4-Bromo-phenyl)-5-ethoxycarbonyl-methyl-morpholine-4-carboxylic acid (79) (1.94 g, 4.2 mmol) in anhydrous THF was added (42 ml) LiBH$_4$ (95%) (0.183 g, 8.4 mmol) at 0° C. under an atmosphere of argon and the resulting mixture was stirred at 0° C. for 2 hours. The cooling bath was removed and the reaction mixture was then stirred overnight (~14 hours). LCMS showed only partial reduction of the ester so the mixture was left stirring for an additional 24 hours at rt. Once LCMS showed complete disappearance of the ester, the mixture was cooled to 0° C. and 20 ml of water was slowly added. After 30 min, the cooling bath was removed and reaction was stirred for another 4 hours. Another 20 ml of water was added and the product was extracted with ethyl acetate (50 ml×2). The combined organic phases were then washed with water (40 ml) and brine (40 ml), dried over sodium sulfate, concentrated, and purified by flash chromatography (80 g silica column, ethyl acetate gradient in heptane from 0 to 100%; 81 eluted at 30% gradient and cyclic product (80) eluted at 70% gradient). Fractions were concentrated to obtain 0.49 g of 81 and 0.70 g of 80. Combined yield: 84%; 81:80=1:1.8. $^1$H NMR (300 MHz, CDCl$_3$) for 81: δ 7.43-7.32 (m, 9H), 5.38 (d, J=12 Hz, 1H), 5.22-5.14 (m, 1H), 4.51 (d, J=21 Hz, 1H), 4.24-4.22 (m, 1H), 3.88-3.79 (m, 3H), 3.23-3.15 (m, 1H), 2.99-2.92 (m, 1H), 1.52-1.44 (m, 1H). Compound 80 was very pure by LCMS. MS (ESI) m/z [M+H]$^+$; calcd for C13H15BrNO3; 312.0. found 312.5.

To the solution of 4-(4-Bromo-phenyl)-hexahydro-[1,4]oxazino[4,3-c][1,3]oxazin-6-one (80) (0.70 g, 2.25 mmol) in methanol (20 ml) was added sodium hydroxide (0.36 g, 9 mmol) as 4 N solution in water and the resulting mixture was heated to reflux for 36 hours. Once LCMS showed complete hydrolysis of the carbamate 80 to the alcohol 82, the mixture was concentrated and 20 ml of water was added. The aqueous phase was extracted with dichloromethane (20 ml×2) and the combined organic phases were washed with brine (20 ml), dried over sodium sulfate, and concentrated to afford 0.59 g (yield=92%) of 82 as a colorless sticky solid. $^1$H NMR (300 MHz, CDCl$_3$): δ 7.48 (d, J=9 Hz, 2H), 7.31 (d, J=9 Hz, 2H), 4.11 (d, J=3 Hz, 1H), 3.93-3.58 (m, 6H), 3.15-3.10 (m, 1H), 2.10-2.05 (m, 1H), 1.67-1.60 (m, 1H).

To a stirred solution of 2-[5-(4-Bromo-phenyl)-morpholin-3-yl]-ethanol (82) (0.57 g, 2 mmol) in anhydrous toluene (13.5 ml) at 0° C. was added diphenylphosphoryl azide (DPPA) (0.66 g, 2.4 mmol) followed by 1,8-Diazabicyclo [5.4.0]undec-7-ene (DBU) (0.36 g, 2.4 mmol) and the resulting mixture was stirred for 10 min under an atmosphere of argon. The cooling bath was removed and after 10 min the mixture was placed in a 80° C. oil bath and stirred under argon for 14 hours. Once LCMS showed complete conversion of the alcohol to the azide, 20 ml of ethyl acetate and 20 ml of water were added. The organic phase was separated and the aqueous phase was extracted with another 20 ml of ethyl acetate. The combined organic phases were washed with saturated sodium bicarbonate (20 ml), water (920 ml) and brine (20 ml), dried over sodium sulfate, concentrated, and purified by flash chromatography (40 g silica column, solvent A: dichloromethane, solvent B: dichloromethane+methanol+ammonium hydroxide (28% aq. solution) (90:10:0.2); gradient of B in A: 0 to 100% over 15 column volume (cv) and 100% over 5 cv, product was eluted at 100% gradient). Fractions were combined and concentrated to obtain 0.56 g of 83 as a colorless sticky solid (yield=87%). $^1$H NMR (300 MHz, CDCl$_3$): δ 7.60 (d, J=36 Hz, 2H), 7.45 (d, J=15 Hz, 2H), 4.08 (d, J=9 Hz, 1H), 3.85-3.79 (m, 2H), 3.64-3.39 (m, 4H), 3.09-3.05 (m, 1H), 2.06-1.58 (m, 2H).

To the solution of 3-(2-Azido-ethyl)-5-(4-bromo-phenyl)-morpholine (83) (0.56 g, 1.8 mmol) in 92% of THF+8% of water (total 18 ml) was added triphenylphosphine and the resulting mixture was stirred at 60° C. for 4 hours. Once LCMS showed complete reduction of the azide to the amine, the solvent was evaporated and the residue was dried under high vacuum for 3 hours. The crude product was then dissolved in 20 ml of anhydrous THF, Et$_3$N (3.27 g, 32.4 mmol) was added and the resulting mixture was cooled to 0° C. To this cold solution, di-tert-butyl dicarbonate ((Boc)$_2$O, 1.96 g, 9 mmol) was added and the reaction mixture was stirred for 10 min. The cooling bath was removed and the solution was stirred at 55° C. under an atmosphere of argon for 5 hours. Once LCMS showed complete protection of both amines, the reaction mixture was cooled and ethyl acetate (25 ml) and water (25 ml) were added. The organic layer was separated and the aqueous layer was extracted with ethyl acetate (25 ml). The combined organic layers were washed with water (50 ml) and brine (25 ml), dried over sodium sulfate, concentrated, and purified by flash chromatography (40 g silica column, gradient of ethyl acetate in heptane 0-50% over 15 cv; product was eluted at 30% of gradient). Fractions were combined and concentrated to obtain 0.77 g (yield=88%) of 84 as a colorless sticky solid. It was very pure by LCMS. MS (ESI) m/z [M+Na]$^+$; calcd for C$_{22}$H$_{33}$BrN$_2$NaO$_5$; 509.15. found 509.6.

To a solution of 3-(4-Bromo-phenyl)-5-(2-tert-butoxycarbonylamino-ethyl)-morpholine-4-carboxylic acid tert-butyl ester (84) (0.77 g, 1.6 mmol) in DMSO (10 ml) was added B$_2$(Pin)$_2$ (7a, 0.49 g, 1.92 mmol), potassium acetate (KOAc) (0.47 g, 4.8 mmol) and PdCl$_2$(dppf)CH$_2$Cl$_2$ (0.065 g, 0.08 mmol) and the resulting mixture was degassed using high vacuum, purged with argon twice and stirred at 80° C. under an atmosphere argon for 12 hours. Once LCMS showed complete consumption of 84, the solution was cooled down, 20 ml of water was added, and the aqueous phase was extracted with EtOAc (25 ml×2). During this extraction, emulsion formation occurred which was broken by adding ~3 g of celite. The combined organic phases were then washed with water (25 ml), 14% ammonium hydroxide (25 ml), water (25 ml), and brine (25 ml), dried over sodium sulfate, concentrated, and purified by flash chromatography (40 g silica column, gradient of ethyl acetate in heptane 0 to 50% in 15 cv, product came at ~30% gradient). Fractions were combined and concentrated to obtain 0.60 g (yield=70%) pure 85 as a colorless sticky solid. MS (ESI) m/z [M+Na]$^+$; calcd for C$_{28}$H$_{45}$BN$_2$NaO$_7$; 555.3. found 555.8.

To a solution of 3-(2-tert-Butoxycarbonylamino-ethyl)-5-[4-(4,4,5,5-tetramethyl-[1,3,2]dioxaborolan-2-yl)-phenyl]- morpholine-4-carboxylic acid tert-butyl ester (85) (0.58 g, 1.1 mmol) in methanol (16 ml) was added water (4 ml), 5-iodocytosine (0.29 g, 1.21 mmol), and Cu(OAc)$_2$.H$_2$O (0.22 g, 1.1 mmol) followed by TMEDA (0.26 g, 2.2 mmol) and the mixture was then stirred in open air for 14 hours. Once LCMS showed complete consumption of 85, the mixture was concentrated, 20 ml of water was added, and the aqueous phase was extracted with ethyl acetate (20 ml×2). The combined organic phases were then washed with 14% ammonium hydroxide (20 ml), water (20 ml) and brine (20 ml), dried over sodium sulfate and concentrated to obtain 0.8 g of crude product. This crude product was dissolved in ethyl acetate (20 ml), benzoic anhydride (0.30 g, 1.32 mmol) was added, and the mixture was stirred at 80° C. for 3 hours and 30 min. Once LCMS showed complete benzoylation of the intermediate amine, the reaction mixture was cooled down to room temperature, washed with saturated sodium bicarbonate (10 ml), water (10 ml), and brine (10 ml), dried over sodium sulfate, concentrated, and purified by flash chromatography (40 g silica column, gradient of ethyl acetate in heptane 0 to 100%, product eluted at 70% of gradient) to obtain 0.52 g (yield 63% over two steps) of 86 as a white brittle solid. $^1$H NMR (300 MHz, CDCl$_3$): δ 13.45 (s, br, 1H), 8.41 (d, J=6 Hz, 2H), 7.91 (s, 1H), 7.59-7.31 (m, 8H), 4.98 (s, br, 1H), 4.55-4.50 (m, 1H), 4.08 (s, br, 1H), 3.97-3.77 (m, 3H), 3.40-3.33 (m, 2H), 3.10-3.05 (m, 1H), 2.09-2.05 (m, 1H), 1.92-1.87 (m, 1H), 1.45 (S, 9H), 1.24 (s, 9H). MS (ESI) m/z [M+H]$^+$; calcd for C$_{33}$H$_{41}$IN$_5$O$_7$; 746.2. found 746.7.

A solution of 3-[4-(4-Benzoylamino-5-iodo-2-oxo-2H-pyrimidin-1-yl)-phenyl]-5-(2-tert-butoxycarbonylamino-ethyl)-morpholine-4-carboxylic acid tert-butyl ester (86) (0.52 g, 0.7 mmol) and alkyne 11a (0.264 g, 0.7 mmol) in anhydrous DMF (7 ml) was degassed under high vacuum and purged with argon twice. To this solution was added DIPEA (0.27 g, 2.1 mmol) followed by Pd(PPh$_3$)$_4$ (0.04 g, 0.035 mmol) and CuI (0.013 g, 0.07 mmol). The mixture was then stirred at 70° C. for 12 hours. Once LCMS showed complete consumption of 86, the reaction mixture was cooled to room temperature, methanol (7 ml) was added, and the mixture was stirred at 80° C. for 4 hours. Once LCMS showed complete consumption of the Sonogashira coupled intermediate and formation of debenzoylated cyclized product 87, the mixture was cooled down to room temperature and concentrated. Water (20 ml) was then added and the aqueous phase was extracted with ethyl acetate (20 ml×2). The combined organic phases were washed with water (20 ml), 14% ammonium hydroxide (20 ml), water (20 ml) and brine (20 ml), dried over sodium sulfate, concentrated and purified by flash chromatography (12 g silica column, solvents A=CH$_2$Cl$_2$, B=CH$_2$Cl$_2$:MeOH:28% ammonium hydroxide (90:10:0.2), gradient of B in A 0 to 80%. Product eluted at 60% of B) to obtain 0.45 g (yield=72% over two steps) of 87 as a pure yellow solid. MS (ESI) m/z [M H]$^+$; calcd for C$_{47}$H$_{57}$ClFN$_6$O$_8$; 887.3. found 887.8.

To a stirred solution of 3-(4-{6-[5-(4-Benzyloxycarbonylamino-pentyl)-3-chloro-2-fluoro-phenyl]-2-oxo-2,7-dihydro-pyrrolo[2,3-d]pyrimidin-3-yl}-phenyl)-5-(2-tert-butoxycarbonylamino-ethyl)-morpholine-4-carboxylic acid tert-butyl ester (87) (0.31 g, 0.35 mmol) in dichloromethane (12 ml) was added 4 N solution of HCl in 1,4-dioxane (4.3 ml, 17.5 mmol) and the resulting mixture was stirred for 50 min. Once LCMS showed complete deprotection of the Boc groups, the mixture was concentrated to dryness and the resulting residue was dissolved in anhydrous methanol. To this solution was added N,N'-di-Boc-1H-pyrazole-1-carboxamidine (0.132 g, 0.42 mmol) and i-Pr$_2$NEt (0.45 g, 3.5 mmol) and the resulting mixture was stirred at room temperature for 14 hours. Once LCMS showed complete consumption of the intermediate amine, the mixture was concentrated and the resulting residue was dissolved in trifluoroacetic acid (12 ml). Thioanisole (0.12 ml) was then added to the solution and the resulting mixture was stirred at room temperature for 24 hours. Once LCMS showed complete deprotection of the Cbz and Boc groups, the mixture was concentrated and the product was purified by HPLC chromatography (Varian, 41.4 mm×150 mm Dynamax column packed with of 8 μm irregular size C-18 coated silica gel; solvent A: water+0.15% TFA, solvent B: methanol+0.15% TFA; gradient 20-100 over 55 min., product eluted in ~32 min). Product fractions were concentrated to dryness, suspended in 10 ml of ethanol and concentrated to dryness. The TFA salt of the product was converted to the HCl by using 6 N HCl (10 ml×2 in with 15 min duration each time). The reaction mixture was then concentrated and lyophilized to afford 0.089 g (yield=36% over 4 steps) of compound 353, as a yellow powder. $^1$H NMR (300 MHz, D$_2$O): δ 8.34 (s, 1H), 7.69 (d, J=9 Hz, 2H), 7.50 (d, J=7 Hz, 2H), 7.33 (d, J=6 Hz, 1H), 7.25 (d, J=6 Hz, 1H), 6.73 (s, 1H), 4.80-4.63 (m, 1H), 4.14-4.01 (m, 4H), 3.69-3.61 (m, 1H), 3.31-3.22 (m, 3H), 2.56-2.53 (m, 2H), 2.30-2.26 (m, 1H), 2.01-1.97 (m, 1H), 1.60-1.47 (m, 4H), 1.17 (d, J=9 Hz, 3H), MS (ESI) m/z [M+H]$^+$; calcd for C$_{30}$H$_{37}$ClFN$_8$O$_2$; 595.2. found 595.7.

Synthetic scheme for Compound 357

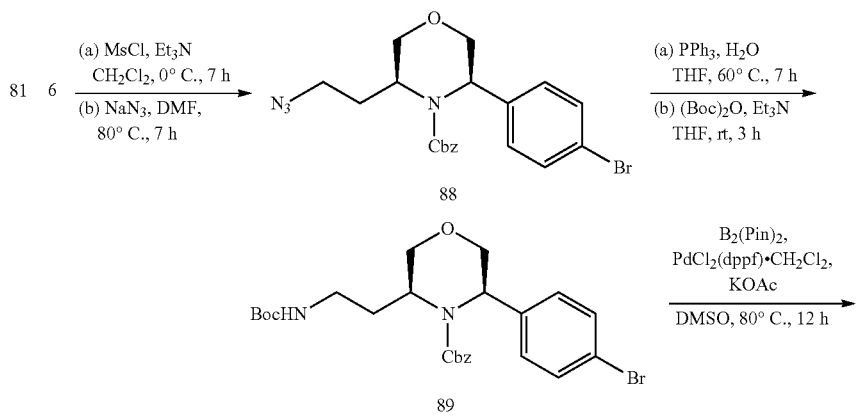

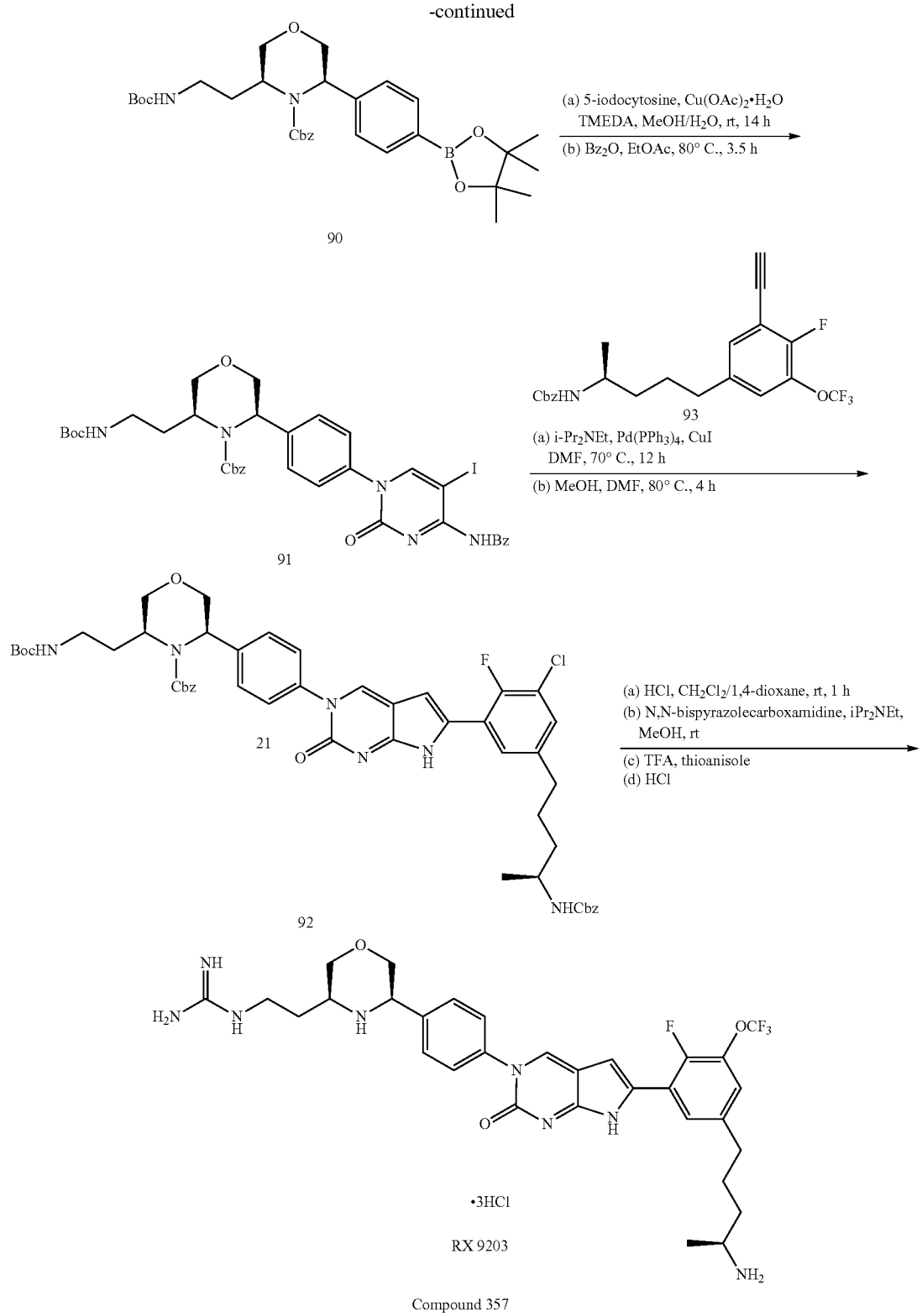

Compound 357

A solution of 3-(4-Bromo-phenyl)-5-(2-hydroxy-ethyl)-morpholine-4-carboxylic acid benzyl ester (81) (0.50 g, 1.2 mmol) in anhydrous dichloromethane (5 ml) was cooled to 0° C. under an atmosphere of argon and Et₃N (0.127 g, 1.26 mmol) was added followed by methanesulfonyl chloride (0.144 g, 1.26 mmol). The resulting mixture was then stirred in an ice bath for 7 hours. Once TLC indicated the complete consumption of the 81, the mixture was concentrated. The residue was then dissolved in of ethyl acetate (15 ml), washed with water (15 ml×2) and brine (15 ml), dried over sodium sulfate, and concentrated to obtain 0.59 g of crude mesylated product which was pure by LCMS. The crude mesylated product was then dissolved in anhydrous DMF (6 ml), sodium azide (0.78 g, 12 mmol) was added and the resulting mixture was stirred at 80° C. under an atmosphere of argon for 7 hours. Once LCMS indicated complete consumption of the mesylate, the mixture was cooled to room temperature. 10 ml of water was then added and the aqueous phase was extracted with ethyl acetate (20 ml×2). The combined organic phases were then washed with water (25 ml) and brine (25 ml), dried over sodium sulfate, concentrated, and purified by flash chromatography (40 g silica column, gradient of ethyl acetate in heptane from 0-50% over 15 column volumes; product was eluted 29-31% gradient). Fractions were concentrated to afford 0.39 g of 88 as a pure colorless sticky solid (yield=73% over two steps). Pure by LCMS. MS (ESI) m/z [M+Na)]$^+$; calcd for $C_{20}H_{21}BrN_4NaO_3$; 467.07. found 467.5.

To a stirred solution of 3-(2-azido-ethyl)-5-(4-bromophenyl)-morpholine-4-carboxylic acid benzyl ester (88) (0.38 g, 0.88 mmol) in THF (9 ml) was added PPh$_3$ (0.57 g, 2.2 mmol) and water (1.2 ml) and the resulting mixture was heated to 55° C. for 4 hours. Once LCMS showed complete consumption of the azide 88, the solvent was evaporated and the resulting crude product was dried under high vacuum for 3 hours. The crude product was then dissolved in 10 ml of anhydrous THF, Et$_3$N (0.79 g, 7.9 mmol) was added, and the mixture was cooled to 0° C. To this cold mixture was added di-tert-butyl dicarbonate ((Boc)$_2$O, 0.57 g, 2.6 mmol) and the resulting mixture was stirred for 10 min. The cooling bath was removed and the mixture was stirred for 3 hours. Once LCMS showed complete consumption of amine, 25 ml of water was added and the product was extracted with ethyl acetate (25 ml×2). The combined organic phases were then washed with water (30 ml) and brine (30 ml), dried over sodium sulfate, and concentrated. The product was purified by flash chromatography (40 g silica column; ethyl acetate gradient in heptane from 0-60% in 15 column volumes; product was eluted at 28% gradient). Fractions were concentrated to obtain 0.41 g of 89 as a colorless sticky solid (yield=98%). $^1$H NMR (300 MHz, CDCl$_3$): δ 7.44-7.36 (m, 9H), 5.32-5.17 (m, 3H) 4.51 (d, J=12 Hz, 1H), 4.13-4.08 (m, 1H), 3.84-3.71 (m, 3H), 2.98-2.91 (m, 1H), 2.45-2.50 (m, 1H), 1.39 (s, 9H), 1.30-1.23 (m, 1H).

To a solution of 3-(4-Bromo-phenyl)-5-(2-tert-butoxycarbonylamino-ethyl)-morpholine-4-carboxylic acid tert-butyl ester (89) (0.77 g, 1.6 mmol) in DMSO (10 ml) was added B$_2$(Pin)$_2$ (11a, 0.49 g, 1.92 mmol), potassium acetate (KOAc) (0.47 g, 4.8 mmol) and PdCl$_2$(dppf).CH$_2$Cl$_2$ (0.065 g, 0.08 mmol) and the resulting mixture was degassed using high vacuum, purged with argon twice, and stirred at 80° C. under an atmosphere of argon fir 12 hours. Once LCMS showed the complete consumption of 89, the reaction solution was cooled down, 20 ml of water was added, and the aqueous phase was extracted with EtOAc (25 ml×2). During this extraction, emulsion formation occurred which was broken by adding ~3 g of celite. The combined organic phases were washed with water (25 ml), 14% ammonium hydroxide (25 ml), water (25 ml) and brine (25 ml), dried over sodium sulfate, concentrated and purified by flash chromatography (40 g silica column, gradient of ethyl acetate in heptane 0 to 50% in 15 cv; product came at ~30% gradient). Fractions were combined and concentrated to obtain 90 (yield=84%) as a pure colorless sticky solid. MS (ESI) m/z [M+Na]$^+$; calcd for $C_{31}H_{43}BN_2NaO_7$; 589.3. found 589.7.

To a solution of 3-(2-tert-Butoxycarbonylamino-ethyl)-5-[4-(4,4,5,5-tetramethyl-[1,3,2]dioxaborolan-2-yl)-phenyl]-morpholine-4-carboxylic acid tert-butyl ester (90) (0.58 g, 1.1 mmol) in methanol (16 ml) was added water (4 ml), 5-iodocytosine (0.29 g, 1.21 mmol), and Cu(OAc)$_2$.H$_2$O (0.22 g, 1.1 mmol) followed by TMEDA (0.26 g, 2.2 mmol) and the mixture was then stirred in open air for 14 hours. Once LCMS showed complete consumption of 90, the mixture was concentrated, 20 ml of water was added, and the aqueous phase was extracted with ethyl acetate (20 ml×2). The combined organic phases were then washed with 14% ammonium hydroxide (20 ml), water (20 ml) and brine (20 ml), dried over sodium sulfate and concentrated to obtain 0.8 g of crude product. This crude product was dissolved in ethyl acetate (20 ml), benzoic anhydride (0.30 g, 1.32 mmol) was added, and the mixture was stirred at 80° C. for 3 hours and 30 min. Once LCMS showed complete benzoylation of the intermediate amine, the reaction mixture was cooled down to room temperature, washed with saturated sodium bicarbonate (10 ml), water (10 ml), and brine (10 ml), dried over sodium sulfate, concentrated, and purified by flash chromatography (40 g silica column, gradient of ethyl acetate in heptane 0 to 100%, product eluted at 70% of gradient) to obtain 91 (yield 76% over two steps) as a white brittle solid. $^1$H NMR (300 MHz, CDCl$_3$): δ 13.34 (s, br, 1H), 8.41 (d, J=6 Hz, 2H), 7.92 (s, 1H), 7.75 (d, J=9 Hz, 2H), 7.60-7.30 (m, 10H), 5.33-5.19 (m, 3H), 4.77 (s, br, 1H), 4.56 (d, J=12 Hz, 2H), 4.12-4.09 (m, 1H), 3.87-3.70 (m, 3H), 2.86-2.83 (m, 1H), 2.59-2.55 (m, 1H), 1.48-1.40 (m, 11H). MS (ESI) m/z [M+Na]$^+$; calcd for $C_{36}H_{39}IN_5O_7$; 780.2. found 780.7.

A solution of 3-[4-(4-Benzoylamino-5-iodo-2-oxo-2H-pyrimidin-1-yl)-phenyl]-5-(2-tert-butoxycarbonylamino-ethyl)-morpholine-4-carboxylic acid tert-butyl ester (91) (0.52 g, 0.7 mmol) and alkyne 93 (0.264 g, 0.7 mmol) in anhydrous DMF (7 ml) was degassed under high vacuum and purged with argon twice. To this solution was added DIPEA (0.27 g, 2.1 mmol) followed by Pd(PPh$_3$)$_4$ (0.04 g, 0.035 mmol) and CuI (0.013 g, 0.07 mmol). The mixture was then stirred at 70° C. for 12 hours. Once LCMS showed complete consumption of 91, the reaction mixture was cooled to room temperature, methanol (7 ml) was added, and the mixture was stirred at 80° C. for 4 hours. Once LCMS showed complete consumption of the Sonogashira coupled intermediate and formation of debenzoylated cyclized product 92, the mixture was cooled down to room temperature and concentrated. Water (20 ml) was then added and the aqueous phase was extracted with ethyl acetate (20 ml×2). The combined organic phases were washed with water (20 ml), 14% ammonium hydroxide (20 ml), water (20 ml) and brine (20 ml), dried over sodium sulfate, concentrated and purified by flash chromatography (12 g silica column, solvents A=CH$_2$Cl$_2$, B=CH$_2$Cl$_2$:MeOH: 28% ammonium hydroxide (90:10:0.2), gradient of B in A 0 to 80%, Product eluted at 60% of B) to obtain 92 (yield=68% over two steps) as a pure yellow solid. MS (ESI) m/z [M+H]$^+$; calcd for $C_{51}H_{55}F_3N_6O_9$; 971.4. found 971.8.

To a stirred solution of 92 (0.31 g, 0.35 mmol) in dichloromethane (12 ml) was added 4 N solution of HCl in 1,4-dioxane (4.3 ml, 17.5 mmol) and the resulting mixture was stirred for 50 min. Once LCMS showed complete deprotection of the Boc groups, the mixture was concentrated to dryness and the resulting residue was dissolved in anhydrous methanol. To this solution was added N,N'-di-Boc-1H-pyrazole-1-carboxamidine (0.132 g, 0.42 mmol) and i-Pr$_2$NEt (0.45 g, 3.5 mmol) and the resulting mixture was stirred at room temperature for 14 hours. Once LCMS showed complete consumption of the intermediate amine, the mixture was concentrated and the resulting residue was dissolved in trifluoroacetic acid (12 ml). Thioanisole (0.12 ml) was then added to the solution and the resulting mixture was stirred at room temperature for 24 hours. Once LCMS showed complete deprotection of the Cbz and Boc groups, the mixture was concentrated and the product was purified by HPLC chromatography (Varian, 41.4 mm×150 mm Dynamax column packed with of 8 μm irregular size C-18 coated silica gel; solvent A: water+0.15% TFA, solvent B: methanol+0.15% TFA; gradient 20-100 over 55 min., product eluted in ~32 min). Product fractions were concentrated to dryness, suspended in 10 ml of ethanol and concentrated to dryness. The TFA salt of the product was converted to the HCl by using 6 N HCl (10 ml×2 in with 15 min duration each time). The reaction mixture was then concentrated and lyophilized to afford compound 357 (yield=43% over 4 steps) as a yellow powder. $^1$H NMR (300 MHz, D$_2$O): δ 8.32 (s, 1H), 7.58 (d, J=9 Hz, 2H), 7.44 (d, J=9 Hz, 2H), 7.37 (d, J=6 Hz, 1H), 7.20 (d, J=6 Hz, 1H), 6.71 (s, 1H), 4.55-4.50 (m, 1H), 4.14-4.07 (m, 2H), 3.95 (t, J=24, 1H), 3.67-3.61 (m, 2H), 3.26-3.21 (m, 3H), 2.56-2.53 (m, 2H), 1.86-1.85 (m, 2H), 1.59-1.40 (m, 4H), 1.13 (d, J=9 Hz, 3H). MS (ESI) m/z [M+H]$^+$; calcd for C$_{31}$H$_{37}$F$_4$N$_8$O$_3$; 645.3. found 645.7.

Example 2: Antimicrobial Activity

The compounds of the present invention were tested for antimicrobial activity. These data are presented in Table 2. The Compounds 1-582 were run against *Eschericia coli* (*E. Coli*) strain ATCC25922 and Compounds 320-582 were run against *Staphylococcus aureus* (*S. aureus*) 11540 strain using a standard microdilution assay to determine minimum inhibitory concentrations (MICs). The data is presented whereby a "+" indicates that the compound has an MIC value of 16 micrograms/mL or less and a "−" indicates that the compound has an MIC value greater than 16 micrograms/mL. It will be recognized by one skilled in the art that the compounds can be assessed against other bacterial organisms and that the presentation of data for activity against *Eschericia coli* and *Staphylococcus aureus* are illustrative and in no way is intended to limit the scope of the present invention. The compounds of the present invention can be assayed against a range of other microorganisms depending upon the performance activity desired to be gathered. Furthermore, the "+" and "−" representation and the selection of a cutoff value of 16 micrograms/mL is also illustrative and in no way is intended to limit the scope of the present invention. For example, a "−" is not meant to indicate that the compound necessarily lacks activity or utility, but rather that its MIC value against the indicated microorganism is greater than 16 micrograms/mL.

TABLE 2

| Compound No. | MIC E. Coli | MIC S. aureus |
| --- | --- | --- |
| 1 | + | ND |
| 2 | + | ND |
| 3 | + | ND |
| 4 | + | ND |
| 5 | + | ND |
| 6 | + | ND |
| 7 | + | ND |
| 8 | − | ND |
| 9 | − | ND |
| 10 | + | ND |
| 11 | + | ND |
| 12 | + | ND |

TABLE 2-continued

| Compound No. | MIC E. Coli | MIC S. aureus |
| --- | --- | --- |
| 13 | + | ND |
| 14 | + | ND |
| 15 | + | ND |
| 16 | + | ND |
| 17 | + | ND |
| 18 | + | ND |
| 19 | + | ND |
| 20 | + | ND |
| 21 | + | ND |
| 22 | + | ND |
| 23 | + | ND |
| 24 | + | ND |
| 25 | + | ND |
| 26 | + | ND |
| 27 | + | ND |
| 28 | + | ND |
| 29 | + | ND |
| 30 | + | ND |
| 31 | + | ND |
| 32 | + | ND |
| 33 | + | ND |
| 34 | + | ND |
| 35 | + | ND |
| 36 | + | ND |
| 37 | + | ND |
| 38 | + | ND |
| 39 | + | ND |
| 40 | + | ND |
| 41 | + | ND |
| 42 | + | ND |
| 43 | + | ND |
| 44 | + | ND |
| 45 | + | ND |
| 46 | + | ND |
| 47 | + | ND |
| 48 | + | ND |
| 49 | + | ND |
| 50 | + | ND |
| 51 | + | ND |
| 52 | + | ND |
| 53 | + | ND |
| 54 | + | ND |
| 55 | + | ND |
| 56 | + | ND |
| 57 | + | ND |
| 58 | + | ND |
| 59 | + | ND |
| 60 | − | ND |
| 61 | + | ND |
| 62 | + | ND |
| 63 | + | ND |
| 64 | + | ND |
| 65 | + | ND |
| 66 | + | ND |
| 67 | + | ND |
| 68 | + | ND |
| 69 | + | ND |
| 70 | + | ND |
| 71 | + | ND |
| 72 | + | ND |
| 73 | + | ND |
| 74 | + | ND |
| 75 | + | ND |
| 76 | − | ND |
| 77 | + | ND |
| 78 | + | ND |
| 79 | + | ND |
| 80 | + | ND |
| 81 | + | ND |
| 82 | + | ND |
| 83 | + | ND |
| 84 | + | ND |
| 85 | + | ND |
| 86 | + | ND |
| 87 | + | ND |
| 88 | + | ND |
| 89 | + | ND |

TABLE 2-continued

| Compound No. | MIC E. Coli | MIC S. aureus |
|---|---|---|
| 90 | + | ND |
| 91 | + | ND |
| 92 | + | ND |
| 93 | + | ND |
| 94 | + | ND |
| 95 | + | ND |
| 96 | + | ND |
| 97 | + | ND |
| 98 | + | ND |
| 99 | + | ND |
| 100 | + | ND |
| 101 | + | ND |
| 102 | + | ND |
| 103 | + | ND |
| 104 | + | ND |
| 105 | + | ND |
| 106 | + | ND |
| 107 | + | ND |
| 108 | + | ND |
| 109 | − | ND |
| 110 | + | ND |
| 111 | + | ND |
| 112 | − | ND |
| 113 | − | ND |
| 114 | − | ND |
| 115 | − | ND |
| 116 | − | ND |
| 117 | + | ND |
| 118 | + | ND |
| 119 | − | ND |
| 120 | − | ND |
| 121 | − | ND |
| 122 | − | ND |
| 123 | + | ND |
| 124 | − | ND |
| 125 | − | ND |
| 126 | − | ND |
| 127 | − | ND |
| 128 | − | ND |
| 129 | − | ND |
| 130 | + | ND |
| 131 | − | ND |
| 132 | + | ND |
| 133 | + | ND |
| 134 | + | ND |
| 135 | + | ND |
| 136 | − | ND |
| 137 | − | ND |
| 138 | − | ND |
| 139 | − | ND |
| 140 | − | ND |
| 141 | − | ND |
| 142 | − | ND |
| 143 | + | ND |
| 144 | − | ND |
| 145 | − | ND |
| 146 | − | ND |
| 147 | − | ND |
| 148 | + | ND |
| 149 | − | ND |
| 150 | + | ND |
| 151 | + | ND |
| 152 | + | ND |
| 153 | − | ND |
| 154 | − | ND |
| 155 | + | ND |
| 156 | + | ND |
| 157 | − | ND |
| 158 | − | ND |
| 159 | − | ND |
| 160 | + | ND |
| 161 | − | ND |
| 162 | − | ND |
| 163 | − | ND |
| 164 | + | ND |
| 165 | − | ND |
| 166 | − | ND |
| 167 | + | ND |
| 168 | + | ND |
| 169 | − | ND |
| 170 | − | ND |
| 171 | + | ND |
| 172 | − | ND |
| 173 | + | ND |
| 174 | + | ND |
| 175 | + | ND |
| 176 | + | ND |
| 177 | + | ND |
| 178 | + | ND |
| 179 | + | ND |
| 180 | + | ND |
| 181 | + | ND |
| 182 | + | ND |
| 183 | + | ND |
| 184 | + | ND |
| 185 | + | ND |
| 186 | + | ND |
| 187 | + | ND |
| 188 | + | ND |
| 189 | + | ND |
| 190 | + | ND |
| 191 | + | ND |
| 192 | + | ND |
| 193 | + | ND |
| 194 | + | ND |
| 195 | + | ND |
| 196 | + | ND |
| 197 | + | ND |
| 198 | + | ND |
| 199 | + | ND |
| 200 | + | ND |
| 201 | + | ND |
| 202 | + | ND |
| 203 | + | ND |
| 204 | + | ND |
| 205 | + | ND |
| 206 | + | ND |
| 207 | + | ND |
| 208 | + | ND |
| 209 | + | ND |
| 210 | + | ND |
| 211 | + | ND |
| 212 | + | ND |
| 213 | + | ND |
| 214 | + | ND |
| 215 | + | ND |
| 216 | + | ND |
| 217 | + | ND |
| 218 | + | ND |
| 219 | + | ND |
| 220 | + | ND |
| 221 | + | ND |
| 222 | + | ND |
| 223 | + | ND |
| 224 | + | ND |
| 225 | + | ND |
| 226 | + | ND |
| 227 | + | ND |
| 228 | + | ND |
| 229 | + | ND |
| 230 | + | ND |
| 231 | + | ND |
| 232 | + | ND |
| 233 | + | ND |
| 234 | + | ND |
| 235 | + | ND |
| 236 | + | ND |
| 237 | + | ND |
| 238 | + | ND |
| 239 | + | ND |
| 240 | + | ND |
| 241 | + | ND |
| 242 | + | ND |
| 243 | + | ND |

TABLE 2-continued

| Compound No. | MIC E. Coli | MIC S. aureus |
|---|---|---|
| 244 | + | ND |
| 245 | + | ND |
| 246 | + | ND |
| 247 | + | ND |
| 248 | + | ND |
| 249 | + | ND |
| 250 | + | ND |
| 251 | + | ND |
| 252 | + | ND |
| 253 | + | ND |
| 254 | + | ND |
| 255 | + | ND |
| 256 | + | ND |
| 257 | + | ND |
| 258 | + | ND |
| 259 | + | ND |
| 260 | + | ND |
| 261 | + | ND |
| 262 | + | ND |
| 263 | + | ND |
| 264 | + | ND |
| 265 | + | ND |
| 266 | + | ND |
| 267 | + | ND |
| 268 | + | ND |
| 269 | + | ND |
| 270 | + | ND |
| 271 | + | ND |
| 272 | + | ND |
| 273 | + | ND |
| 274 | + | ND |
| 275 | + | ND |
| 276 | + | ND |
| 277 | + | ND |
| 278 | + | ND |
| 279 | + | ND |
| 280 | + | ND |
| 281 | + | ND |
| 282 | + | ND |
| 283 | + | ND |
| 284 | + | ND |
| 285 | + | ND |
| 286 | + | ND |
| 287 | + | ND |
| 288 | + | ND |
| 289 | + | ND |
| 290 | + | ND |
| 291 | + | ND |
| 292 | + | ND |
| 293 | + | ND |
| 294 | + | ND |
| 295 | + | ND |
| 296 | − | ND |
| 297 | + | ND |
| 298 | + | ND |
| 299 | + | ND |
| 300 | + | ND |
| 301 | + | ND |
| 302 | + | ND |
| 303 | + | ND |
| 304 | + | ND |
| 305 | + | ND |
| 306 | + | ND |
| 307 | + | ND |
| 308 | + | ND |
| 309 | + | ND |
| 310 | + | ND |
| 311 | + | ND |
| 312 | + | ND |
| 313 | + | ND |
| 314 | + | ND |
| 315 | + | ND |
| 316 | + | ND |
| 317 | + | ND |
| 318 | + | ND |
| 319 | + | ND |
| 320 | + | + |

TABLE 2-continued

| Compound No. | MIC E. Coli | MIC S. aureus |
|---|---|---|
| 321 | + | + |
| 322 | + | + |
| 323 | + | + |
| 324 | + | + |
| 325 | + | + |
| 326 | + | + |
| 327 | + | + |
| 328 | + | + |
| 329 | + | + |
| 330 | + | + |
| 331 | + | + |
| 332 | + | + |
| 333 | + | + |
| 334 | + | + |
| 335 | + | + |
| 336 | + | + |
| 337 | + | + |
| 338 | + | + |
| 339 | + | + |
| 340 | + | + |
| 341 | + | + |
| 342 | + | + |
| 343 | + | + |
| 344 | + | + |
| 345 | + | + |
| 346 | + | + |
| 347 | + | + |
| 348 | + | + |
| 349 | + | + |
| 350 | + | + |
| 351 | + | + |
| 352 | + | + |
| 353 | + | + |
| 354 | + | + |
| 355 | + | + |
| 356 | + | + |
| 357 | + | + |
| 358 | + | + |
| 359 | + | + |
| 360 | + | + |
| 361 | + | + |
| 362 | + | + |
| 363 | + | + |
| 364 | − | − |
| 365 | + | + |
| 366 | + | + |
| 367 | + | + |
| 368 | + | + |
| 369 | + | + |
| 370 | + | + |
| 371 | + | + |
| 372 | + | + |
| 373 | + | + |
| 374 | − | − |
| 375 | + | + |
| 376 | + | + |
| 377 | + | + |
| 378 | + | + |
| 379 | + | + |
| 380 | + | + |
| 381 | + | + |
| 382 | + | + |
| 383 | + | + |
| 384 | + | + |
| 385 | + | + |
| 386 | + | + |
| 387 | + | + |
| 388 | + | + |
| 389 | + | + |
| 390 | − | − |
| 391 | − | − |
| 392 | − | + |
| 393 | + | + |
| 394 | + | + |
| 395 | + | + |
| 396 | + | + |
| 397 | + | + |

TABLE 2-continued

| Compound No. | MIC E. Coli | MIC S. aureus |
|---|---|---|
| 398 | + | + |
| 399 | + | + |
| 400 | + | + |
| 401 | + | + |
| 402 | + | + |
| 403 | + | + |
| 404 | + | + |
| 405 | + | + |
| 406 | + | + |
| 407 | + | + |
| 408 | + | + |
| 409 | + | + |
| 410 | + | + |
| 411 | + | + |
| 412 | + | + |
| 413 | + | + |
| 414 | + | + |
| 415 | + | + |
| 416 | + | + |
| 417 | + | + |
| 418 | + | + |
| 419 | + | + |
| 420 | + | + |
| 421 | + | + |
| 422 | + | + |
| 423 | + | + |
| 424 | + | + |
| 425 | + | + |
| 426 | + | + |
| 427 | + | + |
| 428 | + | + |
| 429 | + | + |
| 430 | + | + |
| 431 | + | + |
| 432 | + | + |
| 433 | + | + |
| 434 | + | + |
| 435 | + | + |
| 436 | + | + |
| 437 | + | + |
| 438 | + | + |
| 439 | + | + |
| 440 | + | + |
| 441 | + | + |
| 442 | + | + |
| 443 | + | + |
| 444 | + | + |
| 445 | + | + |
| 446 | + | + |
| 447 | + | + |
| 448 | + | + |
| 449 | − | + |
| 450 | + | + |
| 451 | + | + |
| 452 | − | − |
| 453 | − | − |
| 454 | + | + |
| 455 | + | + |
| 456 | + | + |
| 457 | + | + |
| 458 | − | + |
| 459 | + | + |
| 460 | + | + |
| 461 | + | + |
| 462 | + | + |
| 463 | + | − |
| 464 | + | + |
| 465 | + | + |
| 466 | + | + |
| 467 | + | + |
| 468 | − | + |
| 469 | + | + |
| 470 | + | + |
| 471 | + | + |
| 472 | + | + |
| 473 | + | + |
| 474 | + | + |

TABLE 2-continued

| Compound No. | MIC E. Coli | MIC S. aureus |
|---|---|---|
| 475 | + | + |
| 476 | + | + |
| 477 | + | + |
| 478 | − | − |
| 479 | − | − |
| 480 | + | + |
| 481 | + | + |
| 482 | + | + |
| 483 | + | + |
| 484 | + | + |
| 485 | + | + |
| 486 | + | + |
| 487 | + | + |
| 488 | + | + |
| 489 | − | − |
| 490 | + | + |
| 491 | + | + |
| 492 | + | + |
| 493 | + | + |
| 494 | + | + |
| 495 | − | − |
| 496 | − | − |
| 497 | − | + |
| 498 | − | + |
| 499 | + | + |
| 500 | + | + |
| 501 | − | − |
| 502 | + | + |
| 503 | + | + |
| 504 | − | − |
| 505 | + | + |
| 506 | + | + |
| 507 | + | + |
| 508 | + | + |
| 509 | − | − |
| 510 | − | − |
| 511 | + | + |
| 512 | + | + |
| 513 | − | − |
| 514 | − | − |
| 515 | + | + |
| 516 | + | + |
| 517 | + | + |
| 518 | + | + |
| 519 | + | + |
| 520 | + | + |
| 521 | + | + |
| 522 | + | + |
| 523 | + | + |
| 524 | + | + |
| 525 | + | + |
| 526 | + | + |
| 527 | + | + |
| 528 | + | + |
| 529 | − | − |
| 530 | − | − |
| 531 | + | + |
| 532 | − | + |
| 533 | + | + |
| 534 | + | + |
| 535 | − | + |
| 536 | + | + |
| 537 | + | + |
| 538 | − | + |
| 539 | − | − |
| 540 | + | + |
| 541 | + | + |
| 542 | + | + |
| 543 | − | − |
| 544 | + | + |
| 545 | − | − |
| 546 | − | + |
| 547 | ND | ND |
| 548 | − | + |
| 549 | + | + |
| 550 | − | − |
| 551 | − | − |

TABLE 2-continued

| Compound No. | MIC E. Coli | MIC S. aureus |
|---|---|---|
| 552 | + | + |
| 553 | + | + |
| 554 | + | + |
| 555 | + | + |
| 556 | + | + |
| 557 | + | + |
| 558 | + | + |
| 559 | + | + |
| 560 | + | + |
| 561 | + | + |
| 562 | ND | ND |
| 563 | + | + |
| 564 | + | + |
| 565 | + | + |
| 566 | − | + |
| 567 | − | + |
| 568 | − | + |
| 569 | + | + |
| 570 | + | + |
| 571 | + | + |
| 572 | + | + |
| 573 | + | + |
| 574 | + | − |
| 575 | + | + |
| 576 | + | + |
| 577 | + | + |
| 578 | + | + |
| 579 | + | + |
| 580 | − | − |
| 581 | + | + |
| 582 | − | − |

*ND = not determined

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound of Formula (I)

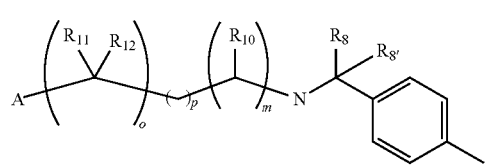

-continued

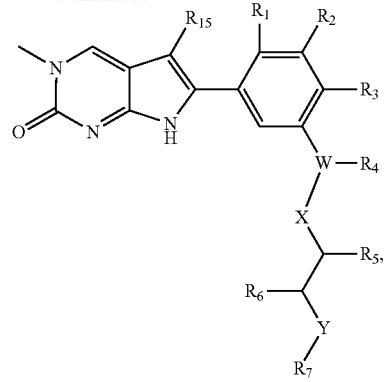

or a tautomer thereof, or a pharmaceutically acceptable salt, or ester of said compound or tautomer wherein:

$R_1$ is H or F, wherein when $R_1$ is H, then $R_2$ is $CF_3$, $OCF_3$, $SCF_3$, $SOCF_3$ or halo and $R_3$ is H; and when $R_1$ is F, then (i) $R_2$ is Cl or $OCF_3$ and $R_3$ is H; or (ii) $R_2$ is H and $R_3$ is $C_1$-$C_6$ alkyl; or (iii) $R_2$ is $C_1$-$C_6$ alkyl optionally substituted with one or more halo and $R_3$ is halo;

$R_4$ is H, OH, $NH_2$, or $C_1$-$C_6$ alkoxyl, or when X is O or $CHR_{17}$, $R_4$ and $R_5$ together with the two atoms to which they are attached and the atom connecting said two atoms form a 5- to 8-membered heterocycloalkyl ring having 1 to 2 heteroatoms; or when X is a bond, $R_4$ and $R_6$ together with the two carbon atoms to which they are attached and the carbon atom connecting said two carbon atoms, form a 5- to 12-membered saturated heterocycloalkyl ring having 1 to 2 heteroatoms;

$R_5$ is H, $CH_2OH$ or $CH_2OC_1$-$C_6$ alkyl, or when X is O or $CHR_{17}$, $R_4$ and $R_5$ together with the two atoms to which they are attached and the atom connecting said two atoms form a 5- to 8-membered heterocycloalkyl ring having 1 to 2 heteroatoms;

$R_6$ is $C_1$-$C_3$ alkyl optionally substituted with one or more substituents independently selected from the group consisting of halo, OH, azido, amino, $C_1$-$C_6$ alkoxyl, $C_1$-$C_6$ alkylthio, $C_2$-$C_3$ alkenyl, $OCOR_a$, $CH_2OCOR_a$, and $-OP(O)(OR_a)_2$, in which $R_a$ is $C_1$-$C_6$ alkyl, amino, or phenyl, and $R_a$ is optionally substituted with COOH, $COOC_1$-$C_6$ alkyl, $OCOC_1$-$C_6$ alkyl, phenyl, or $C_7$-$C_{12}$ arylalkyl; or $R_6$ and $R_7$ together with the two atoms to which they are attached, form a 5- to 12-membered heterocycloalkyl ring having 0 to 1 additional heteroatom optionally substituted with an oxo group; or $R_6$ and $R_{17}$ together with the two carbon atoms to which they are attached and the carbon atom connecting said two carbon atoms, form a 5- to 12-membered saturated heterocycloalkyl ring having 1 to 2 heteroatoms; or when X is a bond, $R_4$ and $R_6$ together with the two carbon atoms to which they are attached and the carbon atom connecting said two carbon atoms, form a 5- to 12-membered saturated heterocycloalkyl ring having 1 to 2 heteroatoms;

$R_7$ is H, C(=NH)$NH_2$, or $COR_b$ in which $R_b$ is $C_1$-$C_6$ alkyl optionally substituted with $C_1$-$C_6$ alkoxyl or amino; or $R_6$ and $R_7$ together with the two atoms to which they are attached, form a 5- to 12-membered heterocycloalkyl ring having 0 to 1 additional heteroatom optionally substituted with an oxo group;

$R_{11}$ is $Q_1$-$T_1$, in which $Q_1$ is a bond or $C_1$-$C_3$ alkyl linker optionally substituted with one or more halo or hydroxyl, and $T_1$ is H, halo, OH, COOH, cyano, azido, $C_1$-$C_3$ alkyl, $C_2$-$C_6$ alkenyl, $C_2$-$C_6$ alkynyl, $C_1$-$C_6$ alkoxyl, $C_2$-$C_6$ haloalkenyl, $C_1$-$C_6$ alkylthio, COOC$_1$-$C_6$ alkyl, —NHC(O)CH$_2$NH$_2$, NHS(O)C$_1$-$C_3$ alkyl, SO$_2$C$_1$-$C_6$ alkyl, or $R_c$, in which $R_c$ is amino, $C_3$-$C_8$ cycloalkyl, $C_6$-$C_{10}$ aryl, 4 to 12-membered heterocycloalkyl, 5- or 6-membered heteroaryl, —O-heteroaryl, —NH-heteroaryl, —S-heteroaryl, or C(O)NR$_d$R$_e$, each of $R_d$ and $R_e$ independently being H or $C_1$-$C_6$ alkyl, or $R_d$ and $R_e$ together with the nitrogen atom to which they are attached forming a 5- to 12-membered heterocycloalkyl ring having 0 to 2 additional heteroatoms; and $R_c$ is optionally substituted with -$Q_2$-$T_2$, in which $Q_2$ is a bond or $C_1$-$C_3$ alkyl and $T_2$ is H, halo, $C_1$-$C_3$ alkyl, amino, 5- or 6-membered heteroaryl or $C_6$-$C_{10}$ aryl wherein the aryl and heteroaryl are optionally substituted with $C_1$-$C_6$ alkoxyl or $C_1$-$C_4$ aminoalkyl;

$R_8$ and $R_{10}$, together with the two carbon atoms to which they are attached and the Z atom connecting said two carbon atoms, form a 5- to 12-membered heterocycloalkyl ring having 0 to 2 additional heteroatoms optionally substituted with one more substituents independently selected from $C_1$-$C_6$ alkyl or —C(=N)NH$_2$;

$R_{8'}$ is H $R_{12}$ is H or $C_1$-$C_6$ alkyl, or $R_{12}$ and $R_{11}$ together with the carbon atom to which they are attached form a 4- to 12-membered saturated heterocycloalkyl ring having 1 to 2 heteroatoms optionally substituted with C(=NH)NH$_2$ each of $R_9$ and $R_{13}$ independently is H, $C_1$-$C_3$ alkyl, $C_2$-$C_4$ alkenyl or —C(O)H, or $R_9$ and $R_{13}$, when Z is NR$_9$, together with the two nitrogen atoms to which they are attached and the carbon atoms connecting said two nitrogen atoms, form a 7- to 12-membered saturated heterocycloalkyl ring having 0 to 1 additional heteroatom, or $R_9$ and A, when Z is NR$_9$ and A is NR$_{13}$R$_{14}$, together with the two atoms to which they are attached and the atoms connecting said atoms form a 5- to 8-membered heterocycloalkyl ring having 2 to 3 heteroatoms optionally substituted with an oxo or an imino group;

$R_{11}$ and $R_{13}$, when A is NR$_{13}$R$_{14}$, together with the atoms to which they are attached form a 5- to 8-membered heterocycloalkyl ring having 0 to 2 additional heteroatoms optionally substituted with oxo;

$R_{14}$ is H, C(O)C$_1$-$C_3$ alkyl, C(O)NH$_2$, C(CH=NO$_2$)NHCH$_3$, C(=NH)H, C(=NH)C$_1$-$C_3$ alkyl, 5- or 6-membered heteroaryl having 1 to 3 heteroatoms, 5 or 6-membered heterocycloalkyl having 1 to 3 heteroatoms, $C_1$-$C_6$ alkyl optionally substituted with one or more substituents independently selected from 5- or 6-membered heteroaryl having 1 to 3 heteroatoms, $C_3$-$C_8$ cycloalkyl, and 5 or 6-membered heterocycloalkyl having 1 to 3 heteroatoms, or C(=NR$_{16}$)NH$_2$, in which $R_{16}$ is H, $C_1$-$C_3$ alkyl, $C_2$-$C_4$ alkenyl, $C_3$-$C_8$ cycloalkyl, or 4- to 12-membered saturated heterocycloalkyl ring having 1 to 2 heteroatoms, or $R_{16}$ and $R_{11}$ together with the two atoms to which they are attached and the atoms connecting said two carbon atoms, form a 5- to 12-membered heterocycloalkyl ring having 0 to 1 additional heteroatom;

$R_{14}$ and $R_{13}$ together with the nitrogen atom to which they are attached form a 5- or 6-membered heteroaryl having 1 to 3 additional heteroatoms optionally substituted with oxo; or $R_{14}$ and $R_{13}$ together with the nitrogen atom to which they are attached form a 5- or 6-membered heterocycloalkyl having 1 to 3 additional heteroatoms optionally substituted with oxo;

$R_{15}$ is H or halo;

A is C(O)NH$_2$, NR$_{13}$R$_{14}$, C(O)NHC$_1$-$C_3$ alkyl, C(O)OH, OH, CN, $C_3$-$C_8$ cycloalkyl, —OP(O)(OR$_b$)$_2$, in which $R_b$ is $C_1$-$C_6$ alkyl, amino, or phenyl, 5 or 6-membered heterocycloalkyl having 1 to 3 heteroatoms optionally substituted with oxo, or 5- or 6-membered heteroaryl having 1 to 4 heteroatoms optionally substituted with $C_1$-$C_4$ alkyl, $C_1$-$C_4$ alkylenyl-aryl, NO$_2$, or amino, wherein the alkyl, alkylenyl, and aryl are optionally substituted with one or more substituents independently selected from $C_1$-$C_3$ alkyl, $C_2$-$C_4$ alkenyl, $C_1$-$C_3$ alkoxy, or halo; or $R_9$ and A, when Z is NR$_9$ and A is NR$_{13}$R$_{14}$, together with the two carbon atoms to which they are attached and the atoms connecting said carbon atoms form a 5- to 8-membered heterocycloalkyl ring having 2 to 3 heteroatoms optionally substituted with an oxo or an imino group;

W is CH or C; or W and Y, when W is C, together with the atoms to which they are attached, form a 5- to 12-membered heterocycloalkyl ring having 0 to 1 additional heteroatom;

X is a bond, O, or CHR$_{17}$, in which $R_{17}$ is H, or $R_{17}$ and $R_6$ together with the two carbon atoms to which they are attached and the carbon atom connecting said two carbon atoms, form a 5- to 12-membered saturated heterocycloalkyl ring having 1 to 2 heteroatoms; or when X is a bond, $R_4$ and $R_6$ together with the two carbon atoms to which they are attached and the carbon atom connecting said two carbon atoms, form a 5- to 12-membered saturated heterocycloalkyl ring having 1 to 2 heteroatoms;

Y is NH; or Y and W together with the atoms to which they are attached, form a 5- to 12-membered heterocycloalkyl ring having 0 to 1 additional heteroatom;

Z is a bond, O, NR$_9$, NH, CH, or CH$_2$; or $R_{11}$ and Z, when Z is NH or CH, together with the atoms to which they are attached and the atoms connecting said two atoms form a 5- to 8-membered heterocycloalkyl ring having 0 to 2 additional heteroatoms;

each m and o is independently 0 or 1;

and p is 0, 1, or 2; and provided that for a compound of Formula (I)

(c) when $R_{14}$ is C(=NR$_{16}$)NH$_2$, X is CH$_2$, and $R_6$ is CH$_2$OCH$_3$, then at least one of $R_4$, $R_5$, $R_7$, $R_8$, $R_{10}$, $R_{11}$, $R_{12}$, or $R_{15}$ is not H.

2. The compound of claim 1 having Formula (Ia):
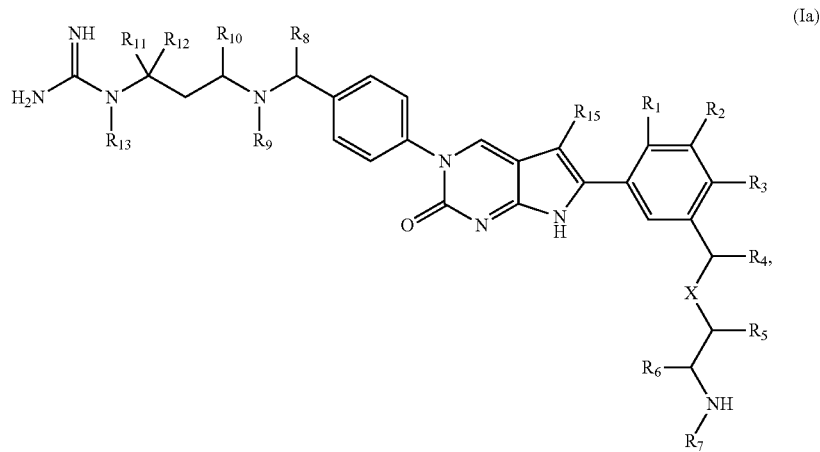
(Ia)
or a tautomer thereof, or a pharmaceutically acceptable salt, or ester of said compound or tautomer, provided that
(c) when X is $CH_2$, $R_6$ is $CH_2OCH_3$, then at least one of $R_4$, $R_5$, $R_7$, $R_8$, $R_{10}$, $R_{11}$, $R_{12}$, or $R_{15}$ is not H.
3. The compound of claim 1 having Formula (Ib), (Ic), or (Id):
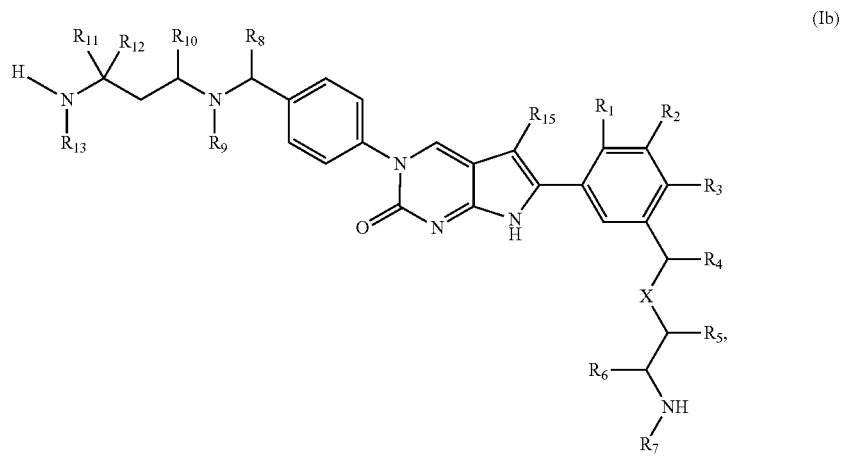
(Ib)
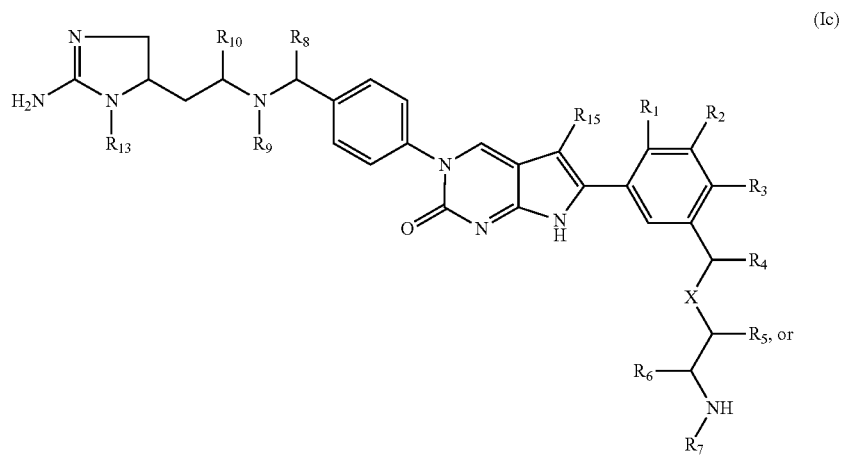
(Ic)

-continued (Id)

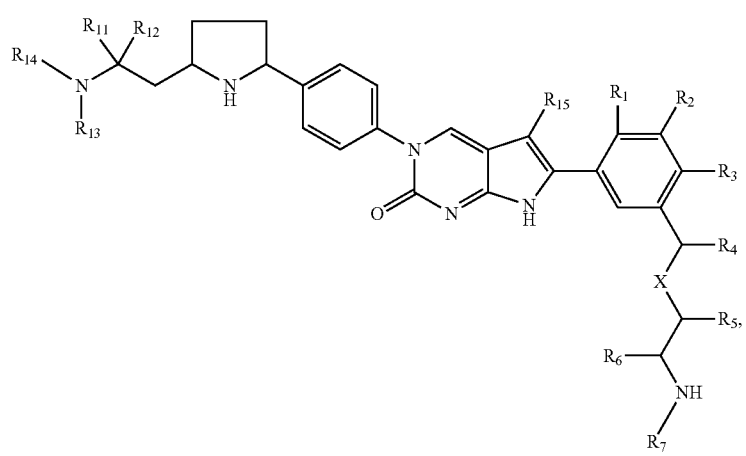

or a tautomer thereof, or a pharmaceutically acceptable salt, or ester of said compound or tautomer.

4. The compound of claim 1 or a tautomer thereof, or a pharmaceutically acceptable salt, or ester of said compound or tautomer, wherein each of $R_1$ and $R_3$ is H and $R_2$ is $CF_3$, $OCF_3$, $SCF_3$, $SOCF_3$ or Cl.

5. The compound of claim 1 or a tautomer thereof, or a pharmaceutically acceptable salt, or ester of said compound or tautomer, wherein $R_1$ is F, $R_3$ is H and $R_2$ is $OCF_3$ or Cl.

6. The compound of claim 1 or a tautomer thereof, or a pharmaceutically acceptable salt, or ester of said compound or tautomer, wherein each of $R_1$ and $R_3$ is F, and $R_2$ is $CF_3$ or ethyl.

7. The compound of claim 1 or a tautomer thereof, or a pharmaceutically acceptable salt, or ester of said compound or tautomer, wherein $R_1$ is F, $R_2$ is H, and $R_3$ is methyl.

8. The compound of claim 1 or a tautomer thereof, or a pharmaceutically acceptable salt, or ester of said compound or tautomer, wherein $R_6$ is methyl, ethyl, $CH_2OH$, $CH_2CH_2OH$, $CH_2F$, $CH_2OCH_3$, $CH_2SCH_3$, $CH(OH)CH_2OH$, $CH_2NH_2$, $CH_2OCOCH_3$, $CH_2OCOC_6H_5$, $CH_2OCONHCH_2C_6H_5$, $CH_2OCOCH_2CH_2COOH$, $CH_2OCOC_6H_4OCOCH_3$, $CH_2OCOCH_2C_6H_4$, $CH_2OP(O)(OH)_2$, or $CH_2OP(O)(OPh)_2$.

9. The compound of claim 1 or a tautomer thereof, or a pharmaceutically acceptable salt, or ester of said compound or tautomer, wherein $R_7$ is H, C(=NH)NH_2, $COOCH_2CH_3$, $COCH_2NH_2$, or $COCH_3$.

10. The compound of claim 1 or a tautomer thereof, or a pharmaceutically acceptable salt, or ester of said compound or tautomer, wherein $R_6$ and $R_7$ together with the atoms to which they are attached, form

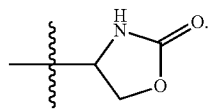

11. The compound of claim 1 or a tautomer thereof, or a pharmaceutically acceptable salt, or ester of said compound or tautomer, wherein X is a bond, and $R_4$ and $R_6$ together with the two carbon atoms to which they are attached and the carbon atom connecting said two carbon atoms, form

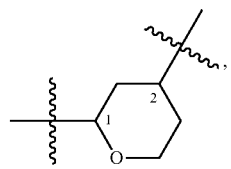

with carbon 1 connected to phenyl and carbon 2 connected to $NHR_7$.

12. The compound of claim 1 or a tautomer thereof, or a pharmaceutically acceptable salt, or ester of said compound or tautomer, wherein each of $R_4$ and $R_5$ is H, X is $CHR_{17}$, in which $R_{17}$ and $R_6$ together with the two carbon atoms to which they are attached and the carbon atom connecting said two carbon atoms, form

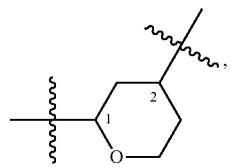

with carbon 1 connected to phenyl and carbon 2 connected to $NHR_7$.

13. The compound of claim 1 or a tautomer thereof, or a pharmaceutically acceptable salt, or ester of said compound or tautomer, wherein X is O.

14. The compound of claim 13 or a tautomer thereof, or a pharmaceutically acceptable salt, or ester of said compound or tautomer, wherein $R_5$ is H and $R_6$ is methyl, ethyl, $CH_2OH$, $CH_2CH_2OH$, $CH_2F$, $CH_2OCH_3$, $CH_2SCH_3$, $CH(OH)CH_2OH$, $CH_2NH_2$, $CH_2OCOCH_3$, $CH_2OCOC_6H_5$, $CH_2OCONHCH_2C_6H_5$, $CH_2OCOCH_2CH_2COOH$, $CH_2OCOC_6H_4OCOCH_3$, $CH_2OCOCH_2C_6H_4$, $CH_2OP(O)(OH)_2$, or $CH_2OP(O)(OPh)_2$.

15. The compound of claim 13 or a tautomer thereof, or a pharmaceutically acceptable salt, or ester of said compound or tautomer, wherein $R_5$ is H and $R_6$ is $CH_2OH$.

16. The compound of claim 1 or a tautomer thereof, or a pharmaceutically acceptable salt, or ester of said compound or tautomer, wherein each of $R_{11}$ and $R_{12}$ is H or $CH_3$, or $R_{11}$ and $R_{12}$ together with the carbon atom to which they are attached form

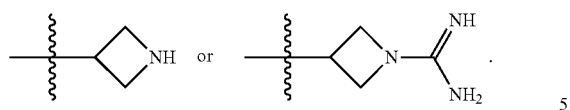
17. A pharmaceutical composition comprising a pharmaceutically acceptable carrier and a compound of claim 1 or a tautomer thereof, or a pharmaceutically acceptable salt, or ester of said compound or tautomer.
* * * * *